United States Patent
Kanouni et al.

(10) Patent No.: US 11,814,384 B2
(45) Date of Patent: Nov. 14, 2023

(54) INHIBTORS OF RAF KINASES

(71) Applicant: Kinnate Biopharma Inc., San Diego, CA (US)

(72) Inventors: Toufike Kanouni, Rancho Santa Fe, CA (US); Jason M. Cox, Rancho Santa Fe, CA (US); John Tyhonas, San Diego, CA (US); Robert S. Kania, Del Mar, CA (US); Subhas J. Chakravorty, Sellersville, PA (US); Young K. Chen, San Marcos, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

(21) Appl. No.: 18/164,326

(22) Filed: Feb. 3, 2023

(65) Prior Publication Data

US 2023/0303566 A1    Sep. 28, 2023

Related U.S. Application Data

(60) Provisional application No. 63/306,195, filed on Feb. 3, 2022.

(51) Int. Cl.
| | | |
|---|---|---|
| *C07D 403/12* | (2006.01) | |
| *C07D 471/04* | (2006.01) | |
| *C07D 487/04* | (2006.01) | |
| *C07D 519/00* | (2006.01) | |
| *C07D 491/147* | (2006.01) | |

(52) U.S. Cl.
CPC ......... *C07D 471/04* (2013.01); *C07D 403/12* (2013.01); *C07D 487/04* (2013.01); *C07D 491/147* (2013.01); *C07D 519/00* (2013.01)

(58) Field of Classification Search
CPC ... C07D 403/12; C07D 471/04; C07D 401/14
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 2004/0157827 | A1 | 8/2004 | Pevarello et al. |
| 2005/0256174 | A1 | 11/2005 | Wood et al. |
| 2008/0114006 | A1 | 5/2008 | Flynn et al. |
| 2008/0176846 | A1 | 7/2008 | Chianelli et al. |
| 2011/0183997 | A1 | 7/2011 | Chianelli et al. |
| 2018/0346457 | A1 | 12/2018 | Zamboni et al. |
| 2021/0300904 | A1 | 9/2021 | Kaldor et al. |

FOREIGN PATENT DOCUMENTS

| | | |
|---|---|---|
| EP | 3663293 A1 | 6/2020 |
| WO | WO-03068229 A1 | 8/2003 |
| WO | WO-2006071940 A2 | 7/2006 |
| WO | WO-2008034008 A2 | 3/2008 |
| WO | WO-2013134298 A1 | 9/2013 |
| WO | WO-2013184119 A1 | 12/2013 |
| WO | WO-2014151616 | 9/2014 |
| WO | WO-2014151616 A1 | 9/2014 |
| WO | WO-2020198058 A1 | 10/2020 |
| WO | WO-2023070053 A1 | 4/2023 |

OTHER PUBLICATIONS

Berge et al. Pharmaceutical Salts. Journal of Pharmaceutical Sciences 66(1):1-19 (Jan. 1977).
Cohn-Cedermark et al. Central nervous system metastases of cutaneous malignant melanoma—A population-based study. Acta Oncol. 37:463-470 (1998).
Di et al. Chapter 3: Free Drug Hypothesis for CNS Drug Candidates. Blood-Brain Barrier in Drug Discovery: Optimizing Brain Exposure of CNS Drugs and Minimizing Brain Side Effects for Peripheral Drugs. Wiley & Sons p. 42-65 (2015).
Di et al. Strategies to assess blood-brain barrier penetration. Expert Opin Drug Disc 3(6):677-687 (2008).
Evans. Synthesis of radiolabeled compounds. J Radioanal Chem 64(1-2):9-32 (1981).
Gynther et al. Large neutral amino acid transporter enables brain drug delivery via prodrugs. J. Med. Chem. 51(4):932-936 (2008).
Kabalka et al. The Synthesis of Radiolabeled Compounds via Organometallic Intermediates. Tetrahedron 45(21):6601-6621 (1989).
Ohtsuki et al. Contribution of carrier-mediated transport systems to the blood-brain barrier as a supporting and protecting interface for the brain; importance for CNS drug discovery and development. Pharm. Res., 24:1745-58 (2007).
PCT/SU2022/078461 International Search Report and Written Opinion dated Jan. 4, 2023.
Pubchem, SID 439173928, Available Date: Dec. 19, 2020 [retrieved on 21 Nov. 1-10, 24-33, 41 2022]., Retrieved from the Internet URL: https://pubchem.ncbi.nlm.nih.gov/substance/439173928 entire document.
Redmer. Deciphering mechanisms of brain metastasis in melanoma—The gist of the matter. Mol. Cancer 17:106 (2018).
Summerfield et al. Examining the Uptake of Central Nervous System Drugs and Candidates across the Blood-Brain Barrier. J. Pharmacol. Exp. Ther. 358:294-305 (2016).
Tawbi et al. New era in the management of melanoma brain metastases. Am. Soc. Clin. Oncol. Educ. Book 38:741-750 (2018).
Nishiguchi et al. Design and Discovery of N-(2-Methyl-5'-morpholino-6'-(((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).
Ramurthy et al. Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).
PCT/US2023/061939 International Search Report and Written Opinion dated Apr. 11, 2023.
CAS Chemical Structure Search dated Jun. 29, 2023.

*Primary Examiner* — Samira J Jean-Louis
(74) *Attorney, Agent, or Firm* — WILSON SONSINI GOODRICH & ROSATI

(57) ABSTRACT

Provided herein are inhibitors of receptor tyrosine kinase effector, RAF, pharmaceutical compositions comprising said compounds, and methods for using said compounds for the treatment of diseases.

30 Claims, No Drawings

INHIBITORS OF RAF KINASES

CROSS-REFERENCE TO RELATED APPLICATION

This application claims the benefit of U.S. Patent Application No. 63/306,195, filed on Feb. 3, 2022 which is hereby incorporated by reference in its entirety.

BACKGROUND

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY OF THE INVENTION

Provided herein are inhibitors of the receptor tyrosine kinase effector Raf (RAF), pharmaceutical compositions comprising said compounds, and methods for using said compounds for the treatment of diseases.

One embodiment provides a compound, or pharmaceutically acceptable salt or solvate thereof, having the structure of Formula (I):

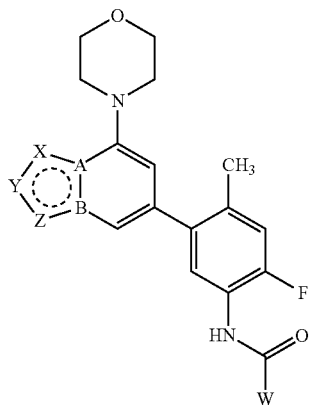

(I)

wherein,
A is N or C; B is N or C; provided if A is N, then B is C; or if A is C, then B is N;
X is N or C—$R^1$;
Y is N or C—$R^2$
Z is N or C—$R^3$;
$R^1$, $R^2$, and $R^3$ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (Ia):

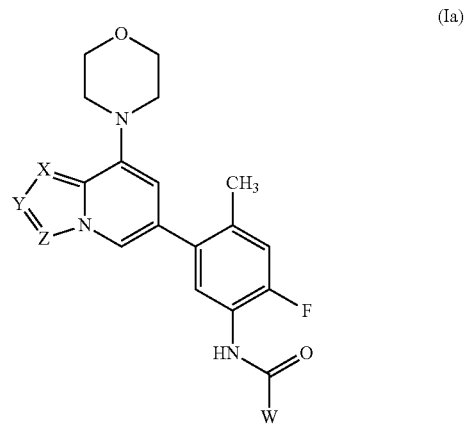

(Ia)

wherein,
X is N or C—$R^1$;
Y is N or C—$R^2$
Z is N or C—$R^3$;
$R^1$, $R^2$, and $R^3$ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (Ib):

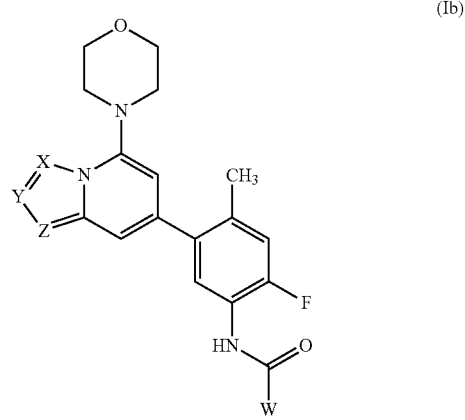

(Ib)

wherein,

X is N or C—R¹;

Y is N or C—R²

Z is N or C—R³;

R¹, R², and R³ are independently selected from H, —CN, halogen, optionally substituted alkyl, optionally substituted cycloalkyl, or optionally substituted cycloalkylalkyl; and W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (II):

(II)

wherein,

X is N or C—R¹;

Z is N or C—R³;

R¹ and R³ are independently selected from H, —CN, halogen, optionally substituted alkyl, optionally substituted cycloalkyl, or optionally substituted cycloalkylalkyl;

R⁴ is selected from optionally substituted alkyl, optionally substituted cycloalkyl, or optionally substituted cycloalkylalkyl; and W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (III):

(III)

wherein,

L is —CO—NH—, or —NH—CO—;

A is N or C; B is N or C; provided if A is N, then B is C; or if A is C, then B is N;

X is N or C—R¹;

Y is N or C—R²

Z is N or C—R³;

R¹, R², and R³ are independently selected from H, —CN, halogen, optionally substituted alkyl, optionally substituted cycloalkyl, or optionally substituted cycloalkylalkyl; or optionally, R¹ and R² may join to form a ring; or optionally R² and R³ may join to form a ring;

R⁴ is selected from H, halogen, or optionally substituted C1-C3 alkyl;

K is N, or C—H;

E is N, or C—H;

M is N, or C—R⁵;

Q is N, or C—R⁵;

T is N, or C—R⁵;

each R⁵ is independently selected from H, halogen, or optionally substituted C1-C3 alkyl;

G is selected from

W is selected from:
- optionally substituted nitrogen-containing heterocyclyl;
- optionally substituted nitrogen-containing heteroaryl;
- optionally substituted carbocyclyl;
- optionally substituted aryl;
- optionally substituted nitrogen-containing heterocyclyl further substituted with an optionally substituted cycloalkyl, or optionally substituted cycloalkylalkyl;
- optionally substituted nitrogen-containing heteroaryl further substituted with an optionally substituted cycloalkyl, or optionally substituted cycloalkylalkyl;
- optionally substituted carbocyclyl further substituted with an optionally substituted cycloalkyl, or optionally substituted cycloalkylalkyl; and
- optionally substituted aryl further substituted with an optionally substituted cycloalkyl, or optionally substituted cycloalkylalkyl.

One embodiment provides a pharmaceutical composition comprising a compound of Formula (I), (Ia), (Ib), (II), or (III), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), (Ia), (Ib), (II), or (III), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl).

In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$(where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$(where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms.

The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$(where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) 7r-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —R-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula -$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O-$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure.

When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para- isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

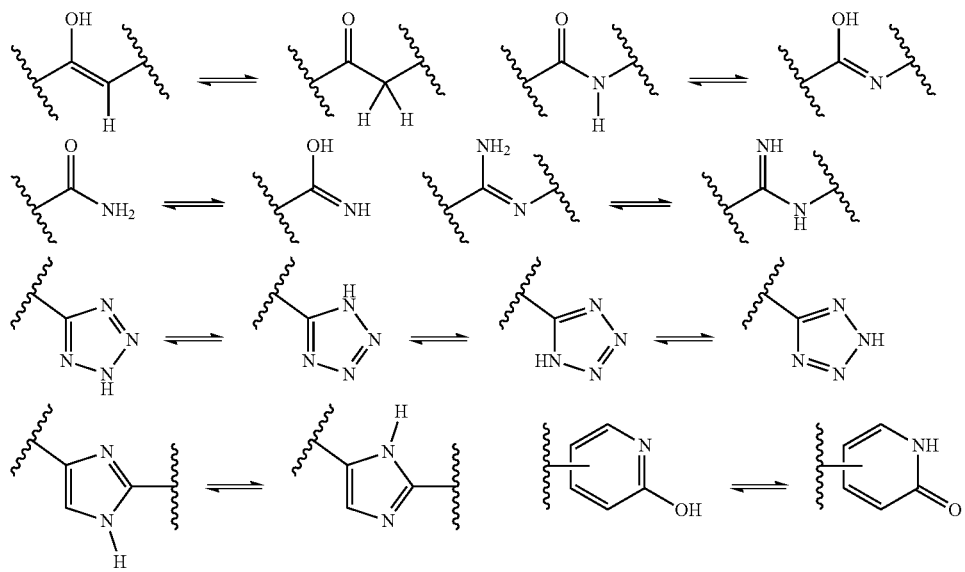

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

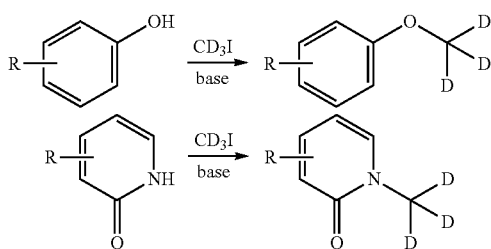

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

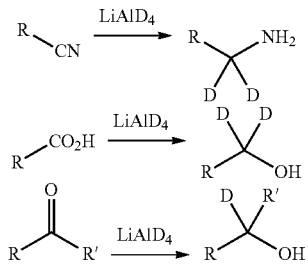

Deuterium gas and palladium catalyst are employed to reduce unsaturated carbon-carbon linkages and to perform a reductive substitution of aryl carbon-halogen bonds as illustrated, by way of example only, in the reaction schemes below.

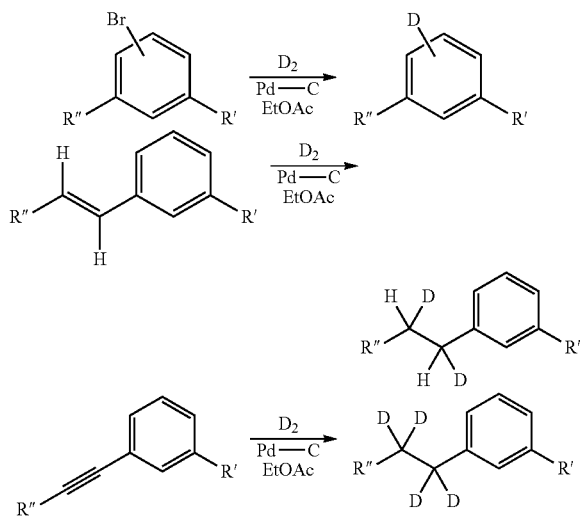

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the RAF inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in unsolvated as well as solvated forms. The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The RAF Family of Kinases

The RAF kinases are a family of serine/thronine protein kinases constitute core components of the RAS-RAF-MEK-ERK mitogen activated protein kinase (MAPK) signalling cascade (also known as the MAPK/ERK pathway), a pathway that mediates signals from cell surface receptors to the nucleus to regulate cell growth, differentiation, and survival. The RAF proteins are related to retroviral oncogenes and are structurally conserved from metazoans to mammals, as is the MAPK/ERK pathway. Their dysregulation leads to uncontrolled cellular proliferation, survival, and dedifferentiation. Consequently, RAF kinases are altered or inappropriately activated in a majority of cancers.

The MAPK/ERK signalling pathway is a network of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, which communicate by adding phosphate groups to a neighboring protein, which acts as a molecular "on" or "off" switch, and overall, the pathway can be divided into 3 steps: (i) Ras activation, (ii) a kinase signal transduction cascade, and (iii) regulation of translation and transcription. Briefly, an extracellular mitogen or a signaling molecule binds to the membrane receptor. This allows Ras (a small GTPase) to swap its GDP for a GTP and become active. Activated Ras activates the protein kinase activity of RAF kinase. RAF kinase phosphorylates and activates MEK (MEK1 and MEK2). MEK then phosphorylates and activates a MAPK (also known as ERK). MAPK activation regulates activities of several transcription factors and also alters the translation of mRNA to proteins. By altering the levels and activities of transcription factors, MAPK leads to altered transcription of genes that are important for the cell cycle.

There are three known mammalian RAF isoforms: C-RAF (also known as RAF-1, or c-RAF-1), BRAF, and A-RAF. All RAF kinases share a common modular structure consisting of 3 conserved regions (CR1, CR2, and CR3) with distinct functions. CR1 contains (i) a Ras-binding domain (RBD), which is necessary for the interaction with Ras and with membrane phospholipids required for membrane recruitment, and (ii) a cysteine-rich domain (CRD), which is a secondary Ras-binding site and also necessary for the interaction of CR1 with the kinase domain for RAF autoinhibition. CR2 contains important inhibitory phosphorylation sites participating in the negative regulation of Ras binding and RAF activation. CR3 features the kinase domain, including the activation segment, whose phosphorylation is crucial for kinase activation.

Functionally, the RAF structure can be split into a regulatory N-terminal region, containing the RBD, which is critical for activation as well as inhibitory phosphorylation sites, and a catalytic C-terminal region, which includes phosphorylation sites necessary for the kinase activation. The regulatory domain restrains the activity of the kinase domain, and its removal results in constitutive oncogenic activation. However, the activity of the isolated C-RAF kinase domain is subjected to further regulation and can be stimulated by phorbol esters, v-Src, and phosphorylation.

The common and key step in the activation of all 3 RAF kinase isoforms is membrane recruitment by a Ras family protein. The RAF kinases are located in the cytosol in their inactive state when bound to 14-3-3 proteins. In the presence of active Ras, they translocate to the plasma membrane. Membrane translocation triggers further activation events, such as the binding of PP2A to dephosphorylate the inhibitory pS259 site in RAF-1 (and presumably the corresponding sites in A-RAF and B-RAF) and the co-localization with the kinases responsible for the multiple activating phosphorylations. The sequences forming the binding interface are well conserved in the RAF as well as Ras family indicating that several members of the Ras family have the ability to bind RAF kinases. H-Ras, N-Ras, and K-Ras stimulate all 3 RAF isoforms and are the only Ras proteins that activate B-RAF. In contrast, A-RAF is also activated by R-Ras3, while C-RAF responds weakly to R-Ras3, Rit, and TC21 as well. But all RAF kinases share MEK1/2 kinases as substrates. MEK1/2 in turn activate ERK1/2, and this pathway regulates many cellular functions such as cell proliferation, differentiation, migration, or apoptosis.

C-RAF

C-RAF was first to be identified and is a ubiquitously expressed isoform. In humans, C-RAF is encoded by the RAF1 gene. C-RAF also has a known splice variant preferentially expressed in the muscle and brain. C-RAF plays a critical role in mediating the cellular effects of growth factor signals. In the inactive state, C-RAF exists in a closed conformation in which the N-terminal regulatory region folds over and occludes the catalytic region. This conformation is stabilized by a 14-3-3 dimer binding to an N-terminal site, phospho-S259 (pS259), and a C-terminal site, pS621. Dephosphorylation of pS259 at the cell membrane by specific phosphatases (PP2A, PP1) releases 14-3-3 from its N-terminal binding site in C-RAF, thereby allowing conformational changes to occur that unmask the RBD and CRD domains in the CR1 region to enable Ras binding and membrane recruitment.

B-RAF

B-RAF is encoded in humans by the BRAF gene, also known as proto-oncogene B-RAF and v-RAF murine sarcoma viral oncogene homolog B. Alternative splicing gives rise to multiple B-RAF isoforms which are differentially expressed in various tissues. Whereas activation of A-RAF and C-RAF requires both phosphorylation and dephosphorylation of certain residues, as well as binding to other proteins, B-RAF becomes activated immediately upon translocation to the plasma membrane. B-RAF exhibits higher basal kinase activity than A-RAF and C-RAF. B-RAF requires Ras and 14-3-3 binding for its activation and is inhibited or activated by PKA depending on the levels of 14-3-3 expression, which need to be high for permitting activation. B-RAF activity is also regulated by splicing. B-RAF isoforms containing exon 8b are more phosphorylated on the inhibitory S365 site, leading to an increased interaction with 14-3-3 and strengthening the inhibitory interaction between N-terminal regulatory domain and kinase domain, altogether resulting in lower kinase activity.

A-RAF

Serine/threonine-protein kinase A-RAF or A-RAF is an enzyme encoded by the ARAF gene in humans. There are 2 known splice isoforms of A-RAF - DA-RAF1 and D-RAF2. They lack the kinase domain and act as dominant inhibitory mutants of Ras and ARF GTPases. DA-RAF1 is a positive regulator of myogenic differentiation by mediating the inhibition of the ERK pathway required for differentiation. There are several ways A-RAF is different from the other RAF kinases. A-RAF is the only steroid hormone-regulated Raf isoform. In addition, the A-RAFprotein has amino acid substitutions in a negatively charged region upstream of the kinase domain (N-region), which contributes to its low basal activity. A-RAF is also only weakly activated by oncogenic H-Ras and Src and also displays low kinase activity towards MEK (the lowest kinase activity towards MEK proteins in the Raf kinase family). In addition to phosphorylating MEK, A-RAF also inhibits MST2, a tumor suppressor and proapoptotic kinase not found in the MAPK pathway. By inhibiting MST2, A-RAF prevents apoptosis from occurring. However, this inhibition only occurs when the splice factor heterogenous nuclear ribonucleoprotein H (hnRNP H) maintains the expression of a full-length A-RAF protein. Tumorous cells often overexpress hnRNP H which leads to full-length expression of A-Raf which then inhibits apoptosis, allowing cancerous cells that should be destroyed to stay alive. A-RAF also binds to pyruvate kinase $M_2$ (PKM2), again outside the MAPK pathway. PKM2 is an isozyme of pyruvate kinase that is responsible for the Warburg effect in cancer cells. A-RAF upregulates the activity of PKM2 by promoting a conformational change in PKM2. This causes PKM2 to transition from its low-activity dimeric form to a highly active tetrameric form. This causes more glucose carbons to be converted to pyruvate and lactate, producing energy for the cell, linking A-Raf to energy metabolism regulation and cell transformation, both of which are very important in tumorigenesis.

BRAF-Targeted Therapy in CNS Tumors and/or Brain Metastases

Patients with cerebral involvement have a dismal prognosis and their treatment is an unmet medical need. In the case of melanoma, brain metastases are frequently the first site of disease-progression (Cohn-Cedermark, G. et al. Central nervous system metastases of cutaneous malignant melanoma-A population-based study. *Acta Oncol.* 1998, 37, 463-470). Metastatic CNS invasion is a multistep process. Primary tumor cells initially enter the circulation and then undergo hematogenous spread until they arrest within capillary beds of organs, where they proliferate and form the metastasis. (Redmer, T. Deciphering mechanisms of brain metastasis in melanoma—The gist of the matter. *Mol. Cancer* 2018, 17, 106; Tawbi, H. A.; et al. New era in the management of melanoma brain metastases. *Am. Soc. Clin. Oncol. Educ. Book* 2018, 38, 741-750). One shortcoming of current therapies is the inability of a small molecule RAF kinase inhibitor to cross the blood-brain barrier and provide a therapeutically effective amount of inhibitor at the location of the CNS tumor and/or brain metastatic tissue.

Determination of Blood-Brain Barrier Penetration by Small Molecules

In drug development, CNS drug candidates have lower success rates and longer development times than those in the other therapeutic areas. (Di, L. et al. *Expert Opinion on Drug Discovery* (2008) 3:6, 677-687. DOI: 10.1517/17460441.3.6.677) Low brain penetration of small molecules can be due to several factors, including, but not limited to, low blood-brain barrier (BBB) permeability, P-glycoprotein (Pgp) efflux, or high plasma protein binding.

There are multiple mechanisms that affect brain penetration of molecules. Compounds may enter the brain by transcellular passive diffusion, which is driven by a concentration gradient between the blood and the brain. Brain penetration of compounds may be enhanced by influx transporters, such as the large neutral amino acid transporter 1 (LAT1) for L-dopa and gabapentin (Ohtsuki,et al. Pharm. Res. 2007, 24, 1745-58; Gynther, et al. J. Med. Chem. 2008, 51(4), 932-936). This requires that the compounds have a certain structural motif to bind to the transporter. Only a few examples have been reported in which this pathway was purposely used to increase brain penetration. Efflux transporters move molecules out of cells. Of primary importance for brain penetration is the efflux transporter Pgp. Plasma protein binding, which reduces the free drug concentration available for BBB penetration, and metabolism and renal excretion, which reduces the total blood concentration, also affect brain penetration. Overall, passive diffusion is the major driving force moving most molecules into the brain; however, the other mechanisms discussed above can reduce brain penetration, depending on the structure and properties of the compound.

Bioanalytical methods and screening strategies provide the rationale for design and evaluation of compounds with desirable BBB distribution properties. (Di, L. et al. Expert Opinion on Drug Discovery (2008) 3:6, 677-687; Summerfield et al. J. Pharmacol. Exp. Ther. (2016) 358:294-305) A superior representation of brain distribution is based on the ratio of unbound compound in the brain extracellular fluid to the unbound blood concentration, represented as Kp,uu. (Liu and Chen, Blood-Brain Barrier in Drug Discovery: Optimizing Brain Exposure of CNS Drugs and Minimizing Brain Side Effects for Peripheral Drugs (2015), p. 42-65, Wiley & Sons). Kp,uu is a steady-state distribution term denoting the unbound concentration gradient across the BBB. If Kp,uu is lower than 1, then drug passage across the BBB is restricted by some factor. IfKp,uu is larger than 1, then drug passage across the BBB is assisted by some factor. AKp,uu value of about 1 indicates passive diffusion across the BBB is predominate, or that active pathways (e.g., influx and efflux) are balanced. (Summerfield et al. vide supra)

RAF Kinase Inhibitors

Aberrant activation of the MAPK/ERK pathway is frequently found in various cancers and is a target for cancer therapeutics. In particular, B-RAF has emerged as one of the most attractive molecular targets for cancer therapeutics because somatic mutations of B-RAF have frequently been found in human tumors. Approximately 20% of all cancer samples tested to date harbor mutations in B-RAF. B-RAF-V600E, a missense mutation in the kinase domain generated by the substitution of glutamic acid with valine at position 600 is the most common B-RAF mutation. C-RAF is mutated in ~1% of the various tumor types tested and the rate of mutations in A-RAF is even lower. B-RAF and C-RAF form both homo- and heterodimers as part of their activation mechanism and A-RAF stabilizes the B-RAF:C-RAF complexes to sustain signaling efficiency. Also, it is C-RAF, not B-RAF, that transmits signals from oncogenic RAS to MEK. Therefore, in different contexts, each of the RAF isoforms act as a potential therapeutic target.

Sorafenib was the first RAF inhibitor to enter clinical trials. Sorafenib is a broad specificity drug that inhibits additional kinases, including vascular endothelial growth factor receptor family (VEGFR-2 and VEGFR-3), platelet-derived growth factor receptor family (PDGFR-b and KIT) and FLT3. Clinical trials showed no correlation between the clinical responses with B-RAF mutation status, indicating it is a poor inhibitor of B-RAF. This led to the development of a new generation of B-RAF inhibitors, including, but not limited to vemurafenib, SB-590885, and dabrafenib (GSK2118436). Although the initial results of the clinical studies in B-RAF-mutant melanoma were encouraging, as clinical testing began in other B-RAF-mutated cancers (such as thyroid and colorectal cancers) it became apparent that tumors of different cell types harboring B-RAF mutations responded differently to selective B-RAF inhibition. Moreover, the existence of both primary and secondary resistance to RAF inhibition poses as one of the greatest challenge to the progress of RAF kinase inhibitor therapy. The mechanisms of resistance fall into two broad categories. Intrinsic/primary resistance is displayed by approximately 50% of patients.

The other 50% of the patients initially respond (>30% tumor shrinkage) to RAF inhibitor but subsequently develop progressive disease associated with acquired/secondary resistance to RAF inhibitor. These two categories are not mutually exclusive because nearly all responders have remaining disease and, thus, may display intrinsic resistance. The determinants of primary RAF inhibitor resistance seem to vary with tumor type, with alteration in RTK signaling also being involved. Potential mechanisms of secondary B-RAF inhibitor resistance include, but are not limited to, reactivation of ERK1/2 pathways, upregulation of RTK signaling, the upregulation of receptor tyrosine kinases, mutations in RAS, and upregulation of COT. B-Raf alternative splicing and amplification of B-RAF-V600E have also been implicated in ~ 30 and 20% of patients, respectively. Moreover, RAF kinase inhibitors cause paradoxical activation of the MAPK pathway, which, in some instances, leads to the development of secondary RAS mutation-driven malignancies. As such, there is a need in the field for new RAF kinase inhibitors that overcome the existing pitfalls and challenges posed by the current inhibitors.

RAF Inhibitory Compounds

In one aspect, provided herein is a RAF inhibitory compound.

One embodiment provides a compound, or pharmaceutically acceptable salt or solvate thereof, having the structure of Formula (I):

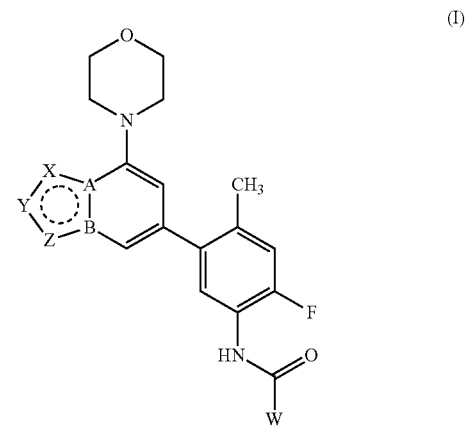

wherein,
A is N or C; B is N or C; provided if A is N, then B is C; or if A is C, then B is N;
X is N or C—R$^1$;
Y is N or C—R$^2$
Z is N or C—R$^3$;
R$^1$, R$^2$, and R$^3$ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (Ia):

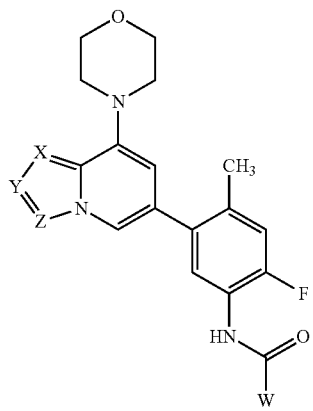

(Ia)

wherein,
X is N or C—R$^1$;
Y is N or C—R$^2$
Z is N or C—R$^3$;
R$^1$, R$^2$, and R$^3$ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides a compound, or pharmaceutically acceptable salt or solvate thereof, having the structure of Formula (Ib):

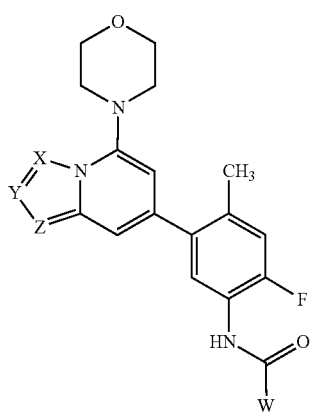

(Ib)

wherein,
X is N or C—R$^1$;
Y is N or C—R$^2$
Z is N or C—R$^3$;
R$^1$, R$^2$, and R$^3$ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides the compound of Formula (I), (Ia), or (Ib), or pharmaceutically acceptable salt or solvate thereof, wherein X is C—R$^1$.

One embodiment provides the compound of Formula (I), (Ia), or (Ib), or pharmaceutically acceptable salt or solvate thereof, wherein Y is N, and Z is N.

One embodiment provides the compound of Formula (I), (Ia), or (Ib), or pharmaceutically acceptable salt or solvate thereof, wherein Y is C—R$^2$, and Z is N.

One embodiment provides the compound of Formula (I), (Ia), or (Ib), or pharmaceutically acceptable salt or solvate thereof, wherein Y is N, and Z is C—R$^3$.

One embodiment provides the compound of Formula (I), (Ia), or (Ib), or pharmaceutically acceptable salt or solvate thereof, wherein Y is C—R$^2$, and Z is C—R$^3$.

One embodiment provides the compound of Formula (I), (Ia), or (Ib), or pharmaceutically acceptable salt or solvate thereof, wherein X is C—R$^1$, Y is N, and Z is N.

One embodiment provides the compound of Formula (I), (Ia), or (Ib), or pharmaceutically acceptable salt or solvate thereof, wherein X is C—R$^1$, Y is C—R$^2$, and Z is N.

One embodiment provides the compound of Formula (I), (Ia), or (Ib), or pharmaceutically acceptable salt or solvate thereof, wherein X is C—R$^1$, Y is N, and Z is C—R$^3$.

One embodiment provides the compound of Formula (I), (Ia), or (Ib), or pharmaceutically acceptable salt or solvate thereof, wherein X is C—R$^1$, Y is C—R$^2$, and Z is C—R$^3$.

One embodiment provides the compound of Formula (I), (Ia), or (Ib), or pharmaceutically acceptable salt or solvate thereof, wherein Y is C—R$^2$.

One embodiment provides the compound of Formula (I), (Ia), or (Ib), or pharmaceutically acceptable salt or solvate thereof, wherein X is N, and Z is N.

One embodiment provides the compound of Formula (I), (Ia), or (Ib), or pharmaceutically acceptable salt or solvate thereof, wherein X is C—R$^1$, and Z is N.

One embodiment provides the compound of Formula (I), (Ia), or (Ib), or pharmaceutically acceptable salt or solvate thereof, wherein X is N, and Z is C—R$^3$.

One embodiment provides the compound of Formula (I), (Ia), or (Ib), or pharmaceutically acceptable salt or solvate thereof, wherein X is C—R$^1$, and Z is C—R$^3$.

One embodiment provides the compound of Formula (I), (Ia), or (Ib), or pharmaceutically acceptable salt or solvate thereof, wherein Y is C—R$^2$, X is N, and Z is N.

One embodiment provides the compound of Formula (I), (Ia), or (Ib), or pharmaceutically acceptable salt or solvate thereof, wherein Y is C—R$^2$, X is C—R$^1$, and Z is N.

One embodiment provides the compound of Formula (I), (Ia), or (Ib), or pharmaceutically acceptable salt or solvate thereof, wherein Y is C—R$^2$, X is N, and Z is C—R$^3$.

One embodiment provides the compound of Formula (I), (Ia), or (Ib), or pharmaceutically acceptable salt or solvate thereof, wherein Y is C—R$^2$, X is C—R$^1$, and Z is C—R$^3$.

One embodiment provides the compound of Formula (I), (Ia), or (Ib), or pharmaceutically acceptable salt or solvate thereof, wherein Z is C—R$^3$.

One embodiment provides the compound of Formula (I), (Ia), or (Ib), or pharmaceutically acceptable salt or solvate thereof, wherein X is N, and Y is N.

One embodiment provides the compound of Formula (I), (Ia), or (Ib), or pharmaceutically acceptable salt or solvate thereof, wherein X is C—$R^1$, and Y is N.

One embodiment provides the compound of Formula (I), (Ia), or (Ib), or pharmaceutically acceptable salt or solvate thereof, wherein X is N, and Y is C—$R^2$.

One embodiment provides the compound of Formula (I), (Ia), or (Ib), or pharmaceutically acceptable salt or solvate thereof, wherein X is C—$R^1$, and Y is C—$R^2$.

One embodiment provides the compound of Formula (I), (Ia), or (Ib), or pharmaceutically acceptable salt or solvate thereof, wherein Z is C—$R^3$, X is N, and Y is N.

One embodiment provides the compound of Formula (I), (Ia), or (Ib), or pharmaceutically acceptable salt or solvate thereof, wherein Z is C—$R^3$, X is C—$R^1$, and Y is N.

One embodiment provides the compound of Formula (I), (Ia), or (Ib), or pharmaceutically acceptable salt or solvate thereof, wherein Z is C—$R^3$, X is N, and Y is C—$R^2$.

One embodiment provides the compound of Formula (I), (Ia), or (Ib), or pharmaceutically acceptable salt or solvate thereof, wherein Z is C—$R^3$, X is C—$R^1$, and Y is C—$R^2$.

One embodiment provides the compound of Formula (I), (Ia), or (Ib), or pharmaceutically acceptable salt or solvate thereof, wherein $R^2$ is H.

One embodiment provides the compound of Formula (I), (Ia), or (Ib), or pharmaceutically acceptable salt or solvate thereof, wherein $R^2$ is halogen.

One embodiment provides the compound of Formula (I), (Ia), or (Ib), or pharmaceutically acceptable salt or solvate thereof, wherein $R^2$ is fluorine.

One embodiment provides the compound of Formula (I), (Ia), or (Ib), or pharmaceutically acceptable salt or solvate thereof, wherein $R^2$ is optionally substituted alkyl. Another embodiment provides the compound, or pharmaceutically acceptable salt or solvate thereof, wherein the optionally substituted alkyl is selected from a C1-C5 optionally substituted alkyl.

One embodiment provides the compound of Formula (I), (Ia), or (Ib), or pharmaceutically acceptable salt or solvate thereof, wherein $R^2$ is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl.

One embodiment provides the compound of Formula (I), (Ia), or (Ib), or pharmaceutically acceptable salt or solvate thereof, wherein $R^2$ is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

One embodiment provides a compound, or pharmaceutically acceptable salt or solvate thereof, having the structure of Formula (II):

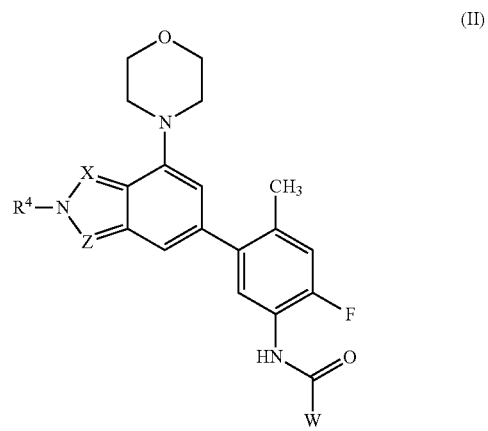

(II)

wherein,
X is N or C—$R^1$;
Z is N or C—$R^3$;
$R^1$ and $R^3$ are independently selected from H, —CN, halogen, optionally substituted alkyl, optionally substituted cycloalkyl, or optionally substituted cycloalkylalkyl;
$R^4$ is selected from optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

One embodiment provides the compound of Formula (II), or pharmaceutically acceptable salt or solvate thereof, wherein X is N, and Z is N.

One embodiment provides the compound of Formula (II), or pharmaceutically acceptable salt or solvate thereof, wherein X is C—$R^1$, and Z is N.

One embodiment provides the compound of Formula (II), or pharmaceutically acceptable salt or solvate thereof, wherein X is N, and Z is C—$R^3$.

One embodiment provides the compound of Formula (II), or pharmaceutically acceptable salt or solvate thereof, wherein X is C—$R^1$, and Z is C—$R^3$.

One embodiment provides the compound of Formula (II), or pharmaceutically acceptable salt or solvate thereof, wherein $R^4$ is selected from optionally substituted alkyl. Another embodiment provides the compound, or pharmaceutically acceptable salt or solvate thereof, wherein the optionally substituted alkyl is selected from a C1-C5 optionally substituted alkyl. Another embodiment provides the compound, or pharmaceutically acceptable salt or solvate thereof, wherein the optionally substituted alkyl is selected from a C1-C5 optionally substituted alkyl. One embodiment provides the compound of Formula (II), or pharmaceutically acceptable salt or solvate thereof, wherein $R^4$ is selected from optionally substituted cycloalkyl. Another embodiment provides the compound, or pharmaceutically acceptable salt or solvate thereof, wherein the optionally substituted cycloalkyl is selected from a C3-C4 optionally substituted cycloalkyl. One embodiment provides the compound of Formula (II), or pharmaceutically acceptable salt or solvate thereof, wherein $R^4$ is selected from optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

One embodiment provides the compound of Formula (I), (Ia), (Ib), or (II), or pharmaceutically acceptable salt or solvate thereof, wherein $R^1$ is H.

One embodiment provides the compound of Formula (I), (Ia), (Ib), or (II), or pharmaceutically acceptable salt or solvate thereof, wherein $R^1$ is halogen.

One embodiment provides the compound of Formula (I), (Ia), (Ib), or (II), or pharmaceutically acceptable salt or solvate thereof, wherein $R^1$ is fluorine.

One embodiment provides the compound of Formula (I), (Ia), (Ib), or (II), or pharmaceutically acceptable salt or solvate thereof, wherein $R^1$ is optionally substituted alkyl. Another embodiment provides the compound, or pharmaceutically acceptable salt or solvate thereof, wherein the optionally substituted alkyl is selected from a C1-C5 optionally substituted alkyl.

One embodiment provides the compound of Formula (I), (Ia), (Ib), or (II), or pharmaceutically acceptable salt or solvate thereof, wherein $R^1$ is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl.

One embodiment provides the compound of Formula (I), (Ia), (Ib), or (II), or pharmaceutically acceptable salt or solvate thereof, wherein $R^1$ is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

One embodiment provides the compound of Formula (I), (Ia), (Ib), or (II), or pharmaceutically acceptable salt or solvate thereof, wherein $R^3$ is H.

One embodiment provides the compound of Formula (I), (Ia), (Ib), or (II), or pharmaceutically acceptable salt or solvate thereof, wherein $R^3$ is halogen.

One embodiment provides the compound of Formula (I), (Ia), (Ib), or (II), or pharmaceutically acceptable salt or solvate thereof, wherein $R^3$ is fluorine.

One embodiment provides the compound of Formula (I), (Ia), (Ib), or (II), or pharmaceutically acceptable salt or solvate thereof, wherein $R^3$ is optionally substituted alkyl. Another embodiment provides the compound, or pharmaceutically acceptable salt or solvate thereof, wherein the optionally substituted alkyl is selected from a C1-C5 optionally substituted alkyl.

One embodiment provides the compound of Formula (I), (Ia), (Ib), or (II), or pharmaceutically acceptable salt or solvate thereof, wherein $R^3$ is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl.

One embodiment provides the compound of Formula (I), (Ia), (Ib), or (II), or pharmaceutically acceptable salt or solvate thereof, wherein $R^3$ is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

One embodiment provides the compound of Formula (I), (Ia), (Ib), or (II), or pharmaceutically acceptable salt or solvate thereof, wherein W is an optionally substituted nitrogen-containing heterocyclyl. One embodiment provides the compound, or pharmaceutically acceptable salt or solvate thereof, wherein W is selected from an optionally substituted pyrrolidine, an optionally substituted 2,5-dihydro-1H-pyrrole, an optionally substituted piperidine, or an optionally substituted 1,2,3,6-tetrahydropyridine. One embodiment provides the compound, or pharmaceutically acceptable salt or solvate thereof, wherein W is selected from:

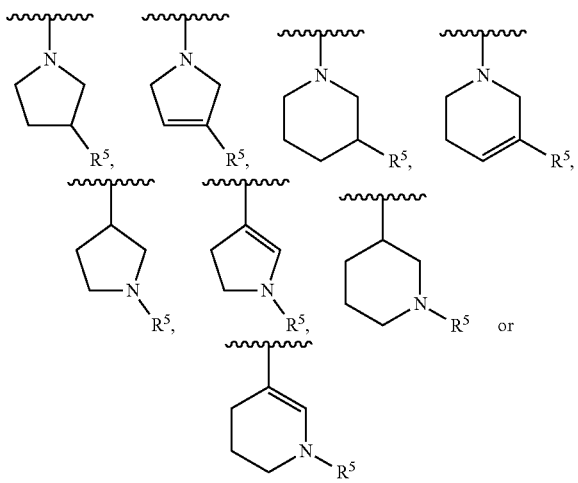

and
wherein $R^5$ is selected from —$CH_3$, —$CH_2CH_3$, —$CH(CH_3)_2$, —$C(CH_3)_3$, —$CF_3$, —$CH_2CF_3$, —$CH(CH_3)CF_3$, —$CH_2CHF_2$, or —$C(CH_3)_2CF_3$.

One embodiment provides the compound of Formula (I), (Ia), (Ib), or (II), or pharmaceutically acceptable salt or solvate thereof, wherein W is an optionally substituted nitrogen-containing heteroaryl. One embodiment provides the compound, or pharmaceutically acceptable salt or solvate thereof, wherein W is an optionally substituted pyridyl, optionally substituted pyrimidyl, optionally substituted triazinyl, or optionally substituted pyrrolyl. One embodiment provides the compound, or pharmaceutically acceptable salt or solvate thereof, wherein W is selected from:

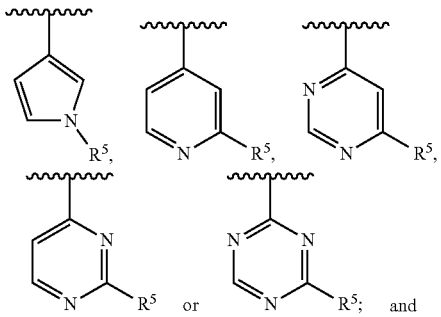

wherein $R^5$ is selected from —$CH_3$, —$CH_2CH_3$, —$CH(CH_3)_2$, —$C(CH_3)_3$, —$CF_3$, —$CH_2CF_3$, —$CH(CH_3)CF_3$, —$CH_2CHF_2$, or —$C(CH_3)_2CF_3$.

One embodiment provides the compound of Formula (I), (Ia), (Ib), or (II), or pharmaceutically acceptable salt or solvate thereof, wherein W is an optionally substituted pyrazyl, optionally substituted imidazyl, optionally substituted triazyl, or optionally substituted tetrazyl.

One embodiment provides the compound of Formula (I), (Ia), (Ib), or (II), or pharmaceutically acceptable salt or solvate thereof, wherein W is an optionally substituted pyraz-3-yl, optionally substituted pyraz-4-yl, optionally substituted pyraz-5-yl, optionally substituted imidaz-4-yl, or optionally substituted imidaz-5-yl.

One embodiment provides the compound of Formula (I), (Ia), (Ib), or (II), or pharmaceutically acceptable salt or solvate thereof, wherein W is an optionally substituted 1,2,3-triaz-4-yl, optionally substituted 1,2,3-triaz-5-yl, or optionally substituted 1,2,4-oxadiaz-5-yl.

One embodiment provides the compound of Formula (I), (Ia), (Ib), or (II), or pharmaceutically acceptable salt or solvate thereof, wherein W is an optionally substituted oxaz-2-yl, optionally substituted oxaz-4-yl, or optionally substituted oxaz-5-yl.

One embodiment provides the compound of Formula (I), (Ia), (Ib), or (II), or pharmaceutically acceptable salt or solvate thereof, wherein W is an optionally substituted thiaz-2-yl, optionally substituted thiaz-4-yl, or optionally substituted thiaz-5-yl.

One embodiment provides the compound of Formula (I), (Ia), (Ib), or (II), or pharmaceutically acceptable salt or solvate thereof, wherein W is an optionally substituted nitrogen-containing heterocyclyl further substituted with an optionally substituted cycloalkyl, or optionally substituted nitrogen-containing heteroaryl further substituted with an optionally substituted cycloalkyl.

One embodiment provides the compound of Formula (I), (Ia), (Ib), or (II), or pharmaceutically acceptable salt or solvate thereof, wherein W is selected from:

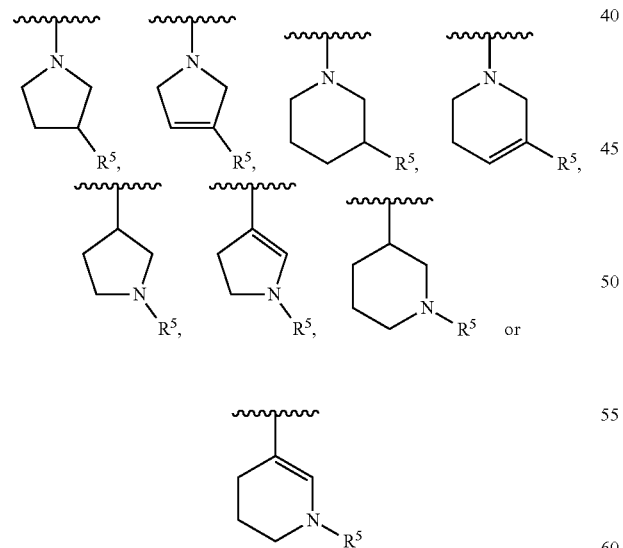

and $R^5$ is 1-trifluoromethylcyclopropyl, or a cyclopropyl substituted with at least one fluorine.

One embodiment provides the compound of Formula (I), (Ia), (Ib), or (II), or pharmaceutically acceptable salt or solvate thereof, wherein W is selected from:

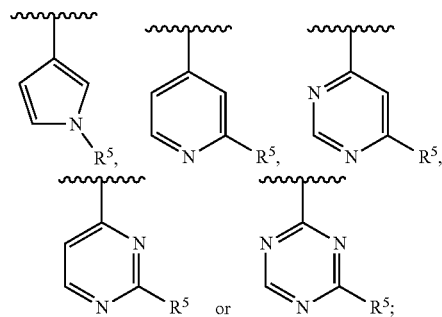

and $R^5$ is 1-trifluoromethylcyclopropyl, or a cyclopropyl substituted with at least one fluorine.

One embodiment provides the compound of Formula (I), (Ia), (Ib), or (II), or pharmaceutically acceptable salt or solvate thereof, wherein W is selected from:

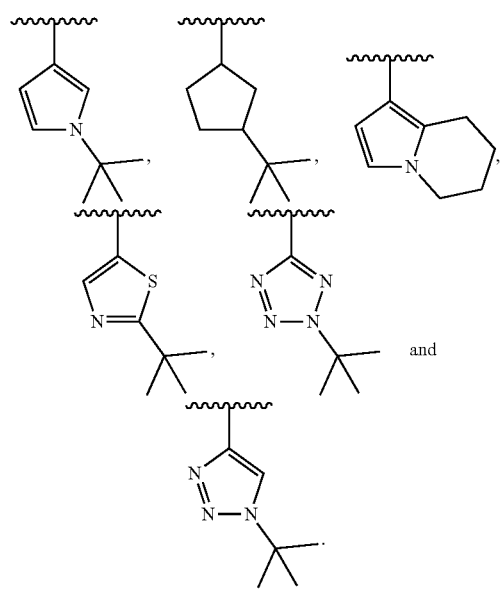

One embodiment provides the compound of Formula (I), (Ia), (Ib), or (II), or pharmaceutically acceptable salt or solvate thereof, wherein W is selected from:

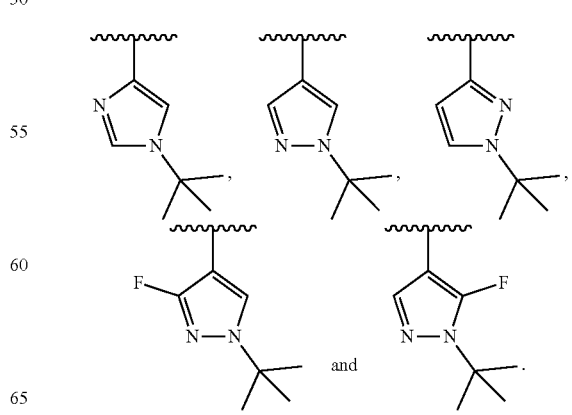

One embodiment provides the compound of Formula (I), (Ia), (Ib), or (II), or pharmaceutically acceptable salt or solvate thereof, wherein W is selected from:

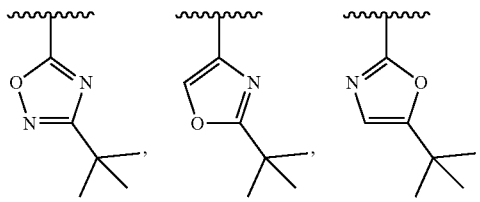

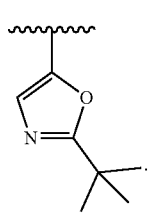

One embodiment provides the compound of Formula (I), (Ia), (Ib), or (II), or pharmaceutically acceptable salt or solvate thereof, wherein W is optionally substituted aryl. One embodiment provides the compound, or pharmaceutically acceptable salt or solvate thereof, wherein W is an optionally substituted phenyl. One embodiment provides the compound, or pharmaceutically acceptable salt or solvate thereof, wherein W is

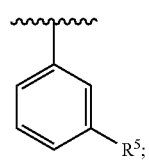

and $R^5$ is selected from —$CH_3$, —$CH_2CH_3$, —$CH(CH_3)_2$, —$C(CH_3)_3$, —$CF_3$, —$CH_2CF_3$, —$CH(CH_3)CF_3$, —$CH_2CHF_2$, or —$C(CH_3)_2CF_3$.

One embodiment provides the compound of Formula (I), (Ia), (Ib), or (II), or pharmaceutically acceptable salt or solvate thereof, wherein W is optionally substituted aryl further substituted with an optionally substituted cycloalkyl. One embodiment provides the compound, or pharmaceutically acceptable salt or solvate thereof, wherein W is

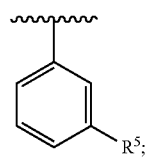

and $R^5$ is selected from is 1-trifluoromethylcyclopropyl, or a cyclopropyl substituted with at least one fluorine.

One embodiment provides a compound, or pharmaceutically acceptable salt or solvate thereof, having the structure of Formula (III):

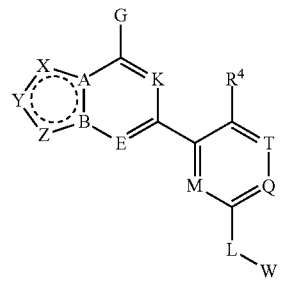

wherein,
L is —CO—NH—, or —NH—CO—;
A is N or C; B is N or C; provided if A is N, then B is C; or if A is C, then B is N;
X is N or C—$R^1$;
Y is N or C—$R^2$
Z is N or C—$R^3$;
$R^1$, $R^2$, and $R^3$ are independently selected from H, —CN, halogen, optionally substituted alkyl, optionally substituted cycloalkyl, or optionally substituted cycloalkylalkyl; or optionally, $R^1$ and $R^2$ may join to form a ring; or optionally $R^2$ and $R^3$ may join to form a ring;
$R^4$ is selected from H, halogen, or optionally substituted C1-C3 alkyl;
K is N, or C—H;
E is N, or C—H;
M is N, or C—$R^5$;
Q is N, or C—$R^5$;
T is N, or C—$R^5$;
each $R^5$ is independently selected from H, halogen, or optionally substituted C1-C3 alkyl;

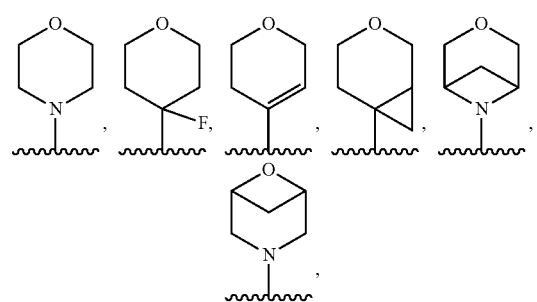

G is selected from

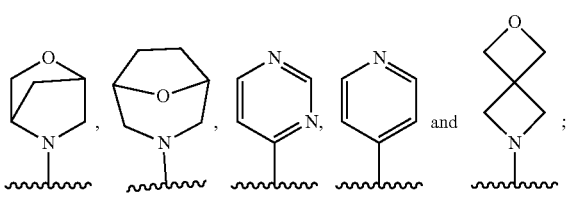

W is selected from:
optionally substituted nitrogen-containing heterocyclyl;
optionally substituted nitrogen-containing heteroaryl;

optionally substituted carbocyclyl;

optionally substituted aryl;

optionally substituted nitrogen-containing heterocyclyl further substituted with an optionally substituted cycloalkyl, or optionally substituted cycloalkylalkyl;

optionally substituted nitrogen-containing heteroaryl further substituted with an optionally substituted cycloalkyl, or optionally substituted cycloalkylalkyl;

optionally substituted carbocyclyl further substituted with an optionally substituted cycloalkyl, or optionally substituted cycloalkylalkyl; and optionally substituted aryl further substituted with an optionally substituted cycloalkyl, or optionally substituted cycloalkylalkyl.

Another embodiment provides the compound of Formula (III), or pharmaceutically acceptable salt or solvate thereof, wherein A is N and B is C.

Another embodiment provides the compound of Formula (III), or pharmaceutically acceptable salt or solvate thereof, wherein A is C and B is N.

Another embodiment provides the compound of Formula (III), or pharmaceutically acceptable salt or solvate thereof, wherein L is —CO—NH—.

Another embodiment provides the compound of Formula (III), or pharmaceutically acceptable salt or solvate thereof, wherein L is —NH—CO—.

Another embodiment provides the compound of Formula (III), or pharmaceutically acceptable salt or solvate thereof, wherein G is

[Structure: morpholine ring attached via N]

Another embodiment provides the compound of Formula (III), or pharmaceutically acceptable salt or solvate thereof, wherein X is C—$R^1$.

Another embodiment provides the compound of Formula (III), or pharmaceutically acceptable salt or solvate thereof, wherein Y is N, and Z is N.

Another embodiment provides the compound of Formula (III), or pharmaceutically acceptable salt or solvate thereof, wherein Y is C—$R^2$, and Z is N.

Another embodiment provides the compound of Formula (III), or pharmaceutically acceptable salt or solvate thereof, wherein Y is N, and Z is C—$R^3$.

Another embodiment provides the compound of Formula (III), or pharmaceutically acceptable salt or solvate thereof, wherein Y is C—$R^2$, and Z is C—$R^3$.

Another embodiment provides the compound of Formula (III), or pharmaceutically acceptable salt or solvate thereof, wherein Y is C—$R^2$.

Another embodiment provides the compound of Formula (III), or pharmaceutically acceptable salt or solvate thereof, wherein X is N, and Z is N.

Another embodiment provides the compound of Formula (III), or pharmaceutically acceptable salt or solvate thereof, wherein X is C—$R^1$, and Z is N.

Another embodiment provides the compound of Formula (III), or pharmaceutically acceptable salt or solvate thereof, wherein X is N, and Z is C—$R^3$.

Another embodiment provides the compound of Formula (III), or pharmaceutically acceptable salt or solvate thereof, wherein X is C—$R^1$, and Z is C—$R^3$.

Another embodiment provides the compound of Formula (III), or pharmaceutically acceptable salt or solvate thereof, wherein Z is C—$R^3$.

Another embodiment provides the compound of Formula (III), or pharmaceutically acceptable salt or solvate thereof, wherein X is N, and Y is N.

Another embodiment provides the compound of Formula (III), or pharmaceutically acceptable salt or solvate thereof, wherein X is C—$R^1$, and Y is N.

Another embodiment provides the compound of Formula (III), or pharmaceutically acceptable salt or solvate thereof, wherein X is N, and Y is C—$R^2$.

Another embodiment provides the compound of Formula (III), or pharmaceutically acceptable salt or solvate thereof, wherein X is C—$R^1$, and Y is C—$R^2$.

Another embodiment provides the compound of Formula (III), or pharmaceutically acceptable salt or solvate thereof, wherein K is N; and E is C—H.

Another embodiment provides the compound of Formula (III), or pharmaceutically acceptable salt or solvate thereof, wherein K is C—H; and E is N.

Another embodiment provides the compound of Formula (III), or pharmaceutically acceptable salt or solvate thereof, wherein M is C—$R^5$; Q is C—$R^5$; and T is N.

Another embodiment provides the compound of Formula (III), or pharmaceutically acceptable salt or solvate thereof, wherein M is C—$R^5$; Q is N; and T is C—$R^5$.

Another embodiment provides the compound of Formula (III), or pharmaceutically acceptable salt or solvate thereof, wherein M is N; Q is C—$R^5$; and T is C—$R^5$.

Another embodiment provides the compound of Formula (III), or pharmaceutically acceptable salt or solvate thereof, wherein $R^1$ is H. Another embodiment provides the compound of Formula (III), or pharmaceutically acceptable salt or solvate thereof, wherein $R^1$ is halogen. Another embodiment provides the compound of Formula (III), or pharmaceutically acceptable salt or solvate thereof, wherein $R^1$ is fluorine. Another embodiment provides the compound of Formula (III), or pharmaceutically acceptable salt or solvate thereof, wherein $R^1$ is optionally substituted alkyl. Another embodiment provides the compound, or pharmaceutically acceptable salt or solvate thereof, wherein the optionally substituted alkyl is selected from a C1-C5 optionally substituted alkyl. Another embodiment provides the compound of Formula (III), or pharmaceutically acceptable salt or solvate thereof, wherein $R^1$ is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl. Another embodiment provides the compound of Formula (III), or pharmaceutically acceptable salt or solvate thereof, wherein $R^1$ is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

Another embodiment provides the compound of Formula (III), or pharmaceutically acceptable salt or solvate thereof, wherein $R^2$ is H. Another embodiment provides the compound of Formula (III), or pharmaceutically acceptable salt or solvate thereof, wherein $R^2$ is halogen. Another embodiment provides the compound of Formula (III), or pharmaceutically acceptable salt or solvate thereof, wherein $R^2$ is fluorine. Another embodiment provides the compound of Formula (III), or pharmaceutically acceptable salt or solvate thereof, wherein R² is optionally substituted alkyl. Another embodiment provides the compound, or pharmaceutically acceptable salt or solvate thereof, wherein the optionally substituted alkyl is selected from a C1-C5 optionally substituted alkyl. Another embodiment provides the compound of Formula (III), or pharmaceutically acceptable salt or solvate thereof, wherein R² is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl. Another embodiment provides the compound of Formula (III), or pharmaceutically acceptable salt or solvate thereof, wherein R² is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

Another embodiment provides the compound of Formula (III), or pharmaceutically acceptable salt or solvate thereof, wherein R³ is H. Another embodiment provides the compound of Formula (III), or pharmaceutically acceptable salt or solvate thereof, wherein R³ is halogen. Another embodiment provides the compound of Formula (III), or pharmaceutically acceptable salt or solvate thereof, wherein R³ is fluorine. Another embodiment provides the compound of Formula (III), or pharmaceutically acceptable salt or solvate thereof, wherein R³ is optionally substituted alkyl. Another embodiment provides the compound, or pharmaceutically acceptable salt or solvate thereof, wherein the optionally substituted alkyl is selected from a C1-C5 optionally substituted alkyl. Another embodiment provides the compound of Formula (III), or pharmaceutically acceptable salt or solvate thereof, wherein R³ is optionally substituted cycloalkyl. Another embodiment provides the compound, or pharmaceutically acceptable salt or solvate thereof, wherein the optionally substituted cycloalkyl is selected from a C3-C4 optionally substituted cycloalkyl. Another embodiment provides the compound of Formula (III), or pharmaceutically acceptable salt or solvate thereof, wherein R³ is optionally substituted cycloalkylalkyl. Another embodiment provides the compound, or pharmaceutically acceptable salt or solvate thereof, wherein the optionally substituted cycloalkylalkyl is selected from a C4-C7 optionally substituted cycloalkylalkyl.

Another embodiment provides the compound of Formula (III), or pharmaceutically acceptable salt or solvate thereof, wherein R⁴ is F or CH₃.

Another embodiment provides the compound of Formula (III), or pharmaceutically acceptable salt or solvate thereof, wherein M is C—H.

Another embodiment provides the compound of Formula (III), or pharmaceutically acceptable salt or solvate thereof, wherein Q is C—F.

Another embodiment provides the compound of Formula (III), or pharmaceutically acceptable salt or solvate thereof, wherein T is C—H.

Another embodiment provides the compound of Formula (III), or pharmaceutically acceptable salt or solvate thereof, wherein W is an optionally substituted nitrogen-containing heterocyclyl.

Another embodiment provides the compound of Formula (III), or pharmaceutically acceptable salt or solvate thereof, wherein W is selected from an optionally substituted pyrrolidine, an optionally substituted 2,5-dihydro-1H-pyrrole, an optionally substituted piperidine, or an optionally substituted 1,2,3,6-tetrahydropyridine.

Another embodiment provides the compound of Formula (III), or pharmaceutically acceptable salt or solvate thereof, wherein W is an optionally substituted nitrogen-containing heteroaryl.

Another embodiment provides the compound of Formula (III), or pharmaceutically acceptable salt or solvate thereof, wherein W is an optionally substituted pyridyl, optionally substituted pyrimidyl, optionally substituted triazinyl, or optionally substituted pyrrolyl.

Another embodiment provides the compound of Formula (III), or pharmaceutically acceptable salt or solvate thereof, wherein W is an optionally substituted pyrazyl, optionally substituted imidazyl, optionally substituted triazyl, or optionally substituted tetrazyl.

Another embodiment provides the compound of Formula (III), or pharmaceutically acceptable salt or solvate thereof, wherein W is an optionally substituted pyraz-3-yl, optionally substituted pyraz-4-yl, optionally substituted pyraz-5-yl, optionally substituted imidaz-4-yl, or optionally substituted imidaz-5-yl.

Another embodiment provides the compound of Formula (III), or pharmaceutically acceptable salt or solvate thereof, wherein W is an optionally substituted 1,2,3-triaz-4-yl, optionally substituted 1,2,3-triaz-5-yl, or optionally substituted 1,2,4-oxadiaz-5-yl.

Another embodiment provides the compound of Formula (III), or pharmaceutically acceptable salt or solvate thereof, wherein W is an optionally substituted oxaz-2-yl, optionally substituted oxaz-4-yl, or optionally substituted oxaz-5-yl.

Another embodiment provides the compound of Formula (III), or pharmaceutically acceptable salt or solvate thereof, wherein W is an optionally substituted thiaz-2-yl, optionally substituted thiaz-4-yl, or optionally substituted thiaz-5-yl.

Another embodiment provides the compound of Formula (III), or pharmaceutically acceptable salt or solvate thereof, wherein W is an optionally substituted nitrogen-containing heterocyclyl further substituted with an optionally substituted cycloalkyl, or optionally substituted cycloalkylalkyl.

Another embodiment provides the compound of Formula (III), or pharmaceutically acceptable salt or solvate thereof, wherein W is an optionally substituted nitrogen-containing heteroaryl further substituted with an optionally substituted cycloalkyl, or optionally substituted cycloalkylalkyl.

One embodiment provides the compound of Formula (III), or pharmaceutically acceptable salt or solvate thereof, wherein W is an optionally substituted nitrogen-containing heterocyclyl. One embodiment provides the compound, or pharmaceutically acceptable salt or solvate thereof, wherein W is selected from an optionally substituted pyrrolidine, an optionally substituted 2,5-dihydro-1H-pyrrole, an optionally substituted piperidine, or an optionally substituted 1,2,3,6-tetrahydropyridine. One embodiment provides the compound, or pharmaceutically acceptable salt or solvate thereof, wherein W is selected from:

-continued

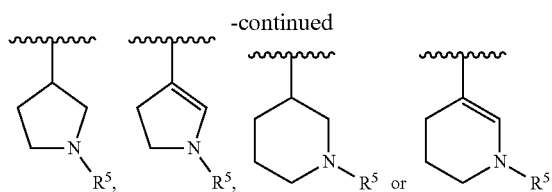

and wherein R⁵ is selected from —CH₃, —CH₂CH₃, —CH(CH₃)₂, —C(CH₃)₃, —CF₃, —CH₂CF₃, —CH(CH₃)CF₃, —CH₂CHF₂, or —C(CH₃)₂CF₃.

One embodiment provides the compound of Formula (III), or pharmaceutically acceptable salt or solvate thereof, wherein W is an optionally substituted nitrogen-containing heteroaryl. One embodiment provides the compound, or pharmaceutically acceptable salt or solvate thereof, wherein W is an optionally substituted pyridyl, optionally substituted pyrimidyl, optionally substituted triazinyl, or optionally substituted pyrrolyl. One embodiment provides the compound, or pharmaceutically acceptable salt or solvate thereof, wherein W is selected from:

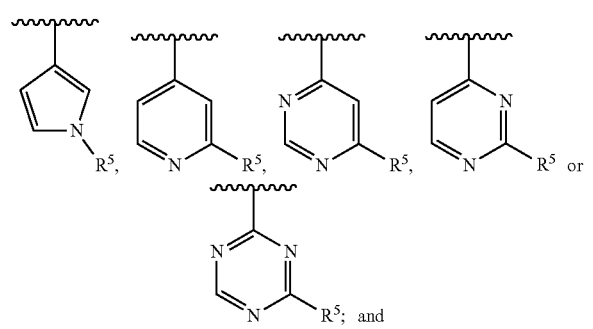

wherein R⁵ is selected from —CH₃, —CH₂CH₃, —CH(CH₃)₂, —C(CH₃)₃, —CF₃, —CH₂CF₃, —CH(CH₃)CF₃, —CH₂CHF₂, or —C(CH₃)₂CF₃.

One embodiment provides the compound of Formula (III), or pharmaceutically acceptable salt or solvate thereof, wherein W is an optionally substituted pyrazyl, optionally substituted imidazyl, optionally substituted triazyl, or optionally substituted tetrazyl.

One embodiment provides the compound of Formula (III), or pharmaceutically acceptable salt or solvate thereof, wherein W is an optionally substituted pyraz-3-yl, optionally substituted pyraz-4-yl, optionally substituted pyraz-5-yl, optionally substituted imidaz-4-yl, or optionally substituted imidaz-5-yl.

One embodiment provides the compound of Formula (III), or pharmaceutically acceptable salt or solvate thereof, wherein W is an optionally substituted 1,2,3-triaz-4-yl, optionally substituted 1,2,3-triaz-5-yl, or optionally substituted 1,2,4-oxadiaz-5-yl.

One embodiment provides the compound of Formula (III), or pharmaceutically acceptable salt or solvate thereof, wherein W is an optionally substituted oxaz-2-yl, optionally substituted oxaz-4-yl, or optionally substituted oxaz-5-yl.

One embodiment provides the compound of Formula (III), or pharmaceutically acceptable salt or solvate thereof, wherein W is an optionally substituted thiaz-2-yl, optionally substituted thiaz-4-yl, or optionally substituted thiaz-5-yl.

One embodiment provides the compound of Formula (III), or pharmaceutically acceptable salt or solvate thereof, wherein W is an optionally substituted nitrogen-containing heterocyclyl further substituted with an optionally substituted cycloalkyl, or optionally substituted nitrogen-containing heteroaryl further substituted with an optionally substituted cycloalkyl.

One embodiment provides the compound of Formula (III), or pharmaceutically acceptable salt or solvate thereof, wherein W is selected from:

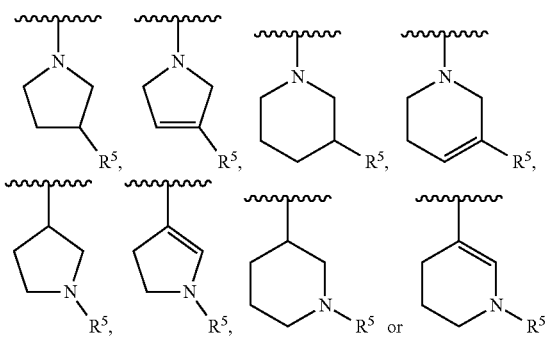

and R⁵ is 1-trifluoromethylcyclopropyl, or a cyclopropyl substituted with at least one fluorine.

One embodiment provides the compound of Formula (III), or pharmaceutically acceptable salt or solvate thereof, wherein W is selected from:

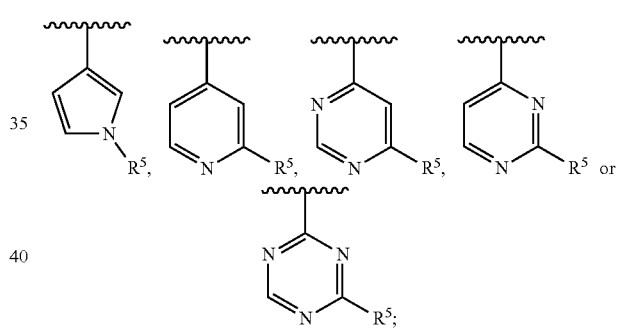

and R⁵ is 1-trifluoromethylcyclopropyl, or a cyclopropyl substituted with at least one fluorine.

One embodiment provides the compound of Formula (III), or pharmaceutically acceptable salt or solvate thereof, wherein W is selected from:

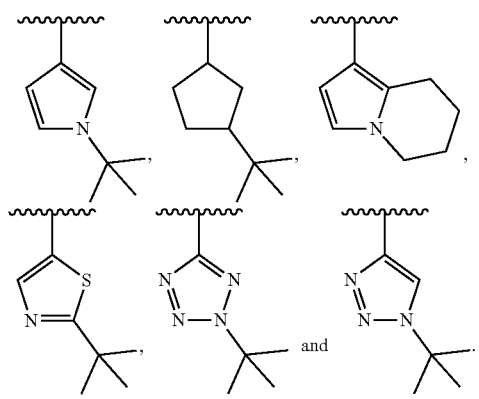

One embodiment provides the compound of Formula (III), or pharmaceutically acceptable salt or solvate thereof, wherein W is selected from:

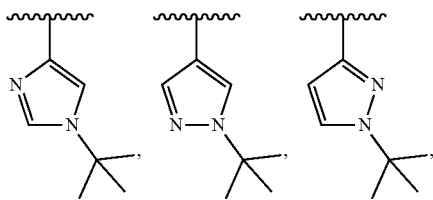

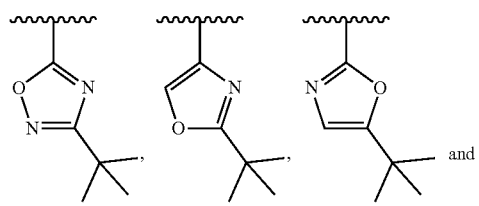

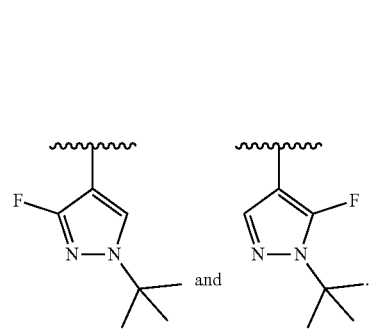

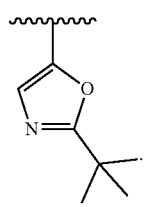

One embodiment provides the compound of Formula (III), or pharmaceutically acceptable salt or solvate thereof, wherein W is selected from:

In some embodiments, the RAF kinase inhibitory compound as described herein has a structure provided in Table 1.

TABLE 1

| Synthetic Chemistry Example | Compound Structure | Compound Name |
|---|---|---|
| 1 | 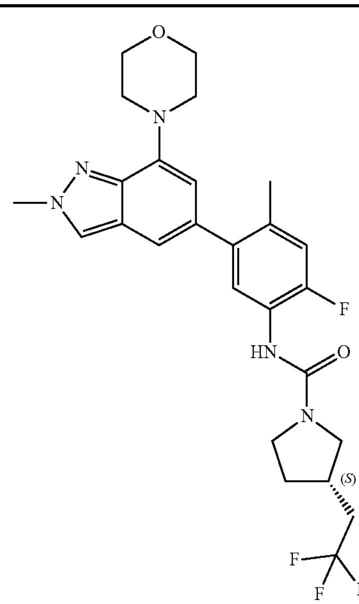 | (3S)-N-[2-Fluoro-4-methyl-5-[2-methyl-7-(morpholin-4-yl)indazol-5-yl]phenyl]-3-(2,2,2-trifluoroethyl)pyrrolidine-1-carboxamide |

TABLE 1-continued
| Synthetic Chemistry Example | Compound Structure | Compound Name |
|---|---|---|
| 2 | 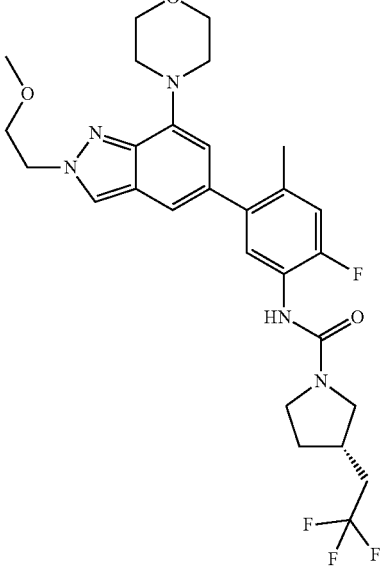 | (S)-N-(2-Fluoro-5-(2-(2-methoxyethyl)-7-morpholino-2H-indazol-5-yl)-4-methylphenyl)-3-(2,2,2-trifluoroethyl)pyrrolidine-1-carboxamide |
| 3 | 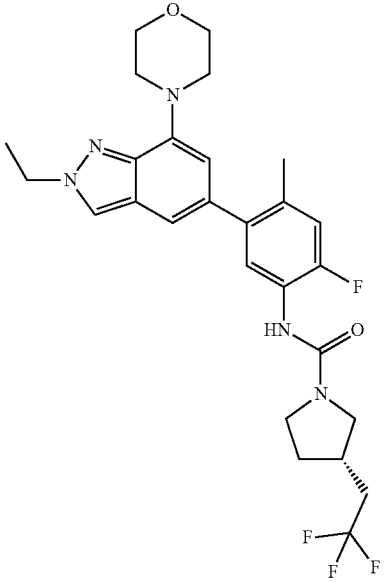 [SMILES: CCn1cc2cc(-c3cc(NC(=O)N4CC[C@@H](CC(F)(F)F)C4)c(F)cc3C)cc(N3CCOCC3)c2n1] | (S)-N-(5-(2-Ethyl-7-morpholino-2H-indazol-5-yl)-2-fluoro-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 4 | 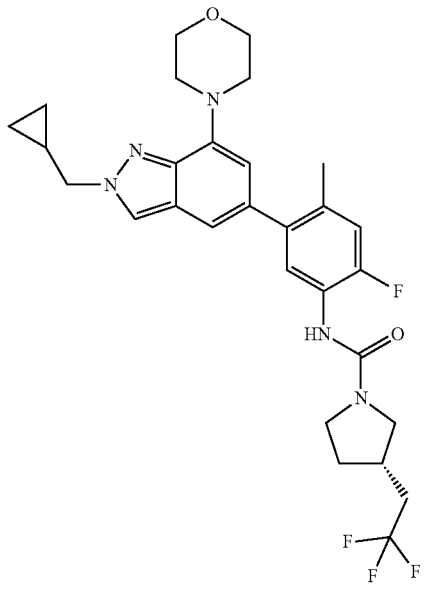 [SMILES: Cc1cc(F)c(NC(=O)N2CC[C@@H](CC(F)(F)F)C2)cc1-c1cc(N2CCOCC2)c2nn(CC3CC3)cc2c1] | (S)-N-(5-(2-(Cyclopropylmethyl)-7-morpholino-2H-indazol-5-yl)-2-fluoro-4-methylphenyl)-3-(2,2,2-trifluoroethyl)pyrrolidine-1-carboxamide |
| 5 | 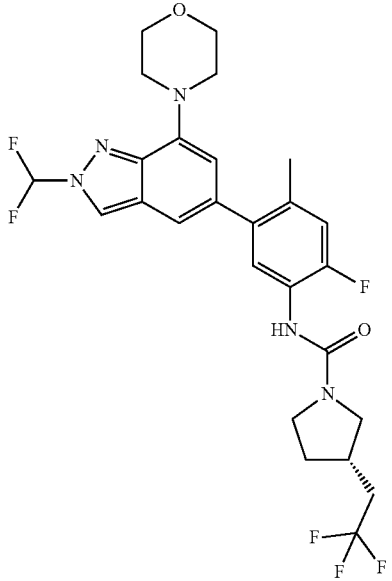 [SMILES: Cc1cc(F)c(NC(=O)N2CC[C@@H](CC(F)(F)F)C2)cc1-c1cc(N2CCOCC2)c2nn(C(F)F)cc2c1] | (S)-N-(5-(2-(Difluoromethyl)-7-morpholino-2H-indazol-5-yl)-2-fluoro-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 6 | 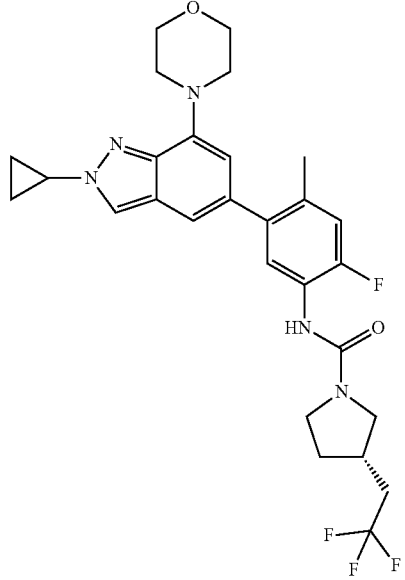 [SMILES: Cc1cc(F)c(NC(=O)N2CC[C@@H](CC(F)(F)F)C2)cc1-c1cc(N2CCOCC2)c2nn(C3CC3)cc2c1] | (S)-N-(5-(2-Cyclopropyl-7-morpholino-2H-indazol-5-yl)-2-fluoro-4-methylphenyl)-3-(2,2,2-trifluoroethyl)pyrrolidine-1-carboxamide |
| 7 | 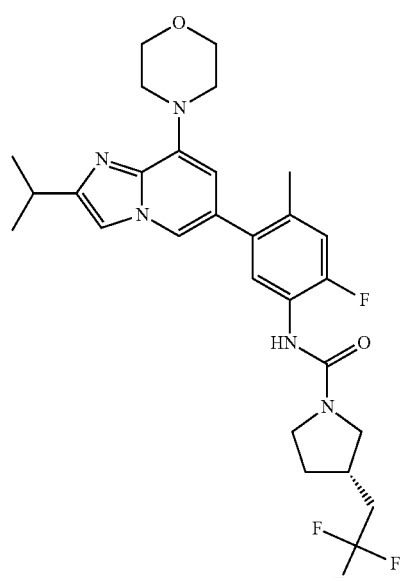 | (S)-N-(2-Fluoro-5-(2-isopropyl-8-morpholinoimidazo[1,2-a]pyridin-6-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 8 | 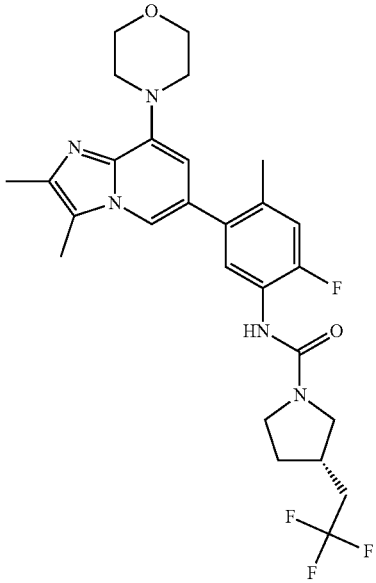 | (S)-N-(5-(2,3-Dimethyl-8-morpholinoimidazo[1,2-a]pyridin-6-yl)-2-fluoro-4-methylphenyl)-3-(2,2,2-trifluoroethyl)pyrrolidine-1-carboxamide |
| 9 | 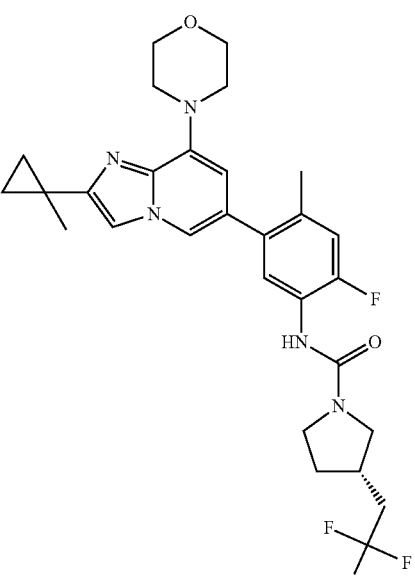 | (S)-N-(2-Fluoro-4-methyl-5-(2-(1-methylcyclopropyl)-8-morpholinoimidazo[1,2-a]pyridin-6-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 10 | 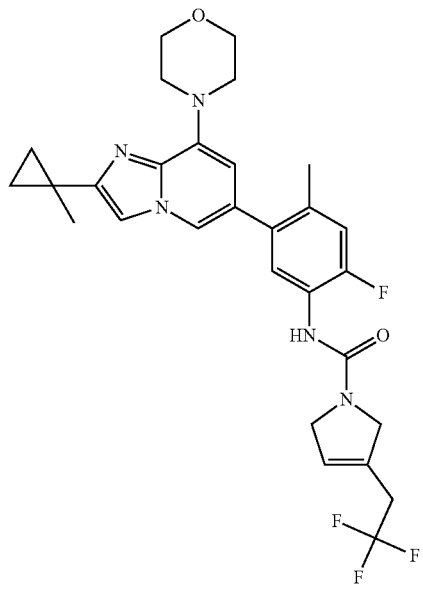 [SMILES: Cc1cc(F)c(NC(=O)N2CC[C@@H](CC(F)(F)F)C2)cc1-c1cc(N2CCOCC2)c2nc(C3(C)CC3)cn2c1] | N-(2-Fluoro-4-methyl-5-(2-(1-methylcyclopropyl)-8-morpholinoimidazo[1,2-a]pyridin-6-yl)phenyl)-3-(2,2,2-trifluoroethyl)-2,5-dihydro-1H-pyrrole-1-carboxamide |
| 11 | 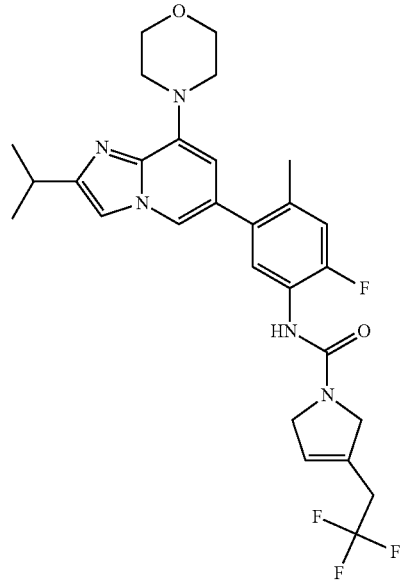 [SMILES: Cc1cc(F)c(NC(=O)N2CC=C(CC(F)(F)F)C2)cc1-c1cc(N2CCOCC2)c2nc(C(C)C)cn2c1] | N-(2-Fluoro-5-(2-isopropyl-8-morpholinoimidazo[1,2-a]pyridin-6-yl)-4-methylphenyl)-3-(2,2,2-trifluoroethyl)-2,5-dihydro-1H-pyrrole-1-carboxamide |

TABLE 1-continued

| Synthetic Chemistry Example | Compound Structure | Compound Name |
|---|---|---|
| 12 | 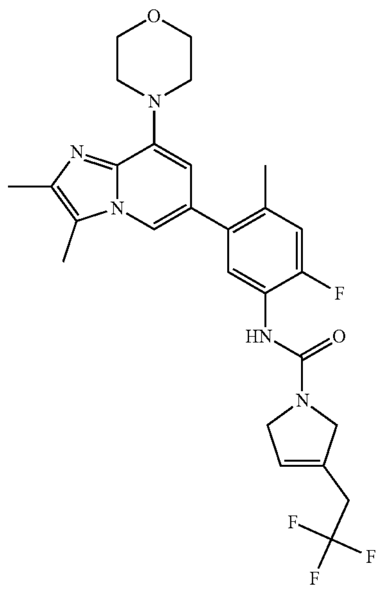 [SMILES: Cc1cc(F)c(NC(=O)N2CC=C(CC(F)(F)F)C2)cc1-c1cc(N2CCOCC2)c2nc(C)c(C)n2c1] | N-(5-(2,3-Dimethyl-8-morpholinoimidazo[1,2-a]pyridin-6-yl)-2-fluoro-4-methylphenyl)-3-(2,2,2-trifluoroethyl)-2,5-dihydro-1H-pyrrole-1-carboxamide |
| 13 | 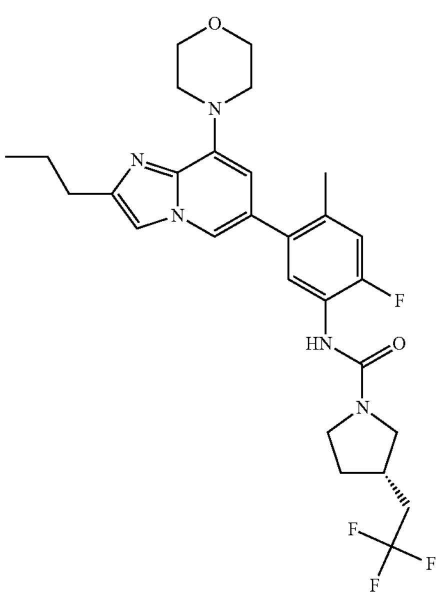 [SMILES: CCCc1cn2cc(-c3cc(NC(=O)N4CC[C@@H](CC(F)(F)F)C4)c(F)cc3C)cc(N3CCOCC3)c2n1] | (S)-N-(2-fluoro-4-methyl-5-(8-morpholino-2-propylimidazo[1,2-a]pyridin-6-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 14 | 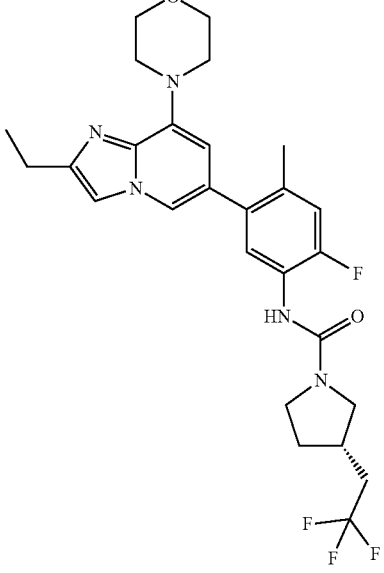 | (S)-N-(5-(2-Ethyl-8-morpholinoimidazo[1,2-a]pyridin-6-yl)-2-fluoro-4-methylphenyl)-3-(2,2,2-trifluoroethyl)pyrrolidine-1-carboxamide |
| 15 | 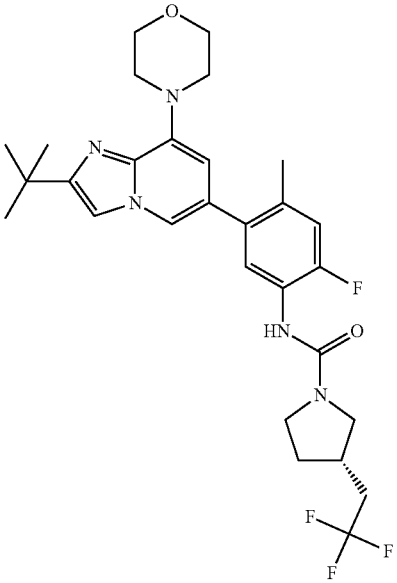 [SMILES: Cc1cc(F)c(NC(=O)N2CC[C@@H](CC(F)(F)F)C2)cc1-c1cc(N2CCOCC2)c2nc(C(C)(C)C)cn2c1] | (S)-N-(5-(2-(Tert-butyl)-8-morpholinoimidazo[1,2-a]pyridin-6-yl)-2-fluoro-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 16 | 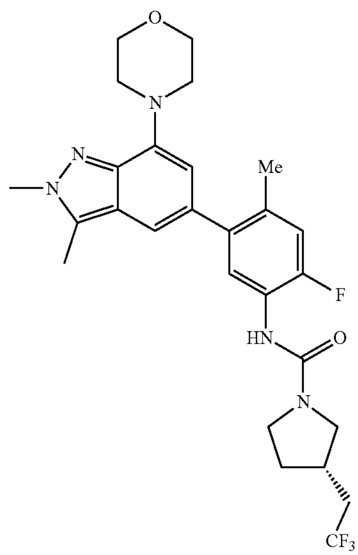 [SMILES: Cc1cc(F)c(NC(=O)N2CC[C@@H](CC(F)(F)F)C2)cc1-c1cc(N2CCOCC2)c2nn(C)c(C)c2c1] | (S)-N-(5-(2,3-dimethyl-7-morpholino-2H-indazol-5-yl)-2-fluoro-4-methylphenyl)-3-(2,2,2-trifluoroethyl)pyrrolidine-1-carboxamide |
| 17 | 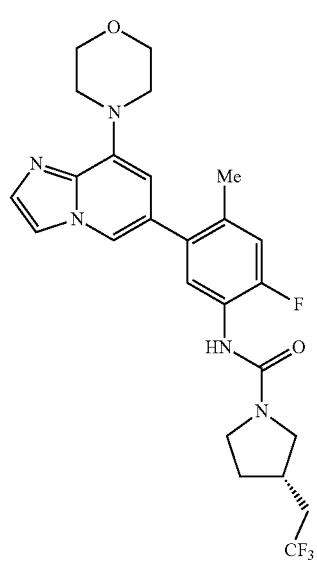 [SMILES: Cc1cc(F)c(NC(=O)N2CC[C@@H](CC(F)(F)F)C2)cc1-c1cc(N2CCOCC2)c2nccn2c1] | (S)-N-(2-fluoro-4-methyl-5-(8-morpholinoimidazo[1,2-a]pyridin-6-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 18 | 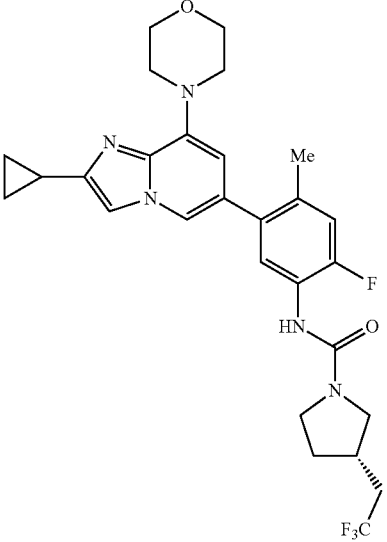 [SMILES: Cc1cc(F)c(NC(=O)N2CC[C@@H](CC(F)(F)F)C2)cc1-c1cc(N2CCOCC2)c2nc(C3CC3)cn2c1] | (S)-N-(5-(2-cyclopropyl-8-morpholinoimidazo[1,2-a]pyridin-6-yl)-2-fluoro-4-methylphenyl)-3-(2,2,2-trifluoroethyl)pyrrolidine-1-carboxamide |
| 19 | 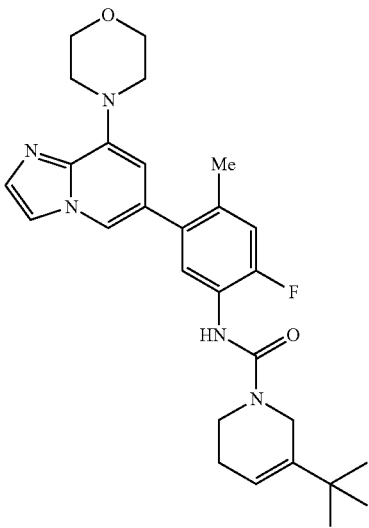 [SMILES: Cc1cc(F)c(NC(=O)N2CCC=C(C(C)(C)C)C2)cc1-c1cc(N2CCOCC2)c2nccn2c1] | 3-(tert-butyl)-N-(2-fluoro-4-methyl-5-(8-morpholinoimidazo[1,2-a]pyridin-6-yl)phenyl)-5,6-dihydropyridine-1(2H)-carboxamide |

TABLE 1-continued
| Synthetic Chemistry Example | Compound Structure | Compound Name |
|---|---|---|
| 20 | 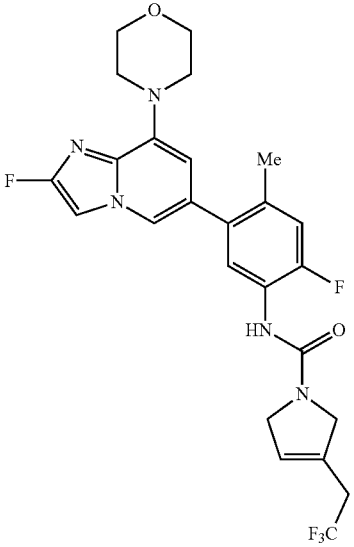 [SMILES: Cc1cc(F)c(NC(=O)N2CC=C(CC(F)(F)F)C2)cc1-c1cc(N2CCOCC2)c2nc(F)cn2c1] | N-(2-fluoro-5-(2-fluoro-8-morpholinoimidazo[1,2-a]pyridin-6-yl)-4-methylphenyl)-3-(2,2,2-trifluoroethyl)-2,5-dihydro-1H-pyrrole-1-carboxamide |
| 21 | 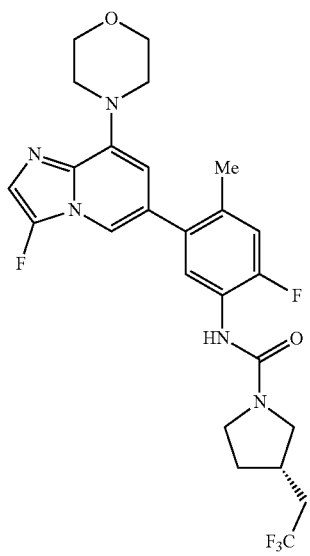 [SMILES: Cc1cc(F)c(NC(=O)N2CC[C@@H](CC(F)(F)F)C2)cc1-c1cc(N2CCOCC2)c2ncc(F)n2c1] | (S)-N-(2-fluoro-5-(3-fluoro-8-morpholinoimidazo[1,2-a]pyridin-6-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 22 | 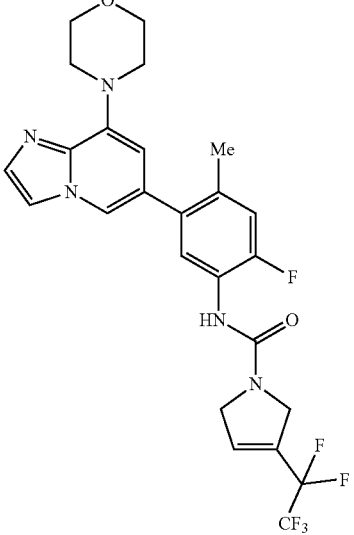 | N-(2-fluoro-4-methyl-5-(8-morpholinoimidazo[1,2-a]pyridin-6-yl)phenyl)-3-(perfluoroethyl)-2,5-dihydro-1H-pyrrole-1-carboxamide |
| 23 | 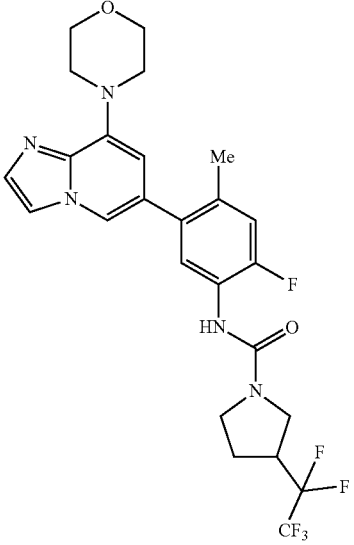 [SMILES: Cc1cc(F)c(NC(=O)N2CCC(C(F)(F)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(perfluoroethyl)pyrrolidine-1-carboxamide |

TABLE 1-continued
| Synthetic Chemistry Example | Compound Structure | Compound Name |
|---|---|---|
| 24 | 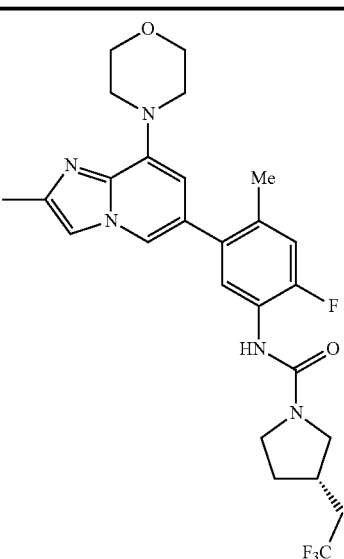 | (S)-N-(2-fluoro-4-methyl-5-(2-methyl-8-morpholinoimidazo[1,2-a]pyridin-6-yl)phenyl)-3-(2,2,2-trifluoroethyl)pyrrolidine-1-carboxamide |
| 25 | 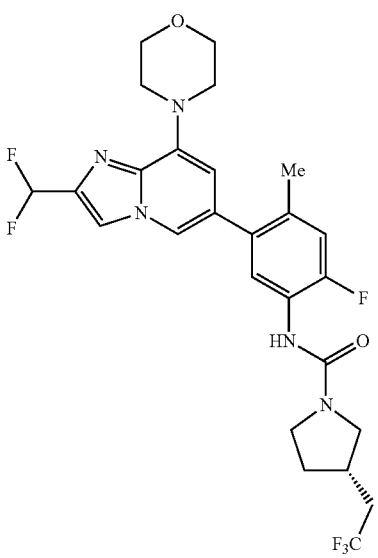 [SMILES: Cc1cc(F)c(NC(=O)N2CC[C@@H](CC(F)(F)F)C2)cc1-c1cc(N2CCOCC2)c2nc(C(F)F)cn2c1] | (S)-N-(5-(2-(difluoromethyl)-8-morpholinoimidazo[1,2-a]pyridin-6-yl)-2-fluoro-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 26 | 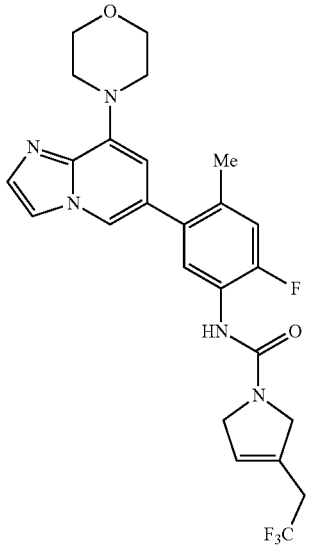 [SMILES: Cc1cc(F)c(NC(=O)N2CC=C(CC(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(2,2,2-trifluoroethyl)-2,5-dihydro-1H-pyrrole-1-carboxamide |
| 27 | 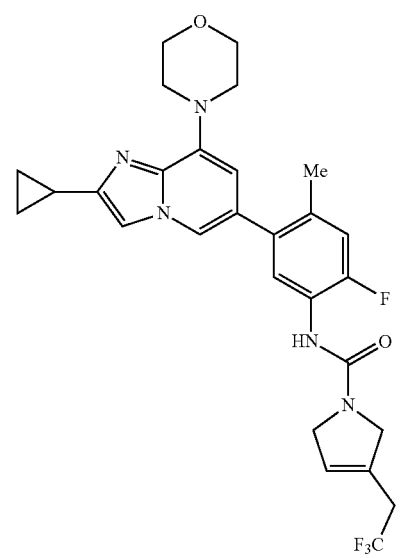 [SMILES: Cc1cc(F)c(NC(=O)N2CC=C(CC(F)(F)F)C2)cc1-c1cc(N2CCOCC2)c2nc(C3CC3)cn2c1] | N-(5-(2-cyclopropyl-8-morpholinoimidazo[1,2-a]pyridin-6-yl)-2-fluoro-4-methylphenyl)-3-(2,2,2-trifluoroethyl)-2,5-dihydro-1H-pyrrole-1-carboxamide |

TABLE 1-continued
| Synthetic Chemistry Example | Compound Structure | Compound Name |
|---|---|---|
| 28 | 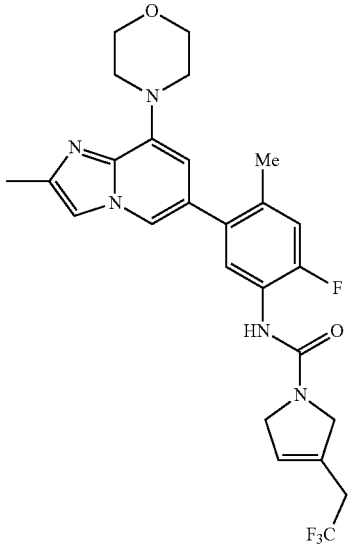 [SMILES: Cc1cn2cc(-c3cc(NC(=O)N4CC=C(CC(F)(F)F)C4)c(F)cc3C)cc(N3CCOCC3)c2n1] | N-(2-fluoro-4-methyl-5-(2-methyl-8-morpholinoimidazo[1,2-a]pyridin-6-yl)phenyl)-3-(2,2,2-trifluoroethyl)-2,5-dihydro-1H-pyrrole-1-carboxamide |
| 29 | 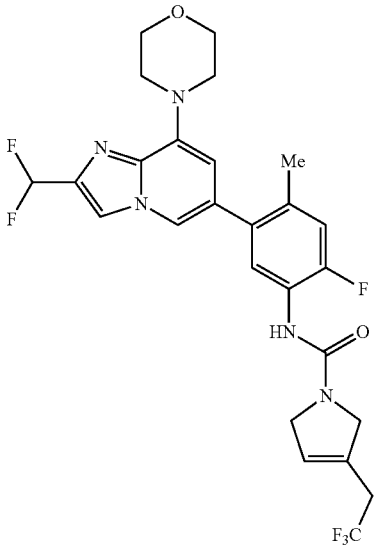 [SMILES: Cc1cc(F)c(NC(=O)N2CC=C(CC(F)(F)F)C2)cc1-c1cc(N2CCOCC2)c2nc(C(F)F)cn2c1] | N-(5-(2-(difluoromethyl)-8-morpholinoimidazo[1,2-a]pyridin-6-yl)-2-fluoro-4-methylphenyl)-3-(2,2,2-trifluoroethyl)-2,5-dihydro-1H-pyrrole-1-carboxamide |

TABLE 1-continued
| Synthetic Chemistry Example | Compound Structure | Compound Name |
|---|---|---|
| 30 | 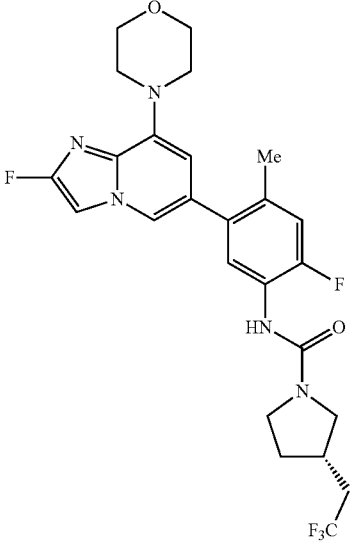 [SMILES: Cc1cc(F)c(NC(=O)N2CC[C@@H](CC(F)(F)F)C2)cc1-c1cc(N2CCOCC2)c2nc(F)cn2c1] | (S)-N-(2-fluoro-5-(2-fluoro-8-morpholinoimidazo[1,2-a]pyridin-6-yl)-4-methylphenyl)-3-(2,2,2-trifluoroethyl)pyrrolidine-1-carboxamide |
| 31 | 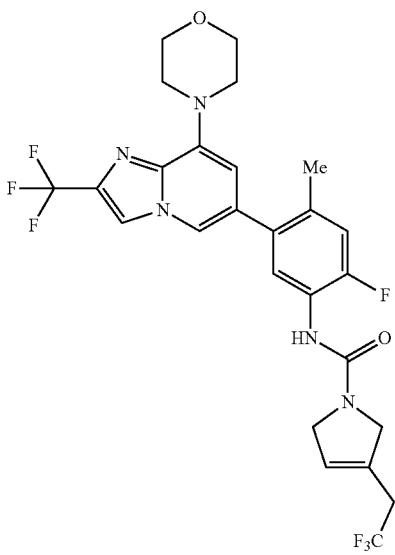 [SMILES: Cc1cc(F)c(NC(=O)N2CC=C(CC(F)(F)F)C2)cc1-c1cc(N2CCOCC2)c2nc(C(F)(F)F)cn2c1] | N-(2-fluoro-4-methyl-5-(8-morpholino-2-(trifluoromethyl)imidazo[1,2-a]pyridin-6-yl)phenyl)-3-(2,2,2-trifluoroethyl)-2,5-dihydro-1H-pyrrole-1-carboxamide |

TABLE 1-continued
| Synthetic Chemistry Example | Compound Structure | Compound Name |
|---|---|---|
| 32 | 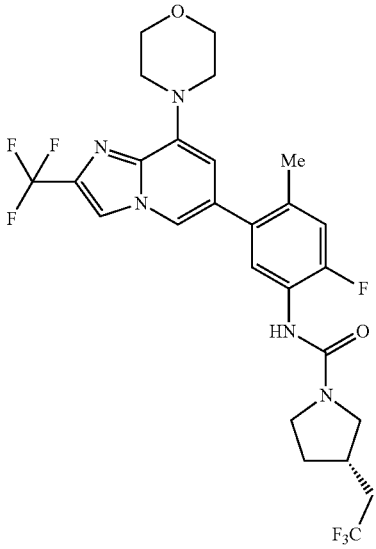 [SMILES: Cc1cc(F)c(NC(=O)N2CC[C@@H](CC(F)(F)F)C2)cc1-c1cc(N2CCOCC2)c2nc(C(F)(F)F)cn2c1] | (S)-N-(2-fluoro-4-methyl-5-(8-morpholino-2-(trifluoromethyl)imidazo[1,2-a]pyridin-6-yl)phenyl)-3-(2,2,2-trifluoroethyl)pyrrolidine-1-carboxamide |
| 33 | 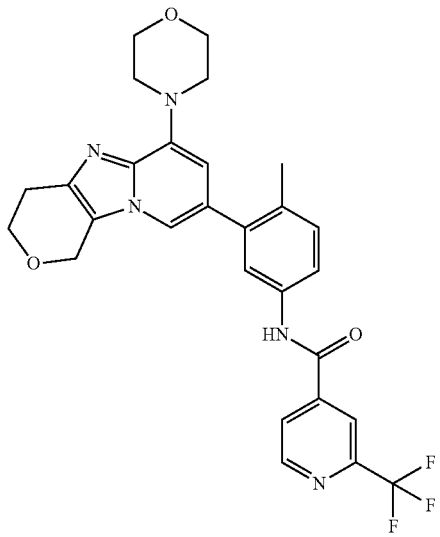 [SMILES: Cc1ccc(NC(=O)c2ccnc(C(F)(F)F)c2)cc1-c1cc(N2CCOCC2)c2nc3c(n2c1)COCC3] | N-(4-Methyl-3-(6-morpholino-3,4-dihydro-1H-pyrano[4',3':4,5]imidazo[1,2-a]pyridin-8-yl)phenyl)-2-(trifluoromethyl)isonicotinamide |

TABLE 1-continued
| Synthetic Chemistry Example | Compound Structure | Compound Name |
|---|---|---|
| 34 | 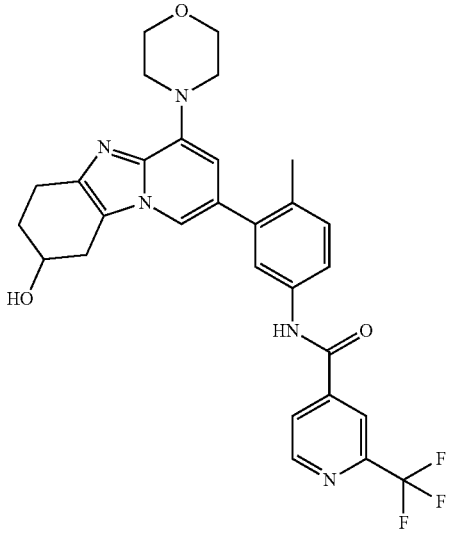 [SMILES: Cc1ccc(NC(=O)c2ccnc(C(F)(F)F)c2)cc1-c1cc(N2CCOCC2)c2nc3c(n2c1)CC(O)CC3] | N-(3-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide |
| 35 | 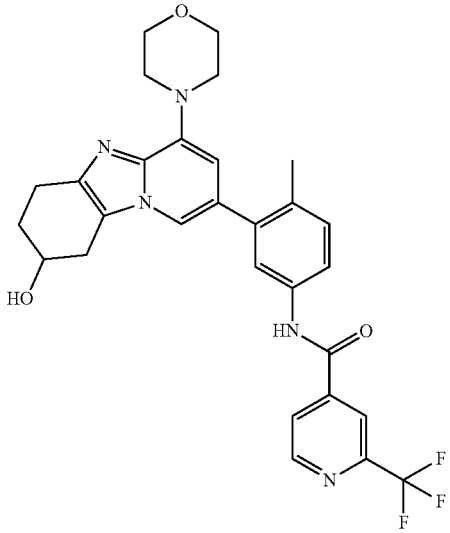 [SMILES: Cc1ccc(NC(=O)c2ccnc(C(F)(F)F)c2)cc1-c1cc(N2CCOCC2)c2nc3c(n2c1)CC(O)CC3] | N-(3-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide |

TABLE 1-continued
| Synthetic Chemistry Example | Compound Structure | Compound Name |
|---|---|---|
| 36 | 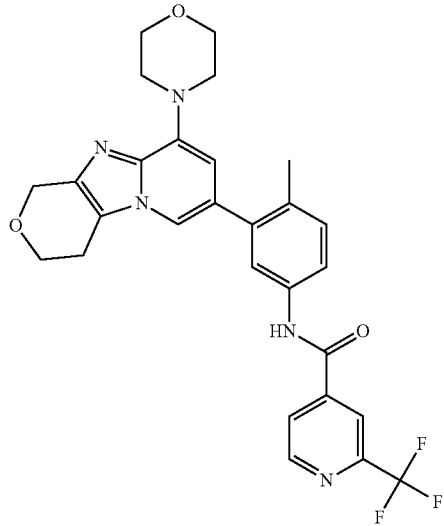 [SMILES: Cc1ccc(NC(=O)c2ccnc(C(F)(F)F)c2)cc1-c1cc(N2CCOCC2)c2nc3c(n2c1)CCOC3] | N-(4-methyl-3-(9-morpholino-3,4-dihydro-1H-pyrano[3',4':4,5]imidazo[1,2-a]pyridin-7-yl)phenyl)-2-(trifluoromethyl)isonicotinamide |
| 37 | 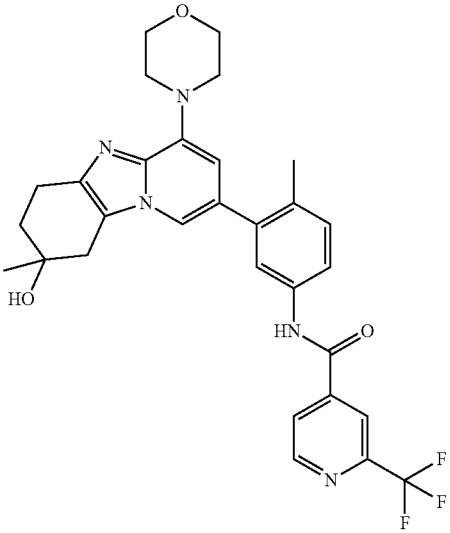 [SMILES: Cc1ccc(NC(=O)c2ccnc(C(F)(F)F)c2)cc1-c1cc(N2CCOCC2)c2nc3c(n2c1)CC(C)(O)CC3] | N-(3-(8-Hydroxy-8-methyl-4-morpholino-6,7,8,9-tetrahydrobenzo[4,5]imidazo[1,2-a]pyridin-2-yl)-4-methylphenyl)-2-(trifluoromethyl)isonicotinamide |

TABLE 1-continued

| Synthetic Chemistry Example | Compound Structure | Compound Name |
|---|---|---|
| 38 | 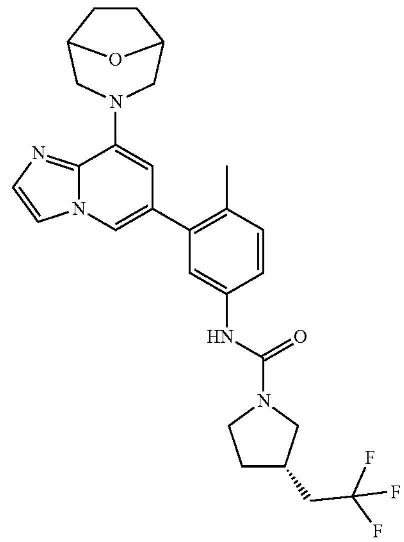 [SMILES: Cc1ccc(NC(=O)N2CC[C@@H](CC(F)(F)F)C2)cc1-c1cc(N2CC3CCC(C2)O3)c2nccn2c1] | (3S)-N-[4-Methyl-3-(8-[8-oxa-3-azabicyclo[3.2.1]octan-3-yl]imidazo[1,2-a]pyridin-6-yl)phenyl]-3-(2,2,2-trifluoroethyl)pyrrolidine-1-carboxamide |
| 39 | 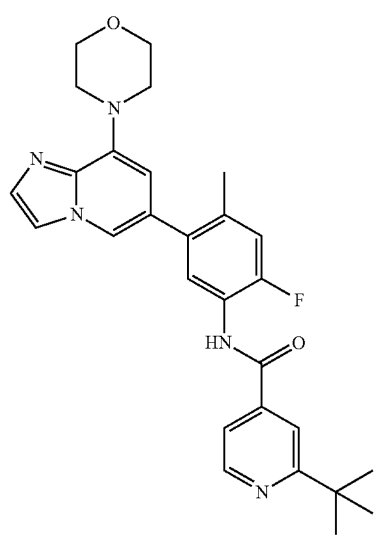 [SMILES: Cc1cc(F)c(NC(=O)c2ccnc(C(C)(C)C)c2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}pyridine-4-carboxamide |

TABLE 1-continued
| Synthetic Chemistry Example | Compound Structure | Compound Name |
|---|---|---|
| 40 | 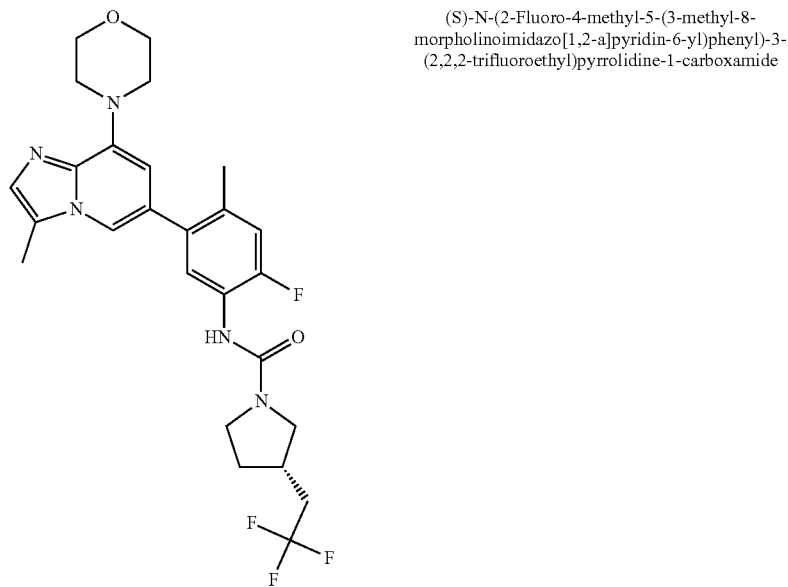 | (S)-N-(2-Fluoro-4-methyl-5-(3-methyl-8-morpholinoimidazo[1,2-a]pyridin-6-yl)phenyl)-3-(2,2,2-trifluoroethyl)pyrrolidine-1-carboxamide |
| 41 | 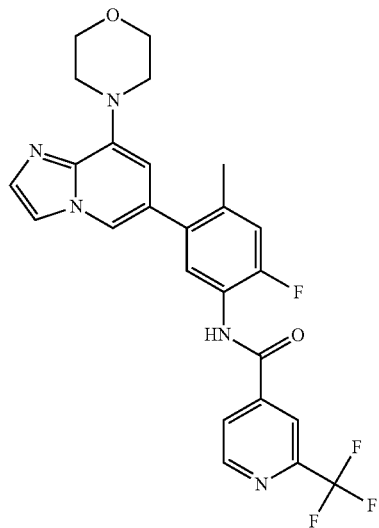 [SMILES: Cc1cc(F)c(NC(=O)c2ccnc(C(F)(F)F)c2)cc1-c1cc(N2CCOCC2)c2nccn2c1] | N-(2-Fluoro-4-methyl-5-(8-morpholinoimidazo[1,2-a]pyridin-6-yl)phenyl)-2-(trifluoromethyl)isonicotinamide |

TABLE 1-continued
| Synthetic Chemistry Example | Compound Structure | Compound Name |
|---|---|---|
| 42 | 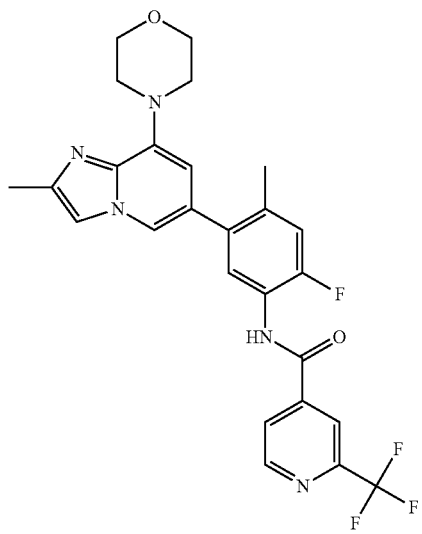 [SMILES: Cc1cn2cc(-c3cc(NC(=O)c4ccnc(C(F)(F)F)c4)c(F)cc3C)cc(N3CCOCC3)c2n1] | N-(2-Fluoro-4-methyl-5-(2-methyl-8-morpholinoimidazo[1,2-a]pyridin-6-yl)phenyl)-2-(trifluoromethyl)isonicotinamide |
| 43 | 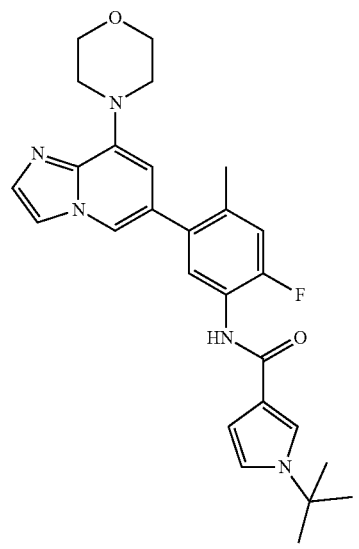 [SMILES: Cc1cc(F)c(NC(=O)c2ccn(C(C)(C)C)c2)cc1-c1cc(N2CCOCC2)c2nccn2c1] | 1-tert-Butyl-N-{2-fluoro-4-methyl-5-[8-(morpholin-4-yl)imidazo[1,2-a]pyridin-6-yl]phenyl}pyrrole-3-carboxamide |

TABLE 1-continued
| Synthetic Chemistry Example | Compound Structure | Compound Name |
|---|---|---|
| 44 | 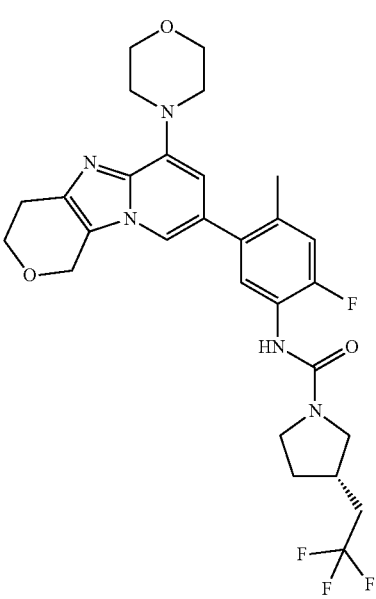 [SMILES: Cc1cc(F)c(NC(=O)N2CC[C@@H](CC(F)(F)F)C2)cc1-c1cc(N2CCOCC2)c2nc3c(n2c1)COCC3] | (S)-N-(2-Fluoro-4-methyl-5-(6-morpholino-3,4-dihydro-1H-pyrano[4',3':4,5]imidazo[1,2-a]pyridin-8-yl)phenyl)-3-(2,2,2-trifluoroethyl)pyrrolidine-1-carboxamide |
| 45 | 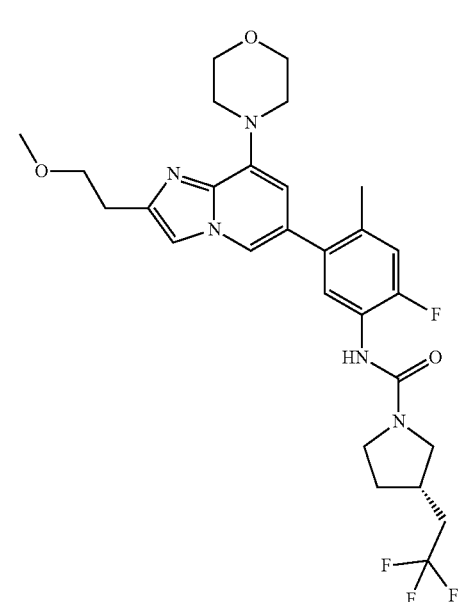 [SMILES: COCCc1cn2cc(-c3cc(NC(=O)N4CC[C@@H](CC(F)(F)F)C4)c(F)cc3C)cc(N3CCOCC3)c2n1] | (S)-N-(2-Fluoro-5-(2-(2-methoxyethyl)-8-morpholinoimidazo[1,2-a]pyridin-6-yl)-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 46 | 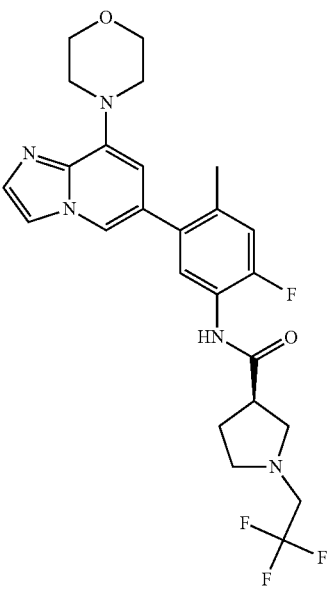 [SMILES: Cc1cc(F)c(NC(=O)[C@@H]2CCN(CC(F)(F)F)C2)cc1-c1cc(N2CCOCC2)c2nccn2c1] | (R)-N-(2-Fluoro-4-methyl-5-(8-morpholinoimidazo[1,2-a]pyridin-6-yl)phenyl)-1-(2,2,2-trifluoroethyl)pyrrolidine-3-carboxamide |
| 47 | 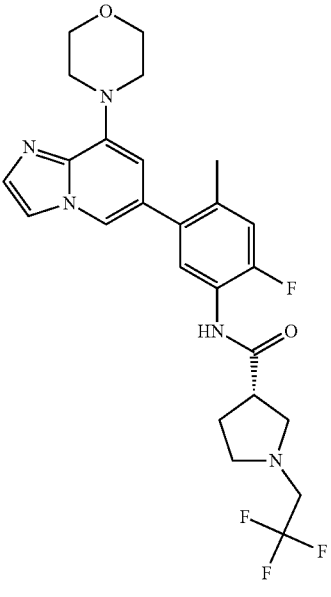 [SMILES: Cc1cc(F)c(NC(=O)[C@H]2CCN(CC(F)(F)F)C2)cc1-c1cc(N2CCOCC2)c2nccn2c1] | (S)-N-(2-Fluoro-4-methyl-5-(8-morpholinoimidazo[1,2-a]pyridin-6-yl)phenyl)-1-(2,2,2-trifluoroethyl)pyrrolidine-3-carboxamide |

TABLE 1-continued
| Synthetic Chemistry Example | Compound Structure | Compound Name |
|---|---|---|
| 48 | 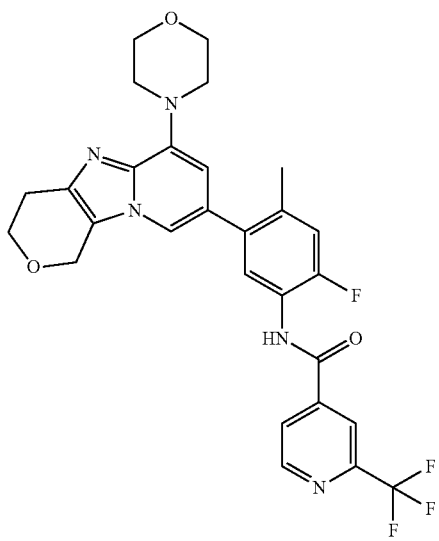 [SMILES: Cc1cc(F)c(NC(=O)c2ccnc(C(F)(F)F)c2)cc1-c1cc(N2CCOCC2)c2nc3c(n2c1)COCC3] | N-(2-Fluoro-4-methyl-5-(6-morpholino-3,4-dihydro-1H-pyrano[4',3':4,5]imidazo[1,2-a]pyridin-8-yl)phenyl)-2-(trifluoromethyl)isonicotinamide |
| 49 | 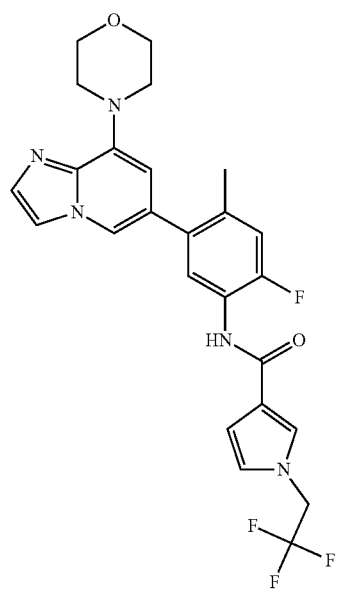 [SMILES: Cc1cc(F)c(NC(=O)c2ccn(CC(F)(F)F)c2)cc1-c1cc(N2CCOCC2)c2nccn2c1] | N-(2-Fluoro-4-methyl-5-(8-morpholinoimidazo[1,2-a]pyridin-6-yl)phenyl)-1-(2,2,2-trifluoroethyl)-1H-pyrrole-3-carboxamide |

TABLE 1-continued

| Synthetic Chemistry Example | Compound Structure | Compound Name |
|---|---|---|
| 50 | 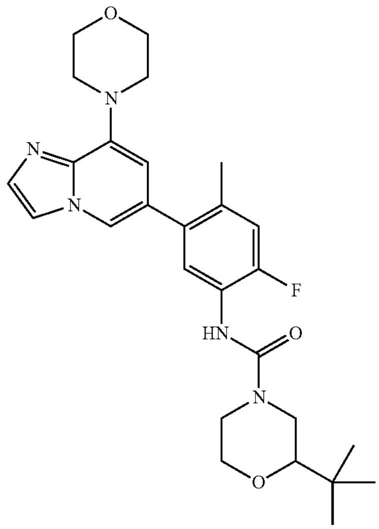 [SMILES: Cc1cc(F)c(NC(=O)N2CCOC(C(C)(C)C)C2)cc1-c1cc(N2CCOCC2)c2nccn2c1] | 2-(tert-Butyl)-N-(2-fluoro-4-methyl-5-(8-morpholinoimidazo[1,2-a]pyridin-6-yl)phenyl)morpholine-4-carboxamide |
| 51 | 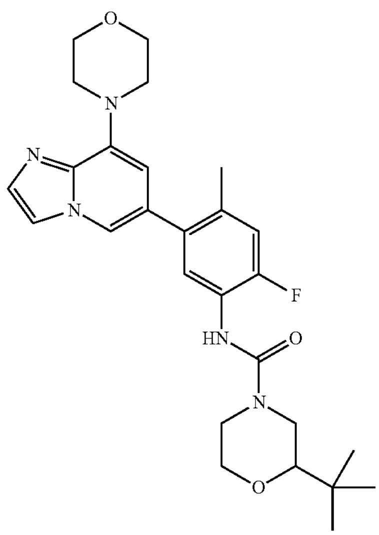 [SMILES: Cc1cc(F)c(NC(=O)N2CCOC(C(C)(C)C)C2)cc1-c1cc(N2CCOCC2)c2nccn2c1] | 2-(tert-Butyl)-N-(2-fluoro-4-methyl-5-(8-morpholinoimidazo[1,2-a]pyridin-6-yl)phenyl)morpholine-4-carboxamide |
| 52 | 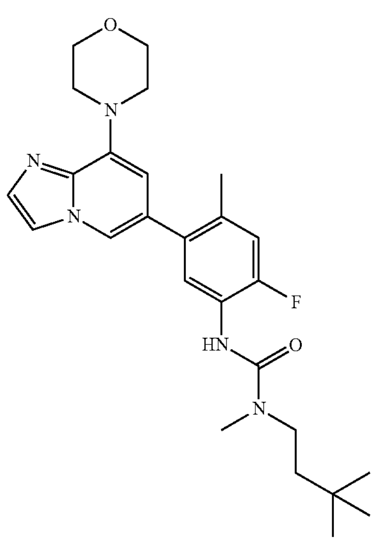 [SMILES: Cc1cc(F)c(NC(=O)N(C)CCC(C)(C)C)cc1-c1cc(N2CCOCC2)c2nccn2c1] | 1-(3,3-Dimethylbutyl)-3-(2-fluoro-4-methyl-5-(8-morpholinoimidazo[1,2-a]pyridin-6-yl)phenyl)-1-methylurea |

TABLE 1-continued
| Synthetic Chemistry Example | Compound Structure | Compound Name |
|---|---|---|
| 53 | 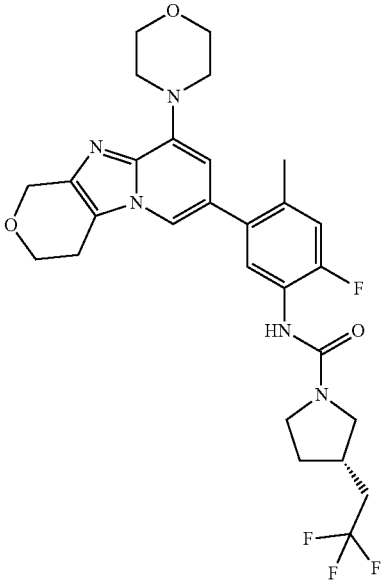 [SMILES: Cc1cc(F)c(NC(=O)N2CC[C@@H](CC(F)(F)F)C2)cc1-c1cc(N2CCOCC2)c2nc3c(n2c1)CCOC3] | (S)-N-(2-Fluoro-4-methyl-5-(9-morpholino-3,4-dihydro-1H-pyrano[3',4':4,5]imidazo[1,2-a]pyridin-7-yl)phenyl)-3-(2,2,2-trifluoroethyl)pyrrolidine-1-carboxamide |
| 54 | 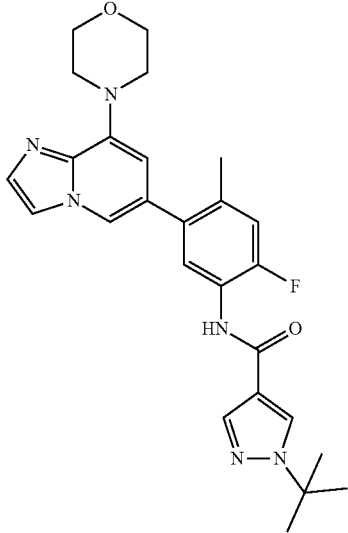 [SMILES: Cc1cc(F)c(NC(=O)c2cnn(C(C)(C)C)c2)cc1-c1cc(N2CCOCC2)c2nccn2c1] | 1-(Tert-butyl)-N-(2-fluoro-4-methyl-5-(8-morpholinoimidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 55 | 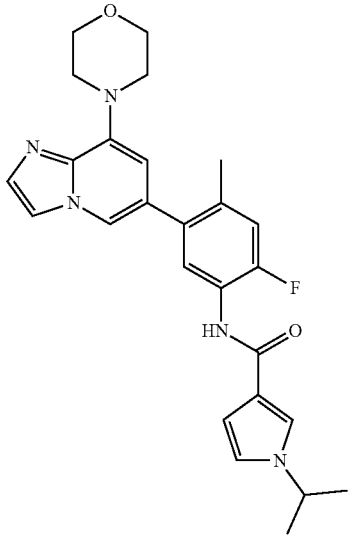 [SMILES: Cc1cc(F)c(NC(=O)c2ccn(C(C)C)c2)cc1-c1cc(N2CCOCC2)c2nccn2c1] | N-(2-Fluoro-4-methyl-5-(8-morpholinoimidazo[1,2-a]pyridin-6-yl)phenyl)-1-isopropyl-1H-pyrrole-3-carboxamide |
| 56 | 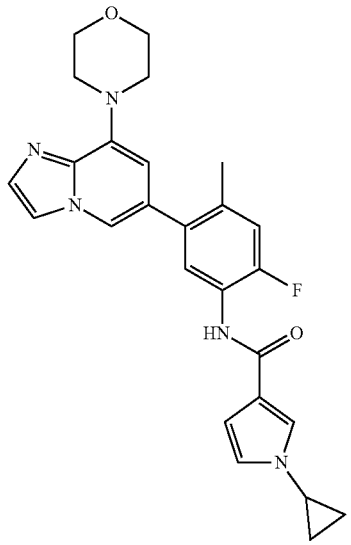 [SMILES: Cc1cc(F)c(NC(=O)c2ccn(C3CC3)c2)cc1-c1cc(N2CCOCC2)c2nccn2c1] | 1-Cyclopropyl-N-(2-fluoro-4-methyl-5-(8-morpholinoimidazo[1,2-a]pyridin-6-yl)phenyl)-1H-pyrrole-3-carboxamide |

TABLE 1-continued
| Synthetic Chemistry Example | Compound Structure | Compound Name |
|---|---|---|
| 57 | 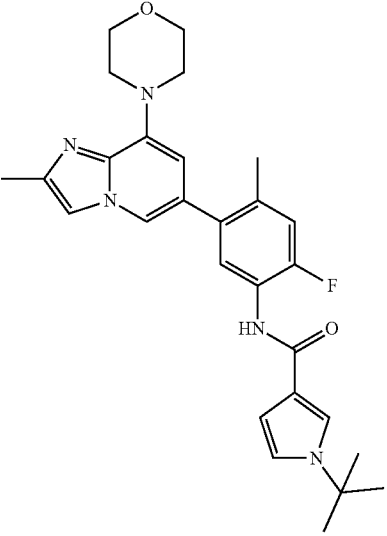 [SMILES: Cc1cn2cc(-c3cc(NC(=O)c4ccn(C(C)(C)C)c4)c(F)cc3C)cc(N3CCOCC3)c2n1] | 1-(Tert-butyl)-N-(2-fluoro-4-methyl-5-(2-methyl-8-morpholinoimidazo[1,2-a]pyridin-6-yl)phenyl)-1H-pyrrole-3-carboxamide |
| 58 | 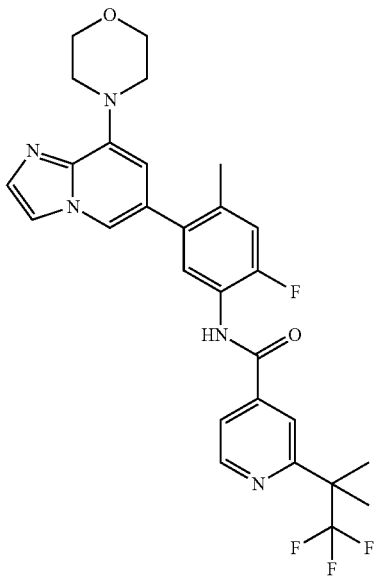 [SMILES: Cc1cc(F)c(NC(=O)c2ccnc(C(C)(C)C(F)(F)F)c2)cc1-c1cc(N2CCOCC2)c2nccn2c1] | N-(2-Fluoro-4-methyl-5-(8-morpholinoimidazo[1,2-a]pyridin-6-yl)phenyl)-2-(1,1,1-trifluoro-2-methylpropan-2-yl)isonicotinamide |

TABLE 1-continued
| Synthetic Chemistry Example | Compound Structure | Compound Name |
|---|---|---|
| 59 | 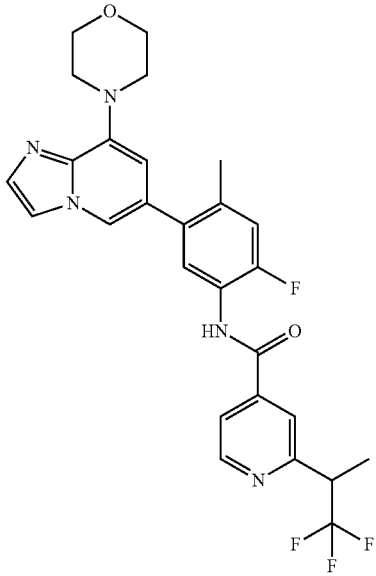 [SMILES: Cc1cc(F)c(NC(=O)c2ccnc(C(C)C(F)(F)F)c2)cc1-c1cc(N2CCOCC2)c2nccn2c1] | N-(2-Fluoro-4-methyl-5-(8-morpholinoimidazo[1,2-a]pyridin-6-yl)phenyl)-2-(1,1,1-trifluoropropan-2-yl)isonicotinamide |
| 60 | 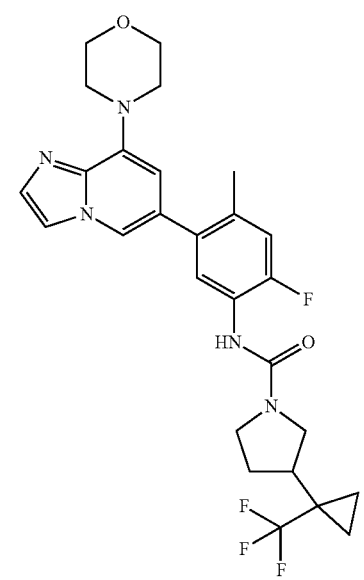 [SMILES: Cc1cc(F)c(NC(=O)N2CCC(C3(C(F)(F)F)CC3)C2)cc1-c1cc(N2CCOCC2)c2nccn2c1] | N-(2-fluoro-4-methyl-5-(8-morpholinoimidazo[1,2-a]pyridin-6-yl)phenyl)-3-(1-(trifluoromethyl)cyclopropyl)pyrrolidine-1-carboxamide |

TABLE 1-continued
| Synthetic Chemistry Example | Compound Structure | Compound Name |
|---|---|---|
| 61 | 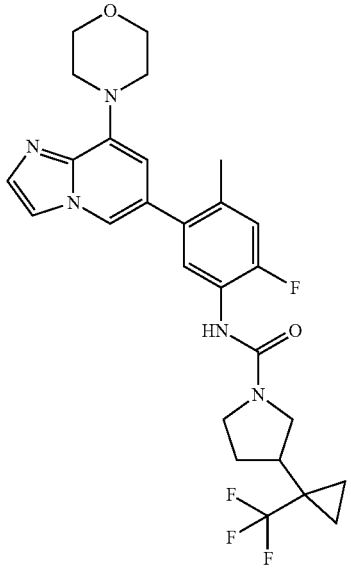 [SMILES: Cc1cc(F)c(NC(=O)N2CCC(C3(C(F)(F)F)CC3)C2)cc1-c1cc(N2CCOCC2)c2nccn2c1] | N-(2-fluoro-4-methyl-5-(8-morpholinoimidazo[1,2-a]pyridin-6-yl)phenyl)-3-(1-(trifluoromethyl)cyclopropyl)pyrrolidine-1-carboxamide |
| 62 | 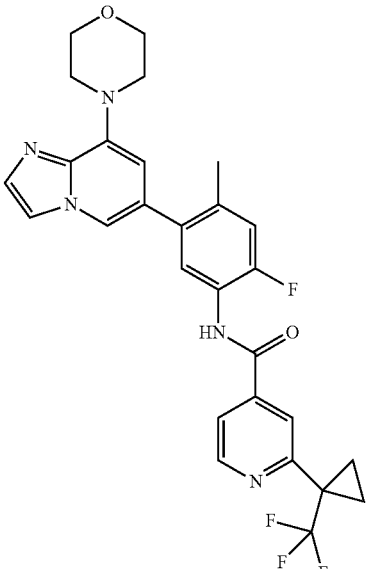 | 2-Fluoro-4-methyl-5-(8-morpholinoimidazo[1,2-a]pyridin-6-yl)phenyl 2-(1-(trifluoromethyl)cyclopropyl)isonicotinate |

TABLE 1-continued
| Synthetic Chemistry Example | Compound Structure | Compound Name |
|---|---|---|
| 63 | 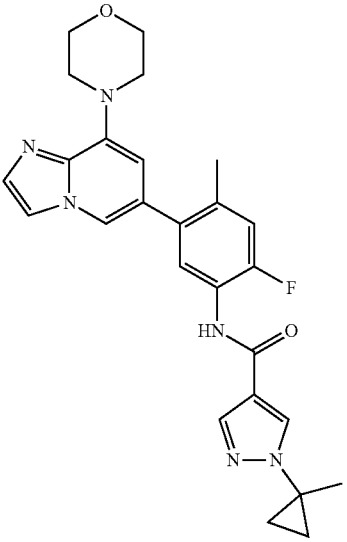 [SMILES: Cc1cc(F)c(NC(=O)c2cnn(C3(C)CC3)c2)cc1-c1cc(N2CCOCC2)c2nccn2c1] | N-(2-Fluoro-4-methyl-5-(8-morpholinoimidazo[1,2-a]pyridin-6-yl)phenyl)-1-(1-methylcyclopropyl)-1H-pyrazole-4-carboxamide |
| 64 | 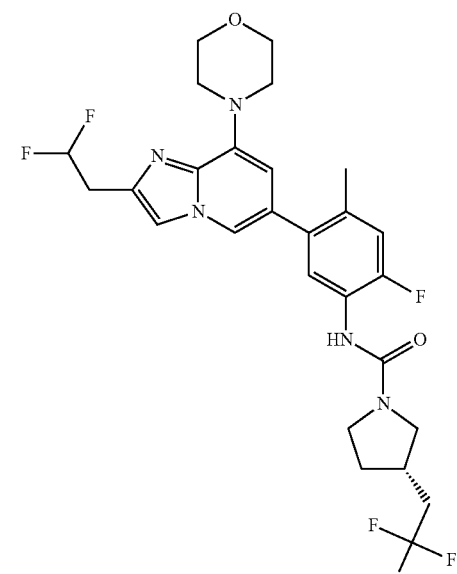 | (S)-N-(5-(2-(2,2-Difluoroethyl)-8-morpholinoimidazo[1,2-a]pyridin-6-yl)-2-fluoro-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 65 | 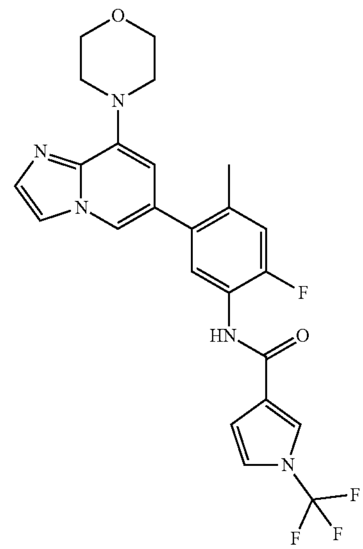 [SMILES: Cc1cc(F)c(NC(=O)c2ccn(C(F)(F)F)c2)cc1-c1cc(N2CCOCC2)c2nccn2c1] | N-(2-Fluoro-4-methyl-5-(8-morpholinoimidazo[1,2-a]pyridin-6-yl)phenyl)-1-(trifluoromethyl)-1H-pyrrole-3-carboxamide |
| 66 | 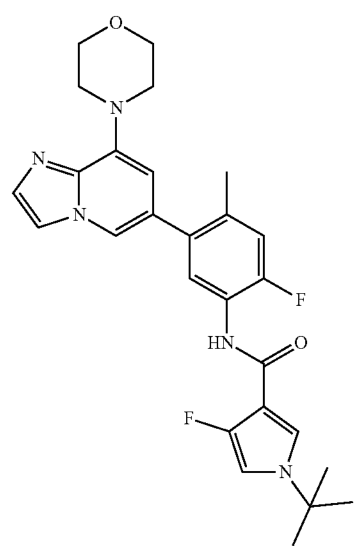 [SMILES: Cc1cc(F)c(NC(=O)c2cn(C(C)(C)C)cc2F)cc1-c1cc(N2CCOCC2)c2nccn2c1] | 1-Tert-butyl-4-fluoro-N-{2-fluoro-4-methyl-5-[8-(morpholin-4-yl)imidazo[1,2-a]pyridin-6-yl]phenyl}pyrrole-3-carboxamide |

TABLE 1-continued
| Synthetic Chemistry Example | Compound Structure | Compound Name |
|---|---|---|
| 67 | 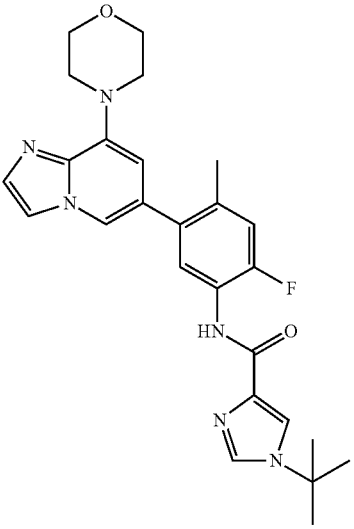 [SMILES: Cc1cc(F)c(NC(=O)c2cn(C(C)(C)C)cn2)cc1-c1cc(N2CCOCC2)c2nccn2c1] | 1-Tert-butyl-N-{2-fluoro-4-methyl-5-[8-(morpholin-4-yl)imidazo[1,2-a]pyridin-6-yl]phenyl}imidazole-4-carboxamide |
| 68 | 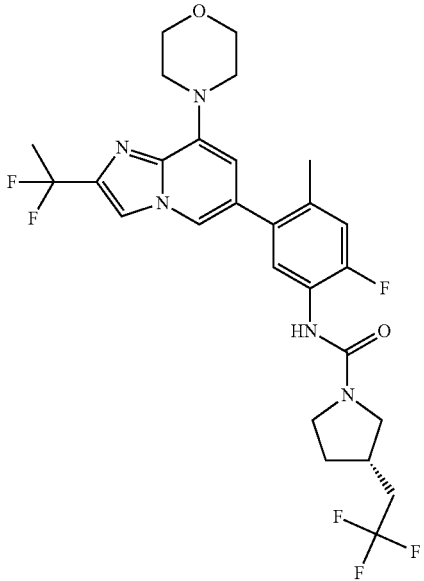 [SMILES: Cc1cc(F)c(NC(=O)N2CC[C@@H](CC(F)(F)F)C2)cc1-c1cc(N2CCOCC2)c2nc(C(C)(F)F)cn2c1] | (S)-N-(5-(2-(1,1-Difluoroethyl)-8-morpholinoimidazo[1,2-a]pyridin-6-yl)-2-fluoro-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 69 | 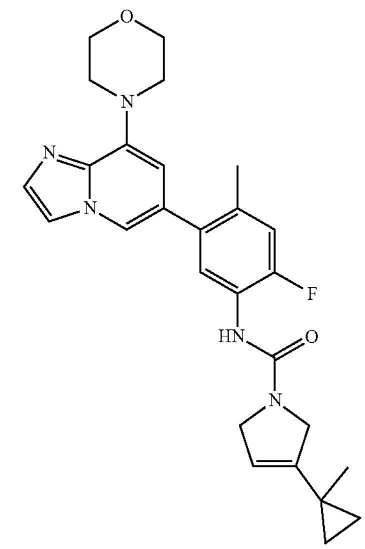 [SMILES: Cc1cc(F)c(NC(=O)N2CC=C(C3(C)CC3)C2)cc1-c1cc(N2CCOCC2)c2nccn2c1] | N-{2-Fluoro-4-methyl-5-[8-(morpholin-4-yl)imidazo[1,2-a]pyridin-6-yl]phenyl}-3-(1-methylcyclopropyl)-2,5-dihydropyrrole-1-carboxamide |
| 70 | 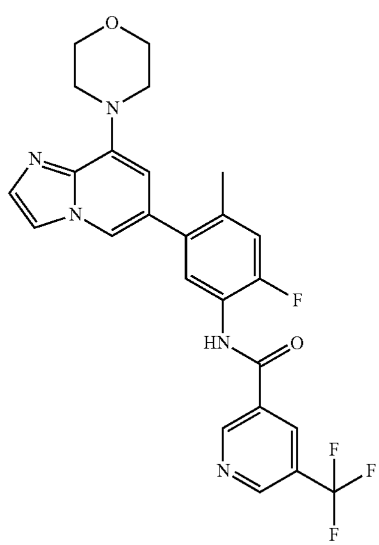 [SMILES: Cc1cc(F)c(NC(=O)c2cncc(C(F)(F)F)c2)cc1-c1cc(N2CCOCC2)c2nccn2c1] | N-{2-Fluoro-4-methyl-5-[8-(morpholin-4-yl)imidazo[1,2-a]pyridin-6-yl]phenyl}-5-(trifluoromethyl)pyridine-3-carboxamide |

TABLE 1-continued
| Synthetic Chemistry Example | Compound Structure | Compound Name |
|---|---|---|
| 71 | 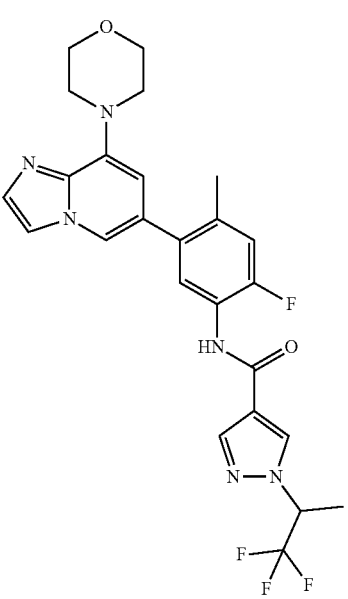 [SMILES: Cc1cc(F)c(NC(=O)c2cnn(C(C)C(F)(F)F)c2)cc1-c1cc(N2CCOCC2)c2nccn2c1] | N-(2-fluoro-4-methyl-5-(8-morpholinoimidazo[1,2-a]pyridin-6-yl)phenyl)-1-(1,1,1-trifluoropropan-2-yl)-1H-pyrazole-4-carboxamide |
| 72 | 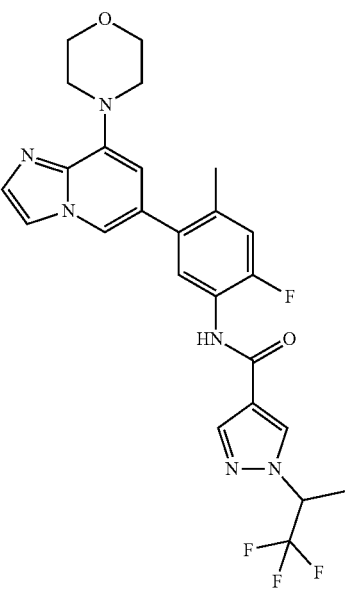 [SMILES: Cc1cc(F)c(NC(=O)c2cnn(C(C)C(F)(F)F)c2)cc1-c1cc(N2CCOCC2)c2nccn2c1] | N-(2-fluoro-4-methyl-5-(8-morpholinoimidazo[1,2-a]pyridin-6-yl)phenyl)-1-(1,1,1-trifluoropropan-2-yl)-1H-pyrazole-4-carboxamide |

TABLE 1-continued
| Synthetic Chemistry Example | Compound Structure | Compound Name |
|---|---|---|
| 73 | 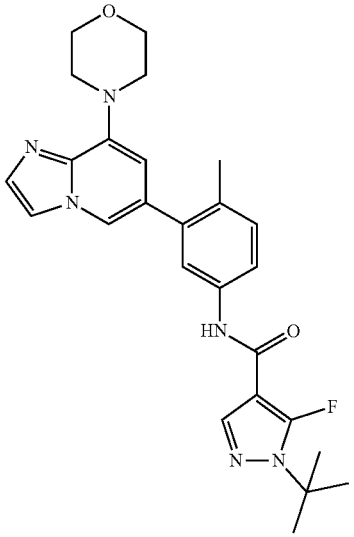 [SMILES: Cc1ccc(NC(=O)c2cnn(C(C)(C)C)c2F)cc1-c1cc(N2CCOCC2)c2nccn2c1] | 1-(tert-butyl)-5-fluoro-N-(4-methyl-3-(8-morpholinoimidazo[1,2-a]pyridin-6-yl)phenyl)-1H-pyrazole-4-carboxamide |
| 74 | 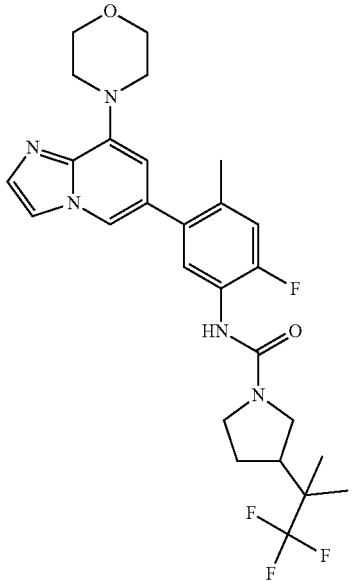 [SMILES: Cc1cc(F)c(NC(=O)N2CCC(C(C)(C)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide |

| Synthetic Chemistry Example | Compound Structure | Compound Name |
|---|---|---|
| 75 | 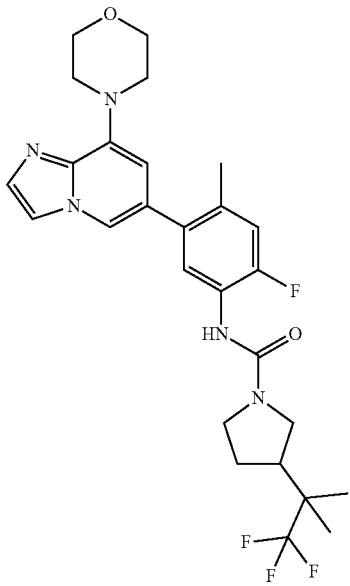 [SMILES: Cc1cc(F)c(NC(=O)N2CCC(C(C)(C)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide |
| 76 | 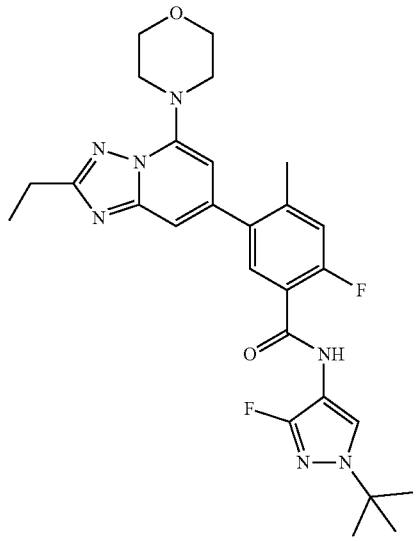 [SMILES: CCc1nc2cc(-c3cc(C(=O)Nc4cn(C(C)(C)C)nc4F)c(F)cc3C)cc(N3CCOCC3)n2n1] | N-(1-(tert-Butyl)-3-fluoro-1H-pyrazol-4-yl)-5-(2-ethyl-5-morpholino-[1,2,4]triazolo[1,5-a]pyridin-7-yl)-2-fluoro-4-methylbenzamide |

TABLE 1-continued

| Synthetic Chemistry Example | Compound Structure | Compound Name |
|---|---|---|
| 77 | 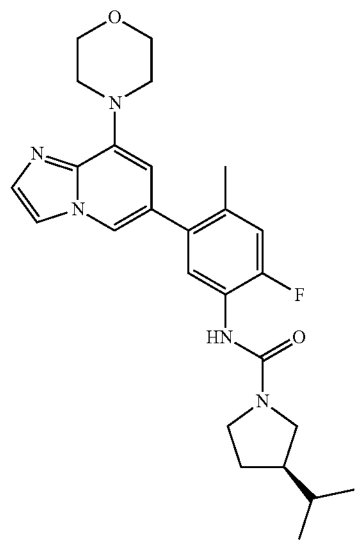 [SMILES: Cc1cc(F)c(NC(=O)N2CC[C@H](C(C)C)C2)cc1-c1cc(N2CCOCC2)c2nccn2c1] | (R)-N-(2-Fluoro-4-methyl-5-(8-morpholinoimidazo[1,2-a]pyridin-6-yl)phenyl)-3-isopropylpyrrolidine-1-carboxamide |
| 78 | 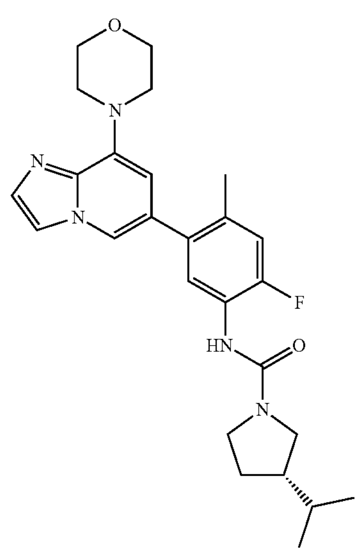 [SMILES: Cc1cc(F)c(NC(=O)N2CC[C@@H](C(C)C)C2)cc1-c1cc(N2CCOCC2)c2nccn2c1] | (S)-N-(2-Fluoro-4-methyl-5-(8-morpholinoimidazo[1,2-a]pyridin-6-yl)phenyl)-3-isopropylpyrrolidine-1-carboxamide |

TABLE 1-continued
| Synthetic Chemistry Example | Compound Structure | Compound Name |
|---|---|---|
| 79 | 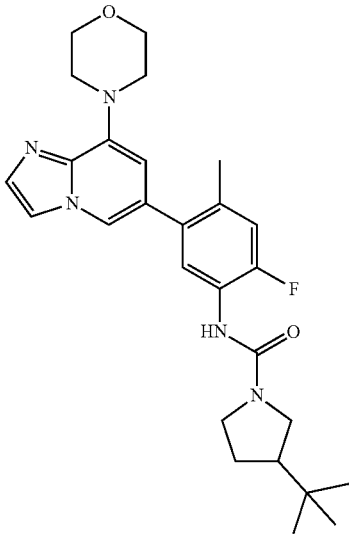 [SMILES: Cc1cc(F)c(NC(=O)N2CCC(C(C)(C)C)C2)cc1-c1cc(N2CCOCC2)c2nccn2c1] | 3-(tert-butyl)-N-(2-fluoro-4-methyl-5-(8-morpholinoimidazo[1,2-a]pyridin-6-yl)phenyl)pyrrolidine-1-carboxamide |
| 80 | 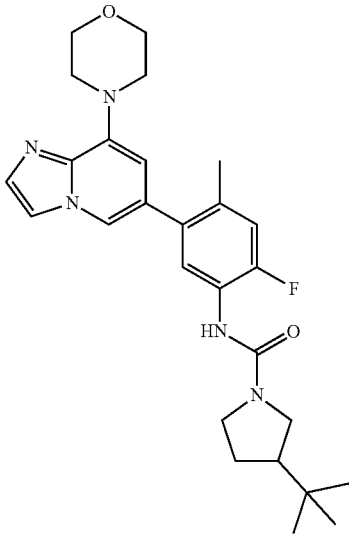 [SMILES: Cc1cc(F)c(NC(=O)N2CCC(C(C)(C)C)C2)cc1-c1cc(N2CCOCC2)c2nccn2c1] | 3-(tert-butyl)-N-(2-fluoro-4-methyl-5-(8-morpholinoimidazo[1,2-a]pyridin-6-yl)phenyl)pyrrolidine-1-carboxamide |

TABLE 1-continued
| Synthetic Chemistry Example | Compound Structure | Compound Name |
|---|---|---|
| 81 | 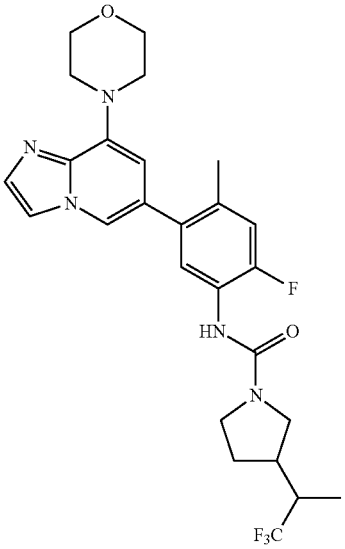 [SMILES: Cc1cc(F)c(NC(=O)N2CCC(C(C)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(1,1,1-trifluoropropan-2-yl)pyrrolidine-1-carboxamide |
| 82 | 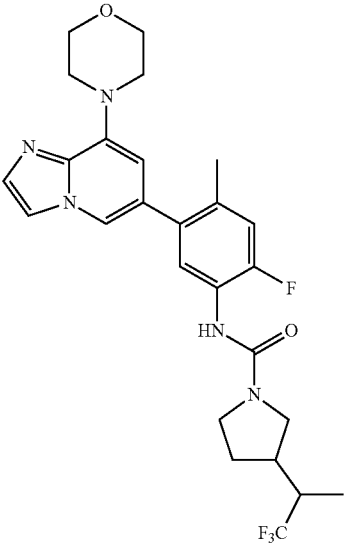 [SMILES: Cc1cc(F)c(NC(=O)N2CCC(C(C)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(1,1,1-trifluoropropan-2-yl)pyrrolidine-1-carboxamide |

TABLE 1-continued
| Synthetic Chemistry Example | Compound Structure | Compound Name |
|---|---|---|
| 83 | 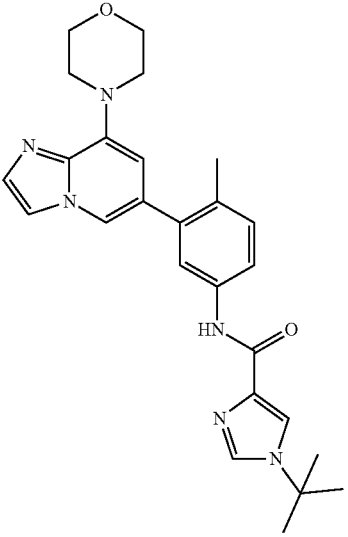 [SMILES: Cc1ccc(NC(=O)c2cn(C(C)(C)C)cn2)cc1-c1cc(N2CCOCC2)c2nccn2c1] | 1-(Tert-butyl)-N-(4-methyl-3-(8-morpholinoimidazo[1,2-a]pyridin-6-yl)phenyl)-1H-imidazole-4-carboxamide |
| 84 | 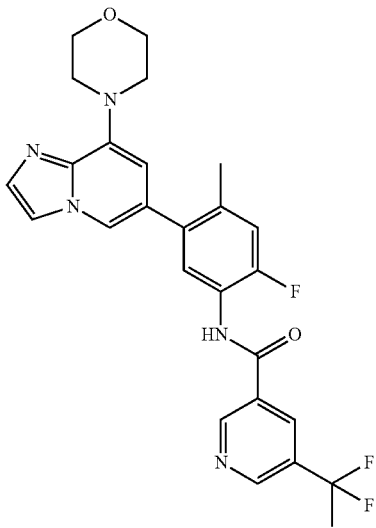 [SMILES: Cc1cc(F)c(NC(=O)c2cncc(C(C)(F)F)c2)cc1-c1cc(N2CCOCC2)c2nccn2c1] | 5-(1,1-Difluoroethyl)-N-{2-fluoro-4-methyl-5-[8-(morpholin-4-yl)imidazo[1,2-a]pyridin-6-yl]phenyl}pyridine-3-carboxamide |

TABLE 1-continued
| Synthetic Chemistry Example | Compound Structure | Compound Name |
|---|---|---|
| 85 | 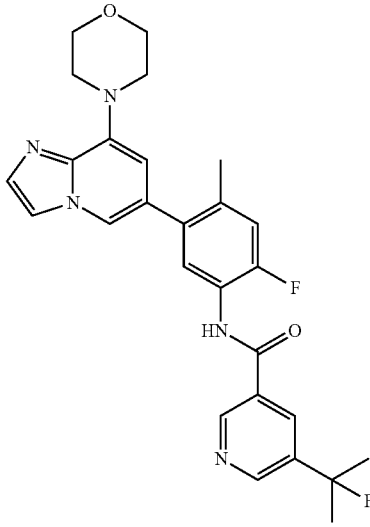 | N-(2-Fluoro-4-methyl-5-(8-morpholinoimidazo[1,2-a]pyridin-6-yl)phenyl)-5-(2-fluoropropan-2-yl)nicotinamide |
| 86 | 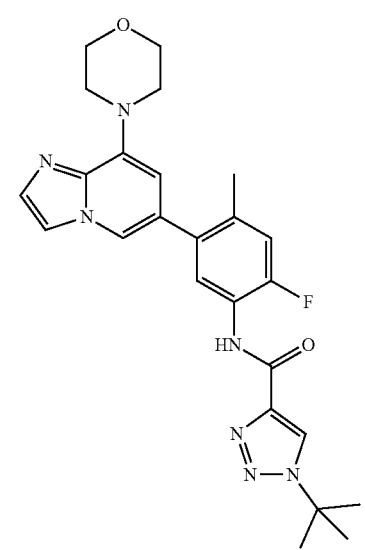 [SMILES: Cc1cc(F)c(NC(=O)c2cn(C(C)(C)C)nn2)cc1-c1cc(N2CCOCC2)c2nccn2c1] | 1-Tert-butyl-N-{2-fluoro-4-methyl-5-[8-(morpholin-4-yl)imidazo[1,2-a]pyridin-6-yl]phenyl}-1,2,3-triazole-4-carboxamide |

TABLE 1-continued
| Synthetic Chemistry Example | Compound Structure | Compound Name |
|---|---|---|
| 87 | 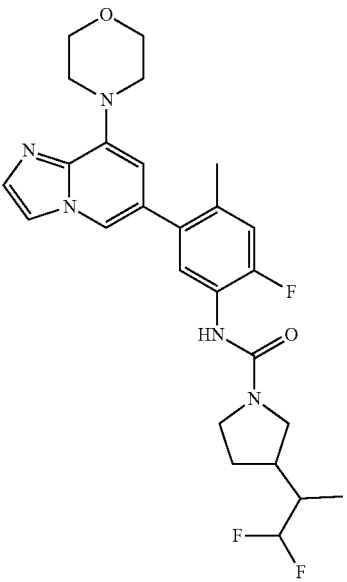 [SMILES: Cc1cc(F)c(NC(=O)N2CCC(C(C)C(F)F)C2)cc1-c1cc(N2CCOCC2)c2nccn2c1] | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |
| 88 | 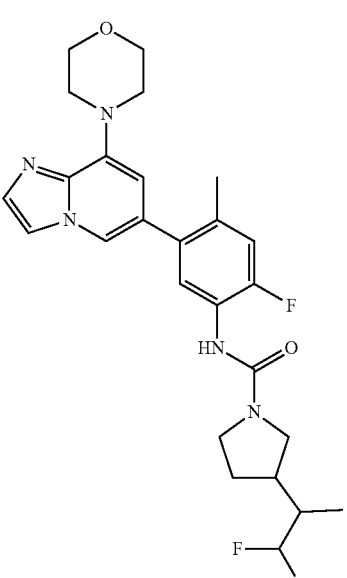 | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |

TABLE 1-continued
| Synthetic Chemistry Example | Compound Structure | Compound Name |
|---|---|---|
| 89 | 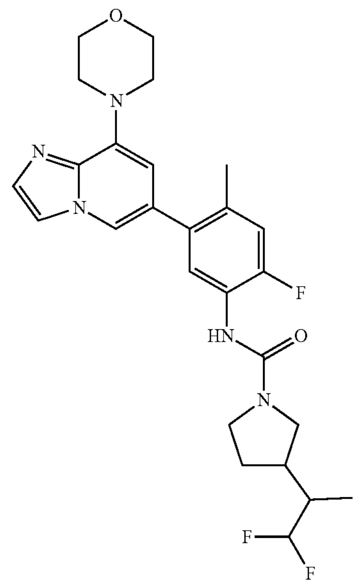 [SMILES: Cc1cc(F)c(NC(=O)N2CCC(C(C)C(F)F)C2)cc1-c1cc(N2CCOCC2)c2nccn2c1] | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |
| 90 | 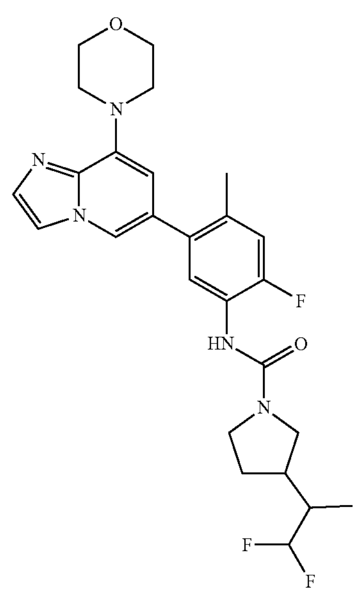 [SMILES: Cc1cc(F)c(NC(=O)N2CCC(C(C)C(F)F)C2)cc1-c1cc(N2CCOCC2)c2nccn2c1] | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |

TABLE 1-continued
| Synthetic Chemistry Example | Compound Structure | Compound Name |
|---|---|---|
| 91 | 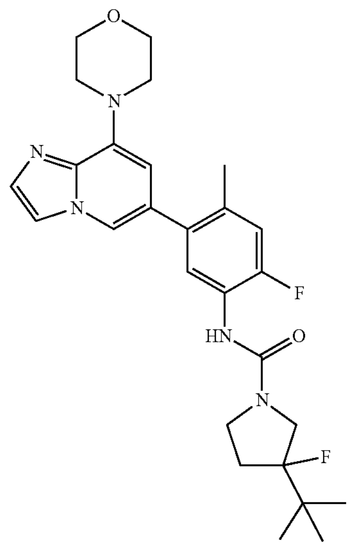 [SMILES: Cc1cc(F)c(NC(=O)N2CCC(F)(C(C)(C)C)C2)cc1-c1cc(N2CCOCC2)c2nccn2c1] | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |
| 92 | 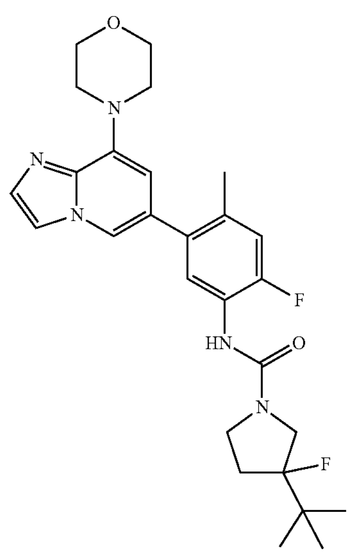 [SMILES: Cc1cc(F)c(NC(=O)N2CCC(F)(C(C)(C)C)C2)cc1-c1cc(N2CCOCC2)c2nccn2c1] | 3-(1,1-difluoropropan-2-yl)-N-(2-fluoro-4-methyl-5-(8-morpholinoimidazo[1,2-a]pyridin-6-yl)phenyl)pyrrolidine-1-carboxamide |

TABLE 1-continued
| Synthetic Chemistry Example | Compound Structure | Compound Name |
|---|---|---|
| 93 | 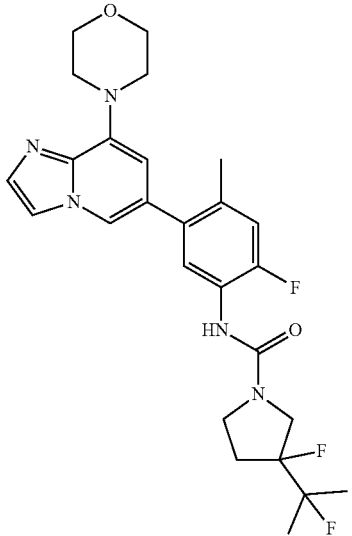 [SMILES: Cc1cc(F)c(NC(=O)N2CCC(F)(C(C)(C)F)C2)cc1-c1cc(N2CCOCC2)c2nccn2c1] | 3-fluoro-N-(2-fluoro-4-methyl-5-(8-morpholinoimidazo[1,2-a]pyridin-6-yl)phenyl)-3-(2-fluoropropan-2-yl)pyrrolidine-1-carboxamide |
| 94 | 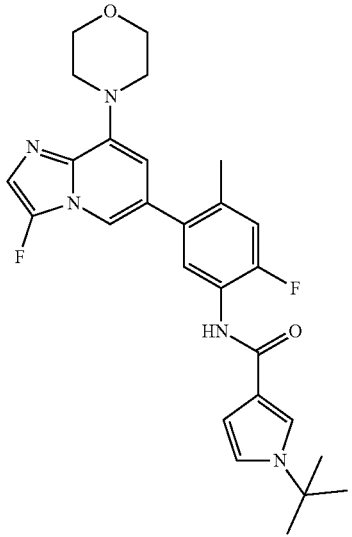 [SMILES: Cc1cc(F)c(NC(=O)c2ccn(C(C)(C)C)c2)cc1-c1cc(N2CCOCC2)c2ncc(F)n2c1] | 1-(Tert-butyl)-N-(2-fluoro-5-(3-fluoro-8-morpholinoimidazo[1,2-a]pyridin-6-yl)-4-methylphenyl)-1H-pyrrole-3-carboxamide |

TABLE 1-continued
| Synthetic Chemistry Example | Compound Structure | Compound Name |
|---|---|---|
| 95 | 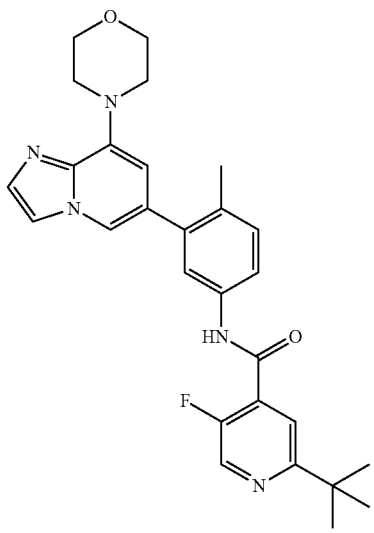 [SMILES: Cc1ccc(NC(=O)c2cc(C(C)(C)C)ncc2F)cc1-c1cc(N2CCOCC2)c2nccn2c1] | 2-Tert-butyl-5-fluoro-N-{4-methyl-3-[8-(morpholin-4-yl)imidazo[1,2-a]pyridin-6-yl]phenyl}pyridine-4-carboxamide |
| 96 | 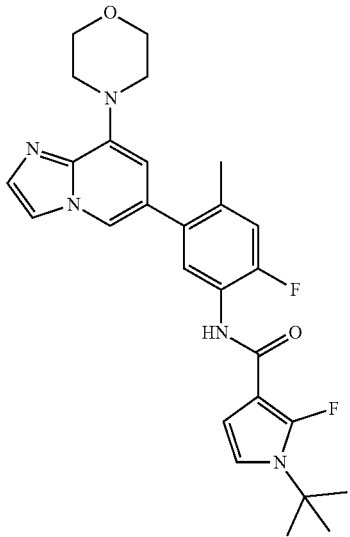 [SMILES: Cc1cc(F)c(NC(=O)c2ccn(C(C)(C)C)c2F)cc1-c1cc(N2CCOCC2)c2nccn2c1] | 1-(Tert-butyl)-2-fluoro-N-(2-fluoro-4-methyl-5-(8-morpholinoimidazo[1,2-a]pyridin-6-yl)phenyl)-1H-pyrrole-3-carboxamide |

TABLE 1-continued
| Synthetic Chemistry Example | Compound Structure | Compound Name |
|---|---|---|
| 97 | 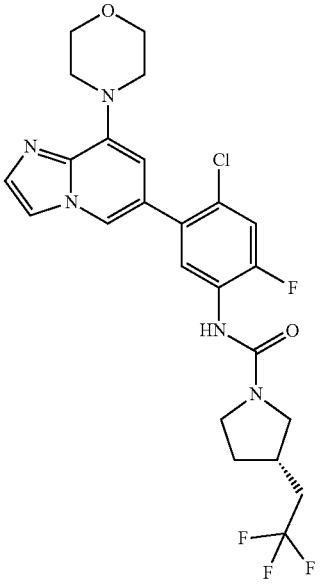 [SMILES: O=C(Nc1cc(-c2cc(N3CCOCC3)c3nccn3c2)c(Cl)cc1F)N1CC[C@@H](CC(F)(F)F)C1] | 1-(Tert-butyl)-2-fluoro-N-(2-fluoro-4-methyl-5-(8-morpholinoimidazo[1,2-a]pyridin-6-yl)phenyl)-1H-pyrrole-3-carboxamide |
| 98 | 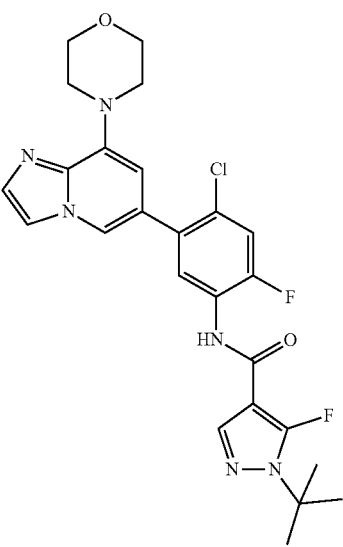 [SMILES: CC(C)(C)n1ncc(C(=O)Nc2cc(-c3cc(N4CCOCC4)c4nccn4c3)c(Cl)cc2F)c1F] | 1-(tert-butyl)-N-(4-chloro-2-fluoro-5-(8-morpholinoimidazo[1,2-a]pyridin-6-yl)phenyl)-5-fluoro-1H-pyrazole-4-carboxamide |

TABLE 1-continued
| Synthetic Chemistry Example | Compound Structure | Compound Name |
|---|---|---|
| 99 | 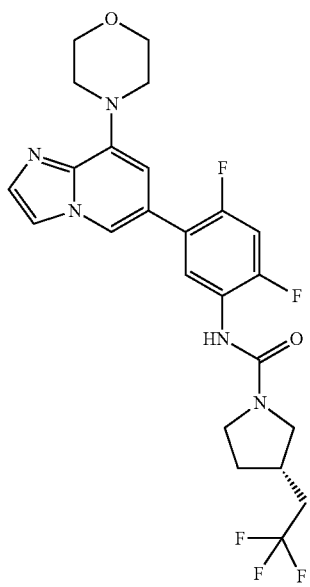 [SMILES: O=C(Nc1cc(-c2cc(N3CCOCC3)c3nccn3c2)c(F)cc1F)N1CC[C@@H](CC(F)(F)F)C1] | (3S)-N-{2,4-Difluoro-5-[8-(morpholin-4-yl)imidazo[1,2-a]pyridin-6-yl]phenyl}-3-(2,2,2-trifluoroethyl)pyrrolidine-1-carboxamide |
| 100 | 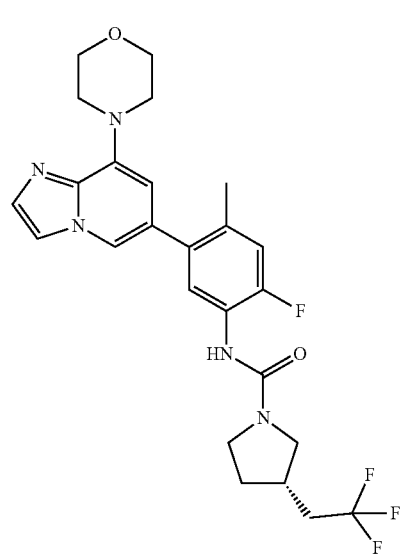 [SMILES: Cc1cc(F)c(NC(=O)N2CC[C@@H](CC(F)(F)F)C2)cc1-c1cc(N2CCOCC2)c2nccn2c1] | (S)-N-(2-fluoro-4-methyl-5-(8-morpholinoimidazo[1,2-a]pyridin-6-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 101 | 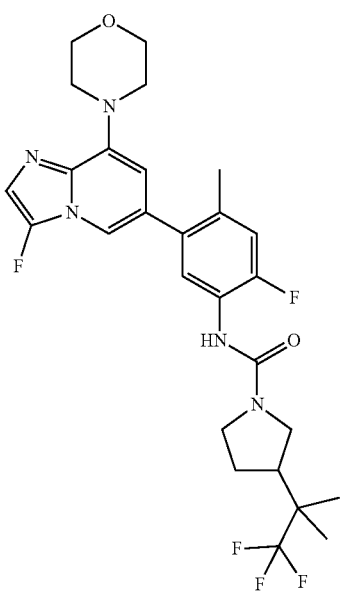 [SMILES: Cc1cc(F)c(NC(=O)N2CCC(C(C)(C)C(F)(F)F)C2)cc1-c1cc(N2CCOCC2)c2ncc(F)n2c1] | N-(2-fluoro-5-(3-fluoro-8-morpholinoimidazo[1,2-a]pyridin-6-yl)-4-methylphenyl)-3-(1,1,1-trifluoro-2-methylpropan-2-yl)pyrrolidine-1-carboxamide |
| 102 | 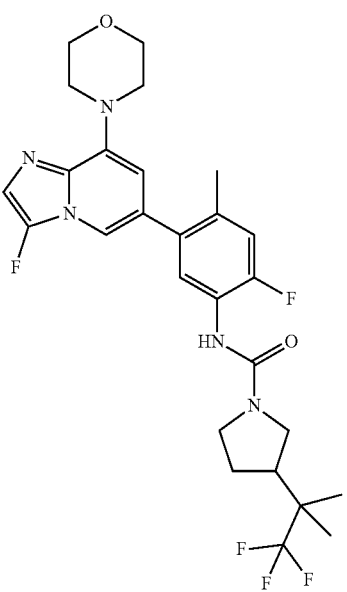 [SMILES: Cc1cc(F)c(NC(=O)N2CCC(C(C)(C)C(F)(F)F)C2)cc1-c1cc(N2CCOCC2)c2ncc(F)n2c1] | N-(2-fluoro-5-(3-fluoro-8-morpholinoimidazo[1,2-a]pyridin-6-yl)-4-methylphenyl)-3-(1,1,1-trifluoro-2-methylpropan-2-yl)pyrrolidine-1-carboxamide |

TABLE 1-continued
| Synthetic Chemistry Example | Compound Structure | Compound Name |
|---|---|---|
| 103 | 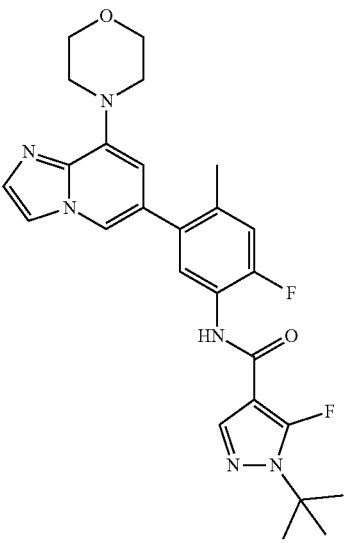 [SMILES: Cc1cc(F)c(NC(=O)c2cnn(C(C)(C)C)c2F)cc1-c1cc(N2CCOCC2)c2nccn2c1] | 1-Tert-butyl-5-fluoro-N-{2-fluoro-4-methyl-5-[8-(morpholin-4-yl)imidazo[1,2-a]pyridin-6-yl]phenyl}pyrazole-4-carboxamide |
| 104 | 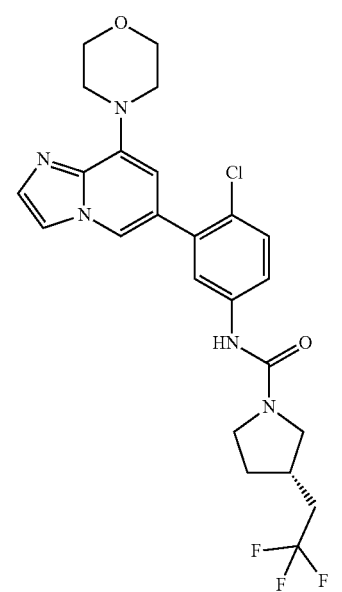 [SMILES: O=C(Nc1ccc(Cl)c(-c2cc(N3CCOCC3)c3nccn3c2)c1)N1CC[C@@H](CC(F)(F)F)C1] | (S)-N-(4-Chloro-3-(8-morpholinoimidazo[1,2-a]pyridin-6-yl)phenyl)-3-(2,2,2-trifluoroethyl)pyrrolidine-1-carboxamide |

TABLE 1-continued
| Synthetic Chemistry Example | Compound Structure | Compound Name |
|---|---|---|
| 105 | 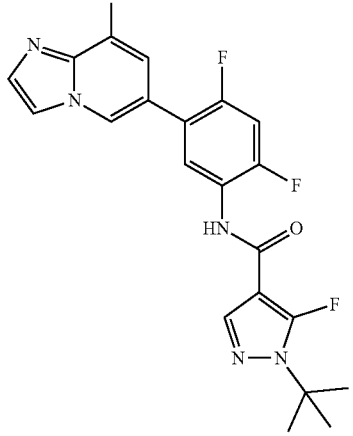 | 1-(Tert-butyl)-N-(2,4-difluoro-5-(8-morpholinoimidazo[1,2-a]pyridin-6-yl)phenyl)-5-fluoro-1H-pyrazole-4-carboxamide |
| 106 | 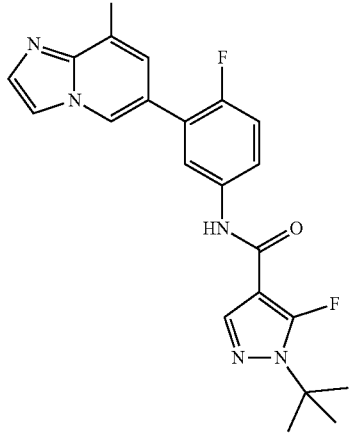 | 1-(Tert-butyl)-5-fluoro-N-(4-fluoro-3-(8-morpholinoimidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 107 | 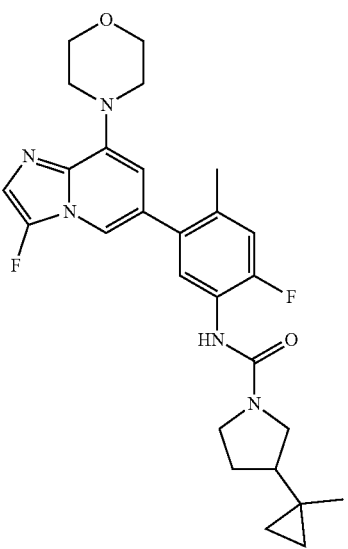 [SMILES: Cc1cc(F)c(NC(=O)N2CCC(C3(C)CC3)C2)cc1-c1cc(N2CCOCC2)c2ncc(F)n2c1] | N-(2-fluoro-5-(3-fluoro-8-morpholinoimidazo[1,2-a]pyridin-6-yl)-4-methylphenyl)-3-(1-methylcyclopropyl)pyrrolidine-1-carboxamide |
| 108 | 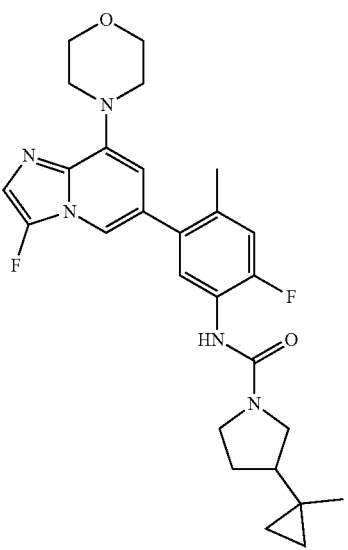 [SMILES: Cc1cc(F)c(NC(=O)N2CCC(C3(C)CC3)C2)cc1-c1cc(N2CCOCC2)c2ncc(F)n2c1] | N-(2-fluoro-5-(3-fluoro-8-morpholinoimidazo[1,2-a]pyridin-6-yl)-4-methylphenyl)-3-(1-methylcyclopropyl)pyrrolidine-1-carboxamide |

TABLE 1-continued
| Synthetic Chemistry Example | Compound Structure | Compound Name |
|---|---|---|
| 109 | 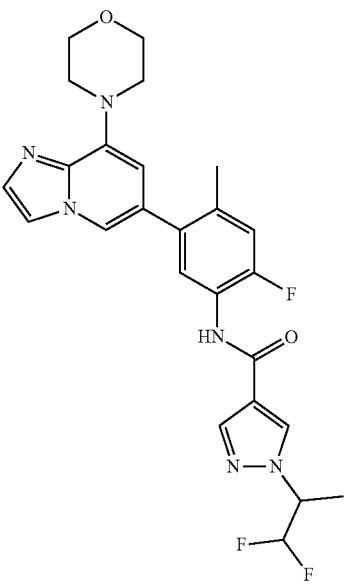 [SMILES: Cc1cc(F)c(NC(=O)c2cnn(C(C)C(F)F)c2)cc1-c1cc(N2CCOCC2)c2nccn2c1] | 1-(1,1-Difluoropropan-2-yl)-N-(2-fluoro-4-methyl-5-(8-morpholinoimidazo[1,2-a]pyridin-6-yl)phenyl)-1H-pyrazole-4-carboxamide |
| 110 | 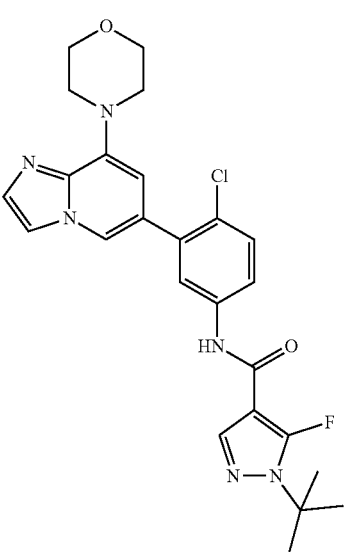 [SMILES: CC(C)(C)n1ncc(C(=O)Nc2ccc(Cl)c(-c3cc(N4CCOCC4)c4nccn4c3)c2)c1F] | 1-(tert-butyl)-N-(4-chloro-3-(8-morpholinoimidazo[1,2-a]pyridin-6-yl)phenyl)-5-fluoro-1H-pyrazole-4-carboxamide |

TABLE 1-continued

| Synthetic Chemistry Example | Compound Structure | Compound Name |
|---|---|---|
| 111 | 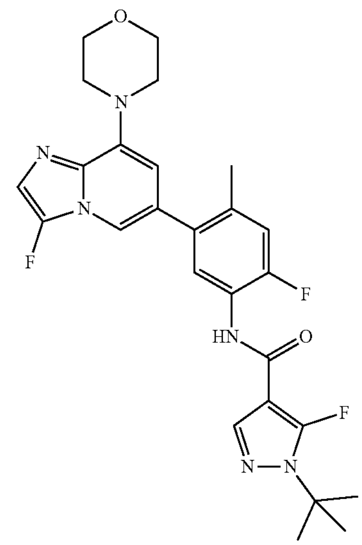 [SMILES: Cc1cc(F)c(NC(=O)c2cnn(C(C)(C)C)c2F)cc1-c1cc(N2CCOCC2)c2ncc(F)n2c1] | 1-Tert-butyl-5-fluoro-N-{2-fluoro-5-[3-fluoro-8-(morpholin-4-yl)imidazo[1,2-a]pyridin-6-yl]-4-methylphenyl}pyrazole-4-carboxamide |
| 112 | 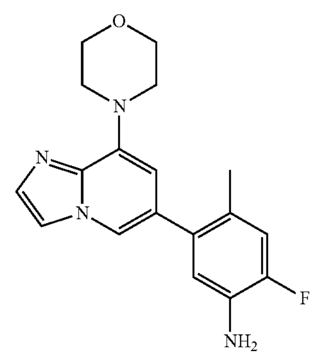 [SMILES: Cc1cc(F)c(N)cc1-c1cc(N2CCOCC2)c2nccn2c1] | 2-Fluoro-4-methyl-5-[8-(morpholin-4-yl)imidazo[1,2-a]pyridin-6-yl]aniline |
| 113 | 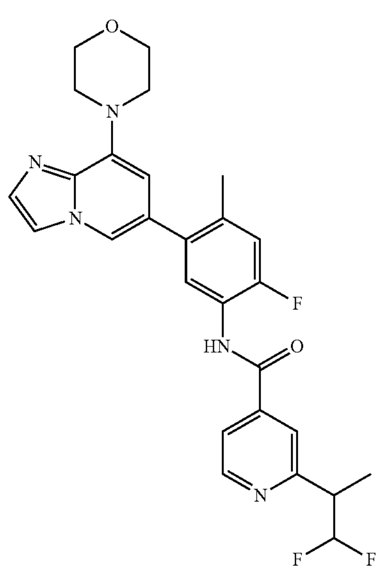 [SMILES: Cc1cc(F)c(NC(=O)c2ccnc(C(C)C(F)F)c2)cc1-c1cc(N2CCOCC2)c2nccn2c1] | 2-(1,1-difluoropropan-2-yl)-N-(2-fluoro-4-methyl-5-(8-morpholinoimidazo[1,2-a]pyridin-6-yl)phenyl)isonicotinamide |

TABLE 1-continued

| Synthetic Chemistry Example | Compound Structure | Compound Name |
|---|---|---|
| 114 | 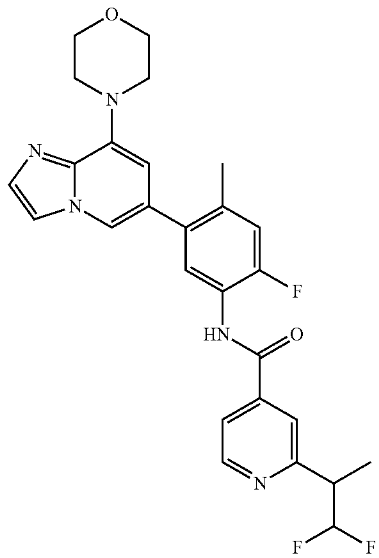 [SMILES: Cc1cc(F)c(NC(=O)c2ccnc(C(C)C(F)F)c2)cc1-c1cc(N2CCOCC2)c2nccn2c1] | 2-(1,1-difluoropropan-2-yl)-N-(2-fluoro-4-methyl-5-(8-morpholinoimidazo[1,2-a]pyridin-6-yl)phenyl)isonicotinamide |
| 115 | 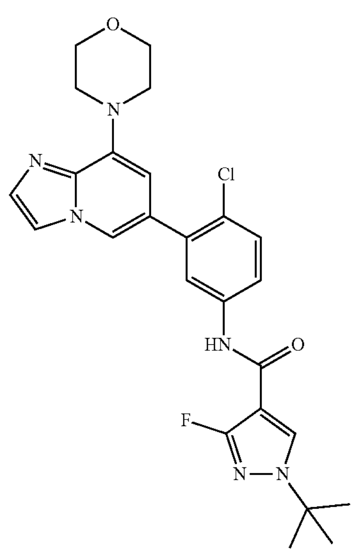 [SMILES: CC(C)(C)n1cc(C(=O)Nc2ccc(Cl)c(-c3cc(N4CCOCC4)c4nccn4c3)c2)c(F)n1] | 1-(Tert-butyl)-N-(4-chloro-3-(8-morpholinoimidazo[1,2-a]pyridin-6-yl)phenyl)-3-fluoro-1H-pyrazole-4-carboxamide |

TABLE 1-continued
| Synthetic Chemistry Example | Compound Structure | Compound Name |
|---|---|---|
| 116 | 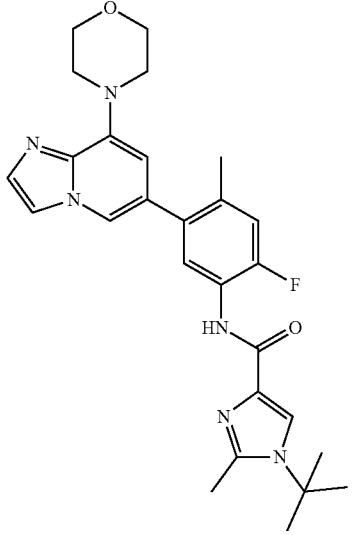 [SMILES: Cc1cc(F)c(NC(=O)c2cn(C(C)(C)C)c(C)n2)cc1-c1cc(N2CCOCC2)c2nccn2c1] | 1-(Tert-butyl)-N-(2-fluoro-4-methyl-5-(8-morpholinoimidazo[1,2-a]pyridin-6-yl)phenyl)-2-methyl-1H-imidazole-4-carboxamide |
| 117 | 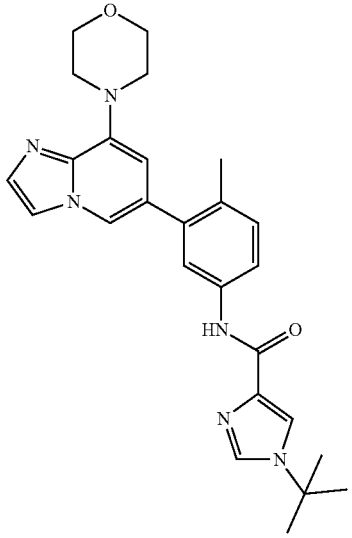 [SMILES: Cc1ccc(NC(=O)c2cn(C(C)(C)C)cn2)cc1-c1cc(N2CCOCC2)c2nccn2c1] | 1-(Tert-butyl)-N-(4-methyl-3-(8-morpholinoimidazo[1,2-a]pyridin-6-yl)phenyl)-1H-imidazole-4-carboxamide |

TABLE 1-continued
| Synthetic Chemistry Example | Compound Structure | Compound Name |
|---|---|---|
| 118 | 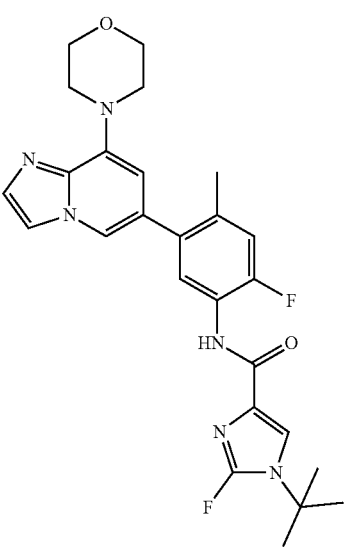 [SMILES: Cc1cc(F)c(NC(=O)c2cn(C(C)(C)C)c(F)n2)cc1-c1cc(N2CCOCC2)c2nccn2c1] | 1-Tert-butyl-2-fluoro-N-{2-fluoro-4-methyl-5-[8-(morpholin-4-yl)imidazo[1,2-a]pyridin-6-yl]phenyl}imidazole-4-carboxamide |
| 119 | 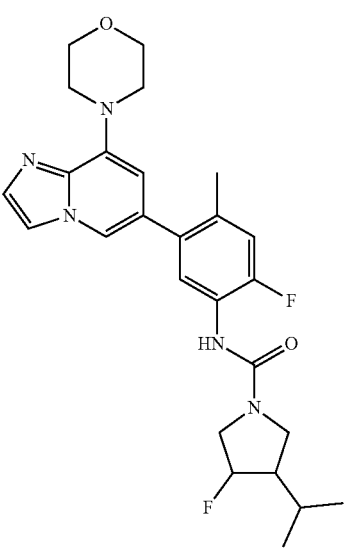 [SMILES: Cc1cc(F)c(NC(=O)N2CC(F)C(C(C)C)C2)cc1-c1cc(N2CCOCC2)c2nccn2c1] | 3-fluoro-N-(2-fluoro-4-methyl-5-(8-morpholinoimidazo[1,2-a]pyridin-6-yl)phenyl)-4-isopropylpyrrolidine-1-carboxamide |

TABLE 1-continued
| Synthetic Chemistry Example | Compound Structure | Compound Name |
|---|---|---|
| 120 | 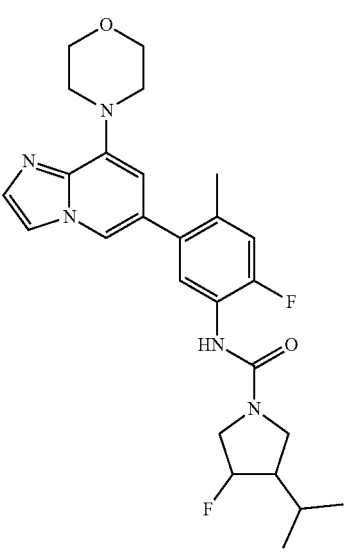 [SMILES: Cc1cc(F)c(NC(=O)N2CC(F)C(C(C)C)C2)cc1-c1cc(N2CCOCC2)c2nccn2c1] | 3-fluoro-N-(2-fluoro-4-methyl-5-(8-morpholinoimidazo[1,2-a]pyridin-6-yl)phenyl)-4-isopropylpyrrolidine-1-carboxamide |
| 121 | 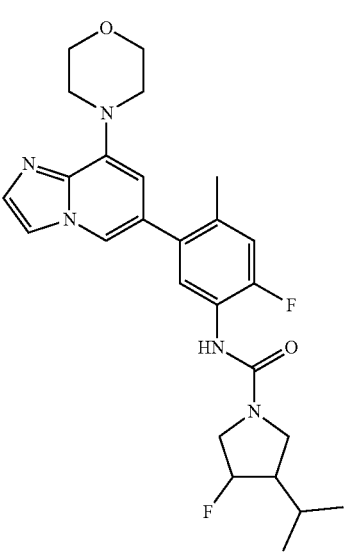 [SMILES: Cc1cc(F)c(NC(=O)N2CC(F)C(C(C)C)C2)cc1-c1cc(N2CCOCC2)c2nccn2c1] | 3-fluoro-N-(2-fluoro-4-methyl-5-(8-morpholinoimidazo[1,2-a]pyridin-6-yl)phenyl)-4-isopropylpyrrolidine-1-carboxamide |

TABLE 1-continued
| Synthetic Chemistry Example | Compound Structure | Compound Name |
|---|---|---|
| 122 | 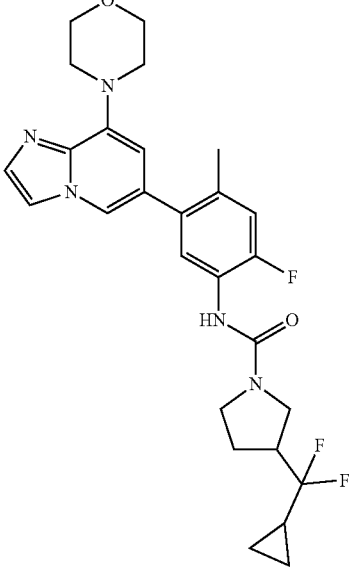 | N-(2-fluoro-4-methyl-5-(8-morpholinoimidazo[1,2-a]pyridin-6-yl)phenyl)-3-(1-(trifluoromethyl)cyclopropyl)pyrrolidine-1-carboxamide |
| 123 | 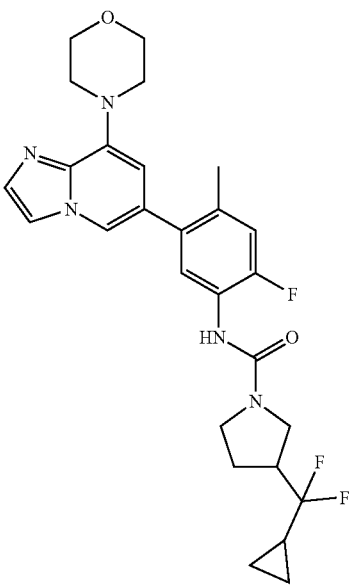 [SMILES: Cc1cc(F)c(NC(=O)N2CCC(C(F)(F)C3CC3)C2)cc1-c1cc(N2CCOCC2)c2nccn2c1] | N-(2-fluoro-4-methyl-5-(8-morpholinoimidazo[1,2-a]pyridin-6-yl)phenyl)-3-(1-(trifluoromethyl)cyclopropyl)pyrrolidine-1-carboxamide |

TABLE 1-continued
| Synthetic Chemistry Example | Compound Structure | Compound Name |
|---|---|---|
| 124 | 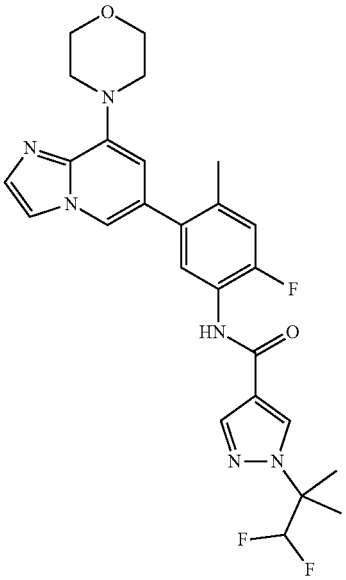 [SMILES: Cc1cc(F)c(NC(=O)c2cnn(C(C)(C)C(F)F)c2)cc1-c1cc(N2CCOCC2)c2nccn2c1] | 1-(1,1-Difluoro-2-methylpropan-2-yl)-N-{2-fluoro-4-methyl-5-[8-(morpholin-4-yl)imidazo[1,2-a]pyridin-6-yl]phenyl}pyrazole-4-carboxamide |
| 125 | 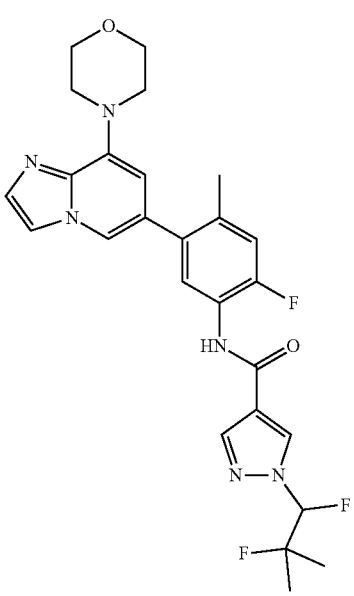 [SMILES: Cc1cc(F)c(NC(=O)c2cnn(C(F)C(C)(C)F)c2)cc1-c1cc(N2CCOCC2)c2nccn2c1] | 1-(1,2-Difluoro-2-methylpropyl)-N-(2-fluoro-4-methyl-5-(8-morpholinoimidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 126 | 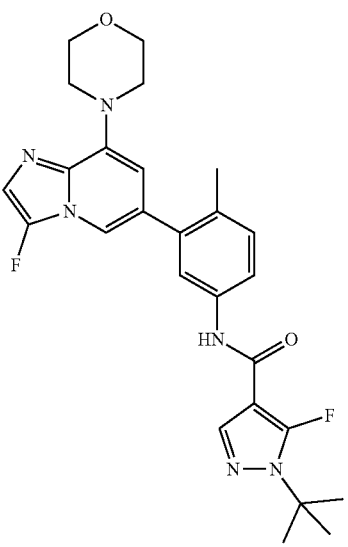 [SMILES: Cc1ccc(NC(=O)c2cnn(C(C)(C)C)c2F)cc1-c1cc(N2CCOCC2)c2ncc(F)n2c1] | 1-(Tert-butyl)-5-fluoro-N-(3-(3-fluoro-8-morpholinoimidazo[1,2-a]pyridin-6-yl)-4-methylphenyl)-1H-pyrazole-4-carboxamide |
| 127 | 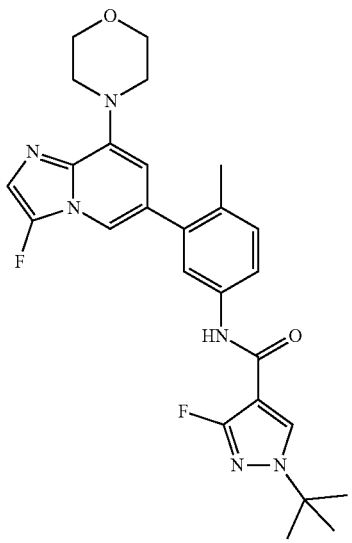 [SMILES: Cc1ccc(NC(=O)c2cn(C(C)(C)C)nc2F)cc1-c1cc(N2CCOCC2)c2ncc(F)n2c1] | 1-(Tert-butyl)-3-fluoro-N-(3-(3-fluoro-8-morpholinoimidazo[1,2-a]pyridin-6-yl)-4-methylphenyl)-1H-pyrazole-4-carboxamide |

TABLE 1-continued
| Synthetic Chemistry Example | Compound Structure | Compound Name |
|---|---|---|
| 128 | 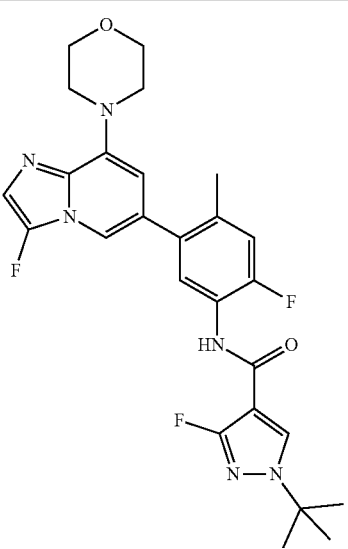 [SMILES: Cc1cc(F)c(NC(=O)c2cn(C(C)(C)C)nc2F)cc1-c1cc(N2CCOCC2)c2ncc(F)n2c1] | 1-(Tert-butyl)-3-fluoro-N-(2-fluoro-5-(3-fluoro-8-morpholinoimidazo[1,2-a]pyridin-6-yl)-4-methylphenyl)-1H-pyrazole-4-carboxamide |
| 129 | 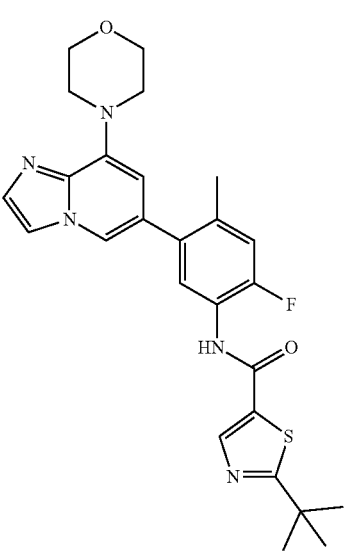 [SMILES: Cc1cc(F)c(NC(=O)c2cnc(C(C)(C)C)s2)cc1-c1cc(N2CCOCC2)c2nccn2c1] | 2-(Tert-butyl)-N-(2-fluoro-4-methyl-5-(8-morpholinoimidazo[1,2-a]pyridin-6-yl)phenyl)thiazole-5-carboxamide |

TABLE 1-continued
| Synthetic Chemistry Example | Compound Structure | Compound Name |
|---|---|---|
| 130 | 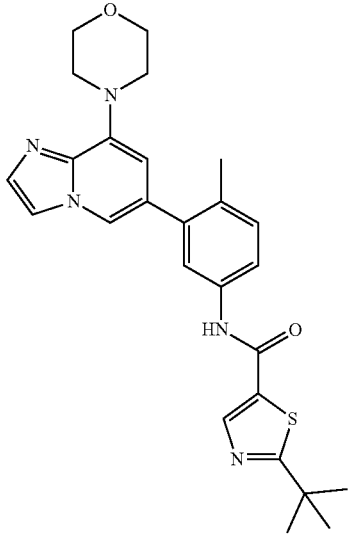 [SMILES: Cc1ccc(NC(=O)c2cnc(C(C)(C)C)s2)cc1-c1cc(N2CCOCC2)c2nccn2c1] | 2-(Tert-butyl)-N-(4-methyl-3-(8-morpholinoimidazo[1,2-a]pyridin-6-yl)phenyl)thiazole-5-carboxamide |
| 131 | 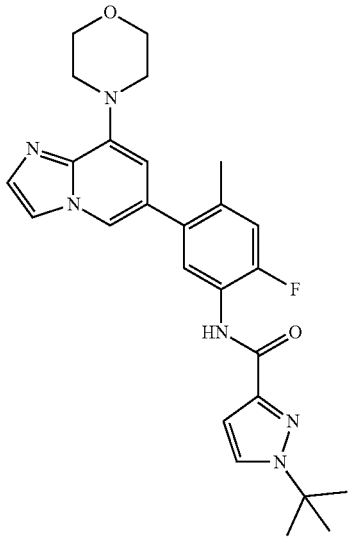 [SMILES: Cc1cc(F)c(NC(=O)c2ccn(C(C)(C)C)n2)cc1-c1cc(N2CCOCC2)c2nccn2c1] | 1-(Tert-butyl)-N-(2-fluoro-4-methyl-5-(8-morpholinoimidazo[1,2-a]pyridin-6-yl)phenyl)-1H-pyrazole-3-carboxamide |

TABLE 1-continued
| Synthetic Chemistry Example | Compound Structure | Compound Name |
|---|---|---|
| 132 | 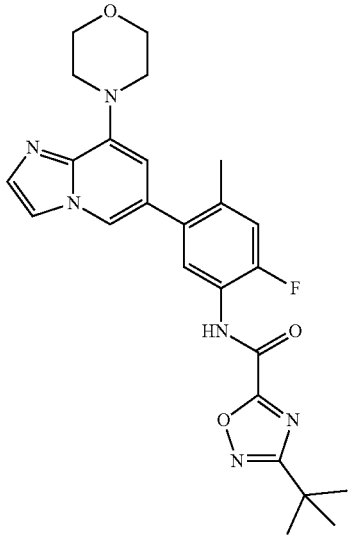 [SMILES: Cc1cc(F)c(NC(=O)c2nc(C(C)(C)C)no2)cc1-c1cc(N2CCOCC2)c2nccn2c1] | 3-(Tert-butyl)-N-(2-fluoro-4-methyl-5-(8-morpholinoimidazo[1,2-a]pyridin-6-yl)phenyl)-1,2,4-oxadiazole-5-carboxamide |
| 133 | 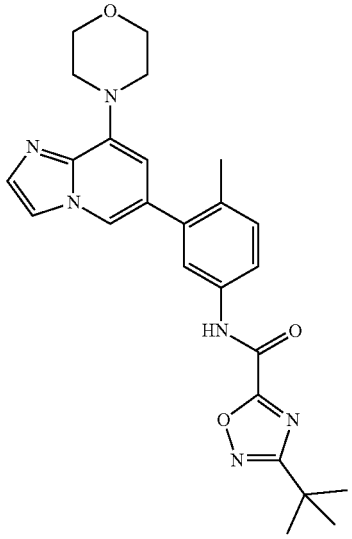 [SMILES: Cc1ccc(NC(=O)c2nc(C(C)(C)C)no2)cc1-c1cc(N2CCOCC2)c2nccn2c1] | 3-(Tert-butyl)-N-(4-methyl-3-(8-morpholinoimidazo[1,2-a]pyridin-6-yl)phenyl)-1,2,4-oxadiazole-5-carboxamide |

TABLE 1-continued
| Synthetic Chemistry Example | Compound Structure | Compound Name |
|---|---|---|
| 134 | 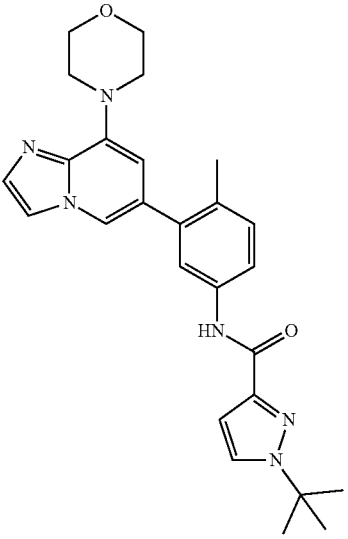 [SMILES: Cc1ccc(NC(=O)c2ccn(C(C)(C)C)n2)cc1-c1cc(N2CCOCC2)c2nccn2c1] | 1-(Tert-butyl)-N-(4-methyl-3-(8-morpholinoimidazo[1,2-a]pyridin-6-yl)phenyl)-1H-pyrazole-3-carboxamide |
| 135 | 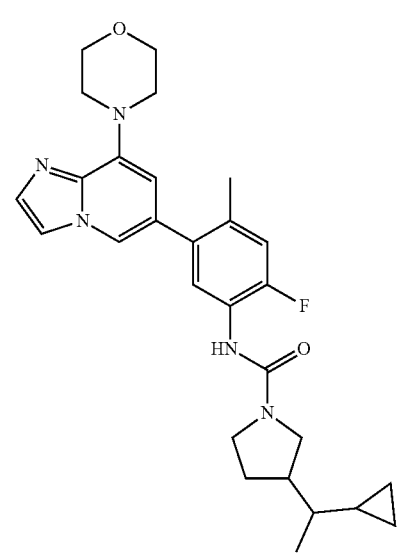 [SMILES: Cc1cc(F)c(NC(=O)N2CCC(C(C)C3CC3)C2)cc1-c1cc(N2CCOCC2)c2nccn2c1] | 3-(1-Cyclopropylethyl)-N-(2-fluoro-4-methyl-5-(8-morpholinoimidazo[1,2-a]pyridin-6-yl)phenyl)pyrrolidine-1-carboxamide |

TABLE 1-continued
| Synthetic Chemistry Example | Compound Structure | Compound Name |
|---|---|---|
| 136 | 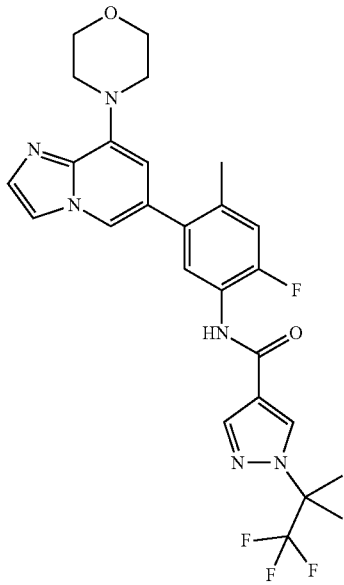 [SMILES: Cc1cc(F)c(NC(=O)c2cnn(C(C)(C)C(F)(F)F)c2)cc1-c1cc(N2CCOCC2)c2nccn2c1] | N-{2-fluoro-4-methyl-5-[8-(morpholin-4-yl)imidazo[1,2-a]pyridin-6-yl]phenyl}-1-(1,1,1-trifluoro-2-methylpropan-2-yl)pyrazole-4-carboxamide |
| 137 | 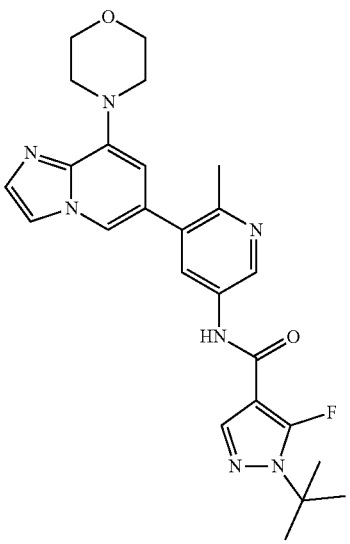 [SMILES: Cc1ncc(NC(=O)c2cnn(C(C)(C)C)c2F)cc1-c1cc(N2CCOCC2)c2nccn2c1] | 1-(tert-Butyl)-5-fluoro-N-(6-methyl-5-(8-morpholinoimidazo[1,2-a]pyridin-6-yl)pyridin-3-yl)-1H-pyrazole-4-carboxamide |

TABLE 1-continued

| Synthetic Chemistry Example | Compound Structure | Compound Name |
|---|---|---|
| 138 | | 1-(tert-Butyl)-5-fluoro-N-(5-methyl-4-(8-morpholinoimidazo[1,2-a]pyridin-6-yl)pyridin-2-yl)-1H-pyrazole-4-carboxamide |
| 138 | | 1-Tert-butyl-5-fluoro-N-{6-methyl-5-[8-(morpholin-4-yl)imidazo[1,2-a]pyridin-6-yl]pyridin-3-yl}pyrazole-4-carboxamide |

TABLE 1-continued
| Synthetic Chemistry Example | Compound Structure | Compound Name |
|---|---|---|
| 140 | 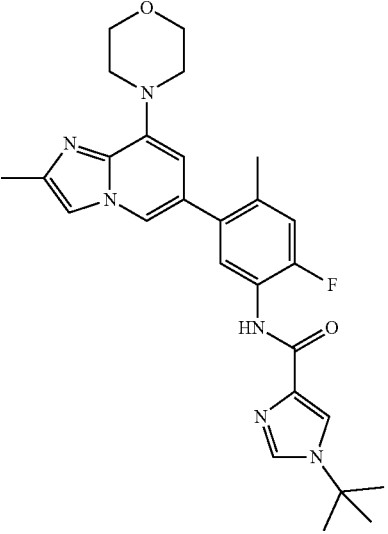 [SMILES: Cc1cn2cc(-c3cc(NC(=O)c4cn(C(C)(C)C)cn4)c(F)cc3C)cc(N3CCOCC3)c2n1] | 1-(Tert-butyl)-N-(2-fluoro-4-methyl-5-(2-methyl-8-morpholinoimidazo[1,2-a]pyridin-6-yl)phenyl)-1H-imidazole-4-carboxamide |
| 141 | 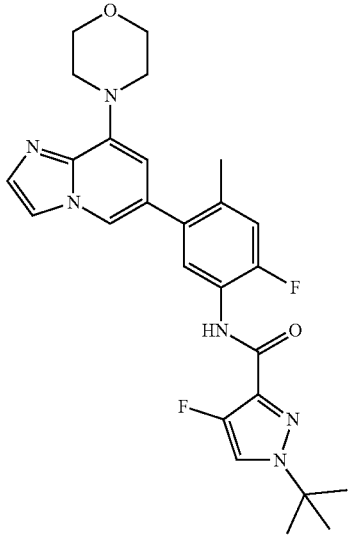 [SMILES: Cc1cc(F)c(NC(=O)c2nn(C(C)(C)C)cc2F)cc1-c1cc(N2CCOCC2)c2nccn2c1] | 1-Tert-butyl-4-fluoro-N-{2-fluoro-4-methyl-5-[8-(morpholin-4-yl)imidazo[1,2-a]pyridin-6-yl]phenyl}pyrazole-3-carboxamide |

TABLE 1-continued
| Synthetic Chemistry Example | Compound Structure | Compound Name |
|---|---|---|
| 142 | 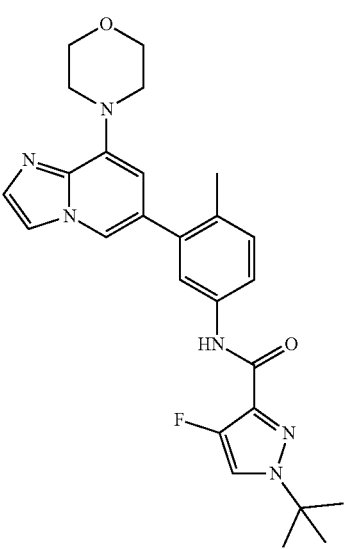 [SMILES: Cc1ccc(NC(=O)c2nn(C(C)(C)C)cc2F)cc1-c1cc(N2CCOCC2)c2nccn2c1] | 1-Tert-butyl-4-fluoro-N-{4-methyl-3-[8-(morpholin-4-yl)imidazo[1,2-a]pyridin-6-yl]phenyl}pyrazole-3-carboxamide |
| 143 | 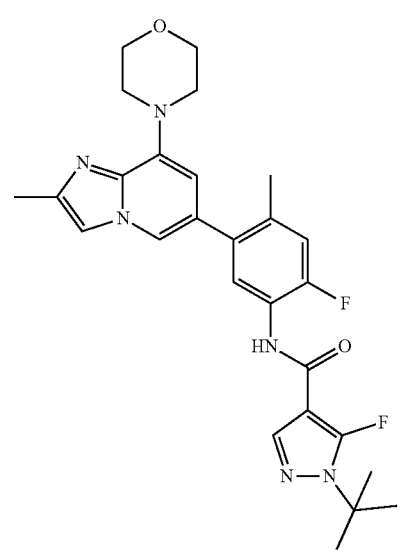 [SMILES: Cc1cn2cc(-c3cc(NC(=O)c4cnn(C(C)(C)C)c4F)c(F)cc3C)cc(N3CCOCC3)c2n1] | 1-(tert-Butyl)-5-fluoro-N-(2-fluoro-4-methyl-5-(2-methyl-8-morpholinoimidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 144 | 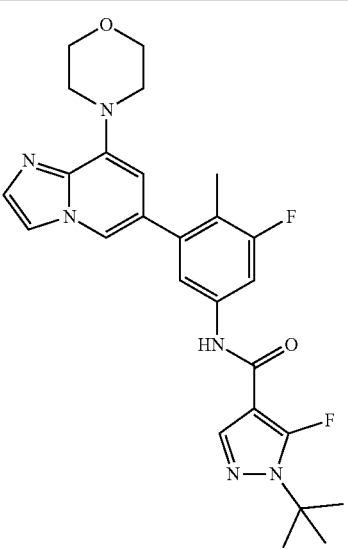 [SMILES: Cc1c(F)cc(NC(=O)c2cnn(C(C)(C)C)c2F)cc1-c1cc(N2CCOCC2)c2nccn2c1] | 1-(Tert-butyl)-5-fluoro-N-(3-fluoro-4-methyl-5-(8-morpholinoimidazo[1,2-a]pyridin-6-yl)phenyl)-1H-pyrazole-4-carboxamide |
| 145 | 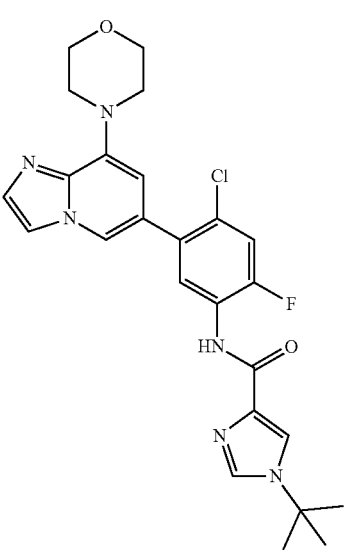 [SMILES: CC(C)(C)n1cnc(C(=O)Nc2cc(-c3cc(N4CCOCC4)c4nccn4c3)c(Cl)cc2F)c1] | 1-Tert-butyl-N-{4-chloro-2-fluoro-5-[8-(morpholin-4-yl)imidazo[1,2-a]pyridin-6-yl]phenyl}imidazole-4-carboxamide |

TABLE 1-continued
| Synthetic Chemistry Example | Compound Structure | Compound Name |
|---|---|---|
| 146 | 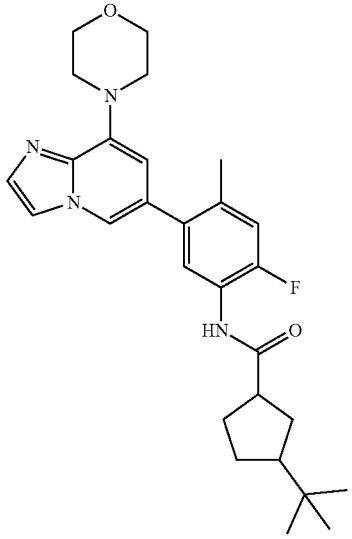 [SMILES: Cc1cc(F)c(NC(=O)C2CCC(C(C)(C)C)C2)cc1-c1cc(N2CCOCC2)c2nccn2c1] | 3-(tert-Buty))-N-(2-fluoro-4-methyl-5-(8-morpholinoimidazo[1,2-a]pyridin-6-yl)phenyl)cyclopentane-1-carboxamide |
| 147 | 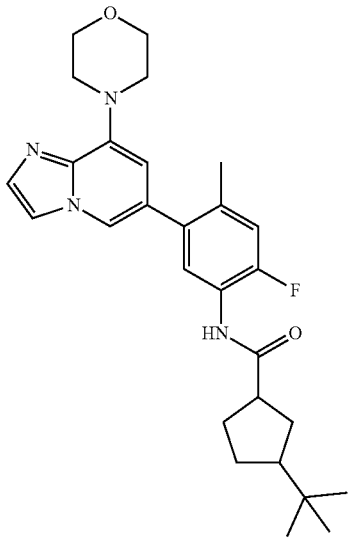 [SMILES: Cc1cc(F)c(NC(=O)C2CCC(C(C)(C)C)C2)cc1-c1cc(N2CCOCC2)c2nccn2c1] | 3-(tert-Butyl)-N-(2-fluoro-4-methyl-5-(8-morpholinoimidazo[1,2-a]pyridin-6-yl)phenyl)cyclopentane-1-carboxamide |

TABLE 1-continued
| Synthetic Chemistry Example | Compound Structure | Compound Name |
|---|---|---|
| 148 | 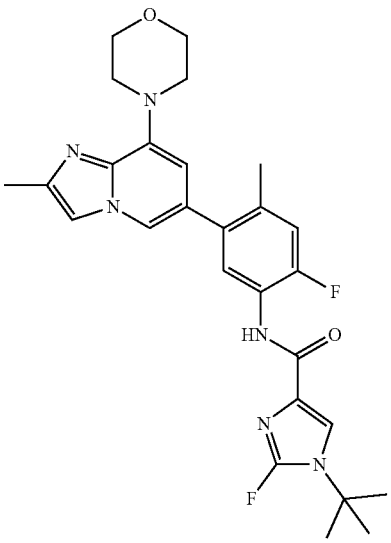 [SMILES: Cc1cn2cc(-c3cc(NC(=O)c4cn(C(C)(C)C)c(F)n4)c(F)cc3C)cc(N3CCOCC3)c2n1] | 1-Tert-butyl-2-fluoro-N-{2-fluoro-4-methyl-5-[2-methyl-8-(morpholin-4-yl)imidazo[1,2-a]pyridin-6-yl]phenyl}imidazole-4-carboxamide |
| 149 | 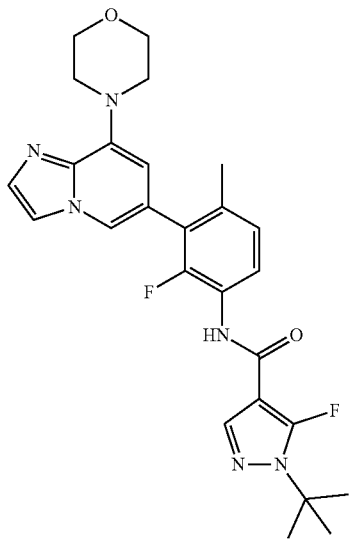 [SMILES: Cc1ccc(NC(=O)c2cnn(C(C)(C)C)c2F)c(F)c1-c1cc(N2CCOCC2)c2nccn2c1] | 1-Tert-butyl-5-fluoro-N-{2-fluoro-4-methyl-3-[8-(morpholin-4-yl)imidazo[1,2-a]pyridin-6-yl]phenyl}pyrazole-4-carboxamide |

TABLE 1-continued
| Synthetic Chemistry Example | Compound Structure | Compound Name |
|---|---|---|
| 150 | 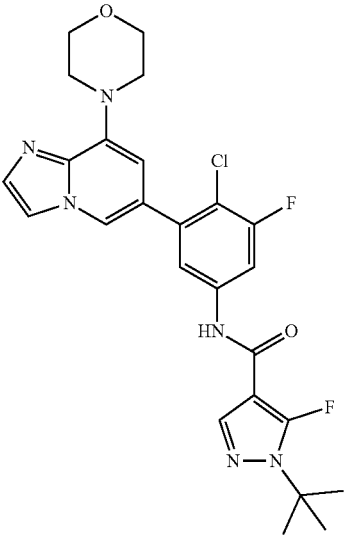 | 1-(Tert-butyl)-N-(4-chloro-3-fluoro-5-(8-morpholinoimidazo[1,2-a]pyridin-6-yl)phenyl)-5-fluoro-1H-pyrazole-4-carboxamide |
| 151 | 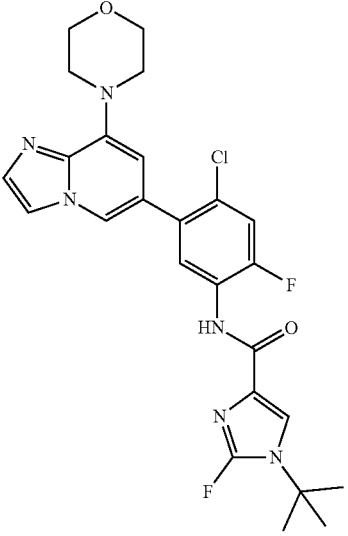 [SMILES: CC(C)(C)n1cc(C(=O)Nc2cc(-c3cc(N4CCOCC4)c4nccn4c3)c(Cl)cc2F)nc1F] | 1-Tert-butyl-N-{4-chloro-2-fluoro-5-[8-(morpholin-4-yl)imidazo[1,2-a]pyridin-6-yl]phenyl}-2-fluoroimidazole-4-carboxamide |

TABLE 1-continued
| Synthetic Chemistry Example | Compound Structure | Compound Name |
|---|---|---|
| 152 | 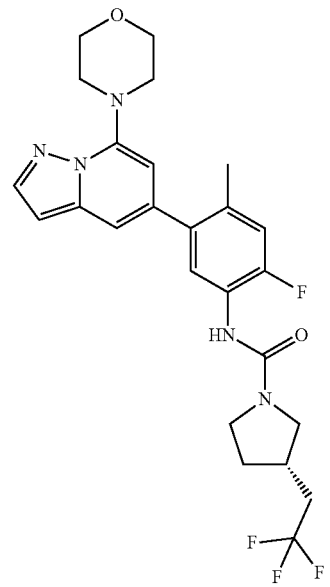 [SMILES: Cc1cc(F)c(NC(=O)N2CC[C@@H](CC(F)(F)F)C2)cc1-c1cc(N2CCOCC2)n2nccc2c1] | (3S)-N-{2-fluoro-4-methyl-5-[7-(morpholin-4-yl)pyrazolo[1,5-a]pyridin-5-yl]phenyl}-3-(2,2,2-trifluoroethyl)pyrrolidine-1-carboxamide |
| 153 | 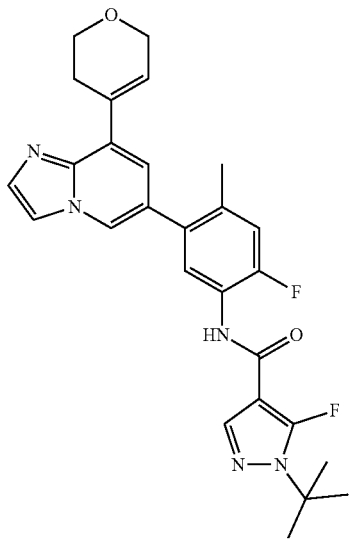 [SMILES: Cc1cc(F)c(NC(=O)c2cnn(C(C)(C)C)c2F)cc1-c1cc(C2=CCOCC2)c2nccn2c1] | 1-(tert-Butyl)-N-(5-(8-(3,6-dihydro-2H-pyran-4-yl)imidazo[1,2-a]pyridin-6-yl)-2-fluoro-4-methylphenyl)-5-fluoro-1H-pyrazole-4-carboxamide |

TABLE 1-continued

| Synthetic Chemistry Example | Compound Structure | Compound Name |
|---|---|---|
| 154 | 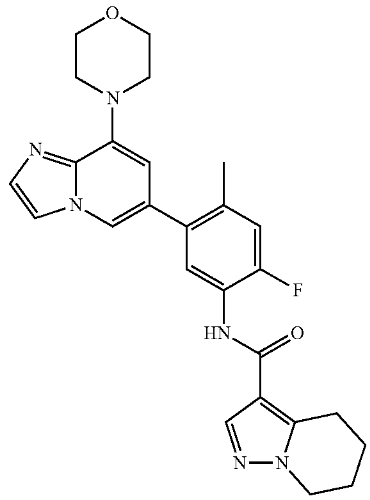 [SMILES: Cc1cc(F)c(NC(=O)c2cnn3c2CCCC3)cc1-c1cc(N2CCOCC2)c2nccn2c1] | N-(2-Fluoro-4-methyl-5-(8-morpholinoimidazo[1,2-a]pyridin-6-yl)phenyl)-4,5,6,7-tetrahydropyrazolo[1,5-a]pyridine-3-carboxamide |
| 155 | 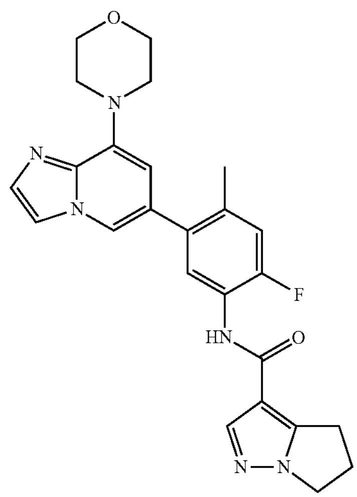 [SMILES: Cc1cc(F)c(NC(=O)c2cnn3c2CCC3)cc1-c1cc(N2CCOCC2)c2nccn2c1] | N-(2-fluoro-4-methyl-5-(8-morpholinoimidazo[1,2-a]pyridin-6-yl)phenyl)-5,6-dihydro-4H-pyrrolo[1,2-b]pyrazole-3-carboxamide |
| 156 | 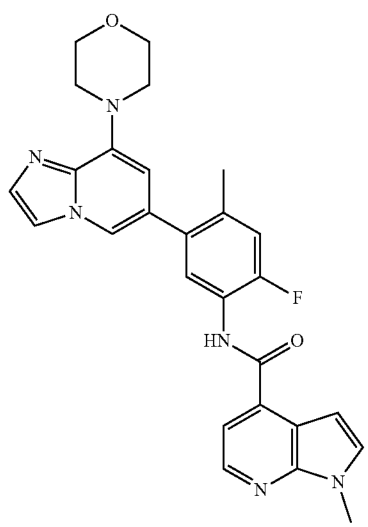 [SMILES: Cc1cc(F)c(NC(=O)c2ccnc3c2ccn3C)cc1-c1cc(N2CCOCC2)c2nccn2c1] | N-(2-fluoro-4-methyl-5-(8-morpholinoimidazo[1,2-a]pyridin-6-yl)phenyl)-1-methyl-1H-pyrrolo[2,3-b]pyridine-4-carboxamide |

TABLE 1-continued
| Synthetic Chemistry Example | Compound Structure | Compound Name |
|---|---|---|
| 157 | 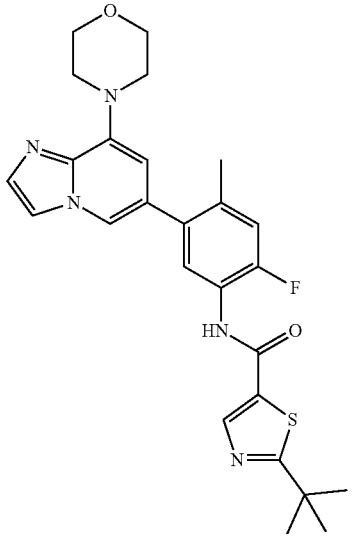 [SMILES: Cc1cc(F)c(NC(=O)c2cnc(C(C)(C)C)s2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}-1,3-thiazole-5-carboxamide |
| 158 | 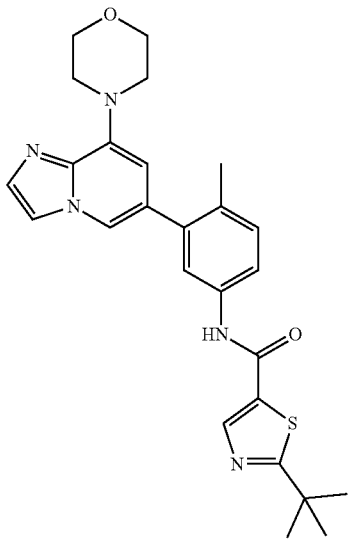 [SMILES: Cc1ccc(NC(=O)c2cnc(C(C)(C)C)s2)cc1-c1cc(N2CCOCC2)c2nccn2c1] | 2-Tert-butyl-N-{4-methyl-3-[8-(morpholin-4-yl)imidazo[1,2-a]pyridin-6-yl]phenyl}-1,3-thiazole-5-carboxamide |

TABLE 1-continued

| Synthetic Chemistry Example | Compound Structure | Compound Name |
|---|---|---|
| 159 | 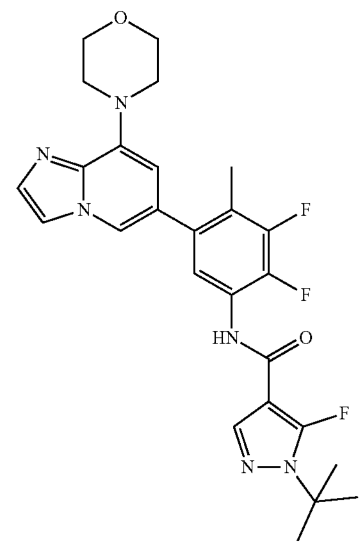 [SMILES: Cc1c(-c2cc(N3CCOCC3)c3nccn3c2)cc(NC(=O)c2cnn(C(C)(C)C)c2F)c(F)c1F] | 1-(tert-Butyl)-N-(2,3-difluoro-4-methyl-5-(8-morpholinoimidazo[1,2-a]pyridin-6-yl)phenyl)-5-fluoro-1H-pyrazole-4-carboxamide |
| 160 | 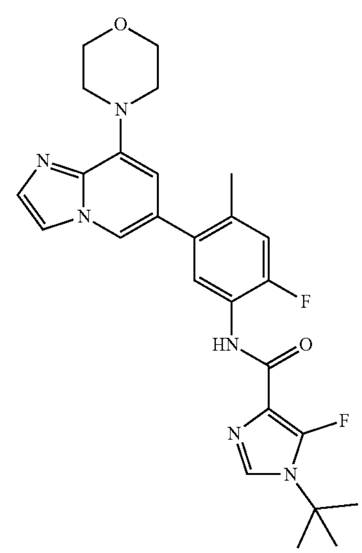 [SMILES: Cc1cc(F)c(NC(=O)c2ncn(C(C)(C)C)c2F)cc1-c1cc(N2CCOCC2)c2nccn2c1] | 1-Tert-butyl-5-fluoro-N-{2-fluoro-4-methyl-5-[8-(morpholin-4-yl)imidazo[1,2-a]pyridin-6-yl]phenyl}imidazole-4-carboxamide |

TABLE 1-continued

| Synthetic Chemistry Example | Compound Structure | Compound Name |
|---|---|---|
| 161 | 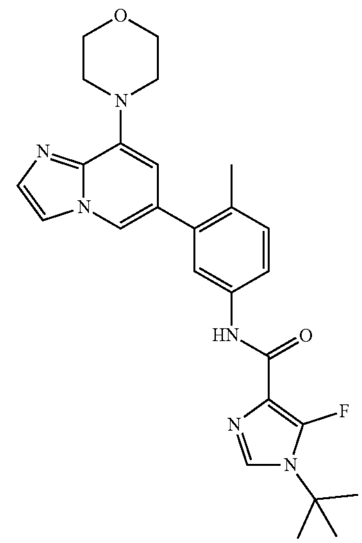 [SMILES: Cc1ccc(NC(=O)c2ncn(C(C)(C)C)c2F)cc1-c1cc(N2CCOCC2)c2nccn2c1] | 1-(Tert-butyl)-5-fluoro-N-(4-methyl-3-(8-morpholinoimidazo[1,2-a]pyridin-6-yl)phenyl)-1H-imidazole-4-carboxamide |
| 162 | 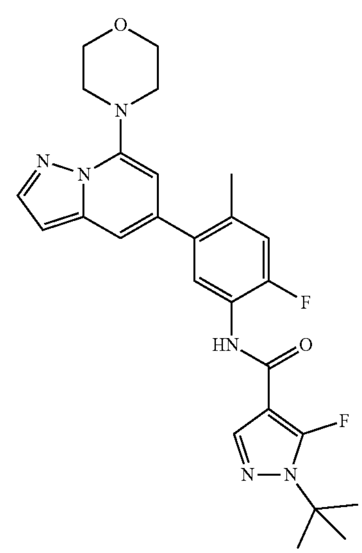 [SMILES: Cc1cc(F)c(NC(=O)c2cnn(C(C)(C)C)c2F)cc1-c1cc(N2CCOCC2)n2nccc2c1] | 1-(tert-Butyl)-5-fluoro-N-(2-fluoro-4-methyl-5-(7-morpholinopyrazolo[1,5-a]pyridin-5-yl)phenyl)-1H-pyrazole-4-carboxamide |

TABLE 1-continued
| Synthetic Chemistry Example | Compound Structure | Compound Name |
|---|---|---|
| 163 | 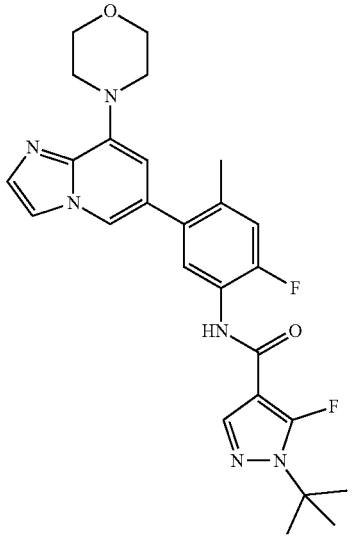 [SMILES: Cc1cc(F)c(NC(=O)c2cnn(C(C)(C)C)c2F)cc1-c1cc(N2CCOCC2)c2nccn2c1] | 1-(tert-Butyl)-5-fluoro-N-(2-fluoro-4-methyl-5-(8-(tetrahydro-2H-pyran-4-yl)imidazo[1,2-a]pyridin-6-yl)phenyl)-1H-pyrazole-4-carboxamide |
| 164 | 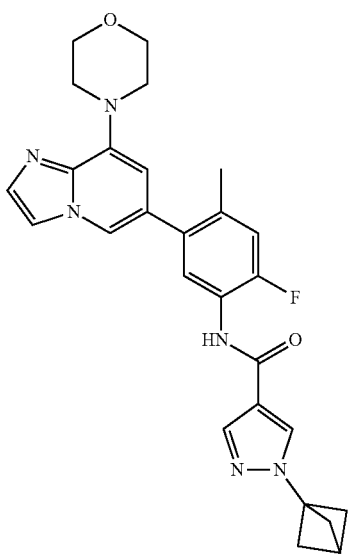 [SMILES: Cc1cc(F)c(NC(=O)c2cnn(C34CC(C3)C4)c2)cc1-c1cc(N2CCOCC2)c2nccn2c1] | 1-{Bicyclo[1.1.1]pentan-1-yl}-N-{2-fluoro-4-methyl-5-[8-(morpholin-4-yl)imidazo[1,2-a]pyridin-6-yl]phenyl}pyrazole-4-carboxamide |

TABLE 1-continued
| Synthetic Chemistry Example | Compound Structure | Compound Name |
|---|---|---|
| 165 | 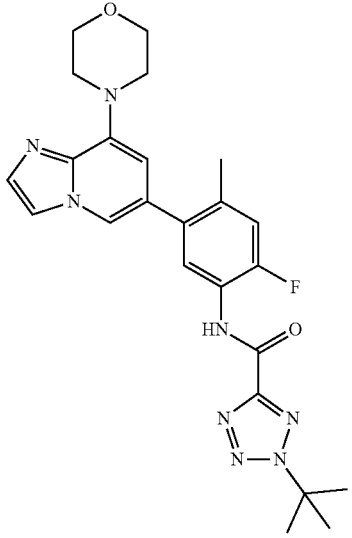 [SMILES: Cc1cc(F)c(NC(=O)c2nnn(C(C)(C)C)n2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}-1,2,3,4-tetrazole-5-carboxamide |
| 166 | 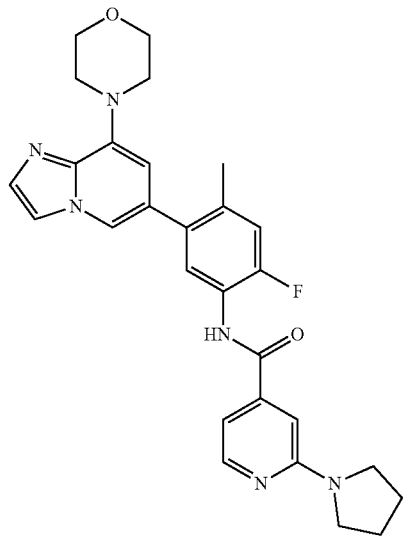 [SMILES: Cc1cc(F)c(NC(=O)c2ccnc(N3CCCC3)c2)cc1-c1cc(N2CCOCC2)c2nccn2c1] | N-{2-fluoro-4-methyl-5-[8-(morpholin-4-yl)imidazo[1,2-a]pyridin-6-yl]phenyl}-2-(pyrrolidin-1-yl)pyridine-4-carboxamide |

TABLE 1-continued
| Synthetic Chemistry Example | Compound Structure | Compound Name |
|---|---|---|
| 167 | 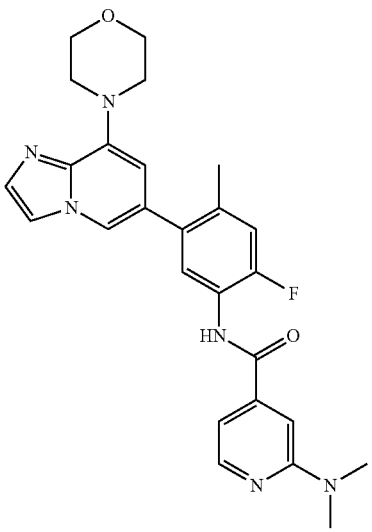 [SMILES: Cc1cc(F)c(NC(=O)c2ccnc(N(C)C)c2)cc1-c1cc(N2CCOCC2)c2nccn2c1] | 2-(Dimethylamino)-N-{2-fluoro-4-methyl-5-[8-(morpholin-4-yl)imidazo[1,2-a]pyridin-6-yl]phenyl}pyridine-4-carboxamide |
| 168 | 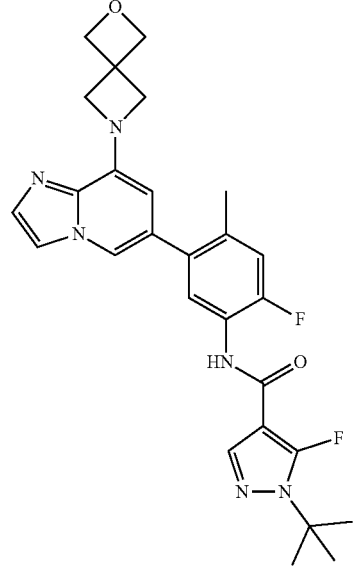 [SMILES: Cc1cc(F)c(NC(=O)c2cnn(C(C)(C)C)c2F)cc1-c1cc(N2CC3(COC3)C2)c2nccn2c1] | N-(5-(8-(2-oxa-6-azaspiro[3.3]heptan-6-yl)imidazo[1,2-a]pyridin-6-yl)-2-fluoro-4-methylphenyl)-1-(tert-butyl)-5-fluoro-1H-pyrazole-4-carboxamide |

TABLE 1-continued
| Synthetic Chemistry Example | Compound Structure | Compound Name |
|---|---|---|
| 169 | 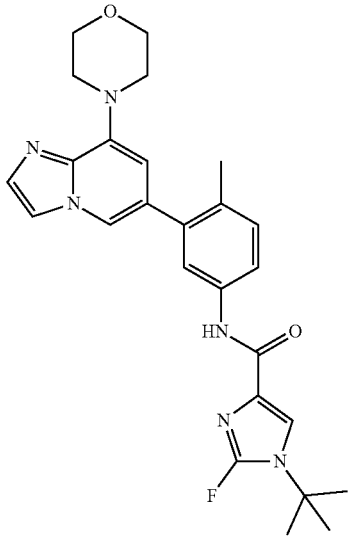 [SMILES: Cc1ccc(NC(=O)c2cn(C(C)(C)C)c(F)n2)cc1-c1cc(N2CCOCC2)c2nccn2c1] | 1-(Tert-butyl)-2-fluoro-N-(4-methyl-3-(8-morpholinoimidazo[1,2-a]pyridin-6-yl)phenyl)-1H-imidazole-4-carboxamide |
| 170 | 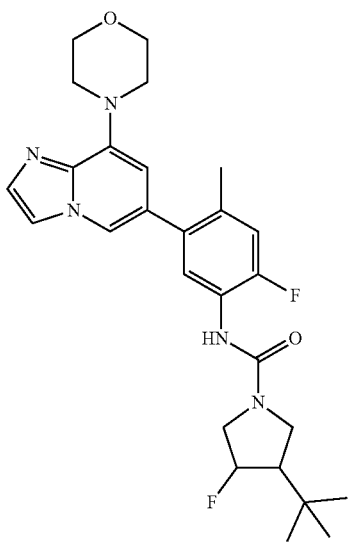 [SMILES: Cc1cc(F)c(NC(=O)N2CC(F)C(C(C)(C)C)C2)cc1-c1cc(N2CCOCC2)c2nccn2c1] | (3R,4S)-3-Tert-butyl-4-fluoro-N-{2-fluoro-4-methyl-5-[8-(morpholin-4-yl)imidazo[1,2-a]pyridin-6-yl]phenyl}pyrrolidine-1-carboxamide |

TABLE 1-continued
| Synthetic Chemistry Example | Compound Structure | Compound Name |
|---|---|---|
| 171 | 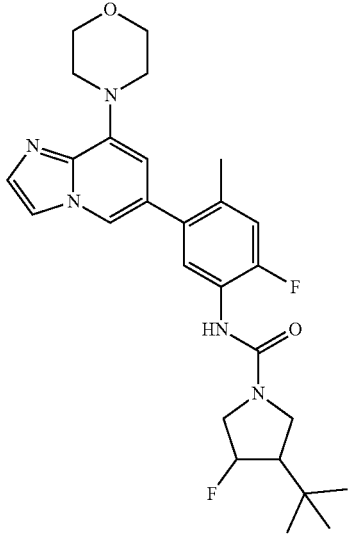 [SMILES: Cc1cc(F)c(NC(=O)N2CC(F)C(C(C)(C)C)C2)cc1-c1cc(N2CCOCC2)c2nccn2c1] | (3R,4R)-3-Tert-butyl-4-fluoro-N-{2-fluoro-4-methyl-5-[8-(morpholin-4-yl)imidazo[1,2-a]pyridin-6-yl]phenyl}pyrrolidine-1-carboxamide |
| 172 | 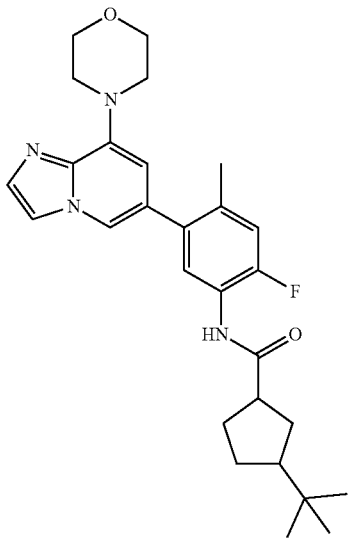 [SMILES: Cc1cc(F)c(NC(=O)C2CCC(C(C)(C)C)C2)cc1-c1cc(N2CCOCC2)c2nccn2c1] | 3-(tert-butyl)-N-(2-fluoro-4-methyl-5-(8-morpholinoimidazo[1,2-a]pyridin-6-yl)phenyl)cyclopentane-1-carboxamide |

TABLE 1-continued
| Synthetic Chemistry Example | Compound Structure | Compound Name |
|---|---|---|
| 173 | 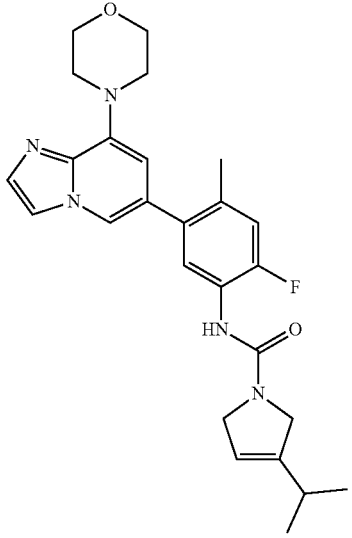 [SMILES: Cc1cc(F)c(NC(=O)N2CC=C(C(C)C)C2)cc1-c1cc(N2CCOCC2)c2nccn2c1] | N-(2-fluoro-4-methyl-5-(8-morpholinoimidazo[1,2-a]pyridin-6-yl)phenyl)-3-isopropyl-2,5-dihydro-1H-pyrrole-1-carboxamide |
| 174 | 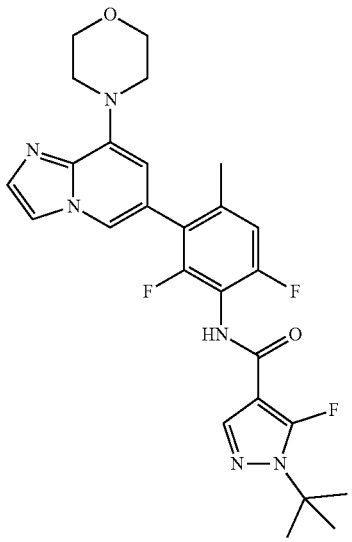 [SMILES: Cc1cc(F)c(NC(=O)c2cnn(C(C)(C)C)c2F)c(F)c1-c1cc(N2CCOCC2)c2nccn2c1] | 1-Tert-butyl-N-{2,6-difluoro-4-methyl-3-[8-(morpholin-4-yl)imidazo[1,2-a]pyridin-6-yl]phenyl}-5-fluoropyrazole-4-carboxamide |

TABLE 1-continued
| Synthetic Chemistry Example | Compound Structure | Compound Name |
|---|---|---|
| 175 | 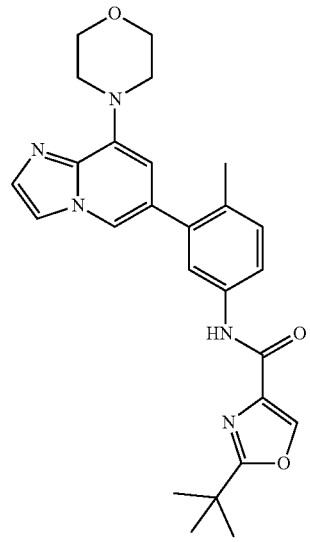 [SMILES: Cc1ccc(NC(=O)c2coc(C(C)(C)C)n2)cc1-c1cc(N2CCOCC2)c2nccn2c1] | 2-Tert-butyl-N-{4-methyl-3-[8-(morpholin-4-yl)imidazo[1,2-a]pyridin-6-yl]phenyl}-1,3-oxazole-4-carboxamide |
| 176 | 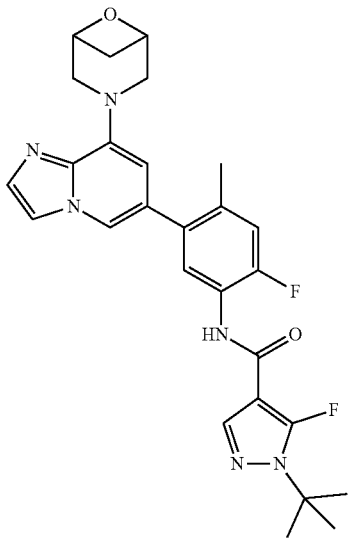 [SMILES: Cc1cc(F)c(NC(=O)c2cnn(C(C)(C)C)c2F)cc1-c1cc(N2CC3CC(C2)O3)c2nccn2c1] | N-(5-(8-(6-oxabicyclo[3.1.1]heptan-3-yl)imidazo[1,2-a]pyridin-6-yl)-2-fluoro-4-methylphenyl)-1-(tert-butyl)-5-fluoro-1H-pyrazole-4-carboxamide |

TABLE 1-continued
| Synthetic Chemistry Example | Compound Structure | Compound Name |
|---|---|---|
| 177 | 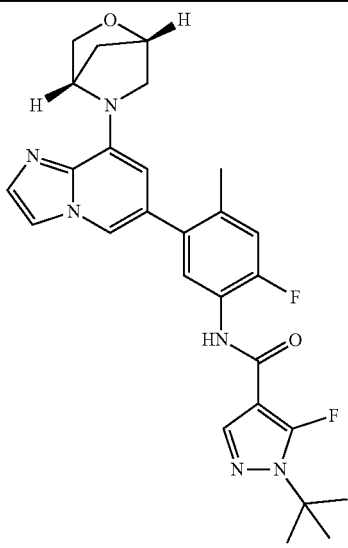 | 1-Tert-butyl-5-fluoro-N-(2-fluoro-4-methyl-5-{8-[(1S,4S)-2-oxa-5-azabicyclo[2.2.1]heptan-5-yl]imidazo[1,2-a]pyridin-6-yl}phenyl)pyrazole-4-carboxamide |
| 178 | 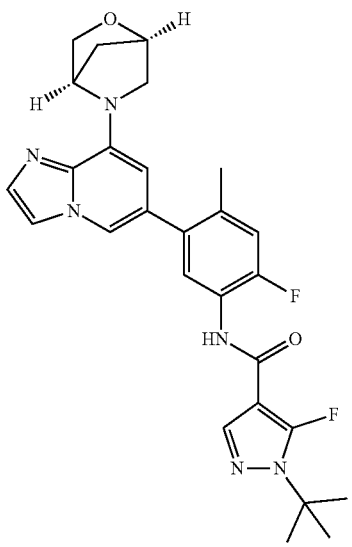 [SMILES: Cc1cc(F)c(NC(=O)c2cnn(C(C)(C)C)c2F)cc1-c1cc(N2C[C@H]3C[C@@H]2CO3)c2nccn2c1] | 1-Tert-butyl-5-fluoro-N-(2-fluoro-4-methyl-5-{8-[(1R,4R)-2-oxa-5-azabicyclo[2.2.1]heptan-5-yl]imidazo[1,2-a]pyridin-6-yl}phenyl)pyrazole-4-carboxamide |

TABLE 1-continued
| Synthetic Chemistry Example | Compound Structure | Compound Name |
|---|---|---|
| 179 | 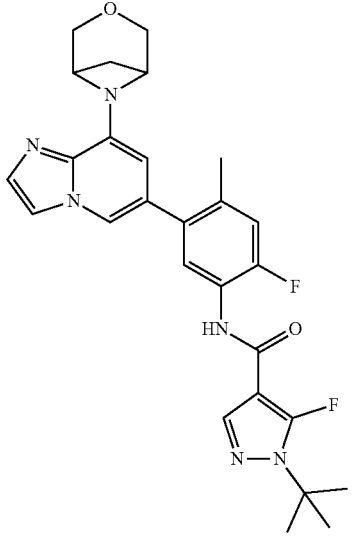 [SMILES: Cc1cc(F)c(NC(=O)c2cnn(C(C)(C)C)c2F)cc1-c1cc(N2C3COCC2C3)c2nccn2c1] | N-(5-(8-(3-oxa-6-azabicyclo[3.1.1]heptan-6-yl)imidazo[1,2-a]pyridin-6-yl)-2-fluoro-4-methylphenyl)-1-(tert-butyl)-5-fluoro-1H-pyrazole-4-carboxamide |
| 180 | 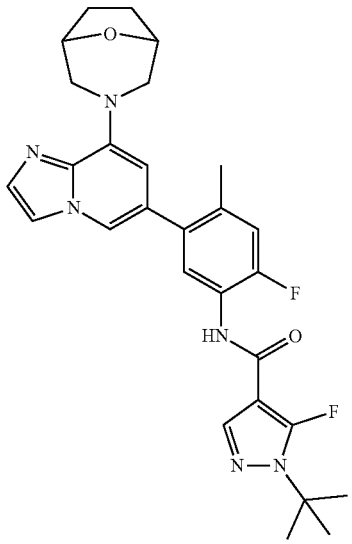 [SMILES: Cc1cc(F)c(NC(=O)c2cnn(C(C)(C)C)c2F)cc1-c1cc(N2CC3CCC(C2)O3)c2nccn2c1] | N-(5-(8-(8-oxa-3-azabicyclo[3.2.1]octan-3-yl)imidazo[1,2-a]pyridin-6-yl)-2-fluoro-4-methylphenyl)-1-(tert-butyl)-5-fluoro-1H-pyrazole-4-carboxamide |

TABLE 1-continued
| Synthetic Chemistry Example | Compound Structure | Compound Name |
|---|---|---|
| 181 | 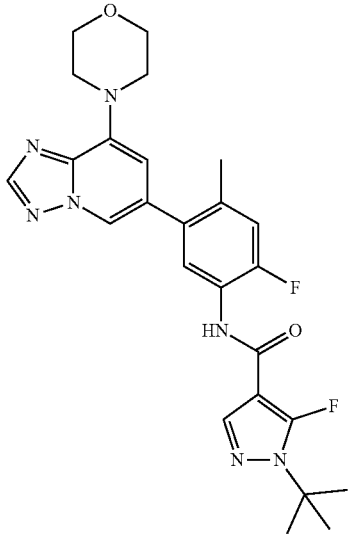 | 1-(tert-Butyl)-5-fluoro-N-(2-fluoro-4-methyl-5-(8-morpholino-[1,2,4]triazolo[1,5-a]pyridin-6-yl)phenyl)-1H-pyrazole-4-carboxamide |
| 182 | 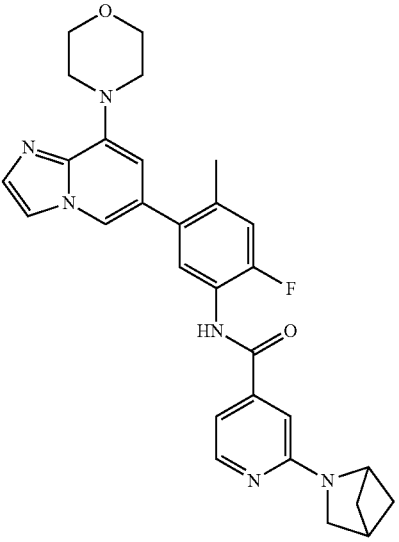 [SMILES: Cc1cc(F)c(NC(=O)c2ccnc(N3CC4CC3C4)c2)cc1-c1cc(N2CCOCC2)c2nccn2c1] | 2-{2-Azabicyclo[2.1.1]hexan-2-yl}-N-{2-fluoro-4-methyl-5-[8-(morpholin-4-yl)imidazo[1,2-a]pyridin-6-yl]phenyl}pyridine-4-carboxamide |

TABLE 1-continued
| Synthetic Chemistry Example | Compound Structure | Compound Name |
|---|---|---|
| 183 | 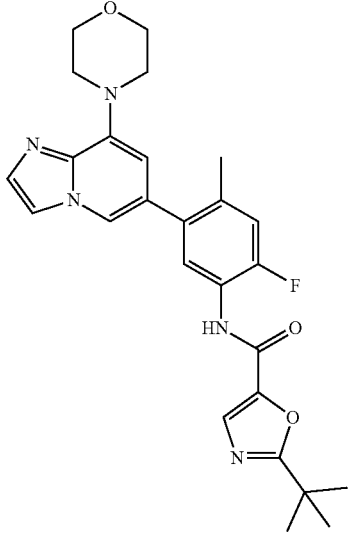 [SMILES: Cc1cc(F)c(NC(=O)c2cnc(C(C)(C)C)o2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}-1,3-oxazole-5-carboxamide |
| 184 | 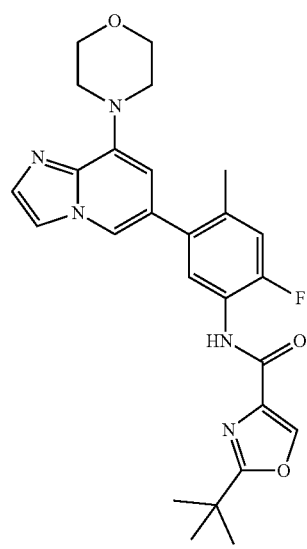 [SMILES: Cc1cc(F)c(NC(=O)c2coc(C(C)(C)C)n2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}-1,3-oxazole-4-carboxamide |

TABLE 1-continued
| Synthetic Chemistry Example | Compound Structure | Compound Name |
|---|---|---|
| 185 | 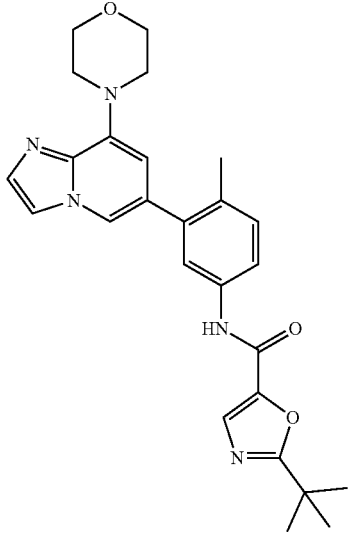 [SMILES: Cc1ccc(NC(=O)c2cnc(C(C)(C)C)o2)cc1-c1cc(N2CCOCC2)c2nccn2c1] | 2-Tert-butyl-N-{4-methyl-3-[8-(morpholin-4-yl)imidazo[1,2-a]pyridin-6-yl]phenyl}-1,3-oxazole-5-carboxamide |
| 186 | 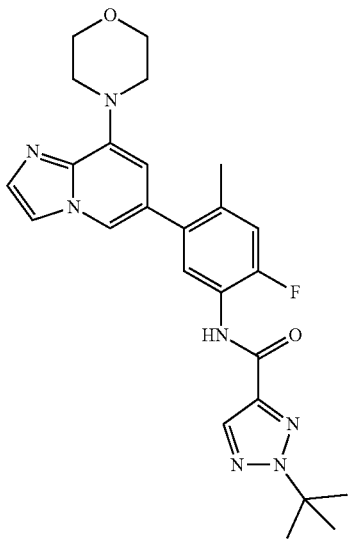 [SMILES: Cc1cc(F)c(NC(=O)c2cnn(C(C)(C)C)n2)cc1-c1cc(N2CCOCC2)c2nccn2c1] | 2-Tert-butyl-N-{2-fluoro-4-methyl-5-[8-(morpholin-4-yl)imidazo[1,2-a]pyridin-6-yl]phenyl}-1,2,3-triazole-4-carboxamide |

| Synthetic Chemistry Example | Compound Structure | Compound Name |
|---|---|---|
| 187 | 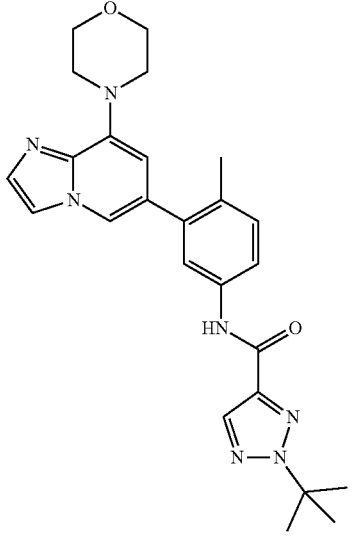 [SMILES: Cc1ccc(NC(=O)c2cnn(C(C)(C)C)n2)cc1-c1cc(N2CCOCC2)c2nccn2c1] | 2-(Tert-butyl)-N-(4-methyl-3-(8-morpholinoimidazo[1,2-a]pyridin-6-yl)phenyl)-2H-1,2,3-triazole-4-carboxamide |
| 188 | 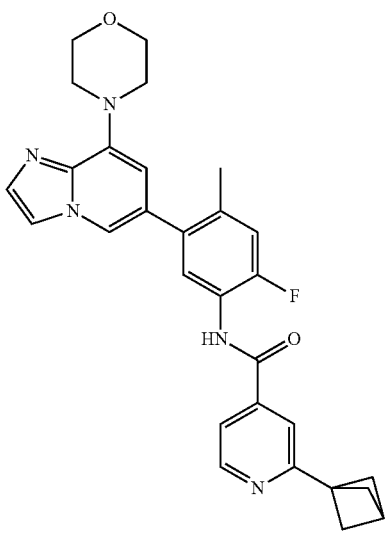 [SMILES: Cc1cc(F)c(NC(=O)c2ccnc(C34CC(C3)C4)c2)cc1-c1cc(N2CCOCC2)c2nccn2c1] | 2-{Bicyclo[1.1.1]pentan-1-yl}-N-{2-fluoro-4-methyl-5-[8-(morpholin-4-yl)imidazo[1,2-a]pyridin-6-yl]phenyl}pyridine-4-carboxamide |

TABLE 1-continued

| Synthetic Chemistry Example | Compound Structure | Compound Name |
|---|---|---|
| 189 | 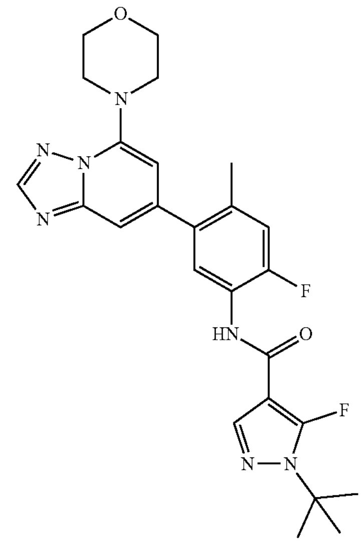 [SMILES: Cc1cc(F)c(NC(=O)c2cnn(C(C)(C)C)c2F)cc1-c1cc(N2CCOCC2)n2ncnc2c1] | 1-(tert-Butyl)-5-fluoro-N-(2-fluoro-4-methyl-5-(5-morpholino-[1,2,4]triazolo[1,5-a]pyridin-7-yl)phenyl)-1H-pyrazole-4-carboxamide |
| 190 | 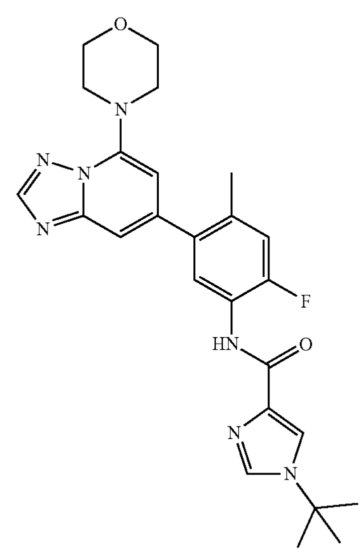 [SMILES: Cc1cc(F)c(NC(=O)c2cn(C(C)(C)C)cn2)cc1-c1cc(N2CCOCC2)n2ncnc2c1] | 1-Tert-butyl-N-{2-fluoro-4-methyl-5-[7-(morpholin-4-yl)pyrazolo[1,5-a]pyridin-5-yl]phenyl}imidazole-4-carboxamide |

TABLE 1-continued
| Synthetic Chemistry Example | Compound Structure | Compound Name |
|---|---|---|
| 191 | 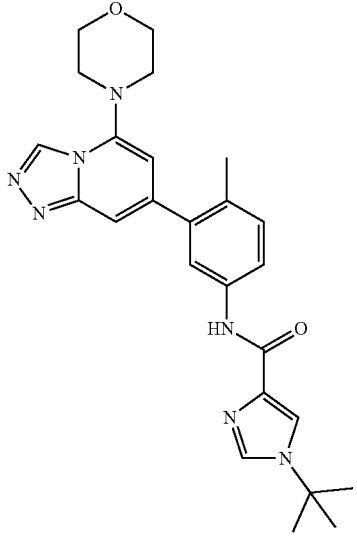 [SMILES: Cc1ccc(NC(=O)c2cn(C(C)(C)C)cn2)cc1-c1cc(N2CCOCC2)n2cnnc2c1] | 1-(Tert-butyl)-N-(4-methyl-3-(5-morpholino-[1,2,4]triazolo[4,3-a]pyridin-7-yl)phenyl)-1H-imidazole-4-carboxamide |
| 192 | 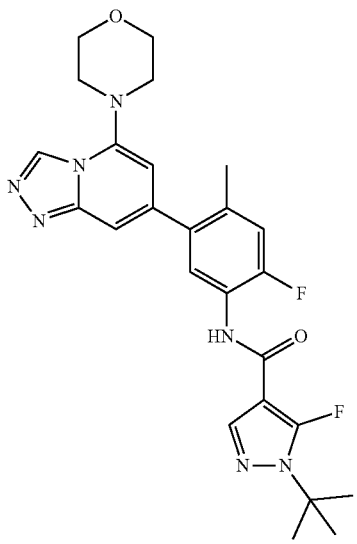 | 1-Tert-butyl-5-fluoro-N-{2-fluoro-4-methyl-5-[5-(morpholin-4-yl)-[1,2,4]triazolo[4,3-a]pyridin-7-yl]phenyl}pyrazole-4-carboxamide |

TABLE 1-continued
| Synthetic Chemistry Example | Compound Structure | Compound Name |
|---|---|---|
| 193 | 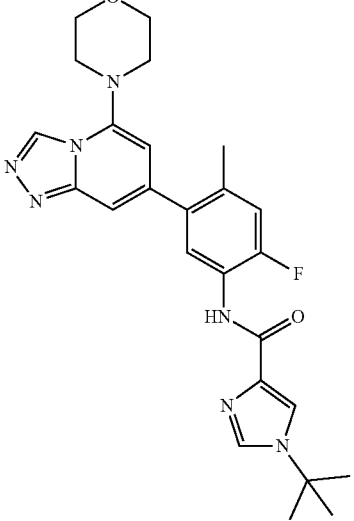 | 1-Tert-butyl-N-{2-fluoro-4-methyl-5-[5-(morpholin-4-yl)-[1,2,4]triazolo[4,3-a]pyridin-7-yl]phenyl}imidazole-4-carboxamide |
| 194 | 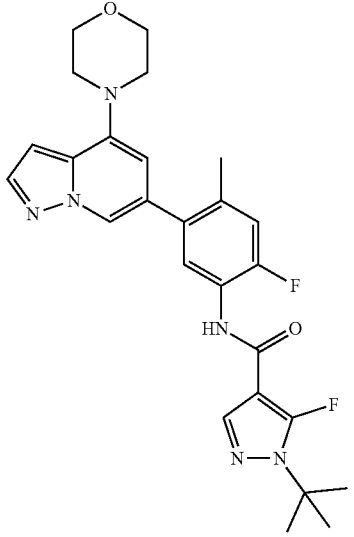 [SMILES: Cc1cc(F)c(NC(=O)c2cnn(C(C)(C)C)c2F)cc1-c1cc(N2CCOCC2)c2ccnn2c1] | 1-Tert-butyl-5-fluoro-N-{2-fluoro-4-methyl-5-[4-(morpholin-4-yl)pyrazolo[1,5-a]pyridin-6-yl]phenyl}pyrazole-4-carboxamide |

TABLE 1-continued
| Synthetic Chemistry Example | Compound Structure | Compound Name |
|---|---|---|
| 195 | 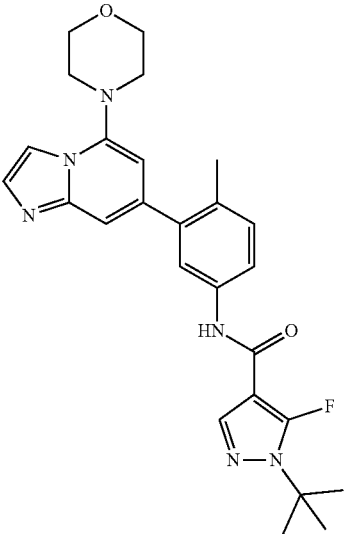 [SMILES: Cc1ccc(NC(=O)c2cnn(C(C)(C)C)c2F)cc1-c1cc(N2CCOCC2)n2ccnc2c1] | 1-Tert-butyl-5-fluoro-N-{4-methyl-3-[5-(morpholin-4-yl)imidazo[1,2-a]pyridin-7-yl]phenyl}pyrazole-4-carboxamide |
| 196 | 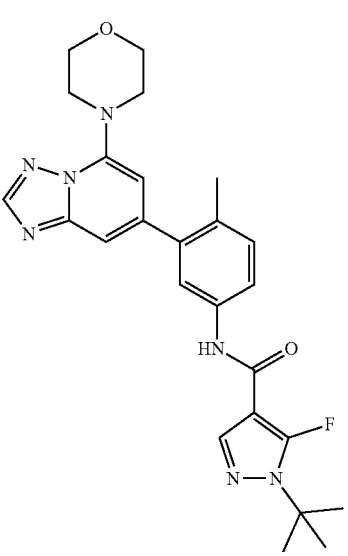 [SMILES: Cc1ccc(NC(=O)c2cnn(C(C)(C)C)c2F)cc1-c1cc(N2CCOCC2)n2ncnc2c1] | 1-Tert-butyl-5-fluoro-N-{4-methyl-3-[5-(morpholin-4-yl)-[1,2,4]triazolo[1,5-a]pyridin-7-yl]phenyl}pyrazole-4-carboxamide |

| Synthetic Chemistry Example | Compound Structure | Compound Name |
|---|---|---|
| 197 | 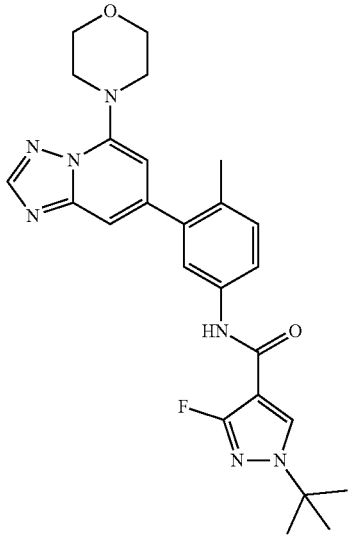 | 1-Tert-butyl-3-fluoro-N-{4-methyl-3-[5-(morpholin-4-yl)-[1,2,4]triazolo[1,5-a]pyridin-7-yl]phenyl}pyrazole-4-carboxamide |
| 198 | 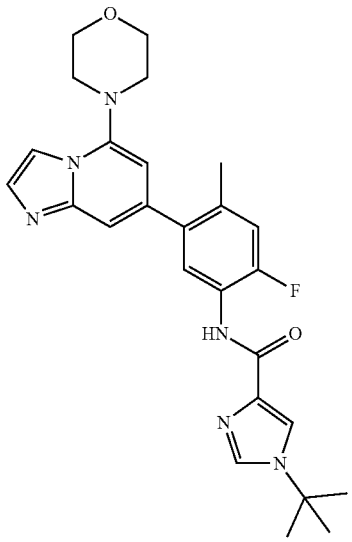 [SMILES: Cc1cc(F)c(NC(=O)c2cn(C(C)(C)C)cn2)cc1-c1cc(N2CCOCC2)n2ccnc2c1] | 1-Tert-butyl-N-{2-fluoro-4-methyl-5-[5-(morpholin-4-yl)imidazo[1,2-a]pyridin-7-yl]phenyl}imidazole-4-carboxamide |

TABLE 1-continued

| Synthetic Chemistry Example | Compound Structure | Compound Name |
|---|---|---|
| 199 | 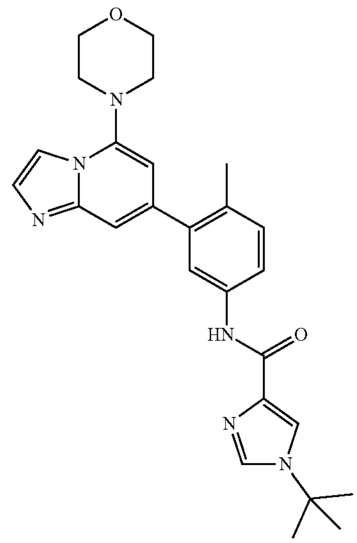 [SMILES: Cc1ccc(NC(=O)c2cn(C(C)(C)C)cn2)cc1-c1cc(N2CCOCC2)n2ccnc2c1] | 1-Tert-butyl-N-{4-methyl-3-[5-(morpholin-4-yl)imidazo[1,2-a]pyridin-7-yl]phenyl}imidazole-4-carboxamide |
| 200 | 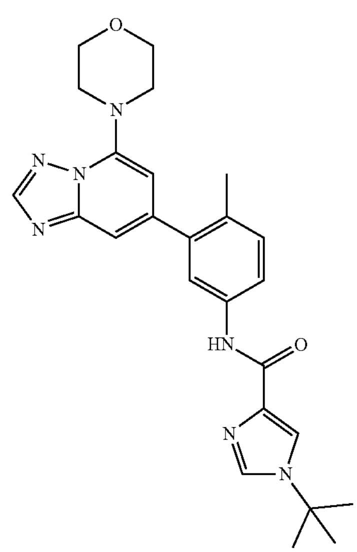 [SMILES: Cc1ccc(NC(=O)c2cn(C(C)(C)C)cn2)cc1-c1cc(N2CCOCC2)n2ncnc2c1] | 1-(Tert-butyl)-N-(4-methyl-3-(5-morpholino-[1,2,4]triazolo[1,5-a]pyridin-7-yl)phenyl)-1H-imidazole-4-carboxamide |

TABLE 1-continued
| Synthetic Chemistry Example | Compound Structure | Compound Name |
|---|---|---|
| 201 | 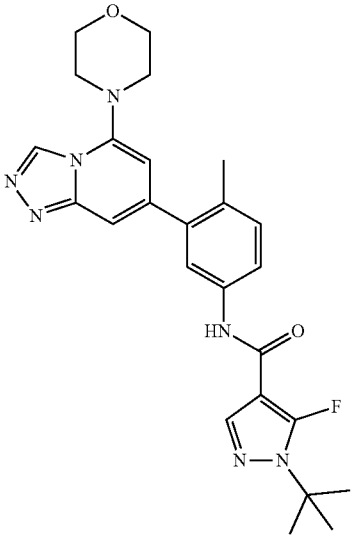 | 1-Tert-butyl-5-fluoro-N-{4-methyl-3-[5-(morpholin-4-yl)-[1,2,4]triazolo[4,3-a]pyridin-7-yl]phenyl}pyrazole-4-carboxamide |
| 202 | 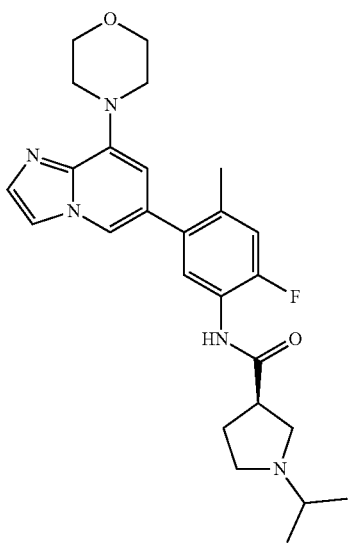 [SMILES: Cc1cc(F)c(NC(=O)[C@@H]2CCN(C(C)C)C2)cc1-c1cc(N2CCOCC2)c2nccn2c1] | (3R)-N-{2-fluoro-4-methyl-5-[8-(morpholin-4-yl)imidazo[1,2-a]pyridin-6-yl]phenyl}-1-isopropylpyrrolidine-3-carboxamide |

TABLE 1-continued
| Synthetic Chemistry Example | Compound Structure | Compound Name |
|---|---|---|
| 203 | 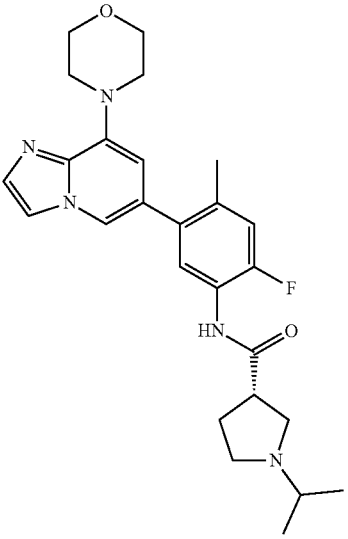 [SMILES: Cc1cc(F)c(NC(=O)[C@H]2CCN(C(C)C)C2)cc1-c1cc(N2CCOCC2)c2nccn2c1] | (3S)-N-{2-fluoro-4-methyl-5-[8-(morpholin-4-yl)imidazo[1,2-a]pyridin-6-yl]phenyl}-1-isopropylpyrrolidine-3-carboxamide |
| 204 | 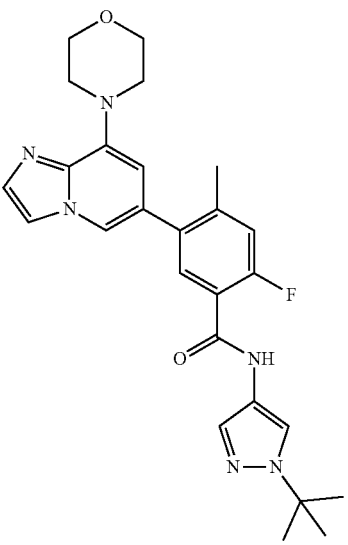 [SMILES: Cc1cc(F)c(C(=O)Nc2cnn(C(C)(C)C)c2)cc1-c1cc(N2CCOCC2)c2nccn2c1] | N-(1-tert-butylpyrazol-4-yl)-2-fluoro-4-methyl-5-[8-(morpholin-4-yl)imidazo[1,2-a]pyridin-6-yl]benzamide |

TABLE 1-continued
| Synthetic Chemistry Example | Compound Structure | Compound Name |
|---|---|---|
| 205 | 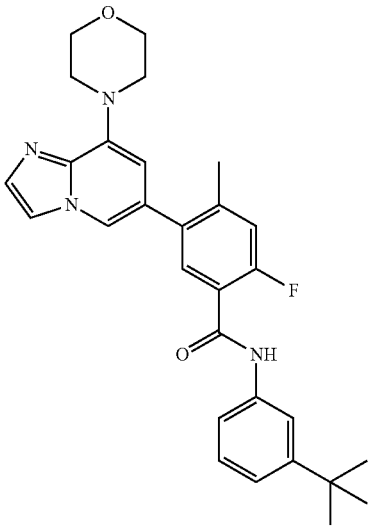 [SMILES: Cc1cc(F)c(C(=O)Nc2cccc(C(C)(C)C)c2)cc1-c1cc(N2CCOCC2)c2nccn2c1] | N-(3-tert-butylphenyl)-2-fluoro-4-methyl-5-[8-(morpholin-4-yl)imidazo[1,2-a]pyridin-6-yl]benzamide |
| 206 | 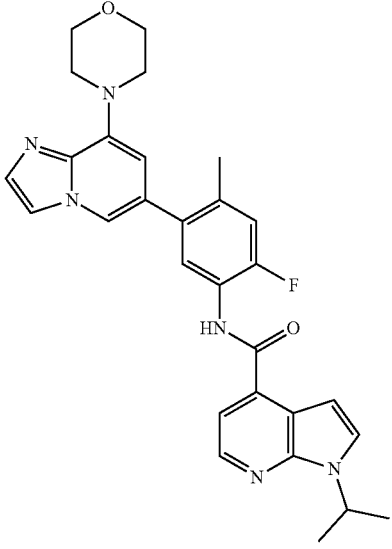 [SMILES: Cc1cc(F)c(NC(=O)c2ccnc3c2ccn3C(C)C)cc1-c1cc(N2CCOCC2)c2nccn2c1] | N-{2-Fluoro-4-methyl-5-[8-(morpholin-4-yl)imidazo[1,2-a]pyridin-6-yl]phenyl}-1-isopropylpyrrolo[2,3-b]pyridine-4-carboxamid |

TABLE 1-continued
| Synthetic Chemistry Example | Compound Structure | Compound Name |
|---|---|---|
| 207 | 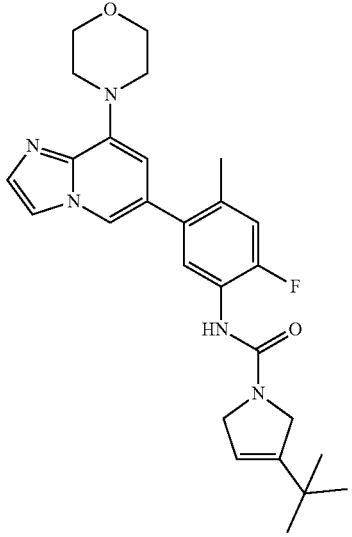 [SMILES: Cc1cc(F)c(NC(=O)N2CC=C(C(C)(C)C)C2)cc1-c1cc(N2CCOCC2)c2nccn2c1] | 3-Tert-butyl-N-{2-fluoro-4-methyl-5-[8-(morpholin-4-yl)imidazo[1,2-a]pyridin-6-yl]phenyl}-2,5-dihydropyrrole-1-carboxamide |
| 208 | 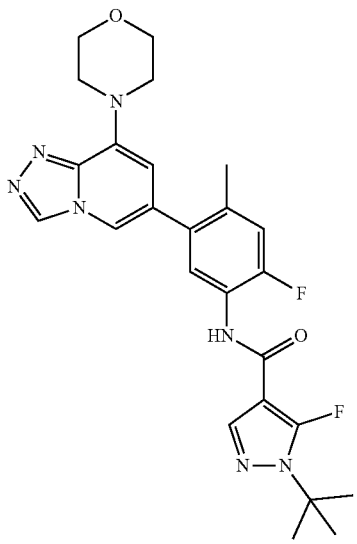 | 1-(Tert-butyl)-5-fluoro-N-(2-fluoro-4-methyl-5-(8-morpholino-[1,2,4]triazolo[4,3-a]pyridin-6-yl)phenyl)-1H-pyrazole-4-carboxamide |

TABLE 1-continued

| Synthetic Chemistry Example | Compound Structure | Compound Name |
|---|---|---|
| 209 | 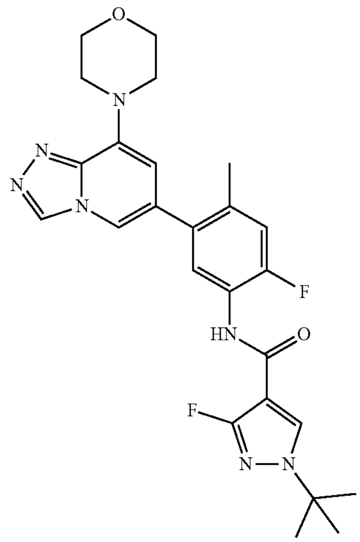 [SMILES: Cc1cc(F)c(NC(=O)c2cn(C(C)(C)C)nc2F)cc1-c1cc(N2CCOCC2)c2nncn2c1] | 1-(Tert-butyl)-3-fluoro-N-(2-fluoro-4-methyl-5-(8-morpholino-[1,2,4]triazolo[4,3-a]pyridin-6-yl)phenyl)-1H-pyrazole-4-carboxamide |
| 210 | 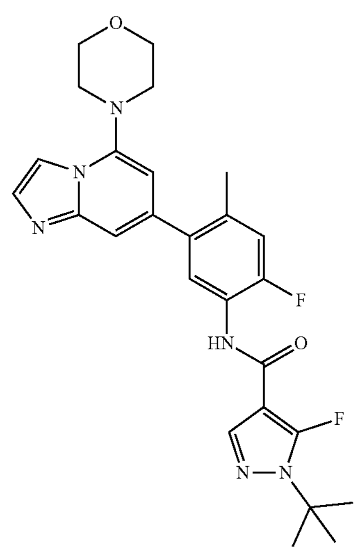 | 1-Tert-butyl-5-fluoro-N-{2-fluoro-4-methyl-5-[5-(morpholin-4-yl)imidazo[1,2-a]pyridin-7-yl]phenyl}pyrazole-4-carboxamide |

TABLE 1-continued
| Synthetic Chemistry Example | Compound Structure | Compound Name |
|---|---|---|
| 211 | 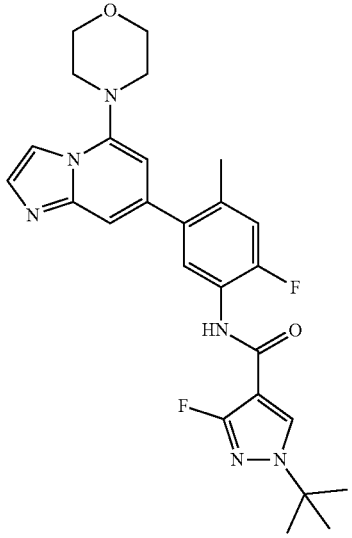 [SMILES: Cc1cc(F)c(NC(=O)c2cn(C(C)(C)C)nc2F)cc1-c1cc(N2CCOCC2)n2ccnc2c1] | 1-Tert-butyl-3-fluoro-N-{2-fluoro-4-methyl-5-[5-(morpholin-4-yl)imidazo[1,2-a]pyridin-7-yl]phenyl}pyrazole-4-carboxamide |
| 212 | 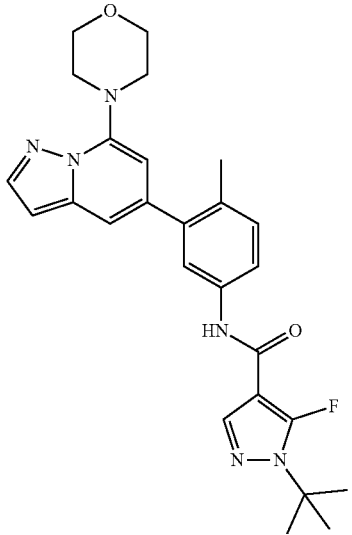 [SMILES: Cc1ccc(NC(=O)c2cnn(C(C)(C)C)c2F)cc1-c1cc(N2CCOCC2)n2nccc2c1] | 1-Tert-butyl-5-fluoro-N-{4-methyl-3-[7-(morpholin-4-yl)pyrazolo[1,5-a]pyridin-5-yl]phenyl}pyrazole-4-carboxamide |

TABLE 1-continued
| Synthetic Chemistry Example | Compound Structure | Compound Name |
|---|---|---|
| 213 | 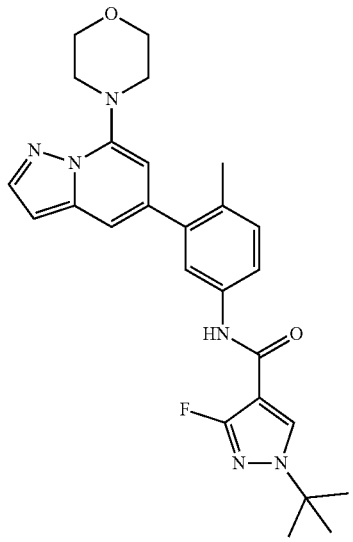 [SMILES: Cc1ccc(NC(=O)c2cn(C(C)(C)C)nc2F)cc1-c1cc(N2CCOCC2)n2nccc2c1] | 1-Tert-butyl-3-fluoro-N-{4-methyl-3-[7-(morpholin-4-yl)pyrazolo[1,5-a]pyridin-5-yl]phenyl}pyrazole-4-carboxamide |
| 214 | 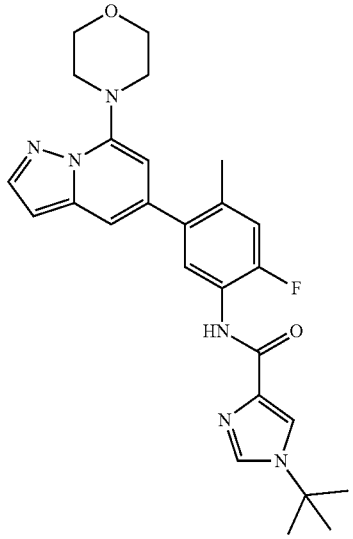 [SMILES: Cc1cc(F)c(NC(=O)c2cn(C(C)(C)C)cn2)cc1-c1cc(N2CCOCC2)n2nccc2c1] | 1-Tert-butyl-N-{2-fluoro-4-methyl-5-[7-(morpholin-4-yl)pyrazolo[1,5-a]pyridin-5-yl]phenyl}imidazole-4-carboxamide |

TABLE 1-continued
| Synthetic Chemistry Example | Compound Structure | Compound Name |
|---|---|---|
| 215 | 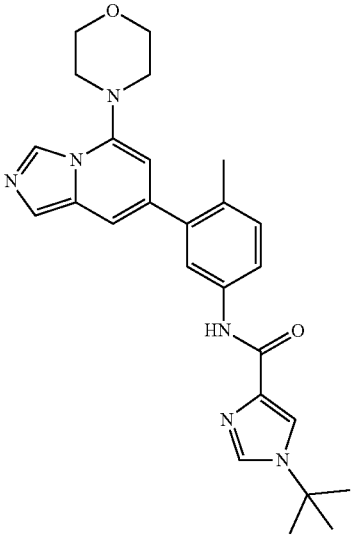 | 1-Tert-butyl-N-{4-methyl-3-[5-(morpholin-4-yl)imidazo[1,5-a]pyridin-7-yl]phenyl}imidazole-4-carboxamide |
| 216 | 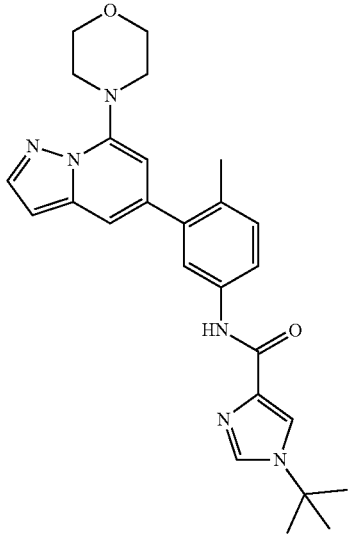 [SMILES: Cc1ccc(NC(=O)c2cn(C(C)(C)C)cn2)cc1-c1cc(N2CCOCC2)n2nccc2c1] | 1-Tert-butyl-N-{4-methyl-3-[7-(morpholin-4-yl)pyrazolo[1,5-a]pyridin-5-yl]phenyl}imidazole-4-carboxamide |

TABLE 1-continued
| Synthetic Chemistry Example | Compound Structure | Compound Name |
|---|---|---|
| 217 | 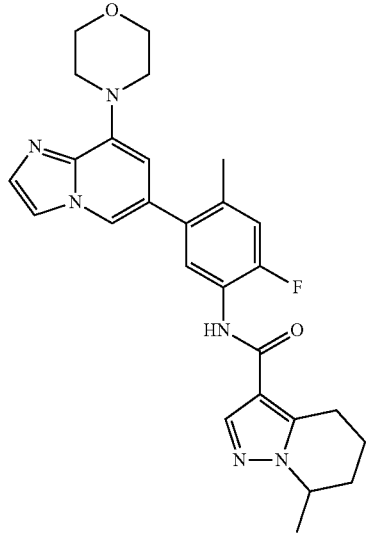 [SMILES: Cc1cc(F)c(NC(=O)c2cnn3c2CCCC3C)cc1-c1cc(N2CCOCC2)c2nccn2c1] | N-(2-fluoro-4-methyl-5-(8-morpholinoimidazo[1,2-a]pyridin-6-yl)phenyl)-7-methyl-4,5,6,7-tetrahydropyrazolo[1,5-a]pyridine-3-carboxamide |
| 218 | 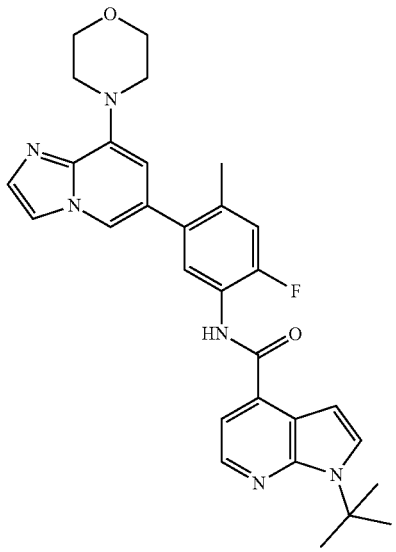 [SMILES: Cc1cc(F)c(NC(=O)c2ccnc3c2ccn3C(C)(C)C)cc1-c1cc(N2CCOCC2)c2nccn2c1] | 1-Tert-butyl-N-{2-fluoro-4-methyl-5-[8-(morpholin-4-yl)imidazo[1,2-a]pyridin-6-yl]phenyl}pyrrolo[2,3-b]pyridine-4-carboxamide |

TABLE 1-continued
| Synthetic Chemistry Example | Compound Structure | Compound Name |
|---|---|---|
| 219 | 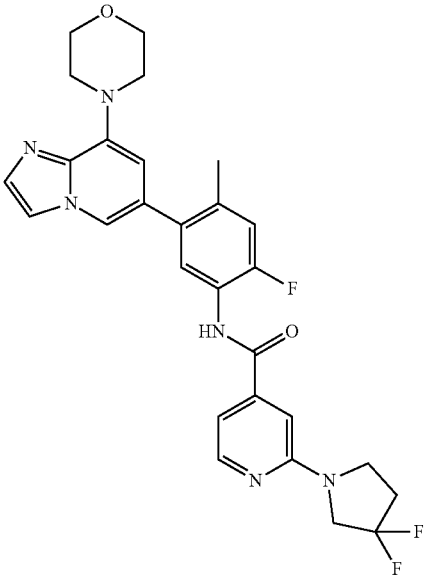 [SMILES: Cc1cc(F)c(NC(=O)c2ccnc(N3CCC(F)(F)C3)c2)cc1-c1cc(N2CCOCC2)c2nccn2c1] | 2-(3,3-Difluoropyrrolidin-1-yl)-N-{2-fluoro-4-methyl-5-[8-(morpholin-4-yl)imidazo[1,2-a]pyridin-6-yl]phenyl}pyridine-4-carboxamide |
| 220 | 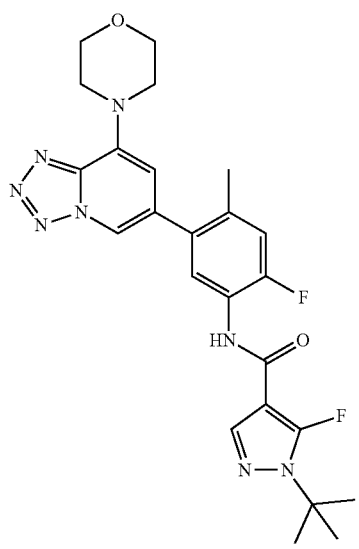 [SMILES: Cc1cc(F)c(NC(=O)c2cnn(C(C)(C)C)c2F)cc1-c1cc(N2CCOCC2)c2nnnn2c1] | 1-Tert-butyl-5-fluoro-N-{2-fluoro-4-methyl-5-[8-(morpholin-4-yl)-[1,2,3,4]tetrazolo[1,5-a]pyridin-6-yl]phenyl}pyrazole-4-carboxamide |

TABLE 1-continued

| Synthetic Chemistry Example | Compound Structure | Compound Name |
|---|---|---|
| 221 | 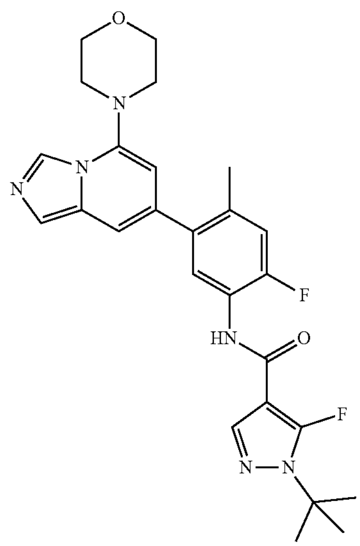 | 1-(Tert-butyl)-5-fluoro-N-(2-fluoro-4-methyl-5-(5-morpholinoimidazo[1,5-a]pyridin-7-yl)phenyl)-1H-pyrazole-4-carboxamide |
| 222 | 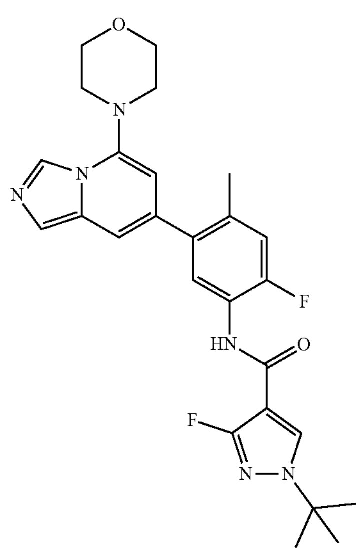 [SMILES: Cc1cc(F)c(NC(=O)c2cn(C(C)(C)C)nc2F)cc1-c1cc(N2CCOCC2)n2cncc2c1] | 1-(Tert-butyl)-3-fluoro-N-(2-fluoro-4-methyl-5-(5-morpholinoimidazo[1,5-a]pyridin-7-yl)phenyl)-1H-pyrazole-4-carboxamide |

TABLE 1-continued
| Synthetic Chemistry Example | Compound Structure | Compound Name |
|---|---|---|
| 223 | 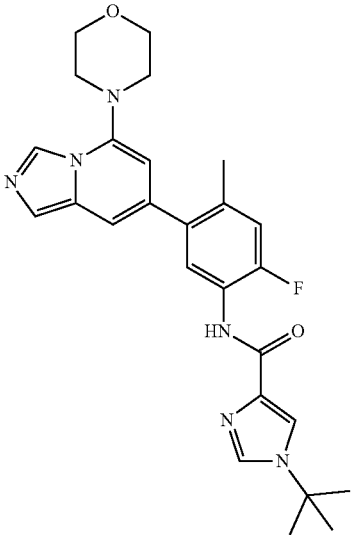 [SMILES: Cc1cc(F)c(NC(=O)c2cn(C(C)(C)C)cn2)cc1-c1cc(N2CCOCC2)n2cncc2c1] | 1-(Tert-butyl)-N-(2-fluoro-4-methyl-5-(5-morpholinoimidazo[1,5-a]pyridin-7-yl)phenyl)-1H-imidazole-4-carboxamide |
| 224 | 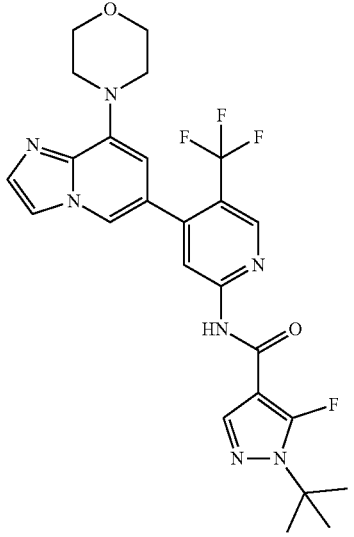 [SMILES: CC(C)(C)n1ncc(C(=O)Nc2cc(-c3cc(N4CCOCC4)c4nccn4c3)c(C(F)(F)F)cn2)c1F] | 1-(Tert-butyl)-5-fluoro-N-(4-(8-morpholinoimidazo[1,2-a]pyridin-6-yl)-5-(trifluoromethyl)pyridin-2-yl)-1H-pyrazole-4-carboxamide |

TABLE 1-continued
| Synthetic Chemistry Example | Compound Structure | Compound Name |
|---|---|---|
| 225 | 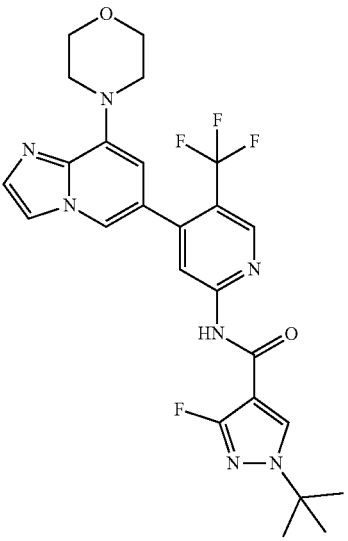 [SMILES: CC(C)(C)n1cc(C(=O)Nc2cc(-c3cc(N4CCOCC4)c4nccn4c3)c(C(F)(F)F)cn2)c(F)n1] | 1-(Tert-butyl)-3-fluoro-N-(4-(8-morpholinoimidazo[1,2-a]pyridin-6-yl)-5-(trifluoromethyl)pyridin-2-yl)-1H-pyrazole-4-carboxamide |
| 226 | 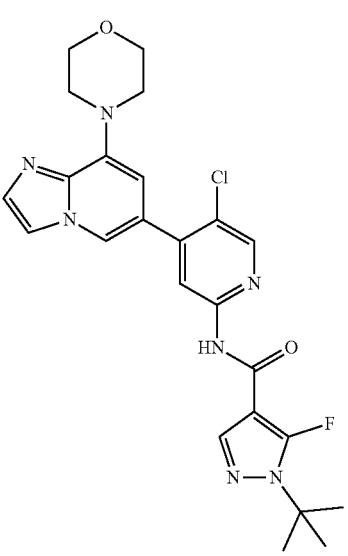 [SMILES: CC(C)(C)n1ncc(C(=O)Nc2cc(-c3cc(N4CCOCC4)c4nccn4c3)c(Cl)cn2)c1F] | 1-(tert-Butyl)-N-(5-chloro-4-(8-morpholinoimidazo[1,2-a]pyridin-6-yl)pyridin-2-yl)-5-fluoro-1H-pyrazole-4-carboxamide |

TABLE 1-continued
| Synthetic Chemistry Example | Compound Structure | Compound Name |
|---|---|---|
| 227 | 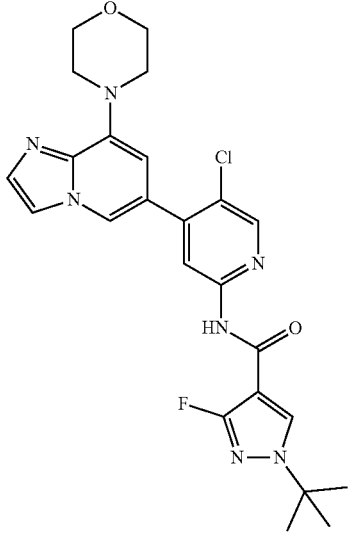 [SMILES: CC(C)(C)n1cc(C(=O)Nc2cc(-c3cc(N4CCOCC4)c4nccn4c3)c(Cl)cn2)c(F)n1] | 1-(Tert-butyl)-N-(5-chloro-4-(8-morpholinoimidazo[1,2-a]pyridin-6-yl)pyridin-2-yl)-3-fluoro-1H-pyrazole-4-carboxamide |
| 228 | 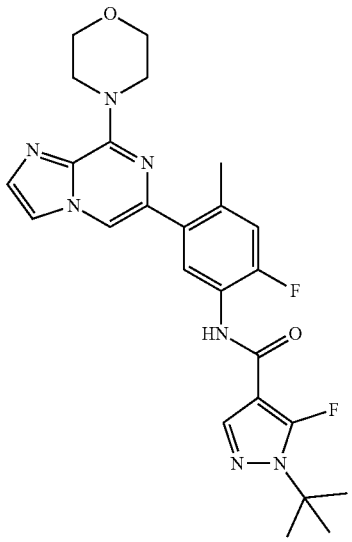 [SMILES: Cc1cc(F)c(NC(=O)c2cnn(C(C)(C)C)c2F)cc1-c1cn2ccnc2c(N2CCOCC2)n1] | 1-(tert-Butyl)-5-fluoro-N-(2-fluoro-4-methyl-5-(8-morpholinoimidazo[1,2-a]pyrazin-6-yl)phenyl)-1H-pyrazole-4-carboxamide |

TABLE 1-continued

| Synthetic Chemistry Example | Compound Structure | Compound Name |
| --- | --- | --- |
| 229 | 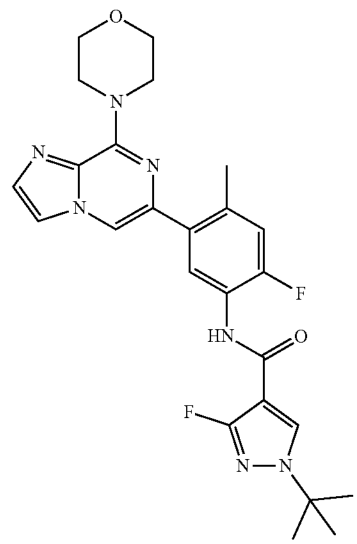 [SMILES: Cc1cc(F)c(NC(=O)c2cn(C(C)(C)C)nc2F)cc1-c1cn2ccnc2c(N2CCOCC2)n1] | 1-(Tert-butyl)-3-fluoro-N-(2-fluoro-4-methyl-5-(8-morpholinoimidazo[1,2-a]pyrazin-6-yl)phenyl)-1H-pyrazole-4-carboxamide |
| 230 | 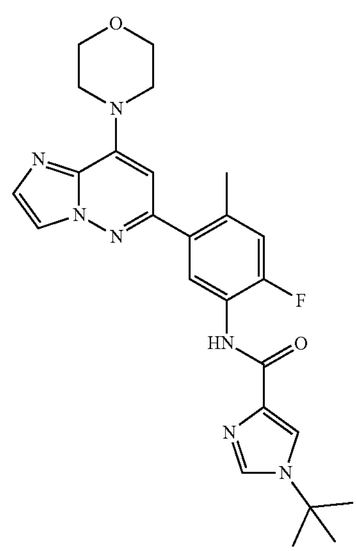 [SMILES: Cc1cc(F)c(NC(=O)c2cn(C(C)(C)C)cn2)cc1-c1cc(N2CCOCC2)c2nccn2n1] | 1-(Tert-butyl)-N-(2-fluoro-4-methyl-5-(8-morpholinoimidazo[1,2-b]pyridazin-6-yl)phenyl)-1H-imidazole-4-carboxamide |

TABLE 1-continued
| Synthetic Chemistry Example | Compound Structure | Compound Name |
|---|---|---|
| 231 | 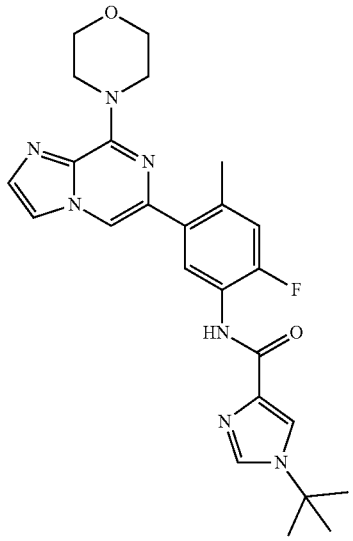 [SMILES: Cc1cc(F)c(NC(=O)c2cn(C(C)(C)C)cn2)cc1-c1cn2ccnc2c(N2CCOCC2)n1] | 1-(Tert-butyl)-N-(2-fluoro-4-methyl-5-(8-morpholinoimidazo[1,2-a]pyrazin-6-yl)phenyl)-1H-imidazole-4-carboxamide |
| 232 | 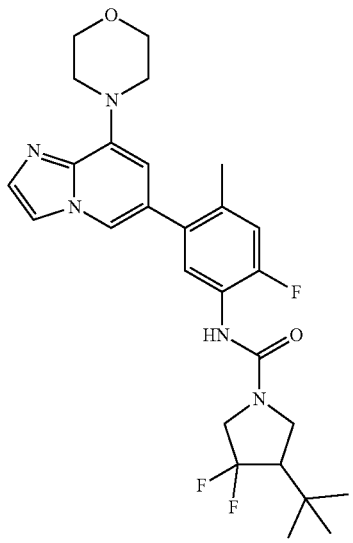 [SMILES: Cc1cc(F)c(NC(=O)N2CC(C(C)(C)C)C(F)(F)C2)cc1-c1cc(N2CCOCC2)c2nccn2c1] | 4-(Tert-butyl)-3,3-difluoro-N-(2-fluoro-4-methyl-5-(8-morpholinoimidazo[1,2-a]pyridin-6-yl)phenyl)pyrrolidine-1-carboxamide |

TABLE 1-continued

| Synthetic Chemistry Example | Compound Structure | Compound Name |
|---|---|---|
| 233 | 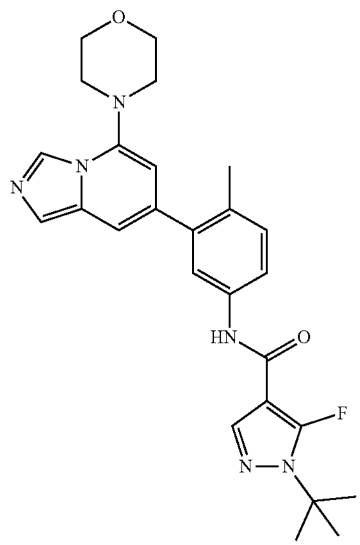 [SMILES: Cc1ccc(NC(=O)c2cnn(C(C)(C)C)c2F)cc1-c1cc(N2CCOCC2)n2cncc2c1] | 1-(Tert-butyl)-5-fluoro-N-(4-methyl-3-(5-morpholinoimidazo[1,5-a]pyridin-7-yl)phenyl)-1H-pyrazole-4-carboxamide |
| 234 | 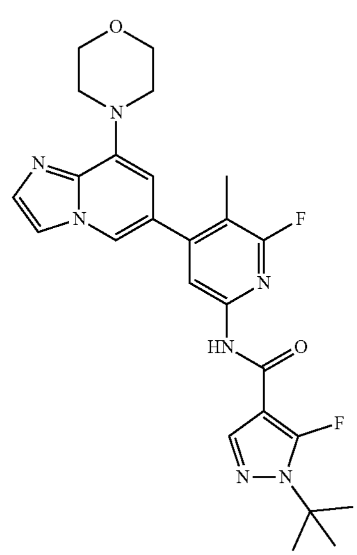 [SMILES: Cc1c(-c2cc(N3CCOCC3)c3nccn3c2)cc(NC(=O)c2cnn(C(C)(C)C)c2F)nc1F] | 1-(Tert-butyl)-5-fluoro-N-(6-fluoro-5-methyl-4-(8-morpholinoimidazo[1,2-a]pyridin-6-yl)pyridin-2-yl)-1H-pyrazole-4-carboxamide |

| Synthetic Chemistry Example | Compound Structure | Compound Name |
|---|---|---|
| 235 | 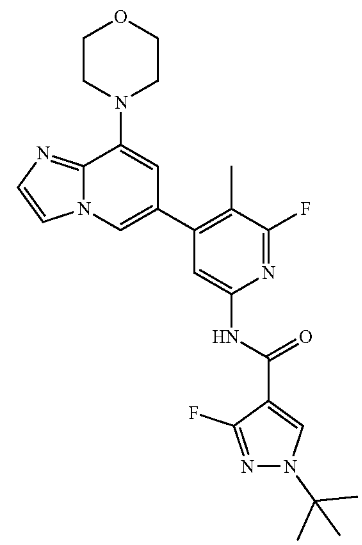 [SMILES: Cc1c(-c2cc(N3CCOCC3)c3nccn3c2)cc(NC(=O)c2cn(C(C)(C)C)nc2F)nc1F] | 1-(Tert-butyl)-3-fluoro-N-(6-fluoro-5-methyl-4-(8-morpholinoimidazo[1,2-a]pyridin-6-yl)pyridin-2-yl)-1H-pyrazole-4-carboxamide |
| 236 | 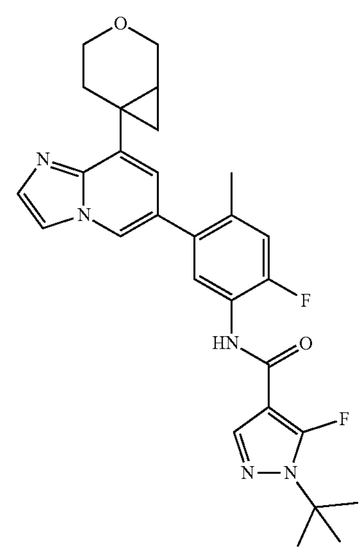 [SMILES: Cc1cc(F)c(NC(=O)c2cnn(C(C)(C)C)c2F)cc1-c1cc(C23CCOCC2C3)c2nccn2c1] | 1-(tert-Butyl)-5-fluoro-N-(2-fluoro-4-methyl-5-(8-morpholinoimidazo[1,2-a]pyrazin-6-yl)phenyl)-1H-pyrazole-4-carboxamide |

TABLE 1-continued
| Synthetic Chemistry Example | Compound Structure | Compound Name |
|---|---|---|
| 237 | 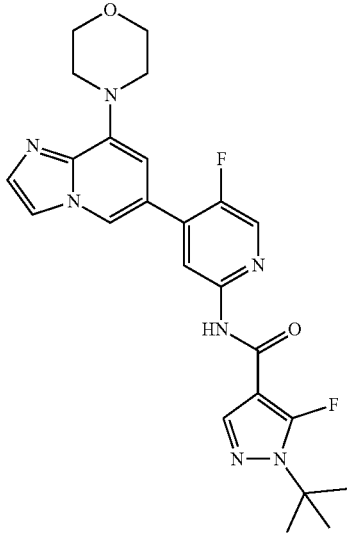 | 1-(Tert-butyl)-5-fluoro-N-(5-fluoro-4-(8-morpholinoimidazo[1,2-a]pyridin-6-yl)pyridin-2-yl)-1H-pyrazole-4-carboxamide |
| 238 | 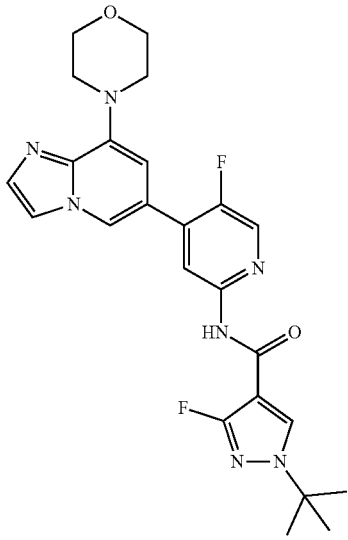 | 1-(Tert-butyl)-3-fluoro-N-(5-fluoro-4-(8-morpholinoimidazo[1,2-a]pyridin-6-yl)pyridin-2-yl)-1H-pyrazole-4-carboxamide |

TABLE 1-continued
| Synthetic Chemistry Example | Compound Structure | Compound Name |
|---|---|---|
| 239 | 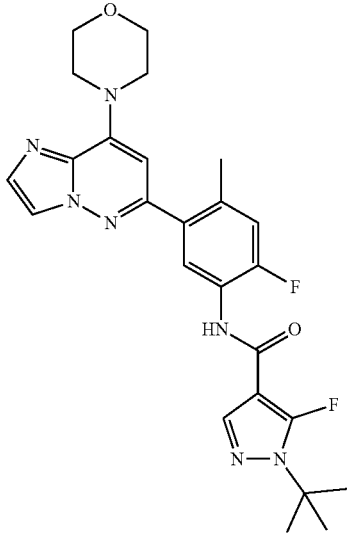 [SMILES: Cc1cc(F)c(NC(=O)c2cnn(C(C)(C)C)c2F)cc1-c1cc(N2CCOCC2)c2nccn2n1] | 1-(tert-Butyl)-5-fluoro-N-(2-fluoro-4-methyl-5-(8-morpholinoimidazo[1,2-b]pyridazin-6-yl)phenyl)-1H-pyrazole-4-carboxamide |
| 240 | 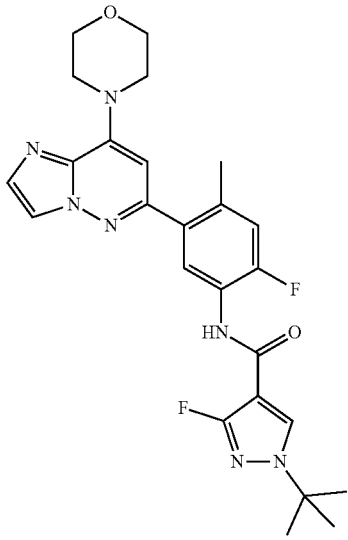 [SMILES: Cc1cc(F)c(NC(=O)c2cn(C(C)(C)C)nc2F)cc1-c1cc(N2CCOCC2)c2nccn2n1] | 1-(Tert-butyl)-3-fluoro-N-(2-fluoro-4-methyl-5-(8-morpholinoimidazo[1,2-b]pyridazin-6-yl)phenyl)-1H-pyrazole-4-carboxamide |

TABLE 1-continued
| Synthetic Chemistry Example | Compound Structure | Compound Name |
|---|---|---|
| 241 | 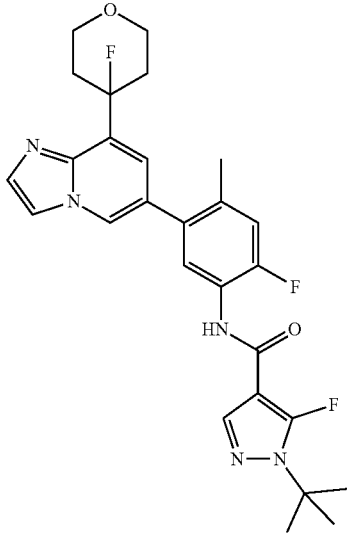 | 1-(Tert-butyl)-5-fluoro-N-(2-fluoro-5-(8-(4-fluorotetrahydro-2H-pyran-4-yl)imidazo[1,2-a]pyridin-6-yl)-4-methylphenyl)-1H-pyrazole-4-carboxamide |
| 242 | 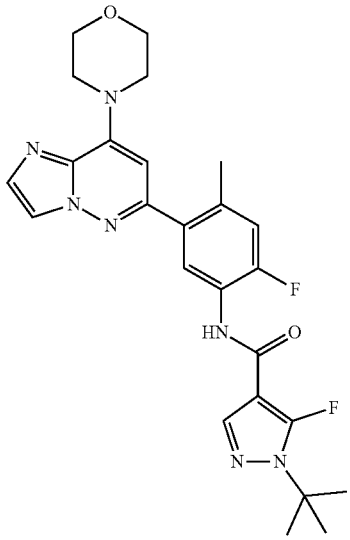 [SMILES: Cc1cc(F)c(NC(=O)c2cnn(C(C)(C)C)c2F)cc1-c1cc(N2CCOCC2)c2nccn2n1] | 1-(tert-Butyl)-5-fluoro-N-(2-fluoro-4-methyl-5-(8-(tetrahydro-2H-pyran-4-yl)imidazo[1,2-b]pyridazin-6-yl)phenyl)-1H-pyrazole-4-carboxamide |

TABLE 1-continued
| Synthetic Chemistry Example | Compound Structure | Compound Name |
|---|---|---|
| 243 | 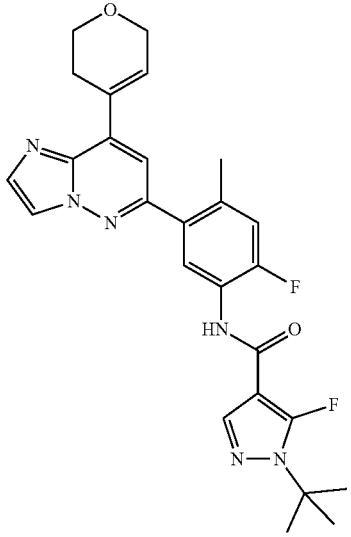 [SMILES: Cc1cc(F)c(NC(=O)c2cnn(C(C)(C)C)c2F)cc1-c1cc(C2=CCOCC2)c2nccn2n1] | 1-(Tert-butyl)-N-(5-(8-(3,6-dihydro-2H-pyran-4-yl)imidazo[1,2-b]pyridazin-6-yl)-2-fluoro-4-methylphenyl)-5-fluoro-1H-pyrazole-4-carboxamide |
| 244 | 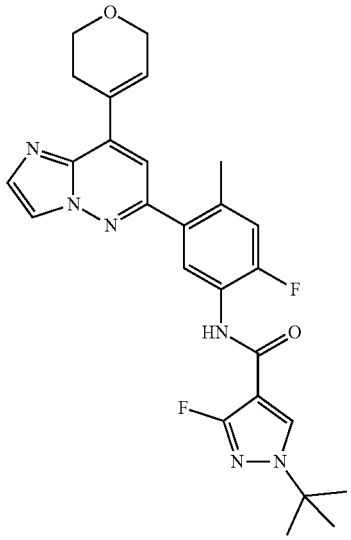 [SMILES: Cc1cc(F)c(NC(=O)c2cn(C(C)(C)C)nc2F)cc1-c1cc(C2=CCOCC2)c2nccn2n1] | 1-(Tert-butyl)-N-(5-(8-(3,6-dihydro-2H-pyran-4-yl)imidazo[1,2-b]pyridazin-6-yl)-2-fluoro-4-methylphenyl)-3-fluoro-1H-pyrazole-4-carboxamide |

TABLE 1-continued
| Synthetic Chemistry Example | Compound Structure | Compound Name |
|---|---|---|
| 245 | 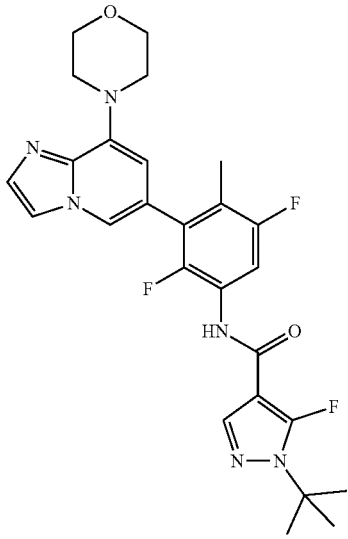 [SMILES: Cc1c(F)cc(NC(=O)c2cnn(C(C)(C)C)c2F)c(F)c1-c1cc(N2CCOCC2)c2nccn2c1] | 1-(Tert-butyl)-N-(2,5-difluoro-4-methyl-3-(8-morpholinoimidazo[1,2-a]pyridin-6-yl)phenyl)-5-fluoro-1H-pyrazole-4-carboxamide |
| 246 | 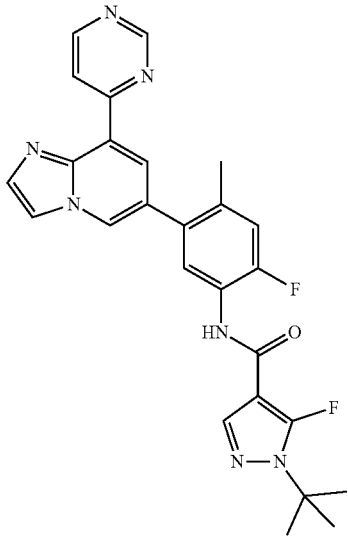 [SMILES: Cc1cc(F)c(NC(=O)c2cnn(C(C)(C)C)c2F)cc1-c1cc(-c2ccncn2)c2nccn2c1] | 1-(Tert-butyl)-5-fluoro-N-(2-fluoro-4-methyl-5-(8-(pyrimidin-4-yl)imidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 247 | 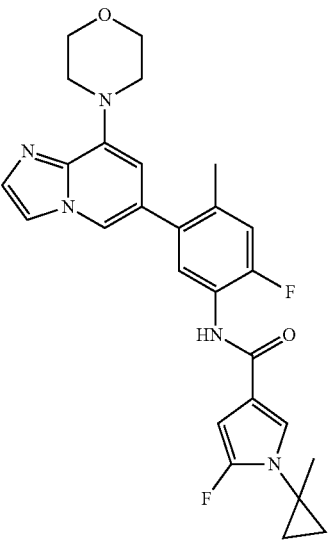 [SMILES: Cc1cc(F)c(NC(=O)c2cc(F)n(C3(C)CC3)c2)cc1-c1cc(N2CCOCC2)c2nccn2c1] | 5-Fluoro-N-{2-fluoro-4-methyl-5-[8-(morpholin-4-yl)imidazo[1,2-a]pyridin-6-yl]phenyl}-1-(1-methylcyclopropyl)pyrrole-3-carboxamide |
| 248 | 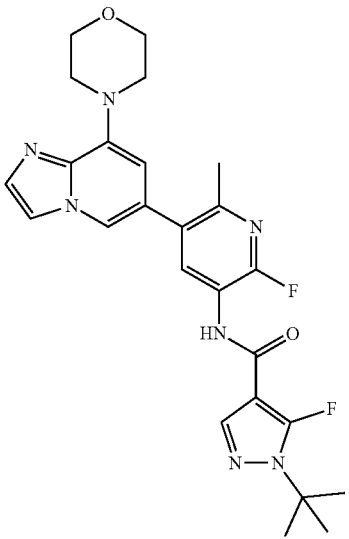 [SMILES: Cc1nc(F)c(NC(=O)c2cnn(C(C)(C)C)c2F)cc1-c1cc(N2CCOCC2)c2nccn2c1] | 1-(tert-Butyl)-5-fluoro-N-(2-fluoro-6-methyl-5-(8-morpholinoimidazo[1,2-a]pyridin-6-yl)pyridin-3-yl)-1H-pyrazole-4-carboxamide |

TABLE 1-continued
| Synthetic Chemistry Example | Compound Structure | Compound Name |
|---|---|---|
| 249 | 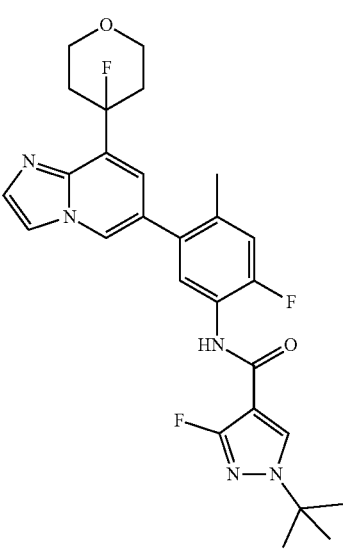 | 1-(Tert-butyl)-3-fluoro-N-(2-fluoro-5-(8-(4-fluorotetrahydro-2H-pyran-4-yl)imidazo[1,2-a]pyridin-6-yl)-4-methylphenyl)-1H-pyrazole-4-carboxamide |
| 250 | 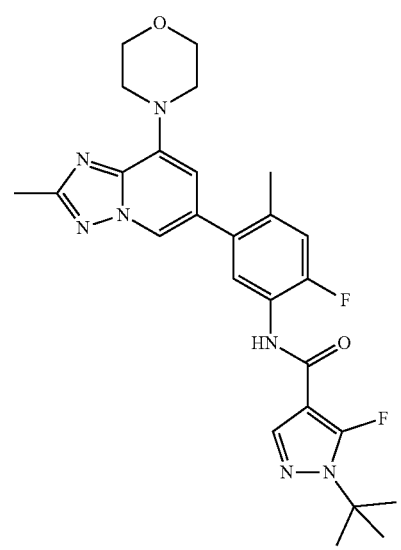 [SMILES: Cc1nc2c(N3CCOCC3)cc(-c3cc(NC(=O)c4cnn(C(C)(C)C)c4F)c(F)cc3C)cn2n1] | 1-(Tert-butyl)-5-fluoro-N-(2-fluoro-4-methyl-5-(2-methyl-8-morpholino-[1,2,4]triazolo[1,5-a]pyridin-6-yl)phenyl)-1H-pyrazole-4-carboxamide |

TABLE 1-continued

| Synthetic Chemistry Example | Compound Structure | Compound Name |
|---|---|---|
| 251 | 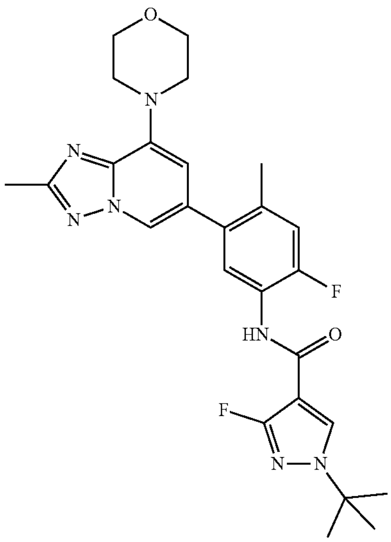 [SMILES: Cc1nc2c(N3CCOCC3)cc(-c3cc(NC(=O)c4cn(C(C)(C)C)nc4F)c(F)cc3C)cn2n1] | 1-Tert-butyl-3-fluoro-N-{2-fluoro-4-methyl-5-[2-methyl-8-(morpholin-4-yl)-[1,2,4]triazolo[1,5-a]pyridin-6-yl]phenyl}pyrazole-4-carboxamide |
| 252 | 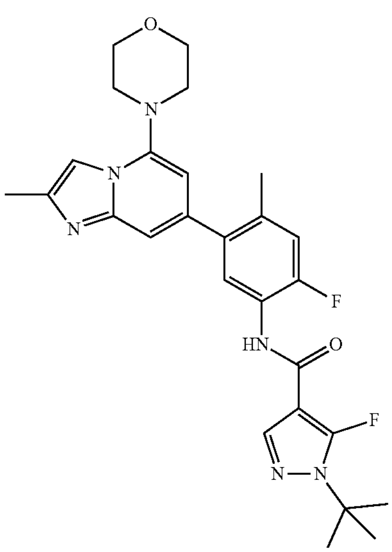 [SMILES: Cc1cn2c(N3CCOCC3)cc(-c3cc(NC(=O)c4cnn(C(C)(C)C)c4F)c(F)cc3C)cc2n1] | 1-(Tert-butyl)-5-fluoro-N-(2-fluoro-4-methyl-5-(2-methyl-5-morpholinoimidazo[1,2-a]pyridin-7-yl)phenyl)-1H-pyrazole-4-carboxamide |

TABLE 1-continued

| Synthetic Chemistry Example | Compound Structure | Compound Name |
|---|---|---|
| 253 | 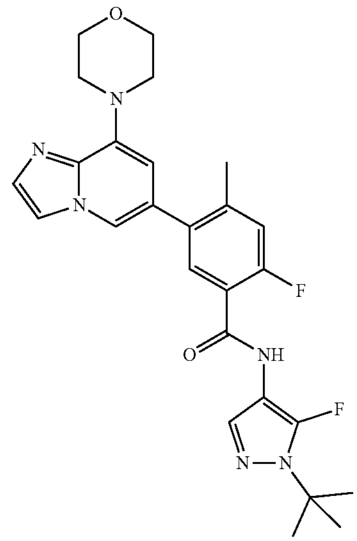 [SMILES: Cc1cc(F)c(C(=O)Nc2cnn(C(C)(C)C)c2F)cc1-c1cc(N2CCOCC2)c2nccn2c1] | 1-(tert-Butyl)-5-fluoro-N-(2-fluoro-4-methyl-5-(2-methyl-8-morpholino-[1,2,4]triazolo[1,5-a]pyridin-6-yl)phenyl)-1H-pyrazole-4-carboxamide |
| 254 | 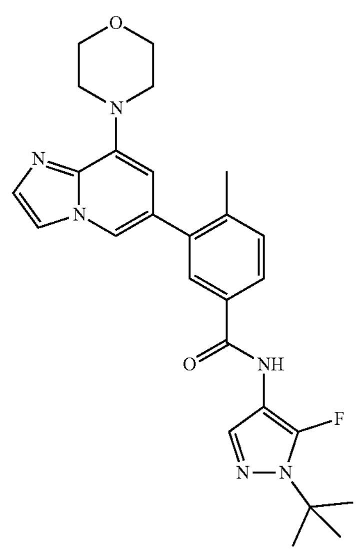 [SMILES: Cc1ccc(C(=O)Nc2cnn(C(C)(C)C)c2F)cc1-c1cc(N2CCOCC2)c2nccn2c1] | N-(1-(Tert-butyl)-5-fluoro-1H-pyrazol-4-yl)-4-methyl-3-(8-morpholinoimidazo[1,2-a]pyridin-6-yl)benzamide |

TABLE 1-continued
| Synthetic Chemistry Example | Compound Structure | Compound Name |
|---|---|---|
| 255 | 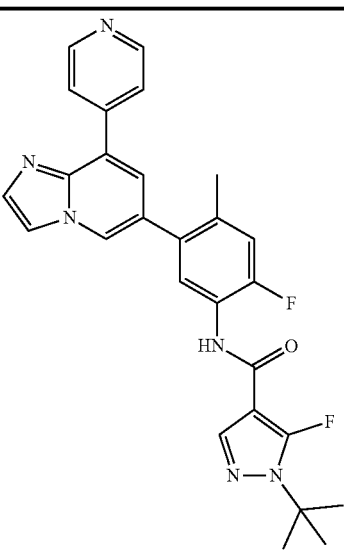 | 1-(Tert-butyl)-5-fluoro-N-(2-fluoro-4-methyl-5-(8-(pyridin-4-yl)imidazo[1,2-a]pyridin-6-yl)phenyl)-1H-pyrazole-4-carboxamide |
| 256 | 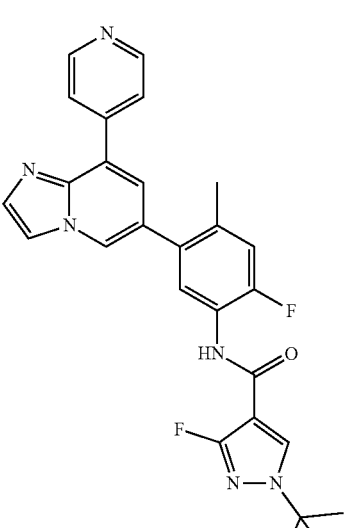 | 1-(Tert-butyl)-3-fluoro-N-(2-fluoro-4-methyl-5-(8-(pyridin-4-yl)imidazo[1,2-a]pyridin-6-yl)phenyl)-1H-pyrazole-4-carboxamide |

TABLE 1-continued
| Synthetic Chemistry Example | Compound Structure | Compound Name |
|---|---|---|
| 257 | 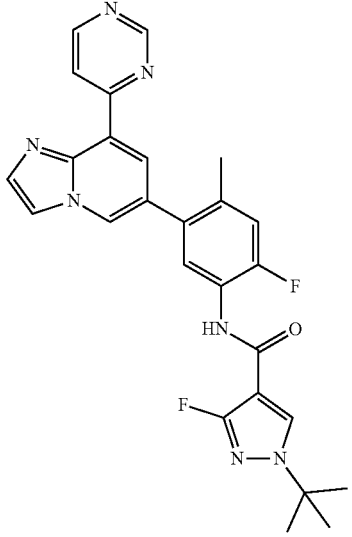 [SMILES: Cc1cc(F)c(NC(=O)c2cn(C(C)(C)C)nc2F)cc1-c1cc(-c2ccncn2)c2nccn2c1] | 1-(Tert-butyl)-3-fluoro-N-(2-fluoro-4-methyl-5-(8-(pyrimidin-4-yl)imidazo[1,2-a]pyridin-6-yl)phenyl)-1H-pyrazole-4-carboxamide |
| 258 | 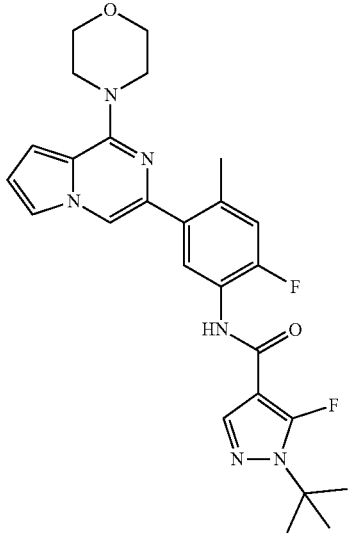 [SMILES: Cc1cc(F)c(NC(=O)c2cnn(C(C)(C)C)c2F)cc1-c1cn2cccc2c(N2CCOCC2)n1] | 1-(Tert-butyl)-5-fluoro-N-(2-fluoro-4-methyl-5-(1-morpholinopyrrolo[1,2-a]pyrazin-3-yl)phenyl)-1H-pyrazole-4-carboxamide |

TABLE 1-continued
| Synthetic Chemistry Example | Compound Structure | Compound Name |
|---|---|---|
| 259 | 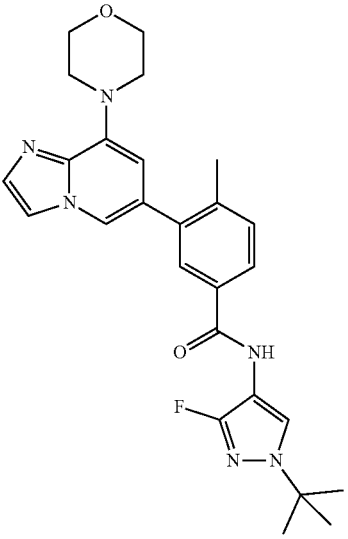 [SMILES: Cc1ccc(C(=O)Nc2cn(C(C)(C)C)nc2F)cc1-c1cc(N2CCOCC2)c2nccn2c1] | N-(1-(Tert-butyl)-3-fluoro-1H-pyrazol-4-yl)-4-methyl-3-(8-morpholinoimidazo[1,2-a]pyridin-6-yl)benzamide |
| 260 | 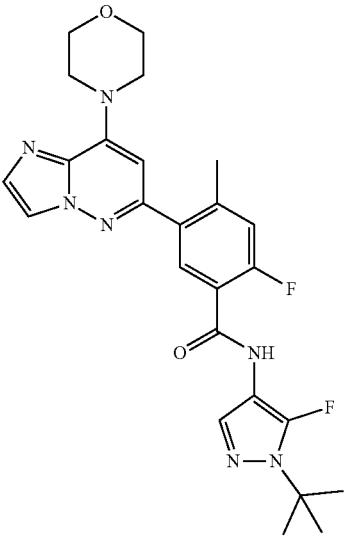 [SMILES: Cc1cc(F)c(C(=O)Nc2cnn(C(C)(C)C)c2F)cc1-c1cc(N2CCOCC2)c2nccn2n1] | N-(1-(tert-butyl)-5-fluoro-1H-pyrazol-4-yl)-2-fluoro-4-methyl-5-(8-morpholinoimidazo[1,2-b]pyridazin-6-yl)benzamide |

TABLE 1-continued
| Synthetic Chemistry Example | Compound Structure | Compound Name |
|---|---|---|
| 261 | 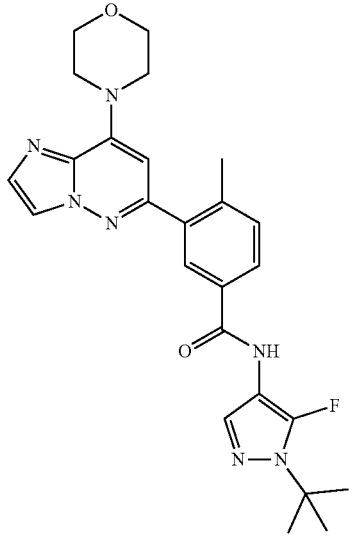 [SMILES: Cc1ccc(C(=O)Nc2cnn(C(C)(C)C)c2F)cc1-c1cc(N2CCOCC2)c2nccn2n1] | N-(1-(Tert-butyl)-5-fluoro-1H-pyrazol-4-yl)-4-methyl-3-(8-morpholinoimidazo[1,2-b]pyridazin-6-yl)benzamide |
| 262 | 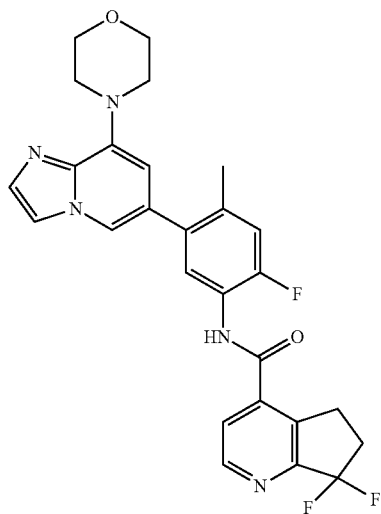 [SMILES: Cc1cc(F)c(NC(=O)c2ccnc3c2CCC3(F)F)cc1-c1cc(N2CCOCC2)c2nccn2c1] | 7,7-difluoro-N-(2-fluoro-4-methyl-5-(8-morpholinoimidazo[1,2-a]pyridin-6-yl)phenyl)-6,7-dihydro-5H-cyclopenta[b]pyridine-4-carboxamide |

| Synthetic Chemistry Example | Compound Structure | Compound Name |
|---|---|---|
| 263 | 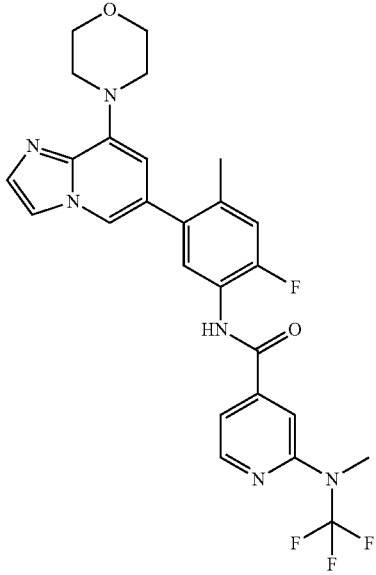 [SMILES: Cc1cc(F)c(NC(=O)c2ccnc(N(C)C(F)(F)F)c2)cc1-c1cc(N2CCOCC2)c2nccn2c1] | N-{2-Fluoro-4-methyl-5-[8-(morpholin-4-yl)imidazo[1,2-a]pyridin-6-yl]phenyl}-2-[methyl(trifluoromethyl)amino]pyridine-4-carboxamide |
| 264 | 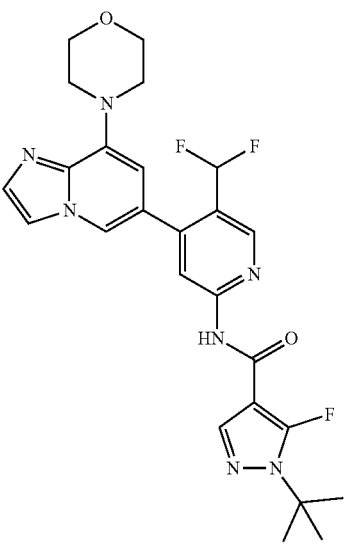 [SMILES: CC(C)(C)n1ncc(C(=O)Nc2cc(-c3cc(N4CCOCC4)c4nccn4c3)c(C(F)F)cn2)c1F] | 1-(Tert-butyl)-N-(5-(difluoromethyl)-4-(8-morpholinoimidazo[1,2-a]pyridin-6-yl)pyridin-2-yl)-5-fluoro-1H-pyrazole-4-carboxamide |

TABLE 1-continued
| Synthetic Chemistry Example | Compound Structure | Compound Name |
|---|---|---|
| 265 | 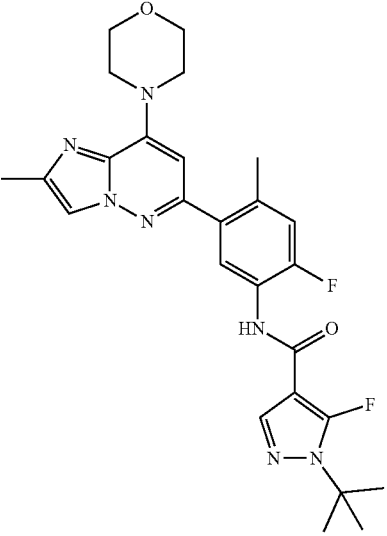 [SMILES: Cc1cn2nc(-c3cc(NC(=O)c4cnn(C(C)(C)C)c4F)c(F)cc3C)cc(N3CCOCC3)c2n1] | 1-(tert-Butyl)-5-fluoro-N-(2-fluoro-4-methyl-5-(2-methyl-8-morpholinoimidazo[1,2-b]pyridazin-6-yl)phenyl)-1H-pyrazole-4-carboxamide |
| 266 | 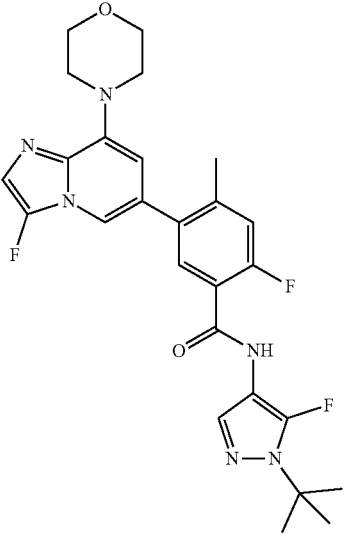 [SMILES: Cc1cc(F)c(C(=O)Nc2cnn(C(C)(C)C)c2F)cc1-c1cc(N2CCOCC2)c2ncc(F)n2c1] | N-(1-(tert-butyl)-5-fluoro-1H-pyrazol-4-yl)-2-fluoro-5-(3-fluoro-8-morpholinoimidazo[1,2-a]pyridin-6-yl)-4-methylbenzamide |

TABLE 1-continued
| Synthetic Chemistry Example | Compound Structure | Compound Name |
|---|---|---|
| 267 | 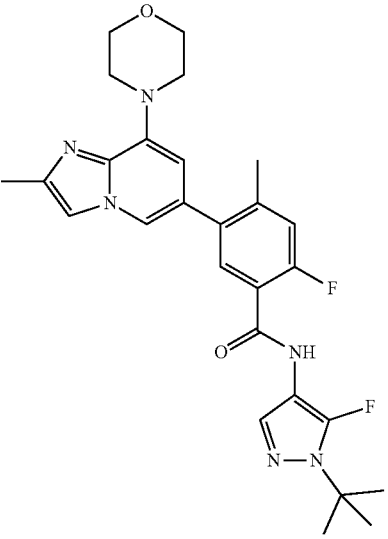 [SMILES: Cc1cn2cc(-c3cc(C(=O)Nc4cnn(C(C)(C)C)c4F)c(F)cc3C)cc(N3CCOCC3)c2n1] | N-(1-(tert-butyl)-5-fluoro-1H-pyrazol-4-yl)-2-fluoro-4-methyl-5-(2-methyl-8-morpholinoimidazo[1,2-a]pyridin-6-yl)benzamide |
| 268 | 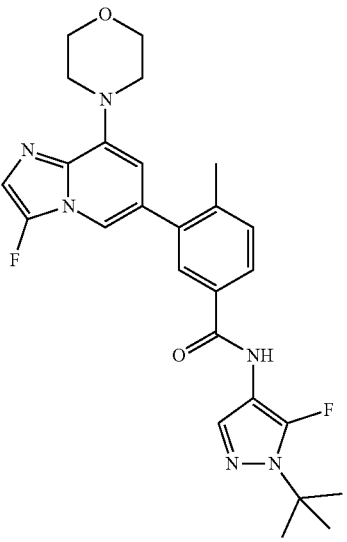 [SMILES: Cc1ccc(C(=O)Nc2cnn(C(C)(C)C)c2F)cc1-c1cc(N2CCOCC2)c2ncc(F)n2c1] | N-(1-(Tert-butyl)-5-fluoro-1H-pyrazol-4-yl)-3-(3-fluoro-8-morpholinoimidazo[1,2-a]pyridin-6-yl)-4-methylbenzamide |

TABLE 1-continued

| Synthetic Chemistry Example | Compound Structure | Compound Name |
|---|---|---|
| 269 | 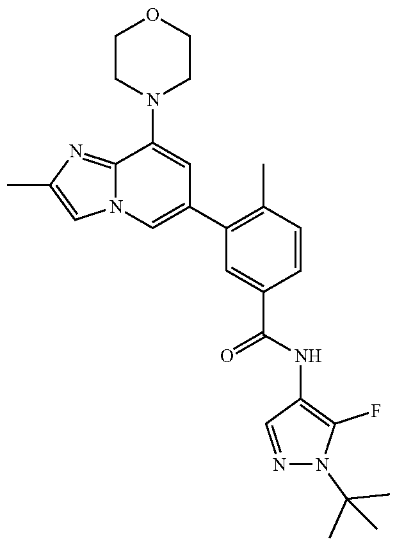 [SMILES: Cc1cn2cc(-c3cc(C(=O)Nc4cnn(C(C)(C)C)c4F)ccc3C)cc(N3CCOCC3)c2n1] | N-(1-(Tert-butyl)-5-fluoro-1H-pyrazol-4-yl)-4-methyl-3-(2-methyl-8-morpholinoimidazo[1,2-a]pyridin-6-yl)benzamide |
| 270 | 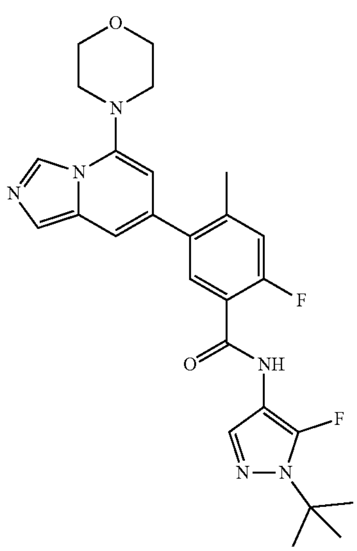 [SMILES: Cc1cc(F)c(C(=O)Nc2cnn(C(C)(C)C)c2F)cc1-c1cc(N2CCOCC2)n2cncc2c1] | N-(1-(Tert-butyl)-5-fluoro-1H-pyrazol-4-yl)-2-fluoro-4-methyl-5-(5-morpholinoimidazo[1,5-a]pyridin-7-yl)benzamide |

TABLE 1-continued
| Synthetic Chemistry Example | Compound Structure | Compound Name |
|---|---|---|
| 271 | 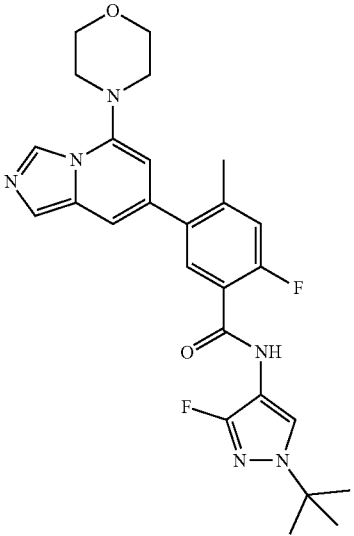 [SMILES: Cc1cc(F)c(C(=O)Nc2cn(C(C)(C)C)nc2F)cc1-c1cc(N2CCOCC2)n2cncc2c1] | N-(1-(Tert-butyl)-3-fluoro-1H-pyrazol-4-yl)-2-fluoro-4-methyl-5-(5-morpholinoimidazo[1,5-a]pyridin-7-yl)benzamide |
| 272 | 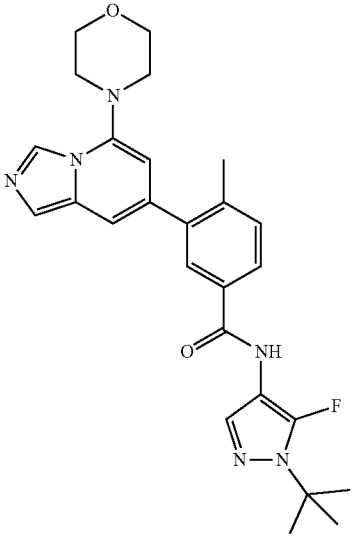 [SMILES: Cc1ccc(C(=O)Nc2cnn(C(C)(C)C)c2F)cc1-c1cc(N2CCOCC2)n2cncc2c1] | N-(1-(Tert-butyl)-5-fluoro-1H-pyrazol-4-yl)-4-methyl-3-(5-morpholinoimidazo[1,5-a]pyridin-7-yl)benzamide |

TABLE 1-continued

| Synthetic Chemistry Example | Compound Structure | Compound Name |
|---|---|---|
| 273 | 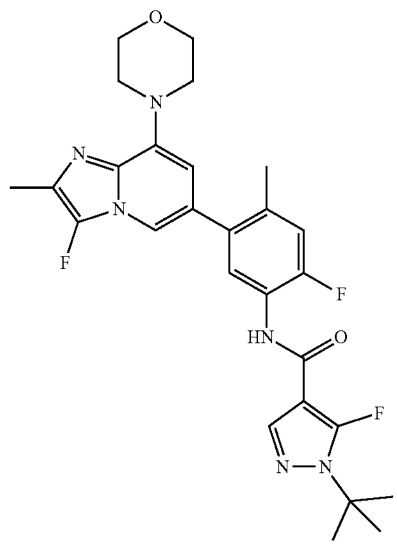 [SMILES: Cc1cc(F)c(NC(=O)c2cnn(C(C)(C)C)c2F)cc1-c1cc(N2CCOCC2)c2nc(C)c(F)n2c1] | 1-(tert-Butyl)-5-fluoro-N-(2-fluoro-5-(3-fluoro-2-methyl-8-morpholinoimidazo[1,2-a]pyridin-6-yl)-4-methylphenyl)-1H-pyrazole-4-carboxamide |
| 274 | 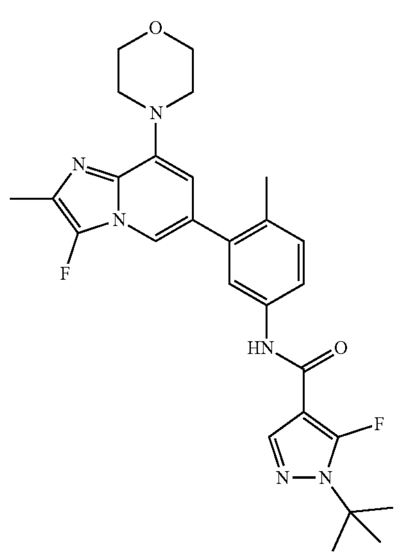 [SMILES: Cc1ccc(NC(=O)c2cnn(C(C)(C)C)c2F)cc1-c1cc(N2CCOCC2)c2nc(C)c(F)n2c1] | 1-(tert-Butyl)-5-fluoro-N-(3-(3-fluoro-2-methyl-8-morpholinoimidazo[1,2-a]pyridin-6-yl)-4-methylphenyl)-1H-pyrazole-4-carboxamide |

TABLE 1-continued
| Synthetic Chemistry Example | Compound Structure | Compound Name |
|---|---|---|
| 275 | 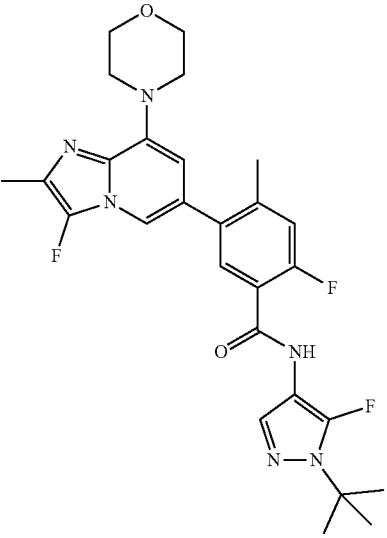 [SMILES: Cc1cc(F)c(C(=O)Nc2cnn(C(C)(C)C)c2F)cc1-c1cc(N2CCOCC2)c2nc(C)c(F)n2c1] | 1-(tert-Butyl)-5-fluoro-N-(3-(3-fluoro-2-methyl-8-morpholinoimidazo[1,2-a]pyridin-6-yl)-4-methylphenyl)-1H-pyrazole-4-carboxamide |
| 276 | 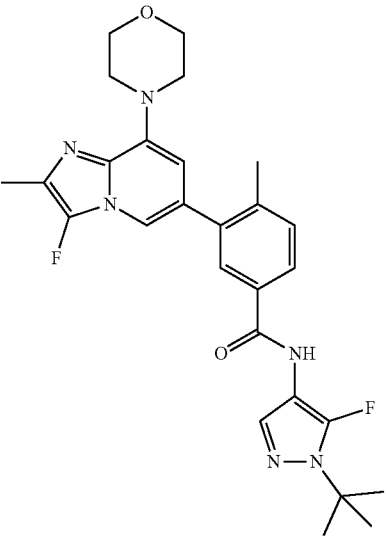 [SMILES: Cc1ccc(C(=O)Nc2cnn(C(C)(C)C)c2F)cc1-c1cc(N2CCOCC2)c2nc(C)c(F)n2c1] | N-(1-(Tert-butyl)-5-fluoro-1H-pyrazol-4-yl)-3-(3-fluoro-2-methyl-8-morpholinoimidazo[1,2-a]pyridin-6-yl)-4-methylbenzamide |

TABLE 1-continued
| Synthetic Chemistry Example | Compound Structure | Compound Name |
|---|---|---|
| 277 | 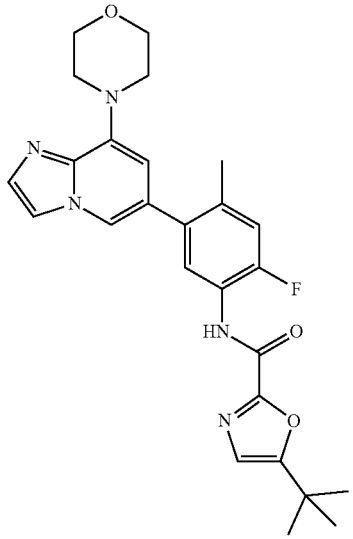 [SMILES: Cc1cc(F)c(NC(=O)c2ncc(C(C)(C)C)o2)cc1-c1cc(N2CCOCC2)c2nccn2c1] | 5-(Tert-butyl)-N-(2-fluoro-4-methyl-5-(8-morpholinoimidazo[1,2-a]pyridin-6-yl)phenyl)oxazole-2-carboxamide |
| 278 | 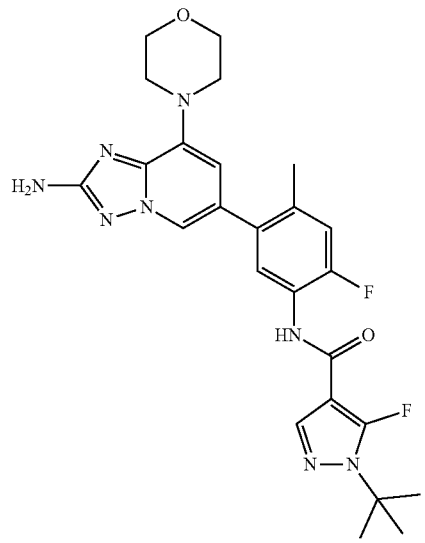 [SMILES: Cc1cc(F)c(NC(=O)c2cnn(C(C)(C)C)c2F)cc1-c1cc(N2CCOCC2)c2nc(N)nn2c1] | N-(5-(2-amino-8-morpholino-[1,2,4]triazolo[1,5-a]pyridin-6-yl)-2-fluoro-4-methylphenyl)-1-(tert-butyl)-5-fluoro-1H-pyrazole-4-carboxamide |

TABLE 1-continued
| Synthetic Chemistry Example | Compound Structure | Compound Name |
|---|---|---|
| 279 | 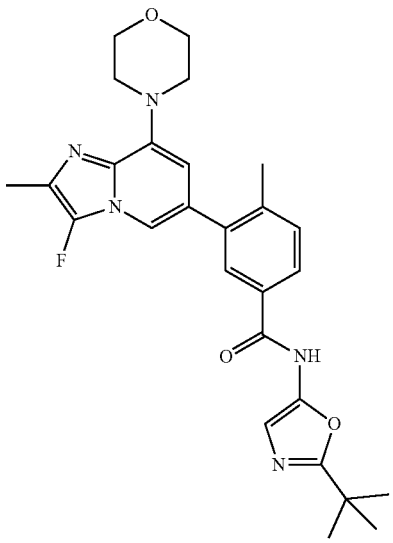 [SMILES: Cc1ccc(C(=O)Nc2cnc(C(C)(C)C)o2)cc1-c1cc(N2CCOCC2)c2nc(C)c(F)n2c1] | N-(2-(Tert-butyl)oxazol-5-yl)-3-(3-fluoro-2-methyl-8-morpholinoimidazo[1,2-a]pyridin-6-yl)-4-methylbenzamide |
| 280 | 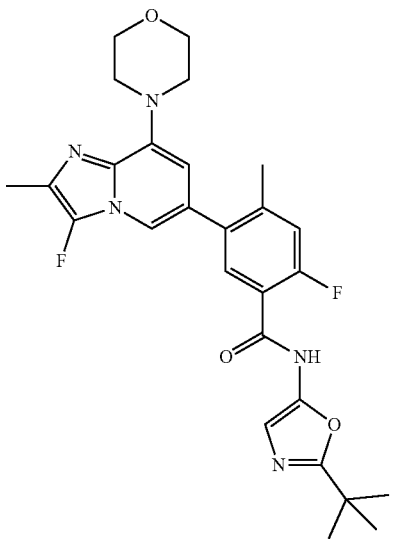 [SMILES: Cc1cc(F)c(C(=O)Nc2cnc(C(C)(C)C)o2)cc1-c1cc(N2CCOCC2)c2nc(C)c(F)n2c1] | N-(2-(Tert-butyl)oxazol-5-yl)-2-fluoro-5-(3-fluoro-2-methyl-8-morpholinoimidazo[1,2-a]pyridin-6-yl)-4-methylbenzamide |

TABLE 1-continued
| Synthetic Chemistry Example | Compound Structure | Compound Name |
|---|---|---|
| 281 | 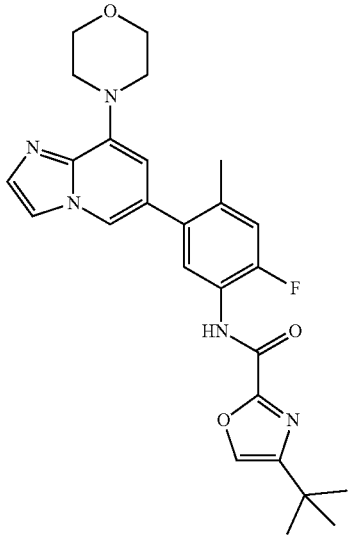 [SMILES: Cc1cc(F)c(NC(=O)c2nc(C(C)(C)C)co2)cc1-c1cc(N2CCOCC2)c2nccn2c1] | 4-(Tert-butyl)-N-(2-fluoro-4-methyl-5-(8-morpholinoimidazo[1,2-a]pyridin-6-yl)phenyl)oxazole-2-carboxamide |
| 282 | 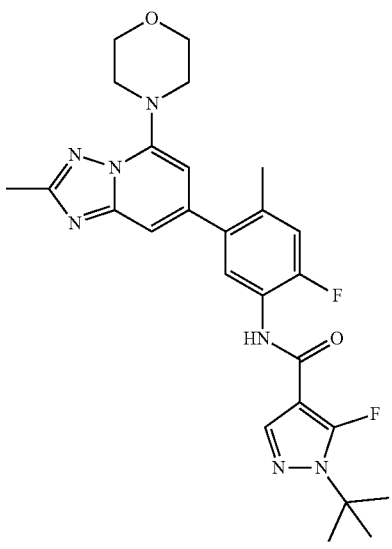 [SMILES: Cc1nc2cc(-c3cc(NC(=O)c4cnn(C(C)(C)C)c4F)c(F)cc3C)cc(N3CCOCC3)n2n1] | 1-(tert-Butyl)-5-fluoro-N-(2-fluoro-4-methyl-5-(2-methyl-5-morpholino-[1,2,4]triazolo[1,5-a]pyridin-7-yl)phenyl)-1H-pyrazole-4-carboxamide |

TABLE 1-continued
| Synthetic Chemistry Example | Compound Structure | Compound Name |
|---|---|---|
| 283 | 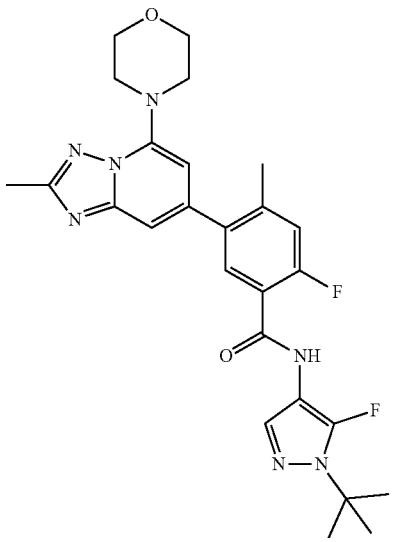 [SMILES: Cc1nc2cc(-c3cc(C(=O)Nc4cnn(C(C)(C)C)c4F)c(F)cc3C)cc(N3CCOCC3)n2n1] | N-(1-(tert-butyl)-5-fluoro-1H-pyrazol-4-yl)-2-fluoro-4-methyl-5-(2-methyl-5-morpholino-[1,2,4]triazolo[1,5-a]pyridin-7-yl)benzamide |
| 284 | 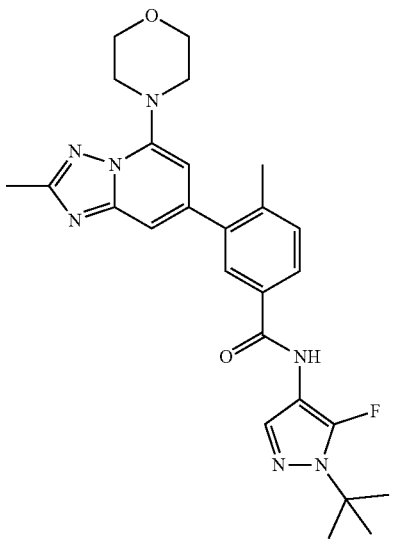 [SMILES: Cc1nc2cc(-c3cc(C(=O)Nc4cnn(C(C)(C)C)c4F)ccc3C)cc(N3CCOCC3)n2n1] | N-(1-(Tert-butyl)-5-fluoro-1H-pyrazol-4-yl)-4-methyl-3-(2-methyl-5-morpholino-[1,2,4]triazolo[1,5-a]pyridin-7-yl)benzamide |

TABLE 1-continued
| Synthetic Chemistry Example | Compound Structure | Compound Name |
|---|---|---|
| 285 | 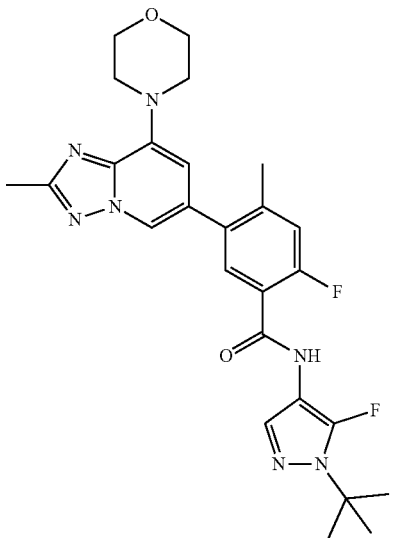 [SMILES: Cc1nc2c(N3CCOCC3)cc(-c3cc(C(=O)Nc4cnn(C(C)(C)C)c4F)c(F)cc3C)cn2n1] | N-(1-(tert-Butyl)-5-fluoro-1H-pyrazol-4-yl)-2-fluoro-4-methyl-5-(2-methyl-8-morpholino-[1,2,4]triazolo[1,5-a]pyridin-6-yl)benzamide |
| 286 | 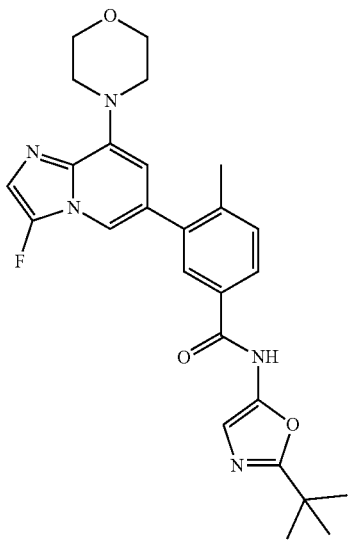 [SMILES: Cc1ccc(C(=O)Nc2cnc(C(C)(C)C)o2)cc1-c1cc(N2CCOCC2)c2ncc(F)n2c1] | N-(2-(Tert-butyl)oxazol-5-yl)-3-(3-fluoro-8-morpholinoimidazo[1,2-a]pyridin-6-yl)-4-methylbenzamide |

TABLE 1-continued
| Synthetic Chemistry Example | Compound Structure | Compound Name |
|---|---|---|
| 287 | 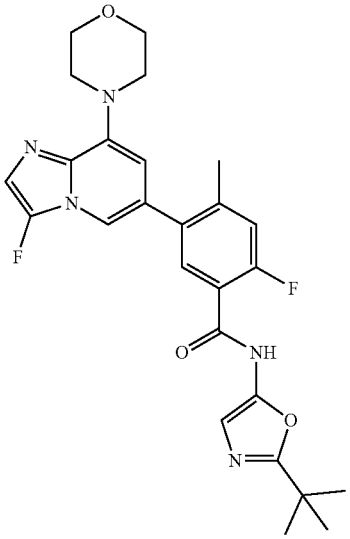 [SMILES: Cc1cc(F)c(C(=O)Nc2cnc(C(C)(C)C)o2)cc1-c1cc(N2CCOCC2)c2ncc(F)n2c1] | N-(2-(Tert-butyl)oxazol-5-yl)-2-fluoro-5-(3-fluoro-8-morpholinoimidazo[1,2-a]pyridin-6-yl)-4-methylbenzamide |
| 288 | 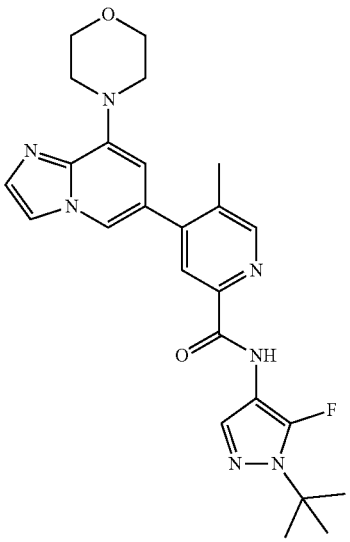 [SMILES: Cc1cnc(C(=O)Nc2cnn(C(C)(C)C)c2F)cc1-c1cc(N2CCOCC2)c2nccn2c1] | N-(1-(Tert-butyl)-5-fluoro-1H-pyrazol-4-yl)-5-methyl-4-(8-morpholinoimidazo[1,2-a]pyridin-6-yl)picolinamide |

TABLE 1-continued

| Synthetic Chemistry Example | Compound Structure | Compound Name |
| --- | --- | --- |
| 289 | 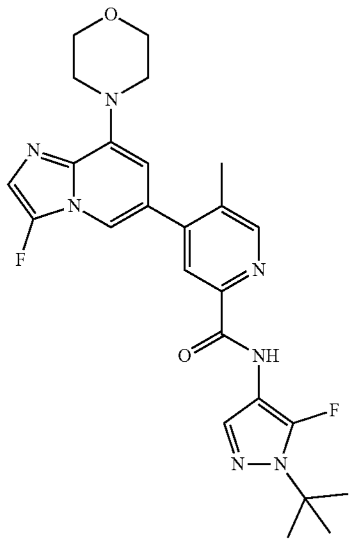 [SMILES: Cc1cnc(C(=O)Nc2cnn(C(C)(C)C)c2F)cc1-c1cc(N2CCOCC2)c2ncc(F)n2c1] | N-(1-(Tert-butyl)-5-fluoro-1H-pyrazol-4-yl)-4-(3-fluoro-8-morpholinoimidazo[1,2-a]pyridin-6-yl)-5-methylpicolinamide |
| 290 | 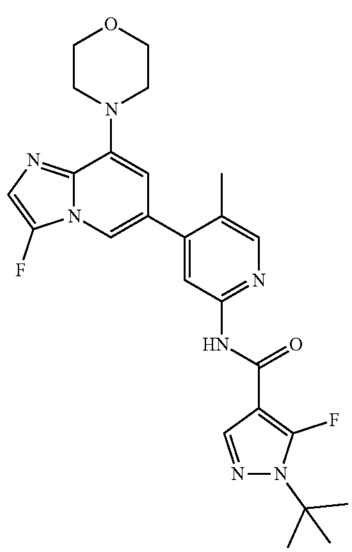 [SMILES: Cc1cnc(NC(=O)c2cnn(C(C)(C)C)c2F)cc1-c1cc(N2CCOCC2)c2ncc(F)n2c1] | 1-(Tert-butyl)-5-fluoro-N-(4-(3-fluoro-8-morpholinoimidazo[1,2-a]pyridin-6-yl)-5-methylpyridin-2-yl)-1H-pyrazole-4-carboxamide |

TABLE 1-continued
| Synthetic Chemistry Example | Compound Structure | Compound Name |
|---|---|---|
| 291 | 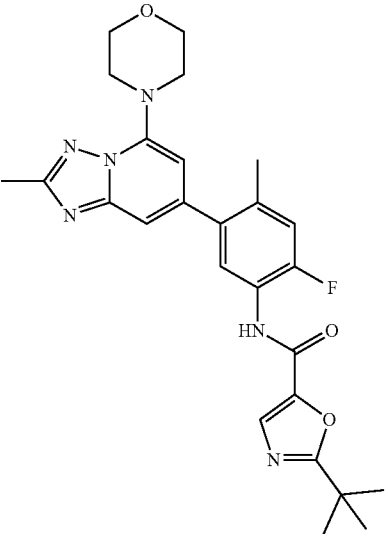 [SMILES: Cc1nc2cc(-c3cc(NC(=O)c4cnc(C(C)(C)C)o4)c(F)cc3C)cc(N3CCOCC3)n2n1] | 2-Tert-butyl-N-{2-fluoro-4-methyl-5-[2-methyl-5-(morpholin-4-yl)-[1,2,4]triazolo[1,5-a]pyridin-7-yl]phenyl}-1,3-oxazole-5-carboxamide |
| 292 | 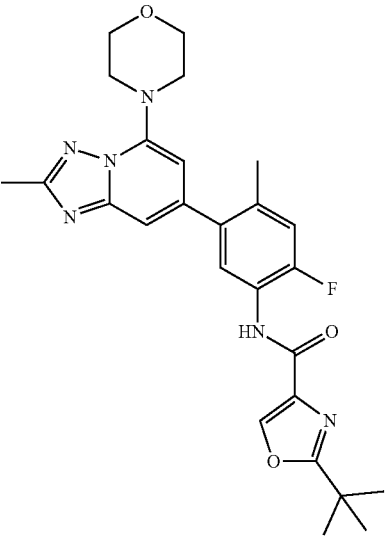 [SMILES: Cc1nc2cc(-c3cc(NC(=O)c4coc(C(C)(C)C)n4)c(F)cc3C)cc(N3CCOCC3)n2n1] | 2-Tert-butyl-N-{2-fluoro-4-methyl-5-[2-methyl-5-(morpholin-4-yl)-[1,2,4]triazolo[1,5-a]pyridin-7-yl]phenyl}-1,3-oxazole-4-carboxamide |

TABLE 1-continued
| Synthetic Chemistry Example | Compound Structure | Compound Name |
|---|---|---|
| 293 | 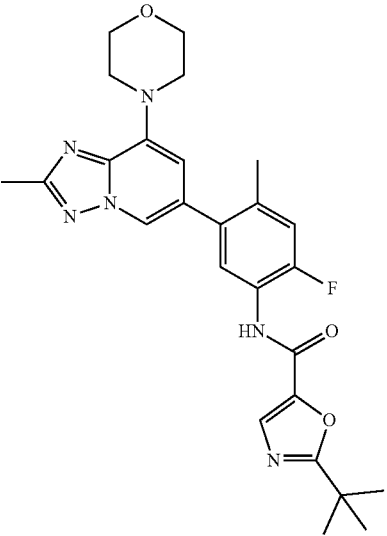 [SMILES: Cc1nc2c(N3CCOCC3)cc(-c3cc(NC(=O)c4cnc(C(C)(C)C)o4)c(F)cc3C)cn2n1] | 2-(Tert-butyl)-N-(2-fluoro-4-methyl-5-(2-methyl-8-morpholino-[1,2,4]triazolo[1,5-a]pyridin-6-yl)phenyl)oxazole-5-carboxamide |
| 294 | 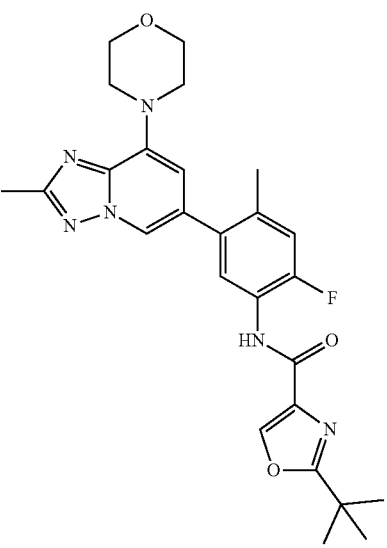 [SMILES: Cc1nc2c(N3CCOCC3)cc(-c3cc(NC(=O)c4coc(C(C)(C)C)n4)c(F)cc3C)cn2n1] | 2-Tert-butyl-N-{2-fluoro-4-methyl-5-[2-methyl-8-(morpholin-4-yl)-[1,2,4]triazolo[1,5-a]pyridin-6-yl]phenyl}-1,3-oxazole-4-carboxamide |

TABLE 1-continued
| Synthetic Chemistry Example | Compound Structure | Compound Name |
|---|---|---|
| 295 | 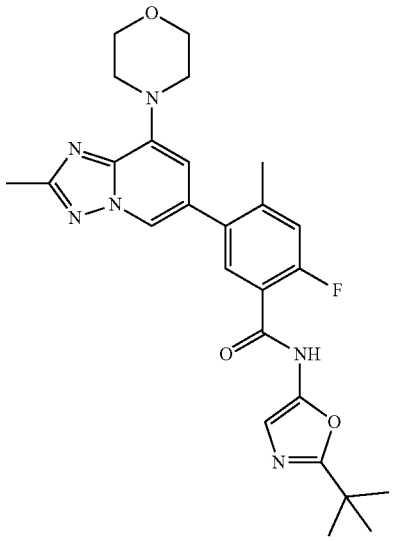 [SMILES: Cc1nc2c(N3CCOCC3)cc(-c3cc(C(=O)Nc4cnc(C(C)(C)C)o4)c(F)cc3C)cn2n1] | N-(2-(Tert-butyl)oxazol-5-yl)-2-fluoro-4-methyl-5-(2-methyl-8-morpholino-[1,2,4]triazolo[1,5-a]pyridin-6-yl)benzamide |
| 296 | 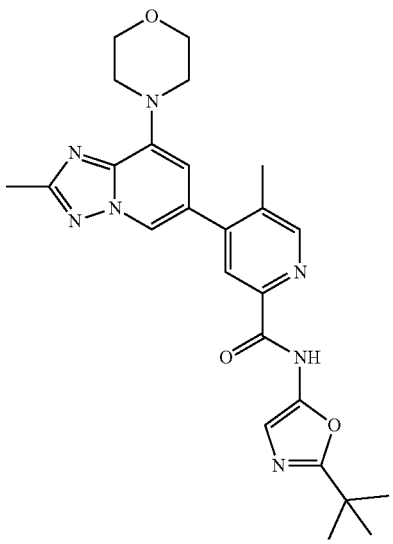 [SMILES: Cc1nc2c(N3CCOCC3)cc(-c3cc(C(=O)Nc4cnc(C(C)(C)C)o4)ncc3C)cn2n1] | N-(2-Tert-butyl-1,3-oxazol-5-yl)-5-methyl-4-[2-methyl-8-(morpholin-4-yl)-[1,2,4]triazolo[1,5-a]pyridin-6-yl]pyridine-2-carboxamide |

TABLE 1-continued
| Synthetic Chemistry Example | Compound Structure | Compound Name |
|---|---|---|
| 297 | 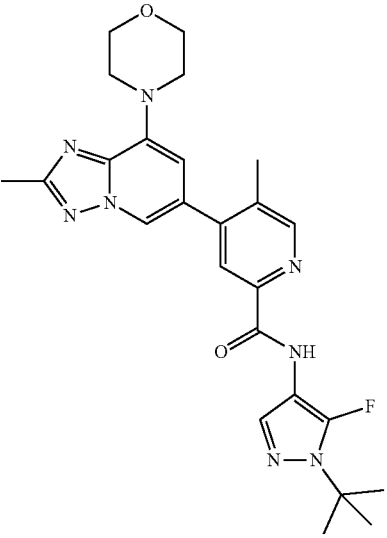 [SMILES: Cc1nc2c(N3CCOCC3)cc(-c3cc(C(=O)Nc4cnn(C(C)(C)C)c4F)ncc3C)cn2n1] | N-(1-Tert-butyl-5-fluoropyrazol-4-yl)-5-methyl-4-[2-methyl-8-(morpholin-4-yl)-[1,2,4]triazolo[1,5-a]pyridin-6-yl]pyridine-2-carboxamide |
| 298 | 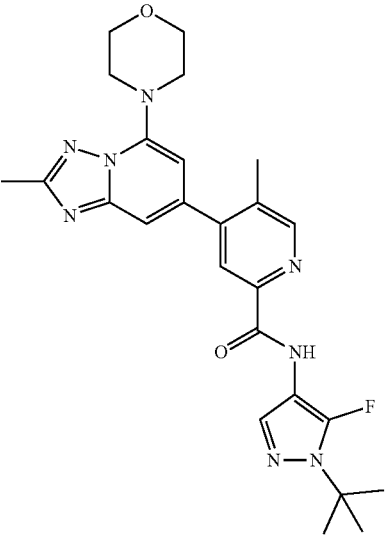 [SMILES: Cc1nc2cc(-c3cc(C(=O)Nc4cnn(C(C)(C)C)c4F)ncc3C)cc(N3CCOCC3)n2n1] | N-(1-Tert-butyl-5-fluoropyrazol-4-yl)-5-methyl-4-[2-methyl-5-(morpholin-4-yl)-[1,2,4]triazolo[1,5-a]pyridin-7-yl]pyridine-2-carboxamide |

TABLE 1-continued

| Synthetic Chemistry Example | Compound Structure | Compound Name |
|---|---|---|
| 299 | 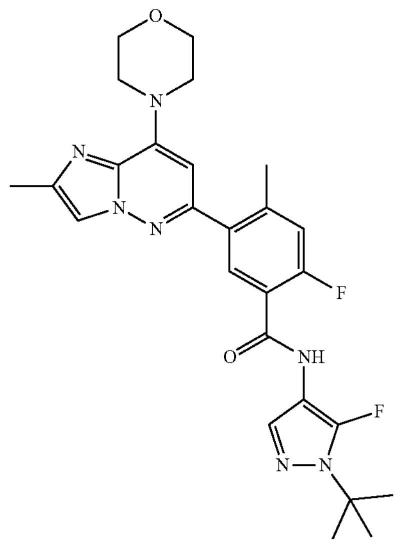 [SMILES: Cc1cn2nc(-c3cc(C(=O)Nc4cnn(C(C)(C)C)c4F)c(F)cc3C)cc(N3CCOCC3)c2n1] | N-(1-Tert-butyl-5-fluoropyrazol-4-yl)-2-fluoro-4-methyl-5-[2-methyl-8-(morpholin-4-yl)imidazo[1,2-b]pyridazin-6-yl]benzamide |
| 300 | 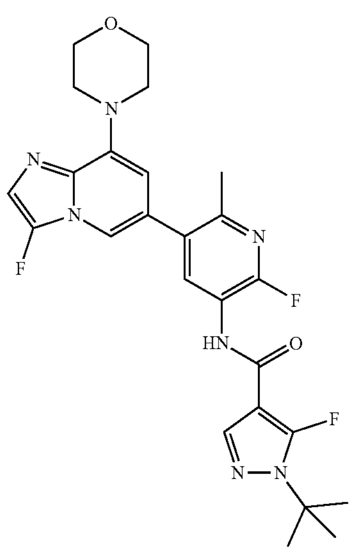 [SMILES: Cc1nc(F)c(NC(=O)c2cnn(C(C)(C)C)c2F)cc1-c1cc(N2CCOCC2)c2ncc(F)n2c1] | 1-Tert-butyl-5-fluoro-N-{2-fluoro-5-[3-fluoro-8-(morpholin-4-yl)imidazo[1,2-a]pyridin-6-yl]-6-methylpyridin-3-yl}pyrazole-4-carboxamide |

TABLE 1-continued
| Synthetic Chemistry Example | Compound Structure | Compound Name |
|---|---|---|
| 301 | 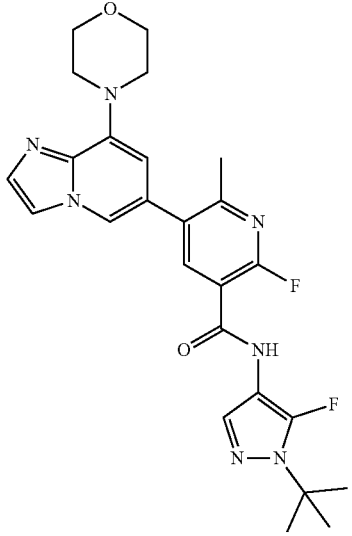 [SMILES: Cc1nc(F)c(C(=O)Nc2cnn(C(C)(C)C)c2F)cc1-c1cc(N2CCOCC2)c2nccn2c1] | N-(1-Tert-butyl-5-fluoropyrazol-4-yl)-2-fluoro-6-methyl-5-[8-(morpholin-4-yl)imidazo[1,2-a]pyridin-6-yl]pyridine-3-carboxamide |
| 302 | 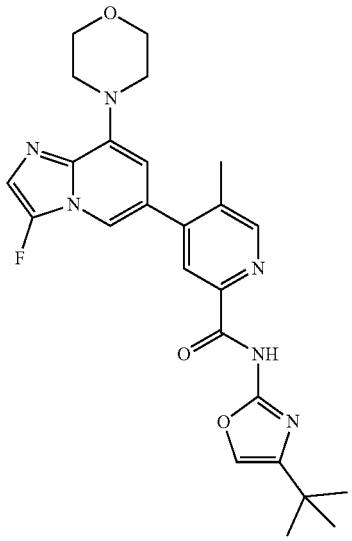 [SMILES: Cc1cnc(C(=O)Nc2nc(C(C)(C)C)co2)cc1-c1cc(N2CCOCC2)c2ncc(F)n2c1] | N-(4-Tert-butyl-1,3-oxazol-2-yl)-4-[3-fluoro-8-(morpholin-4-yl)imidazo[1,2-a]pyridin-6-yl]-5-methylpyridine-2-carboxamide |

TABLE 1-continued
| Synthetic Chemistry Example | Compound Structure | Compound Name |
|---|---|---|
| 303 | 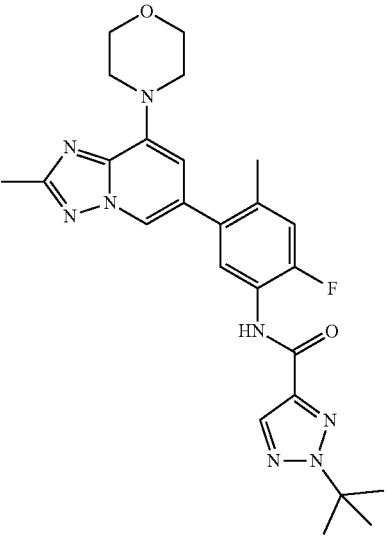 [SMILES: Cc1nc2c(N3CCOCC3)cc(-c3cc(NC(=O)c4cnn(C(C)(C)C)n4)c(F)cc3C)cn2n1] | 2-Tert-butyl-N-{2-fluoro-4-methyl-5-[2-methyl-8-(morpholin-4-yl)-[1,2,4]triazolo[1,5-a]pyridin-6-yl]phenyl}-1,2,3-triazole-4-carboxamide |
| 304 | 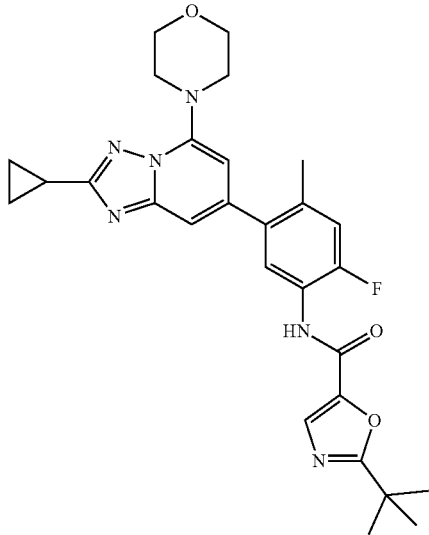 [SMILES: Cc1cc(F)c(NC(=O)c2cnc(C(C)(C)C)o2)cc1-c1cc(N2CCOCC2)n2nc(C3CC3)nc2c1] | 2-Tert-butyl-N-{5-[2-cyclopropyl-5-(morpholin-4-yl)-[1,2,4]triazolo[1,5-a]pyridin-7-yl]-2-fluoro-4-methylphenyl}-1,3-oxazole-5-carboxamide |

TABLE 1-continued
| Synthetic Chemistry Example | Compound Structure | Compound Name |
|---|---|---|
| 305 | 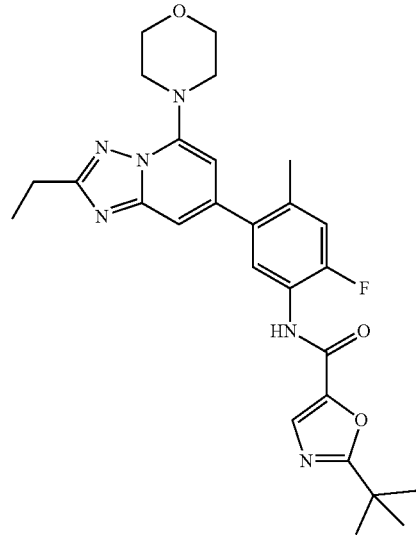 [SMILES: CCc1nc2cc(-c3cc(NC(=O)c4cnc(C(C)(C)C)o4)c(F)cc3C)cc(N3CCOCC3)n2n1] | 2-(Tert-butyl)-N-(5-(2-ethyl-5-morpholino-[1,2,4]triazolo[1,5-a]pyridin-7-yl)-2-fluoro-4-methylphenyl)oxazole-5-carboxamide |
| 306 | 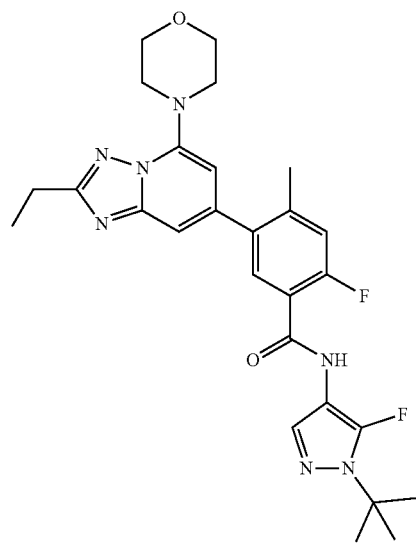 [SMILES: CCc1nc2cc(-c3cc(C(=O)Nc4cnn(C(C)(C)C)c4F)c(F)cc3C)cc(N3CCOCC3)n2n1] | N-(1-(tert-Butyl)-5-fluoro-1H-pyrazol-4-yl)-5-(2-ethyl-5-morpholino-[1,2,4]triazolo[1,5-a]pyridin-7-yl)-2-fluoro-4-methylbenzamide |

TABLE 1-continued
| Synthetic Chemistry Example | Compound Structure | Compound Name |
|---|---|---|
| 307 | 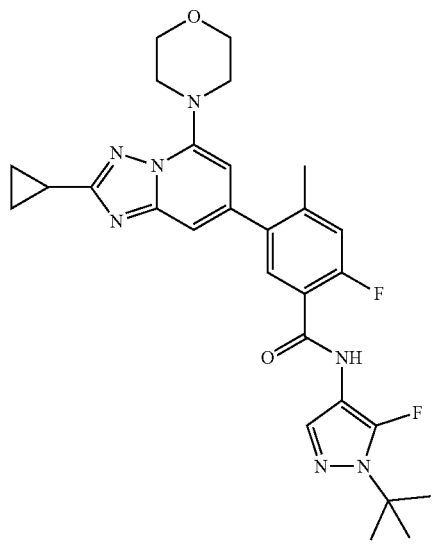 [SMILES: Cc1cc(F)c(C(=O)Nc2cnn(C(C)(C)C)c2F)cc1-c1cc(N2CCOCC2)n2nc(C3CC3)nc2c1] | N-(1-(tert-butyl)-5-fluoro-1H-pyrazol-4-yl)-5-(2-cyclopropyl-5-morpholino-[1,2,4]triazolo[1,5-a]pyridin-7-yl)-2-fluoro-4-methylbenzamide |
| 308 | 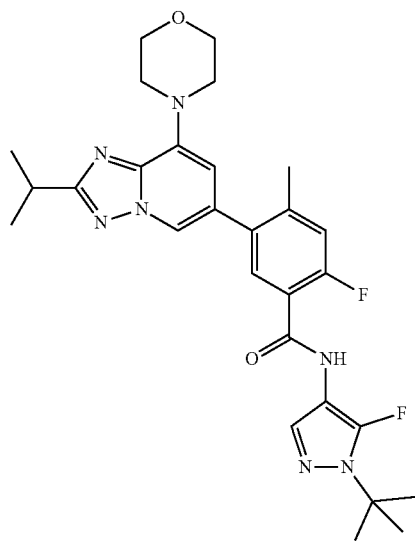 [SMILES: Cc1cc(F)c(C(=O)Nc2cnn(C(C)(C)C)c2F)cc1-c1cc(N2CCOCC2)c2nc(C(C)C)nn2c1] | N-(1-(tert-Butyl)-5-fluoro-1H-pyrazol-4-yl)-2-fluoro-5-(2-isopropyl-8-morpholino-[1,2,4]triazolo[1,5-a]pyridin-6-yl)-4-methylbenzamide |

TABLE 1-continued
| Synthetic Chemistry Example | Compound Structure | Compound Name |
|---|---|---|
| 309 | 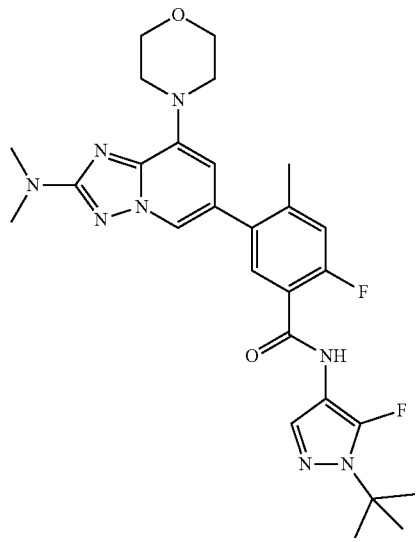 [SMILES: Cc1cc(F)c(C(=O)Nc2cnn(C(C)(C)C)c2F)cc1-c1cc(N2CCOCC2)c2nc(N(C)C)nn2c1] | N-(1-(tert-Butyl)-5-fluoro-1H-pyrazol-4-yl)-5-(2-(dimethylamino)-8-morpholino-[1,2,4]triazolo[1,5-a]pyridin-6-yl)-2-fluoro-4-methylbenzamide |
| 310 | 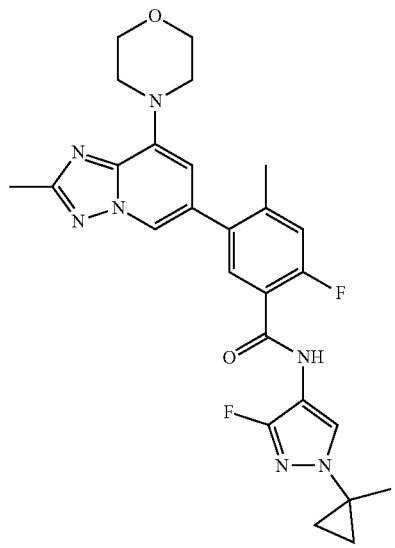 | 2-Fluoro-N-[3-fluoro-1-(1-methylcyclopropyl)pyrazol-4-yl]-4-methyl-5-[2-methyl-8-(morpholin-4-yl)-[1,2,4]triazolo[1,5-a]pyridin-6-yl]benzamide |

TABLE 1-continued

| Synthetic Chemistry Example | Compound Structure | Compound Name |
|---|---|---|
| 311 | 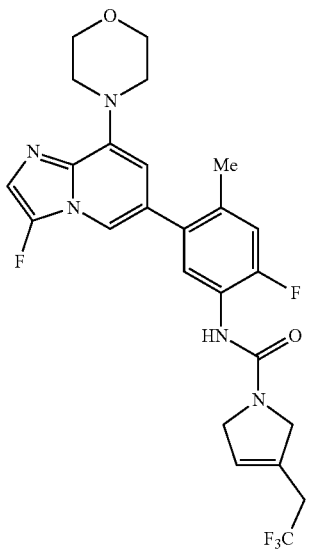 [SMILES: Cc1cc(F)c(NC(=O)N2CC=C(CC(F)(F)F)C2)cc1-c1cc(N2CCOCC2)c2ncc(F)n2c1] | N-(2-fluoro-5-(3-fluoro-8-morpholinoimidazo[1,2-a]pyridin-6-yl)-4-methylphenyl)-3-(2,2,2-trifluoroethyl)-2,5-dihydro-1H-pyrrole-1-carboxamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations, '82nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R.V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the RAF kinase inhibitory compound described herein is administered as a pure chemical. In other embodiments, the RAF kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one RAF kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a pharmaceutical composition comprising a pharmaceutically acceptable excipient and a compound of Formula (Ia), or a pharmaceutically acceptable salt or solvate thereof.

One embodiment provides a pharmaceutical composition comprising a pharmaceutically acceptable excipient and a compound of Formula (Ib), or a pharmaceutically acceptable salt or solvate thereof.

One embodiment provides a pharmaceutical composition comprising a pharmaceutically acceptable excipient and a compound of Formula (II), or a pharmaceutically acceptable salt or solvate thereof.

One embodiment provides a pharmaceutical composition comprising a pharmaceutically acceptable excipient and a compound of Formula (III), or a pharmaceutically acceptable salt or solvate thereof.

One embodiment provides a method of preparing a pharmaceutical composition comprising mixing a compound of Formula (I), (Ia), (Ib), (II), or (III), or a pharmaceutically acceptable salt or solvate thereof, and a pharmaceutically acceptable carrier.

In certain embodiments, the RAF kinase inhibitory compound as described by Formula (I), (Ia), (Ib), (II), or (III), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the RAF kinase inhibitory compound as described by Formula (I), (Ia), (Ib), (II), or (III), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one RAF kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit, e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of cancer or neoplastic disease.

One embodiment provides a pharmaceutical composition comprising a compound of Formula (I), or a pharmaceutically acceptable salt or solvate thereof, and a pharmaceutically acceptable excipient for use in a method of treatment of cancer or neoplastic disease.

One embodiment provides a use of a compound of Formula (I), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (I), or a pharmaceutically acceptable salt or solvate thereof In some embodiments is provided a method of treating cancer, in a patient in need thereof, comprising administering to the patient a pharmaceutical composition comprising a compound of Formula (I), or a pharmaceutically acceptable salt or solvate thereof, and a pharmaceutically acceptable excipient.

One embodiment provides a compound of Formula (Ia), or a pharmaceutically acceptable salt or solvate thereof, for use in a method of treatment of the human or animal body.

One embodiment provides a compound of Formula (Ia), or a pharmaceutically acceptable salt or solvate thereof, for use in a method of treatment of cancer or neoplastic disease.

One embodiment provides a pharmaceutical composition comprising a compound of Formula (Ia), or a pharmaceutically acceptable salt or solvate thereof, and a pharmaceutically acceptable excipient for use in a method of treatment of cancer or neoplastic disease.

One embodiment provides a use of a compound of Formula (Ia), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (Ia), or a pharmaceutically acceptable salt or solvate thereof In some embodiments is provided a method of treating cancer, in a patient in need thereof, comprising administering to the patient a pharmaceutical composition comprising a compound of Formula (Ia), or a pharmaceutically acceptable salt or solvate thereof, and a pharmaceutically acceptable excipient.

One embodiment provides a compound of Formula (Ib), or a pharmaceutically acceptable salt or solvate thereof, for use in a method of treatment of the human or animal body.

One embodiment provides a compound of Formula (Ib), or a pharmaceutically acceptable salt or solvate thereof, for use in a method of treatment of cancer or neoplastic disease.

One embodiment provides a pharmaceutical composition comprising a compound of Formula (Ib), or a pharmaceutically acceptable salt or solvate thereof, and a pharmaceutically acceptable excipient for use in a method of treatment of cancer or neoplastic disease.

One embodiment provides a use of a compound of Formula (Ib), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (Ib), or a pharmaceutically acceptable salt or solvate thereof In some embodiments is provided a method of treating cancer, in a patient in need thereof, comprising administering to the patient a pharmaceutical composition comprising a compound of Formula (Ib), or a pharmaceutically acceptable salt or solvate thereof, and a pharmaceutically acceptable excipient.

One embodiment provides a compound of Formula (II), or a pharmaceutically acceptable salt or solvate thereof, for use in a method of treatment of the human or animal body.

One embodiment provides a compound of Formula (II), or a pharmaceutically acceptable salt or solvate thereof, for use in a method of treatment of cancer or neoplastic disease.

One embodiment provides a pharmaceutical composition comprising a compound of Formula (II), or a pharmaceutically acceptable salt or solvate thereof, and a pharmaceutically acceptable excipient for use in a method of treatment of cancer or neoplastic disease.

One embodiment provides a use of a compound of Formula (II), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (II), or a pharmaceutically acceptable salt or solvate thereof In some embodiments is provided a method of treating cancer, in a patient in need thereof, comprising administering to the patient a pharmaceutical composition comprising a compound of Formula (II), or a pharmaceutically acceptable salt or solvate thereof, and a pharmaceutically acceptable excipient.

One embodiment provides a compound of Formula (III), or a pharmaceutically acceptable salt or solvate thereof, for use in a method of treatment of the human or animal body.

One embodiment provides a compound of Formula (III), or a pharmaceutically acceptable salt or solvate thereof, for use in a method of treatment of cancer or neoplastic disease.

One embodiment provides a pharmaceutical composition comprising a compound of Formula (III), or a pharmaceutically acceptable salt or solvate thereof, and a pharmaceutically acceptable excipient for use in a method of treatment of cancer or neoplastic disease.

One embodiment provides a use of a compound of Formula (III), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (III), or a pharmaceutically acceptable salt or solvate thereof In some embodiments is provided a method of treating cancer, in a patient in need thereof, comprising administering to the patient a pharmaceutical composition comprising a compound of Formula (III), or a pharmaceutically acceptable salt or solvate thereof, and a pharmaceutically acceptable excipient.

In some embodiments described herein, the compound of Formula (I), (Ia), (Ib), (II), or (III) partitions across the blood-brain barrier (BBB) with a $K_{p,uu}$ of greater than 1. In some embodiments described herein, the compound of Formula (I), (Ia), (Ib), (II), or (III) exhibits a $K_{p,uu}$ greater than 0.3. In some embodiments described herein, the compound of Formula (I), (Ia), (Ib), (II), or (III) exhibits a $K_{p,uu}$ greater than 0.4. In some embodiments described herein, the compound of Formula (I), (Ia), (Ib), (II), or (III) exhibits a $K_{p,uu}$ greater than 0.6. In some embodiments described herein, the compound of Formula (I), (Ia), (Ib), (II), or (III) exhibits a $K_{p,uu}$ greater than 0.8. In some embodiments described herein, the compound of Formula (I), (Ia), (Ib), (II), or (III) exhibits a $K_{p,uu}$ greater than 1.0. In some embodiments described herein, the compound of Formula (I), (Ia), (Ib), (II), or (III) exhibits a $K_{p,uu}$ greater than 1.2. In some embodiments described herein, the compound of Formula (I), (Ia), (Ib), (II), or (III) exhibits a $K_{p,uu}$ greater than 1.4. In some embodiments described herein, the compound of Formula (I), (Ia), (Ib), (II), or (III) exhibits a $K_{p,uu}$ greater than 1.6. In some embodiments described herein, the compound of Formula (I), (Ia), (Ib), (II), or (III) exhibits a $K_{p,uu}$ greater than 1.8. In some embodiments described herein, the compound of Formula (I), (Ia), (Ib), (II), or (III) exhibits a $K_{p,uu}$ greater than 2.0. In some embodiments, the $K_{p,uu}$ value is determined in a rat. In some embodiments, the $K_{p,uu}$ value is determined in a mouse. In some embodiments, the $K_{p,uu}$ value is determined in a rodent. In some embodiments, the $K_{p,uu}$ value is determined in a dog. In some embodiments, the $K_{p,uu}$ value is determined in a primate. In some embodiments, the $K_{p,uu}$ value is determined in a human.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the RAF kinase inhibitory compounds disclosed herein are synthesized according to the following examples. As used below, and throughout the description of the invention, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
P micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Intermediate 1: (S)—N-(2-Fluoro-4-methyl-5-(4,4,5,5-tetramethyl-1,3,2-dioxaborolan-2-yl)phenyl)-3-(2,2,2-trifluoroethyl)pyrrolidine-1-carboxamide

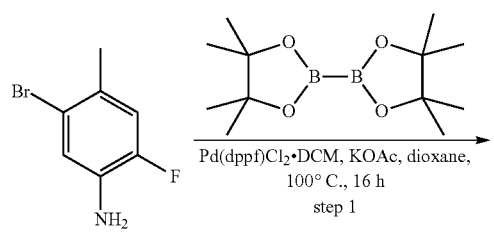

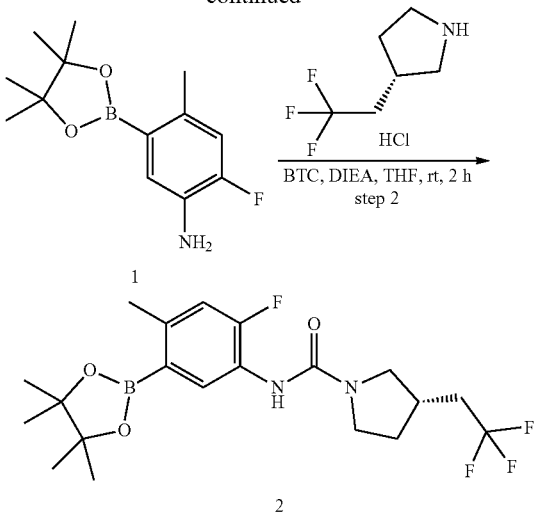

Step 1. 2-Fluoro-4-methyl-5-(4,4,5,5-tetramethyl-1,3,2-dioxaborolan-2-yl)aniline To a stirred mixture of 5-bromo-2-fluoro-4-methylaniline (10 g, 49.01 mmol), 4,4,5,5-tetramethyl-2-(tetramethyl-1,3,2-dioxaborolan-2-yl)-1,3,2-dioxaborolane (14.93 g, 58.81 mmol) and Pd(dppf)Cl$_2$CH$_2$Cl$_2$ (2.00 g, 2.45 mmol) in 1,4-dioxane (120 mL) was added KOAc (14.43 g, 147.03 mmol). The reaction mixture was degassed with nitrogen for three times and stirred for 16 h at 100° C. The resulting mixture was diluted with water (300 mL) at room temperature. The resulting mixture was extracted with CH$_2$Cl$_2$ (3×200 mL). The combined organic layers was washed with brine (3×200 mL), dried over anhydrous Na$_2$SO$_4$. After filtration, the filtrate was concentrated under reduced pressure. The residue was purified by silica gel column chromatography, eluted with PE/EA (4/1). The fractions contained desired product were combined and concentrated to afford 2-fluoro-4-methyl-5-(4,4,5,5-tetramethyl-1,3,2-dioxaborolan-2-yl)aniline (11.6 g, 94%) as a green solid. MS ESI calculated for C$_{13}$H$_{19}$BFNO$_2$ [M+H]$^+$, 252.15, found 252.10; $^1$H NMR (400 MHz, Chloroform-d) δ 7.24 (d, J=10.0 Hz, 1H), 6.82 (d, J=12.0 Hz, 1H), 3.60 (s, 2H), 2.45 (s, 3H), 1.35 (s, 12H); $^{19}$F NMR (376 MHz, Chloroform-d) δ-131.47 (1F)

Step 2. (S)—N-(2-Fluoro-4-methyl-5-(4,4,5,5-tetramethyl-1,3,2-dioxaborolan-2-yl)phenyl)-3-(2,2,2-trifluoroethyl)pyrrolidine-1-carboxamide To a stirred solution of 2-fluoro-4-methyl-5-(4,4,5,5-tetramethyl-1,3,2-dioxaborolan-2-yl)aniline (0.50 g, 1.99 mmol) and DIEA (1.28 g, 9.96 mmol) in THF (42 mL) was added Triphosgene (236 mg, 0.796 mmol) at room temperature under nitrogen atmosphere. The reaction mixture was stirred for 0.5 h at room temperature under nitrogen atmosphere. To the above mixture was added the solution of (3S)-3-(2,2,2-trifluoroethyl)pyrrolidine hydrochloride (0.38 g, 1.99 mmol) in THF (5 mL). The reaction mixture was stirred for additional 2 h at room temperature. The resulting mixture was quenched by the addition of methanol (50 mL) at room temperature. The resulting mixture was concentrated under reduced pressure. The residue was purified by silica gel column chromatography, eluted with petroleum ether/ethyl acetatel (2/1). The fractions contained desired product were combined and concentrated to afford (S)—N-(2-fluoro-4-methyl-5-(4,4,5,5-tetramethyl-1,3,2-dioxaborolan-2-yl)phenyl)-3-(2,2,2-trifluoroethyl)pyrrolidine-1-carboxamide (0.70 g, 82%) as an off-white solid. MS ESI calculated for $C_{20}H_{27}BF_4N_2O_3$ [M+H]$^+$, 431.21, found 431.30; $^1$H NMR (400 MHz, Chloroform-d) δ 8.39 (d, J=9.2 Hz, 1H), 6.88 (d, J=12.8 Hz, 1H), 6.19 (s, 1H), 3.86-3.82 (m, 1H), 3.68-3.63 (m, 1H), 3.50-3.44 (m, 1H), 3.17-3.12 (m, 1H), 2.62-2.54 (m, 1H), 2.49 (s, 3H), 2.33-2.23 (m, 3H), 1.82-1.72 (m, 1H), 1.34 (s, 12H). $^{19}$F NMR (376 MHz, Chloroform-d) δ-64.97 (3F), -128.85 (1F)

Intermediate 2: N-(2-Fluoro-4-methyl-5-(4,4,5,5-tetramethyl-1,3,2-dioxaborolan-2-yl)phenyl)-3-(2,2,2-trifluoroethyl)-2,5-dihydro-1H-pyrrole-1-carboxamide

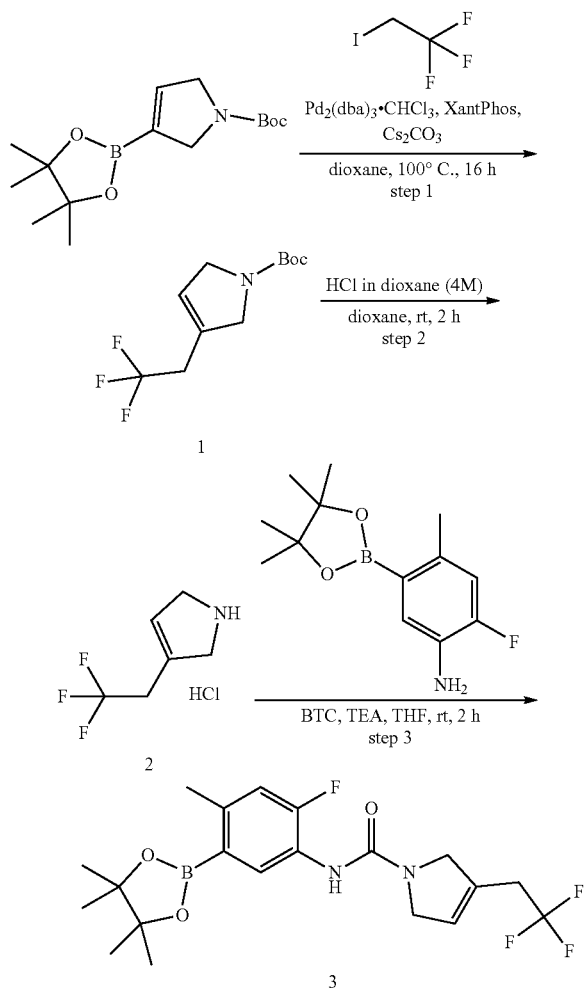

Step 1. Tert-butyl 3-(2,2,2-trifluoroethyl)-2,5-dihydropyrrole-1-carboxylate

To a stirred mixture of cesium carbonate (19.87 g, 60.98 mmol), Tris(dibenzylideneacetone)dipalladium(0)-chloroform adduct (1.58 g, 1.52 mmol) and XantPhos (3.00 g, 5.18 mmol) in dioxane (30 mL) were added tert-butyl 3-(4,4,5,5-tetramethyl-1,3,2-dioxaborolan-2-yl)-2,5-dihydropyrrole-1-carboxylate (4.5 g, 15.24 mmol) and 1,1,1-trifluoro-2-iodoethane (12.80 g, 60.98 mmol). The reaction mixture was degassed with nitrogen for three times and stirred for 16 h at 100° C. The resulting mixture was filtered, the filter cake was washed with dichloromethane (3×200 mL). The filtrate was concentrated under reduced pressure. The residue was purified by silica gel column chromatography, eluted with petroleum ether/ethyl acetatel (5/1). The fractions contained desired product were combined and concentrated to afford tert-butyl 3-(2,2,2-trifluoroethyl)-2,5-dihydropyrrole-1-carboxylate (0.30 g, 8%) as a light brown oil. MS ESI calculated for $C_{11}H_{16}F_3NO_2$ [M–$C_4H_8$+H]$^+$, 196.05, found 195.90; $^1$H NMR (400 MHz, Chloroform-d) δ 5.77 (d, J=20.0 Hz, 1H), 4.17-4.12 (m, 4H), 3.00-2.91 (m, 2H), 1.50 (s, 9H); $^{19}$F NMR (376 MHz, Chloroform-d) δ-64.94 (3F)

Step 2. 3-(2,2,2-Trifluoroethyl)-2,5-dihydro-1H-pyrrole hydrochloride

To a stirred solution of tert-butyl 3-(2,2,2-trifluoroethyl)-2,5-dihydropyrrole-1-carboxylate (0.30 g, 1.19 mmol) in dichloromethane (3 mL) was added HCl (gas) in 1,4-dioxane (3 mL, 4 M) dropwise at 0° C. The resulting mixture was stirred for 2 h at room temperature. The resulting mixture was concentrated under reduced pressure to afford 3-(2,2,2-trifluoroethyl)-2,5-dihydro-1H-pyrrole hydrochloride (0.20 g, crude) as a brown oil. MS ESI calculated for $C_6H_9ClF_3N$ [M -HCl+H]$^+$, 152.06, 154.06, found 152.00, 154.00; $^1$H NMR (400 MHz, DMSO-d$_6$) δ 9.60 (s, 2H), 5.84 (d, J=62.0 Hz, 1H), 3.98-3.91 (m, 4H), 3.41-3.32 (m, 2H); $^{19}$F NMR (376 MHz, DMSO-d$_6$) δ -63.32 (3F).

Step 3. N-[2-Fluoro-4-methyl-5-(4,4,5,5-tetramethyl-1,3,2-dioxaborolan-2-yl)phenyl]-3-(2,2,2-trifluoroethyl)-2,5-dihydropyrrole-1-carboxamide To a stirred solution of 2-fluoro-4-methyl-5-(4,4,5,5-tetramethyl-1,3,2-dioxaborolan-2-yl)aniline (0.10 g, 0.40 mmol) and N,N-diisopropylethylamine (0.26 g, 1.99 mmol) in tetrahydrofuran (5.00 mL) was added triphosgene (47.01 mg, 0.16 mmol) at room temperature under nitrogen atmosphere. The reaction mixture was stirred for 0.5 h at room temperature under nitrogen atmosphere. To the above mixture was added 3-(2,2,2-trifluoroethyl)-2,5-dihydro-1H-pyrrole hydrochloride (67.00 mg, 0.36 mmol) at 0° C. The reaction mixture was stirred for additional 2 h at room temperature. The resulting mixture was quenched by the addition of methanol (20 mL) at room temperature. The resulting mixture was concentrated under reduced pressure. The residue was purified by silica gel column chromatography, eluted with petroleum ether/ethyl acetate (1/1). The fractions contained desired product were combined and concentrated to afford N-[2-fluoro-4-methyl-5-(4,4,5,5-tetramethyl-1,3,2-dioxaborolan-2-yl)phenyl]-3-(2,2,2-trifluoroethyl)-2,5-dihydropyrrole-1-carboxamide (0.10 g, 59%) as an off-white solid. MS ESI calculated for $C_{20}H_{25}BF_4N_2O_3$ [M+H]$^+$, 429.19, found 429.20; $^1$H NMR (400 MHz, Chloroform-d) δ 8.41 (d, J=9.6 Hz, 1H), 6.89 (d, J=12.4 Hz, 1H), 6.19 (d, J=2.8 Hz, 1H), 5.88 (s, 1H), 4.34-4.32 (m, 4H), 3.07-2.99 (m, 2H), 2.50 (s, 3H), 1.34 (s, 12H). $^{19}$F NMR (376 MHz, Chloroform-d) δ-64.84 (3F), -128.78 (1F).

Intermediate 3:
5-Chloro-7-(morpholin-4-yl)-2H-indazole

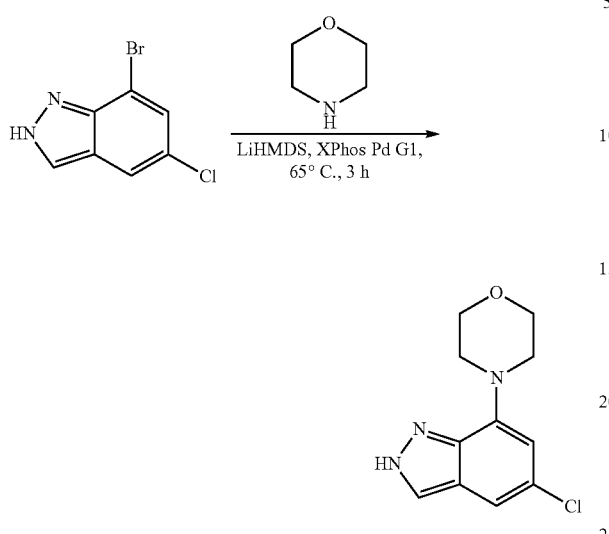

To a stirred solution of 7-bromo-5-chloro-2H-indazole (6 g, 25.92 mmol) and 1-chloro-1-[dicyclohexyl([2-[2,4,6-tris(propan-2-yl)phenyl]phenyl])-1-5]-phosphanyl]-2H,3H,4H-benzo[c]1-aza-2-palladacyclohexane (0.77 g, 1.04 mmol) in morpholine (2.26 g, 25.92 mmol) was added Lithium bis(trimethylsily)amide (LiHMDS, 1 M solution in tetrahydrofuran) (90.7 mL, 90.72 mmol) dropwise at 0° C. under nitrogen atmosphere. The reaction mixture was stirred for 3 h at 65° C. under nitrogen atmosphere. The resulting mixture was quenched with saturated aqueous NH$_4$Cl (200 mL). The resulting mixture was extracted with ethyl acetate (3×200 mL). The combined organic layers was washed with brine (100 mL), dried over anhydrous sodium sulfate. After filtration, the filtrate was concentrated under reduced pressure. The residue was purified by silica gel column chromatography, eluted with petroleum ether/ethyl acetate (1/1). The fractions contained desired product were combined and concentrated to afford 5-chloro-7-(morpholin-4-yl)-2H-indazole (4.1 g, 67%) as a light grey solid. MS ESI calculated for C$_{11}$H$_{12}$ClN$_3$O [M+H]$^+$, 238.07, 240.07, found 237.90, 239.90. $^1$H NMR (400 MHz, Chloroform-d) δ 8.79 (s, 1H), 8.04 (s, 1H), 7.44 (d, J=1.6 Hz, 1H), 6.85 (d, J=1.6 Hz, 1H), 3.98-3.95 (m, 4H), 3.21-3.19 (m, 4H)

The following compounds in Table 2 were prepared using procedures similar to those described in Intermediate 3 using appropriate starting materials.

Intermediate 5:
4-(5-Chloro-2-methyl-2H-indazol-7-yl)morpholine

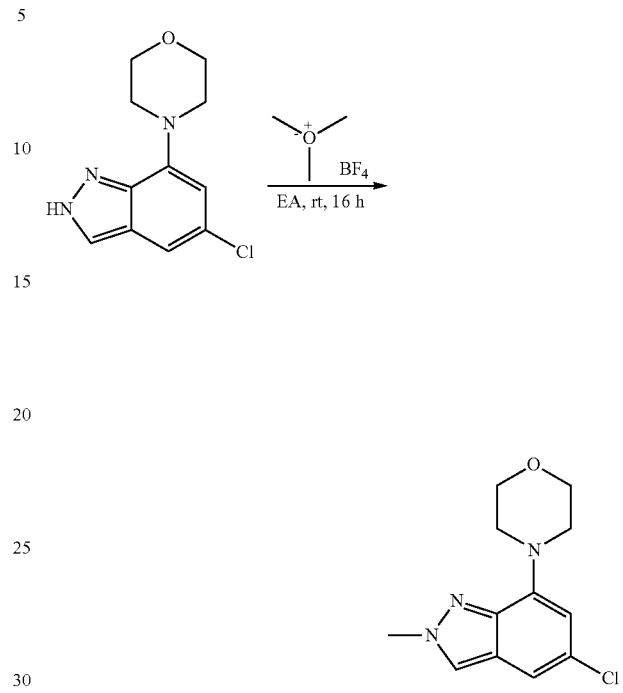

To a stirred solution of 5-chloro-7-(morpholin-4-yl)-1H-indazole (1.00 g, 4.21 mmol) in EA (14 mL) was added trimethyloxonium tetrafluoroborate (0.80 g, 5.43 mmol) at room temperature under nitrogen atmosphere. The reaction mixture was stirred for 16 h at room temperature under nitrogen atmosphere. The resulting mixture was quenched by the addition of sat. NaHCO$_3$ (aq.) (40 mL) at 0° C. The resulting mixture was extracted with EtOAc (3×60 mL). The combined organic layers was washed with brine (1×40 mL), dried over anhydrous Na$_2$SO$_4$. After filtration, the filtrate was concentrated under reduced pressure. The residue was purified by silica gel column chromatography, eluted with (PE/EtOAc/EtOH=4/3/1). The fractions contained desired product were combined and concentrated to afford 5-chloro-2-methyl-7-(morpholin-4-yl)indazole (0.84 g, 79%) as an off-white solid. MS ESI calculated for C$_{12}$H$_{14}$ClN$_3$O [M+H]$^+$, 252.08, 254.08, found 252.10, 254.10; $^1$H NMR (400 MHz, Chloroform-d) δ 7.80 (s, 1H), 7.22 (d, J=1.6 Hz, 1H), 6.54 (s, 1H), 4.19 (s, 3H), 4.02-4.00 (m, 4H), 3.56-3.54 (m, 4H).

TABLE 2

| Intermediate | Structure | IUPAC Name | Exact Mass [M + H]$^+$ | Starting material |
|---|---|---|---|---|
| 4 | (structure: 5-bromo-3-morpholinopyridin-2-amine) | 5-Bromo-3-morpholinopyridin-2-amine | Calc'd 258.02, 260.02, found 258.00, 260.00 | (structure: 3,5-dibromopyridin-2-amine) |

Intermediate 6: 4-(5-Chloro-2-(2-methoxyethyl)-2H-indazol-7-yl)morpholine

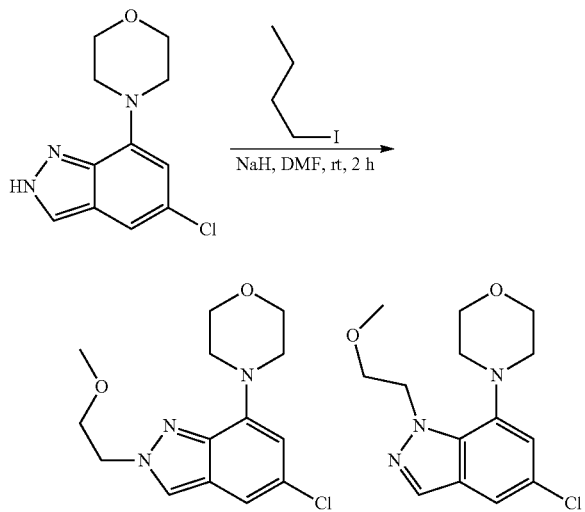

bined and concentrated to afford 4-(5-chloro-2-(2-methoxyethyl)-2H-indazol-7-yl)morpholine (0.22 g, 35%) as a light brown solid. MS ESI calculated for $C_{14}H_{18}ClN_3O_2[M+H]^+$, 296.11, 298.11, found 295.95, 297.95; $^1$H NMR (400 MHz, Chloroform-d) δ 7.93 (s, 1H), 7.22 (d, J=1.6 Hz, 1H), 6.49 (s, 1H), 4.55 (t, J=1.2 Hz, 2H), 3.88-3.86 (m, 4H), 3.86 (t, J=4.8 Hz, 2H), 3.56-3.54 (m, 4H), 3.40 (s, 3H).

And 4-(5-chloro-1-(2-methoxyethyl)-1H-indazol-7-yl)morpholine (0.34 g, 55%) as a light brown solid. MS ESI calculated for $C_{14}H_{18}ClN_3O_2[M+H]^+$, 296.11, 298.11, found 296.00, 298.00; $^1$H NMR (400 MHz, Chloroform-d) δ 7.98 (s, 1H), 7.46 (d, J=1.6 Hz, 1H), 7.04 (d, J=1.6 Hz, 1H), 4.90 (t J=5.6 Hz, 2H), 4.02-3.99 (m, 2H), 3.89-3.84 (m, 4H), 3.31 (s, 3H), 3.16-3.13 (m, 2H), 3.06-3.00 (m, 2H).

The following compounds in Table 3 were prepared using procedures similar to those described in Intermediate 6 using appropriate starting materials.

TABLE 3

| Intermediate | Structure | IUPAC Name | Exact Mass [M + H]⁺ |
| --- | --- | --- | --- |
| 7 | 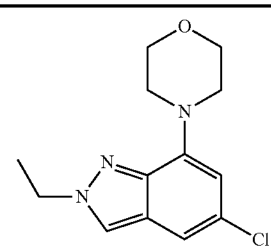 | 4-(5-Chloro-2-ethyl-2H-indazol-7-yl)morpholine | Calc'd, 265.74, 267.74, found 265.95, 267.95 |
| 8 | 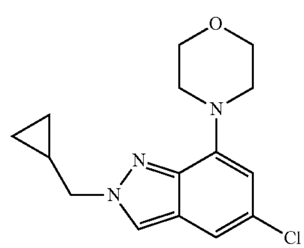 [SMILES: Clc1cc(N2CCOCC2)c2nn(CC3CC3)cc2c1] | 4-(5-Chloro-2-(cyclopropylmethyl)-2H-indazol-7-yl)morpholine | Calc'd 292.11, 294.11, found 292.00, 294.00 |

To a stirred solution of 5-chloro-7-(morpholin-4-yl)-2H-indazole (0.50 g, 2.10 mmol) in N,N-dimethylformamide (5 mL) was added sodium hydride (0.13 g, 3.16 mmol, 60%) at 0° C. under nitrogen atmosphere. The reaction mixture was stirred for 0.5 h at room temperature under nitrogen atmosphere. To the above mixture was added 1-iodo-2-methoxyethane (0.47 g, 2.53 mmol). The reaction mixture was stirred for additional 2 h at room temperature. The resulting mixture was quenched with saturated aqueous NH₄Cl (100 mL). The resulting mixture was extracted with ethyl acetate (3×100 mL). The combined organic layers was washed with saturated brine (100 mL), dried over anhydrous sodium sulfate. After filtration, the filtrate was concentrated under reduced pressure. The residue was purified by silica gel column chromatography, eluted with petroleum ether/ethyl acetate (1/1). The fractions contained desired product were com-

Intermediate 9: 4-(5-Chloro-2-cyclopropyl-2H-indazol-7-yl)morpholine

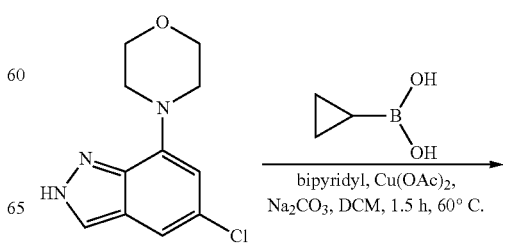

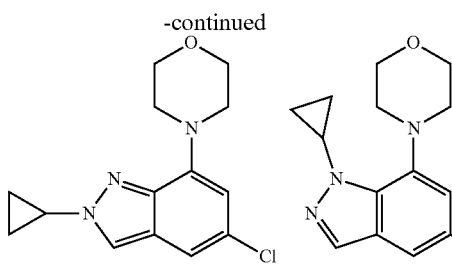

To a stirred mixture of 5-chloro-7-(morpholin-4-yl)-1H-indazole (0.15 g, 0.63 mmol) and cyclopropylboronic acid (0.11 g, 1.26 mmol) and bipyridyl (0.10 g, 0.63 mmol) in DCE (3 mL) were added Cu(OAc)$_2$ (0.11 g, 0.63 mmol) and Na$_2$CO$_3$ (0.13 g, 1.26 mmol) in portions at room temperature. The reaction mixture was degassed with oxygen and stirred for 1.5 h at 60° C. The resulting mixture was filtered, the filter cake was washed with DCM (3×20 mL). The filtrate was concentrated under reduced pressure. The residue was purified by Prep-TLC (PE/EA=1/1). The fractions contained desired product were combined and concentrated to afford 4-(5-chloro-2-cyclopropyl-2H-indazol-7-yl)morpholine (128 mg, 73%) as an off-white solid. MS ESI calculated for C$_{14}$H$_{16}$ClN$_3$O [M+H]$^+$, 278.10, 280.10, found 278.00, 280.00. $^1$H NMR (400 MHz, Chloroform-d) δ 7.89 (s, 1H), 7.18 (d, J=1.6 Hz, 1H), 6.46 (s, 1H), 4.00-3.98 (m, 4H), 3.93-3.89 (m, 1H), 3.55-3.53 (m, 4H), 1.36-1.32 (m, 2H), 1.18-1.14 (m, 2H) And to afford 5-chloro-1-cyclopropyl-7-(morpholin-4-yl)indazole (101 mg, 57%) as an off-white solid. MS ESI calculated for C$_{14}$H$_{16}$ClN$_3$O [M+H]$^+$, 278.10, 280.10, found 278.00, 280.00; $^1$H NMR (400 MHz, Chloroform-d) δ 7.83 (s, 1H), 7.42 (d, J=1.6 Hz, 1H), 6.96 (d, J=2.0 Hz, 1H), 4.58-4.53 (m, 1H), 3.94 (s, 4H), 3.15 (m, 4H), 1.43-1.37 (m, 2H), 1.10-1.05 (m, 2H).

Intermediate 10: 5-Chloro-2-(difluoromethyl)-7-(morpholin-4-yl)indazole

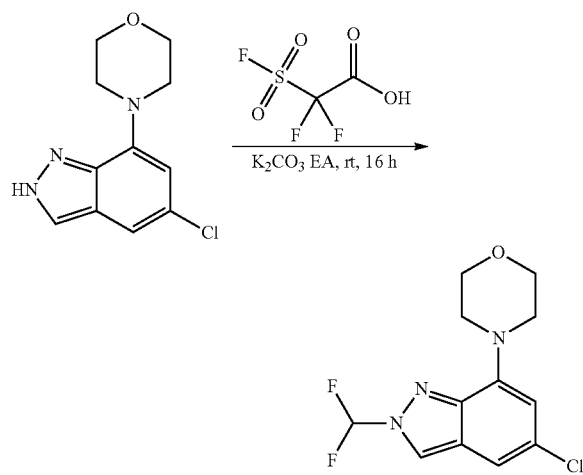

To a stirred solution of 5-chloro-7-(morpholin-4-yl)-2H-indazole (0.50 g, 2.10 mmol) and potassium carbonate (0.87 g, 6.31 mmol) in ethyl acetate (5 mL) was added difluoro(sulfo)acetic acid (0.45 g, 2.53 mmol) dropwise at 0° C. under nitrogen atmosphere. The reaction mixture was stirred for 16 h at room temperature under nitrogen atmosphere. The resulting mixture was quenched with water (100 mL). The resulting mixture was extracted with ethyl acetate (3×100 mL). The combined organic layers was washed with saturated brine (100 mL), dried over anhydrous sodium sulfate. After filtration, the filtrate was concentrated under reduced pressure. The residue was purified by silica gel column chromatography, eluted with ether/ethyl acetate (1/1). The fractions contained desired product were combined and concentrated to afford 5-chloro-2-(difluoromethyl)-7-(morpholin-4-yl)indazole (380 mg, 63%) as a light yellow solid. MS ESI calculated for C$_{12}$H$_{12}$ClF$_2$N$_3$O[M+H]$^+$, 288.06, 290.06, found 287.90, 289.90; $^1$H NMR (400 MHz, DMSO-d$_6$) δ 8.81 (s, 1H), 8.14 (t, J=55.8 Hz, 1H), 7.34 (d, J=1.6 Hz, 1H), 6.46 (d, J=1.6 Hz, 1H), 3.63-3.60 (m, 4H), 3.51-3.49 (m, 4H); $^{19}$F NMR (376 MHz, DMSO-d$_6$) δ -94.76 (2F).

Intermediate 11: 4-{6-Bromo-2-isopropylimidazo[1,2-a]pyridin-8-yl}morpholine

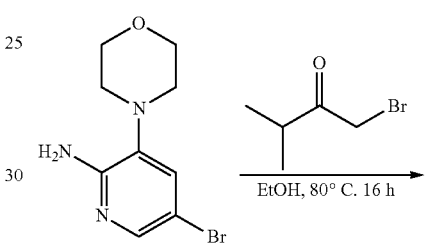

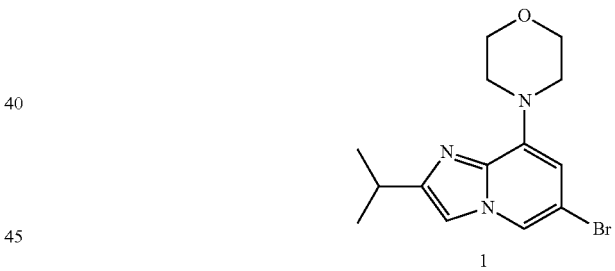

Step 1. 4-{6-Bromo-2-isopropylimidazo[1,2-a]pyridin-8-yl}morpholine To a stirred solution of 5-bromo-3-(morpholin-4-yl)pyridin-2-amine (400 mg, 1.55 mmol) in EtOH (5 mL) was added 1-bromo-3-methylbutan-2-one (511 mg, 3.10 mmol). The reaction mixture was stirred for 16 h at 80° C. The resulting mixture was concentrated under reduced pressure. The residue was purified by silica gel column chromatography, eluted with PE/EA/EtOH (8/3/1) to afford 4-{6-bromo-2-isopropylimidazo[1,2-a]pyridin-8-yl}morpholine (180 mg, 36%) as a grey solid. MS ESI calculated for C$_{14}$H$_{18}$BrN$_3$O [M+H]$^+$, 324.22, 326.22, found 324.05, 326.05; $^1$H NMR (400 MHz, Chloroform-d) δ 7.84 (d, J=1.6 Hz, 1H), 7.21 (s, 1H), 6.44-6.39 (m, 1H), 4.00-3.97 (m, 4H), 3.63-3.56 (m, 4H), 3.13-3.06 (m, 1H), 1.35 (d, J=7.2 Hz, 6H).

The following compounds in Table 4 were prepared using procedures similar to those described in Intermediate 11 using appropriate starting materials.

TABLE 4

| Intermediate | Structure | IUPAC Name | Exact Mass [M + H]+ |
|---|---|---|---|
| 12 | 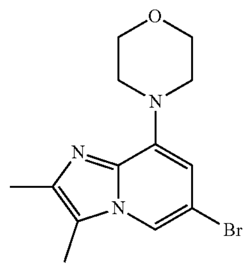 [SMILES: Cc1nc2c(N3CCOCC3)cc(Br)cn2c1C] | 4-(6-Bromo-2,3-dimethylimidazo[1,2-a]pyridin-8-yl)morpholine | Calc'd 310.05, 312.05, found 310.10, 312.10 |
| 13 | 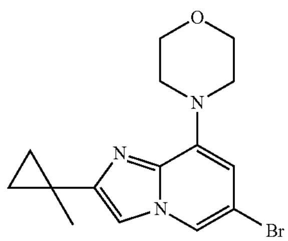 [SMILES: CC1(c2cn3cc(Br)cc(N4CCOCC4)c3n2)CC1] | 4-(6-Bromo-2-(1-methylcyclopropyl)imidazo[1,2-a]pyridin-8-yl)morpholine | Calc'd 336.06, 338.06, found 336.00, 338.00 |
| 14 | 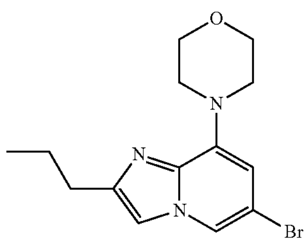 [SMILES: CCCc1cn2cc(Br)cc(N3CCOCC3)c2n1] | 4-(6-Bromo-2-propylimidazo[1,2-a]pyridin-8-yl)morpholine | Calc'd 324.03, 326.06, found 323.75, 325.75 |
| 15 | 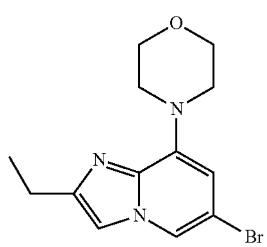 [SMILES: CCc1cn2cc(Br)cc(N3CCOCC3)c2n1] | 4-(6-Bromo-2-ethylimidazo[1,2-a]pyridin-8-yl)morpholine | Calc'd 310.05, 312.05, found 310.00, 312.05 |
| 16 | 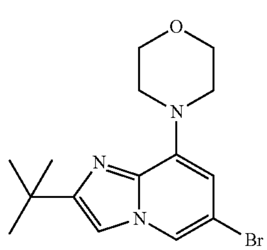 [SMILES: CC(C)(C)c1cn2cc(Br)cc(N3CCOCC3)c2n1] | 4-(6-Bromo-2-(tert-butyl)imidazo[1,2-a]pyridin-8-yl)morpholine | Calc'd 338.08, 340.08, found 337.95, 339.95 |

Example 1: (3S')-N-[2-Fluoro-4-methyl-5-[2-methyl-7-(morpholin-4-yl)indazol-5-yl]phenyl]-3-(2,2,2-tri fluoroethyl)pyrrolidine-1I-carboxamide

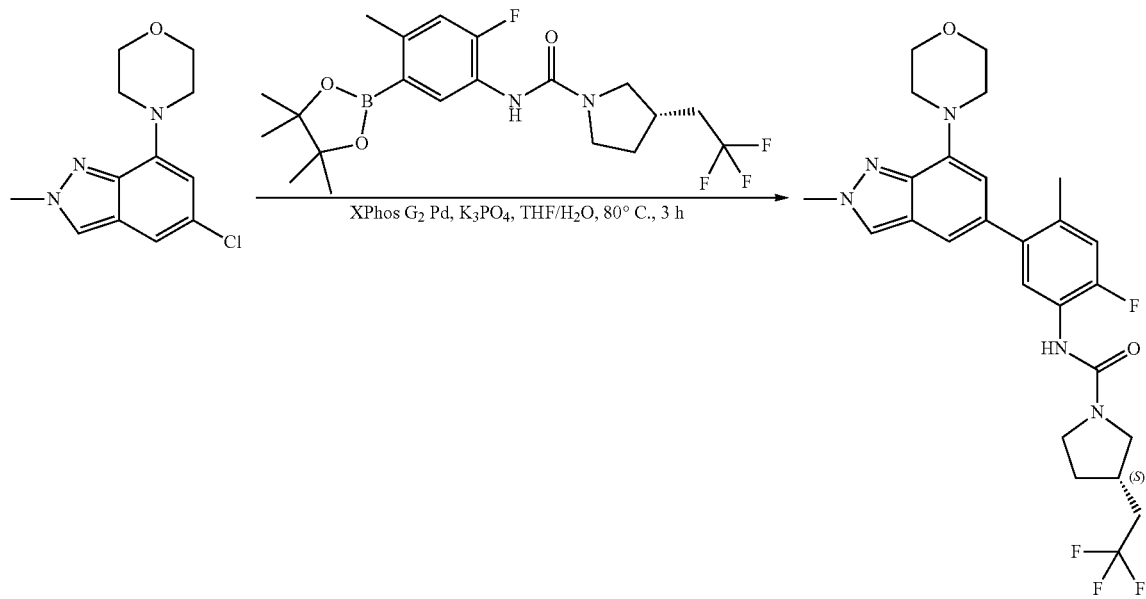

To a stirred mixture of 5-chloro-2-methyl-7-(morpholin-4-yl)indazole (0.12 g, 0.48 mmol) and (3S)-N-[2-fluoro-4-methyl-5-(4,4,5,5-tetramethyl-1,3,2-dioxaborolan-2-yl)phenyl]-3-(2,2,2-trifluoroethyl)pyrrolidine-I-carboxamide (0.21 g, 0.48 mmol), $K_3PO_4$ (0.20 g, 0.95 mmol) in THF (2.00 mL) and $H_2O$ (0.20 mL) was added XPhos palladium (IJ) biphenyl-2-amine chloride (31 mg, 0.05 mmol) in portions at room temperature. The reaction mixture was degassed with nitrogen for three times and stirred for 3 h at 80 TC. The resulting mixture was diluted with water (20 mL). The resulting mixture was extracted with EtOAc (3×20 mL). The combined organic layers were washed with brine (2×20 mL), dried over anhydrous $Na_2SO_4$. After filtration, the filtrate was concentrated under reduced pressure. The residue was purified by Prep-TLC (PE/EtOAc/EtOH=3/1) (1/1) to afford crude product. The crude product was purified by reverse phase flash with the following conditions: Column: WelFlash TM C18-I, 20-40 μm, 40 g; Eluent A: Water (plus 10 mmol/L $NH_4HCO_3$); Eluent B: ACN; Gradient: 25%-80% B in 20 min; Flow rate: 30 mL/min; Detector: 220/254 nm. The fractions contained desired product were combined and concentrated to afford (3S)-N-[2-fluoro-4-methyl-5-[2-methyl-7-(morpholin-4-yl)indazol-5-yl]phenyl]-3-(2,2,2-trifluoroethyl)pyrrolidine-1-carboxamide (132.3 mg, 53%) as a white solid. MS ESI calculated for $C_{26}H_{29}F_4N_5O_2$ $[M+H]^+$, 520.23, found 520.25; $^1H$ NMR (300 MHz, DMSO-$d_6$) δ 8.27 (s, 1H), 7.84 (s, 1H), 7.37-7.35 (m, 1H), 7.12-7.06 (m, 2H), 6.02 (s, 1H), 4.16 (s, 3H), 3.81-3.79 (m, 4H), 3.69-3.63 (m, 1H), 3.55-3.32 (m, 6H), 3.05-2.99 (m, 1H), 2.49-2.40 (m, 3H), 2.21-2.08 (m, 4H), 1.71-1.67 (m, 1H); $^{19}F$ NMR (282 MHz, DMSO-$d_6$) δ -63.39 (3F), -126.58 (1F)

The following compounds in Table 5 were prepared using procedures similar to those described in Example 1 using appropriate starting materials.

TABLE 5

| Ex. | Structure | IUPAC Name | Exact Mass [M + H]+ |
|---|---|---|---|
| 2 | 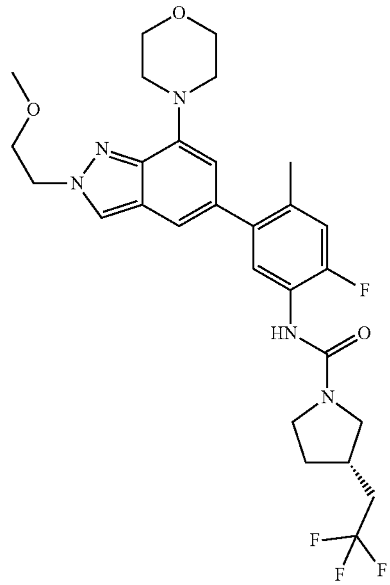 [SMILES: COCCn1cc2cc(-c3cc(NC(=O)N4CC[C@@H](CC(F)(F)F)C4)c(F)cc3C)cc(N3CCOCC3)c2n1] | (S)-N-(2-Fluoro-5-(2-(2-methoxyethyl)-7-morpholino-2H-indazol-5-yl)-4-methylphenyl)-3-(2,2,2-trifluoroethyl)pyrrolidine-1-carboxamide | Calc'd 564.25, found 564.40 |
| 3 | 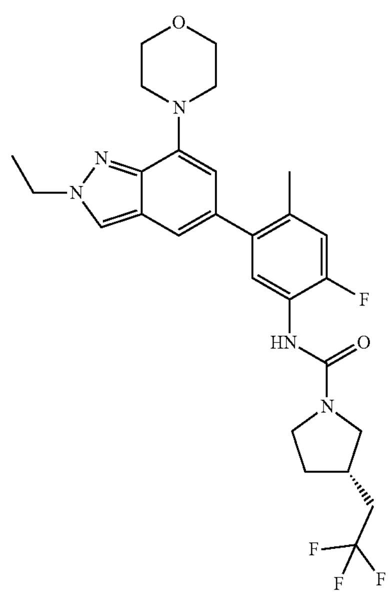 [SMILES: CCn1cc2cc(-c3cc(NC(=O)N4CC[C@@H](CC(F)(F)F)C4)c(F)cc3C)cc(N3CCOCC3)c2n1] | (S)-N-(5-(2-Ethyl-7-morpholino-2H-indazol-5-yl)-2-fluoro-4-methylphenyl)-3-(2,2,2-trifluoroethyl)pyrrolidine-1-carboxamide | Calc'd 534.57, found 534.30 |

TABLE 5-continued

| Ex. | Structure | IUPAC Name | Exact Mass [M + H]+ |
|---|---|---|---|
| 4 | 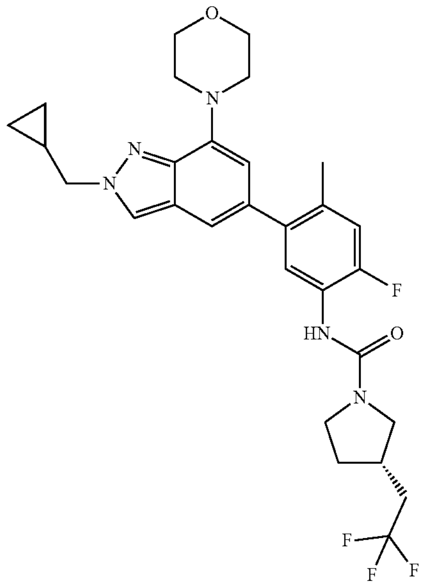 [SMILES: Cc1cc(F)c(NC(=O)N2CC[C@@H](CC(F)(F)F)C2)cc1-c1cc(N2CCOCC2)c2nn(CC3CC3)cc2c1] | (S)-N-(5-(2-(Cyclopropylmethyl)-7-morpholino-2H-indazol-5-yl)-2-fluoro-4-methylphenyl)-3-(2,2,2-trifluoroethyl)pyrrolidine-1-carboxamide | Calc'd 560.26, found 560.10 |
| 5 | 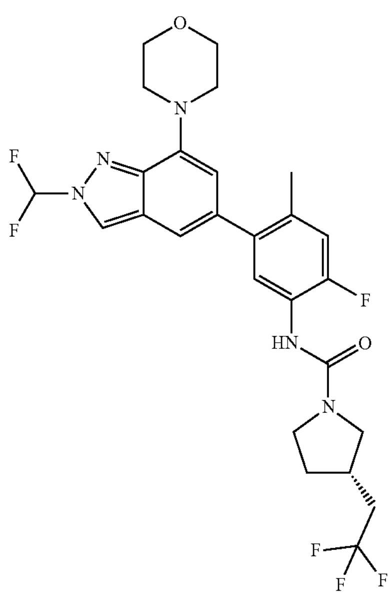 [SMILES: Cc1cc(F)c(NC(=O)N2CC[C@@H](CC(F)(F)F)C2)cc1-c1cc(N2CCOCC2)c2nn(C(F)F)cc2c1] | (S)-N-(5-(2-(Difluoromethyl)-7-morpholino-2H-indazol-5-yl)-2-fluoro-4-methylphenyl)-3-(2,2,2-trifluoroethyl)pyrrolidine-1-carboxamide | Calc'd 556.21, found 556.05 |

TABLE 5-continued
| Ex. | Structure | IUPAC Name | Exact Mass [M + H]+ |
|---|---|---|---|
| 6 | 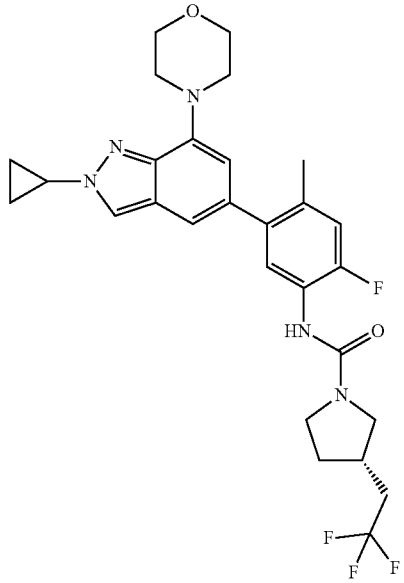 [SMILES: Cc1cc(F)c(NC(=O)N2CC[C@@H](CC(F)(F)F)C2)cc1-c1cc(N2CCOCC2)c2nn(C3CC3)cc2c1] | (S)-N-(5-(2-Cyclopropyl-7-morpholino-2H-indazol-5-yl)-2-fluoro-4-methylphenyl)-3-(2,2,2-trifluoroethyl)pyrrolidine-1-carboxamide | Calc'd 546.24, found. 546.40 |
| 9 | 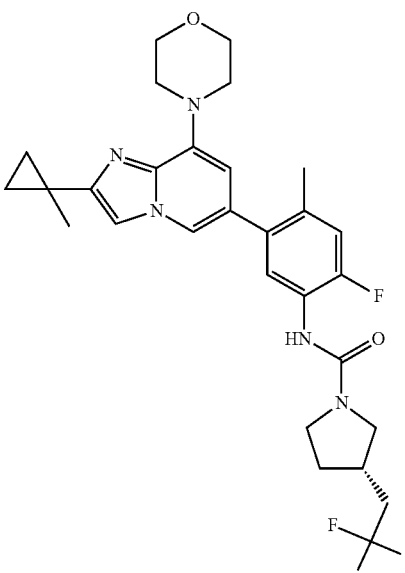 | (S)-N-(2-Fluoro-4-methyl-5-(2-(1-methylcyclopropyl)-8-morpholinoimidazo[1,2-a]pyridin-6-yl)phenyl)-3-(2,2,2-trifluoroethyl)pyrrolidine-1-carboxamide | Calc'd 560.26, found 560.45 |

TABLE 5-continued

| Ex. | Structure | IUPAC Name | Exact Mass [M + H]+ |
|---|---|---|---|
| 10 | 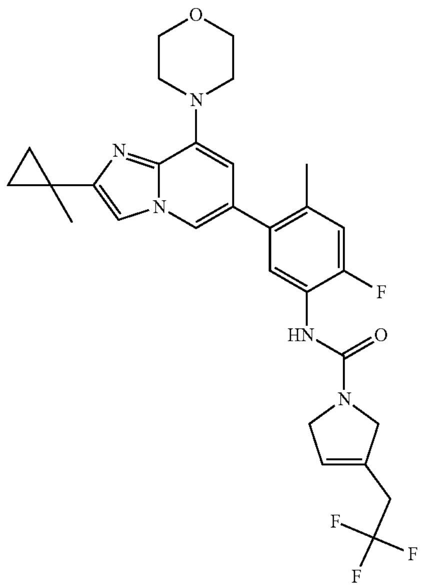 [SMILES: Cc1cc(F)c(NC(=O)N2CC=C(CC(F)(F)F)C2)cc1-c1cc(N2CCOCC2)c2nc(C3(C)CC3)cn2c1] | N-(2-Fluoro-4-methyl-5-(2-(1-methylcyclopropyl)-8-morpholinoimidazo[1,2-a]pyridin-6-yl)phenyl)-3-(2,2,2-trifluoroethyl)-2,5-dihydro-1H-pyrrole-1-carboxamide | Calc'd 558.24, found 558.25 |

Example 7: (S)—N-(2-Fluoro-5-(2-isopropyl-8-morpholinoimidazo[1,2-a]pyridin-6-yl)-4-methylphenyl)-3-(2,2,2-tri fluoroethyl)pyrrolidine-1l-carboxamide

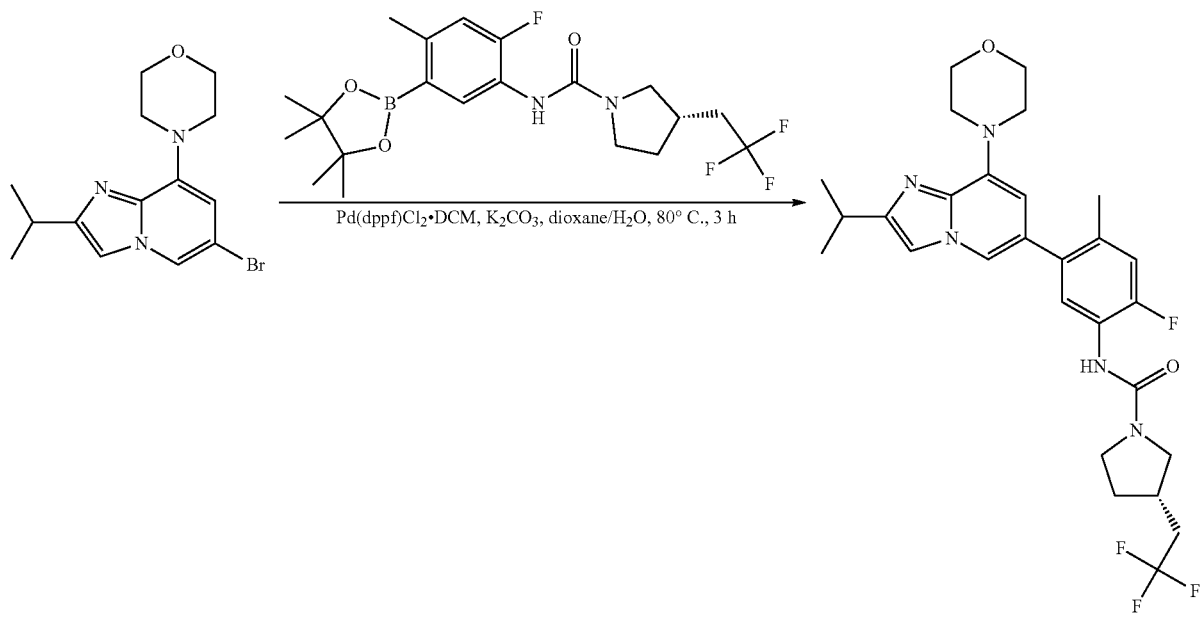

To a stirred of 4-{6-bromo-2-isopropylimidazo[1,2-a]pyridin-8-yl}morpholine (75 mg, 0.23 mmol) and (3S)-N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (100 mg, 0.23 mmol) in dioxane (0.8 mL) and water (0.2 mL) were added K₂CO₃ (96 mg, 0.69 mmol) and Pd(dppf)Cl₂CH₂Cl₂ (19 mg, 0.02 mmol) at room temperature. The reaction mixture was degassed with nitrogen for three times and stirred for 3 h at 80° C. The resulting mixture was concentrated under reduced pressure. The residue was purified by Prep-TLC (petroleum ether/ethyl acetate/ethanol=20/3/1) to afford the crude product. The crude product was purified by reverse phase Flash chromatography with the following conditions: Column: WelFlash TM C18-I, 20-40 μm, 40 g; Eluent A: water (Plus 10 mmol/L NH₄HCO₃); Eluent B: ACN; Gradient: 25% to 80% B in 20 min; Flow rate: 30 mL/min; Detector: 220/254 nm. The fractions contained desired product were combined and concentrated to afford (S)—N-(2-fluoro-5-(2-isopropyl-8-morpholinoimidazo[1,2-a]pyridin-6-yl)-4-methylphenyl)-3-(2,2,2-trifluoroethyl)pyrrolidine-1-carboxamide (70.2 mg, 55%) as a white solid. MS ESI calculated for $C_{28}H_{33}F_4N_5O_2$ [M+H]$^+$, 548.59 found 548.30; $^1$H NMR (400 MHz, Chloroform-d) δ 8.08 (d, J=8.4 Hz, 1H), 7.66 (s, 1H), 7.25 (s, 1H), 7.00 (d, J=12.0 Hz, 1H), 6.32 (d, J=15.2 Hz, 2H), 3.99 (d, J=5.6 Hz, 4H), 3.86-3.82 (m, 1H), 3.72-3.62 (m, 1H), 3.58 (s, 4H), 3.52-3.45 (m, 1H), 3.18-3.10 (m, 2H), 2.60-2.56 (m, 1H), 2.36-2.25 (m, 2H), 2.28 (s, 1H), 2.24 (s, 3H), 1.84-1.74 (m, 1H), 1.38 (d, J=6.9 Hz, 6H). $^{19}$F NMR (376 MHz, Chloroform-d) δ-64.96 (3F), -134.62 (1F).

The following compounds in Table 6 were prepared using procedures similar to those described in Example 7 using appropriate starting materials.

TABLE 6

| Ex. | Structure | IUPACName | Exact Mass [M + H]$^+$ |
|---|---|---|---|
| 8 | 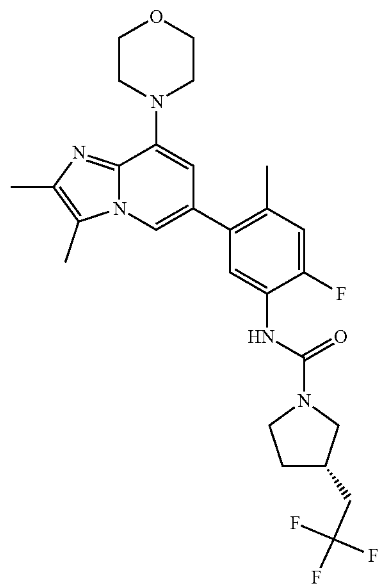 [SMILES: Cc1cc(F)c(NC(=O)N2CC[C@@H](CC(F)(F)F)C2)cc1-c1cc(N2CCOCC2)c2nc(C)c(C)n2c1] | (S)-N-(5-(2,3-Dimethyl-8-morpholinoimidazo[1,2-a]pyridin-6-yl)-2-fluoro-4-methylphenyl)-3-(2,2,2-trifluoroethyl)pyrrolidine-1-carboxamide | Calc'd 534.24, found 534.20 |
| 11 | 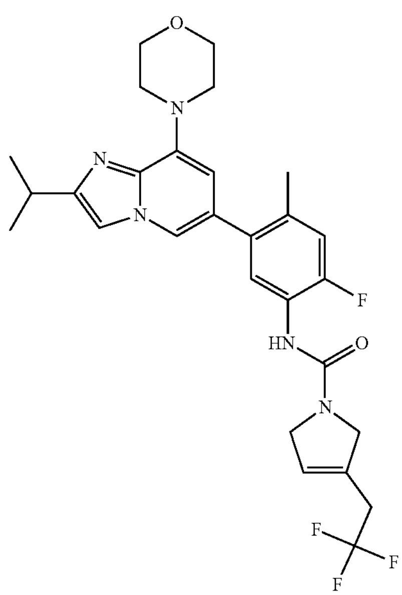 [SMILES: Cc1cc(F)c(NC(=O)N2CC=C(CC(F)(F)F)C2)cc1-c1cc(N2CCOCC2)c2nc(C(C)C)cn2c1] | N-(2-Fluoro-5-(2-isopropyl-8-morpholinoimidazo[1,2-a]pyridin-6-yl)-4-methylphenyl)-3-(2,2,2-trifluoroethyl)-2,5-dihydro-1H-pyrrole-1-carboxamide | Calc'd 546.24, found 546.45 |

TABLE 6-continued

| Ex. | Structure | IUPACName | Exact Mass [M + H]+ |
|---|---|---|---|
| 12 | 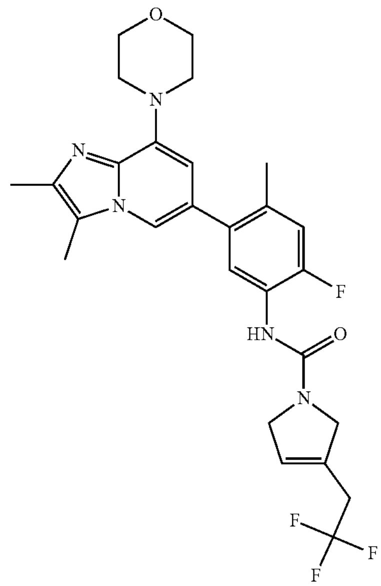 [SMILES: Cc1cc(F)c(NC(=O)N2CC=C(CC(F)(F)F)C2)cc1-c1cc(N2CCOCC2)c2nc(C)c(C)n2c1] | N-(5-(2,3-Dimethyl-8-morpholinoimidazo[1,2-a]pyridin-6-yl)-2-fluoro-4-methylphenyl)-3-(2,2,2-trifluoroethyl)-2,5-dihydro-1H-pyrrole-1-carboxamide | Calc'd 532.23, found 532.20 |
| 13 | 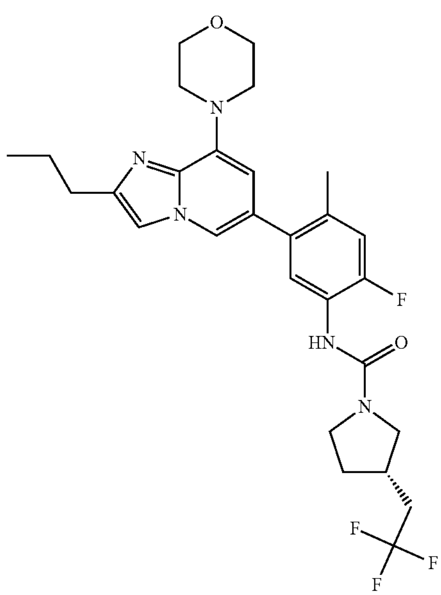 [SMILES: CCCc1cn2cc(-c3cc(NC(=O)N4CC[C@@H](CC(F)(F)F)C4)c(F)cc3C)cc(N3CCOCC3)c2n1] | (S)-N-(2-fluoro-4-methyl-5-(8-morpholino-2-propylimidazo[1,2-a]pyridin-6-yl)phenyl)-3-(2,2,2-trifluoroethyl)pyrrolidine-1-carboxamide | Calc'd 548.26, found 548.30 |

TABLE 6-continued
| Ex. | Structure | IUPACName | Exact Mass [M + H]+ |
|---|---|---|---|
| 14 | 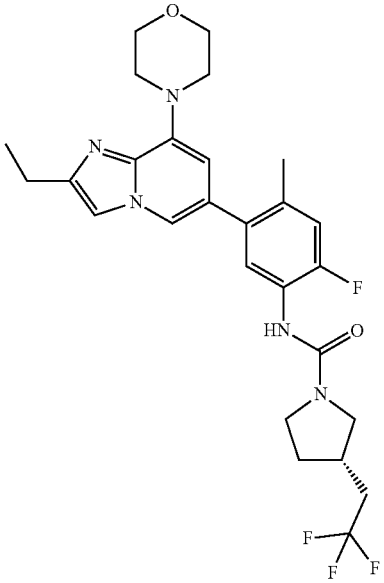 [SMILES: CCc1cn2cc(-c3cc(NC(=O)N4CC[C@@H](CC(F)(F)F)C4)c(F)cc3C)cc(N3CCOCC3)c2n1] | (S)-N-(5-(2-Ethyl-8-morpholinoimidazo[1,2-a]pyridin-6-yl)-2-fluoro-4-methylphenyl)-3-(2,2,2-trifluoroethyl)pyrrolidine-1-carboxamide | Calc'd 534.24, found. 534.20 |
| 15 | 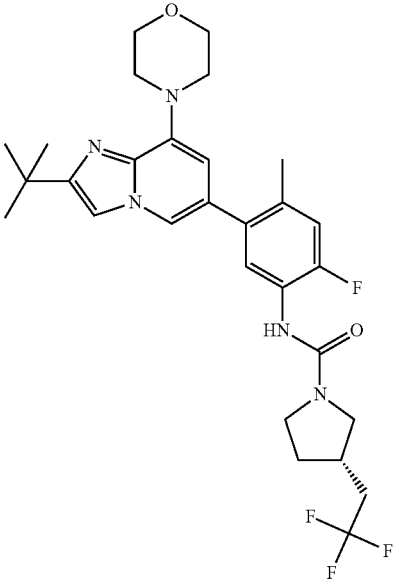 [SMILES: Cc1cc(F)c(NC(=O)N2CC[C@@H](CC(F)(F)F)C2)cc1-c1cc(N2CCOCC2)c2nc(C(C)(C)C)cn2c1] | (S)-N-(5-(2-(Tert-butyl)-8-morpholinoimidazo[1,2-a]pyridin-6-yl)-2-fluoro-4-methylphenyl)-3-(2,2,2-trifluoroethyl)pyrrolidine-1-carboxamide | Calc'd 562.27, found 562.35 |

383

Example 16: (S)—N-(5-(2,3-dimethyl-7-morpholino-2H-indazol-5-yl)-2-fluoro-4-methylphenyl)-3-(2,2,2-trifluoroethyl)pyrrolidine-1l-carboxamide

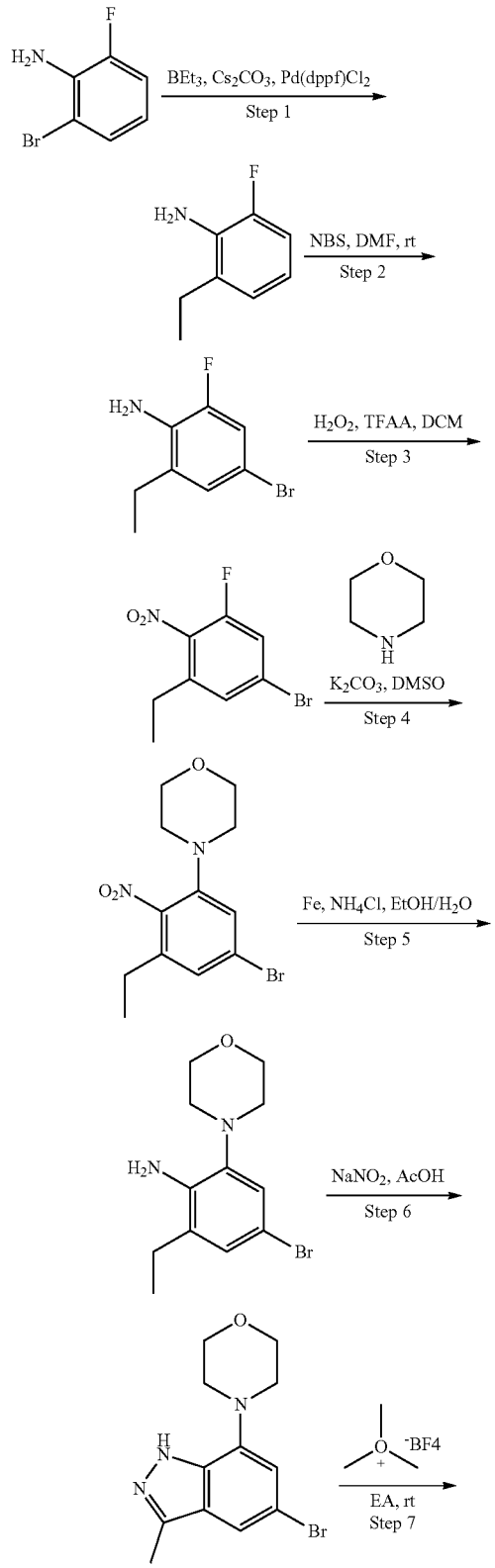

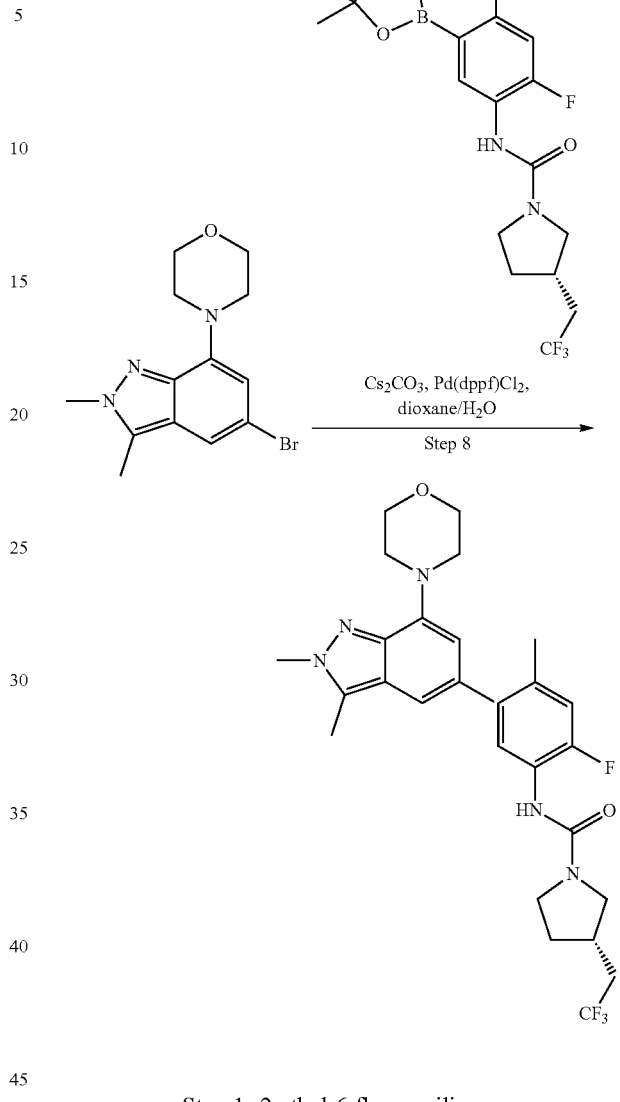

Step 1: 2-ethyl-6-fluoroaniline

A mixture of 2-bromo-6-fluoroaniline (20.0 g, 105.3 mmol), triethylborane (15.7 g, 160.0 mmoL), $Cs_2CO_3$ (102.9 g, 315. 8 mmol) and $Pd(dppf)Cl_2$ (7.7 g, 10.5 mmol) in DMF (500 mL) was stirred at 55° C. for 1 h under $N_2$. To the reaction mixture was cooleded, added water (1000 mL) and extracted with EtOAc (500 mL*3). The combined organic layers were washed with water (500 mL*2) and brine (500 mL), dried over anhydrous $Na_2SO_4$, filtered and concentrated under reduced pressure. The residue was purified by FCC (PE/EA=20/1) to afford 2-ethyl-6-fluoroaniline (9.5 g, 64%) as colorless liquid. MS ESI calculated for $C_8H_{10}FN$ [M+H]$^+$, 140.08, found 140.00.

Step 2: 4-bromo-2-ethyl-6-fluoroaniline

To a mixture of 2-ethyl-6-fluoroaniline (9.5 g, 68.3 mmol) in DMF (200 mL) was added NBS (9.7 g, 54.6 mmol) at 0° C. The reaction mixture was stirred at rt for 1 h. The resulting mixture was added water (500 mL) and extracted with EA (200 mL*2). The combined organic layers were washed with water (200 mL*2) and brine (200 mL), dried over Na$_2$SO$_4$, filtered and concentrated under reduced pressure. The residue was purified by FCC (PE/EA=20/1) to afford 4-bromo-2-ethyl-6-fluoroaniline (11.0 g, 74%) as pale brown oil. MS ESI calculated for C$_8$H$_9$BrFN [M+H]$^+$, 217.99, found 218.00.

Step 3: 5-bromo-1-ethyl-3-fluoro-2-nitrobenzene

To a mixture of H$_2$O$_2$(158.5 g, 30%, 276.5 mmol) in DCM (120 mL) was added TFAA (30.7 mL, 222.0 mmol) at 0° C. The reaction mixture was stirred at 0° C. for 10 min. Then to the reaction mixture was added a solution of 4-bromo-2-ethyl-6-fluoroaniline (10.0 g, 46.0 mmol) in DCM (30 mL) at 0° C. The reaction was stirred at 40° C. for 10h. The resulting mixture was added water (100 mL) and extracted with EA (200 mL). The organic layer was dried over Na$_2$SO$_4$, filtered and concentrated under reduced pressure. The residue was purified by FCC (PE/EA=20/1) to afford 5-bromo-1-ethyl-3-fluoro-2-nitrobenzene (6.0 g, 52%) as a pale brown solid. MS ESI calculated for C$_8$H$_7$BrFNO$_2$ [M+H]$^+$, 247.96, found 247.90.

Step 4: 4-(5-bromo-3-ethyl-2-nitrophenyl)morpholine

To a mixture of 5-bromo-1-ethyl-3-fluoro-2-nitrobenzene (6.0 g, 24.1 mmol) in DMSO (100 mL) was added morpholine (3.1 g, 36.2 mmol) and K$_2$CO$_3$ (6.6 g, 48.3 mmol) at rt. The reaction was stirred at 60° C. for 16h. The resulting mixture was cooleded to rt, added water (200 mL) and extracted with EA (200 mL). The organic layer was dried over Na$_2$SO$_4$, filtered and concentrated under reduced pressure. The residue was purified by FCC (PE/EA=5/1) to afford 4-(5-bromo-3-ethyl-2-nitrophenyl)morpholine (4.3 g, 56.4%) as brown oil. MS ESI calculated for C$_{12}$H$_{15}$BrN$_2$O$_3$ [M+H]$^+$, 315.03, found 315.00.

Step 5: 4-bromo-2-ethyl-6-morpholinoaniline

To a mixture of 4-(5-bromo-3-ethyl-2-nitrophenyl)morpholine (4.3 g, 13.6 mmol) in EtOH/H$_2$O (70/70 mL) was added Fe (7.6 g, 136.5 mmol) and NH$_4$Cl (7.3 g, 136.5 mmol) at rt. The reaction was stirred at 70° C. for 2h. The resulting mixture was cooled to rt, added water (100 mL), filtered and washed with EA (100 mL). The organic layer was concentrated. The residue was diluted with water (100 mL) and extracted with EA (200 mL). The organic layer was dried over Na$_2$SO$_4$, filtered and concentrated under reduced pressure. The residue was purified by FCC (PE/EA=10/1) to afford 4-bromo-2-ethyl-6-morpholinoaniline (3.1 g, 80%) as brown oil. MS ESI calculated for C$_{12}$H$_{17}$BrN$_2$O[M+H]$^+$, 285.05, found 285.00.

Step 6: 4-(5-bromo-3-methyl-1H-indazol-7-yl)morpholine

To a mixture of 4-bromo-2-ethyl-6-morpholinoaniline (1.5 g, 5.2 mmol) in AcOH (35 mL) was added NaNO$_2$ (0.39 g, 5.78 mmol) at 0° C. The reaction mixture was stirred at rt for 4h. The resulting mixture was concentrated. The residue was diluted with EtOAc (100 mL) and adjusted pH 7 with sat NaHCO$_3$. The organic layer was dried over Na$_2$SO$_4$, filtered and concentrated under reduced pressure. The residue was purified by FCC (PE/EA=2/1) to afford 4-(5-bromo-3-methyl-1H-indazol-7-yl)morpholine (340 mg, 22%) as a brown solid. MS ESI calculated for C$_{12}$H$_{14}$BrN$_3$O [M+H]$^+$, 296.03, found 296.00.

Step 7: 4-(5-bromo-2,3-dimethyl-2H-indazol-7-yl)morpholine

To a mixture of 4-(5-bromo-3-methyl-1H-indazol-7-yl)morpholine (290 mg, 0.97 mmol) in EtOAc (35 mL) was added trimethyloxonium tetrafluoroborate (188 mg, 1.27 mmol) at rt. The reaction mixture was stirred at rt for 2h. The reaction mixture was filtered and washed with EA (100 mL). The filtrate was evoparated. The residue was diluted with water (100 mL) and extracted with EA (100 mL). The organic layer was dried over Na$_2$SO$_4$, filtered and concentrated under reduced pressure. The residue was purified by FCC (PE/EA=2/1) to afford 4-(5-bromo-2,3-dimethyl-2H-indazol-7-yl)morpholine (195 mg, 64%) as a brown solid. MS ESI calculated for C$_{13}$H$_{16}$BrN$_3$O [M+H]$^+$, 310.05, found 310.00.

Example 16: (S)—N-(5-(2,3-dimethyl-7-morpholino-2H-indazol-5-yl)-2-fluoro-4-methylphenyl)-3-(2,2,2-trifluoroethyl)pyrrolidine-1-carboxamide A mixture of 4-(5-bromo-2,3-dimethyl-2H-indazol-7-yl)morpholine (50 mg, 0.16 mmol), (S)—N-(2-fluoro-4-methyl-5-(4,4,5,5-tetramethyl-1,3,2-dioxaborolan-2-yl)phenyl)-3-(2,2,2-trifluoroethyl)pyrrolidine-1-carboxamide (69 mg, 0.16 mmol), Cs$_2$CO$_3$ (104 mg, 0.32 mmol) and Pd(dppf)Cl$_2$ (11 mg, 0.01 mmol) in dioxane/H$_2$O (10 mL/2 mL) was stirred at 80° C. for 3h under N$_2$. The reaction mixture was cooled, added water (30 mL) and extracted with EtOAc (30 mL). The organic layer was washed with brine (40 mL), dried over anhydrous Na$_2$SO$_4$, filtered and concentrated under reduced pressure. The residue was purified by prep-HPLC (HCOOH) to afford (S)—N-(5-(2,3-dimethyl-7-morpholino-2H-indazol-5-yl)-2-fluoro-4-methylphenyl)-3-(2,2,2-trifluoroethyl)pyrrolidine-1-carboxamide (23.3 mg, 27.1%) as a white solid. MS ESI calculated for C$_{27}$H$_{31}$F$_4$N$_5$O$_2$ [M+H]$^+$, 534.24, found 534.20. $^1$H NMR (400 MHz, DMSO-d$_6$), δ 7.83 (s, 1H), 7.35 (d, J=8.4 Hz, 1H), 7.10 (d, J=12.0 Hz, 1H), 7.02 (d, J=0.8 Hz, 1H), 6.29 (d, J=0.8 Hz, 1H), 4.03 (s, 3H), 3.80-3.78 (m, 4H), 3.58-3.52 (m, 1H), 3.52-3.44 (m, 1H), 3.41-3.42 (m, 4H), 3.04-3.01 (m, 1H), 2.56 (s, 3H), 2.49-2.41 (m, 4H), 2.20 (s, 3H), 2.10-2.02 (m, 1H), 1.68-1.63 (m, 1H).

Example 17: (S)—N-(2-fluoro-4-methyl-5-(8-morpholinoimidazo[1,2-a]pyridin-6-yl)phenyl)-3-(2,2,2-trifluoroethyl)pyrrolidine-1-carboxamide

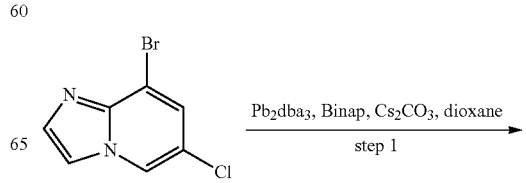

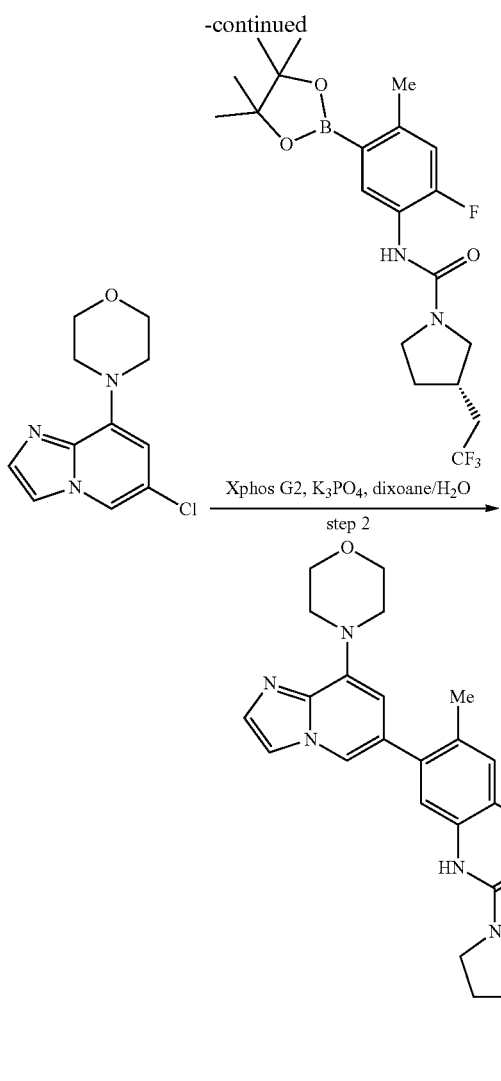

Step 1: 4-(6-chloroimidazo[1,2-a]pyridin-8-yl)morpholine

A mixture of 8-bromo-6-chloroimidazo[1,2-a]pyridine (1.0 g, 4.33 mmol), morpholine (753 mg, 8.66 mmol), Pd$_2$dba$_3$ (394 mg, 0.43 mmol), Binap (280 mg, 0.43 mmol) and Cs$_2$CO$_3$ (2.82 g, 8.66 mmol) in dioxane (30 mL) was stirred at 100° C. for 5h under nitrogen atmosphere. The resulting mixture was cooled, filtered and concentrated under reduced pressure. The residue was purified by FCC (PE/EtOAc=2/1) to afford 4-(6-chloroimidazo[1,2-a]pyridin-8-yl)morpholine (750 mg, 75%) as a yellow solid. MS ESI calculated for C$_1$H$_{12}$ClN$_3$O [M+H]$^+$, 238.07, found 238.1.

Example 17: (S)—N-(2-fluoro-4-methyl-5-(8-morpholinoimidazo[1,2-a]pyridin-6-yl)phenyl)-3-(2,2,2-trifluoroethyl)pyrrolidine-1-carboxamide A mixture of 4-(6-chloroimidazo[1,2-a]pyridin-8-yl)morpholine (100 mg, 0.42 mmol), (S)—N-(2-fluoro-4-methyl-5-(4,4,5,5-tetramethyl-1,3,2-dioxaborolan-2-yl)phenyl)-3-(2,2,2 trifluoroethyl)pyrrolidine-1-carboxamide (180 mg, 0.42 mmol), Xphos G2 (32 mg, 0.04 mmol) and K$_3$PO$_4$ (178 mg, 0.84 mmol) in dioxane (10 mL) and H$_2$O (2 mL) was stirred at 85° C. for 2h under nitrogen atmosphere. The resulting mixture was cooled, added water (20 mL) and extracted with EA (50 mL). The organic layer was dried over Na$_2$SO$_4$, filtered and concentrated under reduced pressure. The residue was purified by prep-HPLC to afford (S)—N-(2-fluoro-4-methyl-5-(8-morpholinoimidazo[1,2-a]pyridin-6-yl)phenyl)-3-(2,2,2-trifluoroethyl)pyrrolidine-1-carboxamide (113.4 mg, 53%) as a white solid. MS ESI calculated for C$_{25}$H$_{27}$F$_4$N$_5$O$_2$ [M+H]$^+$, 506.21, found 506.10. $^1$H NMR (400 MHz, DMSO-d$_6$), δ 8.12 (s, 1H), 7.90 (s, 2H), 7.52 (s, 1H), 7.43 (d, J=8.0 Hz, 1H), 7.17 (d, J=11.6 Hz, 1H), 6.35 (br s, 1H), 3.80 (t, J=4.4 Hz, 4H), 3.68-3.64 (m, 1H), 3.53 (s, 5H), 3.03 (t, J=9.2 Hz, 1H), 2.50-2.41 (m, 4H), 2.25 (s, 3H), 2.14-2.07 (m, 1H), 1.71-1.61 (m, 1H).

Example 18: (S)—N-(5-(2-cyclopropyl-8-morpholinoimidazo[1,2-a]pyridin-6-yl)-2-fluoro-4-methylphenyl)-3-(2,2,2-trifluoroethyl)pyrrolidine-1-carboxamide

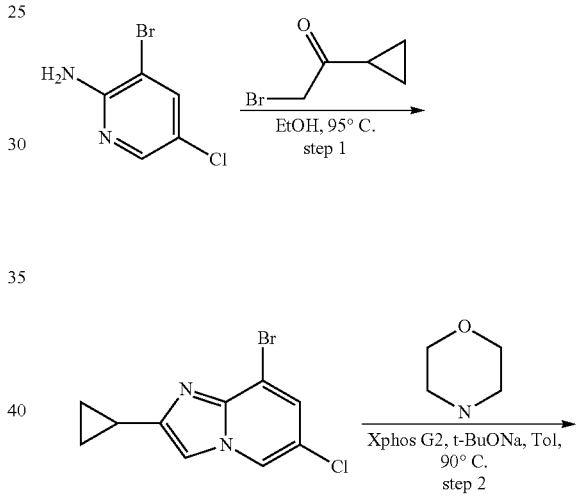

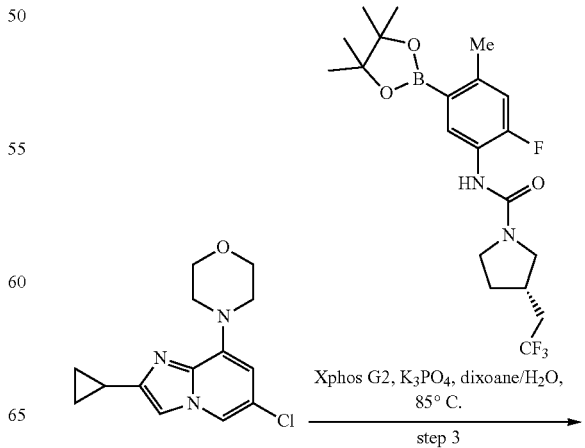

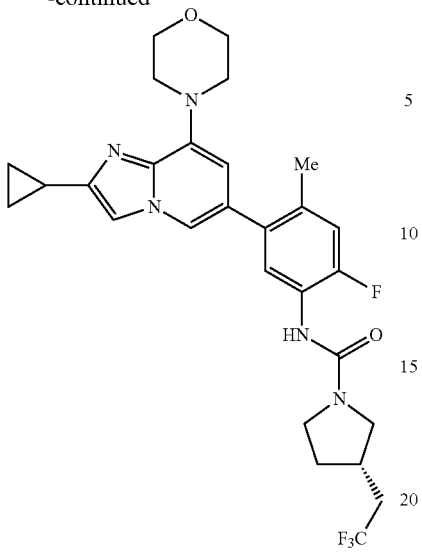

Step 1: 8-bromo-6-chloro-2-cyclopropylimidazo[1,2-a]pyridine

A suspension of 3-bromo-5-chloropyridin-2-amine (5.0 g, 24.2 mmol) and 2-bromo-1-cyclopropylethan-1-one (2.6 mL, 76.6 mmol) in EtOH (100 mL) was stirred at 95° C. for 16h. The reaction mixture was cooled and concentrated. The residue was slurried with EA (30 mL) to afford 8-bromo-6-chloro-2-cyclopropylimidazo[1,2-a]pyridine (5.2 g, 79%) as a gray solid. MS ESI calculated for $C_{10}H_8BrClN_2$ [M+H]$^+$, 270.96, Found:271.00.

Step 2: 4-(6-chloro-2-cyclopropylimidazo[1,2-a]pyridin-8-yl)morpholine

A mixture of 8-bromo-6-chloro-2-cyclopropylimidazo[1,2-a]pyridine (500 mg, 1.85 mmol), morpholine (241 mg, 2.77 mmol), Xphos G2 (145 mg, 0.18 mmol) and t-BuONa (354 mg, 3.69 mmol) in toluene (20 mL) was stirred at 90° C. for 16h under nitrogen atmosphere. The resulting mixture was cooled, added water (50 mL) and extracted with EA (100 mL). The organic layer dried over Na$_2$SO$_4$, filtered and concentrated under reduced pressure. The residue was purified by FCC (PE/EA=1/1) to afford 4-(6-chloro-2-cyclopropylimidazo[1,2-a]pyridin-8-yl)morpholine (115 mg, 23%) as brown oil. MS ESI calculated for $C_{14}H_{16}ClN_3O$ [M+H]$^+$, 278.10, found 278.10.

Example 18: (S)—N-(5-(2-cyclopropyl-8-morpholinoimidazo[1,2-a]pyridin-6-yl)-2-fluoro-4-methylphenyl)-3-(2,2,2-trifluoroethyl)pyrrolidine-1-carboxamide A mixture of 4-(6-chloro-2-cyclopropylimidazo[1,2-a]pyridin-8-yl)morpholine (64 mg, 0.23 mmol), (S)—N-(2-fluoro-4-methyl-5-(4,4,5,5-tetramethyl-1,3,2-dioxaborolan-2-yl)phenyl)-3-(2,2,2-trifluoroethyl)pyrrolidine-1-carboxamide (100 mg, 0.23 mmol), Xphos G2 (18 mg, 0.02 mmol) and K$_3$PO$_4$ (99 mg, 0.46 mmol) in dioxane (15 mL) and H$_2$O (3 mL) was stirred at 85° C. for 1 h under nitrogen atmosphere. The resulting mixture was cooled, added water (50 mL) and extracted with EA (100 mL). The organic layer dried over Na$_2$SO$_4$, filtered and concentrated under reduced pressure to give the crude residue. The residue was purified by Prep-HPLC to afford (S)—N-(5-(2-cyclopropyl-8-morpholinoimidazo[1,2-a]pyridin-6-yl)-2-fluoro-4-methylphenyl)-3-(2,2,2-trifluoroethyl)pyrrolidine-1-carboxamide (67.9 mg, 54%) as a white solid. MS ESI calculated for $C_{28}H_{31}F_4N_5O_2$[M+H]$^+$, 546.24, found 546.30. $^1$H NMR (400 MHz, DMSO-d$_6$) δ 7.95 (d, J=1.2 Hz, 1H), 7.89 (s, 1H), 7.61 (s, 1H), 7.40 (d, J=8.0 Hz, 1H), 7.14 (d, J=11.2 Hz, 1H), 6.27 (s, 1H), 3.80-3.78 (m, 4H), 3.68-3.64 (m, 1H), 3.52-3.49 (m, 5H), 3.30-3.33 (m, 1H), 3.05-3.00 (m, 1H), 2.50-2.40 (m, 3H), 2.22 (s, 3H), 2.07-1.99 (m, 2H), 1.66-1.64 (m, 1H), 0.92-0.88 (m, 2H), 0.80-0.75 (m, 2H).

Example 19: 5-(tert-butyl)-N-(2-fluoro-4-methyl-5-(8-morpholinoimidazo[1,2-a]pyridin-6-yl)phenyl)-3,6-dihydropyridine-1(2H)-carboxamide

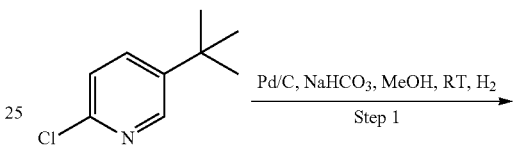

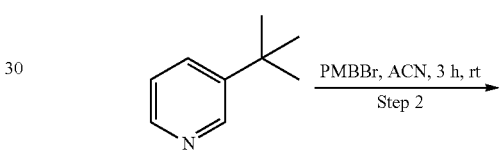

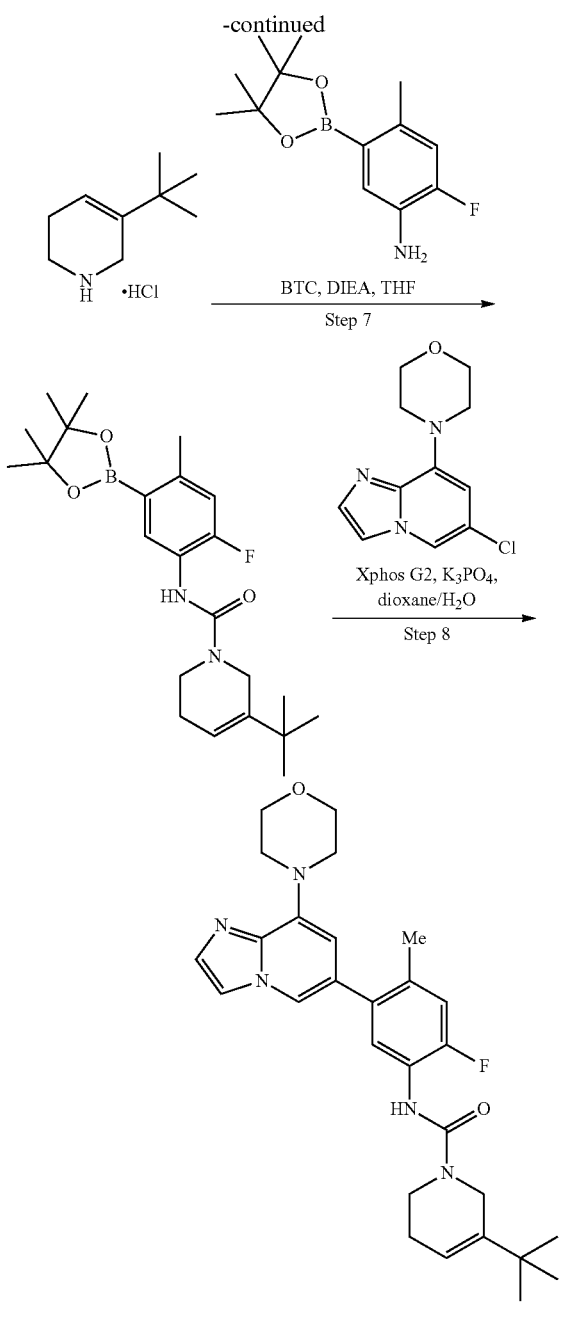

Step 1: 3-(tert-butyl)pyridine

A mixture of 5-(tert-butyl)-2-chloropyridine (5.0 g, 29.5 mmol), Pd/C (1.5g, 5%), NaHCO$_3$ (2.5 g, 29.5 mmol) in MeOH (50 mL) was stirred at rt for 5h under Hydrogen gas balloon atmosphere. The resulting mixture was filtered and concentrated under reduced pressure to afford 3-(tert-butyl) pyridine (3.4 g, 85%) as a white solid. MS ESI calculated for C$_9$H$_{13}$N [M+H]$^+$, 136.10, found 136.10.

Step 2: 3-(tert-butyl)-1-(4-methoxybenzyl)pyridin-1-ium bromide

A mixture of 3-(tert-butyl)pyridine (3.4 g, 25.2 mmol), PMBBr (3.7 mL, 25.2 mmol) in Acetonitrile (50 mL) was stirred at rt for 3h under nitrogen atmosphere. The resulting mixture was eveporated. The residue was stirred with EA (50 mL), poured out solvent to afford 3-(tert-butyl)-1-(4-methoxybenzyl)pyridin-1-ium bromide (5.5 g, 65%) as brown oil. MS ESI calculated for C$_{17}$H$_{22}$BrNO [M+H-79]$^+$, 336.09, found 257.2.

Step 3: 5-(tert-butyl)-1-(4-methoxybenzyl)-1,2,3,6-tetrahydropyridine

A mixture of 3-(tert-butyl)-1-(4-methoxybenzyl)pyridin-1-ium bromide (5.5 g, 21.5 mmol) in MeOH (50 mL) was cooled to 0° C. Then to the mixutre was added NaBH$_4$ (1.6 g, 42.9 mmol) slowley at 0° C. The reaction mixture was stirred at rt for 5h. The resulting mixture was quenched with NaHCO$_3$ solution to adjust pH 9 and extracted with EA (100 mL*2). The combined organic layer was dried over Na$_2$SO$_4$, filtered and concentrated under reduced pressure. The residue was purified by FCC (DCM/MeOH=20/1) to afford 5-(tert-butyl)-1-(4-methoxybenzyl)-1,2,3,6-tetrahydropyridine (4.5 g, 81%) as pale yellow oil. MS ESI calculated for C$_{17}$H$_{25}$NO [M+H]$^+$, 260.19, found 260.1.

Step 4: 5-(tert-butyl)-1,2,3,6-tetrahydropyridine

A mixture of 5-(tert-butyl)-1-(4-methoxybenzyl)-1,2,3,6-tetrahydropyridine (4.5 g, 17.3 mmol) and 1-chloroethyl carbonochloridate (2.2 mL, 20.8 mmol) in DCE (60 mL) was stirred at 70° C. for 16h under nitrogen atmosphere. The resulting mixture was concentrated under reduced pressure. Then to the residue was cooled, added MeOH (60 mL) and stirred at 70° C. for 2h under nitrogen atmosphere. The resulting mixture was cooled and concentrated under reduced pressure. The residue was used to next step directly.

Step 5: tert-butyl 3-(tert-butyl)-5,6-dihydropyridine-1(2H)-carboxylate

A mixture of 5-(tert-butyl)-1,2,3,6-tetrahydropyridine (17.3 mmol, crude) in DCM (30 mL) was cooled to 0° C. Then to the mixture was added DIEA (8.4 mL, 51.6 mmol), followed by di-tert-butyl dicarbonate (4.5 g, 20.7 mmol) and stirred at rt for 5h. The resulting mixture was concentrated under reduced pressure. The residue was purified by FCC (PE/EA=10/1) to afford tert-butyl 3-(tert-butyl)-5,6-dihydropyridine-1(2H)-carboxylate (3.0 g, 73%) as pale yellow oil. MS ESI calculated for C$_{14}$H$_{25}$NO$_2$ [M+H]$^+$, 240.19, found 240.2.

Step 6: 5-(tert-butyl)-1,2,3,6-tetrahydropyridine hydrochloride salt

A mixture of tert-butyl 3-(tert-butyl)-5,6-dihydropyridine-1(2H)-carboxylate (3.0 g, 12.5 mmol) in EA/HCl (20 mL, 2N) was stirred at rt for 3h. The resulting mixture was concentrated under reduced pressure. The residue was used to next step directly.

Step 7: 5-(tert-butyl)-N-(2-fluoro-4-methyl-5-(4,4,5,5-tetramethyl-1,3,2-dioxaborolan-2-yl)phenyl)-3,6-dihydropyridine-1(2H)-carboxamide To a solution of 2-fluoro-4-methyl-5-(4,4,5,5-tetramethyl-1,3,2-dioxaborolan-2-yl)aniline (2.3 g, 9.1 mmol) and DIEA (7.5 mL, 45.8 mmol) in THF (50 mL) was added BTC (1.1 g, 3.6 mmol) at −78° C. under nitrogen atmosphere. The reaction mixture was stirred at −78° C. for 30 min. Then the HCl salt of 5-(tert-butyl)-1,2,3,6-tetrahydropyridine (12.5 mmol) was added to the mixture at −78° C. The mixture was stirred at 0° C. for another 1h. The resulting mixture was dilutedd with H$_2$O (50 mL). The resulting mixture was extracted with EtOAc (50 mL*2). The combined organic layers were washed with brine (40 mL), dried over anhydrous Na$_2$SO$_4$, filtered and concentrated. The residue was purified by FCC (PE/EA=10/1) to afford 5-(tert-butyl)-N-(2-fluoro-4-methyl-5-(4,4,5,5-tetramethyl-1,3,2-dioxaborolan-2-yl)phenyl)-3,6-dihydropyridine-1(2H)-carboxamide (2.6 g, 68%) as a white solid. MS ESI calculated for C$_{23}$H$_{34}$BFN$_2$O$_3$[M+H]$^+$, 417.26, found 417.20.

Example 19: 5-(tert-butyl)-N-(2-fluoro-4-methyl-5-(8-morpholinoimidazo[1,2-a]pyridin-6-yl)phenyl)-3,6-dihydropyridine-1(2H)-carboxamide A mixture of 4-(6-chloroimidazo[1,2-a]pyridin-8-yl)morpholine (60 mg, 0.25 mmol), 5-(tert-butyl)-N-(2-fluoro-4-methyl-5-(4,4,5,5-tetramethyl-1,3,2-dioxaborolan-2-yl)phenyl)-3,6-dihydropyridine-1(2H)-carboxamide (104 mg, 0.25 mmol), Xphos G2 (16 mg, 0.02 mmol) and K$_3$PO$_4$ (106 mg, 0.50 mmol) in dioxane (10 mL) and H$_2$O (2 mL) was stirred at 85° C. for 1 h under nitrogen atmosphere. The resulting mixture was cooled, added water (20 mL) and extracted with EA (50 mL). The organic layer was dried over Na$_2$SO$_4$, filtered and concentrated under reduced pressure. The residue was purified by prep-HPLC to afford 5-(tert-butyl)-N-(2-fluoro-4-methyl-5-(8-morpholinoimidazo[1,2-a]pyridin-6-yl)phenyl)-3,6-dihydropyridine-1(2H)-carboxamide (19.0 mg, 15%) as a white solid. MS ESI calculated for C$_{28}$H$_{34}$FN$_5$O$_2$[M+H]$^+$, 492.27, found 492.1. $^1$H NMR (400 MHz, DMSO-d$_6$), δ 8.27 (s, 1H), 8.10 (s, 1H), 7.88 (s, 1H), 7.49 (s, 1H), 7.33 (d, J=8.0 Hz, 1H), 7.16 (d, J=7.6 Hz, 1H), 6.33 (s, 1H), 5.62-5.60 (m, 1H), 3.95 (d, J=1.6 Hz, 2H), 3.79 (t, J=4.4 Hz, 4H), 3.53 (t, J=4.4 Hz, 4H), 3.43 (t, J=6.0 Hz, 2H), 2.24 (s, 3H), 2.11-2.10 (m, 2H), 1.06 (s, 9H).

Example 20: N-(2-fluoro-5-(2-fluoro-8-morpholinoimidazo[1,2-a]pyridin-6-yl)-4-methylphenyl)-3-(2,2,2-trifluoroethyl)-2,5-dihydro-1H-pyrrole-1-carboxamide

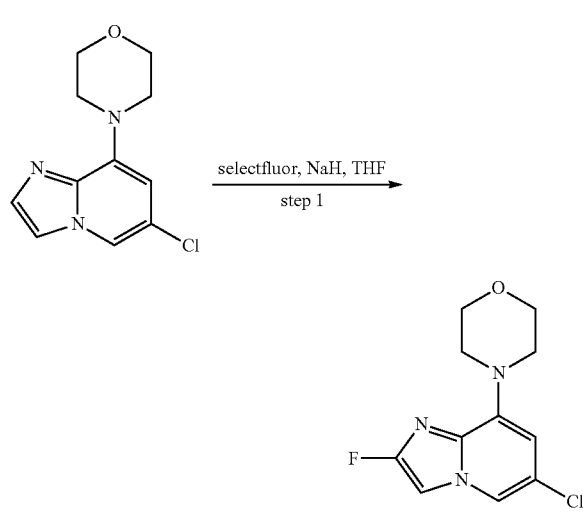

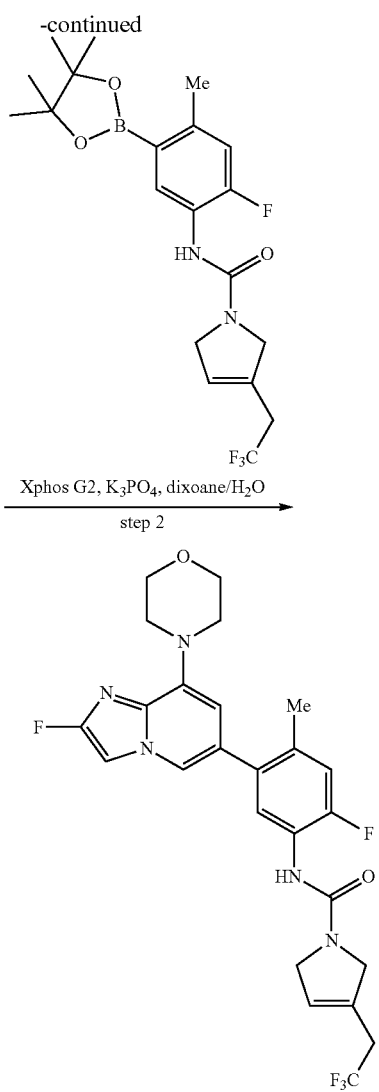

Step 1: 4-(6-chloro-2-fluoroimidazo[1,2-a]pyridin-8-yl)morpholine

To a mixture of 4-(6-chloroimidazo[1,2-a]pyridin-8-yl)morpholine (1.0 g, 4.20 mmol) in THF (30 mL) was added NaH (250 mg, 60%, 6.3 mmol) at 0° C. The reaction mixture was stirred at 0° C. for 15 min. Then to the reaction mixture was added selectfluor (2.98 g, 8.40 mmol) at 0° C.

The reaction mixture was stirred at rt overnight. The reaction mixture was diluted with water (100 mL). The resulting mixture was extracted with EtOAc (100 mL*2). The combined organic layers were washed with brine (100 mL), dried over anhydrous Na$_2$SO$_4$. After filtration, the filtrate was concentrated under reduced pressure. The residue was purified by reversed phase column chromatography (PE/EA=2/1) to afford 4-(6-chloro-2-fluoroimidazo[1,2-a]pyridin-8-yl)morpholine (90 mg, 8%) and 4-(6-chloro-3-fluoroimidazo[1,2-a]pyridin-8-yl)morpholine (150 mg, 14%) as a yellow semi-solid. 4-(6-chloro-2-fluoroimidazo[1,2-a]pyridin-8-yl)morpholine $^1$H NMR (400 MHz, CDCl$_3$) δ 7.88 (d, J=6.0 Hz, 1H), 7.55 (d, J=0.9 Hz, 1H), 7.44 (d, J=0.9 Hz, 1H), 3.92-3.90 (m, 4H), 3.64-3.61 (m, 4H). MS ESI calculated for C$_{11}$H$_{11}$ClFN$_3$O [M+H]$^+$, 256.06, found 256.00. 4-(6-chloro-3-fluoroimidazo[1,2-a]pyridin-8-yl)morpholine ¹H NMR (400 MHz, CDCl₃) δ 7.61 (s, 2H), 6.40 (d, J=6.8 Hz, 1H), 3.97-3.95 (m, 4H), 3.49-3.47 (m, 4H). MS ESI calculated for C₁₁H₁₁ClFN₃O [M+H]⁺, 256.06, found 256.00.

Example 20: N-(2-fluoro-5-(2-fluoro-8-morpholinoimidazo[1,2-a]pyridin-6-yl)-4-methylphenyl)-3-(2,2,2-trifluoroethyl)-2,5-dihydro-1H-pyrrole-1-carboxamide A mixture of 4-(6-chloro-2-fluoroimidazo[1,2-a]pyridin-8-yl)morpholine (40 mg, 0.16 mmol), N-(2-fluoro-4-methyl-5-(4,4,5,5-tetramethyl-1,3,2-dioxaborolan-2-yl)phenyl)-3-(2,2,2-trifluoroethyl)-2,5-dihydro-1H-pyrrole-1-carboxamide (67 mg, 0.16 mmol), Xphos G2 (12 mg, 0.02 mmol) and K₃PO₄ (67 mg, 0.31 mmol) in dioxane (15 mL) and H₂O (3 mL) was stirred at 85° C. for 1 h under nitrogen atmosphere. The resulting mixture was cooled, added water (50 mL) and extracted with EA (100 mL). The organic layer dried over Na₂SO₄, filtered and concentrated under reduced pressure to give crude residue. The residue was purified by Prep-HPLC to afford N-(2-fluoro-4-methyl-5-(4,4,5,5-tetramethyl-1,3,2-dioxaborolan-2-yl)phenyl)-3-(2,2,2-trifluoroethyl)-2,5-dihydro-1H-pyrrole-1-carboxamide (27.2 mg, 34%) as a white solid. MS ESI calculated for C₂₅H₂₄F₅N₅O₂ [M+H]⁺, 522.19, found 522.00. ¹H NMR (400 MHz, DMSO-d₆) δ 8.20 (d, J=6.4 Hz, 1H), 8.03 (s, 1H), 7.86 (s, 1H), 7.51 (d, J=0.8 Hz, 1H), 7.44 (d, J=8.0 Hz, 1H), 7.20 (d, J=11.6 Hz, 1H), 5.92 (s, 1H), 4.20 (s, 4H), 3.76-3.74 (m, 4H), 3.52-3.50 (m, 4H), 3.31-3.29 (m, 2H), 2.16 (s, 3H).

Example 21: (S)—N-(2-fluoro-5-(3-fluoro-8-morpholinoimidazo[1,2-a]pyridin-6-yl)-4-methylphenyl)-3-(2,2,2-trifluoroethyl)pyrrolidine-1-carboxamide A mixture of 4-(6-chloro-3-fluoroimidazo[1,2-a]pyridin-8-yl)morpholine (32 mg, 0.13 mmol), (S)—N-(2-fluoro-4-methyl-5-(4,4,5,5-tetramethyl-1,3,2-dioxaborolan-2-yl)phenyl)-3-(2,2,2-trifluoroethyl)pyrrolidine-1-carboxamide (54 mg, 0.13 mmol), Xphos G2 (10 mg, 0.01 mmol) and K₃PO₄ (53 mg, 0.25 mmol) in dioxane (10 mL) and H₂O (2 mL) was stirred at 85° C. for 1 h under nitrogen atmosphere. The resulting mixture was cooled, added water (50 mL) and extracted with EA (100 mL). The organic layer dried over Na₂SO₄, filtered and concentrated under reduced pressure to give crude residue. The residue was purified by Prep-HPLC to afford (S)—N-(2-fluoro-5-(3-fluoro-8-morpholinoimidazo[1,2-a]pyridin-6-yl)-4-methylphenyl)-3-(2,2,2-trifluoroethyl)pyrrolidine-1-carboxamide (30.5 mg, 46%) as a white solid. MS ESI calculated for C₂₅H₂₆F₅N₅O₂[M+H]⁺, 524.20, found 524.20. ¹H NMR (400 MHz, DMSO-d₆) δ 7.96-7.93 (m, 2H), 7.63 (d, J=0.8 Hz, 1H), 7.46 (d, J=8.0 Hz, 1H), 7.22 (d, J=11.6 Hz, 1H), 6.34 (d, J=6.8 Hz, 1H), 3.81-3.79 (m, 4H), 3.68-3.64 (m, 1H), 3.54-3.45 (m, 5H), 3.34-3.30 (m, 1H), 3.03 (t, J=9.2 Hz, 1H), 2.50-2.41 (m, 3H), 2.17 (s, 3H), 2.10-2.07 (m, 1H), 1.67-1.65 (m, 1H).

The following compounds in Table 7 were prepared using procedures similar to those described in Example 17, 18, or 20 using appropriate starting materials.

TABLE 7

| Ex. | Structure | IUPAC Name | Exact Mass [M + H]⁺ | ¹H NMR Spectrometry Data |
|---|---|---|---|---|
| 21 | 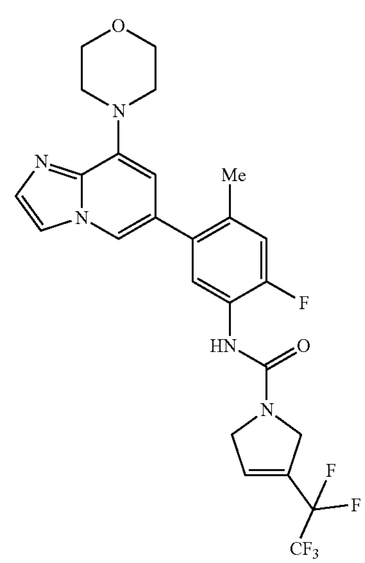 [SMILES: Cc1cc(F)c(NC(=O)N2CC=C(C(F)(F)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(perfluoroethyl)-2,5-dihydro-1H-pyrrole-1-carboxamide | Calc'd 540.18; found 540.10 | ¹H NMR (400 MHz, DMSO-d₆, δ 8.20 (s, 1H), 8.12 (s, 1H), 7.90 (s, 1H), 7.52 (s, 1H), 7.43 (d, J = 8.4 Hz, 1H), 7.20 (d, J = 11.6 Hz, 1H), 6.80 (s, 1H), 6.36 (s, 1H), 4.42 (s, 4H), 3.80 (t, J = 4.4 Hz, 4H), 3.54-3.52 (m, 4H), 2.26 (s, 3H). |

TABLE 7-continued

| Ex. | Structure | IUPAC Name | Exact Mass [M + H]⁺ | ¹H NMR Spectrometry Data |
|---|---|---|---|---|
| 22 | 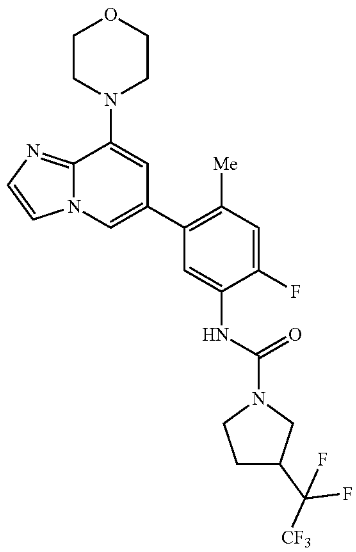 [SMILES: Cc1cc(F)c(NC(=O)N2CCC(C(F)(F)C(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(perfluoroethyl)pyrrolidine-1-carboxamide | Calc'd 542.19; found 542.20 | ¹H NMR (400 MHz, DMSO-$d_6$, δ 8.11-8.10 (m, 2H), 7.90 (s, 1H), 7.51 (s, 1H), 7.40 (d, J = 8.4 Hz, 1H), 7.18 (d, J = 11.6 Hz, 1H), 6.35 (s, 1H), 3.80 (t, J = 4.0 Hz, 4H), 3.72 (t, J = 9.6 Hz, 1H), 3.64 (t, J = 8.4 Hz, 1H), 3.54-3.52 (m, 4H), 3.46-3.37 (m, 2H), 2.51-2.49 (m, 1H), 2.25 (s, 3H), 2.18-2.15 (m, 1H), 2.03-1.98 (m, 1H). |
| 23 | 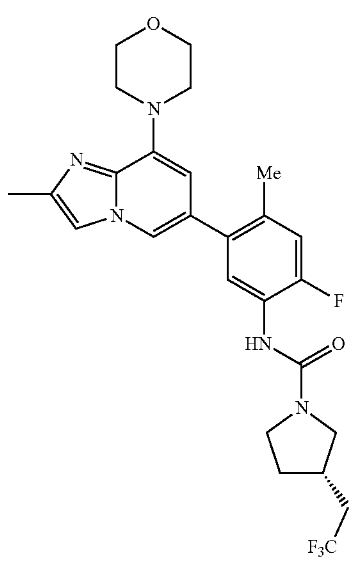 [SMILES: Cc1cn2cc(-c3cc(NC(=O)N4CC[C@@H](CC(F)(F)F)C4)c(F)cc3C)cc(N3CCOCC3)c2n1] | (S)-N-(2-fluoro-4-methyl-5-(2-methyl-8-morpholinoimidazo[1,2-a]pyridin-6-yl)phenyl)-3-(2,2,2-trifluoroethyl)pyrrolidine-1-carboxamide | Calc'd 520.23; found 520.20 | ¹H NMR (400 MHz, DMSO-$d_6$, δ 8.00 (d, J = 1.2 Hz, 1H), 7.88 (s, 1H), 7.60 (s, 1H), 7.41 (d, J = 8.0 Hz, 1H), 7.15 (d, J = 11.6 Hz, 1H), 6.28 (d, J = 0.9 Hz, 1H), 3.80 (t, J = 4.4 Hz, 4H), 3.69-3.64 (m, 1H), 3.54-3.51 (m, 5H), 3.34-3.28 (m, 1H), 3.05-3.02 (m, 1H), 2.50-2.43 (m, 3H), 2.33 (s, 3H), 2.23 (s, 3H), 2.07-2.01 (m, 1H), 1.70-1.65 (m, 1H). |

TABLE 7-continued

| Ex. | Structure | IUPAC Name | Exact Mass [M + H]+ | 1H NMR Spectrometry Data |
|---|---|---|---|---|
| 24 | 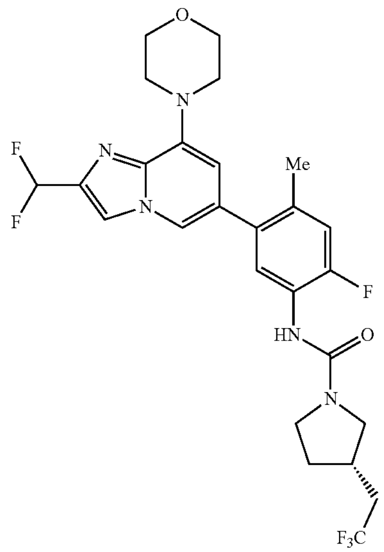 [SMILES: Cc1cc(F)c(NC(=O)N2CC[C@@H](CC(F)(F)F)C2)cc1-c1cc(N2CCOCC2)c2nc(C(F)F)cn2c1] | (S)-N-(5-(2-(difluoromethyl)-8-morpholinoimidazo[1,2-a]pyridin-6-yl)-2-fluoro-4-methylphenyl)-3-(2,2,2-trifluoroethyl)pyrrolidine-1-carboxamide | Calc'd 556.21; found 556.20 | 1H NMR (400 MHz, DMSO-d6, δ 8.22 (s, 1H), 8.15 (s, 1H), 7.93 (s, 1H), 7.44 (d, J = 8.4 Hz, 1H), 7.20 (t, J = 42.8 Hz, 1H), 7.17 (s, 1H), 6.45 (s, 1H), 3.81 (t, J = 4.4 Hz, 4H), 3.69-3.66 (m, 1H), 3.54-3.51 (m, 5H), 3.34-3.31 (m, 1H), 3.02 (t, J = 8.8 Hz, 1H), 2.50-2.43 (m, 3H), 2.25 (s, 3H), 2.07-2.02 (m, 1H), 1.70-1.62 (m, 1H). |
| 25 | 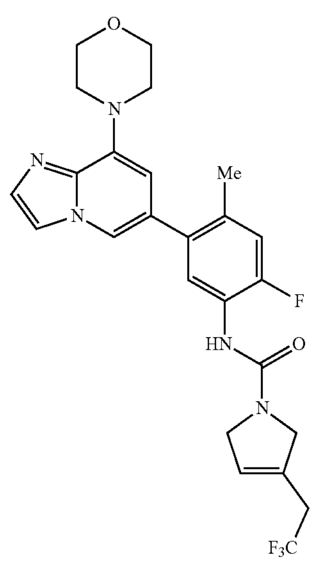 [SMILES: Cc1cc(F)c(NC(=O)N2CC=C(CC(F)(F)F)C2)cc1-c1cc(N2CCOCC2)c2nccn2c1] | N-(2-fluoro-4-methyl-5-(8-morpholinoimidazo[1,2-a]pyridin-6-yl)phenyl)-3-(2,2,2-trifluoroethyl)-2,5-dihydro-1H-pyrrole-1-carboxamide | Calc'd 504.19; found 504.20 | 1H NMR (400 MHz, DMSO-d6, δ 8.11 (s, 1H), 8.02 (s, 1H), 7.89 (s, 1H), 7.50 (s, 1H), 7.44 (d, J = 8.8 Hz, 1H), 7.18 (d, J = 11.6 Hz, 1H), 6.33 (s, 1H), 5.93 (s, 1H), 4.20-4.19 (m, 4H), 3.80 (t, J = 4.4 Hz, 4H), 3.55-3.53 (m, 4H), 3.32-3.30 (m, 2H), 2.25 (s, 3H). |

TABLE 7-continued

| Ex. | Structure | IUPAC Name | Exact Mass [M + H]+ | ¹H NMR Spectrometry Data |
|---|---|---|---|---|
| 26 | 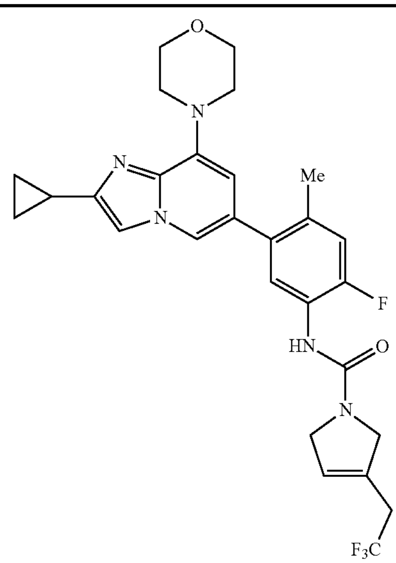 | N-(5-(2-cyclopropyl-8-morpholinoimidazo[1,2-a]pyridin-6-yl)-2-fluoro-4-methylphenyl)-3-(2,2,2-trifluoroethyl)-2,5-dihydro-1H-pyrrole-1-carboxamide | Calc'd 544.23; found 544.20 | ¹H NMR (400 MHz, DMSO-d₆, δ 8.01 (s, 1H), 7.97 (s, 1H), 7.62-7.61 (m, 1H), 7.42-7.40 (m, 1H), 7.18-7.15 (m, 1H), 6.28 (s, 1H), 5.93 (s, 1H), 4.20-4.19 (m, 4H), 3.80-3.79 (m, 4H), 3.52-3.50 (m, 4H), 3.32-3.30 (m, 2H), 2.24 (s, 3H), 0.91-0.90 (m, 2H), 0.78-0.77 (m, 2H). |
| 27 | 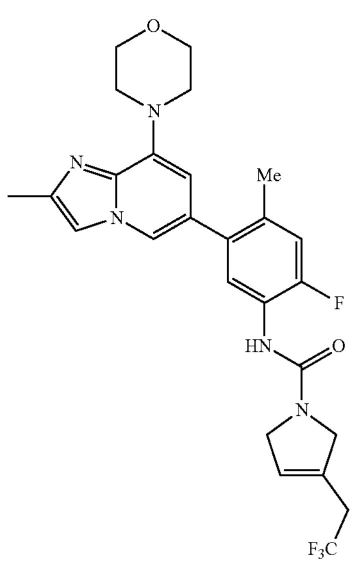 [SMILES: Cc1cn2cc(-c3cc(NC(=O)N4CC=C(CC(F)(F)F)C4)c(F)cc3C)cc(N3CCOCC3)c2n1] | N-(2-fluoro-4-methyl-5-(2-methyl-8-morpholinoimidazo[1,2-a]pyridin-6-yl)phenyl)-3-(2,2,2-trifluoroethyl)-2,5-dihydro-1H-pyrrole-1-carboxamide | Calc'd 518.21; found 518.20 | ¹H NMR (400 MHz, DMSO-d₆, δ 7.98 (s, 1H), 7.58 (s, 1H), 7.45 (d, J = 8.0 Hz, 1H), 7.11 (d, J = 11.6 Hz, 1H), 6.62 (s, 1H), 5.93 (s, 1H), 4.29 (s, 4H), 3.95-3.93 (m, 4H), 3.36-3.33 (m, 4H), 3.20-3.15 (m, 2H), 2.43 (s, 3H), 2.27 (s, 3H). |

TABLE 7-continued

| Ex. | Structure | IUPAC Name | Exact Mass [M + H]+ | 1H NMR Spectrometry Data |
|---|---|---|---|---|
| 28 | 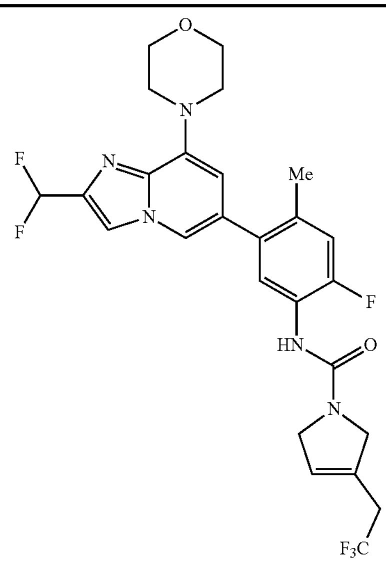 | N-(5-(2-(difluoromethyl)-8-morpholinoimidazo[1,2-a]pyridin-6-yl)-2-fluoro-4-methylphenyl)-3-(2,2,2-trifluoroethyl)-2,5-dihydro-1H-pyrrole-1 carboxamide | Calc'd 554.19; found 554.00 | 1H NMR (400 MHz, DMSO-d6, δ 8.22 (d, J = 1.6 Hz, 1H), 8.15 (s, 1H), 8.03 (s, 1H), 7.46 (d, J = 8.0 Hz, 1H), 7.20 (d, J = 12.0 Hz, 1H), 7.16 (t, J = 55.2 Hz, 1H), 6.45 (s, 1H), 5.93 (s, 1H), 4.20 (s, 4H), 3.82-3.80 (m, 4H), 3.54-3.52 (m, 4H), 3.30-3.28 (m, 2H), 2.25 (s, 3H). |
| 29 | 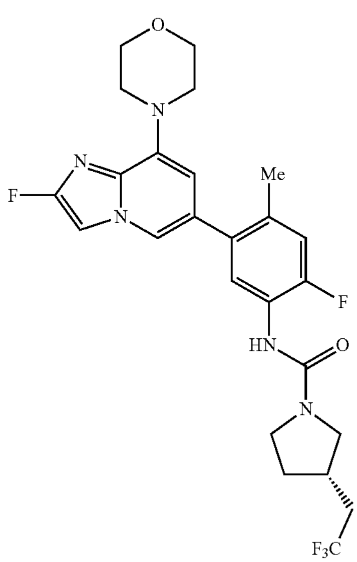 | (S)-N-(2-fluoro-5-(2-fluoro-8-morpholinoimidazo[1,2-a]pyridin-6-yl)-4-methylphenyl)-3-(2,2,2-trifluoroethyl) pyrrolidine-1-carboxamide | Calc'd 524.20; found 524.00 | 1H NMR (400 MHz, DMSO-d6, δ 8.19 (d, J = 6.4 Hz, 1H), 7.91 (s, 1H), 7.85 (d, J = 1.2 Hz, 1H), 7.51 (d, J = 8.0 Hz, 1H), 7.46 (d, J = 9.2 Hz, 1H), 7.20 (d, J = 11.6 Hz, 1H), 3.75-3.73 (m, 4H), 3.68-3.64 (m, 1H), 3.54-3.50 (m, 5H), 3.03 (t, J = 9.2 Hz, 1H), 2.51-2.41 (m, 3H), 2.15 (s, 3H), 2.10-2.05 (m, 1H), 1.70-1.64 (m, 1H). |

TABLE 7-continued

| Ex. | Structure | IUPAC Name | Exact Mass [M + H]⁺ | ¹H NMR Spectrometry Data |
|---|---|---|---|---|
| 30 | 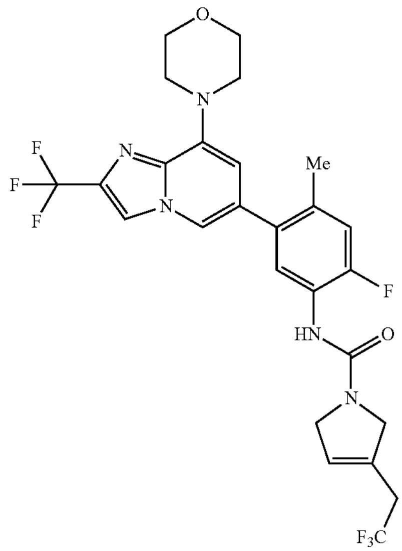 [SMILES: Cc1cc(F)c(NC(=O)N2CC=C(CC(F)(F)F)C2)cc1-c1cc(N2CCOCC2)c2nc(C(F)(F)F)cn2c1] | N-(2-fluoro-4-methyl-5-(8-morpholino-2-(trifluoromethyl)imidazo[1,2-a]pyridin-6-yl)phenyl)-3-(2,2,2-trifluoroethyl)-2,5-dihydro-1H-pyrrole-1-carboxamide | Calc'd 572.18; found 572.20 | ¹H NMR (400 MHz, CD₃OD), δ 8.24 (d, J = 0.8 Hz, 1H), 8.05 (d, J = 1.6 Hz, 1H), 7.48 (d, J = 8.0 Hz, 1H), 7.11 (d, J = 11.6 Hz, 1H), 6.62 (s, 1H), 5.93 (s, 1H), 4.30-4.28 (m, 5H), 3.95-3.93 (m, 4H), 3.50-3.48 (m, 4H), 3.21-3.13 (m, 3H), 2.29 (s, 3H). |
| 31 | 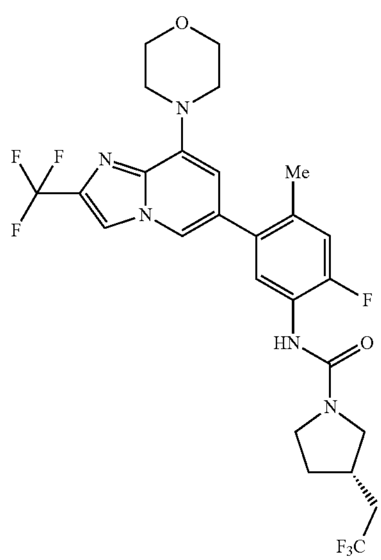 [SMILES: Cc1cc(F)c(NC(=O)N2CC[C@@H](CC(F)(F)F)C2)cc1-c1cc(N2CCOCC2)c2nc(C(F)(F)F)cn2c1] | (S)-N-(2-fluoro-4-methyl-5-(8-morpholino-2-(trifluoromethyl)imidazo[1,2-a]pyridin-6-yl)phenyl)-3-(2,2,2-trifluoroethyl)pyrrolidine-1-carboxamide | Calc'd 574.20; found 574.10 | ¹H NMR (400 MHz, CD₃OD), δ 8.24 (d, J = 0.8 Hz, 1H), 8.05 (d, J = 1.2 Hz, 1H), 7.47 (d, J = 8.0 Hz, 1H), 7.10 (d, J = 11.6 Hz, 1H), 6.63 (d, J = 1.2 Hz, 1H), 3.95-3.93 (m, 4H), 3.80-3.76 (m, 1H), 3.66-3.61 (m, 1H), 3.49-3.42 (m, 5H), 3.13 (t, J = 10.0 Hz, 1H), 2.55-2.53 (m, 1H), 2.40-2.21 (m, 6H), 1.80-1.73 (m, 1H). |

TABLE 7-continued

| Ex. | Structure | IUPAC Name | Exact Mass [M + H]+ | 1H NMR Spectrometry Data |
|---|---|---|---|---|
| 32 | 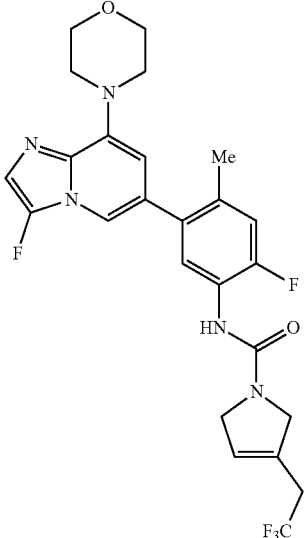 | N-(2-fluoro-5-(3 fluoro-8-morpholinoimidazo[1,2-a]pyridin-6-yl)-4-methylphenyl)-3-(2,2,2-trifluoroethyl)-2,5-dihydro-1H-pyrrole-1-carboxamide | Calc'd 522.19; found 522.20 | 1H NMR (400 MHz, DMSO-d6, δ 8.05 (s, 1H), 7.96 (s, 1H), 7.64 (s, 1H), 7.48 (d, J = 7.6 Hz, 1H), 7.22 (d, J = 11.6 Hz, 1H), 6.35 (d, J = 7.2 Hz, 1H), 5.93 (s, 1H), 4.20-4.18 (m, 4H), 3.81-3.79 (m, 4H), 3.48-3.47 (m, 4H), 3.31-3.28 (m, 2H), 2.18 (s, 3H). |

Example 33: N-(4-Methyl-3-(6-morpholino-3,4-dihydro-1H-pyrano[4',3':4,5]imidazo[1,2-a]pyridin-8-yl)phenyl)-2-(trifluoromethyl)isonicotinamide

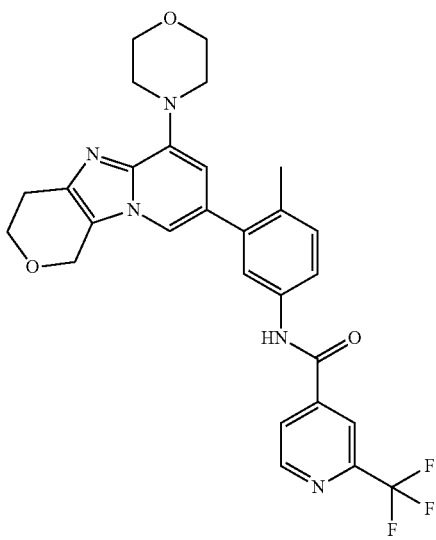 [SMILES: Cc1ccc(NC(=O)c2ccnc(C(F)(F)F)c2)cc1-c1cc(N2CCOCC2)c2nc3c(n2c1)COCC3]

Step 1: To a stirred mixture of 3,5-dibromopyridin-2-amine (20 g, 79.39 mmol) and 1-chloro-1-[dicyclohexyl([2-[2,4,6-tri s(propan-2-yl)phenyl]phenyl])-1A[5]-phosphanyl]-2H,3H,4H-benzo[c]l-aza-2-palladacyclohexane (0.59 g, 0.79 mmol) in THF (200 mL) were added morpholine (6.9 mL, 79.39 mmol) and LiHMDS (1 M in THIF) (198.50 mL, 198.50 mmol) at room temperature under nitrogen atmosphere. The reaction mixture was stirred for 16 h at 65 0 C under nitrogen atmosphere. The reaction mixture was allowed to cool down to room temperature.

The resulting mixture was quenched by the addition of sat. NH4Cl (aq.) (300 mL) at room temperature. The resulting mixture was extracted with EA (3×200 mL). The combined organic layers were washed with brine (2×150 mL), dried over anhydrous Na2SO4. After filtration, the filtrate was concentrated under reduced pressure. The residue was purified by silica gel column chromatography, eluted with PE/EtOAc/EtOH=4/3/1. The fractions containing the desired product were combined and concentrated to afford 5-bromo-3-morpholinopyridin-2-amine (9 g, 44%) as a light-yellow solid. MS ESI calculated for C9H12BrN3O [M+H]+, 258.02, found 258.00. 1H NMR (300 MHz, CDCl3) δ 7.88 (d, J=2.1 Hz, 1H), 7.24 (d, J=2.1 Hz, 1H), 4.77 (s, 2H), 3.86-3.82 (m, 4H), 2.93-2.90 (m, 4H)

Step 2: To a stirred mixture of 5-bromo-3-(morpholin-4-yl)pyridin-2-amine (200.00 mg, 0.78 mmol) in EtOH (5.00 mL) was added 3-bromooxan-4-one (277.41 mg, 1.56 mmol). The reaction mixture was stirred at 80° C. for 48 h. The resulting mixture was concentrated under reduced pressure. The residue was purified by reverse flash chromatography with the following conditions: Column: C18 Column 120 g; Mobile Phase A: Water (Plus 10 mmol/L NH4HCO3), Mobile Phase B: MeCN; Flow rate: 60 mL/min; Gradient: 30% B to 60% B in 30 min; 254/220 nm. The fractions containing the desired product were combined and concentrated to afford 8-bromo-6-morpholino-3,4-dihydro-1H-pyrano[4',3':4,5]imidazo[1,2-a]pyridine (66 mg, 25%) as a brown solid. MS ESI calculated for C14H16BrN3O2[M+H]+, 338.21, found 338.05; 1H NMR (400 MHz, DMSO-d6) δ 7.49 (d, J=1.6 Hz, 1H), 6.50 (d, J=1.6 Hz, 1H), 4.89 (t, J=1.4 Hz, 2H), 4.08 (t, J=5.5 Hz, 2H), 4.03-3.95 (m, 4H), 3.64-3.53 (m, 4H), 2.99 (t, J=5.6 Hz, 2H).

Step 3: To a stirred solution of 2-(trifluoromethyl)pyridine-4-carboxylic acid (1.23 g, 6.43 mmol) and HATU (3.26 g, 8.58 mmol) in DMF (10 mL) were added TEA (2.38 mL, 23.57 mmol) and 4-methyl-3-(4,4,5,5-tetramethyl-1,3,2-dioxaborolan-2-yl)aniline (1 g, 4.29 mmol) at 0° C. under nitrogen atmosphere. The reaction mixture was stirred for 1.5 h at room temperature. The resulting mixture was diluted with water (30 mL) and extracted with EA (3×80 mL). The combined organic layers were washed with brine (5×40 mL), dried over anhydrous Na$_2$SO$_4$ and filtered. The filtrate was concentrated under reduced pressure. The residue was purified by silica gel column chromatography, eluted with PE/EA (3/1). The fractions containing the desired product were combined and concentrated to afford N-(4-methyl-3-(4,4,5,5-tetramethyl-1,3,2-dioxaborolan-2-yl)phenyl)-2-(trifluoromethyl)isonicotinamide (1.45 g, 83%) as an off-white solid. MS ESI calculated for C$_{20}$H$_{22}$BF$_3$N$_2$O$_3$ [M+H]$^+$, 407.17, found 406.90; $^1$H NMR (400 MHz, DMSO-d$_6$) δ 10.63 (s, 1H), 8.98 (d, J=5.0 Hz, 1H), 8.43-8.39 (m, 1H), 8.22 (dd, J=5.1, 1.6 Hz, 1H), 7.98-7.88 (m, 2H), 7.21 (d, J=8.3 Hz, 1H), 2.46 (s, 3H), 1.32 (s, 12H).

Step 4: To a stirred mixture of 8-bromo-6-morpholino-3,4-dihydro-1H-pyrano[4',3':4,5]imidazo[1,2-a]pyridine (66.00 mg, 0.20 mmol) and N-[4-methyl-3-(4,4,5,5-tetramethyl-1,3,2-dioxaborolan-2-yl)phenyl]-2-(trifluoromethyl)pyridine-4-carboxamide (87.20 mg, 0.22 mmol) in dioxane (4.00 mL) and H$_2$O (1.00 mL) were added Pd(dppf)Cl$_2$CH$_2$Cl$_2$ (15.94 mg, 0.02 mmol) and K$_2$CO$_3$ (80.91 mg, 0.59 mmol) at room temperature. The reaction mixture was degassed with nitrogen for three times and stirred for 2 h at 80° C. The resulting mixture was concentrated under reduced pressure. The residue was purified by Prep-TLC, eluted with PE/EA/EtOH (4/3/1) to afford the crude product. The crude product was purified by reverse flash chromatography with the following conditions: Column: C18 Column 120 g; Mobile Phase A: Water (Plus 10 mmol/L NH$_4$HCO$_3$), Mobile Phase B: MeCN; Flow rate: 60 mL/min; Gradient: 35% B to 65% B in 25 min; 254/220 nm. The fractions containing the desired product were combined and concentrated to afford the title compound (45 mg, 42%) as a white solid. MS ESI calculated for C$_{28}$H$_{26}$F$_3$N$_5$O$_3$[M+H]$^+$, 538.54, found 538.20; $^1$H NMR (400 MHz, DMSO-d$_6$) δ 10.71 (s, 1H), 9.00 (d, J=5.0 Hz, 1H), 8.38 (s, 1H), 8.20 (d, J=5.0 Hz, 1H), 7.85-7.68 (m, 3H), 7.35 (d, J=8.3 Hz, 1H), 6.41 (s, 1H), 4.89 (s, 2H), 3.99 (t, J=5.4 Hz, 2H), 3.90-3.74 (m, 4H), 3.54 (t, J=4.5 Hz, 4H), 2.83 (t, J=5.4 Hz, 2H), 2.27 (s, 3H).

Example 34 and 35: N-(2-fluoro-5-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide

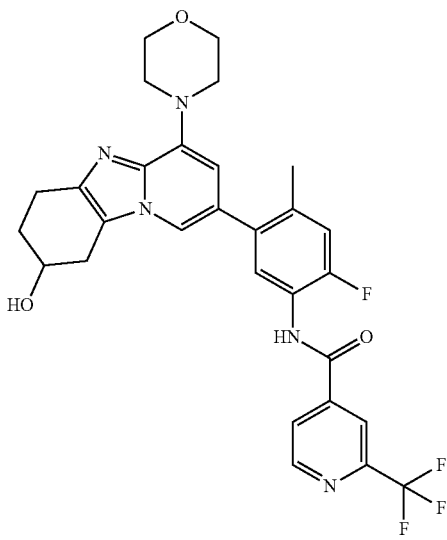 [SMILES: Cc1cc(F)c(NC(=O)c2ccnc(C(F)(F)F)c2)cc1-c1cc(N2CCOCC2)c2nc3c(n2c1)CC(O)CC3]

Step 1 & 2: To a stirred mixture of 1,4-dioxaspiro[4.5]decan-8-one (6.00 g, 38.42 mmol) in THF (100.00 mL) was added LiHMDS (1 M in THF) (76.8 mL, 76.83 mmol) dropwise at −78° C. under nitrogen atmosphere. The reaction mixture was stirred for 30 min at −78° C. under nitrogen atmosphere. To the above mixture was added TMSCI (6.60 mL, 51.64 mmol) dropwise over 20 min at −78° C. The reaction mixture was stirred for additional 30 min at −78° C. The resulting mixture was quenched with NaHCO$_3$ at 0° C. and extracted with EA (3×200 mL). The combined organic layers were washed with brine (2×50 mL), dried over anhydrous sodium sulfate. After filtration, the filtrate was concentrated under reduced pressure. Then the residue was dissolved in THF (50.00 mL) and H$_2$O (50.00 mL). To the above solution were added NaOAc (0.32 g, 3.91 mmol) and NBS (6.84 g, 38.43 mmol) in portions at 0° C. The reaction mixture was stirred for 3 h at room temperature. The resulting mixture was quenched with NaHCO$_3$ (aq.) and extracted with EtOAc (3×300 mL). The combined organic layers were washed with brine (2×100 mL), dried over anhydrous sodium sulfate. After filtration, the filtrate was concentrated under reduced pressure to afford 7-bromo-1,4-dioxaspiro[4.5]decan-8-one (crude). To a stirred mixture of 7-bromo-1,4-dioxaspiro[4.5]decan-8-one (819.66 mg, 3.49 mmol) in EtOH (10.00 mL) was added 5-bromo-3-(morpholin-4-yl)pyridin-2-amine (600.00 mg, 2.33 mmol) in portions at room temperature. The reaction mixture was stirred for 16 h at 80° C. The resulting mixture was concentrated under reduced pressure. The residue was purified by silica gel column chromatography, eluted with PE/EtOAc (1/1). The fractions containing the desired product were combined and concentrated to afford 2-bromo-4-morpholino-6,9-dihydro-7H-spiro[benzo[4,5]imidazo[1,2-a]pyridine-8,2'-[1,3]dioxolane] (0.60 g, 65%) as a brown oil. MS ESI calculated for C$_{17}$H$_2$OBrN$_3$O$_3$[M+H]$^+$, 394.07, found 394.10.

Step 3: A solution of 12-bromo-10-(morpholin-4-yl)-1,8-diazaspiro[1,3-dioxolane-2,4-tricyclo[7.4.0.02,7]]tridecane]-2(7),8,10,12-tetraene (500 mg, 1.53 mmol) in HCl (6 M) (8 mL) was stirred for 1 h at 60° C. The resulting mixture was concentrated under reduced pressure. The resulting mixture was basified to pH 9 with saturated NaHCO$_3$ (aq.). The combined organic layers were washed with brine (2×100 mL), dried over anhydrous sodium sulfate. After filtration, the filtrate was concentrated under reduced pressure The aqueous layer was extracted with EtOAc (3×50 mL). The residue was purified by Prep-TLC, eluted with PE/(EtOAc/EtOH) (1/(3/1)). The fractions containing the desired product were combined and concentrated to afford 2-bromo-4-morpholino-6,9-dihydrobenzo[4,5]imidazo[1,2-a]pyridin-8(7H)-one (0.35 g, 65%) as a dark green oil. MS ESI calculated for C$_{15}$H$_{16}$BrN$_3$O$_2$[M+H]$^+$, 350.04, 352.04, found 350.05, 352.05.

Step 4: To a stirred mixture of 2-bromo-4-morpholino-6,9-dihydrobenzo[4,5]imidazo[1,2-a]pyridin-8(7H)-one (300.00 mg, 0.86 mmol) in MeOH (5.00 mL) was added NaBH$_4$ (38.89 mg, 1.03 mmol) in portions at room temperature. The reaction mixture was stirred for 1 h at room temperature. The resulting mixture was concentrated under reduced pressure. The residue was purified by Prep-TLC, eluted with PE/EtOAc (1/1). The fractions containing the desired product were combined and concentrated to afford 2-bromo-4-morpholino-6,7,8,9-tetrahydrobenzo[4,5]imidazo[1,2-a]pyridin-8-ol (200 mg, 66%) as a light brown solid. MS ESI calculated for C$_{15}$H$_{18}$BrN$_3$O$_2$[M+H]$^+$, 352.06, 354.06, found 352.10, 354.10; $^1$H NMR (300 MHz, CDCl$_3$) δ 7.62 (d, J=1.7 Hz, 1H), 6.51 (d, J=1.7 Hz, 1H), 4.43 (s, 1H), 4.11-3.97 (m, 4H), 3.56-3.52 (m, 4H), 3.14-2.86 (m, 3H), 2.81-2.28 (m, 2H), 2.07-1.76 (m, 2H).

Step 5: To a stirred mixture of N-[4-methyl-3-(4,4,5,5-tetramethyl-1,3,2-dioxaborolan-2-yl)phenyl]-2-(trifluoromethyl)pyridine-4-carboxamide (230.65 mg, 0.57 mmol) and 2-bromo-4-morpholino-6,7,8,9-tetrahydrobenzo[4,5]imidazo[1,2-a]pyridin-8-ol (200.00 mg, 0.57 mmol) in dioxane (6.00 mL) and H$_2$O (1.00 mL) were added Pd(dppf)C$_{12}$CH$_2$Cl$_2$ (46.37 mg, 0.06 mmol) and Na$_2$CO$_3$ (180.54 mg, 1.70 mmol) in portions at room temperature. The reaction mixture was degassed with nitrogen for three times and stirred for 2 h at 80° C. The resulting mixture was concentrated under reduced pressure. The residue was purified by Prep-TLC, eluted with PE/(EtOAc/EtOH) (1/(3/1)) to afford the crude product. The crude product was purified by reverse phase flash with the following conditions: Column: Spherical C18, 20~40 um, 120 g; Mobile Phase A: Water (Plus 10 mmol/L NH$_4$HCO$_3$); Mobile Phase B: ACN; Flow rate: 60 mL/min; Gradient of B: 35%~75%,20 min; Detector: 220 nm. The fractions containing the desired product were combined and concentrated to afford N-(3-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide (200 mg, 64%) as a light yellow solid. MS ESI calculated for C$_{29}$H$_{28}$F$_3$N$_5$O$_2$[M+H]$^+$, 552.21, found 552.15.

Step 6: N-(3-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide (200.00 mg) was purified by Prep-Chiral-HPLC with the following conditions: Column: CHIRALPAK-AD-H-UL001, 20×250m m, 5 pm; Mobile Phase A: Hex (0.5% 2 M NH$_3$-MeOH)--HPLC, Mobile Phase B:IPA--HPLC; Flow rate:20 mL/min; Gradient:20 B to 20 B in 18 min; 220/254 nm; RT1 (Peak1): 10.805 min; Injection Volumn:0.5 mL.

PEAK 1 (EXAMPLE 34, N-(2-fluoro-5-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide): The fractions (RT: 10.8 min) were combined and concentrated to afford the title compound (76.8 mg, 38%) as an off-white solid of undetermined absolute stereochemistry. MS ESI calculated for C$_{29}$H$_{28}$F$_3$N$_5$O$_3$ [M+H]$^+$, 552.21, found 552.20; H NMR (300 MHz, DMSO-d$_6$) δ 10.70 (s, 1H), 8.99 (d, J=5.1 Hz, 1H), 8.37 (d, J=1.5 Hz, 1H), 8.20 (d, J=5.2 Hz, 1H), 7.74-7.70 (m, 3H), 7.34 (d, J=8.3 Hz, 1H), 6.37 (s, 1H), 4.97 (d, J=4.2 Hz, 1H), 4.14 (s, 1H), 3.81-3.77 (m, 4H), 3.55-3.51 (m, 4H), 3.06-3.02 (m, 1H), 2.86-2.51 (m, 3H), 2.28 (s, 3H), 2.07-1.76 (m, 2H).

PEAK 2 (EXAMPLE 35, N-(2-fluoro-5-(8-hydroxy-4-morpholino-6,7,8,9-tetrahydrobenzo[4,5]imidazo[1,2-a]pyridin-2-yl)-4-methylphenyl)-2-(trifluoromethyl)isonicotinamide): The fractions (RT: 14.2 min) were combined and concentrated to afford the title compound (75.6 mg, 38%) as an off-white solid of undetermined absolute stereochemistry. MS ESI calculated for C$_{29}$H$_{28}$F$_3$N$_5$O$_3$ [M+H]$^+$, 552.21, found 552.20; H NMR (300 MHz, DMSO-d$_6$) δ 10.70 (s, 1H), 8.99 (d, J=5.0 Hz, 1H), 8.38 (s, 1H), 8.24-8.16 (m, 1H), 7.81-7.67 (m, 3H), 7.35 (d, J=8.3 Hz, 1H), 6.37 (s, 1H), 4.97 (d, J=4.2 Hz, 1H), 4.14 (s, 1H), 3.81-3.77 (m, 4H), 3.55-3.51 (m, 4H), 3.06-3.02 (m, 1H), 2.88-2.53 (m, 3H), 2.28 (s, 3H), 2.05-1.74 (m, 2H).

Example 36: N-(4-Methyl-3-(9-morpholino-3,4-dihydro-1H-pyrano[3',4':4,5]imidazo[1,2-a]pyridin-7-yl)phenyl)-2-(trifluoromethyl)isonicotinamide

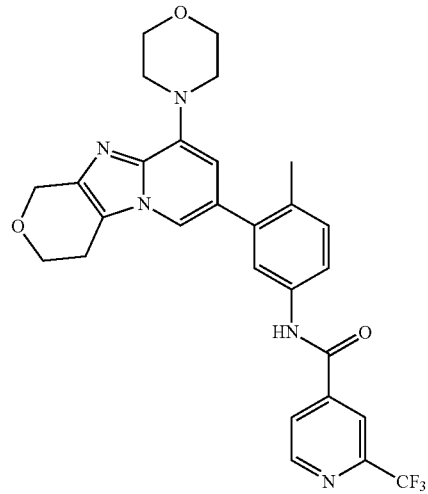 [SMILES: Cc1ccc(NC(=O)c2ccnc(C(F)(F)F)c2)cc1-c1cc(N2CCOCC2)c2nc3c(n2c1)CCOC3]

Step 1: To a stirred mixture of 3,5-dibromopyridin-2-amine (10 g, 39.69 mmol) and oxan-3-one (7.95 g, 79.39 mmol) in dioxane (100 mL) was added sulfur (6.36 g, 198.49 mmol) at room temperature under nitrogen atmosphere. The reaction mixture was stirred for 48 h at 100° C. under nitrogen atmosphere. The resulting mixture was concentrated under reduced pressure. The residue was purified by silica gel column chromatography, eluted with PE/EA (1/1) to afford the crude product. The crude product was purified by Prep-HPLC with the following conditions: Column: XBridge Shield RP18 OBD Column, 30×150 mm, 5 m; Mobile Phase A: Water (Plus 10 mmol/L NH$_4$HCO$_3$), Mobile Phase B: ACN; Flow rate: 60 mL/min; Gradient: 30% B to 40% B in 10 min, 40% B; WaveLength: 254 nm; RT1: 8.5 min. The fractions containing the desired product were combined and concentrated to afford 7,9-dibromo-3,4-dihydro-1H-pyrano[3',4':4,5]imidazo[1,2-a]pyridine (200 mg, 2%) as a light yellow solid. MS ESI calculated for C10H8Br$_2$N$_2$O [M+H]$^+$, 330.90, 332.90, found 330.80 332.80; $^1$H NMR (300 MHz, CDCl$_3$) δ 8.01 (d, J=1.6 Hz, 1H), 7.56 (d, J=1.6 Hz, 1H), 4.93 (d, J=1.4 Hz, 2H), 4.13 (t, J=5.5 Hz, 2H), 2.93 (t, J=5.5 Hz, 2H).

Step 2: To a stirred mixture of 7,9-dibromo-3,4-dihydro-1H-pyrano[3',4':4,5]imidazo[1,2-a]pyridine (185 mg, 0.56 mmol), morpholine (50.98 mg, 0.56 mmol) and 1-chloro-1-[dicyclohexyl([2-[2,4,6-tris(propan-2-yl)phenyl]phenyl])-15]-phosphanyl]-2H,3H,4H-benzo[c]1-aza-2-palladacyclohexane (20.58 mg, 0.03 mmol) in THF (2 mL) was added LiHMDS (2.5 M in THF) (0.56 mL, 1.39 mmol) dropwise at 65° C. under nitrogen atmosphere. The resulting mixture was stirred for 2 h at 65° C. under nitrogen atmosphere. The resulting mixture was concentrated under reduced pressure. The residue was purified by silica gel column chromatography, eluted with PE/EA (1/4). The fractions containing the desired product were combined and concentrated to afford 7-bromo-9-morpholino-3,4-dihydro-1H-pyrano[3',4':4,5]imidazo[1,2-a]pyridine (60 mg, 31.84%) as an off-white solid. MS ESI calculated for C$_{14}$H$_{16}$BrN$_3$O$_2$[M+H]$^+$, 338.04, 340.04, found 337.95, 339.95; $^1$H NMR (300 MHz, CDCl$_3$) δ 7.67 (d, J=1.6 Hz, 1H), 6.53 (d, J=1.6 Hz, 1H), 4.89 (s, 2H), 4.11 (t, J=5.5 Hz, 2H), 4.00-3.96 (m, 4H), 3.56-3.52 (m, 4H), 2.96-2.83 (m, 2H).

Step 3: To a solution of 7-bromo-9-morpholino-3,4-dihydro-1H-pyrano[3',4':4,5]imidazo[1,2-a]pyridine (50 mg, 0.15 mmol) and N-[4-methyl-3-(4,4,5,5-tetramethyl-1,3,2-dioxaborolan-2-yl)phenyl]-2-(trifluoromethyl)pyridine-4-carboxamide (72 mg, 0.18 mmol) in dioxane (5 mL) and H$_2$O (1 mL) were added K$_2$CO$_3$ (40 mg, 0.30 mmol) and Pd(dppf)C$_{12}$CH$_2$Cl$_2$ (12 mg, 0.02 mmol). The reaction mixture was degassed with nitrogen for three times and stirred for 2 h at 80° C. The resulting mixture was concentrated under reduced pressure. The residue was purified by Prep-TLC, eluted with PE/EtOAc (1/5). The fractions containing the desired product were combined and concentrated to afford title compound (19.2 mg, 24%) as a white solid. MS ESI calculated for C$_{28}$H$_{26}$F$_3$N$_5$O$_3$[M+H]$^+$, 538.20, found 538.10; $^1$H NMR (300 MHz, DMSO-d$_6$) δ 10.70 (s, 1H), 8.99 (d, J=5.1 Hz, 1H), 8.38 (d, J=1.4 Hz, 1H), 8.20 (d, J=5.1 Hz, 1H), 7.85 (d, J=1.3 Hz, 1H), 7.81-7.68 (m, 2H), 7.35 (d, J=8.3 Hz, 1H), 6.42 (d, J=1.5 Hz, 1H), 4.74 (s, 2H), 4.01 (t, J=5.4 Hz, 2H), 3.81-3.77 (m, 4H), 3.55-3.51 (m, 4H), 2.91-2.86 (m, 2H), 2.28-2.17 (m, 3H).

Example 38: (3S)-N-[4-Methyl-3-(8-[8-oxa-3-azabicyclo[3.2.1]octan-3-yl]imidazo[1,2-a]pyridin-6-yl)phenyl]-3-(2,2,2-trifluoroethyl)pyrrolidine-1-carboxamide

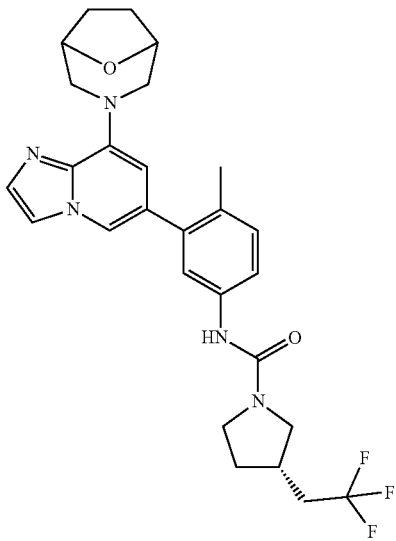 [SMILES: Cc1ccc(NC(=O)N2CC[C@@H](CC(F)(F)F)C2)cc1-c1cc(N2CC3CCC(C2)O3)c2nccn2c1]

Step 1: To a stirred mixture of 4-methyl-3-(4,4,5,5-tetramethyl-1,3,2-dioxaborolan-2-yl)aniline (2.00 g, 8.58 mmol) and DIEA (5.54 g, 42.89 mmol) in THF (100.00 mL) was added triphosgene (1.02 g, 3.44 mmol). The reaction mixture was stirred for 30 min at room temperature under nitrogen atmosphere. To the above mixture was added (3S)-3-(2,2,2-trifluoroethyl)pyrrolidine HCl salt (1.63 g, 8.58 mmol) dropwise at room temperature. The reaction mixture was stirred for additional 3 h at room temperature. The resulting mixture was concentrated under reduced pressure. The residue was purified by silica gel column chromatography, eluted with PE/EA (2/1). The fractions containing the desired product were combined and concentrated to afford (3S)-N-[4-methyl-3-(4,4,5,5-tetramethyl-1,3,2-dioxaborolan-2-yl)phenyl]-3-(2,2,2-trifluoroethyl)pyrrolidine-1-carboxamide (3.1 g, 88%) as an off-white solid. MS ESI calculated for C$_{20}$H$_{28}$BF$_3$N$_2$O$_3$ [M+H]$^+$, 413.21, found 413.15; $^1$H NMR (300 MHz, DMSO-d$_6$) δ 8.14 (s, 1H), 7.67 (d, J=2.3 Hz, 1H), 7.62-7.59 (m, 1H), 7.03 (d, J=8.3 Hz, 1H), 3.69-3.65 (m, 1H), 3.55-3.51 (m, 1H), 3.31-3.27 (m, 1H), 3.04-3.00 (m, 1H), 2.51-2.43 (m, 3H), 2.38 (s, 3H), 2.10-2.06 (m, 1H), 1.70-1.63 (m, 1H), 1.31 (s, 12H).

Step 2: To a stirred mixture of 8-bromo-6-chloroimidazo[1,2-a]pyridine (500 mg, 2.16 mmol), Cs$_2$CO$_3$ (2.1 g, 6.48 mmol) and 8-oxa-3-azabicyclo[3.2.1]octane HCl salt (0.48 g, 3.24 mmol) in dioxane (6.00 mL) was added RuPhos-PdCl-2nd G (0.17 g, 0.22 mmol). The reaction mixture was degassed with nitrogen for three times and stirred for 3 h at 80° C. The resulting mixture was diluted with water (30 mL) and extracted with EtOAc (3×50 mL). The combined organic layers were washed with brine (2×10 mL), dried over anhydrous Na$_2$SO$_4$. After filtration, the filtrate was concentrated under reduced pressure. The residue was purified by silica gel column chromatography, eluted with PE/EA (1/1). The fractions containing the desired product were combined and concentrated to afford 3-[6-chloroimidazo[1,2-a]pyridin-8-yl]-8-oxa-3-azabicyclo[3.2.1]octane (140 mg, 23%) as a light yellow solid; MS ESI calculated for C$_{13}$H$_{14}$ClN$_3$O [M+H]$^+$, 264.08, 266.08, found 264.20, 266.20.

Step 3: To a stirred mixture of 3-[6-chloroimidazo[1,2-a]pyridin-8-yl]-8-oxa-3-azabicyclo[3.2.1]octane (120 mg, 0.46 mmol), (3S)-N-[4-methyl-3-(4,4,5,5-tetramethyl-1,3,2-dioxaborolan-2-yl)phenyl]-3-(2,2,2-trifluoroethyl)pyrrolidine-1-carboxamide (187 mg, 0.46 mmol) and K$_2$CO$_3$ (188 mg, 1.36 mmol) in THF (2.00 mL) and H$_2$O (0.20 mL) was added XPhos Pd G2 (38 mg, 0.05 mmol). The reaction mixture was degassed with nitrogen for three times and stirred for 16 h at 80° C. The resulting mixture was diluted with water (10 mL) and extracted with EA (3×10 mL). The combined organic layers were washed with brine (2×10 mL), dried over anhydrous Na$_2$SO$_4$. After filtration, the filtrate was concentrated under reduced pressure. The residue was purified by prep-TLC, eluted with PE/EA/EtOH (4/3/1) to afford the crude product. The crude product was purified by reverse phase flash with the following conditions: Column: Spherical C18, 20~40 um, 120 g; Mobile Phase A: Water (Plus 10 mmol/L NH$_4$HCO$_3$); Mobile Phase B: ACN; Flow rate: 60 mL/min; Gradient of B: 35%~75%, 20 min; Detector: 220 nm. The fractions containing the desired product were combined and concentrated to afford the title compound (88.9 mg, 37%) as a white solid; MS ESI calculated for C$_{27}$H$_{30}$F$_3$N$_5$O$_2$[M+H]$^+$, 514.24, found 514.30; $^1$H NMR (300 MHz, CDCl$_3$) δ 7.73-7.69 (m, 1H), 7.63-7.61 (m, 1H), 7.54-7.50 (m, 1H), 7.42-7.38 (m, 1H), 7.32-7.30 (m, 1H), 7.22 (d, J=8.2 Hz, 1H), 6.36-6.33 (m, 1H), 6.14 (s, 1H), 4.52-4.48 (m, 2H), 4.14-4.10 (m, 2H), 3.89-3.77 (m, 1H), 3.66 (t, J=8.4 Hz, 1H), 3.47-3.42 (m, 1H), 3.16-3.12 (m, 3H), 2.65-2.51 (m, 1H), 2.32-2.23 (m, 8H), 2.07-2.03 (m, 2H), 1.85-1.71 (m, 1H).

Example 43: 1-tert-Butyl-N-{2-fluoro-4-methyl-5-[8-(morpholin-4-yl)imidazo[1,2-a]pyridin-6-yl]phenyl}pyrrole-3-carboxamide

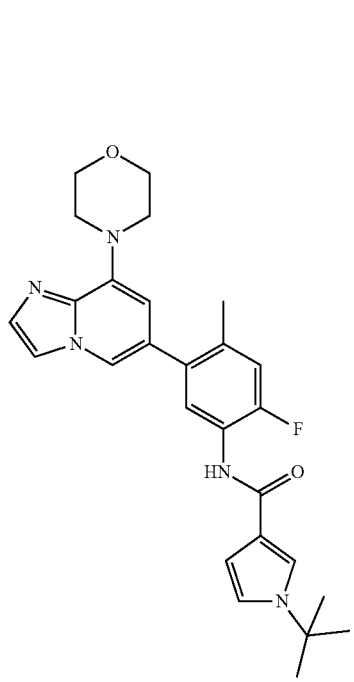 [SMILES: Cc1cc(F)c(NC(=O)c2ccn(C(C)(C)C)c2)cc1-c1cc(N2CCOCC2)c2nccn2c1]

Step 1: To a stirred solution of 1-tert-butylpyrrole-3-carboxylic acid (76.85 mg, 0.46 mmol), HATU (174.75 mg, 0.46 mmol) and TEA (155.03 mg, 1.53 mmol) in THF (1 mL) was added 2-fluoro-4-methyl-5-[8-(morpholin-4-yl)imidazo[1,2-a]pyridin-6-yl]aniline (100 mg, 0.31 mmol) at room temperature under nitrogen atmosphere. The reaction mixture was stirred for 1 h at 60° C. under nitrogen atmosphere. The resulting mixture was concentrated under reduced pressure. The residue was purified by Prep-HPLC with the following conditions: Column: XBridge Shield RP18 OBD Column, 30×150 mm, 5 m; Mobile Phase A: water (Plus 10 mmol/L $NH_4HCO_3$), Mobile Phase B: ACN; Flow rate: 60 mL/min; Gradient: 42% B to 52% B in 10 min, 52% B; Wavelength: 254 nm; RT1: 8.02 min. The fractions containing the desired product were combined and concentrated to afford the title compound (39.3 mg, 26%) as an off-white solid. MS ESI calculated for $C_{27}H_{30}FN_5O_2$ $[M+H]^+$, 476.24, found 476.15; $^1H$ NMR (400 MHz, DMSO-$d_6$) δ 9.32 (s, 1H), 8.14 (d, J=1.4 Hz, 1H), 7.89 (d, J=1.2 Hz, 1H), 7.70 (t, J=2.1 Hz, 1H), 7.54 (d, J=8.0 Hz, 1H), 7.50 (d, J=1.2 Hz, 1H), 7.24 (d, J=11.5 Hz, 1H), 7.01 (t, J=2.7 Hz, 1H), 6.59 (dd, J=3.0, 1.8 Hz, 1H), 6.36 (d, J=1.5 Hz, 1H), 3.83-3.77 (m, 4H), 3.55 (t, J=4.8 Hz, 4H), 2.28 (s, 3H), 1.51 (s, 9H).

Example 46: (R)-N-(2-Fluoro-4-methyl-5-(8-morpholinoimidazo[1,2-a]pyridin-6-yl)phenyl)-1-(2,2,2-trifluoroethyl)pyrrolidine-3-carboxamide

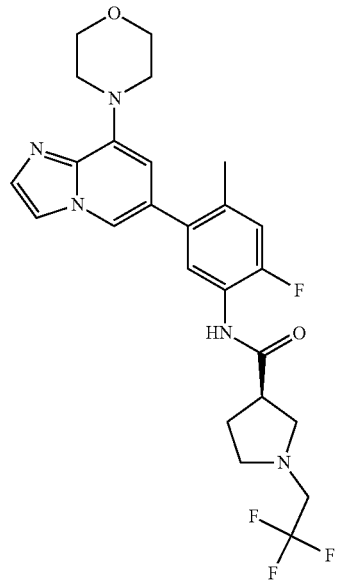 [SMILES: Cc1cc(F)c(NC(=O)[C@@H]2CCN(CC(F)(F)F)C2)cc1-c1cc(N2CCOCC2)c2nccn2c1]

Step 1: To a stirred mixture of methyl (3R)-pyrrolidine-3-carboxylate HCl salt (1.00 g, 6.04 mmol), and potassium carbonate (2.50 g, 18.11 mmol) in N,N-dimethylformamide (10.00 mL) was added 1,1,1-trifluoro-2-iodoethane (1.90 g, 9.06 mmol). The reaction mixture was stirred for 16 h at 100° C. under nitrogen atmosphere. The resulting mixture was diluted with water (80.00 mL) and extracted with ethyl acetate (3×50 mL). The combined organic layers were washed with brine (2×50 mL), dried over anhydrous sodium sulfate. After filtration, the filtrate was concentrated under reduced pressure. The residue was purified by silica gel column chromatography, eluted with PE/EA (5/1). The fractions containing the desired product were combined and concentrated to afford methyl (R)-1-(2,2,2-trifluoroethyl)pyrrolidine-3-carboxylate (800 mg, 62%) as a yellow liquid. MS ESI calculated for $C_8H_{12}F_3NO_2$ $[M+H]^+$, 212.08, found 212.05.

Step 2: To a stirred mixture of methyl (3R)-1-(2,2,2-trifluoroethyl)pyrrolidine-3-carboxylate (850 mg, 4.03 mmol) in THF (3.00 mL) and MeOH (3.00 mL) was added LiOH $H_2O$ (506.66 mg, 12.08 mmol) in water (3.00 mL). The reaction mixture was stirred for 2 h at room temperature. The resulting mixture was acidified to pH 6 with HCl (aq.). The resulting mixture was extracted with ethyl acetate (3×40 mL). The combined organic layers were washed with brine (3×20 mL), dried over anhydrous sodium sulfate. After filtration, the filtrate was concentrated under reduced pressure to afford (R)-1-(2,2,2-trifluoroethyl)pyrrolidine-3-carboxylic acid (0.63 g, 79%) as a yellow oil. MS ESI calculated for $C_7H_{10}F_3NO_2$ $[M+H]^+$, 198.07, found 198.00.

Step 3: To a stirred mixture of (R)-1-(2,2,2-trifluoroethyl)pyrrolidine-3-carboxylic acid (100 mg, 0.51 mmol), HATU (289.29 mg, 0.76 mmol) and trimethylamine (256.63 mg, 2.54 mmol) in acetonitrile (1.00 mL) was added 2-fluoro-4-methyl-5-[8-(morpholin-4-yl)imidazo[1,2-a]pyridin-6-yl]aniline (165.54 mg, 0.51 mmol). The reaction mixture was stirred for 16 h at room temperature. The resulting mixture was concentrated under reduced pressure. The residue was purified by reverse flash chromatography with the following conditions: column, C18 silica gel; mobile phase: ACN in water (Plus 10 mmol/L NH$_4$HCO$_3$), 10% to 50% gradient in 10 min; detector, UV 254 nm. The fractions containing the desired product were combined and concentrated to afford title compound (23.2 mg, 9%) as an off-white solid. MS ESI calculated for C$_{25}$H$_{27}$F$_4$N$_5$O$_2$[M+H]$^+$, 506.21, found 506.20; $^1$H NMR (400 MHz, DMSO-d$_6$) δ 9.74 (s, 1H), 8.13 (d, J=1.5 Hz, 1H), 7.90 (d, J=1.2 Hz, 1H), 7.79 (d, J=8.1 Hz, 1H), 7.53 (s, 1H), 7.24 (d, J=11.8 Hz, 1H), 6.36 (s, 1H), 3.81 (t, J=4.7 Hz, 4H), 3.54 (t, J=4.7 Hz, 4H), 3.32-3.13 (m, 2H), 3.18-3.12 (m, 1H), 3.07-3.03 (m, 1H), 2.88-2.74 (m, 2H), 2.69-2.62 (m, 1H), 2.25 (s, 3H), 2.05-1.96 (m, 2H).

Example 50: 2-(Tert-Butyl)-N-(2-fluoro-4-methyl-5-(8-morpholinoimidazo[1,2-a]pyridin-6-yl)phenyl)morpholine-4-carboxamide

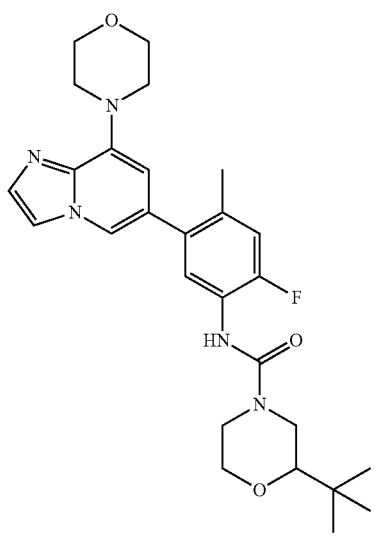 [SMILES: Cc1cc(F)c(NC(=O)N2CCOC(C(C)(C)C)C2)cc1-c1cc(N2CCOCC2)c2nccn2c1]

Step 1: To a stirred solution of 2-fluoro-4-methyl-5-[8-(morpholin-4-yl)imidazo[1,2-a]pyridin-6-yl]aniline (200 mg, 0.61 mmol) and DIEA (0.53 mL, 3.06 mmol) in THF (12.71 mL) was added the solution of triphosgene (72.73 mg, 0.25 mmol) in THF (1 mL) dropwise at room temperature under nitrogen atmosphere. The reaction mixture was stirred for 30 min at room temperature under nitrogen atmosphere. To the above mixture was added 2-tert-butylmorpholine-HCl (110.11 mg, 0.61 mmol) in THF (1 mL) dropwise at room temperature. The reaction mixture was stirred for additional 2 h at room temperature. The resulting mixture was quenched with MeOH at room temperature. The resulting mixture was concentrated under reduced pressure. The residue was purified by silica gel column chromatography, eluted with DCM/MeOH (10/1). The fractions containing the desired product were combined and concentrated to afford 2-tert-butyl-N-{2-fluoro-4-methyl-5-[8-(morpholin-4-yl)imidazo[1,2-a]pyridin-6-yl]phenyl}morpholine-4-carboxamide (185 mg, 61%) as an off-white solid. MS ESI calculated for C$_{27}$H$_{34}$FN$_5$O$_3$ [M+H]$^+$, 496.26, found 496.20.

Step 2: The 2-tert-Butyl-N-{2-fluoro-4-methyl-5-[8-(morpholin-4-yl)imidazo[1,2-a]pyridin-6-yl]phenyl}morpholine-4-carboxamide (230 mg, 0.46 mmol) was purified by Prep-CHIRAL-HPLC with the following conditions: Column: CHIRAL ART Amylose-SA, 2×25 cm, 5 m;

Mobile Phase A: Hex (0.5% 2 M NH$_3$-MeOH)--HPLC, Mobile Phase B: MeOH: DCM=1: 1--HPLC; Flow rate: 20 mL/min; Gradient: 20% B to 20% B in 10 min; Wave Length: 220/254 nm; RT1: 8.00 min; RT2: 9.37 min; Sample Solvent: MeOH--HPLC; Injection Volume: 0.3 mL.

PEAK 1 (EXAMPLE 50,2-(tert-butyl)-N-(2-fluoro-4-methyl-5-(8-morpholinoimidazo[1,2-a]pyridin-6-yl)phenyl)morpholine-4-carboxamide): The fractions (RT: 8.0 min) were combined and concentrated to afford the title compound (71.8 mg, 31%) as an off-white solid of undetermined absolute stereochemistry. MS ESI calculated for C$_{27}$H$_{34}$FN$_5$O$_3$ [M+H]$^+$, 496.26, found 496.25; $^1$H NMR (400 MHz, DMSO-d$_6$) δ 8.34 (s, 1H), 8.11 (d, J=1.4 Hz, 1H), 7.88 (d, J=1.2 Hz, 1H), 7.50 (d, J=1.2 Hz, 1H), 7.33 (d, J=8.2 Hz, 1H), 7.17 (d, J=11.6 Hz, 1H), 6.33 (d, J=1.5 Hz, 1H), 4.01-3.97 (m, 1H), 3.95-3.84 (m, 2H), 3.80 (t, J=4.7 Hz, 4H), 3.54 (t, J=4.7 Hz, 4H), 3.42-3.36 (m, 1H), 2.99-2.97 (m, 1H), 2.91-2.79 (m, 1H), 2.66-2.64 (m, 1H), 2.25 (s, 3H), 0.91 (s, 9H).

Example 60 and 61: N-(2-fluoro-4-methyl-5-(8-morpholinoimidazo[1,2-a]pyridin-6-yl)phenyl)-3-(1-methylcyclopropyl)pyrrolidine-1-carboxamide

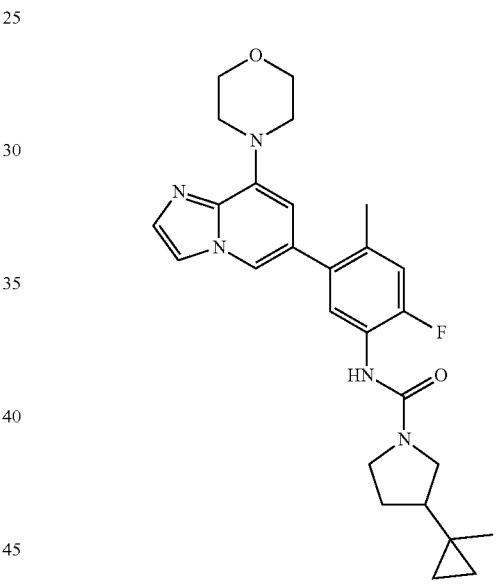

Step 1: To a stirred mixture of 2-fluoro-4-methyl-5-[8-(morpholin-4-yl)imidazo[1,2-a]pyridin-6-yl]aniline (100 mg, 0.31 mmol,) and Triethylamine (124 mg, 1.22 mmol) in tetrahydrofuran (1.5 mL) was added in portions at room temperature. To the above mixture was added triphosgene (36 mg, 0.12 mmol) in portions over 30 min at room temperature. To the above mixture was added 2,2,2-trifluoro-113-ethan-1-one compound with 3-(1-(trifluoromethyl)cyclopropyl)pyrrolidine 2,2,2-trifluoroacetate (134 mg, 0.46 mmol) dropwise at room temperature. The reaction mixture was stirred for additional 2 h at room temperature. The resulting mixture was quenched with methanol and concentrated under reduced pressure. The residue was purified by reverse phase Flash chromatography with the following conditions: Column: WelFlash TM C18-I, 20-40 μm, 120 g; Mobile Phase A: Water (Plus 10 mmol/L NH$_4$HCO$_3$); Mobile Phase B: acetonitrile; Gradient: 40%-60% B in 20 min; Flow rate: 60 mL/min; Detector: 220/254 nm. The fractions containing the desired product were combined and concentrated to afford N-{2-fluoro-4-methyl-5-[8-(morpholin-4-yl)imidazo[1,2-a]pyridin-6-yl]phenyl}-3-[1-(trifluoromethyl)cyclopropyl]pyrrolidine-1-carboxamide as an off-white solid. MS ESI calculated for $C_{27}H_{29}F_4N_5O_2$ [M+H]$^+$, 532.23, found 532.15.

Step 2: N-{2-fluoro-4-methyl-5-[8-(morpholin-4-yl)imidazo[1,2-a]pyridin-6-yl]phenyl}-3-[1-(trifluoromethyl)cyclopropyl]pyrrolidine-1-carboxamide (112 mg, 0.21 mmol) was purified by Chiral-Prep-HPLC with the following conditions: Column: Lux 5 pm Cellulose-4, 2.12×25 cm, m; Mobile Phase A: Hex--HPLC, Mobile Phase B: MeOH: EtOH=1: 1--HPLC; Flow rate: 20 mL/min; Gradient: 20% B to 20% B in 25 min; Wave Length: 220/254 nm; RT1: 19.36 min; RT2: 22.26 min; Sample Solvent: MeOH--HPLC; Injection Volume: 0.3 mL.

PEAK 1 (EXAMPLE 60, N-(2-fluoro-4-methyl-5-(8-morpholinoimidazo[1,2-a]pyridin-6-yl)phenyl)-3-(1-methylcyclopropyl)pyrrolidine-1-carboxamide): The fractions (RT 19.36 min) were combined and concentrated to afford the title compound (29 mg, 25%) as an off-white solid of undetermined absolute stereochemistry. MS ESI calculated for $C_{27}H_{29}F_4N_5O_2$ [M+H]$^+$, 532.23, found 532.30; $^1$H NMR (400 MHz, DMSO-d$_6$) δ 8.19 (s, 1H), 7.97-7.96 (m, 1H), 7.91-7.89 (m, 1H), 7.63-7.59 (m, 1H), 7.44 (d, J=8.1 Hz, 1H), 7.18 (d, J=11.6 Hz, 1H), 6.50 (s, 1H), 3.81 (t, J=4.6 Hz, 4H), 3.65-3.63 (m, 1H), 3.49-3.47 (m, 4H), 3.36-3.32 (m, 2H), 2.93-2.91 (m, 1H), 2.74-2.68 (m, 1H), 2.25 (s, 3H), 1.93-1.86 (m, 1H), 1.49-1.44 (m, 1H), 0.91-0.85 (m, 4H).

PEAK 2 (EXAMPLE 61, N-(2-fluoro-4-methyl-5-(8-morpholinoimidazo[1,2-a]pyridin-6-yl)phenyl)-3-(1-methylcyclopropyl)pyrrolidine-1-carboxamide): The fractions (RT 22.26 min) were combined and concentrated to afford the title compound (32 mg, 28%) as an off-white solid of undetermined absolute stereochemistry. MS ESI calculated for $C_{27}H_{29}F_4N_5O_2$ [M+H]$^+$, 532.23, found 532.30; $^1$H NMR (400 MHz, DMSO-d$_6$) δ 8.19 (s, 1H), 7.97-7.96 (m, 1H), 7.91-7.89 (m, 1H), 7.63-7.59 (m, 1H), 7.44 (d, J=8.1 Hz, 1H), 7.18 (d, J=11.6 Hz, 1H), 6.50 (s, 1H), 3.81 (t, J=4.6 Hz, 4H), 3.65-3.63 (m, 1H), 3.57-3.44 (m, 4H), 3.33-3.32 (m, 2H), 2.93-2.91 (m, 1H), 2.74-2.68 (m, 1H), 2.25 (s, 3H), 1.93-1.86 (m, 1H), 1.47-1.45 (m, 1H), 0.91-0.85 (m, 4H).

Example 66: 1-tert-Butyl-4-fluoro-N-{2-fluoro-4-methyl-5-[8-(morpholin-4-yl)imidazo[1,2-a]pyridin-6-yl]phenyl}pyrrole-3-carboxamide

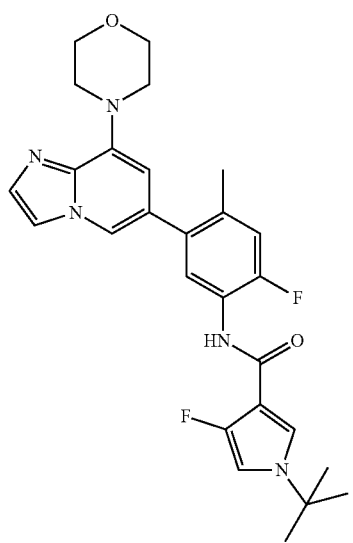 [SMILES: Cc1cc(F)c(NC(=O)c2cn(C(C)(C)C)cc2F)cc1-c1cc(N2CCOCC2)c2nccn2c1]

Step 1: To a stirred solution of 2-methylpropan-2-amine (50 g, 683.63 mmol) in AcOH (150 mL) was added 2,5-dimethoxyoxolane (50 g, 378.33 mmol) dropwise at 0° C. The reaction mixture was stirred for 48 h at 80° C. The mixture was allowed to cool down to room temperature. The resulting mixture was concentrated under reduced pressure. The residue was diluted with water and basified to pH 8 with NaOH (aq.). The resulting mixture was extracted with Diethyl ether (2×200 mL). The combined organic layers were washed with brine (1×200 mL), dried over Na$_2$SO$_4$. After filtration, the filtrate was concentrated under reduced pressure. The resulting mixture was concentrated under reduced pressure. The crude product was purified by distillation under 2 Mpa and the fraction was collected at 80° C. to afford 1-tert-butylpyrrole (5 g, 10%) as a colorless oil. $^1$H NMR (400 MHz, CDCl$_3$) δ 6.84 (t, J=2.0 Hz, 2H), 6.16 (t, J=2.0 Hz, 2H), 1.53 (s, 9H).

Step 2: To a stirred solution of 1-tert-butylpyrrole (3.5 g, 28.41 mmol) in Tetrahydrofuran (40 mL) was added N-Bromosuccinimide (10.11 g, 56.82 mmol) in Tetrahydrofuran (140 mL) dropwise at −80° C. The reaction mixture was stirred for 2 h at −80° C. The resulting mixture was concentrated under reduced pressure. The residue was purified by silica gel column chromatography, eluted with Ethyl acetate. The fractions containing the desired product were combined and concentrated to afford 3,4-dibromo-1-tert-butylpyrrole (7.71 g, 96%) as a colorless oil. $^1$H NMR (400 MHz, CDCl$_3$) δ 6.80 (d, J=1.2 Hz, 2H), 1.49 (s, 9H).

Step 3: To a stirred solution of 3,4-dibromo-1-tert-butylpyrrole (3 g, 10.68 mmol) in Tetrahydrofuran (30 mL) was added 2.5 M n-BuLi in hexane (4.48 mL, 11.21 mmol) dropwise at −78° C. under nitrogen atmosphere. After stirred for 30 min, N-fluorobenzenesulfonimide (5.05 g, 16.01 mmol) in Tetrahydrofuran (30 mL) was added dropwise at −78° C. The reaction mixture was stirred for 1 h at −78° C. The resulting mixture was concentrated under reduced pressure.

The residue was purified by silica gel column chromatography with PE as eluant. The fractions containing the desired product were combined and concentrated to afford 3-bromo-1-tert-butyl-4-fluoropyrrole (1.5 g, 63%) as a colorless oil. $^1$H NMR (400 MHz, CDCl$_3$) δ 6.59-6.55 (m, 2H), 1.47 (s, 9H).

Step 4: To a stirred solution of 3-bromo-1-tert-butyl-4-fluoropyrrole (550 mg, 2.50 mmol) in Tetrahydrofuran (5.5 mL) was added butyllithium (1.05 mL, 2.62 mmol) dropwise at −78° C. under nitrogen atmosphere. The reaction mixture was stirred for 30 min at −78° C. under nitrogen atmosphere. To the above mixture was added propyl carbonochloridate (336.88 mg, 2.75 mmol) dropwise at −78° C. The reaction mixture was stirred for additional 1 h at −78° C. The resulting mixture was quenched by the addition of sat. Ammonium chloride (aq.) (20 mL) at 0° C. The resulting mixture was extracted with Ethyl acetate (2×100 mL). The combined organic layers were washed with brine (1×100 mL), dried over anhydrous Sodium sulfate. After filtration, the filtrate was concentrated under reduced pressure. The residue was purified by silica gel column chromatography, eluted with PE/EA (8/1). The fractions containing the desired product were combined and concentrated to afford propyl 1-tert-butyl-4-fluoropyrrole-3-carboxylate (360 mg, 63%) as a yellow oil. MS ESI calculated for $C_{12}H_{18}FNO_2$ [M+H]$^+$, 228.13, found 228.10; $^1$H NMR (400 MHz, CDCl$_3$) δ 7.18-7.16 (m, 1H), 6.56-6.54 (m, 1H), 4.19 (t, J=6.4 Hz, 2H), 1.78-1.69 (m, 2H), 1.50 (s, 9H), 1.00 (t, J=7.2 Hz, 3H).

Step 5: To a stirred solution of propyl 1-tert-butyl-4-fluoropyrrole-3-carboxylate (320 mg, 1.41 mmol) in Methanol (3.2 mL), Tetrahydrofuran (3.2 mL) and Water (3.2 mL) was added Lithium hydroxide (134.88 mg, 5.63 mmol) dropwise at room temperature. The reaction mixture was stirred for 16 h at 50° C. The resulting mixture was concentrated under reduced pressure. The residue was purified by reverse flash chromatography with the following conditions: column, C18 silica gel; mobile phase, Acetonitrile in Water (Plus 10 mmol/L $NH_4HCO_3$), 10% to 50% gradient in 10 min; detector, UV 254 nm. The fractions containing the desired product were combined and concentrated to afford 1-tert-butyl-4-fluoropyrrole-3-carboxylic acid (200 mg, 76%) as a white solid. MS ESI calculated for $C_9H_{12}FNO_2$ [M+H]$^+$, 186.09, found 186.05; $^1$H NMR (400 MHz, DMSO-$d_6$) δ 7.06 (dd, J=4.2, 3.2 Hz, 1H), 6.85-6.83 (m, 1H), 1.43 (s, 9H).

Step 6: To a stirred mixture of 1-tert-butyl-4-fluoropyrrole-3-carboxylic acid (60.15 mg, 0.32 mmol), 2-fluoro-4-methyl-5-[8-(morpholin-4-yl)imidazo[1,2-a]pyridin-6-yl]aniline (53 mg, 0.16 mmol), EDCI (46.70 mg, 0.24 mmol), HOBt (32.91 mg, 0.24 mmol) in N,N-Dimethylformamide (0.3 mL) was added Triethylamine (65.73 mg, 0.65 mmol) dropwise at room temperature. The reaction mixture was stirred for additional 48 h at 80° C. The resulting mixture was concentrated under reduced pressure. The residue was purified by reverse flash chromatography with the following conditions: column, C18 silica gel; mobile phase, MeCN in Water (Plus 10 mmol/L $NH_4HCO_3$), 10% to 50% gradient in 10 min; detector, UV 254 nm. The fractions containing the desired product were combined and concentrated to afford the title compound (12.1 mg, 15%) as an off-white solid. MS ESI calculated for $C_{27}H_{29}F_2N_5O_2$ [M+H]$^+$, 494.23, found 494.20; $^1$H NMR (400 MHz, DMSO-$d_6$) δ 9.01 (s, 1H), 8.13 (d, J=1.2 Hz, 1H), 7.89 (d, J=1.2 Hz, 1H), 7.69 (d, J=8.0 Hz, 1H), 7.53-7.46 (m, 2H), 7.25 (d, J=11.6 Hz, 1H), 7.07 (t, J=2.8 Hz, 1H), 6.35 (d, J=1.2 Hz, 1H), 3.80 (t, J=4.0 Hz, 4H), 3.55 (t, J=3.6 Hz, 4H), 2.28 (s, 3H), 1.48 (s, 9H).

Example 67: 1-tert-Butyl-N-{2-fluoro-4-methyl-5-[8-(morpholin-4-yl)imidazo[1,2-a]pyridin-6-yl]phenyl}imidazole-4-carboxamide

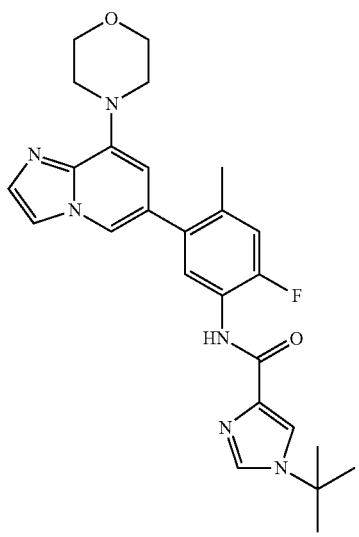 [SMILES: Cc1cc(F)c(NC(=O)c2cn(C(C)(C)C)cn2)cc1-c1cc(N2CCOCC2)c2nccn2c1]

Step 1: To a stirred solution of ethyl 2-isocyanoacetate (5 g, 44.20 mmol) in EtOH (50 mL) was added DMF-DMA (6.46 g, 88.40 mmol) dropwise at 0° C. under nitrogen atmosphere. The reaction mixture was stirred for 16 h at room temperature under nitrogen atmosphere. The resulting mixture was diluted with water (100 mL) and extracted with EtOAc (3×100 mL). The combined organic layers were washed with brine (3×80 mL), dried over anhydrous $Na_2SO_4$.

After filtration, the filtrate was concentrated under reduced pressure. The residue was purified by silica gel column chromatography, eluted with PE/EA (1/1). The fractions containing the desired product were combined and concentrated to afford ethyl (2Z)-3-(dimethylamino)-2-isocyanoprop-2-enoate (5.26 g, 71%) as a yellow solid. MS ESI calculated for $C_8H_{12}N_2O_2$ [M+H]$^+$, 169.19, found 169.10; $^1$H NMR (400 MHz, Chloroform-d) δ 7.20 (s, 1H), 4.24-4.13 (m, 2H), 3.25 (s, 6H), 1.32 (t, J=4.2 Hz, 3H).

Step 2: A solution of ethyl (2Z)-3-(dimethylamino)-2-isocyanoprop-2-enoate (100 mg, 0.60 mmol) in 2-methylpropan-2-amine (1 mL) was stirred for 24 h at 140° C. The resulting mixture was concentrated under reduce pressure. The residue was purified by silica gel column chromatography, eluted with PE/EA/EtOH (4/3/1) to afford the crude product. The crude product was further purified by reverse phase Flash chromatography with the following conditions: Column: WelFlash TM C18-I, 20-40 μm, 40 g; Eluent A: Water (Plus 10 mmol/L $NH_4HCO_3$); Eluent B: ACN; Gradient: 40% to 60% B in 25 min; Flow rate: 30 mL/min; Detector: 220/254 nm. The fractions containing the desired product were combined and concentrated to afford ethyl 1-tert-butylimidazole-4-carboxylate (80 mg, 69%) as a yellow solid. MS ESI calculated for $C_{10}H_{16}N_2O_2$ [M+H]$^+$, 197.25, found 197.10; $^1$H NMR (400 MHz, Chloroform-d) δ 7.76 (d, J=1.6 Hz, 1H), 7.66 (d, J=1.6 Hz, 1H), 4.42-4.36 (m, 2H), 1.61 (s, 9H), 1.41 (t, J=4.2 Hz, 3H).

Step 3: To a stirred solution of ethyl 1-tert-butylimidazole-4-carboxylate (80 mg, 0.41 mmol) in MeOH (1 mL) and THF (1 mL) was added LiOH $H_2O$ (51.31 mg, 1.22 mmol) in $H_2O$ (1 mL). The reaction mixture was stirred for 1 h at 60° C. The resulting mixture was concentrated under reduced pressure to afford 1-tert-butylimidazole-4-carboxylic acid (50 mg, crude). MS ESI calculated for $C_8H_{12}N_2O_2$ [M+H]$^+$, 169.19, found 169.10.

Step 4: To a stirred solution of 1-tert-butylimidazole-4-carboxylic acid (50 mg, 0.29 mmol) in Pyridine (1 mL) were added $T_3P$ (233.98 mg, 0.38 mmol, 50% in EA) and 2-fluoro-4-methyl-5-[8-(morpholin-4-yl)imidazo[1,2-a]pyridin-6-yl]aniline (80 mg, 0.25 mmol) at room temperature. The reaction mixture was stirred for 2 h at 60° C. The resulting mixture was concentrated under reduced pressure. The residue was purified by reverse phase Flash chromatography with the following conditions: Column: WelFlash TM C18-I, 20-40 μm, 40 g; Eluent A: Water (Plus 10 mmol/L $NH_4HCO_3$); Eluent B: ACN; Gradient: 40% to 60% B in 25 min; Flow rate: 30 mL/min; Detector: 220/254 nm. The fractions containing the desired product were combined and concentrated to afford the title compound (4.8 mg, 4%) as a white solid. MS ESI calculated for $C_{26}H_{29}FN_6O_2$ [M+H]$^+$, 477.55 found 477.30; $^1$H NMR (400 MHz, DMSO-$d_6$) δ 9.44 (s, 1H), 8.16 (d, J=1.2 Hz, 1H), 8.05-7.97 (m, 3H), 7.91 (d, J=1.2 Hz, 1H), 7.52 (d, J=1.2 Hz, 1H), 7.30 (d, J=11.8 Hz, 1H), 6.37 (d, J=1.6 Hz, 1H), 3.80 (d, J=4.8 Hz, 4H), 3.56 (d, J=5.2 Hz, 4H), 2.29 (s, 3H), 1.56 (s, 9H).

Example 69: N-(2-Fluoro-4-methyl-5-(8-morpholinoimidazo[1,2-a]pyridin-6-yl)phenyl)-3-(1-methylcyclopropyl)-2,5-dihydro-1H-pyrrole-1-carboxamide

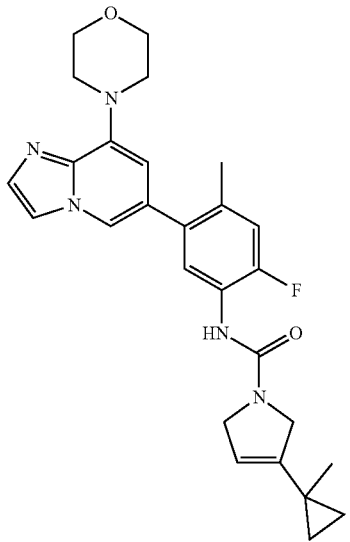 [SMILES: Cc1cc(F)c(NC(=O)N2CC=C(C3(C)CC3)C2)cc1-c1cc(N2CCOCC2)c2nccn2c1]

Step 1: To a stirred solution of tert-butyl 3-oxopyrrolidine-1-carboxylate (10 g, 53.99 mmol) in Tetrahydrofuran (1 L) was added Lithium bis(trimethylsilyl)amide (100 mL, 100.00 mmol) dropwise at −78° C. under a nitrogen atmosphere. The reaction mixture was stirred for 0.5 h at -78° C. under a nitrogen atmosphere. To the above mixture was added 1,1,1-trifluoro-N-phenyl-N-trifluoromethanesulfonylmethanesulfonamide (21.22 g, 59.39 mmol) in THF (20 mL) dropwise at −78° C. The reaction mixture was stirred for additional 2 h at −45° C. The resulting mixture was quenched with sat. Ammonium chloride (aq.) and extracted with EtOAc (2×200 mL). The combined organic layers wad washed with brine (1×100 mL), dried over anhydrous Na$_2$SO$_4$. After filtration, the filtrate was concentrated under reduced pressure. The residue was purified by silica gel column chromatography, eluted with PE/EA (20/1). The fractions containing the desired product were combined and concentrated to afford tert-butyl 3-(trifluoromethanesulfonyloxy)-2,5-dihydropyrrole-1-carboxylate (15 g, 87%) as a brown oil. MS ESI calculated for C$_{10}$H$_{14}$F$_3$NO$_5$S [M+H]$^+$, 318.05, found 318.00.

Step 2: To a stirred solution of tert-butyl 3-(trifluoromethanesulfonyloxy)-2,5-dihydropyrrole-1-carboxylate (4 g, 12.61 mmol), 1,1'-Bis(diphenylphosphino)ferrocene-palladium(II)dichloride dichloromethane complex (1.03 g, 1.26 mmol) and Cesium carbonate (8.22 g, 25.21 mmol) in dioxane (40 mL) and Water (10 mL) was added 4,4,5,5-tetramethyl-2-(prop-1-en-2-yl)-1,3-dioxolane (2.58 g, 15.13 mmol). The reaction mixture was degassed with nitrogen for three times and stirred for 1 h at 100° C. The resulting mixture was diluted with water (200 mL). The resulting mixture was extracted with Ethyl acetate (2×200 mL). The combined organic layers were washed with brine (2×100 mL), dried over anhydrous Sodium sulfate. After filtration, the filtrate was concentrated under reduced pressure. The residue was purified by silica gel column chromatography, eluted with PE/EA (9/1). The fractions containing the desired product were combined and concentrated to afford tert-butyl 3-(prop-i-en-2-yl)-2,5-dihydropyrrole-1-carboxylate (1.3 g, 49%) as a colorless oil. MS ESI calculated for C$_{12}$H$_{19}$NO$_2$ [M+H]$^+$, 210.1 found 210.1.

Step 3: To a stirred solution of diiodomethane (5.62 mL, 69.76 mmol) in dichloromethane (15 mL) was added diethylzinc (11.87 mL, 69.76 mmol) dropwise at 0° C. under nitrogen atmosphere. The reaction mixture was stirred for 15 min at 0° C. under nitrogen atmosphere. To the above mixture was added tert-butyl 3-(prop-i-en-2-yl)-2,5-dihydropyrrole-1-carboxylate (1.46 g, 6.98 mmol) dropwise at 0° C. The reaction mixture was stirred for additional 16 h at room temperature. The resulting mixture was quenched by the addition of sat. ammonium chloride (aq.) (50 mL) at room temperature. The resulting mixture was diluted with water (150 mL) and extracted with Ethyl acetate (2×200 mL). The combined organic layers were washed with brine (1×200 mL), dried over anhydrous sodium sulfate. After filtration, the filtrate was concentrated under reduced pressure. The residue was purified by reverse flash chromatography with the following conditions: column, C18 silica gel; mobile phase, Acetonitrile in Water (Plus 10 mmol/L NH$_4$HCO$_3$), 40% to 60% gradient in 20 min; detector, UV 254 nm. The fractions containing the desired product were combined and concentrated to afford tert-butyl 3-(1-methylcyclopropyl)-2,5-dihydropyrrole-1-carboxylate (80 mg, 5%) as a yellow solid. MS ESI calculated for C$_{13}$H$_{21}$NO$_2$ [M+H]$^+$, 224.1, found 224.1; $^1$H NMR (400 MHz, CDCl$_3$) δ 5.36-5.34 (m, 1H), 4.09-4.06 (m, 2H), 3.92-3.88 (m, 2H), 1.47 (s, 9H), 1.23 (s, 3H), 0.73-0.71 (m, 2H), 0.52-0.50 (m, 2H).

Step 4: To a stirred solution of tert-butyl 3-(1-methylcyclopropyl)-2,5-dihydropyrrole-1-carboxylate (70 mg, 0.31 mmol) in Dichloromethane (4 mL) was added 2,2,2-trifluoroacetic acid (0.8 mL) dropwise at room temperature. The reaction mixture was stirred for 1 h at room temperature. The resulting mixture was concentrated under reduced pressure. The fractions containing the desired product were combined and concentrated to afford 3-(1-methylcyclopropyl)-2,5-dihydro-1H-pyrrole 2,2,2-trifluoroacetate (80 mg, 92%) as a black oil. MS ESI calculated for C$_{10}$H$_{14}$F$_3$NO [M+H]$^+$, 124.10, found 124.10.

Step 5: To a stirred solution of 2-fluoro-4-methyl-5-[8-(morpholin-4-yl)imidazo[1,2-a]pyridin-6-yl]aniline (110.65 mg, 0.34 mmol) and ditrichloromethyl carbonate (40.24 mg, 0.14 mmol) in Tetrahydrofuran (1 mL) was added N,N-Diisopropylethylamine (0.30 mL, 1.70 mmol) dropwise at room temperature under a nitrogen atmosphere. The reaction mixture was stirred for 15 min at room temperature under nitrogen atmosphere. To the above mixture was added 3-(1-methylcyclopropyl)-2,5-dihydro-1H-pyrrole 2,2,2-trifluoroacetate (75 mg, 0.40 mmol) dropwise at room temperature. The reaction mixture was stirred for additional 1 h at room temperature. The resulting mixture was concentrated under reduced pressure. The residue was purified by silica gel column chromatography, eluted with DCM/MeOH (10/1) to afford the crude product. The crude product was purified by Prep-HPLC with the following conditions Column: Xselect CSH F-Phenyl OBD column, 19×250 mm, 5 m; Mobile Phase A: Water (0.1% FA), Mobile Phase B: ACN; Flow rate: 20 mL/min; Gradient: 20% B to 25% B in 8 min, 25% B; Wavelength: 254 nm. The fractions containing the desired product were combined and concentrated to afford the title compound (20 mg, 12%) as a white solid. MS ESI calculated for C$_{27}$H$_{30}$FN$_5$O$_2$[M+H]$^+$, 476.24, found 476.25; $^1$H NMR (400 MHz, DMSO-d$_6$) δ 8.37 (s, 1H), 8.13 (m, 1H), 7.90 (m, 2H), 7.52 (d, J=8.0 Hz, 1H), 7.22 (d, J=11.6 Hz, 1H), 6.88 (s, 1H), 5.54-5.52 (m, 1H), 4.16 (s, 2H), 4.01 (s, 2H), 3.83 (t, J=4.6 Hz, 4H), 3.33 (t, J=4.6 Hz, 4H), 2.25 (s, 3H), 1.23 (s, 3H), 0.79-0.77 (m, 2H), 0.58-0.51 (m, 2H).

Example 70: N-(2-Fluoro-4-methyl-5-(8-morpholinoimidazo[1,2-a]pyridin-6-yl)phenyl)-5-(trifluoromethyl)nicotinamide

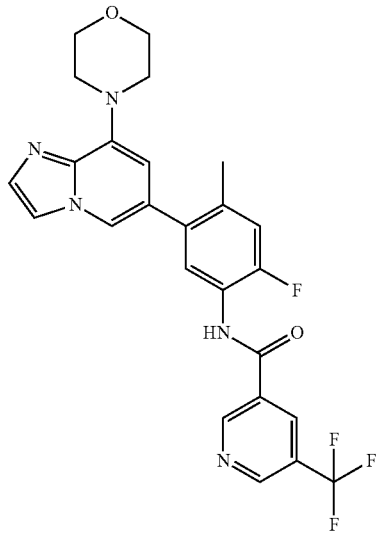 [SMILES: Cc1cc(F)c(NC(=O)c2cncc(C(F)(F)F)c2)cc1-c1cc(N2CCOCC2)c2nccn2c1]

STEP 1. To a stirred solution of 2-fluoro-4-methyl-5-[8-(morpholin-4-yl)imidazo[1,2-a]pyridin-6-yl]aniline (60 mg, 0.18 mmol), 5-(trifluoromethyl)pyridine-3-carboxylic acid (42.16 mg, 0.22 mmol) and 2-(7-Azabenzotriazol-1-yl)-N,N,N',N-tetramethyluronium hexafluorophosphate (104.85 mg, 0.28 mmol) in N,N-Dimethylformamide (1 mL) was added Triethylamine (93.02 mg, 0.92 mmol) dropwise at room temperature. The reaction mixture was stirred for additional 16 h at room temperature. The resulting mixture was diluted with water (20 mL) extracted with Ethyl acetate (3×30 mL). The combined organic layers were washed with brine (3×30 mL), dried over anhydrous Sodium sulfate. After filtration, the filtrate was concentrated under reduced pressure. The residue was purified by reverse flash chromatography with the following conditions: column, C18 silica gel; mobile phase, MeCN in Water (Plus 10 mmol/L $NH_4HCO_3$), 40% to 70% gradient in 30 min; detector, UV 254 nm. The fractions containing the desired product were combined and concentrated to afford N-{2-fluoro-4-methyl-5-[8-(morpholin-4-yl)imidazo[1,2-a]pyridin-6-yl]phenyl}-5-(trifluoromethyl)pyridine-3-carboxamide (67.8 mg, 73%) as a light blue solid. MS ESI calculated for $C_{25}H_{21}F_4N_5O_2$ $[M+H]^+$, 500.16, found 500.20; $^1H$ NMR (400 MHz, $CDCl_3$) δ 9.31 (s, 1H), 9.10 (s, 1H), 8.47 (s, 1H), 8.33 (d, J=8 Hz, 1H), 8.07 (s, 1H), 7.80 (s, 1H), 7.65 (s, 1H), 7.59 (s, 1H), 7.15 (d, J=11.6 Hz, 1H), 6.40 (s, 1H), 4.03-3.96 (m, 4H), 3.59-3.52 (m, 4H), 2.32 (s, 3H).

Example 73: 1-(tert-Butyl)-5-fluoro-N-(4-methyl-3-(8-morpholinoimidazo[1,2-a]pyridin-6-yl)phenyl)-1H-pyrazole-4-carboxamide

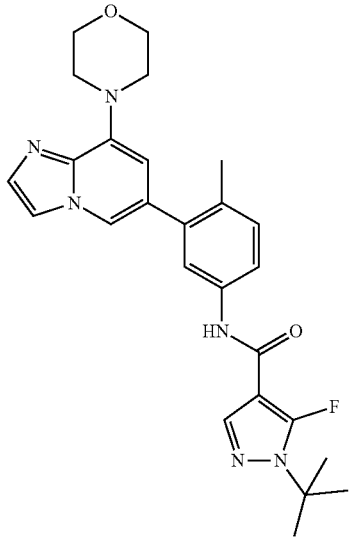 [SMILES: Cc1ccc(NC(=O)c2cnn(C(C)(C)C)c2F)cc1-c1cc(N2CCOCC2)c2nccn2c1]

Step 1: To a stirred solution of 4-bromo-3-fluoro-1H-pyrazole (1 g, 6.06 mmol) in t-BuOH (10 mL) was added $H_2SO_4$ (0.36 mL, 6.67 mmol, 98%) dropwise at room temperature. The reaction mixture was stirred for 6 h at 80° C. under nitrogen atmosphere. The resulting mixture was diluted with water (20 mL). The resulting mixture was extracted with $CH_2Cl_2$ (3×20 mL). The combined organic layers were washed with brine (3×15 mL), dried over anhydrous $Na_2SO_4$. After filtration, the filtrate was concentrated under reduced pressure to afford 4-bromo-1-(tert-butyl)-5-fluoro-1H-pyrazole (1 g, 62%) as a light-yellow oil. MS ESI calculated for $C_7H10BrFN_2$ $[M+H]^+$, 221.00, 223.00, found 221.00, 223.00; $^1H$ NMR (400 MHz, Chloroform-d) δ 7.30 (d, J=2.4 Hz, 1H), 1.59 (s, 9H).

Step 2: To a stirred mixture of 4-{6-chloroimidazo[1,2-a]pyridin-8-yl}morpholine (400 mg, 1.68 mmol) and 4-methyl-3-(4,4,5,5-tetramethyl-1,3,2-dioxaborolan-2-yl) aniline (431.54 mg, 1.85 mmol), $K_3PO_4$ (714.43 mg, 3.37 mmol) in THF (5 mL) and water (0.5 mL) was added 2 nd Generation XPhos Precatalyst (132.41 mg, 0.17 mmol) in portions at room temperature. The reaction mixture was degassed with nitrogen for three times and stirred for 2 h at 80° C. The resulting mixture was concentrated under reduced pressure. The residue was purified by silica gel column chromatography, eluted with PE/EA/EtOH (4/3/1). The fractions containing the desired product were combined and concentrated to afford 4-methyl-3-[8-(morpholin-4-yl) imidazo[1,2-a]pyridin-6-yl]aniline (327 mg, 63%) as a yellow solid. MS ESI calculated for $C_{18}H_2ON_{40}$ $[M+H]^+$, 309.16, found 309.10; $^1H$ NMR (400 MHz, Chloroform-d) δ 7.71 (d, J=1.4 Hz, 1H), 7.60 (d, J=1.3 Hz, 1H), 7.53 (d, J=1.3 Hz, 1H), 7.07 (d, J=8.1 Hz, 1H), 6.66 (dd, J=8.0, 2.6 Hz, 1H), 6.62 (d, J=2.5 Hz, 1H), 6.41 (s, 1H), 4.02-3.95 (m, 4H), 3.57-3.51 (m, 4H), 2.17 (s, 3H).

Step 3: To a stirred mixture of 4-methyl-3-[8-(morpholin-4-yl)imidazo[1,2-a]pyridin-6-yl]aniline (80 mg, 0.26 mmol), $Pd(dppf)C_{12}CH_2Cl_2$ (42.43 mg, 0.05 mmol) and $Co_2(CO)_8$ (26.62 mg, 0.08 mmol) in dioxane (1.5 mL) was added TEA (156.95 mg, 1.55 mmol) and 4-bromo-1-(tert-butyl)-5-fluoro-1H-pyrazole (114.92 mg, 0.52 mmol). The reaction mixture was degassed with nitrogen for three times and stirred for 16 h at 90° C. The resulting mixture was allowed to cool down to room temperature. The resulting mixture was concentrated under reduced pressure. The residue was purified by silica gel column chromatography, eluted with $CH_2Cl_2$/MeOH (10/1) to afford the crude product. The crude product was purified by Prep-HPLC with the following conditions: Column: YMC-Actus Triart C18 ExRS, 30×150 mm, 5 m; Mobile Phase A: Water (Plus 10 mmol/L $NH_4HCO_3$), Mobile Phase B: ACN; Flow rate: 60 mL/min; Gradient: 40% B to 50% B in 10 min, 50% B; Wavelength: 254 nm; RT1: 12.3 min. The fractions were combined and concentrated to afford the title compound (12.2 mg, 9%) as an off-white solid. MS ESI calculated for $C_{26}H_{29}FN_6O_2$ $[M+H]^+$, 477.23, found 477.20; $^1$H NMR (400 MHz, Chloroform-d) δ 7.85-7.79 (m, 2H), 7.69-7.59 (m, 3H), 7.54-7.44 (m, 2H), 7.31-7.28 (m, 1H), 6.52 (s, 1H), 4.03 (t, J=4.6 Hz, 4H), 3.54 (t, J=4.7 Hz, 4H), 2.29 (s, 3H), 1.67 (d, J=1.4 Hz, 9H).

Example 74 and 75: N-(2-Fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide

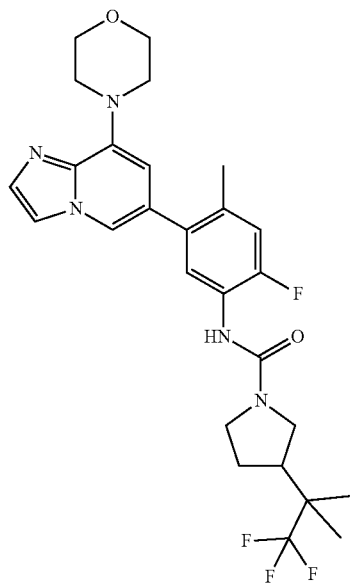 [SMILES: Cc1cc(F)c(NC(=O)N2CCC(C(C)(C)C(F)(F)F)C2)cc1-c1cc(N2CCOCC2)c2nccn2c1]

Step 1: To a stirred solution of maleic anhydride (10 g, 101.98 mmol) in Acetic acid (50 mL) was added (4-methoxyphenyl)methanamine (13.32 mL, 101.98 mmol) dropwise at room temperature under nitrogen atmosphere. The reaction mixture was stirred for 6 h at 120° C. under nitrogen atmosphere. The resulting mixture was concentrated under reduced pressure. The residue was purified by silica gel column chromatography, eluted with PE/EA (4/1). The fractions containing the desired product were combined and concentrated to afford 1-[(4-methoxyphenyl)methyl]pyrrole-2,5-dione (8 g, 36%) as a white solid; $^1$H NMR (400 MHz, $CDCl_3$) δ 7.33-7.26 (m, 2H), 6.87-6.79 (m, 2H), 6.68-6.62 (m, 2H), 4.61 (s, 2H), 3.78 (s, 3H).

Step 2: To a stirred solution of 1-[(4-methoxyphenyl) methyl]pyrrole-2,5-dione (8 g, 36.83 mmol), 3,3,3-trifluoro-2,2-dimethylpropanoic acid (14.37 g, 92.07 mmol) and ammonium persulfate (21.01 g, 92.07 mmol) in dimethyl sulfoxide (160 mL) and water (80 mL) was added potassium phosphate tribasic (19.54 g, 92.07 mmol) at room temperature under nitrogen atmosphere. The reaction mixture was stirred for 16 h at 70° C. under nitrogen atmosphere. The resulting mixture was quenched with sat. sodium bicarbonate (aq.) at room temperature. The resulting mixture was diluted with water (500 mL) and extracted with EA (2×500 mL). The combined organic layers were washed with brine (2×200 mL), dried over anhydrous $Na_2SO_4$. After filtration, the filtrate was concentrated under reduced pressure. The residue was purified by silica gel column chromatography, eluted with PE/EA (9/1). The fractions containing the desired product were combined and concentrated to afford 1-[(4-methoxyphenyl)methyl]-3-(1,1,1-trifluoro-2-methylpropan-2-yl)pyrrole-2,5-dione (3.4 g, 28%) as a yellow oil. $^1$H NMR (400 MHz, $CDCl_3$) δ 7.31-7.27 (m, 2H), 6.87-6.82 (m, 2H), 6.48-6.46 (m, 1H), 4.58 (s, 2H), 3.78 (s, 3H), 1.57-1.51 (s, 6H).

Step 3: To a stirred solution of $LiAlH_4$ (3.22 g, 84.82 mmol) in tetrahydrofuran (35 mL) was added 1-[(4-methoxyphenyl)methyl]-3-(1,1,1-trifluoro-2-methylpropan-2-yl)pyrrole-2,5-dione (3.47 g, 10.60 mmol) dropwise at 0° C. under nitrogen atmosphere. The reaction mixture was stirred for 16 h at room temperature under nitrogen atmosphere. The resulting mixture was quenched by the addition of water (3.2 mL), sodium hydroxide (15%) (3.2 mL) and water (9.6 mL) at 0° C. The resulting mixture was filtered, the filter cake was washed with EA (3×300 mL). The filtrate was concentrated under reduced pressure. The residue was purified by silica gel column chromatography, eluted with PE/EA (2/1). The fractions containing the desired product were combined and concentrated to afford 1-[(4-methoxyphenyl)methyl]-3-(1,1,1-trifluoro-2-methylpropan-2-yl)pyrrolidine (1.6 g, 50%) as a yellow oil. MS ESI calculated for $C_{16}H_{22}F_3NO$ $[M+H]^+$, 302.17, found 302.10; $^1$H NMR (400 MHz, $CDCl_3$) δ 7.26 (d, J=8.4 Hz, 2H), 6.86 (d, J=8.6 Hz, 2H), 3.80 (s, 3H), 3.71-3.48 (m, 2H), 2.76 (d, J=9.2 Hz, 2H), 2.63-2.26 (m, 2H), 1.89-1.86 (m, 1H), 1.78-1.45 (m, 2H), 1.07 (d, J=9.4 Hz, 6H).

Step 4: To a stirred solution of 1-[(4-methoxyphenyl) methyl]-3-(1,1,1-trifluoro-2-methylpropan-2-yl)pyrrolidine (2 g, 6.64 mmol) in EA (2 mL) was added Pd/C (2.00 g, 18.78 mmol, 60%) at room temperature under hydrogen atmosphere. The reaction mixture was stirred for 48 h at room temperature under hydrogen atmosphere. To the above mixture was added HCl (g) in EA (10 mL, 40.000 mmol) dropwise at room temperature. The resulting mixture was stirred for additional 5 min at room temperature. The resulting mixture was filtered, the filter cake was washed with EA (2×20 mL). The filtrate was concentrated under reduced pressure to afford 3-(1,1,1-trifluoro-2-methylpropan-2-yl) pyrrolidine HCl salt (1.5 g, crude) as a yellow oil. MS ESI calculated for $C_8H_{14}F_3N$ $[M+H]^+$, 182.11, found 182.10.

Step 5: To a stirred solution of 3-(1,1,1-trifluoro-2-methylpropan-2-yl)pyrrolidine HCl salt(250.09 mg, 1.15 mmol) and triphosgene (90.92 mg, 0.31 mmol) in Tetrahydrofuran (2.5 mL) was added N,N-Diisopropylethylamine (0.53 mL, 3.06 mmol) dropwise at room temperature under nitrogen atmosphere. The reaction mixture was stirred for 15 min at room temperature. To the above mixture was added 2-fluoro-4-methyl-5-(8-morpholinoimidazo[1,2-a]pyridin-6-yl)aniline (251.09 mg, 0.77 mmol) at room temperature. The reaction mixture was stirred for additional 1 h at room temperature. The resulting mixture was diluted with water (20 mL) and extracted with EA (3×20 mL). The combined organic layers were washed with brine (1×20 mL), dried over anhydrous sodium sulfate. After filtration, the filtrate was concentrated under reduced pressure. The residue was purified by silica gel column chromatography, eluted with EA to afford the crude product. The crude product was purified by Prep-HPLC with the following conditions Column: XBridge Prep OBD C18 Column, 30×150 mm, 5 m; Mobile Phase A: Water (Plus 10 mmol/L $NH_4HCO_3$), Mobile Phase B: ACN; Flow rate: 60 mL/min; Gradient: 49% B to 57% B in 8 min, 57% B; Wavelength: 220 nm. The fractions containing the desired product were combined and concentrated to afford N-(2-fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide (0.19 g, 46%) as a yellow oil. MS ESI calculated for $C_{27}H_{31}F_4N_5O_2$ $[M+H]^+$, 534.24, found 534.15.

Step 6: The N-(2-fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide (0.19 g) was purified by Prep-Chiral-HPLC with the following conditions: Column: CHIRAL ART Cellulose-SB, 2×25 cm, 5 m; Mobile Phase A: Hex (0.5% 2 M $NH_3$-MeOH)--HPLC, Mobile Phase B: IPA: DCM=1: 1--HPLC; Flow rate: 20 mL/min; Gradient: 30% B to 30% B in 11 min; Wave Length: 254/220 nm; RT1: 7.70 min; RT2: 8.70 min; Sample Solvent: MeOH: DCM=1: 1--HPLC; Injection Volume: 0.3 mL.

PEAK 1 (EXAMPLE 74: N-(2-Fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide). The fractions (RT 7.7 min) were combined and concentrated to afford the title compound (61.3 mg, 15%) as a white solid of undetermined absolute stereochemistry. MS ESI calculated for $C_{27}H_{31}F_4N_5O_2$ $[M+H]^+$, 534.24, found 534.20; $^1H$ NMR (400 MHz, DMSO-$d_6$) δ 8.10 (d, J=1.6 Hz, 1H), 7.91-7.86 (m, 2H), 7.50 (d, J=1.2 Hz, 1H), 7.43 (d, J=8.2 Hz, 1H), 7.16 (d, J=11.6 Hz, 1H), 6.33 (d, J=1.5 Hz, 1H), 3.83-3.77 (m, 4H), 3.60-3.50 (m, 6H), 3.28-3.26 (m, 1H), 3.16-3.13 (m, 1H), 2.47-2.35 (m, 1H), 2.25 (s, 3H), 1.95-1.87 (m, 1H), 1.81-1.73 (m, 1H), 1.12 (d, J=8.9 Hz, 6H).

PEAK 2 (EXAMPLE 75: N-(2-Fluoro-4-methyl-5-(8-morpholinoimidazo[1,2-a]pyridin-6-yl)phenyl)-3-(1,1,1-trifluoro-2-methylpropan-2-yl)pyrrolidine-1-carboxamide). The fractions (RT 8.7 min) were combined and concentrated to afford title compound (61.5 mg, 15%) as a white solid of undetermined absolute stereochemistry. MS ESI calculated for $C_{27}H_{31}F_4N_5O_2$ $[M+H]^+$, 534.24, found 534.20; $^1H$ NMR (400 MHz, DMSO-$d_6$) δ 8.10 (d, J=1.6 Hz, 1H), 7.91-7.86 (m, 2H), 7.50 (d, J=1.2 Hz, 1H), 7.43 (d, J=8.2 Hz, 1H), 7.16 (d, J=11.6 Hz, 1H), 6.33 (d, J=1.5 Hz, 1H), 3.83-3.77 (m, 4H), 3.60-3.50 (m, 6H), 3.28-3.26 (m, 1H), 3.16-3.13 (m, 1H), 2.47-2.35 (m, 1H), 2.25 (s, 3H), 1.95-1.87 (m, 1H), 1.81-1.73 (m, 1H), 1.12 (d, J=8.9 Hz, 6H).

Example 84: 5-(1,1-Difluoroethyl)-N-{2-fluoro-4-methyl-5-[8-(morpholin-4-yl)imidazo[1,2-a]pyridin-6-yl]phenyl}pyridine-3-carboxamide

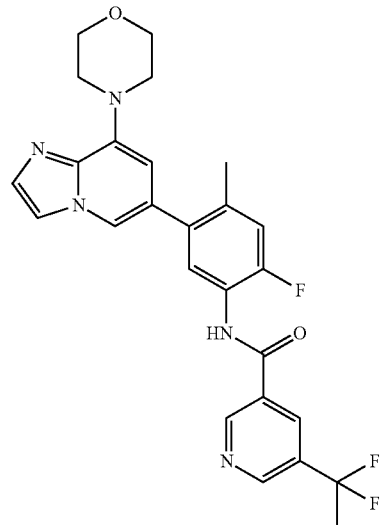 [SMILES: Cc1cc(F)c(NC(=O)c2cncc(C(C)(F)F)c2)cc1-c1cc(N2CCOCC2)c2nccn2c1]

Step 1: A solution of 1-(5-bromopyridin-3-yl)ethanone (3 g, 14.99 mmol) in BAST (4.98 g, 22.49 mmol) was stirred for 6 h at 80° C. under nitrogen atmosphere. The resulting mixture was allowed to cool down to room temperature. The resulting mixture was quenched by the addition of sat. $NaHCO_3$ (aq.) (100 mL) and extracted with EA (3×100 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EA (2/1). The fractions were combined and concentrated to afford 3-bromo-5-(1,1-difluoroethyl)pyridine (1.11 g, 33%) as a yellow oil. MS ESI calculated for $C_7H_6BrF_2N$ $[M+H]^+$, 221.97, found 222.00.

Step 2: To a solution of 3-bromo-5-(1,1-difluoroethyl)pyridine (1 g, 4.50 mmol) in MeOH (10 mL) was added Pd(dppf)$Cl_2$$CH_2Cl_2$ (366.89 mg, 0.45 mmol) and TEA (1.88 mL, 13.51 mmol). The reaction mixture was stirred for 16 h at 100° C. under carbon monoxide atmosphere (30 psi). The resulting mixture was allowed to cool down to room temperature. The resulting mixture was concentrated under reduced pressure. The residue was purified by silica gel column chromatography, eluted with PE/EA (2/1). The fractions containing the desired product were combined and concentrated to afford methyl 5-(1,1-difluoroethyl)pyridine-3-carboxylate (800 mg, 88%) as an off-white oil. MS ESI calculated for $C_9H_9F_2NO_2$ $[M+H]^+$, 202.06, found 202.10; H NMR (400 MHz, DMSO-$d_6$) δ 9.30 (d, J=2 Hz, 1H), 8.95 (d, J=2.4 Hz, 1H), 8.45-8.43 (m, 1H), 4.00 (s, 3H), 1.99 (t, J=18.3 Hz, 3H).

Step 3: To a stirred solution of 2-fluoro-4-methyl-5-[8-(morpholin-4-yl)imidazo[1,2-a]pyridin-6-yl]aniline (162.24 mg, 0.49 mmol) in LiHMDS (1 mL, 1 M in THF) was added methyl 5-(1,1-difluoroethyl)pyridine-3-carboxylate (100 mg, 0.49 mmol) in THF (1 mL) dropwise at 0° C. under nitrogen atmosphere. The reaction mixture was stirred for 1 h at room temperature under nitrogen atmosphere. The resulting mixture was quenched by the addition of sat. $NH_4Cl$ (aq.) (10 mL) and extracted with EtOAc (3×20 mL).

The combined organic layers were washed with brine (2×20 mL), dried over anhydrous $Na_2SO_4$. After filtration, the filtrate was concentrated under reduced pressure. The residue was purified by Prep-TLC, eluted with PE/EA/EtOH (4/3/1) to afford the crude product. The crude product was purified by reversed phase flash chromatography with the following conditions: column, C18 silica gel; mobile phase, MeCN in Water (Plus 10 mmol/L $NH_4HCO_3$), 5% to 95% gradient in 30 min; detector: UV 254 nm. The fractions were combined and concentrated to afford the title compound (132.7 mg, 53%) as a white solid. MS ESI calculated for $C_{26}H_{24}F_3N_5O_2[M+H]^+$, 496.19, found 496.15; $^1H$ NMR (400 MHz, DMSO-$d_6$) δ 10.52 (s, 1H), 9.23 (d, J=2.1 Hz, 1H), 9.00 (d, J=2.1 Hz, 1H), 8.49 (s, 1H), 8.17 (s, 1H), 7.90 (s, 1H), 7.58 (d, J=7.8 Hz, 1H), 7.52 (d, J=2.4 Hz, 1H), 7.33 (d, J=11.4 Hz, 1H), 6.39 (s, 1H), 3.80 (t, J=4.6 Hz, 4H), 3.55 (t, J=4.6 Hz, 4H), 2.31 (s, 3H), 2.09 (t, J=19.2 Hz, 3H).

Example 86: 1-tert-Butyl-N-{2-fluoro-4-methyl-5-[8-(morpholin-4-yl)imidazo[1,2-a]pyridin-6-yl]phenyl}-1,2,3-triazole-4-carboxamide

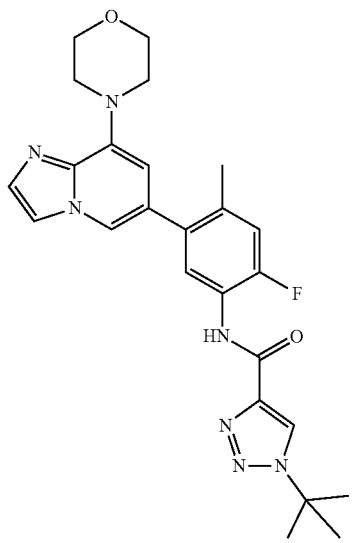 [SMILES: Cc1cc(F)c(NC(=O)c2cn(C(C)(C)C)nn2)cc1-c1cc(N2CCOCC2)c2nccn2c1]

Step 1: To a stirred solution of 1-tert-butyl-1,2,3-triazole-4-carboxylic acid (51.84 mg, 0.306 mmol) in Pyridine (1 mL) and propylphosphonic anhydride solution (1 mL, 50% in EA) was added 2-fluoro-4-methyl-5-[8-(morpholin-4-yl) imidazo[1,2-a]pyridin-6-yl]aniline (100 mg, 0.306 mmol). The reaction mixture was stirred for 16 h at room temperature under nitrogen atmosphere. The resulting mixture was concentrated under reduced pressure. The residue was purified by reverse phase flash chromatography with the following conditions: Column: WelFlash TM C18-I, 20-40 μm, 40 g; mobile phase A: Water (Plus 10 mmol/L $NH_4HCO_3$); mobile phase B: ACN; Gradient: 45% to 55% B in 20 min; Flow rate: 30 mL/min; Detector: 254 nm. The fractions were combined and concentrated to afford the title compound (119.9 mg, 81%) as an off-white solid. MS ESI calculated for $C_{25}H_{28}FN_7O_2[M+H]^+$, 478.23, found 478.25; H NMR (400 MHz, DMSO-$d_6$) δ 10.02 (s, 1H), 8.85 (s, 1H), 8.16 (d, J=1.5 Hz, 1H), 7.90 (d, J=1.4 Hz, 1H), 7.64 (d, J=7.8 Hz, 1H), 7.51 (d, J=1.1 Hz, 1H), 7.29 (d, J=11.5 Hz, 1H), 6.37 (d, J=1.7 Hz, 1H), 3.80 (t, J=4.7 Hz, 4H), 3.55 (t, J=4.8 Hz, 4H), 2.30 (s, 3H), 1.67 (d, J=1.1 Hz, 9H).

Example 87-90: 3-(1,1-difluoropropan-2-yl)-N-(2-fluoro-4-methyl-5-(8-morpholinoimidazo[1,2-a]pyridin-6-yl)phenyl)pyrrolidine-1-carboxamide

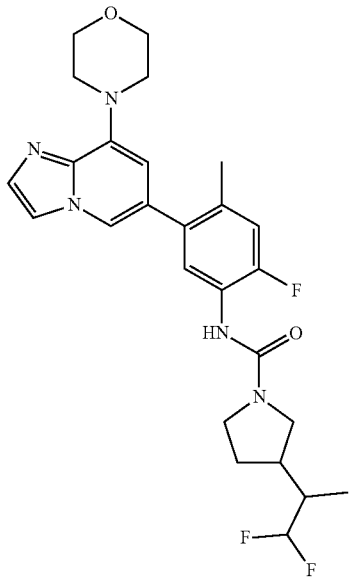 [SMILES: Cc1cc(F)c(NC(=O)N2CCC(C(C)C(F)F)C2)cc1-c1cc(N2CCOCC2)c2nccn2c1]

Step 1: To a stirred solution of tert-butyl 3-(2-methoxy-2-oxoethyl)pyrrolidine-1-carboxylate (2 g, 8.22 mmol) in THF (80 mL) was added 1 M LiHMDS in THF (20.55 mL, 20.55 mmol) dropwise at −10° C. under nitrogen atmosphere. The reaction mixture was stirred for 1 h at -10° C. To the above mixture was added $CH_3I$ (1.28 mL, 20.55 mmol) at −10° C. The reaction mixture was warmed to room temperature and stirred for 4 h under nitrogen atmosphere. The resulting mixture was quenched with water at room temperature and extracted with EtOAc (3×80 mL). The combined organic layers were washed with brine (2×60 mL), dried over anhydrous $Na_2SO_4$, filtered and concentrated under reduced pressure. The residue was purified by silica gel column chromatography, eluted with PE/EA (4/1). The fractions containing the desired product were combined and concentrated to afford tert-butyl 3-(1-methoxy-1-oxopropan-2-yl)pyrrolidine-1-carboxylate (0.7 g, 33%) as a light yellow oil. MS ESI calculated for $C_{13}H_{23}NO_4 [M+H]^+$, 258.33, found, 258.16.

Step 2: To a stirred mixture of $LiAlH_4$ (786 mg, 20.72 mmol) in THF (30 mL) was added tert-butyl 3-(1-methoxy-1-oxopropan-2-yl)pyrrolidine-1-carboxylate (2.6 g, 10.41 mmol) in THF (6 mL) at 0° C. under nitrogen atmosphere. The reaction mixture was stirred for 1 h at room temperature. The resulting mixture was quenched by 15% sodium hydroxide solution (0.6 mL). The resulting mixture was filtered, the filter cake was washed with EtOAc (5 mL). The filtrate was concentrated under reduced pressure. The residue was purified by silica gel column chromatography, eluted with PE/EA (1/1). The fractions containing the desired product were combined and concentrated to afford tert-butyl 3-(1-hydroxypropan-2-yl)pyrrolidine-1-carboxylate (2 g, 83%) as a colorless oil. MS ESI calculated for $C_{12}H_{23}NO_3 [M+H]^+$, 230.32, found 230.15.

Step 3: To a stirred solution of tert-butyl 3-(1-hydroxypropan-2-yl)pyrrolidine-1-carboxylate (2 g, 8.72 mmol) in DCM (40 mL) was added Dess-Martin (7.4 g, 17.44 mmol)

at room temperature. The reaction mixture was stirred for 1 h at room temperature. The resulting mixture was concentrated under reduced pressure. The residue was purified by silica gel column chromatography, eluted with PE/EA (3/1). The fractions containing the desired product were combined and concentrated to afford tert-butyl 3-(1-oxopropan-2-yl)pyrrolidine-1-carboxylate (1.4 g, 70%) as a colorless oil. MS ESI calculated for $C_{12}H_{21}NO_3$ [M+H]$^+$, 228.30, found 228.30.

Step 4: To a stirred solution of tert-butyl 3-(1-oxopropan-2-yl)pyrrolidine-1-carboxylate (1.4 g, 6.15 mmol) in DCM (20 mL) was added DAST (3971 mg, 24.63 mmol) dropwise at 0° C. under nitrogen atmosphere. The reaction mixture was stirred for 1 h at room temperature. The resulting mixture was quenched with NaHCO$_3$ (aq.) at 0° C. and extracted with CH$_2$Cl$_2$ (3×40 mL). The combined organic layers were washed with brine (2×30 mL), dried over anhydrous Na$_2$SO$_4$, filtered and concentrated under reduced pressure. The residue was purified by silica gel column chromatography, eluted with PE/EA (4/1). The fractions containing the desired product were combined and concentrated to afford tert-butyl 3-(1,1-difluoropropan-2-yl)pyrrolidine-1-carboxylate (1.1 g, 71%) as a yellow oil. MS ESI calculated for $C_{12}H_{21}F_2NO_2$ [M+H]$^+$, 250.30, found 250.15.

Step 5: To a stirred mixture of tert-butyl 3-(1,1-difluoropropan-2-yl)pyrrolidine-1-carboxylate (1.1 g, 4.41 mmol) in DCM (10 mL) was added HCl (gas) in EA (0.48 g, 13.23 mmol) at room temperature. The reaction mixture was stirred for 1 h at room temperature. The resulting mixture was concentrated under reduced pressure to afford 3-(1,1-difluoropropan-2-yl) pyrrolidine HCl salt (700 mg, crude) as a yellow solid. MS ESI calculated for $C_7H_{13}F_2N$ [M+H]$^+$, 150.10, found 150.15

Step 6: To a stirred mixture of 2-fluoro-4-methyl-5-[8-(morpholin-4-yl)imidazo[1,2-a]pyridin-6-yl]aniline (300 mg, 0.91 mmol) in THF (22 mL) were added triphosgene (109 mg, 0.36 mmol) and DIEA (356.41 mg, 2.76 mmol) at room temperature under nitrogen atmosphere. The reaction mixture was stirred for 30 min at room temperature under nitrogen atmosphere. To the above mixture was added 3-(1,1-difluoropropan-2-yl) pyrrolidine HCl salt (204.29 mg, 1.10 mmol) at room temperature. The reaction mixture was stirred for additional 2 h at room temperature. The resulting mixture was quenched with MeOH (5 mL) and concentrated under reduced pressure. The residue was purified by reversed phase flash chromatography with the following conditions: column, C18 silica gel; mobile phase, MeCN in Water (Plus 10 mmol/L NH$_4$HCO$_3$), 5% to 95% gradient in 30 min; detector: UV 254 nm. The fractions containing the desired product were combined and concentrated to afford 3-(1,1-difluoropropan-2-yl)-N-{2-fluoro-4-methyl-5-[8-(morpholin-4-yl)imidazo[1,2-a]pyridin-6-yl]phenyl}pyrrolidine-1-carboxamide (170 mg, 36%) as a yellow solid. The solid was further purified by Prep-Chiral-HPLC with the following conditions: Column: CHIRAL-PAK IE, 2×25 cm, 5 m; Mobile Phase A: Hex (0.5% 2 M NH$_3$-MeOH)--HPLC, Mobile Phase B: IPA: DCM=1:1--HPLC; Flow rate: 20 mL/min; Gradient: 40% B to 40% B in 30 min; Wave Length: 254/220 nm; RT1: 20.27 min; RT2: 25.06 min; Sample Solvent: MeOH: DCM=1:1--HPLC; Injection Volume: 0.3 mL.

PEAK 1 (EXAMPLE 87: 3-(1,1-difluoropropan-2-yl)-N-(2-fluoro-4-methyl-5-(8-morpholinoimidazo[1,2-a]pyridin-6-yl)phenyl)pyrrolidine-1-carboxamide): The fractions (RT 20.27 min) were combined and concentrated to afford the title compound (16 mg, 9%) of undetermined absolute stereochemistry. MS ESI calculated for $C_{26}H_{30}F_3N_5O_2$[M+H]$^+$, 502.55, found 502.25; $^1$H NMR (400 MHz, DMSO-d$_6$) δ 8.11 (d, J=1.4 Hz, 1H), 7.91-7.85 (m, 2H), 7.50 (d, J=1.2 Hz, 1H), 7.43 (d, J=8.2 Hz, 1H), 7.17 (d, J=11.6 Hz, 1H), 6.33 (d, J=1.5 Hz, 1H), 6.06-5.98 (m, 1H), 3.80 (t, J=4.7 Hz, 4H), 3.69-3.48 (m, 6H), 3.28-3.26 (m, 1H), 3.01 (t, J=10.0 Hz, 1H), 2.25 (s, 3H), 2.20-1.86 (m, 3H), 1.71-1.61 (m, 1H), 0.96 (d, J=6.9 Hz, 3H).

PEAK 2 (EXAMPLE 88: 3-(1,1-difluoropropan-2-yl)-N-(2-fluoro-4-methyl-5-(8-morpholinoimidazo[1,2-a]pyridin-6-yl)phenyl)pyrrolidine-1-carboxamide): The fractions (RT 25.06 min) were combined and concentrated to afford the title compound (17.2 mg, 10%) of undetermined absolute stereochemistry. MS ESI calculated for $C_{26}H_{30}F_3N_5O_2$[M+H]$^+$, 502.55, found 502.25; $^1$H NMR (400 MHz, DMSO-d$_6$) δ 8.10 (d, J=1.4 Hz, 1H), 7.91-7.84 (m, 2H), 7.50 (d, J=1.1 Hz, 1H), 7.44 (d, J=8.2 Hz, 1H), 7.17 (d, J=11.6 Hz, 1H), 6.33 (s, 1H), 6.25-5.84 (m, 1H), 3.80 (t, J=4.6 Hz, 4H), 3.70-3.51 (m, 6H), 3.26 (dd, J=11.6, 8.1 Hz, 1H), 3.01 (t, J=10.1 Hz, 1H), 2.25 (s, 3H), 2.17-2.15 (m, 1H), 2.12-1.88 (m, 2H), 1.71-1.62 (m, 1H), 0.96 (d, J=6.9 Hz, 3H).

The solid was further purified by Prep-Chiral-HPLC with the following conditions: Column: CHIRAL ART Cellulose-SC, 2×25 cm, 5 m; Mobile Phase A: Hex (0.5% 2 M NH$_3$-MeOH)--HPLC, Mobile Phase B: MeOH: DCM=1:1--HPLC; Flow rate: 20 mL/min; Gradient: 30% B to 30% B in 17 min; Wave Length: 254/220 nm; RT1: 14.45 min; RT2: 16.30 min; Sample Solvent: MeOH: DCM=1:1--HPLC; Injection Volume: 0.5 mL.

PEAK 3 (EXAMPLE 89: 3-(1,1-difluoropropan-2-yl)-N-(2-fluoro-4-methyl-5-(8-morpholinoimidazo[1,2-a]pyridin-6-yl)phenyl)pyrrolidine-1-carboxamide): The fractions (14.45 min) were combined and concentrated to afford the title compound (14.6 mg, 8%) of undetermined absolute stereochemistry. MS ESI calculated for $C_{26}H_{30}F_3N_5O_2$[M+H]$^+$, 502.55, found 502.25; $^1$H NMR (400 MHz, DMSO-d$_6$) δ 8.11 (d, J=1.4 Hz, 1H), 7.91-7.82 (m, 2H), 7.50 (d, J=1.2 Hz, 1H), 7.45 (d, J=8.2 Hz, 1H), 7.16 (d, J=11.6 Hz, 1H), 6.33 (d, J=1.5 Hz, 1H), 5.99-5.92 (m, 1H), 3.80 (t, J=4.6 Hz, 4H), 3.67 (t, J=8.9 Hz, 1H), 3.53 (dd, J=10.1, 6.2 Hz, 5H), 3.28-3.19 (m, 1H), 3.05-3.03 (m, 1H), 2.25 (s, 3H), 2.20-1.86 (m, 3H), 1.60-1.52 (m, 1H), 0.99 (d, J=6.9 Hz, 3H).

PEAK 4 (EXAMPLE 90: 3-(1,1-difluoropropan-2-yl)-N-(2-fluoro-4-methyl-5-(8-morpholinoimidazo[1,2-a]pyridin-6-yl)phenyl)pyrrolidine-1-carboxamide): The fractions (RT 16.30 min) were combined and concentrated to afford the title compound (11.8 mg, 6%) as a white solid of undetermined absolute stereochemistry. MS ESI calculated for $C_{26}H_{30}F_3N_5O_2$[M+H]$^+$, 502.55, found 502.25; $^1$H NMR (400 MHz, DMSO-d$_6$) δ 8.10 (d, J=1.4 Hz, 1H), 7.88 (d, J=1.2 Hz, 1H), 7.83 (s, 1H), 7.50 (d, J=1.2 Hz, 1H), 7.45 (d, J=8.2 Hz, 1H), 7.16 (d, J=11.6 Hz, 1H), 6.33 (d, J=1.5 Hz, 1H), 6.25-5.84 (m, 1H), 3.83-3.76 (m, 4H), 3.68-3.66 (m, 1H), 3.56-3.52 (m, 5H), 3.25-3.23 (m, 1H), 3.05-3.03 (m, 1H), 2.24 (s, 3H), 2.14-2.12 (m, 1H), 2.09-1.82 (m, 2H), 1.71-1.62 (m, 1H), 0.99 (d, J=6.9 Hz, 3H).

Example 91 and 92: 3-(tert-Butyl)-3-fluoro-N-(2-fluoro-4-methyl-5-(8-morpholinoimidazo[1,2-a]pyridin-6-yl)phenyl)pyrrolidine-1-carboxamide

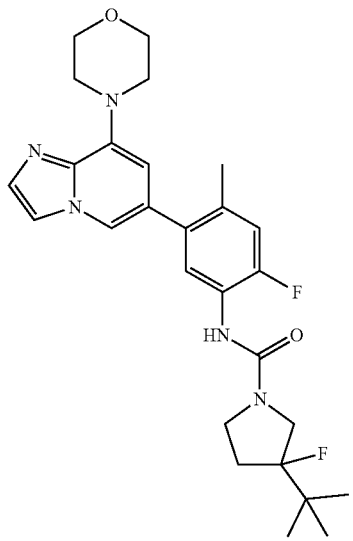 [SMILES: Cc1cc(F)c(NC(=O)N2CCC(F)(C(C)(C)C)C2)cc1-c1cc(N2CCOCC2)c2nccn2c1]

STEP 1: To a stirred solution of tert-butyl 3-oxopyrrolidine-1-carboxylate (3 g, 16.20 mmol) in THF (30 mL) was added tert-butyllithium (14.33 mL, 18.63 mmol, 1.3 M in THF) dropwise at -78° C. under nitrogen atmosphere. The reaction mixture was stirred for 2 h at –78° C. under nitrogen atmosphere. The resulting mixture was quenched by the addition of sat. NH$_4$Cl (aq.) (300 mL) at room temperature. The resulting mixture was extracted with EtOAc (3×300 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EA (2/1). The fractions containing the desired product were combined and concentrated to afford tert-butyl 3-tert-butyl-3-hydroxypyrrolidine-1-carboxylate (1.3 g, 16%) as a colorless oil. MS ESI calculated for C$_{13}$H$_{25}$NO$_3$ [M+H]$^+$, 24418, found 244.15; $^1$H NMR (400 MHz, Chloroform-d) δ 3.81-3.77 (m, 2H), 3.59-3.46 (m, 2H), 2.07-1.98 (m, 1H), 1.75-1.64 (m, 1H), 1.49 (s, 9H), 1.03 (s, 9H).

Step 2: To a stirred solution of tert-butyl 3-tert-butyl-3-hydroxypyrrolidine-1-carboxylate (1 g, 4.11 mmol) in DCM (40 mL) was added DAST (3.31 g, 20.55 mmol) in DCM (40 mL) dropwise at 0° C. under nitrogen atmosphere. The reaction mixture was stirred for 1 h at room temperature under nitrogen atmosphere. The resulting mixture was quenched by the addition of sat. NaHCO$_3$ (aq.) (200 mL) at 0° C. The resulting mixture was extracted with EtOAc (3×300 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EA (2/1). The fractions containing the desired product were combined and concentrated to afford tert-butyl 3-tert-butyl-3-fluoropyrrolidine-1-carboxylate (560 mg, crude) as a colorless oil. MS ESI calculated for C$_{13}$H$_{24}$FNO$_2$ [M+H]$^+$, 246.18, found 246.15.

Step 3: To a stirred solution of tert-butyl 3-tert-butyl-3-fluoropyrrolidine-1-carboxylate (560 mg, 2.283 mmol) in DCM (6 mL) was added HCl (gas) (6 mL, 2 M in EtOAc). The reaction mixture was stirred for 16 at room temperature under nitrogen atmosphere. The resulting mixture was concentrated under reduced pressure to afford 3-tert-butyl-3-fluoropyrrolidine HCl salt (530 mg, crude) as an off-white solid. MS ESI calculated for C$_8$H$_{16}$FN [M+H]$^+$, 182.10, found 182.25.

Step 4: To a stirred solution of 2-fluoro-4-methyl-5-[8-(morpholin-4-yl)imidazo[1,2-a]pyridin-6-yl]aniline (300 mg, 0.92 mmol) and DIEA (594 mg, 4.60 mmol) in THF (18 mL) was added Triphosgene (109 mg, 0.37 mmol) in THF (2 mL) dropwise at room temperature under nitrogen atmosphere. The reaction mixture was stirred for 30 min at room temperature under nitrogen atmosphere. To the above mixture was added 3-tert-butyl-3-fluoropyrrolidine HCl salt (250 mg, 1.38 mmol) in THF (2 mL) dropwise at room temperature. The resulting mixture was stirred for additional 2 h at room temperature. The reaction mixture was quenched by the addition of MeOH (10 mL) and concentrated under reduced pressure. The residue was purified by Prep-HPLC to afford 3-tert-butyl-3-fluoro-N-{2-fluoro-4-methyl-5-[8-(morpholin-4-yl)imidazo[1,2-a]pyridin-6-yl]phenyl}pyrrolidine-1-carboxamide (40 mg, 6%) as an off-white solid. MS ESI calculated for C$_{27}$H$_{33}$F$_2$N$_5$O$_2$ [M+H]$^+$, 498.26, found 498.25.

Step 5: The 3-tert-Butyl-3-fluoro-N-{2-fluoro-4-methyl-5-[8-(morpholin-4-yl)imidazo[1,2-a]pyridin-6-yl]phenyl}pyrrolidine-1-carboxamide (40 mg, 0.08 mmol) was purified by Chiral-Prep-HPLC with the following conditions: Column: CHIRAL ART Cellulose-SB, 2×25 cm, 5 m; Mobile Phase A: Hex (0.5% 2 M NH$_3$-MeOH)--HPLC, Mobile Phase B: IPA: DCM=1: 1--HPLC; Flow rate: 20 mL/min; Gradient: 40% B to 40% B in 7 min; Wave Length: 254/220 nm; RT1: 4.42 min; RT2: 6.49 min; Sample Solvent: MeOH: DCM=1: 1--HPLC; Injection Volume: 0.8 mL.

PEAK 1 (EXAMPLE 91: 3-(tert-Butyl)-3-fluoro-N-(2-fluoro-4-methyl-5-(8-morpholinoimidazo[1,2-a]pyridin-6-yl)phenyl)pyrrolidine-1-carboxamide): The fractions (RT 4.42 min) were combined and concentrated to afford the title compound (12.3 mg, 27%) as an off-white solid of undetermined absolute stereochemistry. MS ESI calculated for C$_{27}$H$_{33}$F$_2$N$_5$O$_2$ [M+H]$^+$, 498.26, found 498.20; $^1$H NMR (400 MHz, Chloroform-d) δ 8.12 (d, J=8.0 Hz, 1H), 7.77 (d, J=1.6 Hz, 1H), 7.63 (s, 1H), 7.54 (d, J=0.8 Hz, 1H), 7.02 (d, J=11.6 Hz, 1H), 6.42-6.36 (m, 2H), 4.02-4.00 (m, 4H), 3.75-3.60 (m, 4H), 3.56-3.52 (m, 4H), 2.25-2.12 (m, 5H), 1.09 (s, 9H).

PEAK 2 (EXAMPLE 92: 3-(tert-Butyl)-3-fluoro-N-(2-fluoro-4-methyl-5-(8-morpholinoimidazo[1,2-a]pyridin-6-yl)phenyl)pyrrolidine-1-carboxamide): The fractions (RT 6.49 min) were combined and concentrated to afford the title compound (11.5 mg, 29%) as an off-white solid of undetermined absolute stereochemistry. MS ESI calculated for C$_{27}$H$_{33}$F$_2$N$_5$O$_2$ [M+H]$^+$, 498.26, found 498.25; $^1$H NMR (400 MHz, Chloroform-d) δ 8.13 (d, J=8.4 Hz, 1H), 7.77 (d, J=1.2 Hz, 1H), 7.64 (s, 1H), 7.54 (d, J=1.2 Hz, 1H), 7.02 (d, J=11.6 Hz, 1H), 6.45 (s, 1H), 6.37 (d, J=2.4 Hz, 1H), 4.03-4.00 (m, 4H), 3.72-3.61 (m, 4H), 3.56-3.53 (m, 4H), 2.28-2.12 (m, 5H), 1.09 (s, 9H).

Example 95: 2-Tert-butyl-5-fluoro-N-{4-methyl-3-[8-(morpholin-4-yl)imidazo[1,2-a]pyridin-6-yl]phenyl}pyridine-4-carboxamide

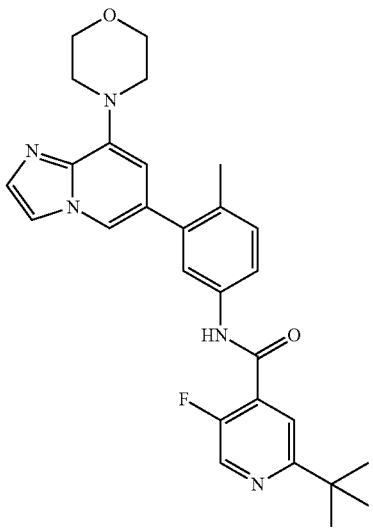 [SMILES: Cc1ccc(NC(=O)c2cc(C(C)(C)C)ncc2F)cc1-c1cc(N2CCOCC2)c2nccn2c1]

STEP 1: To a stirred mixture of methyl 3-fluoropyridine-4-carboxylate (4 g, 25.79 mmol) in DCM (50 mL) was added m-CPBA (6.67 g, 38.68 mmol). The reaction mixture was stirred for 16 h at room temperature. The resulting mixture was quenched with saturated aqueous NaHCO$_3$ (200 mL) and extracted with EtOAc (3×200 mL). The combined organic layers were washed with saturated brine (100 mL), dried over anhydrous Na$_2$SO$_4$. After filtration, the filtrate was concentrated under reduced pressure. The residue was purified by silica gel column chromatography, eluted with PE/EtOAc/EtOH (4/3/1). The fractions containing the desired product were combined and concentrated to afford 3-fluoro-4-(methoxycarbonyl)pyridin-1-ium-1-olate (4.3 g, 97%) as an off-white solid. MS ESI calculated for C$_7$H$_6$FNO$_3$ [M+H]$^+$, 172.03, found 172.15; $^1$H NMR (400 MHz, CDCl$_3$) δ 8.18-8.16 (m, 1H), 8.14-8.08 (m, 1H), 7.87-7.85 (m, 1H), 3.97 (s, 3H).

Step 2: To a stirred mixture of 3-fluoro-4-(methoxycarbonyl)pyridin-1-ium-1-olate (1 g, 5.84 mmol) [Ir(dtbbpy)(ppy)$_2$][PF$_6$] (0.05 g, 0.06 mmol) in ACN (12 mL) was added 2,2-dimethylpropanoyl chloride (1.55 g, 12.86 mmol). The reaction mixture was stirred for 15 min at room temperature under nitrogen atmosphere. The reaction mixture was stirred and irradiated with a blue LED lamp (7 cm away, with cooling fan to keep the reaction temperature at 25° C.) for 16 h. The resulting mixture was quenched with saturated aqueous NaHCO$_3$ (100 mL) and extracted with DCM (3×100 mL). The combined organic layers were washed with brine (100 mL), dried over anhydrous Na$_2$SO$_4$. After filtration, the filtrate was concentrated under reduced pressure. The residue was purified by silica gel column chromatography, eluted with PE/EtOAc/EtOH (1/1). The fractions containing the desired product were combined and concentrated to afford the mixture of methyl 2-tert-butyl-5-fluoropyridine-4-carboxylate and methyl 2-tert-butyl-3-fluoropyridine-4-carboxylate as a light-yellow oil. C$_{11}$H$_{14}$FNO$_2$ [M+H]$^+$, 212.03, found 212.15.

Step 3: To a stirred mixture of mixture of methyl 2-tert-butyl-5-fluoropyridine-4-carboxylate (300 mg, 1.42 mmol) and methyl 2-tert-butyl-3-fluoropyridine-4-carboxylate (mixture) in MeOH (1 mL) and THF (1 mL) was added LiOH H$_2$O (178.78 mg, 4.26 mmol) in H$_2$O (1 mL). The reaction mixture was stirred for 2 h at room temperature. The resulting mixture was concentrated under reduced pressure. The resulting mixture was acidified to pH 4 with HCl (aq.). The resulting mixture was extracted with EtOAc (3×30 mL). The combined organic layers were washed with brine (20 mL), dried over anhydrous Na$_2$SO$_4$. After filtration, the filtrate was concentrated under reduced pressure to afford the mixture of 2-tert-butyl-5-fluoropyridine-4-carboxylic acid and 2-tert-butyl-3-fluoropyridine-4-carboxylic acid (160 mg, crude) as a light-yellow solid. MS ESI calculated for C$_{10}$H$_{12}$FNO$_2$ [M+H]$^+$, 198.09, found 198.15.

Step 4: To a stirred solution of 2-tert-butyl-5-fluoropyridine-4-carboxylic acid (41.57 mg, 0.211 mmol) in T$_3$P (0.5 mL) was stirred for 15 min at room temperature under nitrogen atmosphere. To the above mixture was added the solution of 4-methyl-3-[8-(morpholin-4-yl)imidazo[1,2-a]pyridin-6-yl]aniline (50 mg, 0.162 mmol) in Pyridine (0.5 mL) at room temperature. The reaction mixture was stirred for 2 h at room temperature. The resulting mixture was concentrated under reduced pressure. The residue was purified by silica gel column chromatography, eluted with PE/EA (1/1) to afford the crude product. The crude product was purified by Prep-Chiral-SFC with the following conditions: Column: DAICEL DC Pak P4VP, 3×25 cm, 5 m; Mobile Phase A: CO$_2$, Mobile Phase B: MeOH (0.1% 2 M NH$_3$-MEOH); Flow rate: 75 mL/min; Gradient: isocratic 25% B; Column Temperature: 35° C.; Back Pressure: 100 bar; Wave Length: 254 nm; RT1: 4.58 min; RT2: 5.18 min; Sample Solvent: MeOH--HPLC; Injection Volume: 2 mL.

PEAK 2 (5.18 min): The fractions were combined and concentrated to afford the title compound (7.4 mg, 9%) as a white solid. MS ESI calculated for C$_{28}$H$_{30}$FN$_5$O$_2$[M+H]$^+$, 488.24, found 488.25; $^1$H NMR (400 MHz, DMSO-d$_6$) δ 10.68 (s, 1H), 8.65 (s, 1H), 8.16 (d, J=1.4 Hz, 1H), 7.91 (d, J=1.2 Hz, 1H), 7.70-7.60 (m, 3H), 7.51 (d, J=1.2 Hz, 1H), 7.32 (d, J=8.3 Hz, 1H), 6.37 (d, J=1.5 Hz, 1H), 3.81 (t, J=4.6 Hz, 4H), 3.55 (t, J=4.6 Hz, 4H), 2.27 (s, 3H), 1.34 (s, 9H).

Example 98: 1-(tert-butyl)-N-(4-chloro-2-fluoro-5-(8-morpholinoimidazo[1,2-a]pyridin-6-yl)phenyl)-5-fluoro-1H-pyrazole-4-carboxamide

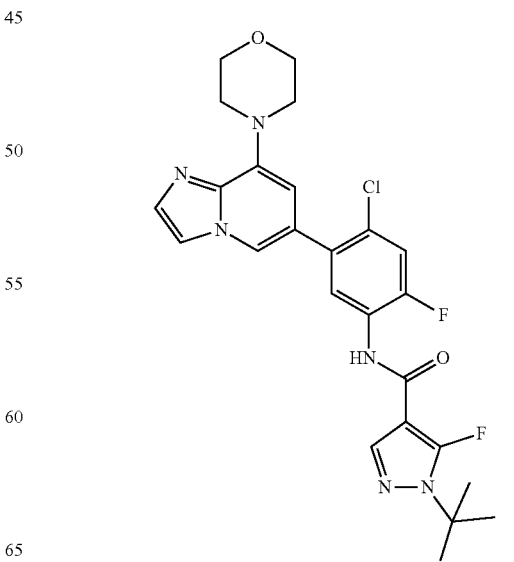

Step 1: To a stirred solution of 4-{6-chloroimidazo[1,2-a]pyridin-8-yl}morpholine (3 g, 12.62 mmol), bis(pinacolato)diboron (4.81 g, 18.93 mmol) and KOAc (3.72 g, 37.86 mmol) in dioxane (30 mL) was added 2 nd Generation XPhos Precatalyst (0.99 g, 1.26 mmol) at room temperature. The reaction mixture was degassed with nitrogen for three times and stirred for 2 h at 100° C. The resulting mixture was filtered, the filter cake was washed with EtOAc (3×100 mL). The filtrate was concentrated under reduced pressureto afford 4-[6-(4,4,5,5-tetramethyl-1,3,2-dioxaborolan-2-yl) imidazo[1,2-a]pyridin-8-yl]morpholine (4 g, crude) as a black oil. MS ESI calculated for $C_{17}H_{24}BN_3O_3$[M+H]$^+$, 330.19, found 329.85.

Step 2: To a stirred solution of 5-bromo-4-chloro-2-fluoroaniline (300 mg, 1.33 mmol), Pd(PPh$_3$)$_2$C$_{12}$ (93.81 mg, 0.13 mmol) and Na$_2$CO$_3$ (424.97 mg, 4.01 mmol) in dioxane (3 mL) and H$_2$O (0.6 mL) was added 4-[6-(4,4,5,5-tetramethyl-1,3,2-dioxaborolan-2-yl)imidazo[1,2-a]pyridin-8-yl]morpholine (1.32 g, 2.00 mmol, 50%) in portions at room temperature. The reaction mixture was degassed with nitrogen for three times and stirred for 1 h at 80° C. The resulting mixture was filtered, the filter cake was washed with EtOAc (3×100 mL). The filtrate was concentrated under reduced pressure. The residue was purified by silica gel column chromatography, eluted with PE/EA/EtOH (8/3/1). The fractions desired product were combined and concentrated to afford 4-chloro-2-fluoro-5-[8-(morpholin-4-yl)imidazo[1,2-a]pyridin-6-yl]aniline (328 mg, 70%) as a yellow solid. MS ESI calculated for $C_{17}H_{16}C_1FN_4O$ [M+H]$^+$, 347.10, 349.10, found 347.10, 349.10; $^1$H NMR (400 MHz, Chloroform-d) δ 7.82 (d, J=1.5 Hz, 1H), 7.62 (d, J=1.3 Hz, 1H), 7.56 (d, J=1.3 Hz, 1H), 7.17 (d, J=10.6 Hz, 1H), 6.81 (d, J=9.3 Hz, 1H), 6.47 (d, J=1.5 Hz, 1H), 4.05-3.97 (m, 4H), 3.63-3.50 (m, 4H).

Step 3: To a stirred mixture of 4-chloro-2-fluoro-5-[8-(morpholin-4-yl)imidazo[1,2-a]pyridin-6-yl]aniline (80 mg, 0.23 mmol) and bis(lambda2-cobalt(2+)) octakis(methanidylidyneoxidanium) (23.59 mg, 0.07 mmol) in dioxane (1 mL) were added TEA (69.69 mg, 0.69 mmol) and 4-bromo-1-(tert-butyl)-5-fluoro-1H-pyrazole (101.66 mg, 0.46 mmol) at room temperature. The reaction mixture was degassed with nitrogen for three times and stirred for 16 h at 90° C. The resulting mixture was concentrated under reduced pressure. The residue mixture was purified by reversed-phase flash chromatography with the following conditions: column, C18 silica gel; mobile phase, MeCN in Water (Plus 10 mmol/L NH$_4$HCO$_3$), 10% to 50% gradient in 10 min; detector, UV 254 nm. The fractions containing the desired product was combined and concentrated to afford crude product. The crude product (35 mg) was purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 41% B to 51% B in 10 min, 51% B; Wavelength: 220/254 nm; RT1: 7.88-8.78 min. The fractions were combined and concentrated to afford the title compound (16.8 mg, 8%) as an off-white solid. MS ESI calculated for $C_{25}H_{25}C_1F_2N_6O_2$ [M+H]$^+$, 515.17, 517.17, found 515.20, 517.20; $^1$H NMR (400 MHz, Chloroform-d) δ 8.58 (d, J=8.4 Hz, 1H), 7.90 (d, J=1.4 Hz, 1H), 7.85 (d, J=2.6 Hz, 1H), 7.72 (s, 1H), 7.64 (s, 1H), 7.58 (d, J=1.3 Hz, 1H), 7.34 (d, J=10.5 Hz, 1H), 6.54 (s, 1H), 4.05-3.98 (m, 4H), 3.59 (t, J=4.7 Hz, 4H), 1.68 (s, 9H).

Example 99: (3S)-N-{2,4-difluoro-5-[8-(morpholin-4-yl)imidazo[1,2-a]pyridin-6-yl]phenyl}-3-(2,2,2-trifluoroethyl)pyrrolidine-1-carboxamide

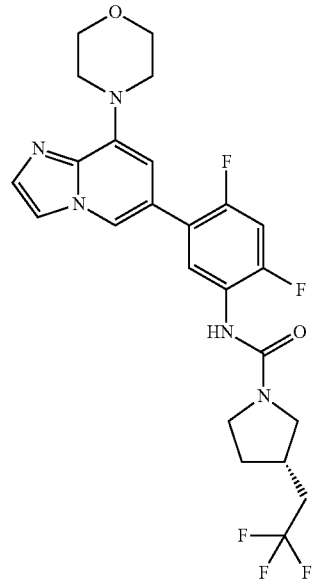 [SMILES: O=C(Nc1cc(-c2cc(N3CCOCC3)c3nccn3c2)c(F)cc1F)N1CC[C@@H](CC(F)(F)F)C1]

Step 1: To a stirred mixture of 5-bromo-2,4-difluoroaniline (2 g, 9.62 mmol), bis(pinacolato)diboron (2.93 g, 11.54 mmol) and Potassium Acetate (2.83 g, 28.85 mmol) in dioxane (20 mL) was added 1,1'-Bis(diphenylphosphino) ferrocene-palladium (II)dichloride dichloromethane complex (0.39 g, 0.48 mmol) in portions at room temperature. The reaction mixture was degassed with nitrogen for three times and stirred for additional 16 h at 100° C. The resulting mixture was concentrated under reduced pressure. The residue was purified by silica gel column chromatography, eluted with PE/EA (3/1). The fractions containing the desired product were combined and concentrated to afford 2,4-difluoro-5-(4,4,5,5-tetramethyl-1,3,2-dioxaborolan-2-yl) aniline (1.4 g, 57%) as a light-yellow oil. MS ESI calculated for $C_{12}H_{16}BF_2NO_2$ [M+H]$^+$, 256.12, found 256.15.

Step 2: To a stirred mixture of 2,4-difluoro-5-(4,4,5,5-tetramethyl-1,3,2-dioxaborolan-2-yl)aniline (800 mg, 3.14 mmol), 4-{6-chloroimidazo[1,2-a]pyridin-8-yl}morpholine (0.75 g, 3.14 mmol) and Potassium phosphate tribasic (1.33 g, 6.27 mmol) in Tetrahydrofuran (8 mL) and water (0.8 mL) was added 2nd Generation XPhos Pd (0.25 g, 0.31 mmol) in portions at room temperature. The reaction mixture was degassed with nitrogen for three times and stirred for 2 h at 80° C. The resulting mixture was concentrated under reduced pressure. The residue was purified by silica gel column chromatography, eluted with PE/EA/EtOH (1/3/1). The fractions containing the desired product were combined and concentrated to afford 2,4-difluoro-5-[8-(morpholin-4-yl)imidazo[1,2-a]pyridin-6-yl]aniline (800 mg, 77%) as a brown solid. MS ESI calculated for $C_{17}H_{16}F_2N_4O$ [M+H]$^+$, 331.13, found 331.10.

Step 3: To a stirred mixture of 2,4-difluoro-5-[8-(morpholin-4-yl)imidazo[1,2-a]pyridin-6-yl]aniline (100 mg, 0.30 mmol) and triphosgene (35.93 mg, 0.12 mmol) in Tetrahydrofuran (5.5 mL) was added N,N-Diisopropylethylamine (195.63 mg, 1.52 mmol) dropwise at room temperature under nitrogen atmosphere. The reaction mixture was stirred for additional 30 min at room temperature. To the above mixture was added (3S)-3-(2,2,2-trifluoroethyl) pyrrolidine HCl salt (57.40 mg, 0.30 mmol) in Tetrahydrofuran (1.5 mL) dropwise at room temperature. The reaction mixture was stirred for additional 2 h at room temperature. The residue was purified by reversed-phase flash chromatography with the following conditions: column, C18 silica gel; mobile phase, MeCN in water (Plus 10 mmol/L $NH_4HCO_3$), 50% to 80% gradient in 20 min; detector, UV 254 nm. The fractions containing the desired product were combined and concentrated to afford the title compound (52.8 mg, 34%) as a white solid. MS ESI calculated for $C_{24}H_{24}F_5N_5O_2[M+H]^+$, 510.19, found 510.30; $^1$H NMR (400 MHz, DMSO-$d_6$) δ 8.35 (d, J=1.7 Hz, 1H), 8.05 (s, 1H), 7.95 (d, J=1.2 Hz, 1H), 7.68-7.66 (m, 1H), 7.52 (d, J=1.2 Hz, 1H), 7.41-7.39 (m, 1H), 6.50 (s, 1H), 3.81 (t, J=4.7 Hz, 4H), 3.73-3.64 (m, 1H), 3.58-3.55 (m, 5H), 3.34-3.28 (m, 1H), 3.07-3.02 (m, 1H), 2.48-2.43 (m, 3H), 2.10-1.99 (m, 1H), 1.70-1.62 (m, 1H).

Example 103: 1-(tert-Butyl)-5-fluoro-N-(2-fluoro-4-methyl-5-(8-morpholinoimidazo[1,2-a]pyridin-6-yl)phenyl)-1H-pyrazole-4-carboxamide

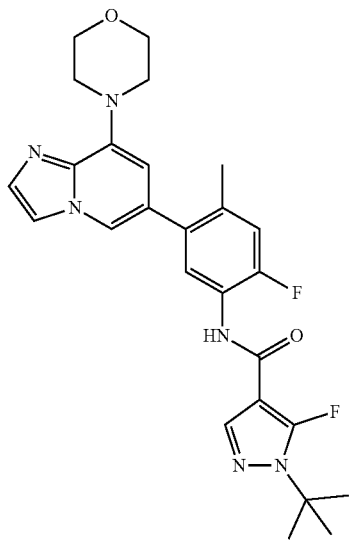

Step 1: To a stirred solution of ethyl (2E)-2-cyano-3-ethoxyprop-2-enoate (7 g, 41.37 mmol) and EtONa (2.67 g, 39.30 mmol) in EtOH (50 mL) was added tert-butylhydrazine HCl salt (5.16 g, 41.37 mmol) in portions at room temperature under nitrogen atmosphere. The reaction mixture was stirred for 16 h at 70° C. under nitrogen atmosphere. The resulting mixture was concentrated under reduced pressure. The residue was purified by silica gel column chromatography, eluted with PE/EA (5/1). The fractions containing the desired product were combined and concentrated to afford ethyl 5-amino-1-tert-butylpyrazole-4-carboxylate (8.4 g, crude) as a yellow oil. MS ESI calculated for $C_{10}H_{17}N_3O_2$ [M+H]$^+$, 212.13, found 212.15.

Step 2: To a stirred solution of ethyl 5-amino-1-tert-butylpyrazole-4-carboxylate (500 mg, 2.36 mmol) and $CuBr_2$ (634.33 mg, 2.84 mmol) in ACN (5 mL) was added t-BuONO (317.27 mg, 3.07 mmol) in portions at room temperature under nitrogen atmosphere. The reaction mixture was stirred for 2 h at 45° C. under nitrogen atmosphere. The resulting mixture was quenched with sat. $NH_4Cl$ (aq.) and extracted with EtOAc (3×50 mL). The combined organic layers were washed with brine (2×50 mL), dried over anhydrous $Na_2SO_4$. After filtration, the filtrate was concentrated under reduced pressure. The resulting mixture was concentrated under reduced pressure. The residue was purified by silica gel column chromatography, eluted with PE/EA (1/1). The fractions containing the desired product were combined and concentrated to afford ethyl 5-bromo-1-tert-butylpyrazole-4-carboxylate (490 mg, 75%) as a white solid. MS ESI calculated for $C_{10}H_{15}BrN_2O_2[M+H]^+$, 275.03, 277.03, found 275.00, 277.00; $^1$H NMR (400 MHz, CDCl$_3$) δ 7.87 (s, 1H), 4.34-4.28 (m, 2H), 1.77 (s, 9H), 1.35 (t, J=7.1 Hz, 3H).

Step 3: To a stirred solution of ethyl 5-bromo-1-tert-butylpyrazole-4-carboxylate (200 mg, 0.90 mmol) in THF (4 mL) was added n-BuLi (0.99 mL, 0.99 mmol, 1 M in hexane) dropwise at -78° C. under nitrogen atmosphere. The reaction mixture was stirred for 30 min at -78° C. under nitrogen atmosphere. To the above mixture was added NFSI (427.91 mg, 1.35 mmol) at -78° C. The reaction mixture was stirred for 2 h at room temperature under nitrogen atmosphere. The resulting mixture was quenched with $NH_4Cl$ (aq.) and extracted with EtOAc (3×20 mL). The combined organic layers were washed with brine (2×30 mL), dried over anhydrous $Na_2SO_4$. After filtration, the filtrate was concentrated under reduced pressure. The residue was purified by silica gel column chromatography, eluted with PE/EA (1/1). The fractions containing the desired product were combined and concentrated to afford ethyl 1-tert-butyl-5-fluoropyrazole-4-carboxylate (80 mg, 41%) as an off-white oil. MS ESI calculated for $C_{10}H_{15}FN_2O_2[M+H]^+$, 215.11, found 215.10; $^1$H NMR (400 MHz, DMSO-$d_6$) δ 7.73 (d, J=2.5 Hz, 1H), 4.34-4.30 (m, 2H), 1.63 (s, 9H), 1.36 (t, J=7.1 Hz, 3H).

Step 4: To a stirred solution of 2-fluoro-4-methyl-5-[8-(morpholin-4-yl)imidazo[1,2-a]pyridin-6-yl]aniline (45.70 mg, 0.14 mmol) in LiHMDS (1 mL, 1 M in THF) was added ethyl 1-tert-butyl-5-fluoropyrazole-4-carboxylate (30 mg, 0.14 mmol) in THF (1 mL) dropwise at 0° C. under nitrogen atmosphere. The resulting mixture was stirred for 1 h at room temperature under nitrogen atmosphere. The resulting mixture was quenched by the addition of sat. $NH_4Cl$ (aq.) (15 mL) and extracted with EtOAc (2×20 mL). The combined organic layers were washed with brine (2×20 mL), dried over anhydrous $Na_2SO_4$. After filtration, the filtrate was concentrated under reduced pressure. The residue was purified by Prep-TLC, eluted with $CH_2Cl_2$/MeOH (10/1) to afford crude product (50 mg). The crude product (50 mg) was purified by Prep-HPLC with the following conditions: Column: XBridge Shield RP18 OBD Column, 19×250 mm, 10 m; Mobile Phase A: Water (Plus 10 mmol/L $NH_4HCO_3$), Mobile Phase B: ACN; Flow rate: 60 mL/min; Gradient: 20% B to 30% B in 8 min; Wavelength: 254/220 nm; RT1: 6.48 min. The fractions containing the desired product were combined and concentrated to afford title compound (22.3 mg, 32%) as a white solid. MS ESI calculated for $C_{26}H_{28}F_2N_6O_2[M+H]^+$, 495.22, found 495.20; $^1$H NMR (400 MHz, DMSO-$d_6$) δ 9.67 (s, 1H), 8.15 (d, J=1.4 Hz, 1H), 8.00 (d, J=2.5 Hz, 1H), 7.90 (d, J=1.2 Hz, 1H), 7.56-7.49 (m, 2H), 7.28 (d, J=11.5 Hz, 1H), 6.36 (d, J=1.5 Hz, 1H), 3.84 (t, J=4.7 Hz, 4H), 3.55 (t, J=4.7 Hz, 4H), 2.29 (s, 3H), 1.58 (d, J=1.4 Hz, 9H).

Example 110: 1-(tert-butyl)-N-(4-chloro-3-(8-morpholinoimidazo[1,2-a]pyridin-6-yl)phenyl)-5-fluoro-1H-pyrazole-4-carboxamide

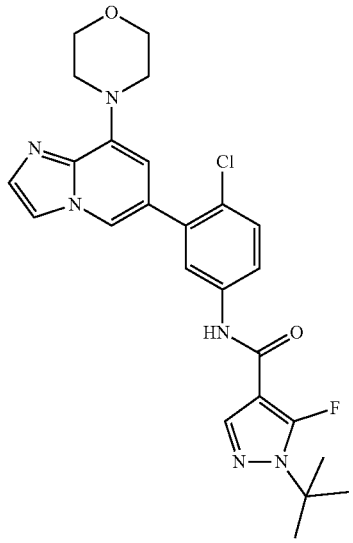

Step 1: To a stirred solution of 4-chloro-3-iodoaniline (1 g, 3.94 mmol), KOAc (801.49 mg, 7.88 mmol) and bis(pinacolato)diboron (1.50 g, 5.91 mmol) in DMF (10 mL) was added Pd(dppf)C$_{12}$ CH$_2$Cl$_2$ (160.69 mg, 0.19 mmol) in portions at room temperature under nitrogen atmosphere. The reaction mixture was stirred for 2 h at 120° C. under nitrogen atmosphere. The resulting mixture was diluted with water (50 mL) and extracted with EtOAc (3×100 mL). The combined organic layers were washed with brine (1×300 mL), dried over anhydrous Na$_2$SO$_4$. After filtration, the filtrate was concentrated under reduced pressure. The residue was purified by silica gel column chromatography, eluted with PE/EA (5/1). The fractions containing the desired product were combined and concentrated to afford 4-chloro-3-(4,4,5,5-tetramethyl-1,3,2-dioxaborolan-2-yl)aniline (1.56 g, crude) as a yellow oil. MS ESI calculated for C$_{12}$H$_{17}$BClNO2 [M+H]$^+$, 254.10, 256.10, found 254.10, 256.10.

Step 2: To a stirred solution of 4-{6-chloroimidazo[1,2-a]pyridin-8-yl}morpholine (500 mg, 2.10 mmol) and XPhos palladium(II) biphenyl-2-amine chloride (165.51 mg, 0.21 mmol) in K$_3$PO$_4$ (10 mL, 0.5 M) and THF (5 mL) was added 4-chloro-3-(4,4,5,5-tetramethyl-1,3,2-dioxaborolan-2-yl)aniline (533.32 mg, 2.10 mmol) in portions at room temperature. The reaction mixture was degassed with nitrogen for three times and stirred for 2 h at 40° C. The resulting mixture was diluted with water (40 mL) and extracted with EtOAc (3×50 mL). The combined organic layers were washed with brine (1×200 mL), dried over anhydrous Na$_2$SO$_4$. After filtration, the filtrate was concentrated under reduced pressure. The residue was purified by silica gel column chromatography, eluted with PE/EA (1/1). The fractions containing the desired product were combined and concentrated to afford 4-chloro-3-[8-(morpholin-4-yl)imidazo[1,2-a]pyridin-6-yl]aniline (433 mg, 62%) as a white solid. MS ESI calculated for C$_{17}$H$_{17}$ClN$_4$O [M+H]$^+$, 329.11, 331.11, found 329.05, 331.05; $^1$H NMR (400 MHz, CDCl$_3$) δ 7.86 (d, J=1.4 Hz, 1H), 7.62 (d, J=1.2 Hz, 1H), 7.57 (d, J=1.2 Hz, 1H), 7.27 (d, J=8.5 Hz, 1H), 6.74-6.63 (m, 2H), 6.52 (d, J=1.5 Hz, 1H), 4.00 (t, J=5.7 Hz, 4H), 3.62 (t, J=5.7 Hz, 4H).

Step 3: To a stirred mixture of 4-chloro-3-[8-(morpholin-4-yl)imidazo[1,2-a]pyridin-6-yl]aniline (100 mg, 0.30 mmol), bis(lambda2-cobalt(2+)) octakis(methanidylidyneoxidanium) (31.20 mg, 0.09 mmol) and Pd(dppf)Cl$_2$ CH$_2$Cl$_2$ (24.78 mg, 0.03 mmol) in dioxane (2 mL) was added TEA (92.33 mg, 0.91 mmol) and 4-bromo-1-(tert-butyl)-5-fluoro-1H-pyrazole (100.85 mg, 0.45 mmol) at room temperature. The reaction mixture was degassed with nitrogen for three times and stirred for 16 h at 90° C. The resulting mixture was concentrated under reduced pressure. The residue was purified by silica gel column chromatography, eluted with PE/EA (1/2) to afford the crude product. The crude product (100 mg) was purified by Prep-HPLC with the following conditions: Column: XSelect CSH Prep C$_{1s}$ OBD Column, 19×250 mm, 5 m; Mobile Phase A: water (Plus 10 mmol/L NH$_4$HCO$_3$), Mobile Phase B: ACN; Flow rate: 20 mL/min; Gradient: 52% B to 57% B in 8 min, 57% B; Wavelength: 254 nm; RT1: 9 min. The fractions containing the desired product were combined desired product were combined and concentrated to afford the title compound (38.5 mg, 24%) as a white solid. MS ESI calculated for C$_{25}$H$_{26}$C$_1$FN$_6$O2 [M+H]$^+$, 497.18 found 497.20; $^1$H NMR (400 MHz, DMSO-d$_6$) δ 10.02 (s, 1H), 8.28 (d, J=1.4 Hz, 1H), 8.03 (d, J=2.5 Hz, 1H), 7.95 (d, J=1.2 Hz, 1H), 7.85 (d, J=2.6 Hz, 1H), 7.77 (dd, J=8.8, 2.6 Hz, 1H), 7.59-7.51 (m, 2H), 6.46 (d, J=1.5 Hz, 1H), 3.81 (t, J=4.6 Hz, 4H), 3.55 (t, J=4.7 Hz, 4H), 1.57 (s, 9H).

Example 111: 1-tert-Butyl-5-fluoro-N-{2-fluoro-5-[3-fluoro-8-(morpholin-4-yl)imidazo[1,2-a]pyridin-6-yl]-4-methylphenyl}pyrazole-4-carboxamide

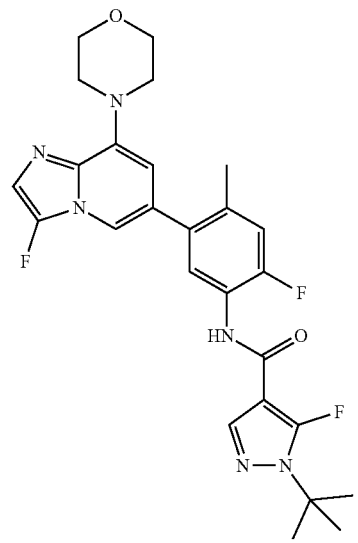

Step 1: To a stirred solution of 8-bromo-6-chloroimidazo[1,2-a]pyridine (10 g, 43.20 mmol) and NaH (1.90 g, 47.52 mmol, 60%) in THF (100 mL) was added Select fluor (15.30 g, 43.20 mmol) in portions at 0° C. under nitrogen atmosphere. The reaction mixture was stirred for 16 h at 60° C. under nitrogen atmosphere. The resulting mixture was diluted with NH$_4$Cl (20 mL) and extracted with EtOAc (3×50 mL). The combined organic layers were washed with brine (3×50 mL), dried over anhydrous Na₂SO₄. After filtration, the filtrate was concentrated under reduced pressure. The residue was purified by silica gel column chromatography, eluted with PE/EA (6/1). The fractions containing the desired product were combined and concentrated to afford 8-bromo-6-chloro-3-fluoroimidazo[1,2-a] pyridine (3.3 g, 30%) as a light-yellow solid. MS ESI calculated for C₇H₃BrClF2 [M+H]⁺, 248.92, found, 248.85.

Step 2: To a stirred solution of 8-bromo-6-chloro-3-fluoroimidazo[1,2-a] pyridine (300 mg, 1.21 mmol), morpholine (105.27 mg, 1.21 mmol) and K₃PO₄ (765 mg, 3.60 mmol) in dioxane (3 mL) were added Pd(OAc)₂ (27 mg, 0.12 mmol) and Dppf (199 mg, 0.36 mmol) in portions at room temperature. The reaction mixture was degassed with nitrogen for three times and stirred for 16 h at 80° C. under nitrogen atmosphere. The resulting mixture was diluted with water (30 mL). and extracted with EtOAc (3×30 mL). The combined organic layers were washed with brine (3×30 mL), dried over anhydrous Na₂SO₄. After filtration, the filtrate was concentrated under reduced pressure. The residue was purified by silica gel column chromatography, eluted with PE/EA (5/1). The fractions containing the desired product were combined and concentrated to afford 4-{6-chloro-3-fluoroimidazo[1,2-a] pyridin-8-yl}morpholine (200 mg, 65%) as an off-white solid. MS ESI calculated for CnHnClFN₃O [M+H]⁺, 256.68, found, 256.70.

Step 3: To a stirred mixture of 4-{6-chloro-3-fluoroimidazo[1,2-a]pyridin-8-yl}morpholine (200 mg, 0.78 mmol) and 2-fluoro-4-methyl-5-(4,4,5,5-tetramethyl-1,3,2-dioxaborolan-2-yl)aniline (256.54 mg, 0.86 mmol) in THF (5 mL) and H₂O (0.5 mL) were added 2nd Generation XPhos Precatalyst (61 mg, 0.07 mmol) and K₃PO₄ (332 mg, 1.56 mmol) at room temperature under nitrogen atmosphere. The mixture was allowed to cool down to room temperature. The resulting mixture was concentrated under reduced pressure. The residue was purified by silica gel column chromatography, eluted with PE/EA (5/1) to afford 2-fluoro-5-(3-fluoro-8-morpholinoimidazo[1,2-a]pyridin-6-yl)-4-methylaniline (190 mg, 71%) as a yellow solid. MS ESI calculated for C₁₈H₁₈F₂N₄O [M+H]⁺. 345.14, found 345.10.

Step 4: To a stirred solution of 2-fluoro-5-[3-fluoro-8-(morpholin-4-yl)imidazo[1,2-a]pyridin-6-yl]-4-methylaniline (80 mg, 0.23 mmol), bis(lambda2-cobalt(2+)) octakis(methanidylidyneoxidanium) (23.83 mg, 0.07 mmol) and Pd(dppf)C₁₂ CH₂Cl₂ (18.92 mg, 0.02 mmol) in dioxane (1 mL) were added TEA (139.38 mg, 1.38 mmol) and 4-bromo-1-(tert-butyl)-5-fluoro-1H-pyrazole (102.79 mg, 0.46 mmol) and at room temperature. The reaction mixture was degassed with nitrogen for three times and stirred for 16 h at 90° C. The resulting mixture was concentrated under reduced pressure. The residue was purified by silica gel column chromatography, eluted with PE/EA (1/1) to afford the crude product which was purified by Prep-HPLC with the following conditions: column: XBridge Prep OBD C18 Column, 30×150 mm, 5 m; Mobile Phase A: Water (Plus 10 mmol/L NH₄HCO₃), Mobile Phase B: ACN; Flow rate: 60 mL/min; Gradient: 47% B to 57% B in 10 min, 57% B; Wave Length: 220/254 nm; RT1: 8.73 min. The fractions containing the desired product were combined and concentrated to afford the title compound (7.2 mg, 6%). MS ESI calculated for C₂₆H₂₇F₃N₆O₂ [M+H]⁺513.21, found 513.30; ¹H NMR (400 MHz, DMSO-d₆) δ 9.69 (s, 1H), 8.00 (d, J=2.5 Hz, 1H), 7.78 (d, J=1.4 Hz, 1H), 7.55 (d, J=7.9 Hz, 1H), 7.34-7.24 (m, 2H), 6.36 (d, J=1.4 Hz, 1H), 3.83-3.77 (m, 4H), 3.57-3.42 (m, 4H), 2.30 (s, 3H), 1.58 (d, J=1.5 Hz, 9H).

Example 112: 2-Fluoro-4-methyl-5-[8-(morpholin-4-yl)imidazo[1,2-a]pyridin-6-yl]aniline

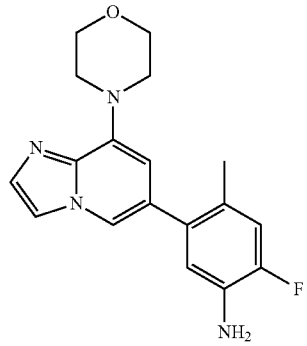 [SMILES: Cc1cc(F)c(N)cc1-c1cc(N2CCOCC2)c2nccn2c1]

Step 1: To a stirred mixture of 8-bromo-6-chloroimidazo[1,2-a] pyridine (1 g, 4.32 mmol), morpholine (0.38 g, 4.36 mmol) and Pd(OAc)₂ (0.10 g, 0.43 mmol) in dioxane (10 mL, 118.04 mmol) were added Dppf (0.72 g, 1.29 mmol) and K₃PO₄ (2.75 g, 12.96 mmol). The reaction mixture was degassed with nitrogen for three times and stirred for 3 h at 80° C. The resulting mixture was diluted with water (50 mL) and extracted with EtOAc (3×50 mL). The combined organic layers were washed with brine (2×80 mL), dried over anhydrous Na₂SO₄. After filtration, the filtrate was concentrated under reduced pressure. The residue was purified by silica gel column chromatography, eluted with PE/EA (1/1). The fractions containing the desired product were combined and concentrated to afford 4-{6-chloroimidazo[1,2-a]pyridin-8-yl}morpholine (1.52 g, 76%) as an off-white solid. MS ESI calculated for C₁₁H₁₂ClN₃O [M+H]⁺, 238.07, 240.07, found 238.10, 240.10; ¹H NMR (400 MHz, CDCl₃) δ 7.85 (d, J=1.6 Hz, 1H), 7.59 (d, J=1.6 Hz, 1H), 7.50 (d, J=1.2 Hz, 1H), 6.39 (d, J=1.6 Hz, 1H), 3.99 (t, J=4.8 Hz, 4H), 3.59 (t, J=4.8 Hz, 4H).

Step 2: To a stirred mixture of 4-{6-chloroimidazo[1,2-a]pyridin-8-yl}morpholine (180 mg, 0.76 mmol) and 2-fluoro-4-methyl-5-(4,4,5,5-tetramethyl-1,3,2-dioxaborolan-2-yl)aniline (190 mg, 0.76 mmol), K₃PO₄ (321 mg, 1.51 mmol) in THF (2 mL) and H₂O (0.2 mL) was added 2nd Generation XPhos Precatalyst (59 mg, 0.08 mmol) in portions at room temperature. The reaction mixture was degassed with nitrogen for three times and stirred for 16 h at 80° C. The resulting mixture was diluted with water (30 mL) and extracted with EtOAc (3×30 mL). The combined organic layers were washed with brine (2×30 mL), dried over anhydrous Na₂SO₄. After filtration, the filtrate was concentrated under reduced pressure. The residue was purified by reverse flash chromatography with the following conditions: column, C18 silica gel; mobile phase, MeCN in water (Plus 10 mmol/L NH₄HCO₃), 5% to 95% gradient in 25 min; detector, UV 254 nm. The fractions containing the desired product were combined and concentrated to afford 2-fluoro-4-methyl-5-[8-(morpholin-4-yl)imidazo[1,2-a]pyridin-6-yl]aniline (178 mg, 72%) as a white solid. MS ESI calculated for C₁₈H₁₉FN₄O [M+H]⁺, 327.15, found 327.15; ¹H NMR (400 MHz, DMSO-d₆) δ 8.07 (d, J=1.2 Hz, 1H), 7.88 (d, J=1.2 Hz, 1H), 7.49 (d, J=1.2 Hz, 1H), 6.95 (d, J=12.4 Hz, 1H), 6.72 (d, J=9.2 Hz, 1H), 6.31 (d, J=1.6 Hz, 1H), 5.01 (s, 2H), 3.81 (t, J=4.8 Hz, 4H), 3.53 (t, J=4.8 Hz, 4H), 2.12 (s, 3H).

Example 113 and 114: 2-(1,1-Difluoropropan-2-yl)-N-(2-fluoro-4-methyl-5-(8-morpholinoimidazo[1,2-a]pyridin-6-yl)phenyl)isonicotinamide

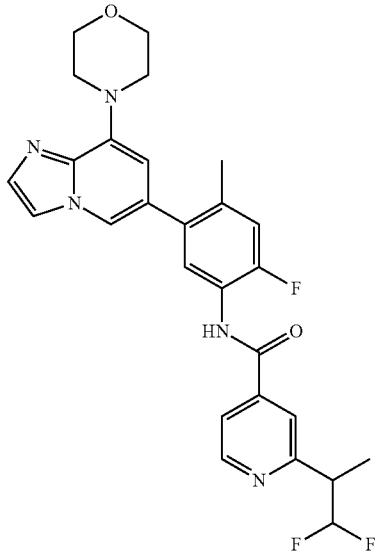 [SMILES: Cc1cc(F)c(NC(=O)c2ccnc(C(C)C(F)F)c2)cc1-c1cc(N2CCOCC2)c2nccn2c1]

Step 1: To a stirred solution of methyl 2-acetylpyridine-4-carboxylate (500 mg, 2.79 mmol) in DMF (6 mL) was added difluoro(triphenylphosphaniumyl)acetate (1.99 g, 5.58 mmol) at room temperature under nitrogen atmosphere. The reaction mixture was stirred for 3 h at 60° C. under nitrogen atmosphere. The resulting mixture was diluted with water (80 mL) and extracted with ethyl acetate (3×60 mL). The combined organic layers were washed with brine (50 mL), dried over anhydrous sodium sulfate. After filtration, the filtrate was concentrated under reduced pressure. The residue was purified by silica gel column chromatography, eluted with PE/EA (1/1) to afford the crude product. The crude product was further purified by reverse flash chromatography with the following conditions: column, C18 silica gel; mobile phase, acetonitrile in water, 30% to 70% gradient in 15 min; detector, UV 254/210 nm. The fractions containing the desired product were combined and concentrated to afford methyl 2-(1,1-difluoroprop-1-en-2-yl)pyridine-4-carboxylate (190 mg, 32%) as a pink oil. MS ESI calculated for $C_{10}H_9F_2NO_2$ [M+H]$^+$, 214.06, found 213.95; $^1$H NMR (400 MHz, CDCl$_3$) δ 8.79 (dd, J=5.2, 1.2 Hz, 1H), 8.07-8.05 (m, 1H), 7.73 (dd, J=5.2, 1.6 Hz, 1H), 3.99 (s, 3H), 2.12 (t, J=3.6 Hz, 3H).

Step 2: To a stirred solution of methyl 2-(1,1-difluoro-prop-1-en-2-yl)pyridine-4-carboxylate (170 mg, 0.80 mmol) in THF (3 mL) was added Pd/C (170 mg, 1.59 mmol, 10%) under nitrogen atmosphere. The reaction mixture was degassed with hydrogen atmosphere for three times and stirred for 5 h under hydrogen atmosphere. The resulting mixture was filtered, the filter cake was washed with MeOH (3×10 mL). The filtrate was concentrated under reduced pressure. The residue was purified by reverse flash chromatography with the following conditions: column, C18 silica gel; mobile phase, acetonitrile in water, 20% to 80% gradient in 20 min; detector, UV 210/278 nm. The fractions containing the desired product were combined and concentrated to afford methyl 2-(1,1-difluoropropan-2-yl)pyridine-4-carboxylate (105 mg, 41%) (67.7% Purity) as a light yellow oil. MS ESI calculated for $C_{10}HnF_2NO_2$ [M+H]$^+$, 216.08, found 216.05; $^1$H NMR (400 MHz, CDCl$_3$) δ 8.76 (dd, J=4.8, 0.8 Hz, 1H), 7.81 (t, J=1.2 Hz, 1H), 7.78 (dd, J=4.8, 1.6 Hz, 1H), 6.27-5.98 (m, 1H), 3.99 (s, 3H), 1.48 (d, J=7.2 Hz, 3H).

Step 3: To a stirred solution of methyl 2-(1,1-difluoropropan-2-yl)pyridine-4-carboxylate (105 mg, 0.49 mmol) in MeOH (1 mL), H$_2$O (1 mL) and THF (1 mL) was added LiOH H$_2$O (61 mg, 1.47 mmol) in portions at 0° C. The reaction mixture was stirred for 2 h at room temperature. The resulting mixture was acidified to pH 4 with HCl (aq.) and concentrated under reduced pressure. The residue was purified by reverse flash chromatography with the following conditions: column, C18 silica gel; mobile phase, acetonitrile in water, 5% to 95% gradient in 20 min; detector, UV 200/273 nm. The fractions containing the desired product were combined and concentrated to afford 2-(1,1-difluoropropan-2-yl)pyridine-4-carboxylic acid (80 mg, 73%) (89% Purity) as an off-white solid. MS ESI calculated for $C_9H_9F_2NO_2$ [M+H]$^+$, 202.06, found 202.10; $^1$H NMR (400 MHz, DMSO-d$_6$) δ 8.68 (dd, J=4.8, 0.8 Hz, 1H), 7.80 (t, J=1.2 Hz, 1H), 7.71 (dd, J=4.8, 1.6 Hz, 1H), 6.46-6.16 (m, 1H), 3.61-3.47 (m, 1H), 1.35 (d, J=6.8 Hz, 3H).

Step 4: To a stirred mixture of 2-(1,1-difluoro-2-methyl-propan-2-yl)pyridine-4-carboxylic acid (80 mg, 0.37 mmol) in T$_3$P (1 mL) and Pyridine (1 mL) was added 2-fluoro-4-methyl-5-[8-(morpholin-4-yl)imidazo[1,2-a]pyridin-6-yl] aniline (110 mg, 0.37 mmol). The reaction mixture was stirred for 2 h at room temperature. The resulting mixture was diluted with water (50 mL) and extracted with ethyl acetate (3×50 mL). The combined organic layers were washed with saturated brine (50 mL), dried over anhydrous sodium sulfate. After filtration, the filtrate was concentrated under reduced pressure. The residue was purified by Prep-TLC, eluted with PE/EA/EtOH=8/3/1 to afford the crude product. The crude product was purified by reverse flash chromatography with the following conditions: column, C18 silica gel; mobile phase, acetonitrile in water (10 mmol NH$_4$HCO3), 5% to 95% gradient in 15 min; detector, UV 254 nm. The fractions containing the desired product were combined and concentrated to afford 2-(1,1-difluoropropan-2-yl)-N-{2-fluoro-4-methyl-5-[8-(morpholin-4-yl)imidazo[1,2-a]pyridin-6-yl]phenyl}pyridine-4-carboxamide (70 mg, 41%) as an off-white solid. MS ESI calculated for $C_{27}H_{26}F_3N_5O_2$[M+H]$^+$, 510.20, found 510.15; $^1$H NMR (400 MHz, CDCl$_3$) δ 8.86 (dd, J=5.2, 0.8 Hz, 1H), 8.36 (d, J=8.0 Hz, 1H), 8.06 (s, 1H), 7.79 (d, J=1.6 Hz, 1H), 7.68-7.61 (m, 3H), 7.58 (d, J=1.2 Hz, 1H), 7.13 (d, J=12.0 Hz, 1H), 6.41 (s, 1H), 6.29-5.99 (m, 1H), 4.03-4.00 (m, 4H), 3.60-3.57 (m, 4H), 3.55-3.41 (m, 4H), 2.31 (s, 3H), 1.51 (d, J=6.8 Hz, 3H).

Step 5: The 2-(1,1-difluoropropan-2-yl)-N-{2-fluoro-4-methyl-5-[8-(morpholin-4-yl)imidazo[1,2-a]pyridin-6-yl]phenyl}pyridine-4-carboxamide (70 mg, 0.14 mmol) was purified by Chiral-Prep-HPLC with the following conditions: Column: CHIRAL ART Cellulose-SC, 2×25 cm, 5 m; Mobile Phase A: Hex (0.1% 2 M NH$_3$-MeOH)--HPLC, Mobile Phase B: MeOH: DCM=1: 1--HPLC; Flow rate: 20 mL/min; Gradient: 40% B to 40% B in 13.5 min; Wave Length: 220254 nm; RT1: 8.996 min; RT2: 11.239 min; Sample Solvent: EtOH: DCM=1: 1--HPLC; Injection Volume: 1.3 mL.

PEAK 1 (EXAMPLE 113: 2-(1,1-difluoropropan-2-yl)-N-(2-fluoro-4-methyl-5-(8-morpholinoimidazo[1,2-a]pyridin-6-yl)phenyl)isonicotinamide): The fractions (RT 8.996 min) were combined and concentrated to afford the title compound (26.9 mg, 38%) as an off-white solid of undetermined absolute stereochemistry. MS ESI calculated for C$_{27}$H$_{26}$F$_3$N$_5$O$_2$ [M+H]$^+$, 510.20, found 510.25; $^1$H NMR (400 MHz, CDCl$_3$) δ 8.80 (d, J=4.8 Hz, 1H), 8.36 (d, J=8.0 Hz, 1H), 8.08 (d, J=2.0 Hz, 1H), 7.80 (d, J=1.6 Hz, 1H), 7.68-7.54 (m, 4H), 7.13 (d, J=11.6 Hz, 1H), 6.42 (s, 1H), 6.29-5.99 (m, 1H), 4.03-4.00 (m, 4H), 3.59-3.57 (m, 4H), 3.53-3.41 (m, 1H), 2.31 (s, 3H), 1.51 (d, J=6.8 Hz, 3H).

PEAK 2 (EXAMPLE 114: 2-(1,1-difluoropropan-2-yl)-N-(2-fluoro-4-methyl-5-(8-morpholinoimidazo[1,2-a]pyridin-6-yl)phenyl)isonicotinamide): The fractions (RT 11.239 min) were combined and concentrated to afford the title compound (26.2 mg, 37%) as an off-white solid of undetermined absolute stereochemistry. MS ESI calculated for C$_{27}$H$_{26}$F$_3$N$_5$O$_2$ [M+H]$^+$, 510.20, found 510.20; $^1$H NMR (400 MHz, CDCl$_3$) δ 8.80 (d, J=4.8 Hz, 1H), 8.35 (d, J=8.0 Hz, 1H), 8.08 (d, J=3.2 Hz, 1H), 7.78 (d, J=1.6 Hz, 1H), 7.68 (d, J=1.6 Hz, 1H), 7.63-7.61 (m, 2H), 7.57 (d, J=1.2 Hz, 1H), 7.13 (d, J=11.6 Hz, 1H), 6.38 (s, 1H), 6.29-5.99 (m, 1H), 4.02-3.99 (m, 4H), 3.60-3.57 (m, 4H), 3.54-3.41 (m, 1H), 2.31 (s, 3H), 1.51 (d, J=7.2 Hz, 3H).

Example 115: 1-tert-Butyl-2-fluoro-N-{2-fluoro-4-methyl-5-[8-(morpholin-4-yl)imidazo[1,2-a]pyridin-6-yl]phenyl}imidazole-4-carboxamide

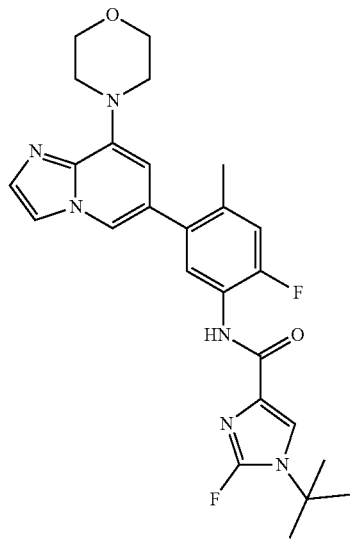

Step 1: To a stirred mixture of ethyl 1-tert-butylimidazole-4-carboxylate (300 mg, 1.53 mmol) and sodium bicarbonate (385.25 mg, 4.59 mmol) in acetonitrile (10 mL) was added Selectfluor (2.71 g, 7.65 mmol). The reaction mixture was stirred for 16 h at room temperature under nitrogen atmosphere. The resulting mixture was diluted with water (10 mL) and extracted with ethyl acetate (3×10 mL). The combined organic layers were washed with brine (3×20 mL), dried over anhydrous sodium sulfate. After filtration, the filtrate was concentrated under reduced pressure. The residue was purified by silica gel column chromatography, eluted with PE/EA (1/1). The fractions containing the desired product were combined and concentrated to afford ethyl 1-tert-butyl-2-fluoroimidazole-4-carboxylate (100 mg, 31%) as a brown oil. MS ESI calculated for C$_{10}$H$_{15}$FN$_2$O$_2$. [M+H]$^+$, 215.11, found 215.05.

Step 2: To a stirred solution of 2-fluoro-4-methyl-5-[8-(morpholin-4-yl)imidazo[1,2-a]pyridin-6-yl]aniline (137.11 mg, 0.42 mmol) in Lithium bis(trimethylsilyl)amide (2 mL) was added ethyl 1-tert-butyl-2-fluoroimidazole-4-carboxylate (90 mg, 0.42 mmol) (was dissolved in tetrahydrofuran (1 mL) dropwise at 0° C. under nitrogen atmosphere. The reaction mixture was stirred for 2 h at room temperature under nitrogen atmosphere. The resulting mixture was quenched with sat. ammonium chloride (aq.) at room temperature. The resulting mixture was extracted with ethyl acetate (3×10 mL). The combined organic layers were washed with brine (3×15 mL), dried over anhydrous sodium sulfate. After filtration, the filtrate was concentrated under reduced pressure. The residue was purified by Prep-TLC, eluted with DCM/MeOH (20/1) to afford the crude product. The crude product was purified by reverse phase Flash chromatography with the following conditions: Column: XBridge Prep OBD C18 Column, 30×150 mm, 5 m; Mobile Phase A: Water (Plus 10 mmol/L NH$_4$HCO$_3$), Mobile Phase B: acetonitrile; Flow rate: 60 mL/min; Gradient: 39% B to 49% B in 10 min, 49% B; Wavelength: 254 nm; RT1: 10 min. The fractions containing the desired product were combined and concentrated to afford 1-tert-butyl-2-fluoro-N-{2-fluoro-4-methyl-5-[8-(morpholin-4-yl)imidazo[1,2-a]pyridin-6-yl]phenyl}imidazole-4-carboxamide (67.1 mg, 21%) as an off-white solid. MS ESI calculated for C$_{26}$H$_{28}$F$_2$N$_6$O$_2$. [M+H]$^+$, 495.22, found 495.20; $^1$H NMR (400 MHz, DMSO-d$_6$) δ 9.41 (s, 1H), 8.48 (s, 1H), 8.22 (s, 1H), 8.03 (s, 1H), 7.94 (d, J=7.9 Hz, 1H), 7.67 (s, 1H), 7.34 (d, J=11.6 Hz, 1H), 7.07 (s, 1H), 3.84 (t, J=4.6 Hz, 4H), 3.28 (d, J=5.6 Hz, 4H), 2.28 (s, 3H), 1.59 (d, J=1.1 Hz, 9H).

Example 119-121: 3-Fluoro-N-(2-fluoro-4-methyl-5-(8-morpholinoimidazo[1,2-a]pyridin-6-yl)phenyl)-4-isopropylpyrrolidine-1-carboxamide

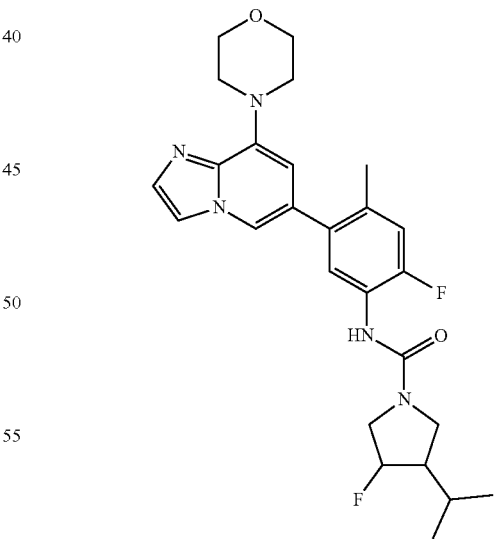

Step 1: To a stirred solution of benzyl 6-oxa-3-azabicyclo[3.1.0]hexane-3-carboxylate (5 g, 22.80 mmol) and copper (I) bromide; dimethyl sulfide (0.94 g, 4.56 mmol) in THF (200 mL) was added bromo(isopropyl)magnesium (13.4 g, 91.22 mmol) dropwise at −20° C. under nitrogen atmosphere. The reaction mixture was stirred for 1 h at −20° C. under nitrogen atmosphere. The resulting mixture was quenched by the addition of sat. NH₄Cl (aq.) (300 mL) at 0° C. The resulting mixture was extracted with EtOAc (3×300 mL). The combined organic layers were washed with brine (2×200 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in water (Plus 10 mmol/L NH₄HCO₃), 25% to 95% gradient in 35 min; detector, UV 254 nm. The fractions containing the desired product were combined and concentrated to afford benzyl 3-hydroxy-4-isopropylpyrrolidine-1-carboxylate (2.05 g, 34%) as a colorless oil. MS ESI calculated for $C_{15}H_{21}NO_3$ [M+H]⁺, 264.33, found, 264.15.

Step 2: To a stirred mixture of benzyl 3-isopropyl-4-oxopyrrolidine-1-carboxylate (700 mg, 2.67 mmol) in DAST (10 mL, 8.03 mmol) at 0° C. under nitrogen atmosphere. The reaction mixture was stirred for 4 h at room temperature under nitrogen atmosphere. The resulting mixture was quenched by the addition of NH₄HCO₃ (aq.) at 0° C. The resulting mixture was extracted with EtOAc (3×50 mL). The combined organic layers were washed with brine (3×50 mL), dried over anhydrous Na₂SO₄. After filtration, the filtrate was concentrated under reduced pressure. The residue was purified by silica gel column chromatography, eluted with PE/EA (5/1). The fractions containing the desired product were combined and concentrated to afford benzyl 3,3-difluoro-4-isopropylpyrrolidine-1-carboxylate (250 mg, 32%) as a yellow oil. MS ESI calculated for $C_{15}H_2OFNO_2$ [M+H]⁺. 266.32, found 266.15.

Step 3: A solution of benzyl 3-fluoro-4-isopropylpyrrolidine-1-carboxylate (300 mg, 1.13 mmol) in TFA (3 mL) was stirred for 16 h at 60° C. The resulting mixture was allowed to cool down to room temperature. The resulting mixture was concentrated under reduced pressure to afford 3-fluoro-4-isopropylpyrrolidine (100 mg, crude) as a yellow oil. MS ESI calculated for $C_7H_{14}FN$ [M+H]⁺, 132.19, found 132.60.

Step 4: To a stirred mixture of 2-fluoro-4-methyl-5-[8-(morpholin-4-yl)imidazo[1,2-a]pyridin-6-yl]aniline (150 mg, 0.46 mmol) and DIEA (297 mg, 2.30 mmol) in THF (7.6 mL) was added triphosgene (54 mg, 0.18 mmol). The reaction mixture was stirred for 15 min at room temperature under nitrogen atmosphere. To the above mixture was added 3-fluoro-4-isopropylpyrrolidine (60 mg, 0.46 mmol). The reaction mixture was stirred for 2 h at room temperature under nitrogen atmosphere. The resulting mixture was quenched with MeOH (2 mL) and concentrated under reduced pressure. The residue was purified by silica gel column chromatography, eluted with CH₂Cl₂/MeOH (10/1). The fractions containing the desired product were combined and concentrated to afford 3-fluoro-N-(2-fluoro-4-methyl-5-(8-morpholinoimidazo[1,2-a]pyridin-6-yl)phenyl)-4-isopropylpyrrolidine-1-carboxamide (100 mg, 45%) as a yellow solid. MS ESI calculated for $C_{26}H_{31}F_2N_5O_2$[M+H]⁺, 484.56, found 484.25.

Step 5: The 3-fluoro-N-(2-fluoro-4-methyl-5-(8-morpholinoimidazo[1,2-a]pyridin-6-yl)phenyl)-4-isopropylpyrrolidine-1-carboxamide (100 mg) was purified by Prep-HPLC with the following conditions: Column: CHIRALPAK IH, 2×25 cm, 5 m; Mobile Phase A: Hex (0.5% 2 M NH₃-MeOH) HPLC, Mobile Phase B: MeOH:DCM=1: 1 HPLC; Flow rate: 20 mL/min; Gradient: 20% B to 20% B in 15 min; Wave Length: 254/220 nm; RT1: 8.19 min; RT2: 11.76 min; Sample Solvent: MeOH: DCM=1: 1-HPLC; Injection Volume: 0.5 mL.

PEAK 1 (EXAMPLE 119: 3-Fluoro-N-(2-fluoro-4-methyl-5-(8-morpholinoimidazo[1,2-a]pyridin-6-yl)phenyl)-4-isopropylpyrrolidine-1-carboxamide): The fractions (RT 8.19 min) were combined and concentrated to afford the title compound (33.3 mg, 14%) as an off-white solid of undetermined absolute stereochemistry. MS ESI calculated for $C_{26}H_{31}F_2N_5O_2$[M+H]⁺, 484.56, found 484.30; ¹H NMR (400 MHz, DMSO-d₆) δ 8.12 (d, J=1.4 Hz, 1H), 8.02 (s, 1H), 7.89 (d, J=1.2 Hz, 1H), 7.50 (d, J=1.2 Hz, 1H), 7.42 (d, J=8.1 Hz, 1H), 7.18 (d, J=11.6 Hz, 1H), 6.34 (d, J=1.5 Hz, 1H), 5.23 (d, J=53.4 Hz, 1H), 3.80 (t, J=4.6 Hz, 4H), 3.78-3.59 (m, 3H), 3.53 (t, J=4.7 Hz, 4H), 3.10 (t, J=10.5 Hz, 1H), 2.25 (s, 3H), 1.98-1.96 (m, 1H), 1.74-1.70 (m, 1H), 1.01 (d, J=6.5 Hz, 3H), 0.92 (d, J=6.6 Hz, 3H).

PEAK 2 (EXAMPLE 120: 3-Fluoro-N-(2-fluoro-4-methyl-5-(8-morpholinoimidazo[1,2-a]pyridin-6-yl)phenyl)-4-isopropylpyrrolidine-1-carboxamide): The fractions (RT 11.76 min) were combined and concentrated to afford the title compound (29.7 mg, 13%) as an off-white solid of undetermined absolute stereochemistry. MS ESI calculated for $C_{26}H_{31}F_2N_5O_2$[M+H]⁺, 484.56, found 484.35; ¹H NMR (400 MHz, DMSO-d₆) δ 8.12 (d, J=1.4 Hz, 1H), 8.03 (s, 1H), 7.89 (d, J=1.2 Hz, 1H), 7.50 (d, J=1.2 Hz, 1H), 7.42 (d, J=8.2 Hz, 1H), 7.18 (d, J=11.6 Hz, 1H), 6.34 (d, J=1.5 Hz, 1H), 5.23 (d, J=53.5 Hz, 1H), 3.83 (t, J=4.7 Hz, 4H), 3.76-3.63 (m, 3H), 3.53 (t, J=4.7 Hz, 4H), 3.11-3.09 (m, 1H), 2.25 (s, 3H), 2.15-1.86 (m, 1H), 1.83-1.65 (m, 1H), 1.01 (d, J=6.5 Hz, 3H), 0.92 (d, J=6.6 Hz, 3H).

PEAK 3 (EXAMPLE 121: 3-Fluoro-N-(2-fluoro-4-methyl-5-(8-morpholinoimidazo[1,2-a]pyridin-6-yl)phenyl)-4-isopropylpyrrolidine-1-carboxamide): The fractions (RT 8.2-11.76 min) were combined and concentrated to afford the title compound (1.7 mg, 0.56%) as an off-white solid of undetermined absolute stereochemistry. MS ESI calculated for $C_{26}H_{31}F_2N_5O_2$[M+H]⁺, 484.56, found 484.35; ¹H NMR (400 MHz, Chloroform-d) δ 8.10 (d, J=8.2 Hz, 1H), 7.76-7.71 (m, 1H), 7.59 (d, J=1.7 Hz, 1H), 7.54-7.49 (m, 1H), 7.00 (d, J=11.5 Hz, 1H), 6.35 (d, J=12.4 Hz, 2H), 5.18-5.16 (m, 1H), 3.98 (t, J=5.0 Hz, 4H), 3.91-3.60 (m, 3H), 3.58-3.42 (m, 5H), 2.23 (d, J=2.0 Hz, 3H), 2.16-1.84 (m, 2H), 1.06-1.04 (m, 6H).

Example 122 and 123: 3-(Cyclopropyldifluoromethyl)-N-(2-fluoro-4-methyl-5-(8-morpholinoimidazo[1,2-a]pyridin-6-yl)phenyl)pyrrolidine-1-carboxamide

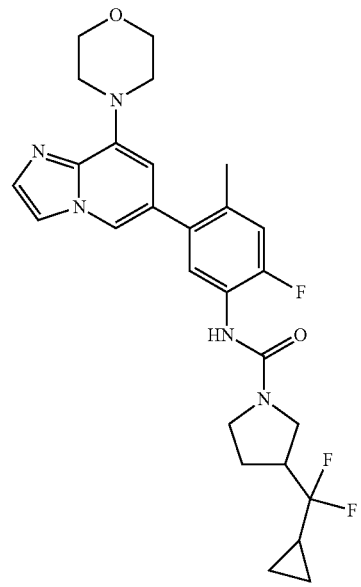 [SMILES: Cc1cc(F)c(NC(=O)N2CCC(C(F)(F)C3CC3)C2)cc1-c1cc(N2CCOCC2)c2nccn2c1]

Step 1: To a stirred solution of 1-(tert-butoxycarbonyl) pyrrolidine-3-carboxylic acid (5 g, 23.23 mmol) and N,O-dimethylhydroxylamine HCl salt (3.40 g, 34.84 mmol) in THF (50 mL) were added EDCI (6.68 g, 34.84 mmol) and TEA (7.05 g, 69.69 mmol) at room temperature under nitrogen atmosphere. The reaction mixture was stirred for 2 h at room temperature under nitrogen atmosphere. The resulting mixture was diluted with water (300 mL) and extracted with EtOAc (3×200 mL). The combined organic layers were washed with brine (3×200 mL), dried over anhydrous $Na_2SO_4$. After filtration, the filtrate was concentrated under reduced pressure. The residue was purified by silica gel column chromatography, eluted with PE/EA (1/3). The fractions containing the desired product were combined and concentrated to afford tert-butyl 3-[methoxy(methyl)carbamoyl]pyrrolidine-1-carboxylate (3.2 g, 53%) as a yellow oil. $^1$H NMR (400 MHz, Chloroform-d) δ 3.74-3.72 (m, 3H), 3.71-3.52 (m, 2H), 3.50-3.30 (m, 3H), 3.22 (s, 3H), 2.23-2.02 (m, 2H), 1.48 (d, J=1.0 Hz, 9H).

Step 2: To a stirred solution of tert-butyl 3-[methoxy(methyl)carbamoyl]pyrrolidine-1-carboxylate (4.6 g, 17.81 mmol) in THF (30 mL) was added bromo(cyclopropyl)magnesium (10.35 g, 71.23 mmol) dropwise at −78° C. The reaction mixture was stirred for 2 h at room temperature under nitrogen atmosphere. The resulting mixture was quenched by the addition of sat. $NH_4Cl$ (aq.) (100 mL) at room temperature. The resulting mixture was extracted with EtOAc (3×150 mL). The combined organic layers were washed with brine (3×100 mL), dried over anhydrous $Na_2SO_4$. After filtration, the filtrate was concentrated under reduced pressure. The residue was purified by silica gel column chromatography, eluted with PE/EA (3/1). The fractions containing the desired product were combined and concentrated to afford tert-butyl 3-cyclopropanecarbonylpyrrolidine-1-carboxylate (3.16 g, 74%) as a light-yellow oil. $^1$H NMR (300 MHz, Chloroform-d) δ 3.70-3.52 (m, 2H), 3.53-3.22 (m, 3H), 2.21-2.06 (m, 2H), 1.99-1.74 (m, 1H), 1.48 (s, 9H), 1.10-1.07 (m, 2H), 1.03-0.88 (m, 2H).

Step 3: To a stirred solution of tert-butyl 3-cyclopropanecarbonylpyrrolidine-1-carboxylate (1 g, 4.18 mmol) in DCM (5 mL) was added HCl (g) (5 mL, 4 M in EA). The reaction mixture was stirred for 1 h at room temperature. The resulting mixture was concentrated under reduced pressure to afford cyclopropyl(pyrrolidin-3-yl)methanone HCl salt (720 mg, crude). To a stirred solution of cyclopropyl(pyrrolidin-3-yl)methanone HCl salt (720 mg, crude) in ACN (5 mL) were added $NaHCO_3$ (905 mg, 10.78 mmol) and benzyl chloroformate (1226 mg, 7.18 mmol) dropwise at 0° C. The reaction mixture was stirred for 2 h at room temperature under nitrogen atmosphere. The resulting mixture was diluted with water (50 mL) and extracted with EtOAc (3×50 mL). The combined organic layers were washed with brine (3×40 mL), dried over anhydrous $Na_2SO_4$. After filtration, the filtrate was concentrated under reduced pressure. The residue was purified by silica gel column chromatography, eluted with PE/EA (3/1). The fractions containing the desired product were combined and concentrated to afford benzyl 3-cyclopropanecarbonylpyrrolidine-1-carboxylate (650 mg, 57%) as a colorless oil. MS ESI calculated for $C_{16}H_{19}NO_3$ [M+H]$^+$, 274.33, found 274.35.

Step 4: A solution of benzyl 3-cyclopropanecarbonylpyrrolidine-1-carboxylate (640 mg, 2.34 mmol) in BAST (5 mL) was stirred for 16 h at 60° C. under nitrogen atmosphere. The resulting mixture was quenched by the addition of sat. $NaHCO_3$ (aq) (10 mL) at room temperature. The resulting mixture was diluted with water (30 mL) and extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EA (3/1). The fractions containing the desired product were combined and concentrated to afford benzyl 3-(cyclopropyldifluoromethyl)pyrrolidine-1-carboxylate (180 mg, 26%) as a yellow oil. MS ESI calculated for $C_{16}H_{19}F_2NO_2$ [M+H]$^+$, 296.33, found 296.25.

Step 5: A solution of 3-(cyclopropyldifluoromethyl)pyrrolidine-1-carboxylate (180 mg, 26%) in TFA (2 mL) was stirred for 1 h. The resulting mixture was concentrated under reduced pressure to afford 3-(cyclopropyldifluoromethyl)pyrrolidine 2,2,2-trifluoroacetate (213 mg, crude). MS ESI calculated for $C_8H_{13}F_2N$ [M+H]$^+$, 162.10, found 162.10.

Step 6: To a stirred solution of 2-fluoro-4-methyl-5-[8-(morpholin-4-yl)imidazo[1,2-a]pyridin-6-yl]aniline (90 mg, 0.28 mmol) in THF (8 mL) was added DIEA (178 mg, 1.38 mmol) and triphosgene (32.73 mg, 0.11 mmol). The reaction mixture was stirred for 30 min at room temperature under nitrogen atmosphere. To the above mixture was added 3-(cyclopropyldifluoromethyl)pyrrolidine 2,2,2-trifluoroacetate (213 mg, 0.28 mmol, 36%). The reaction mixture was stirred for 1 h at room temperature under nitrogen atmosphere. The reaction was quenched with MeOH and concentrated under reduced pressure. The residue was purified by silica gel column chromatography, eluted with PE/EA/EtOH (4/3/1) to afford the crude product. The crude product (120 mg) was purified by Prep-HPLC with the following conditions: Column: XSelect CSH Prep C18 OBD Column, 19×250 mm, 5 m; Mobile Phase A: water (Plus 10 mmol/L $NH_4HCO_3$), Mobile Phase B: ACN; Flow rate: 20 mL/min; Gradient: 49% B to 54% B in 8 min, 54% B; Wavelength: 254 nm; RT1: 7 min. The fractions containing the desired product were combined and concentrated to afford 3-(cyclopropyldifluoromethyl)-N-{2-fluoro-4-methyl-5-[8-(morpholin-4-yl)imidazo[1,2-a]pyridin-6-yl]phenyl}pyrrolidine-1-carboxamide (50 mg, 35%) as a white solid. MS ESI calculated for $C_{27}H_{30}F_3N_5O_2$ [M+H]$^+$, 514.56, found 514.15.

Step 7: The 3-(cyclopropyldifluoromethyl)-N-{2-fluoro-4-methyl-5-[8-(morpholin-4-yl)imidazo[1,2-a]pyridin-6-yl]phenyl}pyrrolidine-1-carboxamide (50 mg, 0.10 mmol) was purified by Prep-Chiral-HPLC with the following conditions: Column: CHIRAL ART Cellulose-SB, 2×25 cm, 5 m; Mobile Phase A: Hex (0.5% 2 M $NH_3$-MeOH)--HPLC, Mobile Phase B: MeOH: DCM=1: 1--HPLC; Flow rate: 20 mL/min; Gradient: 15% B to 15% B in 19 min; Wave Length: 254/220 nm; RT1: 16 min; RT2: 17.49 min; Sample Solvent: MeOH: DCM=1: 1--HPLC; Injection Volume: 0.5 mL.

PEAK1 (EXAMPLE 121: 3-(Cyclopropyldifluoromethyl)-N-(2-fluoro-4-methyl-5-(8-morpholinoimidazo[1,2-a]pyridin-6-yl)phenyl)pyrrolidine-1-carboxamide): The fractions (RT 16 min) were combined and concentrated to afford the title compound (16.1 mg, 32%) as an off-white solid of undetermined absolute stereochemistry. MS ESI calculated for $C_{27}H_{30}F_3N_5O_2$ [M+H]$^+$, 514.56, found 514.15; $^1$H NMR (400 MHz, DMSO-d$_6$) δ 8.12 (d, J=1.6 Hz, 1H), 7.98 (s, 1H), 7.89 (d, J=1.2 Hz, 1H), 7.51 (d, J=1.2 Hz, 1H), 7.43 (d, J=8.2 Hz, 1H), 7.18 (d, J=11.6 Hz, 1H), 6.34 (d, J=1.6 Hz, 1H), 3.81 (t, J=4.6 Hz, 4H), 3.66-3.52 (m, 6H), 3.45-3.34 (m, 2H), 2.97-2.90 (m, 1H), 2.26 (s, 3H), 2.10-2.08 (m, 1H), 2.00-1.92 (m, 1H), 1.50-1.37 (m, 1H), 0.68-0.55 (m, 4H).

PEAK2 (EXAMPLE 122: 3-(Cyclopropyldifluoromethyl)-N-(2-fluoro-4-methyl-5-(8-morpholinoimidazo[1,2-a]pyridin-6-yl)phenyl)pyrrolidine-1-carboxamide): The fractions (RT 17.5 min) were combined and concentrated to afford the title compound (16.9 mg, 33%) as an off-white solid of undetermined absolute stereochemistry. MS ESI calculated for C$_{27}$H$_{30}$F$_3$N$_5$O$_2$ [M+H]$^+$, 514.24, found 514.15; $^1$H NMR (400 MHlz, DMSO-d$_6$) δ 8.12 (d, J=1.4 Hz, 1H), 7.98 (s, 1H), 7.90 (d, J=1.2 Hz, 1H), 7.51 (d, J=1.2 Hz, 1H), 7.43 (d, J=8.0 Hz, 1H), 7.18 (d, J=11.6 Hz, 1H), 6.34 (d, J=1.4 Hz, 1H), 3.81 (t, J=4.6 Hz, 4H), 3.65-3.59 (m, 1H), 3.57-3.53 (m, 5H), 3.45-3.34 (m, 2H), 3.00-2.90 (m, 1H), 2.26 (s, 3H), 2.10-2.08 (m, 1H), 1.98-1.93 (m, 1H), 1.51-1.37 (m, 1H), 0.68-0.55 (m, 4H).

Example 124: 1-(1,1-Difluoro-2-methylpropan-2-yl)-N-{2-fluoro-4-methyl-5-[8-(morpholin-4-yl)imidazo[1,2-a]pyridin-6-yl]phenyl}pyrazole-4-carboxamide

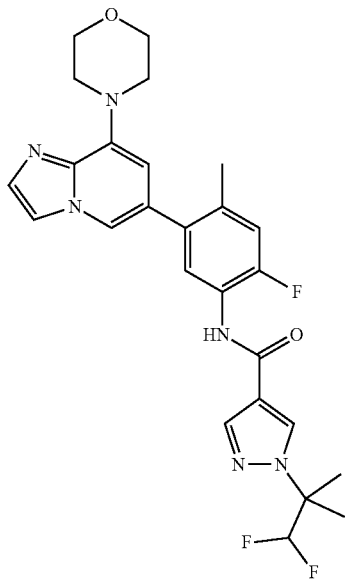 [SMILES: Cc1cc(F)c(NC(=O)c2cnn(C(C)(C)C(F)F)c2)cc1-c1cc(N2CCOCC2)c2nccn2c1]

Step 1: To a stirred mixture of 4-bromopyrazole (5 g, 34.02 mmol) in DMF (50 mL) was added NaH (1.63 g, 40.82 mmol, 60%) in portions at 0° C. under nitrogen atmosphere. The reaction mixture was stirred for 15 min at room temperature under nitrogen atmosphere. To the above mixture was added methyl 2-bromo-2-methylpropanoate (11.09 g, 61.23 mmol) at room temperature. The reaction mixture was stirred for additional 2 h at room temperature. The resulting mixture was quenched with sat. NH$_4$Cl (aq.) at 0° C. The resulting mixture was extracted with EtOAc (3×300 mL). The combined organic layers were washed with brine (6×300 mL), dried over anhydrous Na$_2$SO$_4$. After filtration, the filtrate was concentrated under reduced pressure. The residue was purified by silica gel column chromatography, eluted with PE/EA (2/1). The fractions containing the desired product were combined and concentrated to afford methyl 2-(4-bromopyrazol-1-yl)-2-methylpropanoate (5.2 g, 61%) as a colorless oil. MS ESI calculated for C8H11BrN$_2$O$_2$[M+H]$^+$, 247.00, 248.00, found, 246.85, 248.85; $^1$H NMR (400 MHz, DMSO-d$_6$) δ 8.20 (d, J=0.8 Hz, 1H), 7.59 (d, J=0.8 Hz, 1H), 3.63 (s, 3H), 1.75 (s, 6H).

Step 2: To a stirred mixture of methyl 2-(4-bromopyrazol-1-yl)-2-methylpropanoate (4.5 g, 18.21 mmol) in THE (45 mL) was added LiAlH$_4$ (1.04 g, 27.32 mmol) dropwise at 0° C. under nitrogen atmosphere. The resulting mixture was stirred for 2 h at room temperature under nitrogen atmosphere. The resulting mixture was quenched with NaOH (aq.) (15%) and water at 0° C., after filtered, the filter cake were washed with THE (3×20 mL). The filtrate was concentrated under reduced pressure. The residue was purified by reversed phase flash chromatography with the following conditions: column, C18 silica gel; mobile phase, MeCN in water (Plus 0.1% TFA), 5% to 95% gradient in 10 min; detector, UV 254 nm. The fractions containing the desired product were combined and concentrated to afford 2-(4-bromopyrazol-1-yl)-2-methylpropan-1-ol (2.7 g, 67%) as a white solid. MS ESI calculated for C$_7$HirBrN$_2$O[M+H]$^+$, 219.01, 221.01, found 219.15, 221.15; $^1$H NMR (400 MHz, DMSO-d$_6$) δ 7.96 (d, J=0.8 Hz, 1H), 7.53 (d, J=0.8 Hz, 1H), 4.98 (t, J=5.6 Hz, 1H), 3.55 (d, J=5.6 Hz, 2H), 1.44 (s, 6H).

Step 3: To a stirred mixture of 2-(4-bromopyrazol-1-yl)-2-methylpropan-1-ol (1 g, 4.56 mmol) and TEA (1.9 mL, 13.7 mmol) in DMSO (6 mL) was added SO$_3$-pyridine (2.18 g, 13.7 mmol) in DMSO (4 mL) at room temperature under nitrogen atmosphere. The reaction mixture was stirred for 3 h at room temperature under nitrogen atmosphere. The resulting mixture was quenched by the addition of Water/Ice (50 mL). The resulting mixture was extracted with EtOAc (3×50 mL). The combined organic layers were washed with brine (6×50 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (Plus 10 mmol/L NH$_4$HCO$_3$), 5% to 95% gradient in 10 min; detector, UV 254 nm. The fractions containing the desired product were combined and concentrated to afford 2-(4-bromopyrazol-1-yl)-2-methylpropanal (650 mg, 32%) as a colorless oil. MS ESI calculated for C$_7$H$_9$BrN$_2$O[M+H]$^+$, 216.99, 218.99, found 216.80, 218.80; $^1$H NMR (400 MHz, DMSO-d$_6$) δ 9.50 (s, 1H), 8.24 (s, 1H), 7.68 (s, 1H), 1.60 (s, 6H).

Step 4: To a stirred mixture of 2-(4-bromopyrazol-1-yl)-2-methylpropanal (500 mg, 2.30 mmol) in DCM (5 mL) was added DAST (371.2 mg, 23.03 mmol) in DCM (5 mL) at 0° C. under nitrogen atmosphere. The reaction mixture was stirred for 16 h at room temperature under nitrogen atmosphere. The resulting mixture was quenched with NaHCO$_3$ (aq.) (50 mL) at ° C. The resulting mixture was extracted with CH$_2$Cl$_2$ (3×50 mL). The combined organic layers were washed with brine (2×50 mL), dried over anhydrous Na$_2$SO$_4$. After filtration, the filtrate was concentrated under reduced pressure. The residue was purified by reversed phase flash chromatography with the following conditions: column, C18 silica gel; mobile phase, MeCN in water (Plus 10 mmol/L NH$_4$HCO$_3$), 5% to 95% gradient in 10 min; detector, UV 220 nm. The fractions containing the desired product were combined and concentrated to afford the mixture of 4-bromo-1-(1,1-difluoro-2-methylpropan-2-yl)-1H-pyrazole & 4-bromo-1-(1,2-difluoro-2-methylpropyl)-1H-pyrazole (371 mg, 67%) as a light-yellow oil. MS ESI calculated for C$_7$H$_9$BrF$_2$N$_2$[M+H]$^+$, 238.99, 240.99, found 239.10, 240.10.

Step 5: To a stirred mixture of 2-fluoro-4-methyl-5-[8-(morpholin-4-yl)imidazo[1,2-a]pyridin-6-yl]aniline (75 mg, 0.23 mmol), Pd(dppf)Cl$_2$ CH$_2$Cl$_2$ (37 mg, 0.05 mmol), bis(lambda2-cobalt(2+)) octakis(methanidylidyneoxidanium) (23 mg, 0.07 mmol) and 4-bromo-1-(1,1-difluoro-2-methylpropan-2-yl)-1H-pyrazole & 4-bromo-1-(1,2-difluoro-2-methylpropyl)-1H-pyrazole (109 mg, 0.46 mmol) in dioxane (1.5 mL) was added TEA (139 mg, 1.38 mmol) at room temperature. The reaction mixture was degassed with nitrogen for three times and stirred for 16 h at 90° C. The resulting mixture was concentrated under reduced pressure. The residue was purified by silica gel column chromatography, eluted with PE/EA/EtOH (1/3/1) (1:1) to afford crude product. The crude product was purified by reversed phase flash chromatography with the following conditions: column, C18 silica gel; mobile phase, MeCN in Water (Plus 10 mmol/L NH$_4$HCO$_3$), 5% to 95% gradient in 25 min; detector, UV 254 nm. The fractions containing the desired product were combined and concentrated to afford the mixture of 1-(1,1-difluoro-2-methylpropan-2-yl)-N-(2-fluoro-4-methyl-5-(8-morpholinoimidazo[1,2-a]pyridin-6-yl)phenyl)-1H-pyrazole-4-carboxamide and 1-(1,2-difluoro-2-methylpropyl)-N-(2-fluoro-4-methyl-5-(8-morpholinoimidazo[1,2-a]pyridin-6-yl)phenyl)-1H-pyrazole-4-carboxamide (43 mg, 36%) as a white solid. MS ESI calculated for C$_{26}$H$_{27}$F$_3$N$_6$O$_2$ [M+H]$^+$, 513.21, found 513.15.

Step 6: The mixture of 1-(1,1-difluoro-2-methylpropan-2-yl)-N-(2-fluoro-4-methyl-5-(8-morpholinoimidazo[1,2-a]pyridin-6-yl)phenyl)-1H-pyrazole-4-carboxamide and 1-(1,2-difluoro-2-methylpropyl)-N-(2-fluoro-4-methyl-5-(8-morpholinoimidazo[1,2-a]pyridin-6-yl)phenyl)-1H-pyrazole-4-carboxamide (43 mg) was purified by Achiral-SFC with the following conditions: Column: DAICEL DCpak P4VP, 3×25 cm, 5 m; Mobile Phase A: CO$_2$, Mobile Phase B: ETOH (0.1% 2 M N$_{13}$-MEOH); Flow rate: 60 mL/min; Gradient: isocratic 27% B; Column Temperature: 35° C.; Back Pressure: 100 bar; Wave Length: 254 nm; RT1: 6.77 min; RT2: 8.08 min; Sample Solvent: MeOH--HPLC; Injection Volume: 2 mL.

PEAK 2 (RT2: 8.08 min): The fractions were combined and concentrated to afford the title compound (11.9 mg, 27%) as an off-white solid. MS ESI calculated for C$_{26}$H$_{27}$F$_3$N$_6$O$_2$ [M+H]$^+$, 513.21, found 513.20; $^1$H NMR (400 MHz, DMSO-d$_6$) δ 9.80 (d, J=1.6 Hz, 1H), 8.60 (s, 1H), 8.15 (d, J=1.2 Hz, 1H), 8.10 (s, 1H), 7.89 (d, J=1.2 Hz, 1H), 7.54 (d, J=8.0 Hz, 1H), 7.51 (d, J=1.2 Hz, 1H), 7.29 (d, J=11.2 Hz, 1H), 6.37 (d, J=1.6 Hz, 1H), 6.30-6.28 (m, 1H), 3.80 (t, J=4.8 Hz, 4H), 3.54 (t, J=4.8 Hz, 4H), 2.29 (s, 3H), 1.66 (s, 6H).

Example 125: 1-(1,2-Difluoro-2-methylpropyl)-N-(2-fluoro-4-methyl-5-(8-morpholinoimidazo[1,2-a]pyridin-6-yl)phenyl)-1H-pyrazole-4-carboxamide

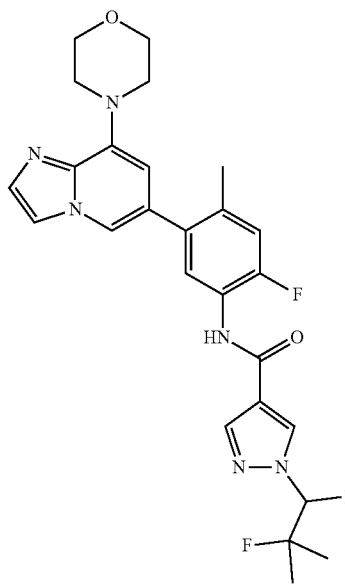

Step 1: The mixture of 1-(1,1-difluoro-2-methylpropan-2-yl)-N-(2-fluoro-4-methyl-5-(8-morpholinoimidazo[1,2-a]pyridin-6-yl)phenyl)-1H-pyrazole-4-carboxamide and 1-(1,2-difluoro-2-methylpropyl)-N-(2-fluoro-4-methyl-5-(8-morpholinoimidazo[1,2-a]pyridin-6-yl)phenyl)-1H-pyrazole-4-carboxamide (43 mg) was purified by Achiral-SFC with the following conditions: Column: DAICEL DCpak P4VP, 3×25 cm, 5 m; Mobile Phase A: CO$_2$, Mobile Phase B: ETOH (0.1% 2 M N$_{13}$-MEOH); Flow rate: 60 mL/min; Gradient: isocratic 27% B; Column Temperature: 35° C.; Back Pressure: 100 bar; Wave Length: 254 nm; RT1: 6.77 min; RT2: 8.08 min; Sample Solvent: MeOH--HPLC; Injection Volume: 2 mL.

PEAK 1 (R$^{6.77}$ min): The fractions were combined and concentrated to afford the title compound (22.6 mg, 52%) as an off-white solid. MS ESI calculated for C$_{26}$H$_{27}$F$_3$N$_6$O$_2$ [M+H]$^+$, 513.21, found 513.20; $^1$H NMR (400 MHz, DMSO-d$_6$) δ 10.01 (s, 1H), 8.68 (s, 1H), 8.20 (s, 1H), 8.16 (d, J=1.2 Hz, 1H), 7.90 (d, J=1.2 Hz, 1H), 7.56 (d, J=8.0 Hz, 1H), 7.52 (d, J=1.2 Hz, 1H), 7.30 (d, J=11.2 Hz, 1H), 6.70-6.54 (m, 1H), 6.38 (d, J=1.2 Hz, 1H), 3.81 (t, J=4.4 Hz, 4H), 3.56 (t, J=4.8 Hz, 4H), 2.30 (s, 3H), 1.51-1.37 (m, 6H).

Example 136: N-{2-fluoro-4-methyl-5-[8-(morpholin-4-yl)imidazo[1,2-a]pyridin-6-yl]phenyl}-1-(1,1,1-trifluoro-2-methylpropan-2-yl)pyrazole-4-carboxamide

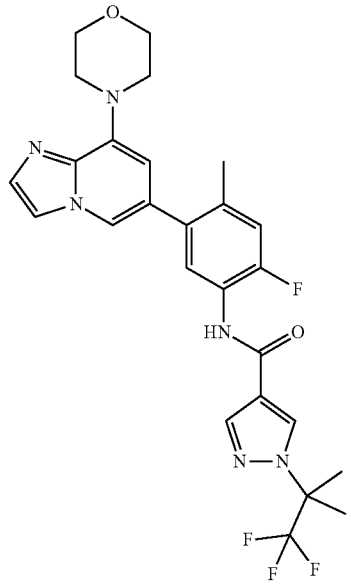 [SMILES: Cc1cc(F)c(NC(=O)c2cnn(C(C)(C)C(F)(F)F)c2)cc1-c1cc(N2CCOCC2)c2nccn2c1]

Step 1: To a stirred mixture of benzohydrazide (10 g, 73.44 mmol) in Toluene (150 mL) was added acetone (6.40 g, 110.17 mmol) at room temperature under nitrogen atmosphere. The reaction mixture was stirred for 16 h at 110° C. under nitrogen atmosphere. The resulting mixture was concentrated under reduced pressure. The residue was purified by silica gel column chromatography, eluted with CH$_2$Cl$_2$/MeOH (20/1). The fractions containing the desired product were combined and concentrated to afford N-(propan-2-ylidene)benzohydrazide (9.8 g, 75%) as a white solid. MS ESI calculated for C$_1$H$_{12}$N$_2$O[M+H]$^+$, 177.09, found, 177.15; $^1$H NMR (400 MHz, DMSO-d$_6$) δ 10.42 (s, 1H), 7.84-7.82 (m, 2H), 7.81-7.43 (m, 3H), 2.01 (s, 3H), 1.95 (s, 3H).

Step 2: To a stirred mixture of N-(propan-2-ylidene)benzohydrazide (5 g, 28.37 mmol) in DCE (57 mL) were added allyltrimethylsilane (4.86 g, 42.53 mmol) and BF$_3$-Et$_2$O (6.04 g, 42.56 mmol) at room temperature under nitrogen atmosphere. The reaction mixture was stirred for 5 min at 85° C. under nitrogen atmosphere. The resulting mixture was allowed to cool down to room temperature. To the above mixture were added NaOAc (9.31 g, 113.50 mmol) and trimethyl(trifluoromethyl)silane (8.07 g, 56.75 mmol) in DMF (57 mL) at room temperature under nitrogen atmosphere. The reaction mixture was stirred for 2 h at room temperature under nitrogen atmosphere. The resulting mixture was quenched with sat. NaHCO$_3$ (aq.) (500 mL) and extracted with EtOAc (3×300 mL). The combined organic layers were washed with brine (5×300 mL), dried over anhydrous Na$_2$SO$_4$. After filtration, the filtrate was concentrated under reduced pressure. The residue was purified by silica gel column chromatography, eluted with PE/EA (1/3). The fractions containing the desired product were combined and concentrated to afford N-(1,1,1-trifluoro-2-methylpropan-2-yl)benzohydrazide (4.91 g, 70%) as a light yellow solid. MS ESI calculated for C$_{11}$H$_{13}$F$_3$N$_2$O[M+H]$^+$, 247.10, found 247.00. $^1$H NMR (400 MHz, DMSO-d$_6$) δ 9.93 (d, J=6.0 Hz, 1H), 7.85-7.82 (m, 2H), 7.58-7.41 (m, 3H), 5.42 (d, J=6.0 Hz, 1H), 1.28 (s, 6H).

Step 3: To a stirred mixture of N-(1,1,1-trifluoro-2-methylpropan-2-yl)benzohydrazide (4.5 g, 18.28 mmol) in MeOH (26 mL) was added HCl (aq.) (73 mL, 292.58 mmol) dropwise at room temperature. The reaction mixture was stirred for 16 h at 80° C. The resulting mixture was concentrated under reduced pressure to afford (1,1,1-trifluoro-2-methylpropan-2-yl)hydrazine hydrochloride (4.38 g, crude) as a light yellow solid. MS ESI calculated for C$_4$H10ClF$_3$N$_2$[M+H]$^+$, 143.07, found 143.10; $^1$H NMR (400 MHz, DMSO-d$_6$) δ 9.53 (brs, 2H), 6.03 (brs, 1H), 1.34 (s, 6H).

Step 4: To a stirred mixture of (1,1,1-trifluoro-2-methylpropan-2-yl)hydrazine hydrochloride (785 mg, 4.40 mmol) and propane, 1,1,3,3-tetramethoxy-(721 mg, 4.40 mmol) in EtOH (6.25 mL) was added HCl (conc.) (1.25 mL, 14.99 mmol) at room temperature under nitrogen atmosphere. The reaction mixture was stirred for 16 h at 80° C. under nitrogen atmosphere. The resulting mixture was quenched with water/Ice (100 mL) and extracted with CH$_2$Cl$_2$ (3×100 mL). The combined organic layers were washed with brine (2×100 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in water (0.1% TFA), 5% to 95% gradient in 30 min; detector, UV 254 nm. The fractions containing the desired product were combined and concentrated to afford 1-(1,1,1-trifluoro-2-methylpropan-2-yl)pyrazole (1.27 g, 80%) as a light yellow liquid. MS ESI calculated for C$_7$H$_9$F$_3$N$_2$[M+H]$^+$, 179.07, found 179.10; $^1$H NMR (400 MHz, DMSO-d$_6$) δ 8.07-8.06 (m, 1H), 7.57 (t, J=2.4 Hz, 1H), 6.40-6.38 (m, 1H), 1.83 (s, 6H).

Step 5: To a stirred mixture of 1-(1,1,1-trifluoro-2-methylpropan-2-yl)pyrazole (1.1 g, 6.17 mmol) in DCM (11 mL) was added NBS (1.10 g, 6.17 mmol) in portions at 0° C. The reaction mixture was stirred for 6 h at room temperature. The resulting mixture was quenched with sat. sodium hyposulfite (aq.) (100 mL) at room temperature. The resulting mixture was extracted with CH$_2$Cl$_2$ (3×100 mL). The combined organic layers were washed with brine (2×100 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (0.1% TFA), 5% to 95% gradient in 30 min; detector, UV 220 nm. The fractions containing the desired product were combined and concentrated to afford 4-bromo-1-(1,1,1-trifluoro-2-methylpropan-2-yl)pyrazole (1.5 g, 94%) as a light yellow oil. MS ESI calculated for C$_7$H$_8$BrF$_3$N$_2$[M+H]$^+$, 256.98, 258.98, found 256.90, 258.90; $^1$H NMR (400 MHz, DMSO-d$_6$) δ 8.40-8.39 (m, 1H), 7.71-7.70 (m, 1H), 1.81 (s, 6H).

Step 6: To a stirred mixture of 2-fluoro-4-methyl-5-[8-(morpholin-4-yl)imidazo[1,2-a]pyridin-6-yl]aniline (150 mg, 0.46 mmol), Pd(dppf)Cl$_2$ CH$_2$Cl$_2$ (74 mg, 0.09 mmol), bis(lambda2-cobalt(2+)) octakis(methanidylidyneoxidanium) (47 mg, 0.14 mmol) and 4-bromo-1-(1,1,1-trifluoro-2-methylpropan-2-yl)pyrazole (236 mg, 0.92 mmol) in dioxane (2 mL) was added TEA (279 mg, 2.76 mmol). The reaction mixture was degassed with nitrogen atmosphere for three times and stirred for 16 h at 90° C. The resulting mixture was concentrated under reduced pressure. The residue was purified by silica gel column chromatography, eluted with PE/EA/EtOH (3/1/1) to afford crude product. The crude product was purified by reversed-phase flash chromatography with the following (Conditions: column, C18 silica gel; mobile phase, MeCN in water (Plus 10 mmol/L NH$_4$HCO$_3$), 5% to 95% gradient in 30 min; detector, UV 254 nm) to afford the title compound (127.2 mg, 51%) as a white solid. MS ESI calculated for C$_{26}$H$_{26}$F$_4$N$_6$O$_2$ [M+H]$^+$, 531.21, found 531.15; $^1$H NMR (400 MHz, DMSO-d$_6$) δ 9.83 (s, 1H), 8.76-8.75 (m, 1H), 8.16 (d, J=1.2 Hz, 1H), 8.13-8.12 (m, 1H), 7.90 (d, J=1.2 Hz, 1H), 7.56 (d, J=8 Hz, 1H), 7.52 (d, J=1.2 Hz, 1H), 7.30 (d, J=11.6 Hz, 1H), 6.38 (d, J=1.6 Hz, 1H), 3.81 (t, J=4.4 Hz, 4H), 3.55 (t, J=4.8 Hz, 4H), 2.30 (s, 3H), 1.87 (s, 6H).

Example 137: 1-(tert-Butyl)-5-fluoro-N-(6-methyl-5-(8-morpholinoimidazo[1,2-a]pyridin-6-yl)pyridin-3-yl)-1H-pyrazole-4-carboxamide

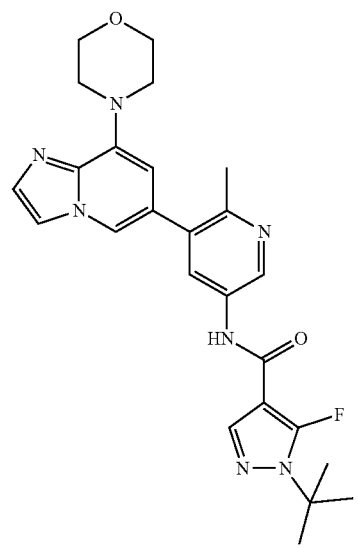

Step 1: To a stirred solution of 4-{6-chloroimidazo[1,2-a]pyridin-8-yl}morpholine (3 g, 12.62 mmol), bis(pinacolato)diboron (4.81 g, 18.93 mmol) and potassium acetate (3.72 g, 37.86 mmol) in dioxane (30 mL) was added Pd(dppf)Cl$_2$ CH₂Cl₂ (1.03 g, 1.26 mmol). The reaction mixture was degassed with nitrogen for three times and stirred for 2 h at 100° C. The resulting mixture was filtered, the filter cake was washed with ethyl acetate (3×100 mL). The filtrate was concentrated under reduced pressure to afford 4-[6-(4,4,5,5-tetramethyl-1,3,2-dioxaborolan-2-yl)imidazo[1,2-a]pyridin-8-yl]morpholine (4 g, crude) as a black oil. MS ESI calculated for $C_{17}H_{24}BN_3O_3$. $[M+H]^+$, 330.19, found 329.85.

Step 2: To a stirred mixture of 5-bromo-6-methylpyridin-3-amine (300 mg, 1.60 mmol) and 4-[6-(4,4,5,5-tetramethyl-1,3,2-dioxaborolan-2-yl)imidazo[1,2-a]pyridin-8-yl]morpholine (1.58 g, 1.60 mmol, 33%) in dioxane (4 mL) and water (1 mL) were added Pd(PPh₃)Cl₂ (112.58 mg, 0.16 mmol) and sodium carbonate (509.99 mg, 4.81 mmol) in portions. The reaction mixture was degassed with nitrogen for three times and stirred for 2 h at 80 C. The resulting mixture was diluted with water (20 mL). The resulting mixture was diluted with water (15 mL) and extracted with ethyl acetate (3×20 mL). The combined organic layers were washed with brine (3×30 mL), dried over anhydrous Na₂SO₄. After filtration, the filtrate was concentrated under reduced pressure. The residue was purified by silica gel column chromatography, eluted with DCM/MeOH (20/1). The fractions containing the desired product were combined and concentrated to afford 6-methyl-5-[8-(morpholin-4-yl)imidazo[1,2-a]pyridin-6-yl]pyridin-3-amine (400 mg, 80%) as a dark grey solid. MS ESI calculated for $C_{17}H_{19}N_5O$. $[M+H]^+$, 310.16, found 310.10.

Step 3: To a stirred mixture of 6-methyl-5-[8-(morpholin-4-yl)imidazo[1,2-a]pyridin-6-yl]pyridin-3-amine (100 mg, 0.32 mmol), bis(lambda2-cobalt(2+)) octakis(methanidylidyneoxidanium) (33.16 mg, 0.09 mmol) and Pd(dppf)Cl₂ CH₂Cl₂ (52.66 mg, 0.06 mmol) in dioxane (1 mL) were added triethylamine (196.25 mg, 1.94 mmol) and 4-bromo-1-(tert-butyl)-5-fluoro-1H-pyrazole (142.92 mg, 0.64 mmol). The reaction mixture was degassed with nitrogen for three times and stirred for 16 h at 90° C. The resulting mixture was diluted with water (10 mL) and extracted with ethyl acetate (3×10 mL). The combined organic layers were washed with brine (3×20 mL), dried over anhydrous sodium sulfate. After filtration, the filtrate was concentrated under reduced pressure. The residue was purified by silica gel column chromatography, eluted with DCM/MeOH (10/1). The residue was purified by Prep-HPLC with the following conditions: Column: XBridge Prep OBD C18 Column, 30×150 mm, 5 m; Mobile Phase A: water (Plus 10 mmol/L NH₄HCO₃), Mobile Phase B: acetonitrile; Flow rate: 60 mL/min; Gradient: 16% B to 26% B in 10 min, 26% B; Wavelength: 220 nm; RT1: 9.45 min.

The fractions containing the desired product were combined and concentrated to afford the title compound (7.7 mg, 5%) as an off-white solid. MS ESI calculated for $C_{25}H_{28}FN_7O_2$. $[M+H]^+$, 478.23, found 478.20; ¹H NMR (400 MHz, DMSO-d₆) δ 10.03 (s, 1H), 8.77 (d, J=2.5 Hz, 1H), 8.24 (d, J=1.4 Hz, 1H), 8.04 (d, J=2.5 Hz, 2H), 7.92-7.91 (m, 1H), 7.54-7.53 (m, 1H), 6.47-6.42 (m, 1H), 3.82 (t, J=4.5 Hz, 4H), 3.57 (t, J=4.6 Hz, 4H), 2.47 (s, 3H), 1.58 (d, J=1.5 Hz, 9H).

Example 138: 1-(tert-Butyl)-5-fluoro-N-(5-methyl-4-(8-morpholinoimidazo[1,2-a]pyridin-6-yl)pyridin-2-yl)-1H-pyrazole-4-carboxamide

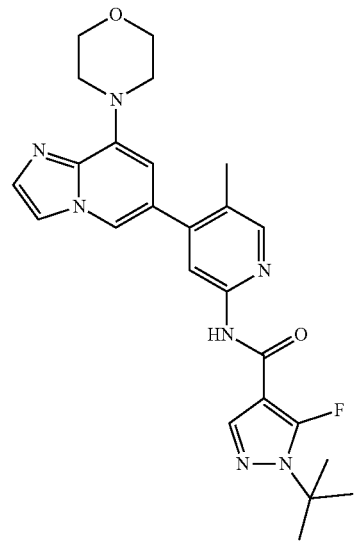

Step 1: To a stirred mixture of 4-bromo-5-methylpyridin-2-amine (300 mg, 1.60 mmol) and 4-[6-(4,4,5,5-tetramethyl-1,3,2-dioxaborolan-2-yl)imidazo[1,2-a]pyridin-8-yl]morpholine (1.58 g, 1.60 mmol, 33%) in dioxane (4 mL) and water (1 mL) were added Pd(PPh₃)₂Cl₂ (112.58 mg, 0.16 mmol) and sodium carbonate (0.51 g, 4.81 mmol). The reaction mixture was degassed with nitrogen for three times and stirred for 2 h at 80 °C. The resulting mixture was diluted with water (20 mL) and extracted with ethyl acetate (3×20 mL). The combined organic layers were washed with brine (3×30 mL), dried over anhydrous sodium sulfate. After filtration, the filtrate was concentrated under reduced pressure. The residue was purified by silica gel column chromatography, eluted with DCM/MeOH (20/1). The fractions containing the desired product were combined and concentrated to afford 5-methyl-4-[8-(morpholin-4-yl)imidazo[1,2-a]pyridin-6-yl]pyridin-2-amine (400 mg, 80%) as a dark grey solid. MS ESI calculated for $C_{17}H_{19}N_5O[M+H]^+$, 310.16, found 310.10.

Step 2: To a stirred solution of 5-methyl-4-[8-(morpholin-4-yl)imidazo[1,2-a]pyridin-6-yl]pyridin-2-amine (100 mg, 0.32 mmol), Pd(dppf)Cl₂ CH₂Cl₂ (26 mg, 0.03 mmol) and 4-bromo-1-(tert-butyl)-5-fluoro-1H-pyrazole (143 mg, 0.65 mmol) in dioxane (1 mL) were added bis(lambda2-cobalt(2+)) octakis(methanidylidyneoxidanium) (33 mg, 0.10 mmol) and TEA (98 mg, 0.96 mmol). The reaction mixture was degassed with nitrogen for three times and stirred for 16 h at 90 °C. The resulting mixture was concentrated under reduced pressure. The residue was purified by silica gel column chromatography, eluted with PE/EA/EtOH (4/3/1) to afford the crude product. The crude product (90 mg) was purified by Prep-HPLC with the following conditions: Column: XBridge Prep OBD C18 Column, 30×150 mm, 5 m; Mobile Phase A: water (Plus 10 mmol/L NH₄HCO₃), Mobile Phase B: ACN; Flow rate: 60 mL/min; Gradient: 33% B to 43% B in 10 min, 43% B; Wavelength: 220/254 nm; RT1: 10.2 min. The fractions containing the desired product were combined and concentrated to afford the title compound (49.5 mg, 32%) as a white solid. MS ESI calculated for C$_{25}$H$_{28}$FN$_7$O$_2$[M+H]$^+$, 478.23, found 478.15; $^1$H NMR (400 MHz, Chloroform-d) δ 8.31-8.29 (m, 1H), 8.25 (d, J=10.6 Hz, 2H), 7.87-7.86 (m, 2H), 7.69-7.63 (m, 1H), 7.61-7.60 (m, 1H), 6.48 (s, 1H), 4.03 (t, J=4.8 Hz, 4H), 3.58 (t, J=4.8 Hz, 4H), 2.32 (s, 3H), 1.68 (d, J=1.6 Hz, 9H).

Example 140: 1-(Tert-butyl)-N-(2-fluoro-4-methyl-5-(2-methyl-8-morpholinoimidazo[1,2-a]pyridin-6-yl)phenyl)-1H-imidazole-4-carboxamide

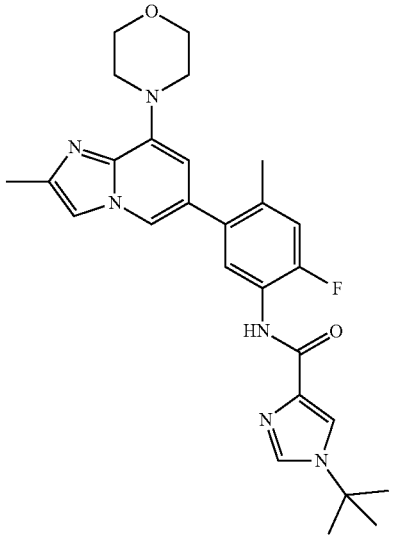 [SMILES: Cc1cn2cc(-c3cc(NC(=O)c4cn(C(C)(C)C)cn4)c(F)cc3C)cc(N3CCOCC3)c2n1]

Step 1: To a stirred solution of 5-bromo-3-(morpholin-4-yl)pyridin-2-amine (2 g, 7.74 mmol) in EtOH (20 mL) was added bromoacetone (2.12 g, 15.49 mmol) dropwise at room temperature under nitrogen atmosphere. The reaction mixture was stirred for 16 h at 80° C. under nitrogen atmosphere. The resulting mixture was concentrated under reduced pressure. The residue was purified by silica gel column chromatography, eluted with PE/EA/EtOH (4/3/1). The fractions containing the desired product were combined and concentrated to afford 4-{6-bromo-2-methylimidazo[1,2-a]pyridin-8-yl}morpholine (1 g, 43%) as a yellow solid. MS ESI calculated for C$_{12}$H$_{14}$BrN$_3$O [M+H]$^+$, 296.03, 298.03, found 295.95, 297.95; $^1$H NMR (400 MHz, Chloroform-d) δ 7.84 (d, J=1.6 Hz, 1H), 7.23 (d, J=1.2 Hz, 1H), 6.45-6.44 (m, 1H), 4.00-3.97 (m, 4H), 3.57-3.55 (m, 4H), 2.44 (s, 3H).

Step 2: To a stirred mixture of 4-{6-bromo-2-methylimidazo[1,2-a]pyridin-8-yl}morpholine (1 g, 3.37 mmol) and 2-fluoro-4-methyl-5-(4,4,5,5-tetramethyl-1,3,2-dioxaborolan-2-yl)aniline (933 mg, 3.71 mmol) in dioxane (10 mL) and H$_2$O (2.5 mL) were added K$_2$CO$_3$ (1.40 g, 10.12 mmol) and Pd(dppf)Cl$_2$CH$_2$Cl$_2$ (275 mg, 0.33 mmol). The reaction mixture was degassed with nitrogen for three times and stirred for 2 h at 80° C. The resulting mixture was diluted with water (50 mL) and extracted with EtOAc (3×200 mL). The combined organic layers were washed with brine (3×100 mL), dried over anhydrous Na$_2$SO$_4$. After filtration, the filtrate was concentrated under reduced pressure. The residue was purified by silica gel column chromatography, eluted with PE/EA (1/1). The fractions containing the desired product were combined and concentrated to afford 2-fluoro-4-methyl-5-[2-methyl-8-(morpholin-4-yl)imidazo[1,2-a]pyridin-6-yl]aniline (400 mg, 34%) as a brown solid. MS ESI calculated for C$_{19}$H$_{21}$FN$_4$O [M+H]$^+$, 341.17, found 341.15.

Step 3: To a stirred mixture of 2-fluoro-4-methyl-5-[2-methyl-8-(morpholin-4-yl)imidazo[1,2-a]pyridin-6-yl]aniline (100 mg, 0.29 mmol) in LiHMDS (1 mL, 1 M) was added ethyl 1-tert-butylimidazole-4-carboxylate (58 mg, 0.29 mmol) in THF (0.5 mL) dropwise at 0° C. under nitrogen atmosphere. The reaction mixture was stirred for 1 h at room temperature under nitrogen atmosphere. The resulting mixture was quenched with NH$_4$Cl (aq.) and extracted with EtOAc (3×50 mL). The combined organic layers were washed with brine (3×20 mL), dried over anhydrous Na$_2$SO$_4$. After filtration, the filtrate was concentrated under reduced pressure. The residue was purified by Prep-TLC, eluted with PE/EA/EtOH (4/3/1) to afford the crude product. The crude product was purified by reversed-phase flash chromatography with the following conditions: column, C18 silica gel; mobile phase, MeCN in water (Plus 0.1% FA), 10% to 50% gradient in 20 min; detector, UV 254 nm. The fractions containing the desired product were combined to afford the title compound (37.8 mg, 26%) as a white solid. MS ESI calculated for C$_{27}$H$_{31}$FN$_6$O$_2$ [M+H]$^+$, 491.25, found 491.20; $^1$H NMR (400 MHz, Chloroform-d) δ 9.20 (s, 1H), 8.42 (d, J=8.0 Hz, 1H), 7.79 (d, J=1.2 Hz, 1H), 7.72-7.71 (m, 1H), 7.63 (d, J=1.2 Hz, 1H), 7.31-7.29 (m, 1H), 7.08 (d, J=11.4 Hz, 1H), 6.45 (s, 1H), 4.04-4.00 (m, 4H), 3.51-3.47 (m, 4H), 2.54 (s, 3H), 2.27 (s, 3H), 1.63 (s, 9H).

Example 141: 1-Tert-butyl-4-fluoro-N-{2-fluoro-4-methyl-5-[8-(morpholin-4-yl)imidazo[1,2-a]pyridin-6-yl]phenyl}pyrazole-3-carboxamide

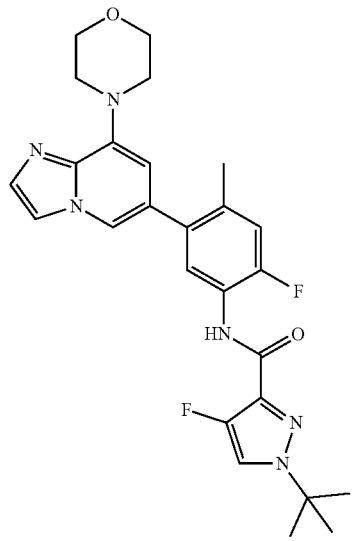 [SMILES: Cc1cc(F)c(NC(=O)c2nn(C(C)(C)C)cc2F)cc1-c1cc(N2CCOCC2)c2nccn2c1]

Step 1: To a stirred solution of 1H-pyrazole-3-carboxylic acid (4.5 g, 40.15 mmol) in tert-Butanol (50 mL) was added H$_2$SO$_4$ (2.18 mL, 40.15 mmol, 98%) dropwise at room temperature under nitrogen atmosphere. The reaction mixture was stirred for 16 h at 100° C. under nitrogen atmosphere. The resulting mixture was concentrated under reduced pressure. The residue was dissolved in water (50 mL) and extracted with dichlormethane (3×50 mL). After filtration, the filtrate was concentrated under reduced pressure to afford 1-tert-butylpyrazole-3-carboxylic acid (5.6 g, crude) as an off-white solid. MS ESI calculated for $C_8H_{12}N_2O_2$ [M+H]$^+$, 169.09, found 169.10.

Step 2: To a stirred solution of 1-tert-butylpyrazole-3-carboxylic acid (5.5 g, 32.70 mmol) in ethyl alcohol (55 mL) was added $H_2SO_4$ (0.18 mL, 3.27 mmol, 98%) dropwise at room temperature under nitrogen atmosphere. The reaction mixture was stirred for 16 h at 80° C. under nitrogen atmosphere. The resulting mixture was concentrated under reduced pressure. The residue was neutralized to pH 7 with saturated sodium bicarbonate (aq.). and extracted with dichlormethane (3×20 mL). The combined organic layers were dried over anhydrous sodium sulfate. After filtration, the filtrate was concentrated under reduced pressure. The residue was purified by silica gel column chromatography, eluted with PE/EA (5/1). The fractions containing the desired product were combined and concentrated to afford ethyl 1-tert-butylpyrazole-3-carboxylate (4 g, 62%) as a light yellow oil. MS ESI calculated for $C_{10}H_{16}MN_2O_2$. [M+H]$^+$, 197.12, found 197.10.

Step 3: To a stirred mixture of ethyl 1-tert-butylpyrazole-3-carboxylate (2 g, 10.19 mmol) in acetonitrile (25 mL) was added Select fluor (3.97 g, 11.21 mmol). The reaction mixture was stirred for 72 h at 80° C. under nitrogen atmosphere. The resulting mixture was concentrated under reduced pressure. The residue was dissolved in dichloromethane (20 mL). The resulting mixture was filtered, the filter cake was washed with dichloromethane (3×20 mL). The filtrate was concentrated under reduced pressure. The residue was purified by reverse phase Flash chromatography with the following conditions: Column: WelFlash TM C18-I, 20-40 μm, 40 g; Eluent A: water (Plus 0.05% TFA); Eluent B: acetonitrile; Gradient: 25% to 45% B in 25 min; Flow rate: 35 mL/min; Detector: 254 nm. The fractions containing the desired product were combined and concentrated to afford ethyl 1-tert-butyl-4-fluoropyrazole-3-carboxylate (690 mg, 31%) as a light yellow oil. MS ESI calculated for $C_{10}H_{15}FN_2O_2$. [M+H]$^+$, 215.11, found 215.05; $^1$H NMR (400 MHz, Chloroform-d) δ 7.44 (d, J=4.8 Hz, 1H), 4.41 (q, J=7.1 Hz, 2H), 1.59 (s, 9H), 1.39 (t, J=7.1 Hz, 3H).

Step 4: To a stirred solution of 2-fluoro-4-methyl-5-[8-(morpholin-4-yl)imidazo[1,2-a]pyridin-6-yl]aniline (100 mg, 0.31 mmol) in LiHMDS (1.5 mL) was added ethyl 1-tert-butyl-4-fluoropyrazole-3-carboxylate (66.34 mg, 0.31 mmol) in THF (1.5 mL) dropwise at 0° C. under nitrogen atmosphere. The reaction mixture was stirred for 1 h at room temperature under nitrogen atmosphere. The reaction was quenched by the addition of sat. NH$_4$Cl (aq.) (10 mL) and extracted with EtOAc (3×10 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EA (1/3) to afford the crude product. The crude product was purified by trituration with acetone (5 mL). The precipitated solids were collected by filtration and washed with acetone (3×2 mL) to afford the title compound (73.2 mg, 48%) as a white solid. MS ESI calculated for $C_{26}H_{28}F_2N_6O2$ [M+H]$^+$, 495.22, found 495.20; $^1$H NMR (400 MHz, DMSO-d$_6$) δ 9.47 (s, 1H), 8.22 (d, J=4.4 Hz, 1H), 8.16 (d, J=1.4 Hz, 1H), 7.90 (d, J=1.2 Hz, 1H), 7.73 (d, J=8.0 Hz, 1H), 7.52 (d, J=1.2 Hz, 1H), 7.30 (d, J=11.6 Hz, 1H), 6.38 (d, J=1.6 Hz, 1H), 3.81 (t, J=4.6 Hz, 4H), 3.56 (t, J=4.6 Hz, 4H), 2.30 (s, 3H), 1.57 (s, 9H).

Example 142: 1-Tert-butyl-4-fluoro-N-{4-methyl-3-[8-(morpholin-4-yl)imidazo[1,2-a]pyridin-6-yl]phenyl}pyrazole-3-carboxamide

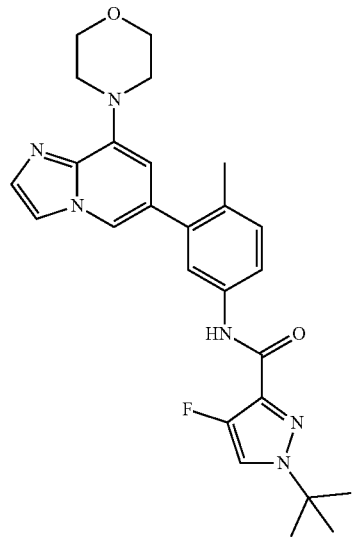 [SMILES: Cc1ccc(NC(=O)c2nn(C(C)(C)C)cc2F)cc1-c1cc(N2CCOCC2)c2nccn2c1]

Step 1: To a stirred solution of 4-methyl-3-[8-(morpholin-4-yl)imidazo[1,2-a]pyridin-6-yl]aniline (100 mg, 0.32 mmol) in LiHMDS (1.5 mL) was added ethyl 1-tert-butyl-4-fluoropyrazole-3-carboxylate (69.47 mg, 0.32 mmol) in THF (1 mL) dropwise at 0° C. under nitrogen atmosphere. The reaction mixture was stirred for 1 h at room temperature under nitrogen atmosphere. The resulting mixture was quenched with sat. NH$_4$Cl (aq.) at room temperature. The resulting mixture was extracted with EA (3×20 mL). The combined organic layers were washed with brine (3×10 mL), dried over anhydrous sodium sulfate. After filtration, the filtrate was concentrated under reduced pressure. The residue was purified by Prep-TLC, eluted with DCM/MeOH (20/1) to afford the crude product. The crude product was purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: acetonitrile; Flow rate: 60 mL/min; Gradient: 36% B to 46% B in 10 min, 46% B; Wavelength: 220/254 nm; RT1: 10.18 min. The fractions containing the desired product were combined and concentrated to afford the title compound (83.6 mg, 54%) as an off-white solid. MS ESI calculated for $C_{26}H_{29}FN_6O_2$. [M+H]$^+$, 477.23, found 477.25; $^1$H NMR (400 MHz, DMSO-d$_6$) δ 9.76 (s, 1H), 8.22-8.14 (m, 2H), 7.91 (d, J=1.2 Hz, 1H), 7.79-7.71 (m, 2H), 7.52 (d, J=1.2 Hz, 1H), 7.29 (d, J=8.2 Hz, 1H), 6.40 (d, J=1.5 Hz, 1H), 3.85 (t, J=4.7 Hz, 4H), 3.56 (t, J=4.7 Hz, 4H), 2.27 (s, 3H), 1.57 (s, 9H).

Example 143: 1-(tert-Butyl)-5-fluoro-N-(2-fluoro-4-methyl-5-(2-methyl-8-morpholinoimidazo[1,2-a]pyridin-6-yl)phenyl)-1H-pyrazole-4-carboxamide

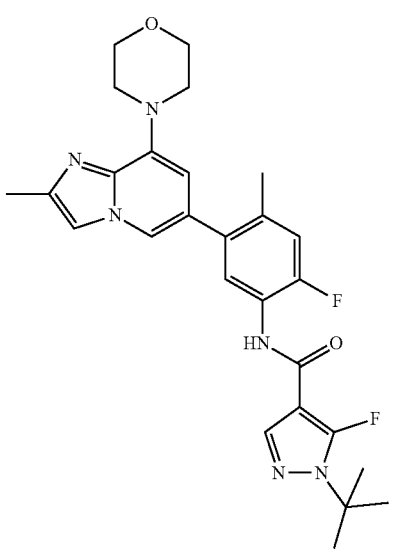 [SMILES: Cc1cn2cc(-c3cc(NC(=O)c4cnn(C(C)(C)C)c4F)c(F)cc3C)cc(N3CCOCC3)c2n1]

Step 1: To a stirred mixture of 2-fluoro-4-methyl-5-[2-methyl-8-(morpholin-4-yl)imidazo[1,2-a]pyridin-6-yl]aniline (100 mg, 0.29 mmol), TEA (0.12 mL, 0.88 mmol) and bis(lambda2-cobalt(2+)) octakis(methanidylidyneoxidanium) (30 mg, 0.09 mmol) in dioxane (1 mL) were added 4-bromo-1-(tert-butyl)-5-fluoro-1H-pyrazole (130 mg, 0.58 mmol) and Pd(dppf)C$_{12}$ CH$_2$Cl$_2$ (48 mg, 0.06 mmol). The reaction mixture was degassed with nitrogen for three times and stirred for 16 h at 80° C. The resulting mixture was diluted with water (20 mL) and extracted with EtOAc (3×50 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EA (1/1) to afford the crude product. The crude product was purified by reversed-phase flash chromatography (Conditions: column, C18 silica gel; mobile phase, MeCN in Water (Plus 0.1% FA), 10% to 50% gradient in 10 min; detector, UV 254 nm) to afford the title compound (12.7 mg, 8%) as a white solid. MS ESI calculated for C$_{27}$H$_{30}$F$_2$N$_6$O$_2$ [M+H]$^+$, 509.24, found 509.25; $^1$H NMR (400 MHz, Chloroform-d) δ 8.34 (d, J=8.4 Hz, 1H), 7.84 (d, J=2.4 Hz, 1H), 7.68-7.67 (m, 2H), 7.29-7.26 (m, 1H), 7.07 (d, J=11.6 Hz, 1H), 6.37 (s, 1H), 4.02-4.00 (m, 4H), 3.56-3.53 (m, 4H), 2.49 (s, 3H), 2.27 (s, 3H), 1.68 (d, J=1.6 Hz, 9H).

Example 148: 1-Tert-butyl-2-fluoro-N-{2-fluoro-4-methyl-5-[2-methyl-8-(morpholin-4-yl)imidazo[1,2-a]pyridin-6-yl]phenyl}imidazole-4-carboxamide

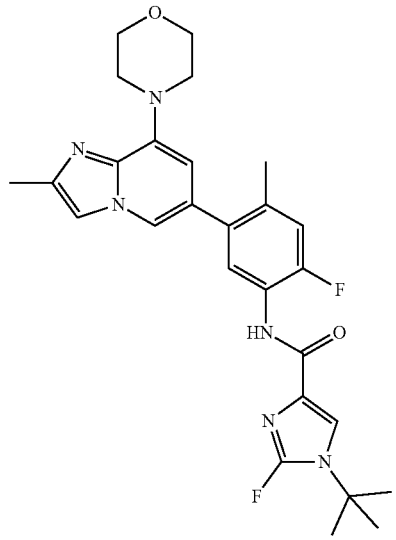 [SMILES: Cc1cn2cc(-c3cc(NC(=O)c4cn(C(C)(C)C)c(F)n4)c(F)cc3C)cc(N3CCOCC3)c2n1]

Step 1: To a stirred mixture of ethyl 1-tert-butylimidazole-4-carboxylate (300 mg, 1.53 mmol) and sodium bicarbonate (385.25 mg, 4.59 mmol) in acetonitrile (10 mL) was added Selectfluor (2.71 g, 7.65 mmol). The reaction mixture was stirred for 16 h at room temperature under nitrogen atmosphere. The resulting mixture was diluted with water (10 mL) and extracted with ethyl acetate (3×10 mL). The combined organic layers were washed with brine (3×20 mL), dried over anhydrous sodium sulfate. After filtration, the filtrate was concentrated under reduced pressure. The residue was purified by silica gel column chromatography, eluted with PE/EA (1/1). The fractions containing the desired product were combined and concentrated to afford ethyl 1-tert-butyl-2-fluoroimidazole-4-carboxylate (100 mg, 30%) as a brown oil. MS ESI calculated for C$_{10}$H$_{15}$FN$_2$O$_2$. [M+H]$^+$, 215.11, found 215.05.

Step 2: To a stirred solution of 2-fluoro-4-methyl-5-[2-methyl-8-(morpholin-4-yl)imidazo[1,2-a]pyridin-6-yl]aniline (100 mg, 0.29 mmol) in LiHMDS (1 mL) was added ethyl 1-tert-butyl-2-fluoroimidazole-4-carboxylate (63 mg, 0.29 mmol) at 0° C. under nitrogen atmosphere. The reaction mixture was stirred for 2 h at room temperature under nitrogen atmosphere. The resulting mixture was quenched with NH$_4$Cl (aq.) and extracted with EtOAc (3×50 mL). The combined organic layers were washed with brine (3×10 mL), dried over anhydrous Na$_2$SO$_4$. After filtration, the filtrate was concentrated under reduced pressure. The residue was purified by Prep-HPLC (Conditions: Column: XBridge Prep OBD C18 Column, 30×150 mm, 5 m; Mobile Phase A: water (Plus 10 mmol/L NH$_4$HCO$_3$), Mobile Phase B: MeCN; Flow rate: 60 mL/min; Gradient: 40% B to 50% B in 10 min, 50% B; Wavelength: 220 nm; RT1: 10.52 min). The fractions containing the desired product were combined and concentrated to afford the title compound (5.8 mg, 3%) as a white solid. MS ESI calculated for C$_{27}$H$_{30}$F$_2$N$_6$O$_2$ [M+H]$^+$, 509.24, found 509.30; $^1$H NMR (400 MHz, Chloroform-d) δ 8.97 (s, 1H), 8.45 (d, J=8.0 Hz, 1H), 7.73-7.72 (m, 1H), 7.31-7.30 (m, 1H), 7.24-7.22 (m, 1H), 7.07 (d, J=11.6 Hz, 1H), 6.51 (s, 1H), 4.06-4.02 (m, 4H), 3.50-3.48 (m, 4H), 2.57 (s, 3H), 2.27 (s, 3H), 1.68 (s, 9H).

Example 151: 1-Tert-butyl-N-{4-chloro-2-fluoro-5-[8-(morpholin-4-yl)imidazo[1,2-a]pyridin-6-yl]phenyl}-2-fluoroimidazole-4-carboxamide

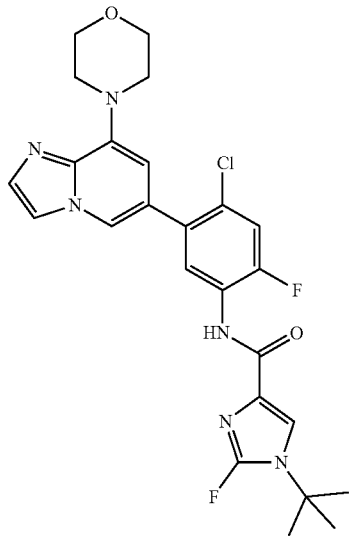 [SMILES: CC(C)(C)n1cc(C(=O)Nc2cc(-c3cc(N4CCOCC4)c4nccn4c3)c(Cl)cc2F)nc1F]

Step 1: To a stirred solution of 5-bromo-2-fluoroaniline (5 g, 26.31 mmol) in ACN (50 mL) was added NCS (3.51 g, 26.31 mmol) at room temperature. The reaction mixture was stirred for 16 h at room temperature. The resulting mixture was concentrated under reduced pressure. The residue was diluted with water (100 mL) and extracted with EtOAc (3×200 mL). The combined organic layers were washed with brine (3×300 mL), dried over anhydrous $Na_2SO_4$. After filtration, the filtrate was concentrated under reduced pressure. The residue was purified by silica gel column chromatography, eluted with PE/EA (1/9). The fractions containing the desired product were combined and concentrated to afford 5-bromo-4-chloro-2-fluoroaniline (4.3 g, 72%) as a red solid. MS ESI calculated for $C_6H_4BrClFN$ $[M+H]^+$, 223.92, found 223.90.

Step 2: To a stirred solution of 5-bromo-4-chloro-2-fluoroaniline (200 mg, 0.89 mmol), $Na_2CO_3$ (283.31 mg, 2.67 mmol) and $Pd(PPh_3)_2Cl_2$ (62.54 mg, 0.08 mmol) in dioxane (2 mL) and $H_2O$ (0.4 mL) was added 4-(6-(4,4,5,5-tetramethyl-1,3,2-dioxaborolan-2-yl)imidazo[1,2-a]pyridin-8-yl)morpholine (888.93 mg, 1.34 mmol) at room temperature. The reaction mixture was degassed with nitrogen for three times and stirred for 1 h at 80° C. The resulting mixture was concentrated under reduced pressure. The residue was purified by silica gel column chromatography, eluted with PE/EA (1/9). The fractions containing the desired product were combined and concentrated to afford 4-chloro-2-fluoro-5-[8-(morpholin-4-yl)imidazo[1,2-a]pyridin-6-yl]aniline (108.2 mg, 35%) as a yellow solid. MS ESI calculated for $C_{17}H_{16}ClFN_4O$ $[M+H]^+$, 347.10, found 347.10; $^1H$ NMR (400 MHz, $CDCl_3$) δ 7.82 (d, J=1.4 Hz, 1H), 7.65-7.51 (m, 2H), 7.17 (d, J=10.5 Hz, 1H), 6.81 (d, J=9.3 Hz, 1H), 6.47 (d, J=1.4 Hz, 1H), 4.13-3.90 (m, 4H), 3.85 (s, 2H), 3.70-3.47 (m, 4H).

Step 3: To a stirred solution of 4-chloro-2-fluoro-5-[8-(morpholin-4-yl)imidazo[1,2-a]pyridin-6-yl]aniline (80 mg, 0.23 mmol) in 1 M LiHMDS in THF (3 mL) was added ethyl 1-tert-butyl-2-fluoroimidazole-4-carboxylate (49.42 mg, 0.23 mmol) in THF (1 mL) dropwise at 0° C. The reaction mixture was stirred for 2 h at room temperature. The reaction was quenched with sat. $NH_4Cl$ (aq.) at room temperature. The resulting mixture was extracted with EtOAc (3×30 mL). The combined organic layers were washed with brine (30 mL), dried over anhydrous $Na_2SO_4$. After filtration, the filtrate was concentrated under reduced pressure. The residue was purified by silica gel column chromatography, eluted with PE/EA/EtOH (2/3/1) to afford the crude product (100 mg). The crude product (100 mg) was purified by Prep-HPLC with the following conditions: Column: XBridge Prep OBD C18 Column, 30×150 mm, 5 m; Mobile Phase A: water (Plus 10 mmol/L $NH_4HCO_3$), Mobile Phase B: ACN; Flow rate: 60 mL/min; Gradient: 40% B to 50% B in 10 min, 50% B; Wavelength: 220/254 nm; RT1: 10.67 min. The fractions containing the desired product were combined and concentrated to afford the title compound (24.8 mg, 20%) as a white solid. MS ESI calculated for $C_{25}H_{25}Cl_1F_2N_6O_2$ $[M+H]^+$, 515.17, 517.17, found 515.15, 517.15; $^1H$ NMR (400 MHz, DMSO-$d_6$) δ 9.54 (s, 1H), 8.27 (d, J=1.4 Hz, 1H), 8.06 (d, J=8.2 Hz, 1H), 7.95 (d, J=1.2 Hz, 1H), 7.73-7.66 (m, 2H), 7.54 (d, J=1.1 Hz, 1H), 6.44 (d, J=1.5 Hz, 1H), 3.81 (t, J=4.7 Hz, 4H), 3.56 (t, J=4.7 Hz, 4H), 1.60 (s, 9H).

Example 153: 1-(tert-Butyl)-N-(5-(8-(3,6-dihydro-2H-pyran-4-yl)imidazo[1,2-a]pyridin-6-yl)-2-fluoro-4-methylphenyl)-5-fluoro-1H-pyrazole-4-carboxamide

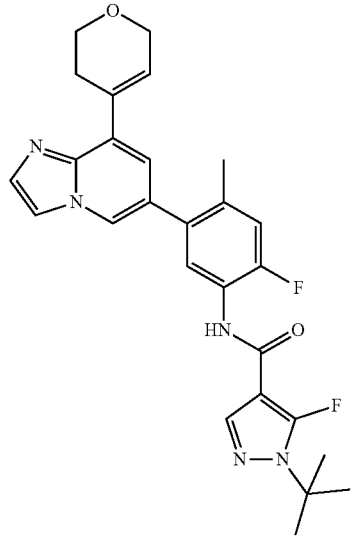 [SMILES: Cc1cc(F)c(NC(=O)c2cnn(C(C)(C)C)c2F)cc1-c1cc(C2=CCOCC2)c2nccn2c1]

Step 1: To a stirred mixture of 8-bromo-6-chloroimidazo[1,2-a]pyridine (1 g, 4.32 mmol) and 2-(3,6-dihydro-2H-pyran-4-yl)-4,4,5,5-tetramethyl-1,3,2-dioxaborolane (1.00 g, 4.75 mmol) in dioxane (10 mL) and water (2.5 mL) were added $Pd(PPh_3)_2Cl_2$ (303.22 mg, 0.43 mmol) and $Na_2CO_3$ (1.37 g, 12.96 mmol) at room temperature. The reaction mixture was degassed with nitrogen for three times and stirred for 1 h at 80° C. The resulting mixture was diluted with water (50 mL) and extracted with ethyl acetate (3×50 mL). The combined organic layers were washed with brine (3×50 mL), dried over anhydrous sodium sulfate. After filtration, the filtrate was concentrated under reduced pressure. The residue was purified by silica gel column chromatography, eluted with DCM/MeOH (20/1). The fractions containing the desired product were combined and concentrated to afford 6-chloro-8-(3,6-dihydro-2H-pyran-4-yl)imidazo[1,2-a]pyridine (0.8 g, 78%) as a light yellow oil. MS ESI calculated for CuH11ClN20. [M+H]$^+$, 235.06, found 235.00.

Step 2: To a stirred mixture of 6-chloro-8-(3,6-dihydro-2H-pyran-4-yl)imidazo[1,2-a]pyridine (0.8 g, 3.41 mmol) and 2-fluoro-4-methyl-5-(4,4,5,5-tetramethyl-1,3,2-dioxaborolan-2-yl)aniline (0.86 g, 3.41 mmol) in THE (10 mL) and water (1 mL) were added XPhos Pd G2 (0.27 g, 0.34 mmol) and K$_3$PO$_4$ (1.45 g, 6.82 mmol) at room temperature. The reaction mixture was degassed with nitrogen for three times and stirred for 1 h at 80° C. The resulting mixture was diluted with water (30 mL) and extracted with ethyl acetate (3×50 mL). The combined organic layers were washed with brine (3×40 mL), dried over anhydrous sodium sulfate. After filtration, the filtrate was concentrated under reduced pressure. The residue was purified by reverse phase Flash chromatography with the following conditions: Column: WelFlash TM C18-I, 20-40 μm, 80 g; Eluent A: water (Plus 0.1% TFA); Eluent B: acetonitrile; Gradient: 10%-30% B in 25 min; Flow rate: 50 mL/min; Detector: 254 nm. The fractions containing the desired fractions were combined and concentrated to afford 5-[8-(3,6-dihydro-2H-pyran-4-yl)imidazo[1,2-a]pyridin-6-yl]-2-fluoro-4-methylaniline (1 g, 90%) as a dark red solid. MS ESI calculated for C$_{19}$H$_{18}$FN$_3$O. [M+H]$^+$, 324.14, found 324.10; $^1$H NMR (400 MHz, DMSO-d$_6$) δ 8.77-8.72 (m, 1H), 8.30 (d, J=2.0 Hz, 1H), 8.14 (d, J=2.0 Hz, 1H), 7.71-7.69 (m, 1H), 7.03 (d, J=12.3 Hz, 1H), 6.75 (d, J=9.1 Hz, 1H), 6.63-6.61 (m, 1H), 4.31(q, J=2.8 Hz, 2H), 3.88 (t, J=5.4 Hz, 2H), 2.59-2.56 (m, 2H), 2.13 (s, 3H). $^{19}$F NMR (376 MHz, DMSO) δ -74.22.

Step 3: To a stirred mixture of 5-[8-(3,6-dihydro-2H-pyran-4-yl)imidazo[1,2-a]pyridin-6-yl]-2-fluoro-4-methylaniline (100 mg, 0.31 mmol) and Pd(dppf)Cl$_2$ DCM (50.38 mg, 0.06 mmol) in dioxane (2 mL) were added 4-bromo-1-(tert-butyl)-5-fluoro-1H-pyrazole (136.73 mg, 0.62 mmol) and triethylamine (187.76 mg, 1.85 mmol) dropwise at room temperature. The reaction mixture was degassed with nitrogen for three times and stirred for 16 h at 90° C. The resulting mixture was concentrated under reduced pressure. The residue was purified by silica gel column chromatography, eluted with DCM/MeOH (10/1) to afford the crude product. The crude product was further purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: acetonitrile; Flow rate: 60 mL/min; Gradient: 43% B to 53% B in 10 min, 53% B; Wavelength: 220/254 nm; RT1: 9.12 min. The fractions containing the desired product were combined and concentrated under reduced pressure to afford the title compound (53.8 mg, 35%) as an off-white solid. MS ESI calculated for C$_{27}$H$_{27}$F$_2$N$_5$O$_2$. [M+H]$^+$, 492.21, found 492.20; $^1$H NMR (400 MHz, DMSO-d$_6$) δ 9.71 (s, 1H), 8.52 (d, J=1.6 Hz, 1H), 7.99 (dd, J=8.5, 1.8 Hz, 2H), 7.73 (d, J=3.0 Hz, 1H), 7.62 (d, J=1.2 Hz, 1H), 7.56 (d, J=7.9 Hz, 1H), 7.31 (d, J=11.4 Hz, 1H), 7.14 (d, J=1.6 Hz, 1H), 4.34 (q, J=2.7 Hz, 2H), 3.87 (t, J=5.4 Hz, 2H), 2.64-2.62 (m, 2H), 2.30 (s, 3H), 1.57 (s, 9H).

Example 159: 1-(tert-Butyl)-N-(2,3-difluoro-4-methyl-5-(8-morpholinoimidazo[1,2-a]pyridin-6-yl)phenyl)-5-fluoro-1H-pyrazole-4-carboxamide

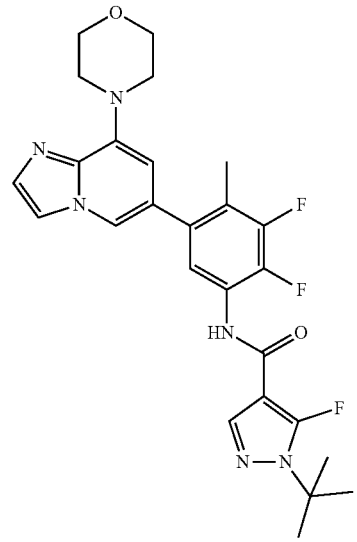 [SMILES: Cc1c(-c2cc(N3CCOCC3)c3nccn3c2)cc(NC(=O)c2cnn(C(C)(C)C)c2F)c(F)c1F]

Step 1: To a stirred solution of 2,3-difluoro-4-methylbenzoic acid (800 mg, 4.65 mmol), H$_2$O (3 mL), HNO$_3$ (3.9 mL) and Br$_2$ (0.5 mL, 9.30 mmol) in CH$_3$COOH (15 mL) was added AgNO$_3$ (1.58 g, 9.30 mmol) in H$_2$O (3 mL) dropwise at 0° C. The reaction mixture was stirred for 3 h at room temperature. The resulting mixture was filtered, the filter cake was washed with CH$_3$COOH (3×20 mL). The filtrate was concentrated under reduced pressure. The residue was purified by reverse flash chromatography with the following conditions: column, C18 silica gel; mobile phase, acetonitrile in water, 5% to 95% gradient in 25 min; detector, UV 208/254 nm. The fractions containing the desired product were combined and concentrated to afford 5-bromo-2,3-difluoro-4-methylbenzoic acid (940 mg, 67%) as a light brown solid. MS ESI calculated for C$_8$H$_5$BrF$_2$O$_2$[M –H]$^+$, 248.94, 250.94, found 248.90, 250.90; $^1$H NMR (400 MHz, DMSO-d$_6$) δ 13.75 (s, 1H), 7.84 (dd, J=6.4, 2.4 Hz, 1H), 2.35 (d, J=2.8 Hz, 3H). $^{19}$F NMR (376 MHz, DMSO-d$_6$) δ -134.39 (1F), - 136.95 (1F).

Step 2: To a stirred solution of 5-bromo-2,3-difluoro-4-methylbenzoic acid (940 mg, 3.75 mmol) and TEA (416 mg, 4.12 mmol) in Toluene (10 mL) was added DPPA (1.13 g, 4.12 mmol) dropwise at room temperature under nitrogen atmosphere. The reaction mixture was stirred for 1 h at 120° C. under nitrogen atmosphere. To the above mixture was added t-BuOH (2 mL) dropwise at room temperature. The reaction mixture was stirred for additional 3 h at 120° C. The resulting mixture was quenched with water (100 mL) and extracted with ethyl acetate (3×60 mL). The combined organic layers were washed with saturated brine (50 mL), dried over anhydrous sodium sulfate. After filtration, the filtrate was concentrated under reduced pressure. The residue was purified by reverse flash chromatography with the following conditions: column, C18 silica gel; mobile phase, acetonitrile in water (Plus 10 mmol/L NH$_4$HCO$_3$), 5% to 95% gradient in 25 min; detector, UV 233/254 nm. The fractions containing the desired product were combined and concentrated to afford tert-butyl N-(5-bromo-2,3-difluoro-4-methylphenyl)carbamate (290 mg, 15%) as a light brown solid. MS ESI calculated for $C_{12}H_{14}BrF_2NO_2$ [M - H]$^+$, 320.02, 322.02, found 319.95, 321.95; $^1$H NMR (400 MHz, Chloroform-d) δ 8.17 (d, J=6.4 Hz, 1H), 6.65 (s, 1H), 2.31 (d, J=2.8 Hz, 3H), 1.55 (s, 9H).

Step 3: To a stirred mixture of tert-butyl N-(5-bromo-2,3-difluoro-4-methylphenyl)carbamate (290 mg, 0.90 mmol), 4-[6-(4,4,5,5-tetramethyl-1,3,2-dioxaborolan-2-yl)imidazo[1,2-a]pyridin-8-yl]morpholine (889 mg, 2.70 mmol, 33%) and $K_2CO_3$ (373 mg, 2.70 mmol) in $H_2O$ (1 mL) and dioxane (4 mL) was added Pd(dppf)Cl$_2$·CH$_2$Cl$_2$ (73 mg, 0.09 mmol). The reaction mixture was degassed with nitrogen for three times and stirred for 2 h at 80° C. The resulting mixture was diluted with water (50 mL) and extracted with ethyl acetate (3×50 mL). The combined organic layers were washed with brine (50 mL), dried over anhydrous sodium sulfate. After filtration, the filtrate was concentrated under reduced pressure. The residue was purified by silica gel column chromatography, eluted with PE/EA/EtOH (8/4/1). The fractions containing the desired product were combined and concentrated to afford tert-butyl N-{2,3-difluoro-4-methyl-5-[8-(morpholin-4-yl)imidazo[1,2-a]pyridin-6-yl]phenyl}carbamate (120 mg, 27%) as a light brown solid. MS ESI calculated for $C_{23}H_{26}F_2N_4O_3$[M - H]$^+$, 443.20, found 443.05; $^1$H NMR (400 MHz, Chloroform-d) δ 7.87 (d, J=7.2 Hz, 1H), 7.82-7.80 (m, 1H), 7.77-7.73 (m, 1H), 7.62-7.61 (m, 1H), 6.76-6.73 (m, 1H), 6.56 (s, 1H), 4.06 (t, J=4.6 Hz, 4H), 3.49 (t, J=4.6 Hz, 4H), 2.19 (d, J=2.4 Hz, 3H), 1.54 (s, 9H).

Step 4: To a stirred solution of tert-butyl N-{2,3-difluoro-4-methyl-5-[8-(morpholin-4-yl)imidazo[1,2-a]pyridin-6-yl]phenyl}carbamate (120 mg, 0.27 mmol) in DCM (2 mL) was added HCl (gas) in EtOAc (2 mL) (4 M) dropwise at 0° C. The reaction mixture was stirred for 2 h at room temperature. The resulting mixture was basified to pH 8 with saturated NaHCO$_3$ (aq.). The resulting mixture was extracted with ethyl acetate (3×30 mL). The combined organic layers were washed with brine (30 mL), dried over anhydrous sodium sulfate. After filtration, the filtrate was concentrated under reduced pressure. The residue was purified by silica gel column chromatography, eluted with PE/EA/EtOH (4/3/1). The fractions containing the desired product were combined and concentrated to afford 2,3-difluoro-4-methyl-5-[8-(morpholin-4-yl)imidazo[1,2-a]pyridin-6-yl]aniline (85 mg, 91%) as a light brown solid. MS ESI calculated for $C_{18}H_{18}F_2N_4O$ [M+H]$^+$, 345.14, found 345.05; $^1$H NMR (400 MHz, Chloroform-d) δ 7.72 (d, J=1.2 Hz, 1H), 7.67-7.64 (m, 1H), 7.58 (d, J=1.2 Hz, 1H), 6.51 (dd, J=8.0, 2.0 Hz, 1H), 6.40-6.36 (m, 1H), 4.03-4.01 (m, 4H), 3.81 (s, 2H), 3.56-3.54 (m, 4H), 2.12 (d, J=2.4 Hz, 3H).

Step 5: To a stirred mixture of 2,3-difluoro-4-methyl-5-[8-(morpholin-4-yl)imidazo[1,2-a]pyridin-6-yl]aniline (80 mg, 0.23 mmol), Pd(dppf)C$_{12}$·CH$_2$Cl$_2$ (38 mg, 0.05 mmol) and bis(lambda2-cobalt(2+)) octakis(methanidylidyneoxidanium) (24 mg, 0.07 mmol) in dioxane (1 mL) were added TEA (141 mg, 1.39 mmol) and 4-bromo-1-(tert-butyl)-5-fluoro-1H-pyrazole (103 mg, 0.46 mmol). The reaction mixture was degassed with nitrogen for three times and stirred for 16 h at 90° C. The resulting mixture was concentrated under reduced pressure. The residue was purified by silica gel column chromatography, eluted with PE/EA/EtOH (4/3/1) to afford the crude product. The crude product (70 mg) was purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: MeCN; Flow rate: 60 mL/min; Gradient: 43% B to 53% B in 10 min, 53% B; Wavelength: 220 nm; RT1: 9.02 min. The fractions containing the desired product were combined and concentrated to afford the title compound (23.7 mg, 20%) as an off-white solid. MS ESI calculated for $C_{26}H_{27}F_3N_6O_2$ [M+H]$^+$, 513.21, found 513.25; $^1$H NMR (400 MHz, Chloroform-d) δ 8.16 (dd, J=6.8, 1.6 Hz, 1H), 7.87 (d, J=0.8 Hz, 1H), 7.78 (d, J=0.8 Hz, 1H), 7.68-7.66 (m, 1H), 7.64-7.60 (m, 1H), 7.57 (d, J=0.8 Hz, 1H), 6.37 (s, 1H), 4.02-4.00 (m, 4H), 3.59-3.57 (m, 4H), 2.24 (d, J=2.8 Hz, 3H), 1.68 (d, J=1.6 Hz, 9H).

Example 160: 1-Tert-butyl-5-fluoro-N-{2-fluoro-4-methyl-5-[8-(morpholin-4-yl)imidazo[1,2-a]pyridin-6-yl]phenyl}imidazole-4-carboxamide

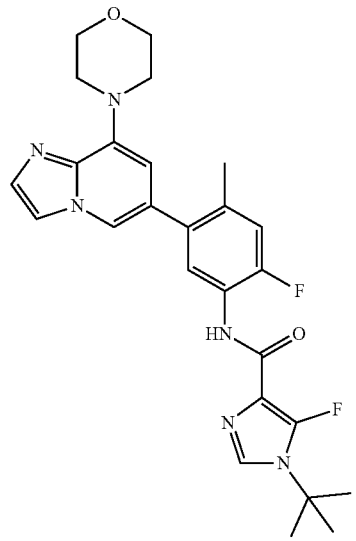

Step 1: To a stirred solution of ethyl 1-tert-butylimidazole-4-carboxylate (500 mg, 2.54 mmol) in ACN (10 mL) was added selectfluor (7.2 g, 20.38 mmol) in portions at room temperature under nitrogen atmosphere. The reaction mixture was stirred for 16 h at room temperature. The resulting mixture was concentrated under reduced pressure. The residue was dissolved in DCM (20 mL). The resulting mixture was filtered, the filter cake was washed with DCM (3×10 mL). The filtrate was concentrated under reduced pressure. The residue was purified by reverse flash chromatography with the following conditions: column, C18 silica gel; mobile phase, acetonitrile in water (Plus 0.1% TFA), 5% to 95% gradient in 25 min; detector, UV 237/254 nm. The fractions containing the desired product were combined and concentrated to afford ethyl 1-(tert-butyl)-5-fluoro-1H-imidazole-4-carboxylate (70 mg, 2%) as a light-yellow oil. MS ESI calculated for $C_{10}H_{15}FN_2O_2$. [M+H]$^+$, 215.11, found 215.09.

Step 2: To a stirred solution of 2-fluoro-4-methyl-5-[8-(morpholin-4-yl)imidazo[1,2-a]pyridin-6-yl]aniline (110 mg, 0.34 mmol) in 1 M LiHMDS in THF (1 mL) was added ethyl 1-(tert-butyl)-5-fluoro-1H-imidazole-4-carboxylate (72 mg, 0.38 mmol) in THF (0.5 mL) dropwise at 0° C. under nitrogen atmosphere. The reaction mixture was stirred for 2 h at room temperature. The resulting mixture was quenched with NH$_4$Cl (20 mL) and extracted with EtOAc (3×50 mL). The combined organic layers were washed with brine (3×40 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in water (Plus 0.1% FA), 10% to 50% gradient in 10 min; detector, UV 254 nm to afford the crude product. The crude product (50 mg) was further purified by Prep-HPLC with the following conditions: Column: XBridge Prep OBD C18 Column, 30×150 mm, 5 m; Mobile Phase A: water (Plus 10 mmol/L $NH_4HCO_3$), Mobile Phase B: MeCN; Flow rate: 60 mL/min; Gradient: 40% B to 50% B in 10 min, 50% B; Wavelength: 220 nm. The fractions containing the desired product were combined and concentrated to afford title compound (5 mg, 3%) as a white solid. MS ESI calculated for $C_{26}H_{28}F_2N_6O_2[M+H]^+$, 495.22, found 495.20; $^1$H NMR (400 MHz, $CDCl_3$) δ 8.81 (d, J=2.4 Hz, 1H), 8.38 (d, J=8.0 Hz, 1H), 7.78 (d, J=1.6 Hz, 1H), 7.63 (s, 1H), 7.56 (d, J=1.2 Hz, 1H), 7.47 (s, 1H), 7.07 (d, J=11.6 Hz, 1H), 6.43-6.41 (m, 1H), 4.02-4.00 (m, 4H), 3.59-3.57 (m, 4H), 2.28 (s, 3H), 1.63 (s, 9H).

Example 162: 1-(tert-Butyl)-5-fluoro-N-(2-fluoro-4-methyl-5-(7-morpholinopyrazolo[1,5-a]pyridin-5-yl) phenyl)-1H-pyrazole-4-carboxamide

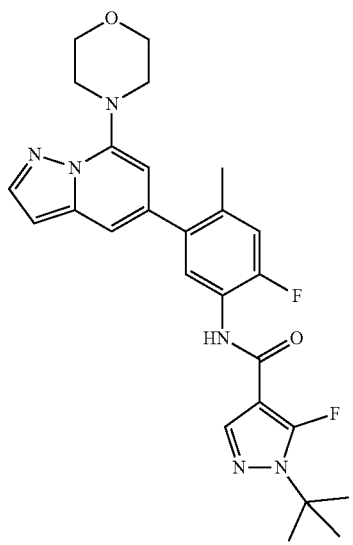 [SMILES: Cc1cc(F)c(NC(=O)c2cnn(C(C)(C)C)c2F)cc1-c1cc(N2CCOCC2)n2nccc2c1]

Step 1: To a stirred mixture of 5-chloro-7-iodopyrazolo [1,5-a]pyridine (900 mg, 3.23 mmol) in THF (10 mL) were added LiHMDS (12 mL, 11.31 mmol), XPhos Pd G2 (102 mg, 0.13 mmol) and morpholine (225 mg, 2.59 mmol) 0° C. under nitrogen atmosphere. The reaction mixture was stirred for 1 h at 60° C. under nitrogen atmosphere. The resulting mixture was quenched by the addition of sat. $NH_4Cl$ (aq.) (20 mL) at room temperature. The resulting mixture was extracted with EtOAc (3×30 mL). The combined organic layers were washed with brine (3×30 mL), dried over anhydrous $Na_2SO_4$. After filtration, the filtrate was concentrated under reduced pressure. The residue was purified by silica gel column chromatography, eluted with PE/EA (3/1). The fractions containing the desired product were combined and concentrated to afford 4-{5-chloropyrazolo[1,5-a]pyri-din-7-yl}morpholine (117 mg, 15%) as a brown oil. MS ESI calculated for $C_{11}H_2ClN_3O$ [M+H]$^+$, 238.07, found 238.15; $^1$H NMR (300 MHz, Chloroform-d) δ 7.98 (d, J=2.1 Hz, 1H), 7.28 (d, J=2.1 Hz, 1H), 6.49 (d, J=2.1 Hz, 1H), 6.15 (d, J=2.1 Hz, 1H), 4.06-3.97 (m, 4H), 3.54-3.44 (m, 4H).

Step 2: To a stirred mixture of 2-fluoro-4-methyl-5-(4,4, 5,5-tetramethyl-1,3,2-dioxaborolan-2-yl)aniline (174 mg, 0.70 mmol) and $K_3PO_4$ (196 mg, 0.93 mmol) in THF (2 mL) and $H_2O$ (0.2 mL) were added XPhos Pd G2 (36 mg, 0.05 mmol) and 4-{5-chloropyrazolo[1,5-a]pyridin-7-yl}morpholine (110 mg, 0.46 mmol) at room temperature. The reaction mixture was degassed with nitrogen for three times and stirred for 2 h at 80° C. The resulting mixture was diluted with water (10 mL). The resulting mixture was diluted with water (10 mL) and extracted with EtOAc (3×20 mL). The combined organic layers were washed with brine (3×20 mL), dried over anhydrous $Na_2SO_4$. After filtration, the filtrate was concentrated under reduced pressure. The residue was purified by silica gel column chromatography, eluted with PE/EA (1/1). The fractions containing the desired product were combined and concentrated to afford 2-fluoro-4-methyl-5-[7-(morpholin-4-yl)pyrazolo[1,5-a] pyridin-5-yl]aniline (130 mg, 86%) as a brown solid. MS ESI calculated for $C_{18}H_{19}FN_4O$ [M+H]$^+$, 327.15, found 327.20; $^1$H NMR (400 MHz, Chloroform-d) δ 8.03 (d, J=2.2 Hz, 1H), 7.16 (d, J=1.6 Hz, 1H), 6.97 (d, J=11.6 Hz, 1H), 6.86 (d, J=8.8 Hz, 1H), 6.55 (d, J=2.2 Hz, 1H), 6.12 (d, J=1.6 Hz, 1H), 4.07-4.00 (m, 4H), 3.50-3.45 (m, 4H), 2.22 (s, 3H).

Step 3: To a stirred solution of 2-fluoro-4-methyl-5-[7-(morpholin-4-yl)pyrazolo[1,5-a]pyridin-5-yl]aniline (73 mg, 0.22 mmol) and bis(lambda2-cobalt(2+)) octakis (methanidylidyneoxidanium) (23 mg, 0.07 mmol) in dioxane (0.5 mL) were added Pd(dppf)$C_{12}$ $CH_2Cl_2$ (36 mg, 0.05 mmol), TEA (136 mg, 1.34 mmol) and 4-bromo-1-(tert-butyl)-5-fluoro-1H-pyrazole (99 mg, 0.45 mmol) at room temperature. The reaction mixture was degassed with nitrogen for three times and stirred for 16 h at 90° C. The resulting mixture was concentrated under reduced pressure. The residue was purified by Prep-TLC, eluted with PE/EA (1:1) to afford the crude product. The crude product (80 mg) was purified by Prep-HPLC with the following conditions: Column: XBridge Prep OBD C18 Column, 30×150 mm, 5 m; Mobile Phase A: water (Plus 10 mmol/L $NH_4HCO_3$), Mobile Phase B: ACN; Flow rate: 60 mL/min; Gradient: 48% B to 58% B in 10 min, 58% B; Wavelength: 220 nm; RT1: 9.42 min. The fractions containing the desired product were combined and concentrated to afford the title compound (31.1 mg, 28%) as a white solid. MS ESI calculated for $C_{26}H_{28}F_2N_6O_2[M+H]^+$, 495.22, found 495.20; $^1$H NMR (400 MHz, DMSO-d$_6$) δ 9.69 (s, 1H), 8.05 (d, J=2.4 Hz, 1H), 8.00 (d, J=2.4 Hz, 1H), 7.55 (d, J=8.0 Hz, 1H), 7.34-7.24 (m, 2H), 6.65 (d, J=2.4 Hz, 1H), 6.23 (d, J=1.6 Hz, 1H), 3.84 (t, J=4.6 Hz, 4H), 3.44 (t, J=4.4 Hz, 4H), 2.31 (s, 3H), 1.58 (d, J=1.6 Hz, 9H).

Example 163: 1-(tert-Butyl)-5-fluoro-N-(2-fluoro-4-methyl-5-(8-(tetrahydro-2H-pyran-4-yl)imidazo[1,2-a]pyridin-6-yl)phenyl)-1H-pyrazole-4-carboxamide

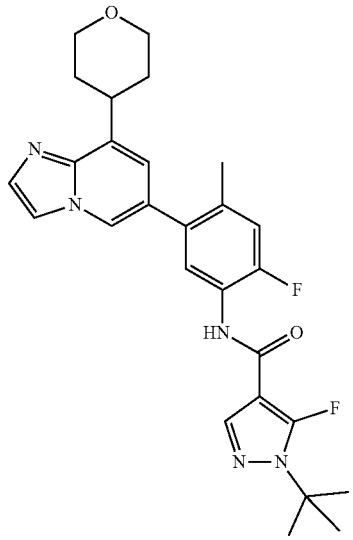 [SMILES: Cc1cc(F)c(NC(=O)c2cnn(C(C)(C)C)c2F)cc1-c1cc(C2CCOCC2)c2nccn2c1]

Step 1: To a stirred solution of 5-[8-(3,6-dihydro-2H-pyran-4-yl)imidazo[1,2-a]pyridin-6-yl]-2-fluoro-4-methyl-aniline (300 mg, 0.93 mmol) in MeOH (3 mL) was added Pd/C (60 mg) in portions at room temperature under nitrogen atmosphere. The resulting mixture was degassed with hydrogen for three times and stirred for 16 h at room temperature. The resulting mixture was filtered and the filter cake was washed with MeOH (3×5 mL). The filtrate was concentrated under reduced pressure to afford 2-fluoro-4-methyl-5-[8-(oxan-4-yl)imidazo[1,2-a]pyridin-6-yl]aniline (200 mg, crude) as an off-white solid. The crude product was directly used to next step without further purification. MS ESI calculated for $C_{19}H_{20}OFN_3O$. [M+H]$^+$, 326.16, found 326.15.

Step 2: To a stirred mixture of 2-fluoro-4-methyl-5-[8-(oxan-4-yl)imidazo[1,2-a]pyridin-6-yl]aniline (200 mg, 0.62 mmol), $Co_2(CO)_8$ (63.05 mg, 0.18 mmol) and Pd(dppf)Cl$_2$ DCM (100.14 mg, 0.12 mmol) in dioxane (4 mL) were added triethylamine (373.19 mg, 3.69 mmol) and 4-bromo-1-(tert-butyl)-5-fluoro-1H-pyrazole (271.77 mg, 1.23 mmol) at room temperature. The reaction mixture was degassed with nitrogen for three times and stirred for 16 h at 90° C. The resulting mixture was concentrated under reduced pressure. The residue was purified by silica gel column chromatography, eluted with DCM/MeOH (10/1) to afford the crude product. The crude product was further purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 40% B to 50% B in 10 min, 50% B; Wavelength: 250 nm; RT1: 9.98 min. The fractions containing the desired fractions were combined and concentrated to afford the title compound (63.3 mg, 20%) as an off-white solid. MS ESI calculated for $C_{27}H_{29}F_2N_5O_2$. [M+H]$^+$, 494.23, found 494.20; $^1$H NMR (400 MHz, DMSO-d$_6$) δ 9.70 (s, 1H), 8.45 (d, J=1.7 Hz, 1H), 8.00 (d, J=2.5 Hz, 1H), 7.96 (d, J=1.3 Hz, 1H), 7.60 (d, J=1.2 Hz, 1H), 7.54 (d, J=7.9 Hz, 1H), 7.29 (d, J=11.4 Hz, 1H), 7.04 (d, J=1.7 Hz, 1H), 4.00-3.98 (m, 2H), 3.57-3.44 (m, 3H), 2.29 (s, 3H), 1.97-1.89 (m, 4H), 1.57 (s, 9H).

Example 164: 1-{Bicyclo[1.1.1]pentan-1-yl}-N-{2-fluoro-4-methyl-5-[8-(morpholin-4-yl)imidazo[1,2-a]pyridin-6-yl]phenyl}pyrazole-4-carboxamide

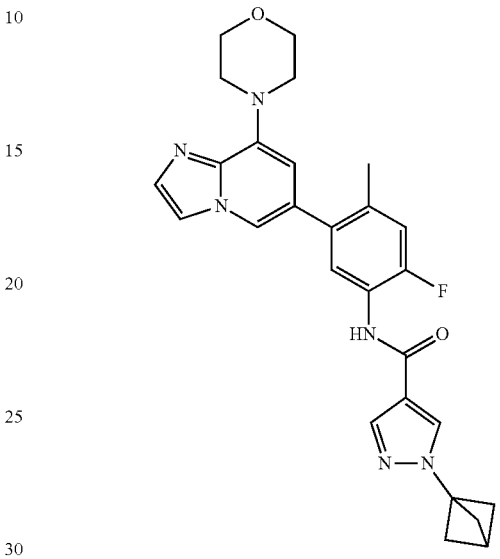

Step 1: To a stirred solution of bicyclo[1.1.1]pentan-1-ylhydrazine dihydrochloride (300 mg, 1.75 mmol) and propane, 1,1,3,3-tetramethoxy- (0.29 mL, 1.75 mmol) in ethanol (3 mL) was added hydrochloric acid (0.30 mL, 3.60 mmol) dropwise at room temperature under nitrogen atmosphere. The reaction mixture was stirred for 16 h at 80° C. The resulting mixture was diluted with water (20 mL) and extracted with ethyl acetate (2×30 mL). The combined organic layers were washed with brine (20 mL), dried over anhydrous Na$_2$SO$_4$. After filtration, the filtrate was concentrated under reduced pressure to afford 1-{bicyclo[1.1.1]pentan-1-yl}pyrazole (180 mg, crude) as a yellow oil. MS ESI calculated for C8H10N$_2$ [M+H]$^+$, 135.08, found 135.10.

Step 2: To a stirred solution of 1-{bicyclo[1.1.1]pentan-1-yl}pyrazole (180 mg, 1.34 mmol) and NIS (301.81 mg, 1.34 mmol) in acetic acid (1.8 mL) at room temperature. The reaction mixture was stirred for 1 h at 80° C. The resulting mixture was diluted with water (20 mL) and extracted with ethyl acetate (2×30 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EA (9/1). The fractions containing the desired product were combined and concentrated to afford 1-{bicyclo[1.1.1]pentan-1-yl}-4-iodopyrazole (210 mg, 60%) as a light yellow oil. MS ESI calculated for $C_8H_9IN_2$ [M+H]$^+$, 260.98, found 261.00.

Step 3: To a stirred solution of 2-fluoro-4-methyl-5-[8-(morpholin-4-yl)imidazo[1,2-a]pyridin-6-yl]aniline (80 mg, 0.25 mmol) and Pd(dppf)Cl$_2$ DCM (39.94 mg, 0.05 mmol) and $Co_2(CO)_8$ (25.15 mg, 0.07 mmol) in dioxane (0.8 mL) were added TEA (0.20 mL, 1.44 mmol) and 1-{bicyclo[1.1.1]pentan-1-yl}-4-iodopyrazole (127.50 mg, 0.49 mmol) in dioxane (0.2 mL) dropwise at room temperature. The reaction mixture was degassed with nitrogen for three times and stirred for 16 h at 90° C. The resulting mixture was concentrated under reduced pressure. The residue was purified by silica gel column chromatography, eluted with EA to afford the crude product. The crude product was further purified by reversed-phase flash chromatography with the following conditions: column, C18 silica gel; mobile phase, ACN in water (Plus 10 mmol/L NH$_4$HCO$_3$), 20% to 50% gradient in 30 min; detector, UV 254 nm. The fractions containing the desired product were combined and concentrated to afford 1-{bicyclo[1.1.1]pentan-1-yl}-N-{2-fluoro-4-methyl-5-[8-(morpholin-4-yl)imidazo[1,2-a]pyridin-6-yl]phenyl}pyrazole-4-carboxamide (79.7 mg, 66%) as a white solid. MS ESI calculated for C$_{27}$H$_{27}$FN$_6$O$_2$[M+H]$^+$, 487.22, found 487.25; $^1$H NMR (400 MHz, DMSO-d$_6$) δ 9.73 (s, 1H), 8.42-8.41 (m, 1H), 8.14 (d, J=1.4 Hz, 1H), 8.02 (s, 1H), 7.89 (d, J=1.2 Hz, 1H), 7.55 (d, J=8.0 Hz, 1H), 7.51 (d, J=1.1 Hz, 1H), 7.27 (d, J=11.5 Hz, 1H), 6.36 (d, J=1.5 Hz, 1H), 3.80 (t, J=4.7 Hz, 4H), 3.54 (t, J=4.7 Hz, 4H), 2.65 (s, 1H), 2.34-2.27 (m, 9H).

Example 166: N-{2-fluoro-4-methyl-5-[8-(morpholin-4-yl)imidazo[1,2-a]pyridin-6-yl]phenyl}-2-(pyrrolidin-1-yl)pyridine-4-carboxamide

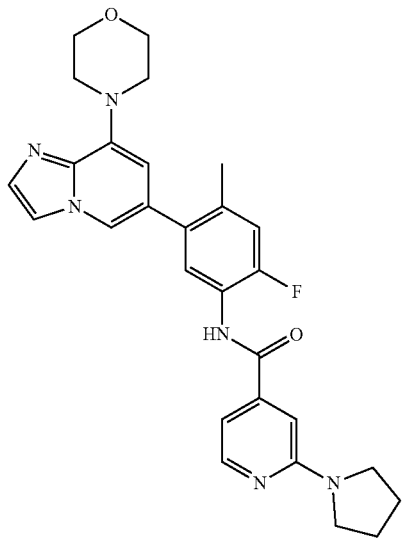 [SMILES: Cc1cc(F)c(NC(=O)c2ccnc(N3CCCC3)c2)cc1-c1cc(N2CCOCC2)c2nccn2c1]

Step 1: To a stirred mixture of 2-(pyrrolidin-1-yl)pyridine-4-carboxylic acid (150 mg, 0.78 mmol) in T$_3$P (1.5 mL, 50% in EA) was added 2-fluoro-4-methyl-5-[8-(morpholin-4-yl)imidazo[1,2-a]pyridin-6-yl]aniline (331.10 mg, 1.01 mmol) in pyridine (1.5 mL) dropwise at room temperature. The reaction mixture was stirred for 2 h at room temperature. The resulting mixture was concentrated under reduced pressure. The residue was purified by reversed-phase flash chromatography with the following conditions: column, C18 silica gel; mobile phase, MeCN in water (Plus 10 mmol/L NH$_4$HCO$_3$), 30% to 60% gradient in 20 min; detector, UV 254 nm. The fractions containing the desired product were combined and concentrated to afford the title compound (125.3 mg, 32%) as a white solid. MS ESI calculated for C$_{28}$H$_{29}$FN$_6$O$_2$ [M+H]$^+$, 501.23, found 501.20; $^1$H NMR (400 MHz, DMSO-d$_6$) δ 10.20 (s, 1H), 8.21 (d, J=5.2 Hz, 1H), 8.16 (d, J=1.4 Hz, 1H), 7.90 (d, J=1.2 Hz, 1H), 7.52-7.50 (m, 2H), 7.31 (d, J=11.6 Hz, 1H), 6.98 (d, J=5.2 Hz, 1H), 6.92 (s, 1H), 6.38 (d, J=0.8 Hz, 1H), 3.81 (d, J=4.4 Hz, 4H), 3.56 (t, J=4.4 Hz, 4H), 3.44-3.40 (m, 4H), 2.31 (s, 3H), 1.99-1.92 (m, 4H).

Example 180: N-(5-(8-(8—Oxa-3-azabicyclo[3.2.1]octan-3-yl)imidazo[1,2-a]pyridin-6-yl)-2-fluoro-4-methylphenyl)-1-(tert-butyl)-5-fluoro-1H-pyrazole-4-carboxamide

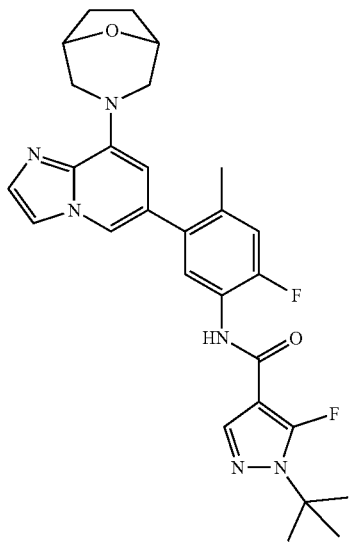 [SMILES: Cc1cc(F)c(NC(=O)c2cnn(C(C)(C)C)c2F)cc1-c1cc(N2CC3CCC(C2)O3)c2nccn2c1]

Step 1: To a stirred mixture of 8-bromo-6-chloroimidazo[1,2-a]pyridine (1 g, 4.32 mmol), 8-oxa-3-azabicyclo[3.2.1]octane hydrochloride (0.65 g, 4.32 mmol), t-BuONa (1.66 g, 17.28 mmol) and BINAP (0.27 g, 0.43 mmol) in toluene (10 mL) was added Pd$_2$(dba)$_3$ (0.20 g, 0.22 mmol) at room temperature. The reaction mixture was degassed with nitrogen for three times and stirred for 3 h at 95° C. The resulting mixture was concentrated under reduced pressure. The residue was purified by reversed-phase flash chromatography with the following conditions: column, C18 silica gel; mobile phase, MeCN in water (Plus 10 mmol/L NH$_4$HCO$_3$), 15% to 95% gradient in 30 min; detector, UV 220 nm. The fractions containing the desired product were combined and concentrated to afford 3-{6-chloroimidazo[1,2-a]pyridin-8-yl}-8-oxa-3-azabicyclo[3.2.1]octane (260 mg, 22%) as an off-white solid. MS ESI calculated for C$_{13}$H$_{14}$ClN$_3$O [M+H]$^+$, 264.08, 266.08, found 264.00, 266.00; $^1$H NMR (400 MHz, CDCl$_3$) δ 7.82-7.81 (m, 1H), 7.62-7.61 (m, 1H), 7.50-7.49 (m, 1H), 6.35-7.34 (m, 1H), 4.55-4.53 (m, 2H), 4.15-4.12 (m, 2H), 3.16-3.13 (m, 2H), 2.26-2.24 (m, 2H), 2.07-2.04 (m, 2H).

Step 2: To a stirred mixture of 3-{6-chloroimidazo[1,2-a]pyridin-8-yl}-8-oxa-3-azabicyclo[3.2.1]octane (200 mg, 0.76 mmol) and 2-fluoro-4-methyl-5-(4,4,5,5-tetramethyl-1,3,2-dioxaborolan-2-yl)aniline (380.86 mg, 1.52 mmol) in THF (2 mL) and K$_3$PO$_4$ (aq.) (4 mL, 0.5 M) was added XPhos Pd G2 (59.67 mg, 0.08 mmol) at room temperature. The reaction mixture was degassed with nitrogen for three times and stirred for 2 h at 80° C. The resulting mixture was concentrated under reduced pressure. The residue was purified by silica gel column chromatography, eluted with PE/EA (3/1). The fractions containing the desired product were combined and concentrated to afford 2-fluoro-4-methyl-5-(8-{8-oxa-3-azabicyclo[3.2.1]octan-3-yl}imidazo

[1,2-a]pyridin-6-yl)aniline (250 mg, 93%) as a brown solid. MS ESI calculated for $C_{20}H_{21}FN_4O$ [M+H]$^+$, 353.17, found 353.15; $^1$H NMR (400 MHz, CDCl$_3$) δ 7.65-7.60 (m, 2H), 7.51 (d, J=1.2 Hz, 1H), 6.90 (d, J=11.8 Hz, 1H), 6.69 (d, J=9.1 Hz, 1H), 6.21-6.20 (m, 1H), 4.50-4.48 (m, 2H), 4.15-4.12 (m, 2H), 3.66 (s, 2H), 3.09 (d, J=11.6 Hz, 2H), 2.23 (t, J=6.4 Hz, 2H), 2.15 (s, 3H), 2.08-1.98 (m, 2H).

Step 3: To a stirred mixture of 2-fluoro-4-methyl-5-(8-{8-oxa-3-azabicyclo[3.2.1]octan-3-yl}imidazo[1,2-a]pyridin-6-yl)aniline (100 mg, 0.28 mmol), Pd(dppf)C$_{12}$ DCM (46.23 mg, 0.06 mmol) and Co$_2$(CO)$_8$ (29.11 mg, 0.09 mmol) in dioxane (1 mL) were added TEA (172.29 mg, 1.70 mmol) and 4-bromo-1-(tert-butyl)-5-fluoro-1H-pyrazole (125.46 mg, 0.57 mmol) at room temperature. The reaction mixture was degassed with nitrogen for three times and stirred for 16 h at 90° C. The resulting mixture was concentrated under reduced pressure. The residue was purified by silica gel column chromatography, eluted with PE/EA/EtOH (2/3/1) to afford the crude product. The crude product (80 mg) was purified by Prep-HPLC with the following conditions Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 44% B to 54% B in 11 min, 54% B; Wavelength: 220 nm; RT1: 10.13 min. The fractions containing the desired product were combined and concentrated to afford the title compound (28.5 mg, 19%) as an off-white solid. MS ESI calculated for $C_{28}H_{30}F_2N_6O_2$[M+H]$^+$, 521.24, found 521.25; $^1$H NMR (400 MHz, CDCl$_3$) δ 8.33 (d, J=8.0 Hz, 1H), 7.84 (d, J=2.8 Hz, 1H), 7.71 (d, J=2.8 Hz, 1H), 7.67 (s, 1H), 7.60 (d, J=8.0 Hz, 1H), 7.54-7.52 (m, 1H), 7.07 (d, J=12 Hz, 1H), 6.25 (s, 1H), 4.52 (m, 2H), 4.18 (d, J=11.2 Hz, 2H), 3.14-3.10 (m, 2H), 2.28-2.24 (m, 5H), 2.06-2.03 (m, 2H), 1.69 (s, 9H).

Example 181: 1-(tert-Butyl)-5-fluoro-N-(2-fluoro-4-methyl-5-(8-morpholino-[1,2,4]triazolo[1,5-a]pyridin-6-yl)phenyl)-1H-pyrazole-4-carboxamide

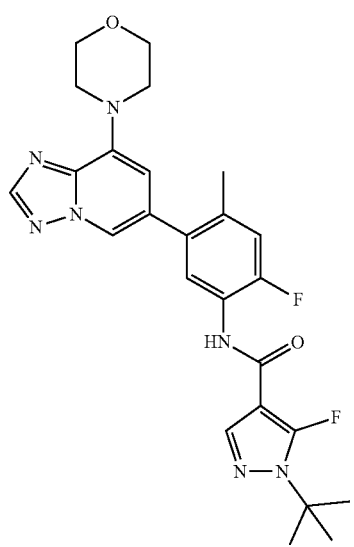

Step 1: To a stirred mixture of 2-fluoro-4-methyl-5-(4,4,5,5-tetramethyl-1,3,2-dioxaborolan-2-yl)aniline (1.14 g, 4.52 mmol), Pd(dppf)Cl$_2$ CH$_2$Cl$_2$ (0.74 g, 0.91 mmol) and Co$_2$(CO)$_8$ (0.46 g, 1.34 mmol) in dioxane (10 mL) were added TEA (2.75 g, 27.14 mmol) and 4-bromo-1-(tert-butyl)-5-fluoro-1H-pyrazole (1 g, 4.52 mmol) at room temperature. The reaction mixture was degassed with nitrogen for three times and stirred for 48 h at 90° C. The resulting mixture was concentrated under reduced pressure. The residue was dissolved in EtOAc (40 mL). The resulting mixture was filtered, the filter cake was washed with EtOAc (3×20 mL). The filtrate was concentrated under reduced pressure. The residue was purified by reversed-phase flash chromatography with the following conditions: column, C18 silica gel; mobile phase, MeCN in water (Plus 10 mmol/L NH$_4$HCO$_3$), 30% to 60% gradient in 20 min; detector, UV 254 nm. The fractions containing the desired product were combined and concentrated to afford 1-(tert-butyl)-5-fluoro-N-(2-fluoro-4-methyl-5-(4,4,5,5-tetramethyl-1,3,2-dioxaborolan-2-yl)phenyl)-1H-pyrazole-4-carboxamide (200 mg, 10%) as a light yellow solid. MS ESI calculated for $C_{21}H_{28}BF_2N_3O_3$. [M+H]$^+$, 420.22, found 420.34.

Step 2: To a stirred mixture of 8-bromo-6-chloro-[1,2,4]triazolo[1,5-a]pyridine (300 mg, 1.29 mmol), morpholine (168.64 mg, 1.94 mmol), K$_3$PO$_4$ (821.78 mg, 3.87 mmol) in 1,4-dioxane (5 mL) were added dppf (213.85 mg, 0.39 mmol) and Pd(OAc)$_2$ (28.97 mg, 0.13 mmol) at room temperature. The reaction mixture was degassed with nitrogen for three times and stirred for 16 h at 80° C. The resulting mixture was concentrated under reduced pressure. The residue was purified by silica gel column chromatography, eluted with PE/EA/EtOH (4/3/1). The fractions containing the desired product were combined and concentrated to afford 4-{6-chloro-[1,2,4]triazolo[1,5-a]pyridin-8-yl}morpholine (230.0 mg, 74%) as a light yellow solid. MS ESI calculated for C10H11ClN$_4$O. [M+H]$^+$, 239.06, 241.06, found 239.00, 241.00; $^1$H NMR (400 MHz, CDCl3) δ 8.28-8.27 (m, 2H), 6.67-6.66 (m, 1H), 3.99-3.94 (m, 4H), 3.64-3.62 (m, 4H).

Step 3: To a stirred mixture of 4-{6-chloro-[1,2,4]triazolo[1,5-a]pyridin-8-yl}morpholine (50 mg, 0.21 mmol), 1-(tert-butyl)-5-fluoro-N-(2-fluoro-4-methyl-5-(4,4,5,5-tetramethyl-1,3,2-dioxaborolan-2-yl)phenyl)-1H-pyrazole-4-carboxamide (87.83 mg, 0.21 mmol) and K$_3$PO$_4$ (88.93 mg, 0.42 mmol) in THF (0.15 mL) and water (0.3 mL) was added 2nd Generation XPhos Precatalyst (16.48 mg, 0.02 mmol) at room temperature. The reaction mixture was degassed with nitrogen for three times and stirred for 2 h at 40° C. The resulting mixture was concentrated under reduced pressure. The residue was purified by silica gel column chromatography, eluted with CH$_2$Cl$_2$/MeOH (10/1) to afford the crude product. The crude product was purified by Prep-HPLC with the following conditions: Column: XBridge Shield RP18 OBD Column, 30×150 mm, 5 m; Mobile Phase A: water (Plus 10 mmol/L NH$_4$HCO$_3$), Mobile Phase B: ACN; Flow rate: 60 mL/min; Gradient: 50% B to 60% B in 10 min; Wavelength: 220 nm; RT1: 10.77 min.

The fractions containing the desired product were combined and concentrated to afford the title compound (22.3 mg, 21%) as a white solid. MS ESI calculated for $C_{25}H_{27}F_2N_7O_2$. [M+H]$^+$, 496.22, found 496.20; $^1$H NMR (400 MHz, DMSO-d$_6$) δ 9.71 (s, 1H), 8.51-8.43 (m, 2H), 8.01 (d, J=2.5 Hz, 1H), 7.57 (d, J=7.9 Hz, 1H), 7.30 (d, J=11.5 Hz, 1H), 6.74 (d, J=1.4 Hz, 1H), 3.82 (t, J=4.8 Hz, 4H), 3.58 (t, J=4.8 Hz, 4H), 2.30 (s, 3H), 1.57 (s, 9H).

Example 183: 2-Tert-butyl-N-{2-fluoro-4-methyl-5-[8-(morpholin-4-yl)imidazo[1,2-a]pyridin-6-yl]phenyl}-1,3-oxazole-5-carboxamide

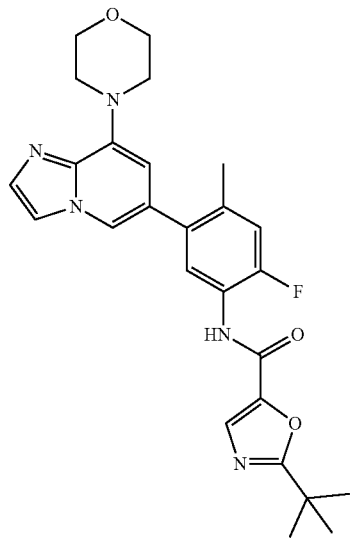 [SMILES: Cc1cc(F)c(NC(=O)c2cnc(C(C)(C)C)o2)cc1-c1cc(N2CCOCC2)c2nccn2c1]

Step 1: To a stirred solution of pivalamide (5 g, 49.43 mmol) and ethyl 2-chloro-3-oxopropanoate (7.44 g, 49.43 mmol) in EtOH (50 mL) was added MgSO$_4$ (17.85 g, 148.30 mmol). The reaction mixture was stirred for 16 h at 80° C. under nitrogen atmosphere. The resulting mixture was concentrated under reduced pressure. The residue was purified by silica gel column chromatography, eluted with PE/EA (10/1) to afford the crude product. The crude product was purified by reverse phase Flash chromatography with the following conditions: Column: WelFlash TM C18-I, 20-40 μm, 120 g; Eluent A: water (Plus 10 mmol/L NH$_4$HCO$_3$); Eluent B: ACN; Gradient: 25%-95% B in 25 min; Flow rate: 60 mL/min; Detector: 220/254 nm. The fractions containing the desire product were combined and concentrated to afford ethyl 2-tert-butyl-1,3-oxazole-5-carboxylate (1.8 g, 18%) as a brown oil. MS ESI calculated for C$_{10}$H$_{15}$NO$_3$ [M+H]$^+$, 198.11, found 198.10; $^1$H NMR (400 MHz, Chloroform-d) δ 7.63 (s, 1H), 4.37 (q, J=7.2 Hz, 2H), 1.43 (s, 9H), 1.38 (t, J=7.2 Hz, 3H).

Step 2: To a stirred mixture of 2-fluoro-4-methyl-5-[8-(morpholin-4-yl)imidazo[1,2-a]pyridin-6-yl]aniline (95 mg, 0.29 mmol) in LiHMDS (1 mL, 1 M in THF) was added ethyl 2-tert-butyl-1,3-oxazole-5-carboxylate (77 mg, 0.29 mmol) in THF (0.5 mL) at 0° C. under nitrogen atmosphere. The reaction mixture was stirred for 1 h at room temperature under nitrogen atmosphere. The resulting mixture was quenched with MeOH at room temperature. The resulting mixture was concentrated under reduced pressure. The residue was purified by silica gel column chromatography, eluted with EA to afford the crude product. The crude product (120 mg) was purified by Prep-HPLC with the following conditions: Column: XBridge Prep OBD C18 Column, 30×150 mm, 5 m; Mobile Phase A: water (Plus 10 mmol/L NH$_4$HCO$_3$+0.1% NH$_3$.H$_2$O), Mobile Phase B: ACN; Flow rate: 60 mL/min; Gradient: 32% B to 62% B in 8 min, 62% B; Wavelength: 254. The fractions containing the desired product were combined and concentrated to afford 2-tert-butyl-N-{2-fluoro-4-methyl-5-[8-(morpholin-4-yl)imidazo[1,2-a]pyridin-6-yl]phenyl}-1,3-oxazole-5-carboxamide (44.9 mg, 32%) as a white solid. MS ESI calculated for C$_{26}$H$_{28}$FN$_5$O$_3$[M+H]$^+$, 478.22, found 478.30; $^1$H NMR (400 MHz, DMSO-d$_6$) δ 10.20 (s, 1H), 8.16 (d, J=1.4 Hz, 1H), 7.92-7.83 (m, 2H), 7.53-7.46 (m, 2H), 7.32 (d, J=11.6 Hz, 1H), 6.37 (d, J=1.6 Hz, 1H), 3.83 (t, J=4.8 Hz, 4H), 3.55 (t, J=4.8 Hz, 4H), 2.31 (s, 3H), 1.38 (s, 9H).

Example 184: 2-Tert-butyl-N-{2-fluoro-4-methyl-5-[8-(morpholin-4-yl)imidazo[1,2-a]pyridin-6-yl]phenyl}-1,3-oxazole-4-carboxamide

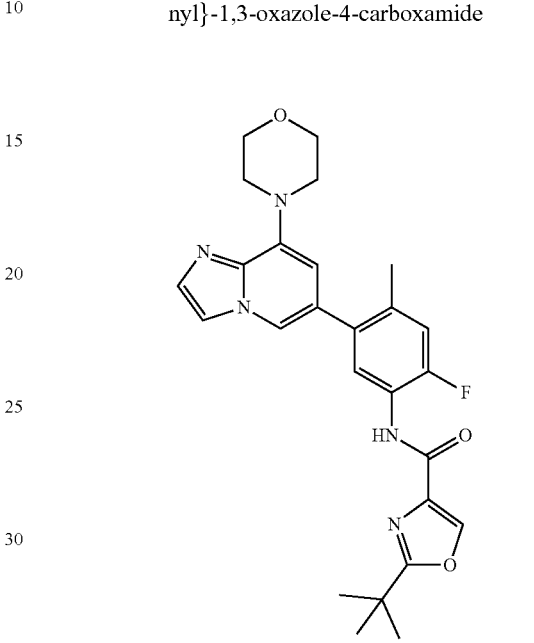

Step 1: To a stirred solution of ethyl 3-bromo-2-oxopropanoate (3.23 mL, 25.71 mmol) in Ethanol (50 mL) was added pivalamide (2.6 g, 25.71 mmol) at room temperature. The reaction mixture was stirred for 16 h at 80° C. The resulting mixture was concentrated under reduced pressure. The residue was purified by silica gel column chromatography, eluted with PE/EA (9/1). The fractions containing the desired product were combined and concentrated to afford ethyl 2-tert-butyl-1,3-oxazole-4-carboxylate (300 mg, 6%) as a light yellow oil. MS ESI calculated for C$_{10}$H$_{15}$NO$_3$ [M+H]$^+$, 198.11, found 198.05; $^1$H NMR (400 MHz, DMSO-d$_6$) δ 8.73 (s, 1H), 4.27 (q, J=7.1 Hz, 2H), 1.34 (s, 9H), 1.28 (t, J=7.1 Hz, 3H).

Step 2: To a stirred solution of 2-fluoro-4-methyl-5-[8-(morpholin-4-yl)imidazo[1,2-a]pyridin-6-yl]aniline (100 mg, 0.31 mmol) in Lithium bis(trimethylsilyl)amide (0.92 mL, 0.92 mmol) was added ethyl 2-tert-butyl-1,3-oxazole-4-carboxylate (60.43 mg, 0.31 mmol) in THE (0.1 mL) dropwise at 0° C. under nitrogen atmosphere. The reaction mixture was stirred for 1 h at room temperature under a nitrogen atmosphere. The resulting mixture was quenched with water/ice and extracted with Ethyl acetate (2×20 mL). The combined organic layers were washed with brine (1×20 mL), dried over anhydrous Sodium sulfate. After filtration, the filtrate was concentrated under reduced pressure. The residue was purified by silica gel column chromatography, eluted with PE/EA (1/9) to afford the crude product. The crude product was purified by Prep-HPLC with the following conditions: Column: XBridge Prep OBD C18 Column, 30×150 mm, 5 m; Mobile Phase A: water (Plus 10 mmol/L NH$_4$HCO$_3$+0.1% NH$_3$.H$_2$O), Mobile Phase B: ACN; Flow rate: 60 mL/min; Gradient: 50% B to 70% B in 8 min, 70%

B; Wavelength: 254. The fractions containing the desired product were combined and concentrated to afford 2-tert-butyl-N-{2-fluoro-4-methyl-5-[8-(morpholin-4-yl)imidazo[1,2-a]pyridin-6-yl]phenyl}-1,3-oxazole-4-carboxamide (56.7 mg, 38%) as a white solid. MS ESI calculated for $C_{26}H_{28}FN_5O_3[M+H]^+$, 478.22, found 478.25; $^1H$ NMR (400 MHz, DMSO-$d_6$) δ 9.59 (s, 1H), 8.70 (s, 1H), 8.15 (d, J=1.4 Hz, 1H), 7.90 (d, J=1.2 Hz, 1H), 7.72 (d, J=8.0 Hz, 1H), 7.51 (d, J=1.2 Hz, 1H), 7.30 (d, J=11.8 Hz, 1H), 6.36 (d, J=1.5 Hz, 1H), 3.80 (t, J=4.7 Hz, 4H), 3.55 (t, J=4.7 Hz, 4H), 2.29 (s, 3H), 1.39 (s, 9H).

Example 185: 2-Tert-butyl-N-{4-methyl-3-[8-(morpholin-4-yl)imidazo[1,2-a]pyridin-6-yl]phenyl}-1,3-oxazole-5-carboxamide

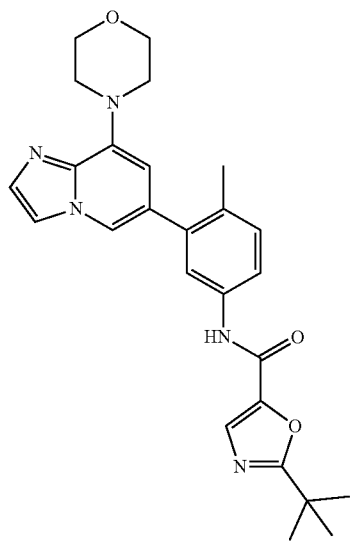 [SMILES: Cc1ccc(NC(=O)c2cnc(C(C)(C)C)o2)cc1-c1cc(N2CCOCC2)c2nccn2c1]

Step 1: To a stirred solution 4-methyl-3-[8-(morpholin-4-yl)imidazo[1,2-a]pyridin-6-yl]aniline (100 mg, 0.32 mmol) in Lithium bis(trimethylsilyl)amide (1.5 mL) was added ethyl 2-tert-butyl-1,3-oxazole-5-carboxylate (127.91 mg, 0.65 mmol) in THF (1 mL) dropwise at 0° C. under nitrogen atmosphere. The reaction mixture was stirred for 1 h at room temperature under nitrogen atmosphere. The resulting mixture was quenched with NH$_4$Cl (aq.) at room temperature. The resulting mixture was concentrated under reduced pressure. The residue was purified by silica gel column chromatography, eluted with DCM/MeOH (20/1) to afford the crude product. The crude product was purified by reverse phase Flash chromatography with the following conditions: Column: WelFlash TM C18-I, 20-40 μm, 40 g; Eluent A: water (Plus 10 mmol/L NH$_4$HCO$_3$); Eluent B: acetonitrile; Gradient: 40%-50% B in 25 min; Flow rate: 30 mL/min; Detector: 254 nm. The fractions containing the desired product were combined and concentrated to afford 2-tert-butyl-N-{4-methyl-3-[8-(morpholin-4-yl)imidazo[1,2-a]pyridin-6-yl]phenyl}-1,3-oxazole-5-carboxamide (85.2 mg, 57%) as an off-white solid. MS ESI calculated for $C_{26}H_{29}N_5O_3$. [M+H]$^+$, 460.23, found 460.25; $^1H$ NMR (400 MHz, DMSO-$d_6$) δ 10.20 (s, 1H), 8.16 (d, J=1.3 Hz, 1H), 7.90 (d, J=1.2 Hz, 1H), 7.84-7.81 (m, 1H), 7.79-7.72 (m, 2H), 7.51 (d, J=1.2 Hz, 1H), 7.32-7.30 (m, 1H), 6.39 (d, J=1.5 Hz, 1H), 3.84-3.77 (m, 4H), 3.55 (t, J=4.7 Hz, 4H), 2.27 (s, 3H), 1.39 (s, 9H).

Example 186: 2-Tert-butyl-N-{2-fluoro-4-methyl-5-[8-(morpholin-4-yl)imidazo[1,2-a]pyridin-6-yl]phenyl}-1,2,3-triazole-4-carboxamide

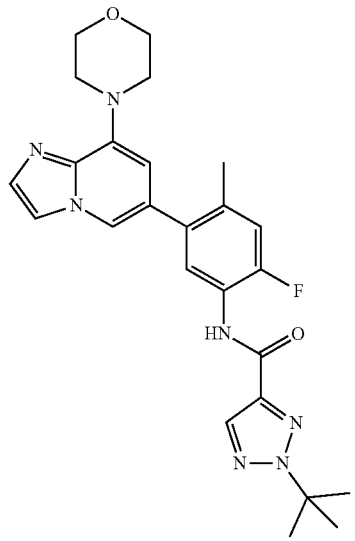 [SMILES: Cc1cc(F)c(NC(=O)c2cnn(C(C)(C)C)n2)cc1-c1cc(N2CCOCC2)c2nccn2c1]

Step 1: To a stirred solution of ethyl 2H-1,2,3-triazole-4-carboxylate (2 g, 14.17 mmol) and tert-butanol (2.10 g, 28.34 mmol) in TFA (30 mL) was added H$_2$SO$_4$ (1.39 g, 14.17 mmol) dropwise at room temperature. The resulting mixture was stirred for 16 h at room temperature. The resulting mixture was diluted with water (50 mL) and extracted with CH$_2$Cl$_2$ (3×100 mL). The combined organic layers were washed with brine (2×50 mL), dried over anhydrous Na$_2$SO$_4$.

After filtration, the filtrate was concentrated under reduced pressure. The residue was purified by silica gel column chromatography, eluted with PE/EA (1/1). The fractions containing the desired product were combined and concentrated to afford ethyl 2-tert-butyl-1,2,3-triazole-4-carboxylate (300 mg, 10%) as a light-yellow oil. MS ESI calculated for $C_9H_{15}N_3O_2$. [M+H]$^+$, 198.12, found 198.15; $^1H$ NMR (300 MHz, CDCl$_3$) δ 8.01 (s, 1H), 4.41 (q, J=7.1 Hz, 2H), 1.70 (s, 9H), 1.40 (t, J=7.1 Hz, 3H).

Step 2: A solution of 2-fluoro-4-methyl-5-[8-(morpholin-4-yl)imidazo[1,2-a]pyridin-6-yl]aniline (100 mg, 0.31 mmol) in LiHMDS (3 mL, 2.5 M) was stirred for 30 min at 0° C. under nitrogen atmosphere. To the above mixture was added ethyl 2-tert-butyl-1,2,3-triazole-4-carboxylate (120.9 mg, 0.62 mmol) in THF (3 mL) dropwise over 5 min at 0° C. The reaction mixture was stirred for 1 h at room temperature. The resulting mixture was quenched with sat. NH$_4$Cl (aq.) (5 mL) at room temperature. The resulting mixture was diluted with water (30 mL) and extracted with EtOAc (3×20 mL). The combined organic layers were washed with brine (2×20 mL), dried over anhydrous Na$_2$SO$_4$. After filtration, the filtrate was concentrated under reduced pressure. The residue was purified by Prep-HPLC with the following conditions: Column: XBridge Prep OBD C18 Column, 30×150 mm, 5 m; Mobile Phase A: water (Plus 10 mmol/L NH$_4$HCO$_3$+0.1% NH$_3$-H$_2$O), Mobile Phase B: ACN; Flow rate: 60 mL/min; Gradient: 39% B to 69% B in 8 min; Wavelength: 254). The fractions containing the desired product were combined and concentrated to afford 2-tert-butyl-N-{2-fluoro-4-methyl-5-[8-(morpholin-4-yl)

imidazo[1,2-a]pyridin-6-yl]phenyl}-1,2,3-triazole-4-carboxamide (56.8 mg, 39%) as a white solid. MS ESI calculated for $C_{25}H_{28}FN_7O_2$. [M+H]$^+$, 478.23, found 478.25; $^1$H NMR (400 MHz, DMSO-d$_6$) δ 10.15 (s, 1H), 8.27 (s, 1H), 8.18 (d, J=1.3 Hz, 1H), 7.92 (d, J=1.2 Hz, 1H), 7.80-7.71 (m, 1H), 7.52 (d, J=1.2 Hz, 1H), 7.31 (d, J=8.2 Hz, 1H), 6.41 (d, J=1.5 Hz, 1H), 3.85-3.78 (m, 4H), 3.59-3.53 (m, 4H), 2.28 (s, 3H), 1.68 (s, 9H).

Example 188: 2-{Bicyclo[1.1.1]pentan-1-yl}-N-{2-fluoro-4-methyl-5-[8-(morpholin-4-yl)imidazo[1,2-a]pyridin-6-yl]phenyl}pyridine-4-carboxamide

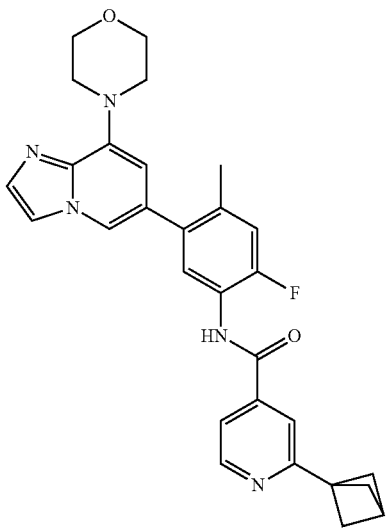 [SMILES: Cc1cc(F)c(NC(=O)c2ccnc(C34CC(C3)C4)c2)cc1-c1cc(N2CCOCC2)c2nccn2c1]

Step 1: To a stirred solution of 4-cyanopyridine (500 mg, 4.80 mmol), bicyclo[1.1.1]pentane-1-carboxylic acid (538.50 mg, 4.80 mmol) and AgNO$_3$ (587.39 mg, 3.46 mmol) in acetonitrile (16 mL) and water (8 mL) was added (NH$_4$)$_2$S$_2$O$_5$(4.38 g, 19.21 mmol) at room temperature. The reaction mixture was stirred for 2 h at 80° C. The resulting mixture was diluted with water (50 mL) and extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with PE/EA (5/1) to afford the crude product which was further purified by reversed-phase flash chromatography with the following conditions: column, C18 silica gel; mobile phase, acetonitrile in water (Plus 10 mmol/L NH$_4$HCO$_3$), 30% to 65% gradient in 25 min; detector, UV 254/210 nm. The fractions containing the desired product were combined and concentrated to afford 2-{bicyclo[1.1.1]pentan-1-yl}pyridine-4-carbonitrile (140 mg, 17%) as a white solid. MS ESI calculated for $C_{11}H_{10}N_2$. [M+H]$^+$, 171.08, found 171.05; $^1$H NMR (300 MHz, CDCl$_3$) δ 8.71 (dd, J=5.0, 1.0 Hz, 1H), 7.39 (dd, J=1.6, 0.9 Hz, 1H), 7.34 (dd, J=5.0, 1.6 Hz, 1H), 2.61 (s, 1H), 2.21 (s, 6H).

Step 2: To a solution of 2-{bicyclo[1.1.1]pentan-1-yl}pyridine-4-carbonitrile (120 mg, 0.71 mmol) in EtOH (2.5 mL) was added NaOH (140.99 mg, 3.53 mmol) in water (2.5 mL) at room temperature. The reaction mixture was stirred for 2 h at 100° C. The resulting mixture was concentrated under reduced pressure. The residue was purified by reversed-phase flash chromatography with the following conditions: column, C18 silica gel; mobile phase, acetonitrile in water (Plus 10 mmol/L NH$_4$HCO$_3$), 5% to 10% gradient in 10 min; detector, UV 254/210 nm. The fractions containing the desired product were combined and concentrated to afford 2-{bicyclo[1.1.1]pentan-1-yl}pyridine-4-carboxylic acid (60 mg, 44%) as a white solid. MS ESI calculated for $C_{11}H_{11}NO_2$. [M+H]$^+$, 190.08, found 190.10.

Step 3: To a stirred mixture of 2-fluoro-4-methyl-5-[8-(morpholin-4-yl)imidazo[1,2-a]pyridin-6-yl]aniline (50 mg, 0.15 mmol), 2-{bicyclo[1.1.1]pentan-1-yl}pyridine-4-carboxylic acid (57.97 mg, 0.31 mmol), HOBt (31.05 mg, 0.23 mmol) and EDCI (44.05 mg, 0.23 mmol) in DMF (2 mL) was added TEA (62.01 mg, 0.61 mmol) dropwise at room temperature. The reaction mixture was stirred for 1 h at room temperature. The resulting mixture was concentrated under reduced pressure. The residue was purified by silica gel column chromatography, eluted with PE/EA (4/1). The residue was purified by reverse phase Flash chromatography with the following conditions: Column: XBridge Prep OBD C18 Column, 30×150 mm, 5 m; Mobile Phase A: Water (Plus 10 mmol/L NH$_4$HCO$_3$), Mobile Phase B: acetonitrile; Flow rate: 60 mL/min; Gradient: 32% B to 62% B in 8 min, 62% B; Wavelength: 254 nm. The fractions containing the desired product were combined and concentrated to afford the title compound (14.2 mg, 18%) as an off-white solid. MS ESI calculated for $C_{29}H_{28}FN_5O_2$. [M+H]$^+$, 498.22, found 498.20; $^1$H NMR (400 MHz, DMSO-d$_6$) δ 10.43 (s, 1H), 8.68 (dd, J=5.1, 0.9 Hz, 1H), 8.16 (d, J=1.5 Hz, 1H), 7.89 (d, J=1.2 Hz, 1H), 7.77-7.68 (m, 2H), 7.55-7.49 (m, 2H), 7.32 (d, J=11.5 Hz, 1H), 6.37 (d, J=1.5 Hz, 1H), 3.80 (t, J=4.6 Hz, 4H), 3.55 (t, J=4.7 Hz, 4H), 2.59 (s, 1H), 2.31 (s, 3H), 2.16 (s, 6H).

Example 189: 1-(tert-Butyl)-5-fluoro-N-(2-fluoro-4-methyl-5-(5-morpholino-[1,2,4]triazolo[1,5-a]pyridin-7-yl)phenyl)-1H-pyrazole-4-carboxamide

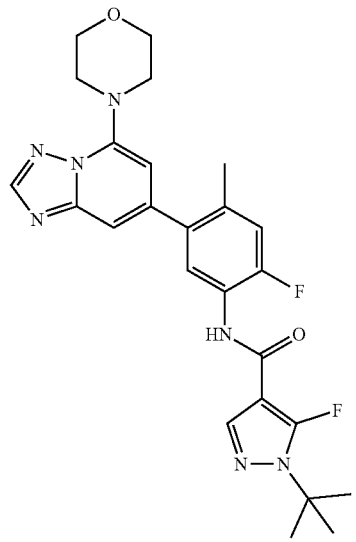 [SMILES: Cc1cc(F)c(NC(=O)c2cnn(C(C)(C)C)c2F)cc1-c1cc(N2CCOCC2)n2ncnc2c1]

Step 1: To a stirred solution of 4,6-dichloropyridin-2-amine (20 g, 122.69 mmol) in DMSO (200 mL, 61.35 mmol) was added morpholine (21.38 g, 245.39 mmol) dropwise at room temperature under nitrogen atmosphere. The reaction mixture was stirred for 16 h at 100° C. under nitrogen atmosphere. The resulting mixture was diluted with water and extracted with EtOAc (3×200 mL). The combined organic layers were washed with brine (2×200 mL), dried over anhydrous Na₂SO₄. After filtration, the filtrate was concentrated under reduced pressure. The residue was purified by silica gel column chromatography, eluted with PE/EA (2/1). The fractions containing the desired product were combined and concentrated to afford 4-chloro-6-(morpholin-4-yl)pyridin-2-amine (6 g, 22%) as a white solid. MS ESI calculated for C₉H₁₂ClN₃O [M+H]⁺, 214.07, 216.07, found 214.10, 216.10.

Step 2: To a stirred solution of 4-chloro-6-(morpholin-4-yl)pyridin-2-amine (1.5 g, 7.02 mmol) in DMF (24.00 mL) was added DMF-DMA (4.18 g, 35.10 mmol). The reaction mixture was stirred for 2 h at 130° C. The resulting mixture was concentrated under reduced pressure. The residue was purified by silica gel column chromatography, eluted with PE/EA/EtOH (8/3/1). The fractions containing the desired product were combined and concentrated to afford (E)-N-[4-chloro-6-(morpholin-4-yl)pyridin-2-yl]-N,N-dimethylmethanimidamide (1.52 g, 80%) as a white solid. MS ESI calculated for C₁₂H₁₇ClN₄O [M+H]⁺, 269.11, 271.11, found 269.10, 271.10; ¹H NMR (400 MHz, Chloroform-a) δ 8.39-8.37 (m, 1H), 6.38-6.33 (m, 1H), 6.22-6.12 (m, 1H), 3.80 (t, J=4.9 Hz, 4H), 3.51 (t, J=4.9 Hz, 4H), 3.08 (s, 6H).

Step 3: To a stirred solution of (E)-N-[4-chloro-6-(morpholin-4-yl)pyridin-2-yl]-N,N-dimethylmethanimidamide (600 mg, 2.23 mmol) and Pyridine (882.98 mg, 11.16 mmol) in MeOH (5 mL) was added aminooxysulfonic acid (504.96 mg, 4.46 mmol) dropwise at room temperature under nitrogen atmosphere. The reaction mixture was stirred for 1 h at 60° C. under nitrogen atmosphere. The resulting mixture was diluited with water (30 mL) and extracted with EtOAc (3×50 mL). The combined organic layers were washed with brine (1×100 mL), dried over anhydrous Na₂SO₄. After filtration, the filtrate was concentrated under reduced pressure.

The residue was purified by silica gel column chromatography, eluted with PE/EA (1/1). The fractions containing the desired product were combined and concentrated to afford 4-{7-chloro-[1,2,4]triazolo[1,5-a]pyridin-5-yl}morpholine (443 mg, 83%) as a white solid. MS ESI calculated for C10H11ClN₄O [M+H]⁺, 239.06, 241.06, found 239.05, 241.05; ¹H NMR (400 MHz, DMSO-d₆) δ 8.50 (s, 1H), 7.60 (d, J=2.0 Hz, 1H), 6.62 (d, J=2.1 Hz, 1H), 3.82 (t, J=4.7 Hz, 4H), 3.55 (t, J=4.7 Hz, 4H).

Step 4: To a stirred solution of 1-(tert-butyl)-5-fluoro-N-(2-fluoro-4-methyl-5-(4,4,5,5-tetramethyl-1,3,2-dioxaborolan-2-yl)phenyl)-1H-pyrazole-4-carboxamide (52.70 mg, 0.13 mmol) and 4-{7-chloro-[1,2,4]triazolo[1,5-a]pyridin-5-yl}morpholine (30 mg, 0.13 mmol) and XPhos Pd G2 (9.89 mg, 0.01 mmol) and K₃PO₄ (53.36 mg, 0.25 mmol) in THF (0.9 mL) and water (0.1 mL) at room temperature. The reaction mixture was degassed with nitrogen for three times and stirred for 1 h at 80° C. The resulting mixture was concentrated under reduced pressure. The residue was purified by silica gel column chromatography, eluted with Ethyl acetate to afford the crude product. The crude product was purified by Prep-HPLC with the following conditions Column: XBridge Prep OBD C18 Column, 30×150 mm, 5 m; Mobile Phase A: water (Plus 10 mmol/L NH₄HCO₃), Mobile Phase B: ACN; Flow rate: 60 mL/min; Gradient: 32% B to 62% B in 8 min, 62% B; Wavelength: 254 nm. The fractions containing the desired product were combined and concentrated to afford the title compound (16.5 mg, 26%) as a white solid. MS ESI calculated for C₂₅H₂₇F₂N₇O₂ [M+H]⁺, 496.22, found 496.20; ¹H NMR (400 MHz, DMSO-d₆) δ 9.73 (s, 1H), 8.51 (s, 1H), 8.00 (d, J=2.6 Hz, 1H), 7.58 (d, J=7.9 Hz, 1H), 7.38 (d, J=1.5 Hz, 1H), 7.31 (d, J=11.5 Hz, 1H), 6.48 (d, J=1.6 Hz, 1H), 3.84 (t, J=4.6 Hz, 4H), 3.50 (t, J=4.6 Hz, 4H), 2.31 (s, 3H), 1.57 (d, J=1.5 Hz, 9H).

Example 204: N-(1-tert-butylpyrazol-4-yl)-2-fluoro-4-methyl-5-[8-(morpholin-4-yl)imidazo[1,2-a]pyridin-6-yl]benzamide

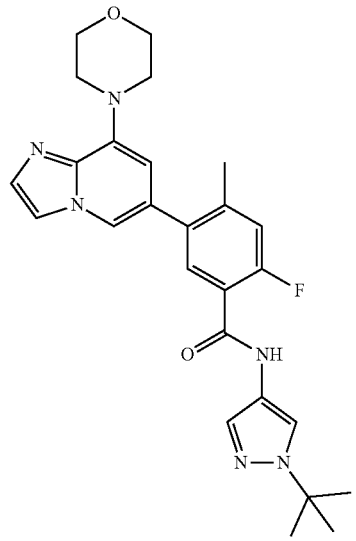 [SMILES: Cc1cc(F)c(C(=O)Nc2cnn(C(C)(C)C)c2)cc1-c1cc(N2CCOCC2)c2nccn2c1]

Step 1: To a stirred solution of methyl 5-bromo-2-fluoro-4-methylbenzoate (1 g, 4.05 mmol), bis(pinacolato)diboron (1.54 g, 6.07 mmol) and KOAc (1.19 g, 12.14 mmol) in 1,4-dioxane (15 mL) was added Pd(dppf)Cl₂ CH₂Cl₂ (329.72 mg, 0.41 mmol) in portions at room temperature. The reaction mixture was degassed with nitrogen for three times and stirred for 16 h at 90° C. The resulting mixture was concentrated under reduced pressure. The residue was purified by silica gel column chromatography, eluted with PE/EA (4/1). The fractions containing the desired product were combined and concentrated to afford methyl 2-fluoro-4-methyl-5-(4,4,5,5-tetramethyl-1,3,2-dioxaborolan-2-yl)benzoate (940 mg, 78%) as an off-white solid. MS ESI calculated for C₁₅H₂₀BFO₄. [M+H]⁺, 295.14, found 295.20; ¹H NMR (400 MHz, CDCl₃) δ 8.45 (d, J=8.4 Hz, 1H), 6.94 (d, J=16.0 Hz, 1H), 3.92 (s, 3H), 2.56 (s, 3H), 1.35 (s, 12H).

Step 2: To a stirred solution of 4-{6-chloroimidazo[1,2-a]pyridin-8-yl}morpholine (400 mg, 1.68 mmol), methyl 2-fluoro-4-methyl-5-(4,4,5,5-tetramethyl-1,3,2-dioxaborolan-2-yl)benzoate (494.98 mg, 1.68 mmol) and K₃PO₄ (714.43 mg, 3.37 mmol) in THF (5 mL) and H₂O (0.5 mL) was added XPhos palladium(II) biphenyl-2-amine chloride (132.41 mg, 0.17 mmol) in portions at room temperature. The reaction mixture was degassed with nitrogen for three times and stirred for 2 h at 80° C. The resulting mixture was diluted with water (20 mL) and extracted with EtOAc (2×20 mL). The combined organic layers were washed with brine (1×20 mL), dried over anhydrous Na₂SO₄. After filtration, the filtrate was concentrated under reduced pressure. The residue was purified by silica gel column chromatography, eluted with PE/EA (5/1). The fractions containing the desired product were combined and concentrated to afford methyl 2-fluoro-4-methyl-5-[8-(morpholin-4-yl)imidazo[1, 2-a]pyridin-6-yl]benzoate (500 mg, 80%) as a green solid. MS ESI calculated for $C_{20}H_{20}FN_3O_3$. [M+H]$^+$, 370.15, found 370.15; $^1$H NMR (400 MHz, CDCl$_3$) δ 7.85 (d, J=7.4 Hz, 1H), 7.72 (d, J=1.4 Hz, 1H), 7.63-7.51 (m, 2H), 7.08 (d, J=11.4 Hz, 1H), 6.30 (d, J=1.5 Hz, 1H), 4.02-3.95 (m, 4H), 3.93 (s, 3H), 3.61-3.49 (m, 4H), 2.33 (s, 3H).

Step 3: To a stirred solution of 1-tert-butylpyrazol-4-amine (20 mg, 0.14 mmol) in LiHMDS (2.5 mL) was added methyl 2-fluoro-4-methyl-5-[8-(morpholin-4-yl)imidazo[1,2-a]pyridin-6-yl]benzoate (53.07 mg, 0.14 mmol) in THF (1 mL) dropwise at 0° C. under nitrogen atmosphere. The reaction mixture was stirred for 1 h at room temperature. The resulting mixture was concentrated under reduced pressure. The residue was purified by silica gel column chromatography, eluted with PE/EA (1/1) to afford the crude product. The crude product (30 mg) was purified by Prep-HPLC with the following conditions: Column: XBridge Prep OBD C18 Column, 30×150 mm, 5 m; Mobile Phase A: water (Plus 10 mmol/L NH$_4$HCO$_3$+0.1% NH$_3$H$_2$O), Mobile Phase B: ACN; Flow rate: 60 mL/min; Gradient: 32% B to 52% B in 8 min; Wavelength: 254 nm. The fractions containing the desired product were combined and concentrated to afford the title compound (3.7 mg, 5%) as a white solid. MS ESI calculated for $C_{26}H_{29}FN_6O_2$. [M+H]$^+$, 477.23, found 477.25; $^1$H NMR (400 MHz, DMSO-d$_6$) δ 10.35 (s, 1H), 8.19 (d, J=1.4 Hz, 1H), 8.06 (s, 1H), 7.90 (d, J=1.2 Hz, 1H), 7.64-7.55 (m, 2H), 7.52 (d, J=1.2 Hz, 1H), 7.35 (d, J=11.3 Hz, 1H), 6.40 (d, J=1.5 Hz, 1H), 3.84 (t, J=4.7 Hz, 4H), 3.56 (t, J=4.7 Hz, 4H), 2.36 (s, 3H), 1.52 (s, 9H).

Example 205: N-(3-tert-butylphenyl)-2-fluoro-4-methyl-5-[8-(morpholin-4-yl)imidazo[1,2-a]pyridin-6-yl]benzamide

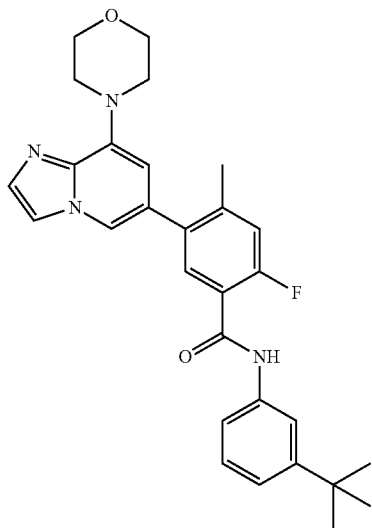 [SMILES: Cc1cc(F)c(C(=O)Nc2cccc(C(C)(C)C)c2)cc1-c1cc(N2CCOCC2)c2nccn2c1]

Step 1: To a stirred solution of methyl 2-fluoro-4-methyl-5-[8-(morpholin-4-yl)imidazo[1,2-a]pyridin-6-yl]benzoate (70 mg, 0.19 mmol) in LiHMDS (1 mL) was added 3-tert-butylaniline (28.28 mg, 0.19 mmol) in THF (1 mL) at 0° C. under nitrogen atmosphere. The reaction mixture was stirred for 1 h at room temperature. The resulting mixture was quenched with sat. NH$_4$Cl (aq) (5 mL) at room temperature. The resulting mixture was diluted with water (30 mL) and extracted with EtOAc (3×20 mL). The combined organic layers were washed with brine (2×20 mL), dried over anhydrous Na$_2$SO$_4$. After filtration, the filtrate was concentrated under reduced pressure. The residue was purified by Prep-HPLC with the following conditions: Column: XBridge Prep OBD C18 Column, 30×150 mm, 5 m; Mobile Phase A: water (Plus 10 mmol/L NH$_4$HCO$_3$+0.1% NH$_3$H$_2$O), Mobile Phase B: ACN; Flow rate: 60 mL/min; Gradient: 50% B to 80% B in 7 min; Wavelength: 254 nm; RT1: 5.87 min. The fractions containing the desired product were combined and concentrated to afford the title compound (45.7 mg, 49%) as a white solid. MS ESI calculated for $C_{29}H_{31}FN_4O_2$. [M+H]$^+$, 487.24, found 487.30; $^1$H NMR (400 MHz, DMSO-d$_6$) δ 10.29 (s, 1H), 8.20 (d, J=1.5 Hz, 1H), 7.89 (d, J=1.2 Hz, 1H), 7.72 (t, J=2.1 Hz, 1H), 7.60 (d, J=7.4 Hz, 2H), 7.52 (d, J=1.2 Hz, 1H), 7.36 (d, J=11.2 Hz, 1H), 7.27 (t, J=7.9 Hz, 1H), 7.14 (dt, J=8.0, 1.3 Hz, 1H), 6.40 (d, J=1.5 Hz, 1H), 3.80 (t, J=4.7 Hz, 4H), 3.56 (t, J=4.8 Hz, 4H), 2.37 (s, 3H), 1.28 (s, 9H).

Example 206: N-{2-Fluoro-4-methyl-5-[8-(morpholin-4-yl)imidazo[1,2-a]pyridin-6-yl]phenyl}-1-isopropylpyrrolo[2,3-b]pyridine-4-carboxamide

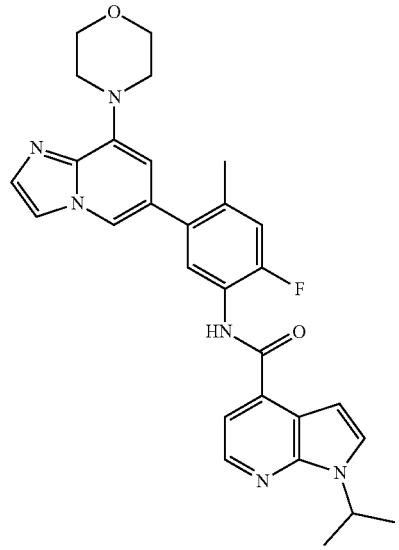 [SMILES: Cc1cc(F)c(NC(=O)c2ccnc3c2ccn3C(C)C)cc1-c1cc(N2CCOCC2)c2nccn2c1]

Step 1: To a stirred solution of methyl 1H-pyrrolo[2,3-b]pyridine-4-carboxylate (200 mg, 1.05 mmol) in THF (2 mL) was added NaH (84 mg, 1.26 mmol, 60%) at 0° C. under nitrogen atmosphere. The reaction mixture was stirred for 30 min at 0° C. To the above mixture was added 2-iodopropane (268 mg, 1.58 mmol) dropwise at 0° C. The reaction mixture was stirred for 16 h at room temperature. The resulting mixture was quenched by the addition of sat. NH$_4$Cl (aq.) (10 mL) at room temperature. The resulting mixture was extracted with EtOAc (3×20 mL). The combined organic layers were washed with brine (3×20 mL), dried over anhydrous Na$_2$SO$_4$. After filtration, the filtrate was concentrated under reduced pressure. The residue was purified by silica gel column chromatography, eluted with PE/EA (5/1). The fractions containing the desired product were combined and concentrated to afford methyl 1-isopropylpyrrolo[2,3-b]pyridine-4-carboxylate (110 mg, 45%) as a colorless oil. MS ESI calculated for $C_{12}H_{14}N_2O_2$ [M+H]$^+$, 219.05, found 219.11; $^1$H NMR (400 MHz, Chloroform-d) δ 8.44 (d, J=5.0

Hz, 1H), 7.72 (d, J=5.0 Hz, 1H), 7.52 (d, J=3.6 Hz, 1H), 7.05 (d, J=3.6 Hz, 1H), 5.33-5.26 (m, 1H), 4.04 (s, 3H), 1.57 (d, J=6.8 Hz, 6H).

Step 2: To a stirred solution of 2-fluoro-4-methyl-5-[8-(morpholin-4-yl)imidazo[1,2-a]pyridin-6-yl]aniline (100 mg, 0.31 mmol) in LiHMDS (1 mL) was added methyl 1-isopropylpyrrolo[2,3-b]pyridine-4-carboxylate (67 mg, 0.31 mmol) in THF (1 mL) dropwise at 0° C. under nitrogen atmosphere. The reaction mixture was stirred for 1 h at room temperature under nitrogen atmosphere. The resulting mixture was quenched with MeOH and concentrated under reduced pressure. The residue was purified by silica gel column chromatography, eluted with $CH_2Cl_2$/MeOH (10/1) to afford the crude product. The crude product (120 mg) was purified by Prep-HPLC with the following conditions: Column: XBridge Prep OBD C18 Column, 30×150 mm, 5 m; Mobile Phase A: water (Plus 10 mmol/L $NH_4HCO_3$+0.1% $NH_3H_2O$), Mobile Phase B: ACN; Flow rate: 60 mL/min; Gradient: 34% B to 64% B in 10 min, 64% B; Wavelength: 254 nm; RT1: 8.5 min. The fractions containing the desired product were combined and concentrated to afford N-{2-fluoro-4-methyl-5-[8-(morpholin-4-yl)imidazo[1,2-a]pyridin-6-yl]phenyl}-1-isopropylpyrrolo[2,3-b]pyridine-4-carboxamide (92.6 mg, 59%) as a white solid. MS ESI calculated for $C_{29}H_{29}FN_6O_2$ [M+H]$^+$, 513.23, found 513.35; $^1$H NMR (400 MHz, DMSO-$d_6$) δ 10.26 (s, 1H), 8.41 (d, J=5.0 Hz, 1H), 8.18 (d, J=1.4 Hz, 1H), 7.90 (d, J=1.2 Hz, 1H), 7.84 (d, J=3.6 Hz, 1H), 7.63 (d, J=7.8 Hz, 1H), 7.58-7.49 (m, 2H), 7.32 (d, J=11.6 Hz, 1H), 6.82 (d, J=3.6 Hz, 1H), 6.38 (d, J=1.6 Hz, 1H), 5.15 (d, J=6.8 Hz, 1H), 3.80 (t, J=4.6 Hz, 4H), 3.56 (t, J=4.8 Hz, 4H), 2.31 (s, 3H), 1.49 (d, J=6.8 Hz, 6H).

Example 220: 1-Tert-butyl-5-fluoro-N-{2-fluoro-4-methyl-5-[8-(morpholin-4-yl)-[1,2,3,4]tetrazolo[1,5-a]pyridin-6-yl]phenyl}pyrazole-4-carboxamide

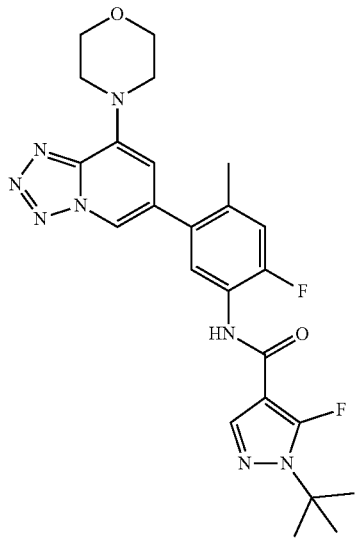 [SMILES: Cc1cc(F)c(NC(=O)c2cnn(C(C)(C)C)c2F)cc1-c1cc(N2CCOCC2)c2nnnn2c1]

Step 1: To a stirred mixture of 3-bromo-2,5-dichloropyridine (2 g, 8.81 mmol) in THF (20 mL) was added hydrazine hydrate (4.41 g, 88.15 mmol) dropwise at room temperature. The reaction mixture was stirred for 16 h at 70° C. under nitrogen atmosphere. The resulting mixture was diluted with water (50 mL) and extracted with EtOAc (3×80 mL). The combined organic layers were washed with NaCl (3×10 mL), dried over anhydrous $Na_2SO_4$ concentrated in vacuo and the residue purified by silica gel column chromatography (PE/EA, 1:1). The fractions containing the desired product were combined and concentrated to afford (E)-3-bromo-5-chloro-2-hydrazineylidene-1,2-dihydropyridine (800 mg, 40%) as a brown solid. MS ESI calculated for $C_5H_5BrClN_3$ [M+H]$^+$, 221.94 found 221.90; $^1$H NMR (400 MHz, DMSO-$d_6$) δ 8.13 (d, J=2.2 Hz, 1H), 7.94 (d, J=2.2 Hz, 1H), 7.68 (s, 1H), 4.27 (s, 2H).

Step 2: To a stirred solution of (E)-3-bromo-5-chloro-2-hydrazineylidene-1,2-dihydropyridine (500 mg, 2.25 mmol) and $H_2O$ (3 mL) in AcOH (9 mL) were added $NaNO_2$ (310 mg, 4.49 mmol) and $H_2O$ (3 mL) dropwise at 0° C. The reaction mixture was stirred for 2 h at 0° C. The resulting mixture was diluted with water (50 mL) and extracted with EtOAc (3×50 mL). The combined organic layers were washed with brine (2×100 mL), dried over anhydrous Sodium sulfate, and filtered. The filtrate was concentrated in vacuo to afford 8-bromo-6-chloro-[1,2,3,4]tetrazolo[1,5-a]pyridine (490 mg, crude) as an off-white solid. MS ESI calculated for $C_5H_2BrClN_4$ [M+H]$^+$, 232.92, found 232.90; $^1$H NMR (400 MHz, Chloroform-d) δ 8.87-8.85 (d, J=1.5 Hz, 1H), 7.91-7.89 (d, J=1.5 Hz, 1H).

Step 3: To a stirred solution of 8-bromo-6-chloro-[1,2,3,4]tetrazolo[1,5-a]pyridine (200 mg, 0.86 mmol) in DMF (5 mL) was added morpholine (149 mg, 1.71 mmol). The reaction mixture was stirred for 3 h at 140° C. The resulting mixture was concentrated in vacuo and the residue purified by reversed-phase flash chromatography with the following conditions: column, C18 silica gel; mobile phase, MeCN in Water (Plus 0.1% TFA), 15% to 85% gradient in 25 min; detector, UV 300 nm. The fractions containing the desired product were combined and concentrated to afford 4-{6-chloro-[1,2,3,4]tetrazolo[1,5-a]pyridin-8-yl}morpholine (82 mg, 39%) as an off-white solid. MS ESI calculated for $C_9H_{10}ClN_5O$ [M+H]$^+$, 240.06, found 240.05; $^1$H NMR (400 MHz, Chloroform-d) δ 8.41-8.40 (d, J=4.0 Hz, 1H), 6.62-6.61 (d, J=4.0 Hz, 1H), 3.98-3.96 (m, 4H), 3.80-3.77 (m, 4H)

Step 4: To a solution of 1-tert-butyl-5-fluoro-N-[2-fluoro-4-methyl-5-(4,4,5,5-tetramethyl-1,3,2-dioxaborolan-2-yl)phenyl]pyrazole-4-carboxamide (8 mg, 0.02 mmol), 2 nd Generation XPhos Precatalyst (1.64 mg, 0.002 mmol) and 4-{6-chloro-[1,2,3,4]tetrazolo[1,5-a]pyridin-8-yl}morpholine (5 mg, 0.02 mmol) in THF (1 mL) and $H_2O$ (0.1 mL) was added $K_3PO_4$ (13 mg, 0.06 mmol). The reaction mixture was purged with nitrogen and stirred for 16 h at 80° C. The resulting mixture was diluted with water (10 mL) and extracted with EtOAc (3×10 mL), dried over anhydrous Sodium sulfate, and filtered. The filtrate was concentrated in vacuo and the residue purified by Prep-HPLC with the following conditions: Column: XBridge Prep OBD C18 Column, 30×150 mm, 5 m; Mobile Phase A: water (Plus 10 mmol/L $NH_4HCO_3$+0.05% $NH_3H_2O$), Mobile Phase B: ACN; Flow rate: 60 mL/min; Gradient: 35% B to 65% B in 8 min, 65% B; Wave Length: 254; 220 nm; RT1: 6.5 min. The fractions containing the desired product were combined and concentrated to afford the title compound (2.8 mg, 26%) as an off-white solid. MS ESI calculated for $C_{24}H_{26}F_2N_8O_2$[M+H]$^+$, 497.21, found 497.40; $^1$H NMR (400 MHz, Chloroform-d) δ 8.43-8.41 (d, J=7.8 Hz, 1H), 8.32-8.31 (d, J=1.2 Hz, 1H), 7.84-7.83 (d, J=2.6 Hz, 1H), 7.72-7.71 (d, J=4.6 Hz, 1H), 7.14-7.11 (d, J=11.8 Hz, 1H), 6.62 (s, 1H), 4.00-3.98 (m, 4H), 3.77-3.75 (m, 4H), 2.29 (s, 3H), 1.68 (s, 9H).

Example 226: 1-(tert-Butyl)-N-(5-chloro-4-(8-morpholinoimidazo[1,2-a]pyridin-6-yl)pyridin-2-yl)-5-fluoro-1H-pyrazole-4-carboxamide

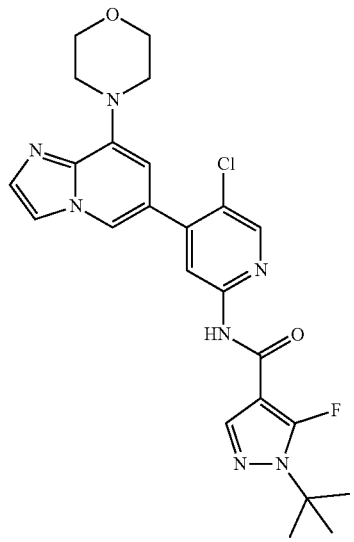 [SMILES: CC(C)(C)n1ncc(C(=O)Nc2cc(-c3cc(N4CCOCC4)c4nccn4c3)c(Cl)cn2)c1F]

Step 1: To a stirred solution of 4-bromo-5-chloropyridin-2-amine (200 mg, 0.96 mmol), Pd(PPh₃)₂C₁₂ (67.67 mg, 0.096 mmol) and Na₂CO₃ (306.53 mg, 2.89 mmol) in dioxane (4 mL) and H₂O (1 mL) was added 4-[6-(4,4,5,5-tetramethyl-1,3,2-dioxaborolan-2-yl)imidazo[1,2-a]pyridin-8-yl]morpholine (1.44 g, 1.44 mmol, 33%) at room temperature. The reaction mixture was purged with nitrogen and stirred for 2 h at 80° C. The resulting mixture was diluted with water (20 mL) and extracted with EtOAc (3×20 mL). The combined organic layers were washed with brine (50 mL), dried over anhydrous Na₂SO₄, filtered, and concentrated in vacuo. The residue purified by silica gel column chromatography (PE/EA, 1:2). The fractions containing the desired product were combined and concentrated to afford 5-chloro-4-[8-(morpholin-4-yl)imidazo[1,2-a]pyridin-6-yl]pyridin-2-amine (240 mg, 75%) as a yellow solid. MS ESI calculated for $C_{16}H_{16}ClN_5O[M+H]^+$, 330.10, 332.10, found 330.15, 332.15; $^1$H NMR (400 MHz, Chloroform-d) δ 8.14 (s, 1H), 7.90 (d, J=1.6 Hz, 1H), 7.59-7.52 (m, 2H), 6.53 (s, 1H), 6.45 (d, J=1.6 Hz, 1H), 4.59 (s, 2H), 3.98 (t, J=4.8 Hz, 4H), 3.58 (dd, J=5.7, 3.5 Hz, 4H).

Step 2: To a stirred solution of 5-chloro-4-[8-(morpholin-4-yl)imidazo[1,2-a]pyridin-6-yl]pyridin-2-amine (50 mg, 0.15 mmol), Pd(dppf)Cl₂.CH₂Cl₂ (24.70 mg, 0.030 mmol), Co₂(CO)₈ (15.55 mg, 0.046 mmol) and 4-bromo-1-(tert-butyl)-5-fluoro-1H-pyrazole (67.03 mg, 0.30 mmol) in dioxane (2.5 mL) was added TEA (0.13 mL, 0.91 mmol) at room temperature. The reaction mixture was purged with nitrogen and stirred for stirred for 16 h at 90° C. The resulting mixture was concentrated in vacuo and the residue purified by silica gel column chromatography (PE/EA/EtOH, 8:3:1) to afford a crude product which (50 mg) was purified by Prep-HPLC with the following conditions:Column: YMC-Actus Triart C18 ExRS, 30×150 mm, 5 m; Mobile Phase A: water (Plus 10 mmol/L NH₄HCO₃+0.1% NH₃·H₂O), Mobile Phase B: ACN; Flow rate: 60 mL/min; Gradient: 47% to 61% in 7 min, 61% B; Wave Length: 220/254 nm; RT: 6.68 min.

The fractions containing the desired product were combined and concentrated to afford the title compound (19.7 mg, 25%) as a white solid. MS ESI calculated for $C_{24}H_{25}C_1FN_7O_2[M+H]^+$, 498.17, found 498.15; $^1$H NMR (400 MHz, DMSO-d₆) δ 10.78 (s, 1H), 8.55 (s, 1H), 8.41 (d, J=1.5 Hz, 1H), 8.31 (s, 1H), 8.22 (d, J=2.4 Hz, 1H), 7.99 (d, J=1.3 Hz, 1H), 7.56 (d, J=1.3 Hz, 1H), 6.52 (d, J=1.6 Hz, 1H), 3.85-3.78 (m, 4H), 3.57-3.50 (m, 4H), 1.57 (d, J=1.4 Hz, 9H).

Example 228: 1-(tert-Butyl)-5-fluoro-N-(2-fluoro-4-methyl-5-(8-morpholinoimidazo[1,2-a]pyrazin-6-yl)phenyl)-1H-pyrazole-4-carboxamide

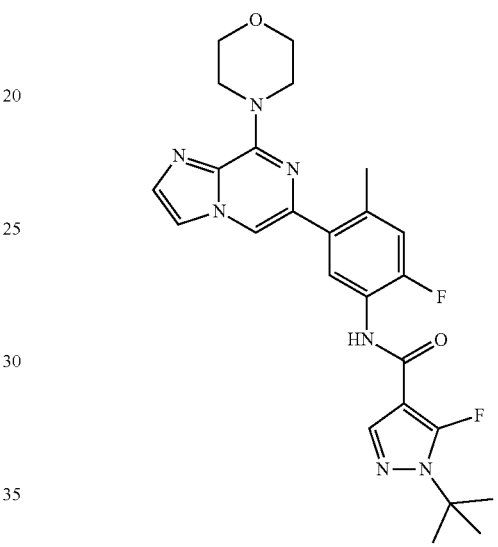

Step 1: To a stirred solution of 6-bromo-8-chloroimidazo[1,2-a]pyrazine (500 mg, 2.15 mmol), morpholine (187.38 mg, 2.15 mmol) and K₃PO₄ (1.37 g, 6.45 mmol) in dioxane (6 mL) were added Pd(OAc)₂ (48.29 mg, 0.22 mmol) and Dppf (356.42 mg, 0.65 mmol) in portions at room temperature. The reaction mixture was purged with nitrogen and stirred for 16 h at 80° C. The resulting mixture was concentrated in vacuo and the residue purified by silica gel column chromatography (PE/EA, 1:1). The fractions containing the desired product were combined and concentrated to afford 4-{6-bromoimidazo[1,2-a]pyrazin-8-yl}morpholine (370 mg, 60%) as a light yellow solid. MS ESI calculated for $C_{10}H_{11}BrN_4O$ $[M+H]^+$, 283.01, found 283.00; $^1$H NMR (400 MHz, Chloroform-d) δ 7.64 (s, 1H), 7.54 (d, J=1.2 Hz, 1H), 7.47 (d, J=1.1 Hz, 1H), 4.35-4.28 (m, 4H), 3.90-3.83 (m, 4H).

Step 2: To a stirred mixture of 4-{6-bromoimidazo[1,2-a]pyrazin-8-yl}morpholine (1 g, 3.53 mmol), 2-fluoro-4-methyl-5-(4,4,5,5-tetramethyl-1,3,2-dioxaborolan-2-yl)aniline (1.06 g, 4.24 mmol) and K₂CO₃ (0.98 g, 7.06 mmol) in dioxane (8 mL) and H₂O (2 mL) was added Pd(dppf)Cl₂—CH₂Cl₂ (0.29 g, 0.35 mmol) in portions at room temperature. The reaction mixture was purged with nitrogen and stirred for 2 h at 80° C. The resulting mixture was concentrated in vacuo and the residue purified by silica gel column chromatography (PE/EA, 1:1). The fractions containing the desired product were combined and concentrated to afford 2-fluoro-4-methyl-5-[8-(morpholin-4-yl)imidazo[1,2-a]pyrazin-6-yl]aniline (800 mg, 66%) as a white solid. MS ESI calculated for $C_{17}H_{18}FN_5O$ [M+H]$^+$, 328.15, found 328.15; $^1$H NMR (400 MHz, Chloroform-d) δ 7.57 (d, J=1.1 Hz, 1H), 7.56-7.50 (m, 2H), 6.89-6.82 (m, 2H), 4.34-4.27 (m, 4H), 3.90-3.84 (m, 4H), 2.29 (s, 3H).

Step 3: To a stirred mixture of 2-fluoro-4-methyl-5-[8-(morpholin-4-yl)imidazo[1,2-a]pyrazin-6-yl]aniline (80 mg, 0.24 mmol), Co$_2$(CO)$_8$ (0.07 mmol, 17.17 mg) and 4-bromo-1-(tert-butyl)-5-fluoro-1H-pyrazole (64.83 mg, 0.29 mmol) in 1,4-dioxane (1 mL) was added Pd(dppf)Cl$_2$—CH$_2$Cl$_2$ (39.81 mg, 0.05 mmol) in portions at room temperature. The reaction mixture was purged with nitrogen and stirred for 16 h at 80° C. The resulting mixture was concentrated in vacuo and the residue purified by silica gel column chromatography (PE/EA, 1:1) to afford a crude product which was further purified by Prep-HPLC with the following conditions: Column: YMC-Actus Triart C18 ExRS, 30×150 mm, 5 m; Mobile Phase A: Water (Plus 10 mmol/L NH$_4$HCO$_3$+ 0.1% NH$_3$-H$_2$O), Mobile Phase B: ACN; Flow rate: 60 mL/min; Gradient: 50% B to 66% B in 7 min; Wave Length: 220/254 nm; RT1: 7.2 min. The fractions containing the desired product were combined and concentrated to afford the title compound (32.1 mg, 26%) as a white solid. MS ESI calculated for $C_{25}H_{27}F_2N_7O_2$. [M+H]$^+$, 496.22, found 496.35; $^1$H NMR (400 MHz, DMSO-d$_6$) δ 9.68 (s, 1H), 8.09 (s, 1H), 7.99 (dd, J=8.5, 1.8 Hz, 2H), 7.65 (d, J=8.1 Hz, 1H), 7.60 (d, J=1.1 Hz, 1H), 7.23 (d, J=11.5 Hz, 1H), 4.20 (t, J=4.6 Hz, 4H), 3.75 (t, J=4.8 Hz, 4H), 2.38 (s, 3H), 1.57 (s, 9H).

Example 236: 1-(tert-Butyl)-5-fluoro-N-(2-fluoro-4-methyl-5-(8-morpholinoimidazo[1,2-a]pyrazin-6-yl) phenyl)-1H-pyrazole-4-carboxamide

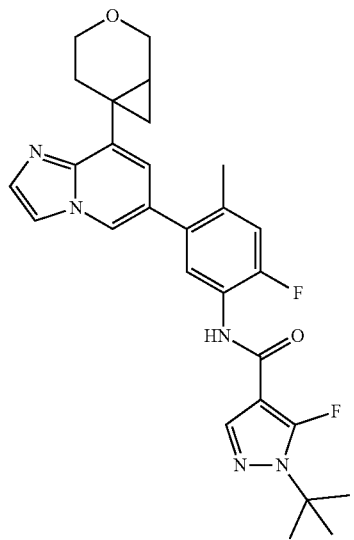 [SMILES: Cc1cc(F)c(NC(=O)c2cnn(C(C)(C)C)c2F)cc1-c1cc(C23CCOCC2C3)c2nccn2c1]

Step 1: To a stirred mixture of 8-bromo-6-chloroimidazo [1,2-a]pyridine (2 g, 8.64 mmol) and 2-(3,6-dihydro-2H-pyran-4-yl)-4,4,5,5-tetramethyl-1,3,2-dioxaborolane (2 g, 9.50 mmol), Na$_2$CO$_3$ (2.75 g, 25.92 mmol) in dioxane (20 mL) and H$_2$O (5 mL) was added Pd(PPh$_3$)$_2$C$_{12}$ (0.61 g, 0.86 mmol). The reaction mixture was purged with nitrogen and stirred for 3 h at 80° C. The resulting mixture was concentrated in vacuo and the residue purified by silica gel column chromatography, eluted with DCM/MeOH (10/1) to afford a crude product which was further purified by reverse phase Flash chromatography with the following conditions: Column: WelFlash TM C18-I, 20-40 μm, 80 g; Eluent A: Water (Plus 10 mmol/L NH$_4$HCO$_3$); Eluent B: ACN; Gradient: 30% B to 45% B in 25 min; Flow rate: 50 mL/min; Detector: 220/254 nm; The fractions containing the desired product were combined and concentrated to afford 6-chloro-8-(3,6-dihydro-2H-pyran-4-yl)imidazo[1,2-a]pyridine (1.3 g, 64%) as a light yellow solid. MS ESI calculated for $C_{12}HiClN20$ [M+H]$^+$, 235.06, found 235.05; $^1$H NMR (400 MHz, Chloroform-d) 6 8.10 (d, J=2.0 Hz, 1H), 7.67 (d, J=1.2 Hz, 1H), 7.56 (d, J=1.2 Hz, 1H), 7.53-7.51 (m, 1H), 7.08 (d, J=2.0 Hz, 1H), 4.48-4.46 (m, 2H), 4.02-3.99 (m, 2H), 2.67-2.63 (m, 2H).

Step 2: To a stirred solution of trimethyl(oxo)-lambda6-sulfanylium iodide (637 mg, 2.90 mmol) in DMSO (5 mL) was added NaH (116 mg, 2.90 mmol, 60%) in portions at 0° C. The reaction mixture was purged with nitrogen and stirred for 0.5 h at room temperature. To the above mixture was added 6-chloro-8-(3,6-dihydro-2H-pyran-4-yl)imidazo[1,2-a]pyridine (170 mg, 0.72 mmol) at room temperature. The reaction mixture was stirred for additional 16 h at 60° C. The resulting mixture was quenched by the addition of saturated aqueous NH$_4$Cl (100 mL) and extracted with EA (3×50 mL). The combined organic layers were washed with brine (3×50 mL), dried over anhydrous Na$_2$SO$_4$ and filtered. The filtrate was concentrated in vacuo and the residue purified by silica gel column chromatography (PE/EA, 4:1). The fractions containing the desired product were combined and concentrated to afford 6-chloro-8-{3-oxabicyclo[4.1.0]heptan-6-yl}imidazo[1,2-a]pyridine (70 mg, 39%) as an off-white solid. MS ESI calculated for $C_{13}H_{13}ClN_2O$[M+H]$^+$, 249.07, found 249.10.

Step 3: To a stirred mixture of 6-chloro-8-{3-oxabicyclo [4.1.0]heptan-6-yl}imidazo[1,2-a]pyridine (70 mg, 0.28 mmol), 2-fluoro-4-methyl-5-(4,4,5,5-tetramethyl-1,3,2-dioxaborolan-2-yl)aniline (85 mg, 0.34 mmol) and K$_3$PO$_4$ (179 mg, 0.84 mmol) in THF (7 mL) and H$_2$O (0.7 mL) was added XPhos palladium(II) G2 (22 mg, 0.03 mmol). The reaction mixture was purged with nitrogen and stirred for 1 h at 80° C. The resulting mixture was diluted with water (50 mL) and extracted with EtOAc (3×50 mL). The combined organic layers were washed with brine (2×30 mL), dried over anhydrous Sodium sulfate, and filtered. The filtrate was concentrated in vacuo and the residue purified by silica gel column chromatography (PE/EA/EtOH, 4:3:1). The fractions containing the desired product were combined and concentrated to afford 2-fluoro-4-methyl-5-(8-{3-oxabicyclo[4.1.0]heptan-6-yl}imidazo[1,2-a]pyridin-6-yl)aniline (50 mg, 53%) as a brown solid. MS ESI calculated for $C_{20}H_2OFN_3O$ [M+H]$^+$, 338.16, found 338.30.

Step 4: To a stirred solution of 2-fluoro-4-methyl-5-(8-{3-oxabicyclo[4.1.0]heptan-6-yl}imidazo[1,2-a]pyridin-6-yl)aniline (45 mg, 0.13 mmol), Pd(dppf)C$_{12}$-CH$_2$Cl$_2$ (11 mg, 0.01 mmol) and Co$_2$(CO)$_8$ (14 mg, 0.04 mmol) in dioxane (1 mL) were added TEA (81 mg, 0.80 mmol) and 4-bromo-1-(tert-butyl)-5-fluoro-1H-pyrazole (0.16 mmol, 35.41 mg). The reaction mixture was purged with nitrogen and stirred for 16 h at 90° C. The resulting mixture was diluted with water (50 mL) and extracted with ethyl acetate (3×50 mL). The combined organic layers were washed with brine (50 mL), dried over anhydrous sodium sulfate, and filtered. The filtrate was concentrated in vacuo and the residue purified by Prep-TLC (PE/EA/EtOH, 4:3:1) to afford a crude product which was further purified by Prep-HPLC with the following conditions: Column: XBridge Prep OBD C18 Column, 30×150 mm, 5 m; Mobile Phase A: Water (Plus 10 mmol/L NH$_4$HCO$_3$+0.05% NH$_3$H$_2$O), Mobile Phase B: MeCN;

Flow rate: 60 mL/min mL/min; Gradient: 17% B to 42% B in 8 min; Wave Length: 254 nm/220 nm nm; RT1: 7.8 min. The fractions containing the desired product were combined and concentrated to afford the title compound (3.0 mg, 4%) as an off-white solid. MS ESI calculated for $C_{28}H_{29}F_2N_5O_2$ [M - H], 504.23, found 504.30; $^1$H NMR (400 MHz, Chloroform-d) δ 8.30 (d, J=8.4 Hz, 1H), 7.94-7.92 (m, 1H), 7.82 (d, J=2.4 Hz, 1H), 7.66-7.63 (m, 1H), 7.48 (d, J=1.6 Hz, 1H), 7.19-7.17 (m, 2H), 7.05 (d, J=11.6 Hz, 1H), 4.48-4.46 (m, 2H), 4.28-4.23 (m, 3H), 4.03-4.00 (m, 2H), 2.70-2.65 (m, 2H), 2.25 (s, 3H), 1.66 (s, 9H).

Example 239: 1-(tert-Butyl)-5-fluoro-N-(2-fluoro-4-methyl-5-(8-morpholinoimidazo[1,2-b]pyridazin-6-yl)phenyl)-1H-pyrazole-4-carboxamide

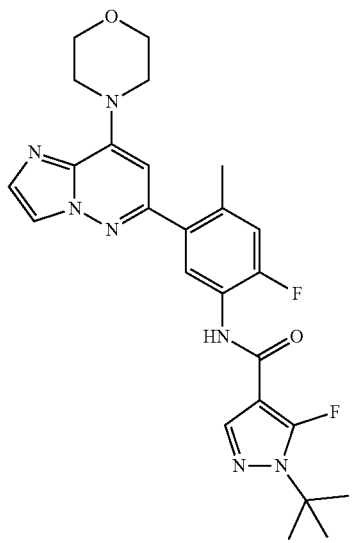 [SMILES: Cc1cc(F)c(NC(=O)c2cnn(C(C)(C)C)c2F)cc1-c1cc(N2CCOCC2)c2nccn2n1]

Step 1: To a stirred solution of 8-bromo-6-chloroimidazo[1,2-b]pyridazine (500.00 mg, 2.15 mmol) in EtOH (5.00 mL) were added morpholine (1.87 g, 21.51 mmol) dropwise at room temperature under nitrogen atmosphere. The reaction mixture was stirred for 3 h at room temperature under nitrogen atmosphere. The resulting mixture was filtered, the filter cake washed with EtOH (3×5 mL) to afford 4-[6-chloroimidazo[1,2-b]pyridazin-8-yl]morpholine (500 mg, crude) as a light yellow solid. MS ESI calculated for $C_{10}H_{11}ClN_4O$ [M+H]$^+$, 239.06, found 239.10.

Step 2: To a stirred mixture of 4-{6-chloroimidazo[1,2-b]pyridazin-8-yl}morpholine (1 g, 4.19 mmol) and 2-fluoro-4-methyl-5-(4,4,5,5-tetramethyl-1,3,2-dioxaborolan-2-yl)aniline (1.05 g, 4.19 mmol) in THF (10 mL) and H$_2$O (2.5 mL) were added XPhos Pd G2 (0.33 g, 0.42 mmol) and K$_3$PO$_4$ (1.78 g, 8.38 mmol) at room temperature. The reaction mixture was purged with nitrogen and stirred for 2 h at 80° C. The resulting mixture was concentrated in vacuo and the residue purified by silica gel column chromatography (PE/EA, 1:1). The fractions containing the desired product were combined and concentrated to afford 2-fluoro-4-methyl-5-[8-(morpholin-4-yl)imidazo[1,2-b]pyridazin-6-yl]aniline (1 g, 72%) as a light yellow solid. MS ESI calculated for $C_{17}H_{18}FN_5O$[M+H]$^+$, 328.15, found 328.15; $^1$H NMR (400 MHz, Chloroform-d) δ 7.84 (d, J=1.2 Hz, 1H), 7.58 (d, J=1.2 Hz, 1H), 6.92 (d, J=11.8 Hz, 1H), 6.83 (d, J=9.0 Hz, 1H), 6.09 (s, 1H), 4.01-3.94 (m, 4H), 3.96-3.89 (m, 4H), 2.24 (s, 3H).

Step 3: To a stirred mixture of 2-fluoro-4-methyl-5-[8-(morpholin-4-yl)imidazo[1,2-b]pyridazin-6-yl]aniline (80 mg, 0.24 mmol), Co$_2$(CO)$_8$ (0.07 mmol, 17.17 mg) and 4-bromo-1-(tert-butyl)-5-fluoro-1H-pyrazole (64.83 mg, 0.29 mmol) in 1,4-dioxane (1 mL) were added Pd(dppf)C$_{12}$·CH$_2$Cl$_2$ (19.91 mg, 0.024 mmol) and TEA (74.19 mg, 0.73 mmol) at room temperature. The reaction mixture was purged with nitrogen and stirred for 16 h at 90° C. The resulting mixture was concentrated in vacuo and the residue purified by silica gel column chromatography (PE/EA, 1:1) to afford a crude product which (80 mg) was purified by Prep-HPLC with the following conditions: Column: XBridge Prep OBD C18 Column, 30×150 mm, 5 m; Mobile Phase A: Water (Plus 10 mmol/L NH$_4$HCO$_3$+0.1% NH$_3$—H$_2$O), Mobile Phase B: ACN; Flow rate: 60 mL/min; Gradient: 34% B to 64% B in 7 min; Wave Length: 254 nm; RT1: 5.87 min. The fractions containing the desired products were combined and concentrated to afford the title compound (27.3 mg, 22%) as a grey solid. MS ESI calculated for $C_{25}H_{27}F_2N_7O_2$ [M+H]$^+$, 496.22, found 496.30; $^1$H NMR (400 MHz, DMSO-d$_6$) δ 9.73 (s, 1H), 8.09 (d, J=1.3 Hz, 1H), 8.00 (d, J=2.5 Hz, 1H), 7.66-7.57 (m, 2H), 7.29 (d, J=11.5 Hz, 1H), 6.34 (s, 1H), 4.03 (t, J=4.8 Hz, 4H), 3.77 (t, J=4.8 Hz, 4H), 2.34 (s, 3H), 1.57 (s, 9H).

Example 242: 1-(tert-Butyl)-5-fluoro-N-(2-fluoro-4-methyl-5-(8-(tetrahydro-2H-pyran-4-yl)imidazo[1,2-b]pyridazin-6-yl)phenyl)-1H-pyrazole-4-carboxamide

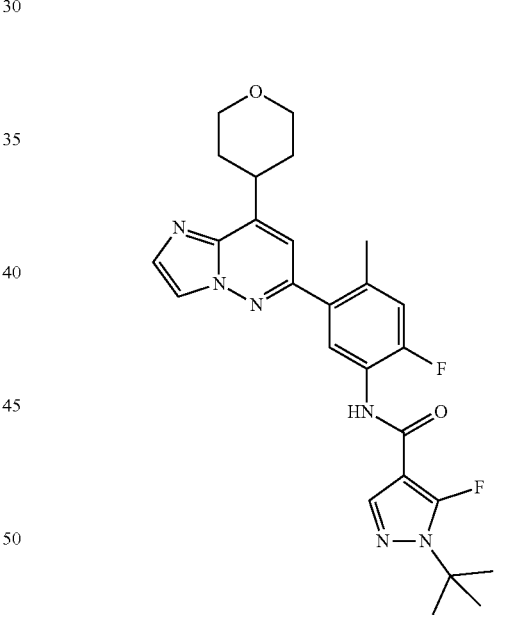

Step 1: To a stirred mixture of 8-bromo-6-chloroimidazo[1,2-b]pyridazine (500 mg, 2.15 mmol), 2-(3,6-dihydro-2H-pyran-4-yl)-4,4,5,5-tetramethyl-1,3,2-dioxaborolane (497.03 mg, 2.37 mmol) and Na$_2$CO$_3$ (683.88 mg, 6.45 mmol) in 1,4-dioxane (5 mL) and H$_2$O (1.2 mL) was added Pd(PPh$_3$)$_2$C$_{12}$ (150.97 mg, 0.21 mmol) in portions at room temperature. The reaction mixture was purged with nitrogen and stirred for 2 h at 80° C. The resulting mixture was concentrated in vacuo and the residue purified by silica gel column chromatography (PE/EA, 1:1). The fractions containing the desired product were combined and concentrated to afford 6-chloro-8-(3,6-dihydro-2H-pyran-4-yl)imidazo[1,2-b]pyridazine (500 mg, 83%) as a yellow solid. MS ESI calculated for C₁₁H₁₀ClN₃O [M+H]⁺, 236.05, found 236.10; ¹H NMR (400 MHz, Chloroform-d) δ 8.04 (d, J=3.2 Hz, 1H), 8.05-7.88 (m, 1H), 7.43-7.28 (m, 1H), 6.91 (s, 1H), 4.49-4.46 (m, 2H), 4.00-3.95 (m, 2H), 2.61-2.54 (m, 2H).

Step 2: To a stirred mixture of 6-chloro-8-(3,6-dihydro-2H-pyran-4-yl)imidazo[1,2-b]pyridazine (500 mg, 2.12 mmol), 2-fluoro-4-methyl-5-(4,4,5,5-tetramethyl-1,3,2-dioxaborolan-2-yl)aniline (799.14 mg, 3.18 mmol) and K₃PO₄ (900.69 mg, 4.24 mmol) in THF (0.5 mL) and H₂O (0.1 mL) were added XPhos Pd G2 (166.93 mg, 0.21 mmol) in portions at room temperature. The reaction mixture was purged with nitrogen and stirred for 16 h at 80° C. The resulting mixture was concentrated in vacuo and the residue purified by silica gel column chromatography (PE/EA, 1:1). The fractions containing the desired product were combined and concentrated to afford 5-[8-(3,6-dihydro-2H-pyran-4-yl)imidazo[1,2-b]pyridazin-6-yl]-2-fluoro-4-methylaniline (270 mg, 38%) as a light yellow solid. MS ESI calculated for C18H₁₇FN₄O [M+H]⁺, 325.14, found 325.15; ¹H NMR (400 MHz, Chloroform-d) δ 8.03-7.95 (m, 2H), 7.76 (d, J=1.2 Hz, 1H), 6.99-6.92 (m, 2H), 6.87 (d, J=9.0 Hz, 1H), 4.50-4.45 (m, 2H), 4.01 (t, J=5.4 Hz, 2H), 3.76 (s, 2H), 2.64-2.58 (m, 2H), 2.26 (s, 3H).

Step 3: To a stirred solution of 5-[8-(3,6-dihydro-2H-pyran-4-yl)imidazo[1,2-b]pyridazin-6-yl]-2-fluoro-4-methylaniline (100 mg, 0.31 mmol) in THF (3 mL) was added Pd/C (10%, 50 mg) under nitrogen atmosphere. The reaction mixture was degassed with hydrogen atmosphere for three times and stirred for 3 h at room temperature under hydrogen atmosphere. The resulting mixture was filtered, the filtrate was concentrated in vacuo to afford 2-fluoro-4-methyl-5-[8-(oxan-4-yl)imidazo[1,2-b]pyridazin-6-yl]aniline (90 mg, crude) as a light yellow solid. MS ESI calculated for C18H₁₉FN₄O [M+H]⁺, 327.16, found 327.15.

Step 4: To a stirred mixture of 2-fluoro-4-methyl-5-[8-(oxan-4-yl)imidazo[1,2-b]pyridazin-6-yl]aniline (80 mg, 0.25 mmol), 4-bromo-1-(tert-butyl)-5-fluoro-1H-pyrazole (65.03 mg, 0.29 mmol), TEA (148.82 mg, 1.47 mmol) and Co₂(CO)₈ (25.15 mg, 0.07 mmol) in 1,4-dioxane (1 mL) was added Pd(dppf)Cl₂ CH₂Cl₂ (39.94 mg, 0.05 mmol) in portions at room temperature. The reaction mixture was purged with nitrogen and stirred for 16 h at 80° C. The resulting mixture was concentrated in vacuo and the residue purified by silica gel column chromatography (PE/EA/EtOH, 4:3:1) to afford a crude product which was further purified by Prep-HPLC with the following conditions: Column: XBridge Prep OBD C18 Column, 30×150 mm, 5 m; Mobile Phase A: water (Plus 10 mmol/L NH₄HCO₃), Mobile Phase B: ACN; Flow rate: 60 mL/min; Gradient: 32% B to 62% B in 7 min; Wave Length: 254 nm/220 nm; RT1: 5.38 min.

The fractions containing the desired product were combined and concentrated to afford the title compound (23.9 mg, 20%) as a white solid. MS ESI calculated for C₂₆H₂₈F₂N₆O2. [M+H]⁺, 495.22, found 495.35; ¹H NMR (400 MHz, DMSO-d₆) δ 9.76 (s, 1H), 8.29 (d, J=1.2 Hz, 1H), 8.01 (d, J=2.5 Hz, 1H), 7.78 (d, J=1.2 Hz, 1H), 7.71 (d, J=7.9 Hz, 1H), 7.34 (d, J=11.5 Hz, 1H), 7.20 (s, 1H), 3.98-3.94 (m, 2H), 3.53-3.45 (m, 3H), 2.37 (s, 3H), 2.05-1.88 (m, 4H), 1.57 (s, 9H).

Example 247: 5-Fluoro-N-{2-fluoro-4-methyl-5-[8-(morpholin-4-yl)imidazo[1,2-a]pyridin-6-yl]phenyl}-1-(1-methylcyclopropyl)pyrrole-3-carboxamide

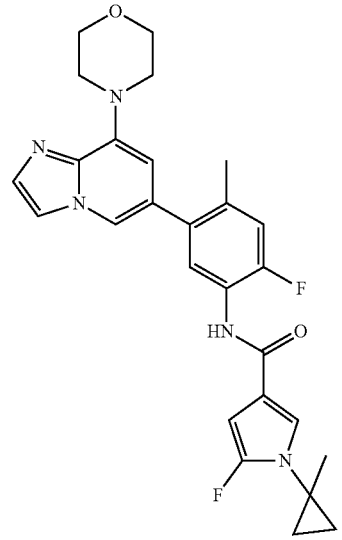 [SMILES: Cc1cc(F)c(NC(=O)c2cc(F)n(C3(C)CC3)c2)cc1-c1cc(N2CCOCC2)c2nccn2c1]

Step 1: To a stirred solution of 1-methylcyclopropan-1-amine hydrochloride (30.00 g, 278.86 mmol) and NaOAc (45.75 g, 557.72 mmol) in AcOH (50 mL) was added 2,5-dimethoxyoxolane (36.03 mL, 278.86 mmol) dropwise at room temperature. The reaction mixture was stirred for 16 h at 80° C. The resulting mixture was diluted with saturated NaHCO₃ (aq.). The resulting mixture was extracted with CH₂Cl₂ (2×300 mL). The combined organic layers were washed with brine (200 mL), dried over anhydrous Na₂SO₄ and filtered. The filtrate was concentrated in vacuo and the residue purified by distillation in vacuo and the fraction was collected at 70° C. This resulted in 1-(1-methylcyclopropyl)pyrrole (5 g, crude) as a colorless oil. ¹H NMR (400 MHz, Chloroform-d) δ 6.77 (t, J=2.1 Hz, 2H), 6.09 (t, J=2.2 Hz, 2H), 1.52 (s, 3H), 1.15-1.08 (m, 2H), 0.82-0.75 (m, 2H).

Step 2: To a stirred solution of 2,3,4-tribromo-1-(1-methylcyclopropyl)pyrrole (10 g, 27.94 mmol) in THF (600 mL) was added NBS (29.37 g, 165.04 mmol) in THF (30 mL) dropwise at -78° C. under nitrogen atmosphere. The reaction mixture was stirred for 2 h at room temperature under nitrogen atmosphere. The resulting mixture was concentrated in vacuo and the residue purified by silica gel column chromatography (PE, 100%). The fractions containing the desired product were combined and concentrated to afford 2,3,4,5-tetrabromo-1-(1-methylcyclopropyl)pyrrole (2.56 g, 14%) as a white solid. ¹H NMR (400 MHz, Chloroform-d) δ 1.45 (s, 3H), 1.27-1.23 (m, 2H), 1.13-1.07 (m, 2H).

Step 3: To a stirred solution of 2,3,4,5-tetrabromo-1-(1-methylcyclopropyl)pyrrole (2.56 g, 5.86 mmol) in THF (25 mL) was added n-BuLi (2.46 mL, 6.15 mmol) dropwise at −78° C. under nitrogen atmosphere. The reaction mixture was stirred for 1 h at −78° C. under nitrogen atmosphere. The resulting mixture was quenched with sat. NH₄Cl (aq.) at 0° C. The resulting mixture was extracted with EtOAc (2×50 mL). The combined organic layers were washed with brine (50 mL), dried over anhydrous Sodium sulfate, and filtered. The filtrate was concentrated in vacuo and the residue purified by silica gel column chromatography (PE, 100%). The fractions containing the desired product were combined and concentrated to afford 2,3,4-tribromo-1-(1-methylcyclopropyl)pyrrole (1.5 g, 71%) as a colorless solid. $^1$H NMR (400 MHz, Chloroform-d) δ 6.87 (s, 1H), 1.48 (s, 3H), 1.17-1.09 (m, 2H), 0.96-0.90 (m, 2H).

Step 4: To a stirred solution of 2,3,4-tribromo-1-(1-methylcyclopropyl)pyrrole (1.5 g, 4.19 mmol) in THF (15 mL) was added n-BuLi (1.76 mL, 4.40 mmol) dropwise at −78° C. under nitrogen atmosphere. The resulting mixture was stirred for 30 min at −78° C. under nitrogen atmosphere. To the above mixture was added NFSI (7.93 g, 25.15 mmol) in THF (15 mL) dropwise at −78° C. The reaction mixture was stirred for additional 1 h at −78° C. The reaction was quenched with sat. NH$_4$Cl (aq.) at 0° C. The resulting mixture was extracted with EtOAc (2×50 mL). The combined organic layers were washed with brine (50 mL), dried over anhydrous sodium sulfate, and filtered. The filtrate was concentrated in vacuo and the residue purified by silica gel column chromatography (PE, 100%). The fractions containing the desired product were combined and concentrated to afford 3,4-dibromo-2-fluoro-1-(1-methylcyclopropyl)pyrrole (640 mg, 25%) as a yellow oil. $^1$H NMR (400 MHz, Chloroform-d) δ 6.39 (d, J=1.9 Hz, 1H), 1.47 (s, 3H), 1.10-1.06 (m, 2H), 0.87-0.82 (m, 2H).

Step 5: To a stirred solution of 3,4-dibromo-2-fluoro-1-(1-methylcyclopropyl)pyrrole (640 mg, 2.16 mmol) in THF (6.4 mL) was added n-BuLi (0.91 mL, 2.26 mmol) dropwise at −78° C. under nitrogen atmosphere. The reaction mixture was stirred for 1 h at −78° C. under nitrogen atmosphere. The reaction was quenched with sat. NH$_4$Cl (aq.) at 0° C. The resulting mixture was extracted with EtOAc (2×30 mL). The combined organic layers were washed with brine (2×20 mL), dried over anhydrous sodium sulfate, and filtered. The filtrate was concentrated in vacuo and the residue purified by silica gel column chromatography (PE, 100%). The fractions containing the desired product were combined and concentrated to afford 4-bromo-2-fluoro-1-(1-methylcyclopropyl) pyrrole (370 mg, 78%) as a light yellow oil. $^1$H NMR (400 MHz, Chloroform-d) δ 6.29-6.23 (m, 1H), 5.48 (dd, J=3.8, 2.2 Hz, 1H), 1.46 (s, 3H), 1.08-1.05 (m, 2H), 0.85-0.78 (m, 2H).

Step 6: To a stirred solution of 4-bromo-2-fluoro-1-(1-methylcyclopropyl)pyrrole (270 mg, 0.99 mmol, 80%) in THF (2.7 mL) was added n-BuLi (0.42 mL, 1.04 mmol) dropwise at −78° C. under nitrogen atmosphere. The reaction mixture was stirred for 30 min at −78° C. under nitrogen atmosphere. To the above mixture was added carbonochloridic acid, propyl ester (0.17 mL, 1.49 mmol) dropwise at −78° C. The reaction mixture was stirred for additional 1 h at −78° C. The resulting mixture was quenched with sat. NH$_4$Cl (aq.) at 0° C. The resulting mixture was diluted with water (10 mL). The resulting mixture was extracted with EtOAc (2×30 mL). The combined organic layers were washed with brine (30 mL), dried over anhydrous sodium sulfate, and filtered. The filtrate was concentrated in vacuo and the residue purified by silica gel column chromatography (PE/EA, 11:1). The fractions containing the desired product were combined and concentrated to afford propyl 5-fluoro-1-(1-methylcyclopropyl)pyrrole-3-carboxylate (170 mg, 76%) as a colorless oil. MS ESI calculated for C$_{12}$H$_{16}$FNO$_2$ [M+H]$^+$, 226.12, found 226.10; $^1$H NMR (400 MHz, Chloroform-d) δ 6.94 (t, J=2.1 Hz, 1H), 5.84 (dd, J=4.0, 2.2 Hz, 1H), 4.15 (t, J=6.8 Hz, 2H), 1.76-1.67 (m, 2H), 1.50 (s, 3H), 1.26 (t, J=7.2 Hz, 1H), 1.11 (t, J=8.0 Hz, 2H), 0.98 (t, J=7.4 Hz, 3H), 0.91-0.84 (m, 2H).

Step 7: To a stirred solution of 2-fluoro-4-methyl-5-[8-(morpholin-4-yl)imidazo[1,2-a]pyridin-6-yl]aniline (70 mg, 0.21 mmol) and LiHMDS (1 M in THF) (0.64 mL, 0.64 mmol) in THF (0.7 mL) was added propyl 5-fluoro-1-(1-methylcyclopropyl)pyrrole-3-carboxylate (48.31 mg, 0.21 mmol) dropwise at 0° C. under nitrogen atmosphere. The reaction mixture was stirred for 1 h at room temperature under nitrogen atmosphere. The resulting mixture was quenched with water at room temperature. The resulting mixture was extracted with EtOAc (2×20 mL). The combined organic layers were washed with brine (10 mL), dried over anhydrous sodium sulfate, and filtered. The filtrate was concentrated in vacuo and the residue purified by silica gel column chromatography (PE/EA, 1:9) to afford a crude product which was further purified by Prep-HPLC with following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 30% B to 60% B in 10 min; Wave Length: 254 nm/220 nm. The fractions containing the desired product were combined and concentrated to afford the title compound (42.9 mg, 40%) as a white solid. MS ESI calculated for C$_{27}$H$_{27}$F$_2$N$_5$O$_2$ [M+H]$^+$, 492.21, found 492.35; $^1$H NMR (400 MHz, DMSO-d$_6$) δ 9.41 (s, 1H), 8.13 (d, J=1.5 Hz, 1H), 7.89 (d, J=1.2 Hz, 1H), 7.53-7.46 (m, 2H), 7.28-7.21 (m, 2H), 6.35 (d, J=1.5 Hz, 1H), 6.06 (dd, J=3.8, 2.3 Hz, 1H), 3.80 (t, J=4.6 Hz, 4H), 3.54 (t, J=4.7 Hz, 4H), 2.28 (s, 3H), 1.47 (s, 3H), 1.14-1.06 (m, 2H), 0.97-0.90 (m, 2H).

Example 248: 1-(tert-Butyl)-5-fluoro-N-(2-fluoro-6-methyl-5-(8-morpholinoimidazo[1,2-a]pyridin-6-yl) pyridin-3-yl)-1H-pyrazole-4-carboxamide

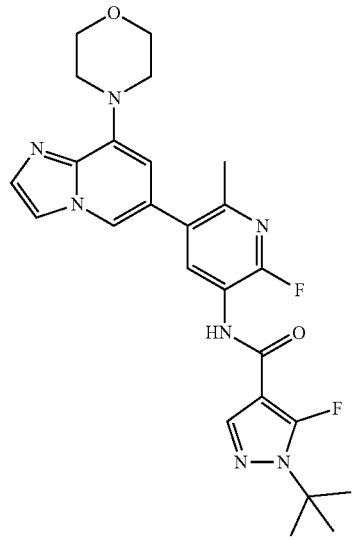 [SMILES: Cc1nc(F)c(NC(=O)c2cnn(C(C)(C)C)c2F)cc1-c1cc(N2CCOCC2)c2nccn2c1]

Step 1: To a stirred mixture of 5-bromo-2-fluoro-6-methylpyridin-3-amine (120 mg, 0.59 mmol), Pd(PPh$_3$)$_2$Cl$_2$ (48 mg, 0.06 mmol) and Na$_2$CO$_3$ (186 mg, 1.76 mmol) in dioxane (4.8 mL) and water (1.2 mL) was added 4-[6-(4,4,5,5-tetramethyl-1,3,2-dioxaborolan-2-yl)imidazo[1,2-a] pyridin-8-yl]morpholine (578 mg, 1.76 mmol, 30%) at room temperature. The reaction mixture was purged with nitrogen and stirred for 2 h at 80° C. The resulting mixture was diluted with water (20 mL) and extracted with EA (2×30 mL). The combined organic layers were washed with brine (100 mL), dried over anhydrous sodium sulfate, and filtered. The filtrate was concentrated in vacuo and the residue purified by silica gel column chromatography (PE/EA/EtOH, 4:3:1). The fractions containing the desired product were combined and concentrated to afford 2-fluoro-6-methyl-5-[8-(morpholin-4-yl)imidazo[1,2-a]pyridin-6-yl]pyridin-3-amine (120 mg, 62%) as a light brown solid. MS ESI calculated for $C_{17}H_{18}FN_5O[M+H]^+$, 328.15, found 328.15; $^1$H NMR (400 MHz, Chloroform-d) δ 7.72 (d, J=1.2 Hz, 1H), 7.63-7.61 (m, 1H), 7.57-7.55 (m, 1H), 7.06-7.02 (m, 1H), 6.33-6.31 (m, 1H), 4.00 (t, J=4.8 Hz, 4H), 3.58 (t, J=4.8 Hz, 4H), 2.35 (s, 3H).

Step 2: To a stirred solution of 2-fluoro-6-methyl-5-[8-(morpholin-4-yl)imidazo[1,2-a]pyridin-6-yl]pyridin-3-amine (70 mg, 0.21 mmol), Pd(dppf)Cl$_2$-DCM (17 mg, 0.02 mmol) and Co$_2$(CO)$_8$ (21.94 mg, 0.06 mmol) in dioxane (1 mL) were added TEA (1.26 mmol, 127.26 mg) and 4-bromo-1-(tert-butyl)-5-fluoro-1H-pyrazole (57 mg, 0.26 mmol) at room temperature. The reaction mixture was purged with nitrogen and stirred for 16 h at 90° C. The resulting mixture was diluted with water (10 mL) and extracted with Ethyl acetate (3×20 mL). The combined organic layers were washed with brine (2×20 mL), dried over anhydrous Sodium sulfate, and filtered. The filtrate was concentrated in vacuo and the residue purified by silica gel column chromatography (PE/EA/EtOH, 8:3:1) to afford a crude product which was further purified by Prep-HPLC with the following conditions: Column: XBridge Prep OBD C18 Column, 30×150 mm, 5 m; Mobile Phase A: Water (Plus 10 mmol/L NH$_4$HCO$_3$), Mobile Phase B: ACN; Flow rate: 60 mL/min; Gradient: 28% B to 58% B in 7 min; Wave Length: 254 nm/220 nm; RT1: 6.4 min. The fractions containing the desired product were combined and concentrated to afford title compound (36.6 mg, 34%) as an off-white solid. MS ESI calculated for $C_{25}H_{27}F_2N_{7O2}$ $[M+H]^+$, 496.22, found 496.20; $^1$H NMR (400 MHz, Chloroform-d) δ 8.76 (d, J=9.6 Hz, 1H), 7.83 (d, J=2.8 Hz, 1H), 7.78 (d, J=2.4 Hz, 1H), 7.65-7.59 (m, 2H), 7.56 (d, J=1.2 Hz, 1H), 6.35 (s, 1H), 4.00-3.99 (m, 4H), 3.64-3.57 (m, 4H), 2.45 (s, 3H), 1.68-1.60 (m, 9H).

Example 250: 1-(tert-Butyl)-5-fluoro-N-(2-fluoro-4-methyl-5-(2-methyl-8-morpholino-[1,2,4]triazolo[1,5-a]pyridin-6-yl)phenyl)-1H-pyrazole-4-carboxamide

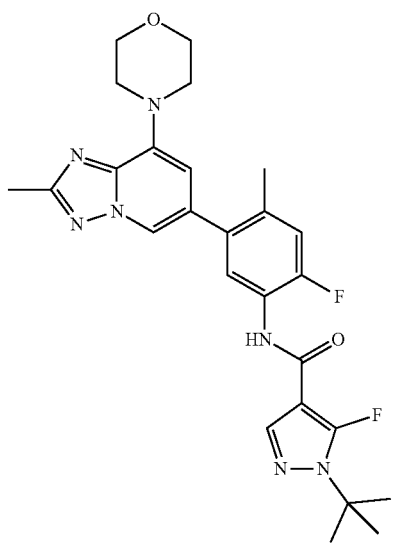 [SMILES: Cc1nc2c(N3CCOCC3)cc(-c3cc(NC(=O)c4cnn(C(C)(C)C)c4F)c(F)cc3C)cn2n1]

Step 1: To a stirred solution of 8-bromo-6-chloro-2-methyl-[1,2,4]triazolo[1,5-a]pyridine (500 mg, 2.03 mmol), BINAP (126 mg, 0.20 mmol), t-BuONa (779 mg, 8.11 mmol) and Pd(OAc)$_2$ (68 mg, 0.30 mmol) in toluene (10 mL) was added morpholine (176 mg, 2.03 mmol). The reaction mixture was purged with nitrogen and stirred for 3 h at 95° C. The resulting mixture was concentrated in vacuo and the residue purified by reversed-phase flash chromatography with the following conditions: column, C18 silica gel; mobile phase, MeCN in Water (Plus 0.1% TFA), 15% to 85% gradient in 25 min; detector, UV 220 nm. The fractions containing the desired product were combined and concentrated to afford 4-{6-chloro-2-methyl-[1,2,4]triazolo[1,5-a]pyridin-8-yl}morpholine (200 mg, 39%) as an off-white solid. MS ESI calculated for $C_{11}H_{13}ClN_4O$ $[M+H]^+$, 253.08, found 253.30; $^1$H NMR (400 MHz, Chloroform-d) δ 8.16-8.13 (m, 1H), 6.63-6.60 (m, 1H), 4.01-3.94 (m, 4H), 3.61-3.54 (m, 4H), 2.59 (s, 3H).

Step 2: To a stirred solution of 4-{6-chloro-2-methyl-[1,2,4]triazolo[1,5-a]pyridin-8-yl}morpholine (160 mg, 0.63 mmol), XPhos Pd G2 (49 mg, 0.06 mmol) and 2-fluoro-4-methyl-5-(4,4,5,5-tetramethyl-1,3,2-dioxaborolan-2-yl)aniline (158 mg, 0.63 mmol) in THF (2 mL) was added K$_3$PO$_4$ (0.5 M, 4 mL). The reaction mixture was purged with nitrogen and stirred for 2 h at 80° C. The resulting mixture was diluted with water (20 mL) and extracted with EtOAc (3×30 mL). The combined organic layers were washed with brine (2×20 mL), dried over anhydrous sodium sulfate, and filtered. The filtrate was concentrated in vacuo and the residue purified by silica gel column chromatography (PE/EA/EtOH, 1:3:1). The fractions containing the desired product were combined and concentrated to afford 2-fluoro-4-methyl-5-[2-methyl-8-(morpholin-4-yl)-[1,2,4]triazolo[1,5-a]pyridin-6-yl]aniline (195 mg, 90%) as an off-white solid. MS ESI calculated for $C_{18}H_{2O}FN_5O[M+H]^+$, 342.17, found 342.15; $^1$H NMR (400 MHz, Chloroform-d) δ 8.02 (d, J=1.4 Hz, 1H), 6.94 (d, J=11.8 Hz, 1H), 6.71-6.68 (m, 1H), 6.58 (d, J=1.5 Hz, 1H), 3.98-3.96 (m, 4H), 3.54-3.52 (m, 4H), 2.60 (s, 3H), 2.15 (s, 3H).

Step 3: To a stirred solution of 2-fluoro-4-methyl-5-[2-methyl-8-(morpholin-4-yl)-[1,2,4]triazolo[1,5-a]pyridin-6-yl]aniline (100 mg, 0.29 mmol), Pd(dppf)Cl$_2$—CH$_2$Cl$_2$ (47 mg, 0.06 mmol) and Co$_2$(CO)$_8$ (30 mg, 0.09 mmol) in dioxane (2 mL) were added TEA (177 mg, 1.74 mmol) and 4-bromo-1-tert-butyl-5-fluoropyrazole (77 mg, 0.35 mmol) dropwise at room temperature. The reaction mixture was purged with nitrogen and stirred for 16 h at 90° C. The resulting mixture was diluted with water (10 mL) and extracted with EtOAc (3×20 mL). The combined organic layers were washed with brine (2×15 mL), dried over anhydrous sodium sulfate, and filtered. The filtrate was concentrated in vacuo and the residue purified by Prep-TLC (PE/EA/EtOH, 8:3:1) to afford crude product. The crude product was further purified by Prep-HPLC with the following conditions: Column: YMC-Actus Triart C 18ExRS, 30×150 mm, 5 m; Mobile Phase A: water (Plus 10 mmol/L NH$_4$HCO$_3$), Mobile Phase B: ACN; Flow rate: 60 mL/min; Gradient: 27% B to 52% B in 8 min; Wave Length: 254 nm/220 nm; RT1: 6.2 min. The fractions containing the desired product were combined and concentrated to afford title compound (24 mg, 16%) as an off-white solid. MS ESI calculated for $C_{26}H_{29}F_2N_{7O2}$ $[M+H]^+$, 510.24, found 510.25; $^1$H NMR (400 MHz, Chloroform-d) δ 8.36 (d, J=8.0 Hz, 1H), 8.06-8.04 (m, 1H), 7.82 (d, J=2.6 Hz, 1H), 7.68-7.64 (m, 1H), 7.09 (d, J=11.6 Hz, 1H), 6.61 (s, 1H), 3.98-3.96 (m, 4H), 3.55-3.52 (m, 4H), 2.61 (s, 3H), 2.25 (s, 3H), 1.66 (s, 9H).

Example 253: N-(1-(tert-Butyl)-5-fluoro-1H-pyrazol-4-yl)-2-fluoro-4-methyl-5-(8-morpholinoimidazo[1,2-a]pyridin-6-yl)benzamide

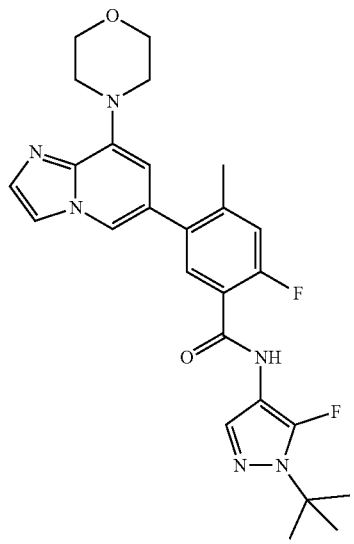 [SMILES: Cc1cc(F)c(C(=O)Nc2cnn(C(C)(C)C)c2F)cc1-c1cc(N2CCOCC2)c2nccn2c1]

Step 1: To a stirred solution of methyl 2-fluoro-4-methyl-5-[8-(morpholin-4-yl)imidazo[1,2-a]pyridin-6-yl]benzoate (230 mg, 0.62 mmol) in dioxane (4 mL) was added $NH_3$-$H_2O$ (4 mL) dropwise at room temperature. The reaction mixture was stirred for 48 h at room temperature. The resulting mixture was concentrated in vacuo and the residue purified by silica gel column chromatography (PE/EA/EtOH, 4:3:1). The fractions containing the desired product were combined and concentrated to afford 2-fluoro-4-methyl-5-[8-(morpholin-4-yl)imidazo[1,2-a]pyridin-6-yl]benzamide (190 mg, 63.20%) as a white solid. MS ESI calculated for $C_{19}H_{19}FN_4O_2$. $[M+H]^+$, 355.15, found 355.15; $^1$H NMR (400 MHz, Chloroform-d) δ 8.04 (d, J=8.2 Hz, 1H), 7.74 (d, J=1.4 Hz, 1H), 7.61 (d, J=1.3 Hz, 1H), 7.55 (d, J=1.3 Hz, 1H), 7.09 (d, J=12.6 Hz, 1H), 6.32 (d, J=1.5 Hz, 1H), 3.99-3.92 (m, 4H), 3.59-3.52 (m, 4H), 2.35 (s, 3H).

Step 2: To a stirred mixture of 2-fluoro-4-methyl-5-[8-(morpholin-4-yl)imidazo[1,2-a]pyridin-6-yl]benzamide (100 mg, 0.28 mmol), methyl[2-(methylamino)ethyl]amine (24.88 mg, 0.28 mmol), 4-bromo-1-(tert-butyl)-5-fluoro-1H-pyrazole (74.86 mg, 0.34 mmol) and $K_3PO_4$ (125.78 mg, 0.59 mmol) in dioxane (0.5 mL) was added CuI (53.74 mg, 0.28 mmol) portionwise at room temperature. The reaction mixture was purged with nitrogen and stirred for 16 h at 100° C. The resulting mixture was concentrated in vacuo and the residue purified by silica gel column chromatography (PE/EA/EtOH, 4:3:1) to afford a crude product which was further purified by Prep-HPLC with the following conditions: Column: XBridge Prep OBD C18 Column, 19×250 mm, 5 m; Mobile Phase A: Water (Plus 10 mmol/L $NH_4HCO_3$+0.05% $NH_3$-$H_2O$), Mobile Phase B: ACN; Flow rate: 25 mL/min; Gradient: 37% B to 67% B in 8 min; Wave Length: 254 nm/220 nm; RT1: 7.43 min. The fractions containing the desired product were combined and concentrated to afford title compound (36.4 mg, 26%) as a white solid. MS ESI calculated for $C_{26}H_{28}F_2N_6O_2$. $[M+H]^+$, 495.22, found 495.30; $^1$H NMR (400 MHz, DMSO-$d_6$) δ 9.91 (s, 1H), 8.19 (d, J=1.4 Hz, 1H), 7.89 (d, J=1.2 Hz, 1H), 7.63-7.54 (m, 2H), 7.52 (d, J=1.2 Hz, 1H), 7.34 (d, J=11.4 Hz, 1H), 6.39 (d, J=1.5 Hz, 1H), 3.84 (t, J=4.8 Hz, 4H), 3.55 (t, J=4.8 Hz, 4H), 2.35 (s, 3H), 1.54 (s, 9H).

Example 260: N-(1-(tert-butyl)-5-fluoro-1H-pyrazol-4-yl)-2-fluoro-4-methyl-5-(8-morpholinoimidazo[1,2-b]pyridazin-6-yl)benzamide

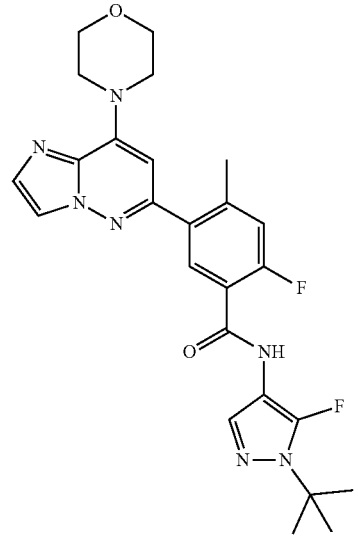 [SMILES: Cc1cc(F)c(C(=O)Nc2cnn(C(C)(C)C)c2F)cc1-c1cc(N2CCOCC2)c2nccn2n1]

Step 1: To a stirred solution of 8-bromo-6-chloroimidazo[1,2-b]pyridazine (500.00 mg, 2.15 mmol) in EtOH (3.30 mL) was added morpholine (1.87 g, 21.51 mmol) dropwise at room temperature under nitrogen atmosphere. The reaction mixture was stirred for 3 h at room temperature under nitrogen atmosphere. The resulting mixture was filtered, the filter cake was washed with EtOH (3×10 mL) to afford 4-[6-chloroimidazo[1,2-b]pyridazin-8-yl]morpholine(500 mg, crude) as a light yellow solid. MS ESI calculated for $C_{10}H_{11}ClN_4O$ $[M+H]^+$, 239.06, found 239.10.

Step 2: To a stirred mixture of 4-{6-chloroimidazo[1,2-b]pyridazin-8-yl}morpholine (243.44 mg, 1.02 mmol) and methyl 2-fluoro-4-methyl-5-(4,4,5,5-tetramethyl-1,3,2-dioxaborolan-2-yl)benzoate (300 mg, 1.02 mmol) in THF (2 mL) and $H_2O$ (0.2 mL) were added $K_3PO_4$ (433.00 mg, 2.04 mmol) and XPhos Pd G2 (80.17 mg, 0.10 mmol) in portions at room temperature. The reaction mixture was purged with nitrogen and stirred for 2 h at 80° C. The resulting mixture was concentrated in vacuo and the residue purified by silica gel column chromatography (PE/EA/EtOH, 4:3:1). The fractions containing the desired product were combined and concentrated to afford methyl 2-fluoro-4-methyl-5-[8-(morpholin-4-yl)imidazo[1,2-b]pyridazin-6-yl]benzoate (260 mg, 55%) as a brown solid. MS ESI calculated for $C_{19}H_{19}FN_4O_3$. $[M+H]^+$, 371.04, found 371.15; $^1$H NMR (400 MHz, Chloroform-d) δ 8.01 (d, J=7.4 Hz, 1H), 7.87 (d, J=1.2 Hz, 1H), 7.62 (d, J=1.2 Hz, 1H), 7.11 (d, J=11.4 Hz, 1H), 6.11 (s, 1H), 3.98-3.89 (m, 8H), 2.44 (s, 3H), 1.27 (s, 3H).

Step 3: To a stirred mixture of methyl 2-fluoro-4-methyl-5-[8-(morpholin-4-yl)imidazo[1,2-b]pyridazin-6-yl]benzoate (200 mg, 0.540 mmol) in 1,4-dioxane (2 mL) was added ammonium hydroxide (2 mL). The reaction mixture was stirred for 48 h at 40° C. The resulting mixture was concentrated in vacuo and the residue purified by silica gel column chromatography (PE/EA/EtOH 4:3:1). The fractions containing the desired product were combined and concentrated to afford 2-fluoro-4-methyl-5-[8-(morpholin-4-yl)imidazo[1,2-b]pyridazin-6-yl]benzamide (90 mg, 46%) as a brown solid. MS ESI calculated for $C_{18}H_{18}FN_5O_2[M+H]^+$, 356.14, found 356.35; $^1$H NMR (400 MHz, Chloroform-d) δ 8.20 (d, J=8.1 Hz, 1H), 7.86 (d, J=1.1 Hz, 1H), 7.65 (s, 1H), 7.12 (d, J=12.6 Hz, 1H), 6.70 (d, J=11.4 Hz, 1H), 4.03-3.93 (m, 8H), 2.46 (s, 3H).

Step 4: To a stirred mixture of 2-fluoro-4-methyl-5-[8-(morpholin-4-yl)imidazo[1,2-b]pyridazin-6-yl]benzamide (70 mg, 0.20 mmol), N, N-dimethylethane-1,2-diamine (17.6 mg, 0.20 mmol) and $K_3PO_4$ (87.80 mg, 0.41 mmol) in 1,4-dioxane (1 mL) were added 4-bromo-1-(tert-butyl)-5-fluoro-1H-pyrazole (53.40 mg, 0.24 mmol) and CuI (37.51 mg, 0.20 mmol) at room temperature. The reaction mixture was purged with nitrogen and stirred for 16 h at 100° C. The resulting mixture was concentrated in vacuo and the residue purified by silica gel column chromatography (PE/EA/EtOH, 4:3:1). The fractions containing the desired product were combined and concentrated to afford the title compound (37.7 mg, 37%) as a white solid. MS ESI calculated for $C_{25}H_{27}F_2N_7O_2[M+H]^+$, 496.22, found 496.35; $^1$H NMR (400 MHz, DMSO-$d_6$) δ 9.98 (s, 1H), 8.10 (d, J=1.2 Hz, 1H), 7.72 (d, J=7.4 Hz, 1H), 7.59 (d, J=10.0, 1.9 Hz, 2H), 7.36 (d, J=11.4 Hz, 1H), 6.40 (s, 1H), 4.04-3.97 (m, 4H), 3.81-3.74 (m, 4H), 2.40 (s, 3H), 1.54 (s, 9H).

Example 263: N-{2-Fluoro-4-methyl-5-[8-(morpholin-4-yl)imidazo[1,2-a]pyridin-6-yl]phenyl}-2-[methyl(trifluoromethyl)amino]pyridine-4-carboxamide

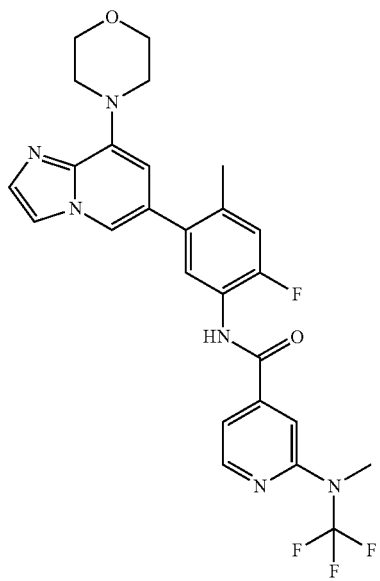 [SMILES: Cc1cc(F)c(NC(=O)c2ccnc(N(C)C(F)(F)F)c2)cc1-c1cc(N2CCOCC2)c2nccn2c1]

Step 1: To a stirred solution of 4-Bromo-N-methylpyridin-2-amine (2 g, 10.69 mmol) in THF (30 mL) was added NaOH (0.86 g, 21.39 mmol). The reaction mixture was stirred for 1 h at room temperature under nitrogen atmosphere and carbon disulfide (1.63 g, 21.39 mmol) was added dropwise at room temperature. The reaction mixture was allowed to stir for 16 h at room temperature followed by addition of $CH_3I$ (3.04 g, 21.39 mmol) dropwise at 0° C. The reaction mixture was stirred for additional 6 h at room temperature. The resulting mixture was diluted with water (50 mL) and extracted with $CH_2Cl_2$ (2×30 mL). The combined organic layers were washed with brine (2×20 mL), dried over anhydrous sodium sulfate, and filtered. The filtrate was concentrated in vacuo and the residue purified by silica gel column chromatography (PE/EA, 2:1). The fractions containing the desired product were combined and concentrated to afford N-(4-bromopyridin-2-yl)-N-methylmethylsulfanylcarbothioamide (1.8 g, 60%) as an off-white solid. MS ESI calculated for $C_8H_9BrN_2S_2[M+H]^+$, 276.94, 278.94, found 276.95, 278.95, H NMR (400 MHz, DMSO-$d_6$) δ 8.26-8.24 (m, 1H), 7.57-7.48 (m, 1H), 7.41 (d, J=1.6 Hz, 1H), 3.20-3.09 (m, 6H)

Step 2: To a stirred solution of tetrabutylazanium dihydrofluoride fluoride (4.89 g, 16.24 mmol) and 1,3-dibromo-5,5-dimethylimidazolidine-2,4-dione (3.71 g, 12.99 mmol) in DCM (13 mL) was added N-(4-bromopyridin-2-yl)-N-methylmethylsulfanylcarbothioamide (900 mg, 3.25 mmol) dropwise at 0° C. The reaction mixture was stirred for 4 h at 0° C. The resulting mixture was basified to pH 10 with NaOH (aq.). The resulting mixture was diluted with water (30 mL) and extracted with EtOAc (3×30 mL). The combined organic layers were washed with brine (2×30 mL), dried over anhydrous sodium sulfate, and filtered. The filtrate was concentrated in vacuo and the residue purified by silica gel column chromatography (PE/EA, 1:1). The fractions containing the desired product were combined and concentrated to afford 4-bromo-N-methyl-N-(trifluoromethyl)pyridin-2-amine (700 mg, 84%) as an off-white solid. MS ESI calculated for $C_7H_6BrF_3N_2[M+H]^+$, 254.97, 256.97, found 254.80, 256.80; $^1$H NMR (400 MHz, DMSO-$d_6$) δ 8.27 (d, J=5.4 Hz, 1H), 7.48-7.42 (m, 1H), 7.37-7.35 (m, 1H), 3.20 (q, J=2.0 Hz, 3H).

Step 3: To a stirred solution of 2-fluoro-4-methyl-5-[8-(morpholin-4-yl)imidazo[1,2-a]pyridin-6-yl]aniline (100 mg, 0.31 mmol), 4-bromo-N-methyl-N-(trifluoromethyl)pyridin-2-amine (78.14 mg, 0.31 mmol) and TEA (186.03 mg, 1.84 mmol) in dioxane (1.5 mL) were added Pd(dppf)Cl$_2$·CH$_2$Cl$_2$ (49.92 mg, 0.06 mmol) and Co$_2$(CO)$_8$ (31.43 mg, 0.09 mmol) in portions at room temperature. The reaction mixture was purged with nitrogen and stirred for 16 h at 90° C. The resulting mixture was diluted with water (40 mL) and extracted with EtOAc (2×50 mL). The combined organic layers were washed with brine (2×40 mL), dried over anhydrous sodium sulfate, and filtered. The filtrate was concentrated in vacuo and the residue purified by Prep-HPLC with the following conditions: Column: XBridge Prep OBD C18 Column, 30×150 mm, 5 m; Mobile Phase A: Water (Plus 10 mmol/L NH$_4$HCO$_3$), Mobile Phase B: ACN; Flow rate: 60 mL/min; Gradient: 32% B to 62% B in 7 min; Wave Length: 254 nm/220 nm; RT: 7 min. The fractions containing the desired product were combined and concentrated to afford the title compound (42.8 mg, 26%) as a white solid. MS ESI calculated for $C_{26}H_{24}F_4N_6O_2[M+H]^+$, 529.19, found 529.35; $^1$H NMR (400 MHz, DMSO-$d_6$) δ 10.50 (s, 1H), 8.57 (d, J=5.1 Hz, 1H), 8.16 (d, J=1.4 Hz, 1H), 7.90 (d, J=1.2 Hz, 1H), 7.65 (dd, J=5.1, 1.4 Hz, 1H), 7.62-7.59 (m, 1H), 7.57-7.49 (m, 2H), 7.33 (d, J=11.4 Hz, 1H), 6.37 (d, J=1.5 Hz, 1H), 3.84-3.77 (t, J=4.7 Hz, 4H), 3.55 (t, J=4.7 Hz, 4H), 3.27 (q, J=2.0 Hz, 3H), 2.31 (s, 3H).

Example 265: 1-(tert-Butyl)-5-fluoro-N-(2-fluoro-4-methyl-5-(2-methyl-8-morpholinoimidazo[1,2-b]pyridazin-6-yl)phenyl)-1H-pyrazole-4-carboxamide

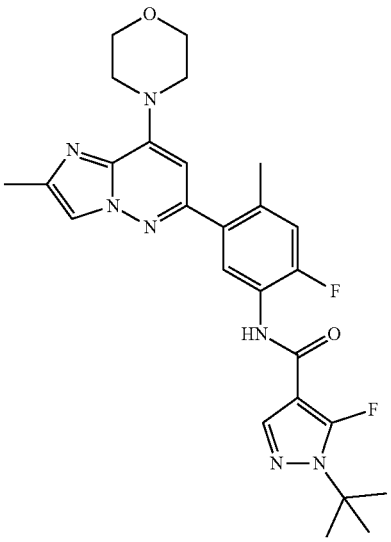 [SMILES: Cc1cn2nc(-c3cc(NC(=O)c4cnn(C(C)(C)C)c4F)c(F)cc3C)cc(N3CCOCC3)c2n1]

Step 1: To a stirred mixture of 8-bromo-6-chloro-2-methylimidazo[1,2-b]pyridazine (950 mg, 3.85 mmol), Cesium carbonate (376.72 mg, 1.16 mmol) and RuPhos Pd G2 (299.36 mg, 0.39 mmol) in dioxane (10 mL) was added morpholine (335.78 mg, 3.85 mmol) dropwise at room temperature. The reaction mixture was purged with nitrogen and stirred for 2 h at 100° C. The resulting mixture was diluted with water (50 mL) and extracted with EA (3×150 mL). The combined organic layers were washed with brine (2×80 mL), dried over anhydrous sodium sulfate, and filtered. The filtrate was concentrated in vacuo and the residue purified by silica gel column chromatography (PE/EA, 4:1). The fractions containing the desired product were combined and concentrated to afford 4-{6-chloro-2-methylimidazo[1,2-b]pyridazin-8-yl}morpholine (820 mg, 84%) as a yellow solid. MS ESI calculated for $C_{11}H_{13}ClN_4O$ [M+H]$^+$, 253.08, 255.08, found 253.00, 255.00; $^1$H NMR (400 MHz, Chloroform-d) δ 7.51 (s, 1H), 6.07 (s, 1H), 4.01-3.87 (m, 8H), 2.43 (s, 3H).

Step 2: To a stirred mixture of 4-{6-chloro-2-methylimidazo[1,2-b]pyridazin-8-yl}morpholine (0.8 g, 3.17 mmol), XPhos Pd G2 (0.25 g, 0.32 mmol) and $K_3PO_4$ (2.02 g, 9.50 mmol) in THF (8 mL) and water (0.8 mL) was added 2-fluoro-4-methyl-5-(4,4,5,5-tetramethyl-1,3,2-dioxaborolan-2-yl)aniline (1.59 g, 6.33 mmol) in portions at room temperature. The reaction mixture was purged with nitrogen and stirred for 3 h at 80° C. The resulting mixture was diluted with water (50 mL) and extracted with EA (3×70 mL). The combined organic layers were washed with brine (2×50 mL), dried over anhydrous sodium sulfate, and filtered. The filtrate was concentrated in vacuo and the residue purified by silica gel column chromatography (PE/EA, 1:1). The fractions containing the desired product were combined and concentrated to afford 2-fluoro-4-methyl-5-[2-methyl-8-(morpholin-4-yl)imidazo[1,2-b]pyridazin-6-yl]aniline (470 mg, 43%) as a white solid. MS ESI calculated for $C_{18}H_2OFN_5O$[M+H]$^+$, 342.17, found 342.15; $^1$H NMR (400 MHz, Chloroform-d) δ 7.60 (s, 1H), 7.26 (s, 1H), 6.91 (d, J=11.8 Hz, 1H), 6.82 (d, J=9.1 Hz, 1H), 3.93-3.80 (m, 8H), 2.46 (s, 3H), 2.22 (s, 3H).

Step 3: To a stirred mixture of 2-fluoro-4-methyl-5-[2-methyl-8-(morpholin-4-yl)imidazo[1,2-b]pyridazin-6-yl]aniline (100 mg, 0.29 mmol), Pd(dppf)$C_{12}$ DCM (47.72 mg, 0.06 mmol) and $Co_2(CO)_8$ (30.05 mg, 0.09 mmol) in dioxane (1 mL) were added TEA (177.85 mg, 1.76 mmol) and 4-bromo-1-(tert-butyl)-5-fluoro-1H-pyrazole (77.71 mg, 0.35 mmol). The reaction mixture was purged with nitrogen and stirred for 16 h at 90° C. The resulting mixture was concentrated in vacuo and the residue purified by silica gel column chromatography (PE/EA/EtOH, 4:3:1). The residue purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 38% B to 68% B in 7 min; Wave Length: 254 nm/220 nm; RT1: 6.2 min. The fractions containing the desired product were combined and concentrated to afford the title compound (27.3 mg, 18%) as a white solid. MS ESI calculated for $C_{26}H_{29}F_2N_7O_2$ [M+H]$^+$, 510.24, found 510.40; $^1$H NMR (400 MHz, Chloroform-d) δ 8.46 (d, J=8.1 Hz, 1H), 7.82 (d, J=2.6 Hz, 1H), 7.67 (s, 1H), 7.61-7.56 (m, 1H), 7.06 (d, J=11.6 Hz, 1H), 6.12 (s, 1H), 3.94-3.86 (m, 8H), 2.46 (s, 3H), 2.33 (s, 3H), 1.65 (s, 9H).

Example 266: N-(1-(tert-butyl)-5-fluoro-1H-pyrazol-4-yl)-2-fluoro-5-(3-fluoro-8-morpholinoimidazo[1,2-a]pyridin-6-yl)-4-methylbenzamide

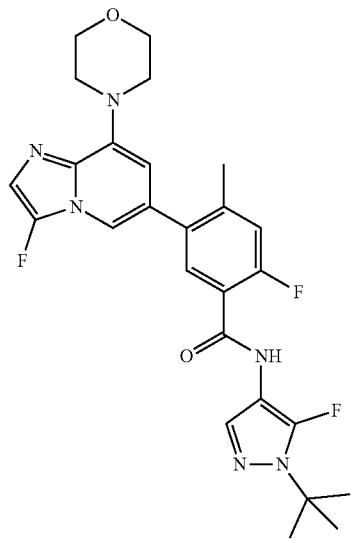 [SMILES: Cc1cc(F)c(C(=O)Nc2cnn(C(C)(C)C)c2F)cc1-c1cc(N2CCOCC2)c2ncc(F)n2c1]

Step 1: To a stirred mixture of 4-{6-chloro-3-fluoroimidazo[1,2-a]pyridin-8-yl}morpholine (880 mg, 3.44 mmol) and methyl 2-fluoro-4-methyl-5-(4,4,5,5-tetramethyl-1,3,2-dioxaborolan-2-yl)benzoate (1.21 g, 4.13 mmol) in THF (10 mL) and H$_2$O (1 mL) were added K$_3$PO$_4$ (2.19 g, 10.33 mmol) and 2nd generation XPhos precatalyst (270.81 mg, 0.34 mmol) in portions at room temperature. The reaction mixture was purged with nitrogen three times and stirred for 2 h at 80° C. The resulting mixture was concentrated in vacuo and the residue purified by silica gel column chromatography (PE/EA/EtOH, 4:3:1). The fractions containing the desired product were combined and concentrated to afford methyl 2-fluoro-5-[3-fluoro-8-(morpholin-4-yl)imidazo[1,2-a]pyridin-6-yl]-4-methylbenzoate (950 mg, 77%) as a brown solid. MS ESI calculated for $C_{20}H_{19}F_2N_3O_3$[M+

H]⁺, 388.14, found 388.35; ¹H NMR (400 MHz, Chloroform-d) δ 7.87 (d, J=7.4 Hz, 1H), 7.49 (d, J=1.4 Hz, 1H), 7.17 (d, J=7.2 Hz, 1H), 7.11 (d, J=11.4 Hz, 1H), 6.25 (d, J=1.5 Hz, 1H), 3.98-3.92 (m, 4H), 3.62-3.55 (m, 4H), 2.34 (s, 3H), 1.27 (s, 3H).

Step 2: To a stirred solution of methyl 2-fluoro-5-[3-fluoro-8-(morpholin-4-yl)imidazo[1,2-a]pyridin-6-yl]-4-methylbenzoate (950 mg, 2.45 mmol) in THF (4 mL), MeOH (4 mL) and water (4 mL) was added LiOH·H₂O (360.15 mg, 8.58 mmol) in portions at room temperature. The reaction mixture was allowed to stir for 1 h at room temperature. The resulting mixture was concentrated in vacuo and acidified to pH 5 with HCl (aq.). The precipitated solids were collected by filtration and washed with water (3×10 mL) to afford 2-fluoro-5-[3-fluoro-8-(morpholin-4-yl)imidazo[1,2-a]pyridin-6-yl]-4-methylbenzoic acid (400 mg, crude) as an off-white solid. MS ESI calculated for C₁₉H₁₇F₂N₃O₃[M+H]⁺, 374.12, found 374.25; ¹H NMR (400 MHz, Chloroform-d) δ 7.85 (d, J=7.4 Hz, 1H), 7.48 (s, 1H), 7.23 (d, J=6.6 Hz, 1H), 7.07 (d, J=11.4 Hz, 1H), 6.32 (s, 1H), 3.93 (t, J=4.8 Hz, 4H), 3.45 (t, J=4.8 Hz, 4H), 2.28 (s, 3H).

Step 3: To a stirred mixture of 2-fluoro-5-[3-fluoro-8-(morpholin-4-yl)imidazo[1,2-a]pyridin-6-yl]-4-methylbenzoic acid (550 mg, 1.47 mmol) in DCM (6 mL) was added and oxalyl chloride (0.25 mL, 2.95 mmol) and DMF (cat.) dropwise at 0° C. The reaction mixture was allowed to stir for 1 h at room temperature. To the above mixture was added NH₃H₂O (2 mL) dropwise at room temperature. The reaction mixture was allowed to stir for additional 5 min at room temperature. The resulting mixture was diluted with water (15 mL) and extracted with DCM (3×20 mL). The combined organic layers were washed with brine (2×15 mL), dried over anhydrous Na₂SO₄ and filtered. The filtrate was concentrated in vacuo and the residue purified by silica gel column chromatography (DCM/MeOH, 10:1). The fractions containing the desired product were combined and concentrate to afford 2-fluoro-5-[3-fluoro-8-(morpholin-4-yl)imidazo[1,2-a]pyridin-6-yl]-4-methylbenzamide (400 mg, 69%) as a yellow solid. MS ESI calculated for C₁₉H₁₈F₂N₄O₂[M+H]⁺, 373.14, found 373.37; ¹H NMR (400 MHz, Chloroform-d) δ 8.06 (d, J=8.1 Hz, 1H), 7.53 (s, 1H), 7.21 (d, J=6.5 Hz, 1H), 7.12 (d, J=12.6 Hz, 1H), 6.71 (d, J=11.6 Hz, 1H), 4.00 (t, J=4.8 Hz, 4H), 3.56 (t, J=4.8 Hz, 4H), 2.37 (s, 3H), 1.27 (s, 2H).

Step 4: To a stirred mixture of 2-fluoro-5-[3-fluoro-8-(morpholin-4-yl)imidazo[1,2-a]pyridin-6-yl]-4-methylbenzamide (400 mg, 1.07 mmol) and K₃PO₄ (478.82 mg, 2.26 mmol) in 1,4-dioxane (5 mL) were added 4-bromo-1-(tert-butyl)-5-fluoro-1H-pyrazole (261.22 mg, 1.18 mmol) and CuI (204.58 mg, 1.07 mmol) at room temperature. The reaction mixture was purged with nitrogen three times and stirred for 16 h at 80° C. The resulting mixture was concentrated in vacuo and the residue purified by silica gel column chromatography (PE/EA/EtOH, 4:3:1). The fractions containing the desired product were combined and concentrated to afford the title compound (166 mg, 29%) as a white solid. MS ESI calculated for C₂₆H₂₇F₃N₆O₂[M+H]⁺, 513.21, found 513.35; ¹H NMR (400 MHz, DMSO-d₆) δ 9.91 (s, 1H), 7.86-7.83 (m, 1H), 7.63 (d, J=7.3 Hz, 1H), 7.57 (d, J=2.4 Hz, 1H), 7.33 (dd, J=13.0, 9.3 Hz, 2H), 6.40 (s, 1H), 3.80 (t, J=4.6 Hz, 4H), 3.57 (t, J=4.6 Hz, 4H), 2.36 (s, 3H), 1.55 (s, 9H).

Example 267: N-(1-(tert-butyl)-5-fluoro-1H-pyrazol-4-yl)-2-fluoro-4-methyl-5-(2-methyl-8-morpholinoimidazo[1,2-a]pyridin-6-yl)benzamide

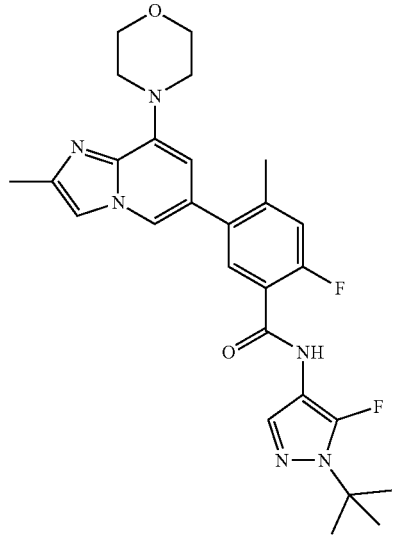 [SMILES: Cc1cn2cc(-c3cc(C(=O)Nc4cnn(C(C)(C)C)c4F)c(F)cc3C)cc(N3CCOCC3)c2n1]

Step 1: To a stirred mixture of 4-{6-bromo-2-methylimidazo[1,2-a]pyridin-8-yl}morpholine (300 mg, 1.01 mmol), Pd(dppf)Cl₂·CH₂Cl₂ (82 mg, 0.10 mmol) and K₂CO₃ (419 mg, 3.04 mmol) in dioxane (4 mL) and water (1 mL) was added methyl 2-fluoro-4-methyl-5-(4,4,5,5-tetramethyl-1,3,2-dioxaborolan-2-yl)benzoate (297 mg, 1.01 mmol). The reaction mixture was purged with nitrogen and stirred for 2 h at 80° C. The resulting mixture was diluted with water (20 mL) and extracted with EA (3×30 mL). The combined organic layers were washed with brine (2×20 mL), dried over anhydrous sodium sulfate, and filtered. The filtrate was concentrated in vacuo.

The residue purified by silica gel column chromatography (PE/EA/EtOH, 4:3:1). The fractions containing the desired product were combined and concentrated to afford methyl 2-fluoro-4-methyl-5-[2-methyl-8-(morpholin-4-yl)imidazo[1,2-a]pyridin-6-yl]benzoate (225 mg, 57%) as an off-white solid. MS ESI calculated for C₂₁H₂₂FN₃O₃[M+H]⁺, 384.16, found 384.15; ¹H NMR (400 MHz, Chloroform-d) δ 7.86 (d, J=7.4 Hz, 1H), 7.65 (m, 1H), 7.31-7.28 (m, 1H), 7.11 (d, J=11.4 Hz, 1H), 6.30-6.26 (m, 1H), 4.02-4.00 (t, J=4.8 Hz, 4H), 3.94 (s, 3H), 3.55-3.53 (t, J=4.8 Hz, 4H), 2.50 (s, 3H), 2.33 (s, 3H).

Step 2: To a stirred solution of methyl 2-fluoro-4-methyl-5-[2-methyl-8-(morpholin-4-yl)imidazo[1,2-a]pyridin-6-yl]benzoate (225 mg, 0.59 mmol) in MeOH (2 mL), THF (2 mL) and H₂O (2 mL) was added LiOH·H₂O (73 mg, 1.76 mmol). The reaction mixture was stirred for 16 h at room temperature. The resulting mixture was concentrated in vacuo to afford 2-fluoro-4-methyl-5-[2-methyl-8-(morpholin-4-yl)imidazo[1,2-a]pyridin-6-yl]benzoic acid (370 mg, crude) as a brown solid. MS ESI calculated for C₂₀H₂₀FN₃O₃[M+H]⁺, 370.15, found 370.15.

Step 3: To a stirred solution of 2-fluoro-4-methyl-5-[2-methyl-8-(morpholin-4-yl)imidazo[1,2-a]pyridin-6-yl]benzoic acid (370 mg, 1.00 mmol) in DCM (40 mL) was added oxalyl chloride (190 mg, 1.50 mmol) and DMF (cat.) dropwise at 0° C. under nitrogen atmosphere. The reaction mixture was stirred for 0.5 h at room temperature. The resulting mixture was quenched with NH₃H₂O (5 mL, 30%) at room temperature. The resulting mixture was concentrated in vacuo and the residue purified by reversed phase flash chromatography with the following conditions: column, C18 silica gel; mobile phase, MeCN in water (Plus 10 mmol/L NH₄HCO₃), 10% to 75% gradient in 20 min; detector, UV 254 nm. The fractions containing the desired product were combined and concentrated to afford 2-fluoro-4-methyl-5-[2-methyl-8-(morpholin-4-yl)imidazo[1,2-a]pyridin-6-yl]benzamide (110 mg, 29%) as an off-white solid. MS ESI calculated for $C_{20}H_{21}FN_4O_2[M+H]^+$, 369.16, found 369.15.

Step 4: To a stirred mixture of 2-fluoro-4-methyl-5-[2-methyl-8-(morpholin-4-yl)imidazo[1,2-a]pyridin-6-yl]benzamide (50 mg, 0.14 mmol), methyl[2-(methylamino)ethyl] amine (12.32 mg, 0.14 mmol) and K₃PO₄ (60.50 mg, 0.29 mmol) in 1,4-dioxane (1 mL) were added 4-bromo-1-(tert-butyl)-5-fluoro-1H-pyrazole (33.00 mg, 0.15 mmol) and CuI (25.85 mg, 0.14 mmol). The reaction mixture was purged with nitrogen and stirred for 16 h at 100° C. The resulting mixture was concentrated in vacuo and the residue purified by silica gel column chromatography (PE/EA/EtOH, 4:3:1). The fractions containing the desired product were combined and concentrated to afford the title compound (19.0 mg, 27%) as a white solid. MS ESI calculated for $C_{27}H_{30}F_2N_6O_2$ [M+H]⁺, 509.24, found 509.35; ¹H NMR (400 MHz, DMSO-d₆) δ 9.94-9.89 (m, 1H), 8.10 (d, J=1.5 Hz, 1H), 7.64-7.54 (m, 3H), 7.34 (d, J=11.3 Hz, 1H), 6.36 (d, J=1.5 Hz, 1H), 3.84 (t, J=4.8 Hz, 4H), 3.53 (t, J=4.8 Hz, 4H), 2.37-2.32 (m, 6H), 1.55 (s, 9H).

Example 273: 1-(tert-Butyl)-5-fluoro-N-(2-fluoro-5-(3-fluoro-2-methyl-8-morpholinoimidazo[1,2-a]pyridin-6-yl)-4-methylphenyl)-1H-pyrazole-4-carboxamide

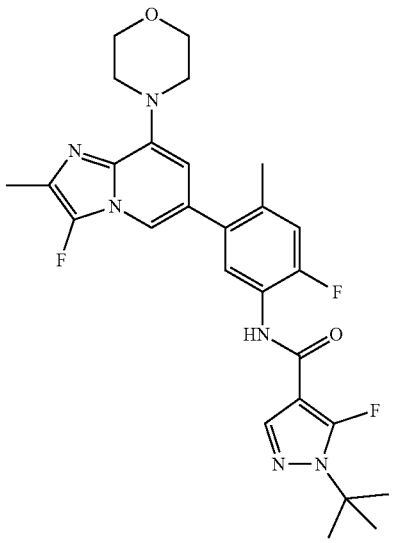 [SMILES: Cc1cc(F)c(NC(=O)c2cnn(C(C)(C)C)c2F)cc1-c1cc(N2CCOCC2)c2nc(C)c(F)n2c1]

Step 1: To a stirred solution of 3-bromo-5-chloropyridin-2-amine (4 g, 19.28 mmol) in EtOH (40 mL) was added bromoacetone (5.28 g, 38.56 mmol) dropwise at room temperature. The reaction mixture was stirred for 16 h at 85° C. The resulting mixture was concentrated in vacuo and the resulting mixture was quenched with saturated aqueous NaHCO₃ (150 mL) and extracted with EA (3×100 mL). The combined organic layers were washed with brine (2×50 mL), dried over anhydrous sodium sulfate, and filtered. The filtrate was concentrated in vacuo and the residue purified by silica gel column chromatography (PE/EA, 1:1) to afford a crude product which (3.5 g) was purified by trituration with (PE/EA, 8:1, 20 mL) to afford 8-bromo-6-chloro-2-methylimidazo[1,2-a]pyridine (2.9 g, 61%) as a pink solid. MS ESI calculated for $C_8H_6BrClN_2$ [M+H]⁺, 244.94, 246.94, found 244.95, 246.95; ¹H NMR (400 MHz, Chloroform-d) δ 8.08 (d, J=1.6 Hz, 1H), 7.41-7.40 (m, 2H), 2.49 (s, 3H).

Step 2: To a stirred solution of Selectfluor (4.60 g, 12.99 mmol) and DMAP (1.44 g, 11.81 mmol) in H₂O (1 mL) was added 8-bromo-6-chloro-2-methylimidazo[1,2-a]pyridine (2.9 g, 11.81 mmol) in CHCl₃ (4 mL) dropwise at 0° C. under nitrogen atmosphere. The reaction mixture was stirred for 2 h at 0° C. and stirred for 16 h at room temperature under nitrogen atmosphere. The resulting mixture was diluted with water (100 mL) and extracted with DCM (3×200 mL). The combined organic layers were washed with saturated brine (2×100 mL), dried over anhydrous sodium sulfate, and filtered. The filtrate was concentrated in vacuo and the residue purified by silica gel column chromatography (PE/EA, 2:1). The fractions containing the desired product were combined and concentrated to afford 8-bromo-6-chloro-3-fluoro-2-methylimidazo[1,2-a]pyridine (1.7 g, 55%) as an off-white solid. MS ESI calculated for $C_8H_5BrClFN_2$ [M+H]⁺, 262.93, 264.93, found 262.90, 264.90; ¹H NMR (400 MHz, Chloroform-d) δ 7.92 (d, J=1.6 Hz, 1H), 7.39 (d, J=2.0 Hz, 1H), 2.47 (s, 3H).

Step 3: To a stirred solution of 8-bromo-6-chloro-3-fluoro-2-methylimidazo[1,2-a]pyridine (1.7 g, 6.45 mmol), morpholine (0.56 g, 6.45 mmol) and Cs₂CO₃ (6.31 g, 19.36 mmol) in dioxane (2 mL) was added RuPhos G2 (0.50 g, 0.65 mmol) at room temperature. The reaction mixture was purged with nitrogen and stirred for 3 h at 65° C. The resulting mixture was diluted with water (150 mL) and extracted with ethyl acetate (3×100 mL). The combined organic layers were washed with brine (70 mL), dried over anhydrous sodium sulfate, and filtered. The filtrate was concentrated in vacuo and the residue purified by silica gel column chromatography (PE/EA, 1:1). The fractions containing the desired product were combined and concentrated to afford 4-{6-chloro-3-fluoro-2-methylimidazo[1,2-a]pyridin-8-yl}morpholine (950 mg, 55%) as an off-white solid. MS ESI calculated for $C_{12}H_{13}ClFN_3O$ [M+H]⁺, 270.07, 272.07, found 270.10, 272.10; ¹H NMR (400 MHz, Chloroform-d) δ 7.53 (d, J=2.0 Hz, 1H), 6.27 (d, J=1.6 Hz, 1H), 3.96-3.94 (m, 4H), 3.57-3.54 (m, 4H), 2.37 (s, 3H).

Step 4: To a stirred mixture of 4-{6-chloro-3-fluoro-2-methylimidazo[1,2-a]pyridin-8-yl}morpholine (200 mg, 0.74 mmol), XPhos Pd G2 (58.35 mg, 0.07 mmol) and K₃PO₄ (472.22 mg, 2.23 mmol) in THF (0.4 mL) and water (0.04 mL) was added 2-fluoro-4-methyl-5-(4,4,5,5-tetramethyl-1,3,2-dioxaborolan-2-yl)aniline (558.64 mg, 2.23 mmol) in portions at room temperature. The reaction mixture was purged with nitrogen and stirred for 2 h at 80° C. The resulting mixture was diluted with water (100 mL) and extracted with EtOAc (3×100 mL), dried over anhydrous sodium sulfate, and filtered. The filtrate was concentrated in vacuo and the residue purified by silica gel column chromatography (PE/EA, 5:1). The fractions containing the desired product were combined and concentrated to afford 2-fluoro-5-[3-fluoro-2-methyl-8-(morpholin-4-yl)imidazo[1,2-a]pyridin-6-yl]-4-methylaniline (240 mg, 90%) as a pink solid. MS ESI calculated for $C_{19}H_{20}F_2N_4O$ [M+H]⁺, 359.16, found 359.15; ¹H NMR (400 MHz, Chloroform-d)

δ 7.41-7.37 (m, 1H), 6.91 (d, J=11.7 Hz, 1H), 6.70 (d, J=9.0 Hz, 1H), 6.32-6.28 (m, 1H), 3.99 (m, 4H), 3.50 (m, 4H), 2.45 (s, 3H), 2.15 (s, 3H).

Step 5: To a stirred mixture of 2-fluoro-5-[3-fluoro-2-methyl-8-(morpholin-4-yl)imidazo[1,2-a]pyridin-6-yl]-4-methylaniline (100 mg, 0.28 mmol), Pd(dppf)C$_{12}$ DCM (45.46 mg, 0.06 mmol) and Co$_2$(CO)$_8$ (28.63 mg, 0.08 mmol) in dioxane (1 mL) were added TEA (169.41 mg, 1.67 mmol) and 4-bromo-1-(tert-butyl)-5-fluoro-1H-pyrazole (74.02 mg, 0.34 mmol) dropwise at room temperature. The reaction mixture was purged with nitrogen and stirred for additional 16 h at 90° C. The resulting mixture was concentrated in vacuo and the residue purified by silica gel column chromatography (PE/EA/EtOH, 4:3:1) to afford a crude product which was further purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 40% B to 70% B in 7 min; Wave Length: 254 nm/220 nm; RT1: 6. min 7. The fractions containing the desired product were combined and concentrated to afford the title compound (3.2 mg, 2%) as a white solid. MS ESI calculated for C$_{27}$H$_{29}$F$_3$N$_6$O$_2$[M+H]$^+$, 527.23, found 527.35; $^1$H NMR (400 MHz, Chloroform-d) δ 8.34 (d, J=8.0 Hz, 1H), 7.82 (d, J=2.8 Hz, 1H), 7.66-7.63 (m, 1H), 7.45-7.41 (m, 1H), 7.06 (d, J=12.0 Hz, 1H), 6.28 (s, 1H), 3.98-3.95 (m, 4H), 3.53-3.49 (m, 4H), 2.42 (s, 3H), 2.25 (s, 3H), 1.66 (s, 9H).

Example 274: 1-(tert-Butyl)-5-fluoro-N-(3-(3-fluoro-2-methyl-8-morpholinoimidazo[1,2-a]pyridin-6-yl)-4-methylphenyl)-1H-pyrazole-4-carboxamide

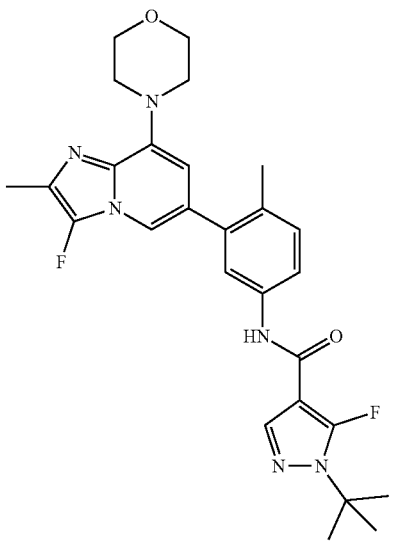 [SMILES: Cc1ccc(NC(=O)c2cnn(C(C)(C)C)c2F)cc1-c1cc(N2CCOCC2)c2nc(C)c(F)n2c1]

Step 1: To a stirred solution of 4-{6-chloro-3-fluoro-2-methylimidazo[1,2-a]pyridin-8-yl}morpholine (200 mg, 0.74 mmol), XPhos Pd G2 (58 mg, 0.07 mmol) and K$_3$PO$_4$ (472 mg, 2.23 mmol) in THF (2 mL) and water (0.2 mL) was added 4-methyl-3-(4,4,5,5-tetramethyl-1,3,2-dioxaborolan-2-yl)aniline (0.89 mmol, 206.90 mg) at room temperature. The reaction mixture was purged with nitrogen and stirred for 2 h at 80° C. The resulting mixture was diluted with water (30 mL) and extracted with Ethyl acetate (3×50 mL). The combined organic layers were washed with brine (2×20 mL), dried over anhydrous Sodium sulfate, and filtered. The filtrate was concentrated in vacuo and the residue purified by silica gel column chromatography (PE/EA/EtOH, 4:3:1). The fractions containing the desired product were combined and concentrated to afford 3-[3-fluoro-2-methyl-8-(morpholin-4-yl)imidazo[1,2-a]pyridin-6-yl]-4-methylaniline (231.8 mg, 91%) as a dark green oil. MS ESI calculated for C$_{19}$H$_{21}$FN$_4$O [M+H]$^+$, 341.17, found 341.20; $^1$H NMR (400 MHz, Chloroform-d) δ 7.42-7.38 (m, 1H), 7.07 (d, J=8.0 Hz, 1H), 6.69-6.59 (m, 2H), 6.31-6.28 (m, 1H), 4.00-3.93 (m, 4H), 3.55-3.49 (m, 4H), 2.41 (s, 3H), 2.16 (s, 3H).

Step 2: To a stirred mixture of 3-[3-fluoro-2-methyl-8-(morpholin-4-yl)imidazo[1,2-a]pyridin-6-yl]-4-methylaniline (100 mg, 0.29 mmol), Co$_2$(CO)$_8$ (28.19 mg, 0.09 mmol) and Pd(dppf)C$_{12}$ DCM (48 mg, 0.06 mmol) in dioxane (1 mL) was added TEA (178 mg, 1.76 mmol) and 4-bromo-1-(tert-butyl)-5-fluoro-1H-pyrazole (78 mg, 0.35 mmol). The reaction mixture was purged with nitrogen and stirred for 16 h at 90° C. The resulting mixture was concentrated under reduced product. The residue purified by Prep-TLC (PE/EA/EtOH, 8:3:1) to afford a crude product which (100 mg) was purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 31% B to 61% B in 10 min; Wave Length: 254 nm/220 nm; RT1: 10.5 min. The fractions containing the desired product were combined and concentrated to afford the title compound (8.1 mg, 5%) as a brown solid. MS ESI calculated for C$_{27}$H$_{30}$F$_2$N$_6$O$_2$ [M+H]$^+$, 509.24, found 509.40; $^1$H NMR (400 MHz, Chloroform-d) δ 7.82 (d, J=2.4 Hz, 1H), 7.53-7.40 (m, 4H), 7.27-7.25 (m, 1H), 6.30 (s, 1H), 3.97-3.96 (m, 4H), 3.54-3.53 (m, 4H), 2.41 (s, 3H), 2.26 (s, 3H), 1.65-1.48 (m, 9H).

Example 275: 1-(tert-Butyl)-5-fluoro-N-(3-(3-fluoro-2-methyl-8-morpholinoimidazo[1,2-a]pyridin-6-yl)-4-methylphenyl)-1H-pyrazole-4-carboxamide

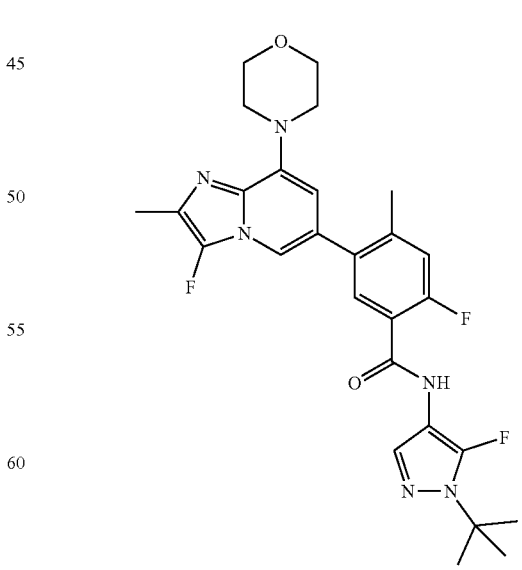

Step 1: To a stirred mixture of 4-{6-chloro-3-fluoro-2-methylimidazo[1,2-a]pyridin-8-yl}morpholine (300 mg, 1.11 mmol) and methyl 2-fluoro-4-methyl-5-(4,4,5,5-tetramethyl-1,3,2-dioxaborolan-2-yl)benzoate (327.17 mg, 1.11 mmol) in THF (4 mL) and water (1 mL) were added XPhos Pd G2 (87.52 mg, 0.11 mmol) and $K_3PO_4$ (708.34 mg, 3.33 mmol) in portions at room temperature. The reaction mixture was degassed with nitrogen atmosphere three times and stirred for 2 h at 80° C. The resulting mixture was concentrated in vacuo and the residue purified by silica gel column chromatography ($CH_2Cl_2$/MeOH, 20:1). The fractions containing the desired product were combined and concentrated to afford methyl 2-fluoro-5-[3-fluoro-2-methyl-8-(morpholin-4-yl)imidazo[1,2-a]pyridin-6-yl]-4-methylbenzoate (240 mg, 53%) as a grey white solid. MS ESI calculated for $C_{21}H_{21}F_2N_3O_3$. $[M+H]^+$, 402.16, found 402.20; $^1$H NMR (400 MHz, Chloroform-d) δ 7.84 (d, J=7.4 Hz, 1H), 7.41-7.39 (m, 1H), 7.08 (d, J=11.4 Hz, 1H), 6.22-6.18 (m, 1H), 3.97 (t, J=4.8 Hz, 4H), 3.93 (s, 3H), 3.54 (t, J=4.8 Hz, 4H), 2.42 (s, 3H), 2.32 (s, 3H).

Step 2: To a stirred solution of methyl 2-fluoro-5-[3-fluoro-2-methyl-8-(morpholin-4-yl)imidazo[1,2-a]pyridin-6-yl]-4-methylbenzoate (140 mg, 0.34 mmol) in THF (3 mL) and MeOH (3 mL) was added LiOH $H_2O$ (73.17 mg, 1.74 mmol) in $H_2O$ (3 mL) dropwise at room temperature. The reaction mixture was stirred for 2 h at room temperature. The resulting mixture was concentrated in vacuo and the residue was acidified to pH 2 with 3 M HCl (aq.). The precipitated solids were collected by filtration and washed with water (3×5 mL). The resulting solid was dried in vacuo to afford 2-fluoro-5-[3-fluoro-2-methyl-8-(morpholin-4-yl)imidazo[1,2-a]pyridin-6-yl]-4-methylbenzoic acid (100 mg, 74%) as an off-white solid. MS ESI calculated for $C_{20}H_{19}F_2N_3O_3$. $[M+H]^+$, 388.14, found 388.05; $^1$H NMR (400 MHz, DMSO-$d_6$) δ 13.19 (s, 1H), 7.79-7.72 (m, 2H), 7.31 (d, J=11.9 Hz, 1H), 6.33 (d, J=1.5 Hz, 1H), 3.82 (t, J=4.8 Hz, 4H), 3.53 (t, J=4.8 Hz, 4H), 2.38-2.25 (m, 6H).

Step 3: To a stirred solution of 2-fluoro-5-[3-fluoro-2-methyl-8-(morpholin-4-yl)imidazo[1,2-a]pyridin-6-yl]-4-methylbenzoic acid (80 mg, 0.21 mmol) in DCM (5 mL) were added oxalyl chloride (52.42 mg, 0.41 mmol) and DMF (cat.) dropwise at 0° C. under nitrogen atmosphere. The reaction mixture was stirred for 30 min at room temperature under nitrogen atmosphere. The resulting mixture was quenched with $NH_3H_2O$ at room temperature. The resulting mixture was concentrated in vacuo and the residue purified by silica gel column chromatography ($CH_2Cl_2$/MeOH, 10:1). The fractions containing the desired product were combined and concentrated to afford 2-fluoro-5-[3-fluoro-2-methyl-8-(morpholin-4-yl)imidazo[1,2-a]pyridin-6-yl]-4-methylbenzamide (30 mg, 37%) as an off-white solid. MS ESI calculated for $C_{20}H_2OF_2N_4O_2$. $[M+H]^+$, 387.16, found 387.35.

Step 4: To a stirred mixture of 2-fluoro-5-[3-fluoro-2-methyl-8-(morpholin-4-yl)imidazo[1,2-a]pyridin-6-yl]-4-methylbenzamide (30 mg, 0.08 mmol), methyl[2-(methylamino)ethyl]amine (6.84 mg, 0.08 mmol), CuI (14.79 mg, 0.08 mmol) and $K_3PO_4$ (34.61 mg, 0.16 mmol) in dioxane (1 mL) was added 4-bromo-1-(tert-butyl)-5-fluoro-1H-pyrazole (20.60 mg, 0.09 mmol) at room temperature. The reaction mixture was degassed with nitrogen atmosphere three times and stirred for 2 h at 100° C. The resulting mixture was concentrated in vacuo and the residue purified by silica gel column chromatography, eluted with ($CH_2Cl_2$/MeOH, 20:1) to afford a crude product which was further purified by prep-HPLC with the following conditions: Column: XBridge Prep OBD C18 Column, 30×150 mm, 5 m; Mobile Phase A: water (Plus 10 mmol/L $NH_4HCO_3$), Mobile Phase B: ACN; Flow rate: 60 mL/min; Gradient: 40% to 70% in 7 min; Wave Length: 254 nm/220 nm. The fractions containing the desired product were combined and concentrated to afford the title compound (4.5 mg, 10%) as an off-white solid. MS ESI calculated for $C_{27}H_{29}F_3N_6O_2$ $[M+H]^+$, 527.23, found 527.40; $^1$H NMR (400 MHz, Chloroform-d) δ 8.09 (d, J=8.1 Hz, 1H), 7.96 (d, J=15.7 Hz, 1H), 7.77 (d, J=2.3 Hz, 1H), 7.48-7.43 (m, 1H), 7.14 (d, J=12.7 Hz, 1H), 6.32 (s, 1H), 4.01-3.97 (m, 4H), 3.49-3.45 (m, 4H), 2.47 (s, 3H), 2.36 (s, 3H), 1.62 (s, 9H).

Example 282: 1-(tert-Butyl)-5-fluoro-N-(2-fluoro-4-methyl-5-(2-methyl-5-morpholino-[1,2,4]triazolo[1,5-a]pyridin-7-yl)phenyl)-1H-pyrazole-4-carboxamide

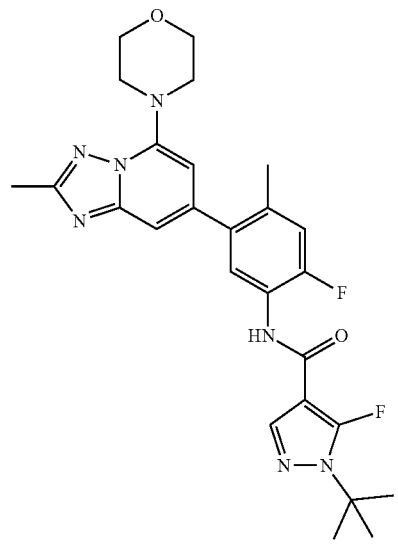 [SMILES: Cc1nc2cc(-c3cc(NC(=O)c4cnn(C(C)(C)C)c4F)c(F)cc3C)cc(N3CCOCC3)n2n1]

Step 1: To a stirred solution of 4-bromo-1-(tert-butyl)-5-fluoro-1H-pyrazole (2 g, 9.05 mmol) in THF (25 mL) was added n-BuLi (3.80 mL, 9.50 mmol, 2.5 M in hexane) at −78° C. under nitrogen atmosphere. The reaction mixture was stirred for 1 h at −78° C. followed by addition of propyl carbonochloridate (1.16 g, 9.50 mmol) in THF (5 mL). The reaction mixture was stirred for another 1 h at −78° C. The resulting mixture was quenched with sat. $NH_4Cl$ (aq.) (10 mL) and extracted with EtOAc (2×50 mL). The combined organic layers were washed with brine (50 mL), dried over anhydrous $Na_2SO_4$. The residue purified by silica gel column chromatography, eluted with PE/EA (4/1). The fractions containing the desired product were combined and concentrated to afford Propyl 1-tert-butyl-5-fluoropyrazole-4-carboxylate (1.26 g, 61%) as a colorless oil. MS ESI calculated for $C_{11}H_{17}FN_2O_2[M+H]^+$, 229.13, found 229.15; $^1$H NMR (400 MHz, DMSO-$d_6$) δ 7.78 (d, J=2.5 Hz, 1H), 4.13 (t, J=6.6 Hz, 2H), 1.65-1.58 (m, 2H), 1.55 (s, 9H), 0.93 (t, J=7.4 Hz, 3H).

Step 2: To a stirred solution of amino 2,4,6-trimethylbenzenesulfonate (7.92 g, 36.81 mmol) in DCM (90 mL) was added 4,6-dichloropyridin-2-amine (3 g, 18.41 mmol) in DCM (90 mL) dropwise at 0° C. The reaction mixture was stirred for 2 h at 50° C. The resulting mixture was concentrated in vacuo and the residue was diluted with DCM (40 mL). The resulting mixture was filtered, the filter cake washed with DCM (3×50 mL). The filtrate was concentrated in vacuo to afford 1,2-diamino-4,6-dichloropyridin-1-ium 2,4,6-trimethylbenzenesulfonate (4.5 g, crude) as an off-white solid. MS ESI calculated for $C_{14}H_{17}C_{12}N_{3}O_3[M+H]^+$, 378.04, found 378.00.

Step 3: To a stirred solution of 1,2-diamino-4,6-dichloro-pyridin-1-ium 2,4,6-trimethylbenzenesulfonate (4.4 g, 11.63 mmol) in $Ac_2O$ (11 mL) was added TsOH (0.40 g, 2.33 mmol). The reaction mixture was stirred for 2 h at 100° C. The resulting mixture was diluted with water (100 mL) and extracted with EtOAc (3×150 mL). The combined organic layers were washed with brine (2×150 mL), dried over anhydrous $Na_2SO_4$, and filtered. The filtrate was concentrated in vacuo and the residue purified by silica gel column chromatography (PE/EA/EtOH, 8:3:1). The fractions containing the desired product were combined and concentrated to afford 5,7-dichloro-2-methyl-[1,2,4]triazolo[1,5-a]pyridine (640 mg, 27%) as an off-white solid. MS ESI calculated for $C_7H_5C_{12}N_3[M+H]^+$, 201.99, 203.98, found 201.85, 203.85; $^1H$ NMR (400 MHz, DMSO-$d_6$) δ 7.62-7.61 (d, J=2.0 Hz, 1H), 7.09-7.08 (d, J=2.0 Hz, 1H), 2.64 (s, 3H).

Step 4: To a stirred solution of 5,7-dichloro-2-methyl-[1,2,4]triazolo[1,5-a]pyridine (0.61 g, 3.02 mmol) and DIEA (1.17 g, 9.06 mmol) in DMSO (10 mL) was added morpholine (0.26 g, 3.02 mmol). The reaction mixture was stirred for 2 h at 130° C. The resulting mixture was allowed to cool to room temperature. The resulting mixture was diluted with water (150 mL) and extracted with EtOAc (3×150 mL). The combined organic layers were washed with brine (2×150 mL), dried over anhydrous $Na_2SO_4$, and filtered. The filtrate was concentrated in vacuo and the residue purified by silica gel column chromatography (PE/EA/EtOH, 4:3:1). The fractions containing the desired product were combined and concentrated to afford 4-{7-chloro-2-methyl-[1,2,4]triazolo[1,5-a]pyridin-5-yl}morpholine (550 mg, 72%) as an off-white solid. MS ESI calculated for $C_{11}H_{13}ClN_4O [M+H]^+$, 253.08, 255.08, found 253.05, 255.05; $^1H$ NMR (400 MHz, Chloroform-d) δ 7.30-7.29 (d, J=1.9 Hz, 1H), 6.27-6.26 (d, J=2.0 Hz, 1H), 4.00-3.98 (m, 4H), 3.52-3.50 (m, 4H), 2.59 (s, 3H).

Step 5: To a stirred solution of 4-{7-chloro-2-methyl-[1,2,4]triazolo[1,5-a]pyridin-5-yl}morpholine (240 mg, 0.95 mmol), XPhos Pd G2 (74 mg, 0.10 mmol) and 2-fluoro-4-methyl-5-(4,4,5,5-tetramethyl-1,3,2-dioxaborolan-2-yl)aniline (286 mg, 1.14 mmol) in THF (3 mL) was added $K_3PO_4$ (0.5 M, 6 mL). The reaction mixture was purged with nitrogen and stirred for 2 h at 40° C. The resulting mixture was diluted with water (20 mL) and extracted with EtOAc (3×30 mL). The combined organic layers were washed with brine (2×30 mL), dried over anhydrous Sodium sulfate, and filtered. The filtrate was concentrated in vacuo and the residue purified by silica gel column chromatography (PE/EA/EtOH, 8:3:1). The fractions containing the desired product were combined and concentrated to afford 2-fluoro-4-methyl-5-[2-methyl-5-(morpholin-4-yl)-[1,2,4]triazolo[1,5-a]pyridin-7-yl]aniline (350 mg, 91%) as a brown solid. MS ESI calculated for $C_{18}H_{20}FN_5O[M+H]^+$, 342.17, found 342.15; $^1H$ NMR (400 MHz, Chloroform-d) δ 7.19 (d, J=1.6 Hz, 1H), 6.93 (d, J=11.8 Hz, 1H), 6.72 (d, J=9.0 Hz, 1H), 6.22 (d, J=1.4 Hz, 1H), 4.01-3.98 (m, 4H), 3.50-3.48 (m, 4H), 2.62 (s, 3H), 2.16 (s, 3H).

Step 6: A solution of 2-fluoro-4-methyl-5-[2-methyl-5-(morpholin-4-yl)-[1,2,4]triazolo[1,5-a]pyridin-7-yl]aniline (60 mg, 0.18 mmol) in Lithium bis(trimethylsilyl)amide (2 mL) was stirred for 1 h at 0° C. under nitrogen atmosphere. To the above mixture was added propyl 1-tert-butyl-5-fluoropyrazole-4-carboxylate (60 mg, 0.26 mmol) in THF (4 mL) dropwise at 0° C. and allowed to stir for additional 1 h at room temperature. The reaction mixture was quenched with sat. $NH_4Cl$ (aq.) (10 mL) and extracted with EA (3×20 mL). The combined organic layers were washed with brine (2×10 mL), dried over anhydrous sodium sulfate, and filtered. The filtrate was concentrated in vacuo and the residue purified by silica gel column chromatography (PE/EA/EtOH, 12:1:3) to afford a crude product which was further purified by reversed phase flash chromatography with the following conditions: column, C18 silica gel; mobile phase, MeCN in water (Plus 10 mmol/L $NH_4HCO_3$), 10% to 50% gradient in 20 min; detector, UV 254 nm. The fractions containing the desired product were combined and concentrated to afford the title compound (8.9 mg, 9%) as an off-white solid. MS ESI calculated for $C_{26}H_{29}F_2N_{7}O_2$ $[M+H]^+$, 510.24, found 510.25; $^1H$ NMR (400 MHz, Chloroform-d) δ 8.35 (d, J=8.0 Hz, 1H), 7.82 (d, J=2.4 Hz, 1H), 7.68-7.65 (m, 1H), 7.26-7.22 (m, 1H), 7.07 (d, J=11.6 Hz, 1H), 6.26 (d, J=1.6 Hz, 1H), 4.01-3.99 (m, 4H), 3.51-3.49 (m, 4H), 2.63 (s, 3H), 2.26 (s, 3H), 1.66 (d, J=1.2 Hz, 9H).

Example 283: N-(1-(tert-butyl)-5-fluoro-1H-pyrazol-4-yl)-2-fluoro-4-methyl-5-(2-methyl-5-morpholino-[1,2,4]triazolo[1,5-a]pyridin-7-yl)benzamide

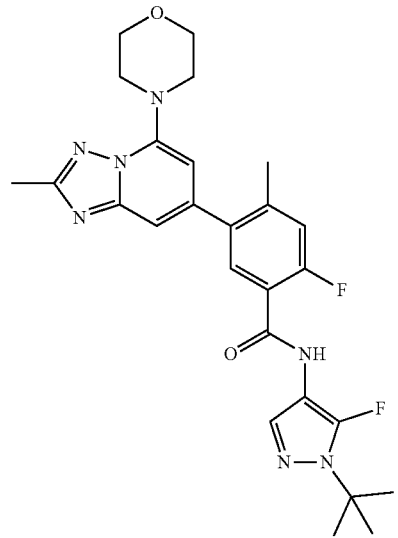 [SMILES: Cc1nc2cc(-c3cc(C(=O)Nc4cnn(C(C)(C)C)c4F)c(F)cc3C)cc(N3CCOCC3)n2n1]

Step 1: To a stirred solution of tert-butyl carbamate (1.59 g, 13.57 mmol) and CuI (1.72 g, 9.05 mmol) and $K_3PO_4$ (4.03 g, 19.00 mmol) and 4-bromo-1-(tert-butyl)-5-fluoro-1H-pyrazole (2 g, 9.05 mmol) in dioxane (20 mL) was added methyl[2-(methylamino)ethyl]amine (0.97 mL, 9.05 mmol) dropwise at room temperature under nitrogen atmosphere. The reaction mixture was stirred for 16 h at 100° C. under nitrogen atmosphere. The resulting mixture was concentrated in vacuo and the residue purified by silica gel column chromatography (PE/EA, 5:1). The fractions containing the desired product were combined and concentrated to afford tert-butyl (1-(tert-butyl)-5-fluoro-1H-pyrazol-4-yl)carbamate (600 mg, 25%) as a white solid. MS ESI calculated for $C_{12}H_{20}FN_3O_2$ $[M+H]^+$, 258.15, found 258.15.

Step 2: To a stirred solution of tert-butyl (1-(tert-butyl)-5-fluoro-1H-pyrazol-4-yl)carbamate (240 mg, 0.93 mmol) in $CH_2Cl_2$ (1.8 mL) was added TFA (0.6 mL) dropwise at room temperature. The reaction mixture was stirred for 1 h at room temperature. The resulting mixture was basified to pH 8 with saturated $NaHCO_3$ (aq.) and extracted with DCM (3×40 mL). The combined organic layers were dried over anhydrous sodium sulfate and filtered. The filtrate was concentrated in vacuo to afford 1-(tert-butyl)-5-fluoro-1H-pyrazol-4-amine (140 mg, 61%) as a light-yellow oil. MS ESI calculated for $C_7H_{12}FN_3$ [M+H]$^+$, 158.10, found 158.30; $^1$H NMR (400 MHz, DMSO-$d_6$) δ 6.94 (d, J=3.3 Hz, 1H), 1.46 (d, J=1.5 Hz, 9H).

Step 3: To a stirred mixture of 4-{7-chloro-2-methyl-[1,2,4]triazolo[1,5-a]pyridin-5-yl}morpholine (660 mg, 2.61 mmol), 4,4,4',4',5,5,5',5'-octamethyl-2,2'-bi(1,3,2-dioxaborolane) (994.86 mg, 3.92 mmol) and KOAc (768.98 mg, 7.83 mmol) in dioxane (7 mL) was added XPhos Pd G2 (205.50 mg, 0.26 mmol) in portions at room temperature. The reaction mixture was purged with nitrogen and stirred for 2 h at 100° C. The resulting mixture was filtered, the filter cake washed with EA (3×20 mL) and the filtrate concentrated in vacuo to afford 2-methyl-5-(morpholin-4-yl)-[1,2,4]triazolo[1,5-a]pyridin-7-ylboronic acid (1.8 g, crude) as a black oil. MS ESI calculated for $C_{11}H_{15}BN_4O_3$[M+H]$^+$, 263.12, found 263.05.

Step 4: To a stirred solution of 2-methyl-5-(morpholin-4-yl)-[1,2,4]triazolo[1,5-a]pyridin-7-ylboronic acid (600 mg, 2.29 mmol), $K_3PO_4$ (728 mg, 3.43 mmol) and methyl 5-bromo-2-fluoro-4-methylbenzoate (282 mg, 1.15 mmol) in THF (8 mL) and $H_2O$ (2 mL) was added Pd(dppf)$C_{12}$·$CH_2Cl_2$ (93 mg, 0.11 mmol). The reaction mixture was purged with nitrogen and stirred for 2 h at 80° C. The resulting mixture was diluted with water (10 mL) and extracted with EtOAc (3×30 mL). The combined organic layers were washed with brine (2×20 mL), dried over anhydrous sodium sulfate, and filtered. The filtrate was concentrated in vacuo and the residue purified by reversed-phase flash chromatography with the following conditions: column, C18 silica gel; mobile phase, MeCN in water (0.1% TFA), 20% to 95% gradient in 20 min; detector, UV 254 nm. The fractions containing the desired product were combined and concentrated to afford methyl 2-fluoro-4-methyl-5-[2-methyl-5-(morpholin-4-yl)-[1,2,4]triazolo[1,5-a]pyridin-7-yl]benzoate (510 mg, 98%) as a brown solid. MS ESI calculated for $C_{20}H_{21}FN_4O_3$[M+H]$^+$, 385.16, found 385.15; $^1$H NMR (400 MHz, Chloroform-d) δ 7.85-7.82 (m, 1H), 7.68-7.64 (m, 1H), 7.14 (d, J=11.4 Hz, 1H), 6.45 (m, 1H), 3.98 (s, 3H), 3.95-3.90 (m, 4H), 3.58-3.54 (m, 4H), 2.74 (s, 3H), 2.35 (s, 3H).

Step 5: To a solution of methyl 2-fluoro-4-methyl-5-[2-methyl-5-(morpholin-4-yl)-[1,2,4]triazolo[1,5-a]pyridin-7-yl]benzoate (510 mg, 1.33 mmol) in THF (5 mL), MeOH (5 mL) and $H_2O$ (5 mL) was added LiOH·$H_2O$ (167 mg, 3.98 mmol). The reaction mixture was stirred for 1 h at room temperature. The resulting mixture was acidified to pH 5 with HCl (3 M, aq.). The resulting mixture was concentrated in vacuo and the residue purified by reversed-phase flash chromatography with the following conditions: column, C18 silica gel; mobile phase, MeCN in water (Plus 0.1% TFA), 15% to 95% gradient in 15 min; detector, UV 254 nm. The fractions containing the desired product were combined and concentrated to afford 2-fluoro-4-methyl-5-[2-methyl-5-(morpholin-4-yl)-[1,2,4]triazolo[1,5-a]pyridin-7-yl]benzoic acid (152 mg, 29%) as an off-white solid. MS ESI calculated for $C_{19}H_{19}FN_4O_3$[M+H]$^+$, 371.14, found 371.05; $^1$H NMR (400 MHz, Chloroform-d) δ 7.84-7.80 (m, 1H), 7.57-7.53 (m, 1H), 7.11 (d, J=11.2 Hz, 1H), 6.42-6.40 (m, 1H), 4.00-3.96 (m, 4H), 3.58-3.54 (m, 4H), 2.76 (s, 3H), 2.35 (s, 3H).

Step 6: A solution of added 2-fluoro-4-methyl-5-[2-methyl-5-(morpholin-4-yl)-[1,2,4]triazolo[1,5-a]pyridin-7-yl]benzoic acid (80 mg, 0.22 mmol) in $T_3P$ (1 mL, 50% in EA) was stirred for 0.5 h at room temperature. To the above mixture was added 1-(tert-butyl)-5-fluoro-1H-pyrazol-4-amine (50 mg, 0.32 mmol) in pyridine (1 mL) dropwise at room temperature. The reaction mixture was stirred for additional 2 h at 60° C. The resulting mixture was concentrated in vacuo and the residue purified by reversed-phase flash chromatography with the following conditions: column, C18 silica gel; mobile phase, MeCN in water (Plus 10 mmol/L $NH_4HCO_3$), 15% to 80% gradient in 20 min; detector, UV 254 nm. The fractions containing the desired product were combined and concentrated to afford the title compound (30 mg, 27%) as an off-white solid. MS ESI calculated for $C_{26}H_{29}F_2N_7O_2$ [M+H]$^+$, 510.24, found 510.45; $^1$H NMR (400 MHz, Chloroform-d) δ 8.12 (d, J=8.0 Hz, 1H), 8.01 (d, J=15.5 Hz, 1H), 7.78 (d, J=2.3 Hz, 1H), 7.28-7.26 (m, 1H), 7.17 (d, J=12.8 Hz, 1H), 6.28 (s, 1H), 4.01 (t, J=4.8 Hz, 4H), 3.54 (t, J=4.8 Hz, 4H), 2.67 (s, 3H), 2.37 (s, 3H), 1.62 (s, 9H).

Example 285: N-(1-(tert-Butyl)-5-fluoro-1H-pyrazol-4-yl)-2-fluoro-4-methyl-5-(2-methyl-8-morpholino-[1,2,4]triazolo[1,5-a]pyridin-6-yl)benzamide

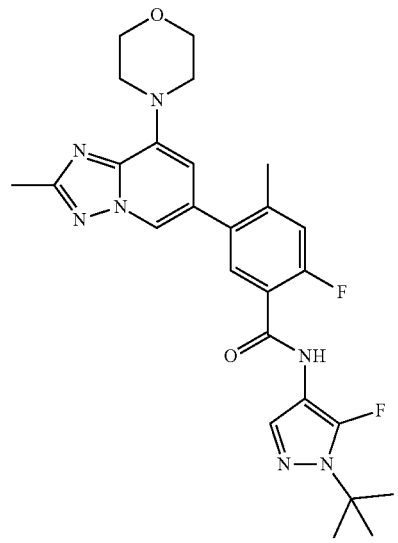 [SMILES: Cc1nc2c(N3CCOCC3)cc(-c3cc(C(=O)Nc4cnn(C(C)(C)C)c4F)c(F)cc3C)cn2n1]

Step 1: To a stirred solution of 4-{6-chloro-2-methyl-[1,2,4]triazolo[1,5-a]pyridin-8-yl}morpholine (1 g, 3.96 mmol), bis(pinacolato)diboron (1.51 g, 5.94 mmol), KOAc (1.17 g, 11.87 mmol) and XPhos Pd G2 (311.37 mg, 0.40 mmol) in dioxane (20 mL) at room temperature. The reaction mixture was purged with nitrogen and stirred for 1.5 h at 100° C. The resulting mixture was filtered, the filter cake was washed with 1,4-dioxane (3×10 mL). The filtrate was concentrated in vacuo to afford 2-methyl-8-(morpholin-4-yl)-[1,2,4]triazolo[1,5-a]pyridin-6-ylboronic acid (3 g, crude) as a black oil. MS ESI calculated for $C_{11}H_{15}BN_4O_3$ [M+H]$^+$, 263.12, found 263.40.

Step 2: To a stirred mixture of 2-methyl-8-(morpholin-4-yl)-[1,2,4]triazolo[1,5-a]pyridin-7-ylboronic acid (1.4 g, 1.60 mmol, 30%) and methyl 5-bromo-2-fluoro-4-methylbenzoate (0.40 g, 1.60 mmol) in dioxane (12 mL) and $H_2O$ (3 mL) were added Pd(PPh$_3$)$_2C_{12}$ (0.11 g, 0.16 mmol) and $Na_2CO_3$ (0.51 g, 4.81 mmol) at room temperature. The reaction mixture was purged with nitrogen and stirred for 1 h at 80° C. The resulting mixture was concentrated in vacuo and the residue purified by silica gel column chromatography (PE/EA/EtOH, 4:3:1). The fractions containing the desired product were combined and concentrated to afford methyl 2-fluoro-4-methyl-5-(2-methyl-8-morpholino-[1,2,4]triazolo[1,5-a]pyridin-6-yl)benzoate (400 mg, 65%) as a yellow solid. MS ESI calculated for $C_{20}H_{21}FN_4O_3[M+H]^+$, 385.16, found 385.40; $^1$H NMR (400 MHz, Chloroform-d) δ 8.06 (d, J=1.4 Hz, 1H), 7.85 (d, J=7.2 Hz, 1H), 7.10 (d, J=11.6 Hz, 1H), 6.55 (d, J=1.4 Hz, 1H), 4.00-3.95 (m, 4H), 3.93 (s, 3H), 3.57-3.53 (m, 4H), 2.62 (s, 3H), 2.32 (s, 3H).

Step 3: To a stirred solution of methyl 2-fluoro-4-methyl-5-[2-methyl-8-(morpholin-4-yl)-[1,2,4]triazolo[1,5-a]pyridin-6-yl]benzoate (400 mg, 1.04 mmol) and in $H_2O$ (3 mL), MeOH (3 mL) and THF (3 mL) was added NaOH (208 mg, 5.21 mmol) at room temperature. The reaction mixture was stirred for 2 h at room temperature. The resulting mixture was concentrated in vacuo and the resulting mixture was diluted with water (5 mL). The resulting mixture was acidified to pH 4 with HCl (aq.). The resulting mixture was filtered, the filter cake was washed with water (3×5 mL) to afford 2-fluoro-4-methyl-5-[2-methyl-8-(morpholin-4-yl)-[1,2,4]triazolo[1,5-a]pyridin-6-yl]benzoic acid (240 mg, 62%) as an off-white solid. MS ESI calculated for $C_{19}H_{19}FN_4O_3[M+H]^+$, 371.14, found 371.15; $^1$H NMR (400 MHz, DMSO-$d_6$) δ 13.28 (s, 1H), 8.42 (d, J=1.4 Hz, 1H), 7.76 (d, J=7.6 Hz, 1H), 7.32 (d, J=11.8 Hz, 1H), 6.70 (d, J=1.6 Hz, 1H), 3.83-3.76 (m, 4H), 3.56-3.52 (m, 4H), 2.48 (s, 3H), 2.32 (s, 3H).

Step 4: To a stirred solution of 2-fluoro-4-methyl-5-[2-methyl-8-(morpholin-4-yl)-[1,2,4]triazolo[1,5-a]pyridin-6-yl]benzoic acid (80 mg, 0.22 mmol) and oxalyl chloride (42 mg, 0.32 mmol) in DCM (1 mL) was added DMF (0.002 mL) at 0° C. under nitrogen atmosphere. The reaction mixture was stirred for 0.5 h at room temperature under nitrogen atmosphere. The resulting mixture was quenched by the addition of $NH_3$-$H_2O$ (1 mL) at 0° C. The resulting mixture was extracted with EtOAc (3×5 mL), dried over anhydrous Sodium sulfate, and filtered. The filtrate was concentrated in vacuo and the residue purified by Prep-TLC (PE/EA/EtOH, 8:3:1). The fractions containing the desired product were combined and concentrated to afford 2-fluoro-4-methyl-5-[2-methyl-8-(morpholin-4-yl)-[1,2,4]triazolo[1,5-a]pyridin-6-yl]benzamide (40 mg, 50%) as a grey solid. MS ESI calculated for $C_{19}H_2OFN_5O_2[M+H]^+$, 370.16, found 370.20; $^1$H NMR (400 MHz, Chloroform-d) δ 7.99-7.96 (m, 1H), 7.04 (d, J=12.6 Hz, 1H), 6.62 (d, J=11.6 Hz, 1H), 6.50 (d, J=1.6 Hz, 1H), 3.93-3.88 (m, 4H), 3.51-3.45 (m, 4H), 2.55 (s, 3H), 2.27 (s, 3H).

Step 5: To a stirred solution of 2-fluoro-4-methyl-5-[2-methyl-8-(morpholin-4-yl)-[1,2,4]triazolo[1,5-a]pyridin-6-yl]benzamide (40 mg, 0.11 mmol) and 4-bromo-1-(tert-butyl)-5-fluoro-1H-pyrazole (30 mg, 0.13 mmol) in dioxane (1 mL) were added methyl[2-(methylamino)ethyl]amine (10 mg, 0.11 mmol), CuI (21 mg, 0.11 mmol) and $K_3PO_4$ (48 mg, 0.23 mmol) at room temperature. The resulting mixture was purged with nitrogen and stirred for 16 h at 100° C. The resulting mixture was concentrated in vacuo and the residue purified by Prep-TLC (PE/EA/EtOH, 8:3:1) to afford a crude product which was further purified by reverse phase Flash chromatography with the following conditions: Column: WelFlash TM C18-I, 20-40 m, 25 g; Eluent A: Water (Plus 10 mmol/L $NH_4HCO_3$); Eluent B: ACN; Gradient: 25% B to 55% B in 30 min; Flow rate: 30 mL/min; Detector: 220/254 nm. The fractions containing the desired product were combined and concentrated to afford N-(1-tert-butyl-3-fluoropyrazol-4-yl)-2-fluoro-4-methyl-5-[2-methyl-8-(morpholin-4-yl)-[1,2,4]triazolo[1,5-a]pyridin-6-yl]benzamide (3.5 mg, 6%) as a white solid. MS ESI calculated for $C_{26}H_{29}F_2N_7O_2$ [M - H], 508.24, found 508.35; $^1$H NMR (400 MHz, DMSO-$d_6$) δ 9.93 (s, 1H), 8.44 (d, J=1.2 Hz, 1H), 7.63 (d, J=7.4 Hz, 1H), 7.57 (d, J=2.4 Hz, 1H), 7.35 (d, J=11.6 Hz, 1H), 6.73 (d, J=1.2 Hz, 1H), 3.80 (t, J=4.8 Hz, 4H), 3.55 (t, J=4.8 Hz, 4H), 2.48 (s, 3H), 2.34 (s, 3H), 1.54 (s, 9H).

Example 291: 2-Tert-butyl-N-{2-fluoro-4-methyl-5-[2-methyl-5-(morpholin-4-yl)-[1,2,4]triazolo[1,5-a]pyridin-7-yl]phenyl}-1,3-oxazole-5-carboxamide

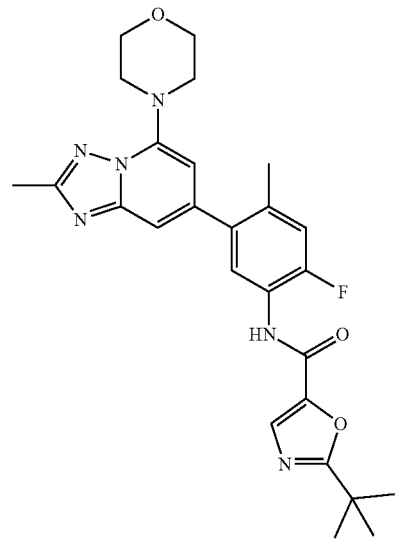 [SMILES: Cc1nc2cc(-c3cc(NC(=O)c4cnc(C(C)(C)C)o4)c(F)cc3C)cc(N3CCOCC3)n2n1]

Step 1: To a stirred solution of 2-tert-butyl-1,3-oxazole-5-carboxylic acid (59 mg, 0.35 mmol) in $T_3P$ (1 ml) was added 2-fluoro-4-methyl-5-[2-methyl-5-(morpholin-4-yl)-[1,2,4]triazolo[1,5-a]pyridin-7-yl]aniline (100 mg, 0.29 mmol) in Pyridine (1 mL) dropwise at room temperature. The reaction mixture was stirred for 1 h at 60° C. The resulting mixture was concentrated in vacuo and the residue purified by Prep-TLC (PE/EA/EtOH, 16:3:1) to afford a crude product which was further purified by reversed-phase flash chromatography with the following conditions: column, C18 silica gel; mobile phase, MeCN in water (Plus 10 mmol/L $NH_4HCO_3$), 10% to 60% gradient in 25 min; detector, UV 254 nm. The fractions containing the desired product were combined and concentrated to afford 2-tert-butyl-N-{2-fluoro-4-methyl-5-[2-methyl-5-(morpholin-4-yl)-[1,2,4]triazolo[1,5-a]pyridin-7-yl]phenyl}-1,3-oxazole-5-carboxamide (58.7 mg, 40%) as an off-white solid. MS ESI calculated for $C_{26}H_{29}FN_6O_3$ [M+H]$^+$, 493.23, found 493.30; $^1$H NMR (400 MHz, Chloroform-d) δ 8.33 (d, J=8.0 Hz, 1H), 8.02 (s, 1H), 7.71 (s, 1H), 7.26-7.23 (m, 1H), 7.11 (d, J=11.6 Hz, 1H), 6.26 (d, J=1.2 Hz, 1H), 4.01 (t, J=4.4 Hz, 4H), 3.52 (t, J=4.4 Hz, 4H), 2.63 (s, 3H), 2.28 (s, 3H), 1.47 (s, 9H).

Example 292: 2-Tert-butyl-N-{2-fluoro-4-methyl-5-[2-methyl-5-(morpholin-4-yl)-[1,2,4]triazolo[1,5-a]pyridin-7-yl]phenyl}-1,3-oxazole-4-carboxamide

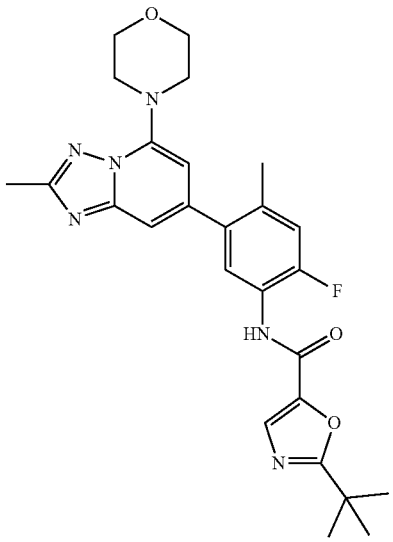 [SMILES: Cc1nc2cc(-c3cc(NC(=O)c4cnc(C(C)(C)C)o4)c(F)cc3C)cc(N3CCOCC3)n2n1]

Step 1: To a stirred solution of ethyl 3-bromo-2-oxopropanoate (40.00 g, 205.12 mmol) in EtOH (350 mL) was added pivalamide (20.75 g, 205.14 mmol) at room temperature. The reaction mixture was stirred for 48 h at 85° C. The resulting mixture was concentrated in vacuo and the residue was diluted with water (200 mL) and extracted with EA (3×100 mL). The combined organic layers were washed with brine (2×100 mL), dried over ahydrous $Na_2SO_4$, filtered and concentrated in vacuo and the residue purified by silica gel column chromatography (PE/EA, 9:1). The fractions containing the desired product were combined and concentrated to afford ethyl 2-tert-butyl-1,3-oxazole-4-carboxylate (6.1 g, 15%) as a light yellow oil. MS ESI calculated for $C_{10}H_{15}NO_3$ [M+H]$^+$, 198.11, found 198.11; $^1$H NMR (400 MHz, Chloroform-d) δ 8.12 (s, 1H), 4.38 (q, J=7.1 Hz, 2H), 1.41 (s, 9H), 1.37 (t, J=7.1 Hz, 3H).

Step 2: To a stirred solution of ethyl 2-tert-butyl-1,3-oxazole-4-carboxylate (6.1 g, 30.93 mmol) in MeOH (50 mL) and THF (50 mL) was added NaOH (3.71 g, 92.78 mmol) in water (50 mL) dropwise at room temperature. The reaction mixture was stirred for 1 h at room temperature. The resulting mixture was concentrated in vacuo and the residue was acidified to pH 2 with HCl (aq.). The precipitated solids were collected by filtration and washed with water (5 mL). The solid was dried in vacuo to afford 2-tert-butyl-1,3-oxazole-4-carboxylic acid (3.1 g, 59%) as a white solid. $^1$H NMR (400 MHz, Chloroform-d) δ 10.83 (s, 1H), 8.24 (s, 1H), 1.42 (s, 9H).

Step 3: To a stirred solution of 2-tert-butyl-1,3-oxazole-4-carboxylic acid (47 mg, 0.28 mmol) in $T_3P$ (1 mL, 50% in EA) was added 2-fluoro-4-methyl-5-[2-methyl-5-(morpholin-4-yl)-[1,2,4]triazolo[1,5-a]pyridin-7-yl]aniline (80 mg, 0.23 mmol) in pyridine (1 mL) dropwise at room temperature. The reaction mixture was stirred for 1 h at 60° C. The resulting mixture was diluted with water (10 mL) and extracted with EtOAc (3×15 mL). The combined organic layers were washed with brine (2×10 mL), dried over anhydrous sodium sulfate, and filtered. The filtrate was concentrated in vacuo and the residue purified by Prep-TLC (PE/EA/EtOH, 8:3:1) to afford a crude product which was further purified by Prep-HPLC with the following conditions: Column: XBridge Prep OBD C18 Column, 30×150 mm, 5 m; Mobile Phase A: water (Plus 10 mmol/L $NH_4HCO_3$+0.05% $NH_3H_2O$), Mobile Phase B: ACN; Flow rate: 60 mL/min; Gradient: 39% B to 69% B in 8 min; Wave Length: 254 nm/220 nm; RT1: 6.98 min. The fractions containing the desired product were combined and concentrated to afford the title compound (42 mg, 36%) as an off-white solid. MS ESI calculated for $C_{26}H_{29}FN_6O_3$ [M+H]$^+$, 493.23, found 493.20; $^1$H NMR (400 MHz, Chloroform-d) δ 9.00 (s, 1H), 8.42 (d, J=8.0 Hz, 1H), 8.19 (s, 1H), 7.28-7.24 (m, 1H), 7.12 (d, J=11.6 Hz, 1H), 6.32-6.28 (m, 1H), 4.03-4.01 (m, 4H), 3.55-3.53 (m, 4H), 2.67-2.65 (m, 3H), 2.29 (s, 3H), 1.45 (s, 9H).

Example 293: 2-(Tert-butyl)-N-(2-fluoro-4-methyl-5-(2-methyl-8-morpholino-[1,2,4]triazolo[1,5-a]pyridin-6-yl)phenyl)oxazole-5-carboxamide

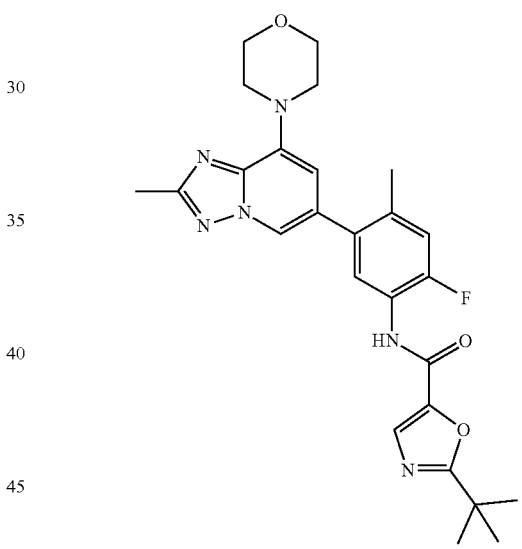

Step 1: To a stirred solution of 2-tert-butyl-1,3-oxazole-5-carboxylic acid (39.64 mg, 0.23 mmol) in $T_3P$ (0.4 mL, 50% in EA) was added 2-fluoro-4-methyl-5-[2-methyl-8-(morpholin-4-yl)-[1,2,4]triazolo[1,5-a]pyridin-6-yl]aniline (80 mg, 0.23 mmol) in pyridine (1 mL) dropwise at room temperature. The reaction mixture was stirred for 1 h at 60° C. The resulting mixture was concentrated in vacuo and the residue purified by reversed-phase flash chromatography with the following conditions: column, C18 silica gel; mobile phase, MeCN in water (Plus 10 mmol/L $NH_4HCO_3$), 30% to 60% gradient in 25 min; detector, UV 254 nm. The fractions contained desired product were combined and concentrated to afford the title compound (85.3 mg, 73%) as a white solid. MS ESI calculated for $C_{26}H_{29}FN_6O_3$ [M+H]$^+$, 493.23, found 493.40; $^1$H NMR (400 MHz, DMSO-$d_6$) δ 10.21 (s, 1H), 8.38 (d, J=1.4 Hz, 1H), 7.85-7.80 (m, 1H), 7.52 (d, J=7.8 Hz, 1H), 7.33 (d, J=11.3 Hz, 1H), 6.70 (s, 1H), 3.80 (t, J=4.8 Hz, 4H), 3.55 (t, J=4.8 Hz, 4H), 2.48 (s, 3H), 2.30 (s, 3H), 1.38 (s, 9H).

Example 294: 2-Tert-butyl-N-{2-fluoro-4-methyl-5-[2-methyl-8-(morpholin-4-yl)-[1,2,4]triazolo[1,5-a]pyridin-6-yl]phenyl}-1,3-oxazole-4-carboxamide

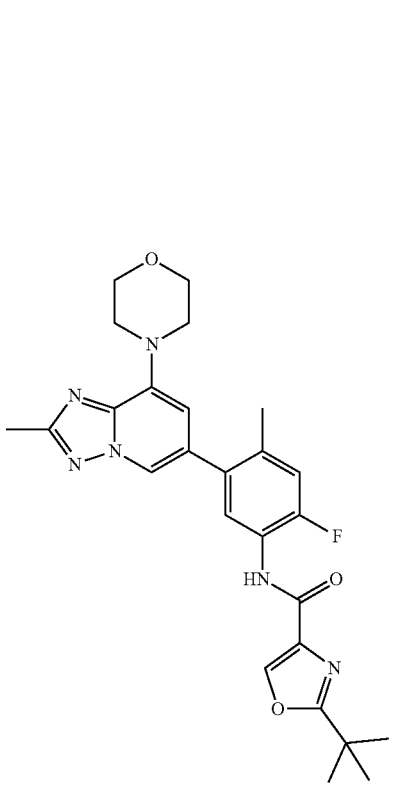 [SMILES: Cc1nc2c(N3CCOCC3)cc(-c3cc(NC(=O)c4coc(C(C)(C)C)n4)c(F)cc3C)cn2n1]

Step 1: To a stirred solution of 2-tert-butyl-1,3-oxazole-4-carboxylic acid (39.64 mg, 0.23 mmol) in T₃P (0.4 mL, 50% in EA) was added 2-fluoro-4-methyl-5-[2-methyl-8-(morpholin-4-yl)-[1,2,4]triazolo[1,5-a]pyridin-6-yl]aniline (80 mg, 0.23 mmol) in pyridine (0.5 mL) at room temperature. The reaction mixture was stirred for 1 h at 60° C. The resulting mixture was concentrated in vacuo and the residue purified by reversed-phase flash chromatography with the following conditions: column, C18 silica gel; mobile phase: MeCN in water (plus 10 mmol/L NH₄HCO₃), 40% to 75% gradient in 25 min; detector, UV 254 nm. The fractions containing the desired product were combined and concentrated to afford title compound (80.0 mg, 69%) as a white solid. MS ESI calculated for $C_{26}H_{29}FN_6O_3$ [M+H]⁺, 493.23, found 493.40; ¹H NMR (400 MHz, DMSO-d₆) δ 9.61 (s, 1H), 8.70 (s, 1H), 8.37 (d, J=1.3 Hz, 1H), 7.73 (d, J=7.9 Hz, 1H), 7.31 (d, J=11.6 Hz, 1H), 6.69 (d, J=1.5 Hz, 1H), 3.84 (t, J=4.8 Hz, 4H), 3.55 (t, J=4.8 Hz, 4H), 2.48 (s, 3H), 2.28 (s, 3H), 1.39 (s, 9H).

Example 299: N-(1-Tert-butyl-5-fluoropyrazol-4-yl)-2-fluoro-4-methyl-5-[2-methyl-8-(morpholin-4-yl)imidazo[1,2-b]pyridazin-6-yl]benzamide

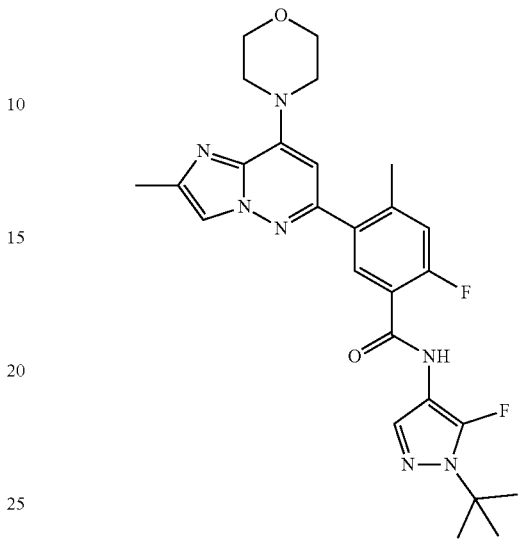

Step 1: To a stirred mixture of 4-{6-chloro-2-methylimidazo[1,2-b]pyridazin-8-yl}morpholine (150 mg, 0.59 mmol), methyl 2-fluoro-4-methyl-5-(4,4,5,5-tetramethyl-1,3,2-dioxaborolan-2-yl)benzoate (209.51 mg, 0.71 mmol) and K₃PO₄ (377.99 mg, 1.78 mmol) in THF (3 mL) and H₂O (0.3 mL) was added 2nd generation XPhos precatalyst (46.70 mg, 0.06 mmol) in portions at room temperature. The reaction mixture was purged with nitrogen three times and stirred for 3 h at 80° C. The resulting mixture was concentrated in vacuo and the residue purified by silica gel column chromatography (DCM/EA, 3:1). The fractions containing the desired product were combined and concentrated to afford methyl 2-fluoro-4-methyl-5-[2-methyl-8-(morpholin-4-yl)imidazo[1,2-b]pyridazin-6-yl]benzoate (200 mg, 87%) as a grey solid. MS ESI calculated for $C_{20}H_{21}FN_4O_3$[M+H]⁺, 385.16, found 385.20.

Step 2: To a stirred solution of methyl 2-fluoro-4-methyl-5-[2-methyl-8-(morpholin-4-yl)imidazo[1,2-b]pyridazin-6-yl]benzoate (200 mg, 0.52 mmol) in THF (1.6 mL) and MeOH (1.6 mL) was added NaOH (104.05 mg, 2.60 mmol) in H₂O (1.6 mL) dropwise at room temperature. The reaction mixture was allowed to stir for 2 h at room temperature. The resulting mixture was concentrated in vacuo and the residue was acidified to pH 6 with HCl (aq.). The precipitated solids were collected by filtration and washed with water (3×10 mL) to afford 2-fluoro-4-methyl-5-[2-methyl-8-(morpholin-4-yl)imidazo[1,2-b]pyridazin-6-yl]benzoic acid (250 mg, crude) as an off-white solid. MS ESI calculated for $C_{19}H_{19}FN_4O_3$[M+H]⁺, 371.14, found 371.30.

Step 3: To a stirred mixture of 2-fluoro-4-methyl-5-[2-methyl-8-(morpholin-4-yl)imidazo[1,2-b]pyridazin-6-yl]benzoic acid (80 mg, 0.22 mmol), EDCI (62.11 mg, 0.32 mmol), HOBT (43.78 mg, 0.32 mmol) and 1-tert-butyl-5-fluoropyrazol-4-amine (80 mg, 0.51 mmol) in DMF (2 mL) was added TEA (87.43 mg, 0.86 mmol) dropwise at room temperature. The reaction mixture was allowed to stir for 2 h at room temperature under nitrogen atmosphere. The resulting mixture was diluted with water (20 mL) and extracted with EtOAc (3×20 mL). The combined organic layers were washed with brine (3×15 mL), dried over anhydrous Na₂SO₄ and filtered. The filtrate was concentrated in vacuo and the residue purified by Prep-TLC (PE/EA, 2:3) to afford the crude product. The crude product was purified by reverse phase Flash chromatography with the following conditions: Column: WelFlash TM C18-I, 20-40 μm, 40 g; Eluent A: Water (Plus 10 mmol/L NH$_4$HCO$_3$); Eluent B: ACN; Gradient: 30% to 50% B in 25 min; Flow rate: 40 mL/min; Detector: 220/254 nm. The fractions containing the desired product were combined and concentrated to afford the title compound (51.2 mg, 46%) as an off-white solid. MS ESI calculated for C$_{26}$H$_{29}$F$_2$N$_{7}$O$_2$ [M+H]$^+$, 510.24, found 510.35; $^1$H NMR (400 MHz, DMSO-d$_6$) δ 9.95 (s, 1H), 7.84 (d, J=1.0 Hz, 1H), 7.71 (d, J=7.4 Hz, 1H), 7.57 (d, J=2.4 Hz, 1H), 7.34 (d, J=11.4 Hz, 1H), 6.35 (s, 1H), 4.04-3.97 (m, 4H), 3.78-3.73 (m, 4H), 2.39-2.23 (m, 6H), 1.54 (d, J=1.5 Hz, 9H).

Example 303: 2-Tert-butyl-N-{2-fluoro-4-methyl-5-[2-methyl-8-(morpholin-4-yl)-[1,2,4]triazolo[1,5-a]pyridin-6-yl]phenyl}-1,2,3-triazole-4-carboxamide

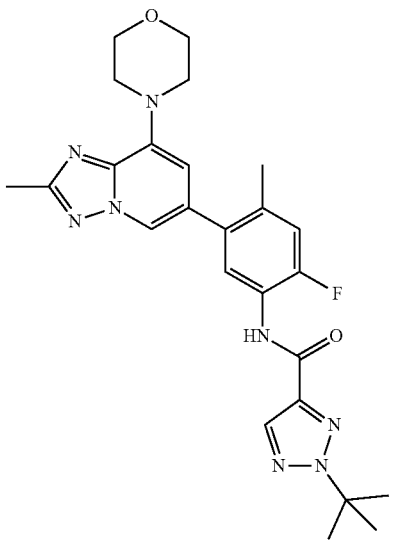 [SMILES: Cc1nc2c(N3CCOCC3)cc(-c3cc(NC(=O)c4cnn(C(C)(C)C)n4)c(F)cc3C)cn2n1]

Step 1: To a stirred solution of 4-{6-chloro-2-methyl-[1,2,4]triazolo[1,5-a]pyridin-8-yl}morpholine (300 mg, 1.18 mmol), 2-fluoro-4-methyl-5-(4,4,5,5-tetramethyl-1,3,2-dioxaborolan-2-yl)aniline (296.18 mg, 1.18 mmol) and XPhos Pd G2 (93.41 mg, 0.12 mmol) in THF (2 mL) was added K$_3$PO$_4$ (0.5 M) (4 mL) at room temperature. The reaction mixture was purged with nitrogen three times and stirred for 2 h at 40° C. The resulting mixture was diluted with water (20 mL) and extracted with EtOAc (3×50 mL). The combined organic layers were washed with brine (2×30 mL), dried over anhydrous Na$_2$SO$_4$ and filtered. The filtrate was concentrated in vacuo and the residue purified by silica gel column chromatography, eluted with PE/EA/EtOH (4/3/1). The fractions containing the desired product were combined and concentrated to afford 2-fluoro-4-methyl-5-[2-methyl-8-(morpholin-4-yl)-[1,2,4]triazolo[1,5-a]pyridin-6-yl]aniline (361.9 mg, 89%) as a yellow solid. MS ESI calculated for C$_{18}$H$_{2}$OFN$_5$O[M+H]$^+$, 342.17, found 342.20; $^1$H NMR (400 MHz, Chloroform-d) δ 8.03 (d, J=1.4 Hz, 1H), 6.94 (d, J=11.8 Hz, 1H), 6.71 (d, J=9.0 Hz, 1H), 6.58 (d, J=1.4 Hz, 1H), 4.02-3.95 (m, 4H), 3.59-3.52 (m, 4H), 2.62 (s, 3H), 2.17 (s, 3H).

Step 2: A solution of 2-fluoro-4-methyl-5-[2-methyl-8-(morpholin-4-yl)-[1,2,4]triazolo[1,5-a]pyridin-6-yl]aniline (100 mg, 0.29 mmol) in LiHMDS (1 mL, 1 M in THF) was allowed to stir for 1 h at 0° C. under nitrogen atmosphere. To the above mixture was added ethyl 2-tert-butyl-1,2,3-triazole-4-carboxylate (57.77 mg, 0.29 mmol) in THF (1 mL) dropwise over 5 min at 0° C. The reaction mixture was allowed to stir for additional 1 h at room temperature. The resulting mixture was quenched by the addition of sat. NH$_4$Cl (aq.) (5 mL) at room temperature. The resulting mixture was diluted with water (30 mL) and extracted with EtOAc (3×20 mL). The combined organic layers were washed with brine (2×20 mL), dried over anhydrous Na$_2$SO$_4$. The resulting mixture was concentrated in vacuo and the residue purified by Prep-HPLC with the following conditions: Column: XBridge Prep OBD C18 Column, 30×150 mm, 5 m; Mobile Phase A: Water (Plus 10 nmol/L NH$_4$HCO$_3$+0.05% NH$_3$H$_2$O), Mobile Phase B: ACN; Flow rate: 60 mL/min; Gradient: 41% B to 71% B in 10 min; Wave Length: 254 nm/220 nm; RT1: 8.5 min. The fractions containing the desired product were combined and concentrated to afford the title compound (74.3 mg, 51%) as a white solid. MS ESI calculated for C$_{25}$H$_{29}$FN$_8$O$_2$ [M+H]$^+$, 493.24, found 493.40; $^1$H NMR (400 MHz, DMSO-d$_6$) δ 10.01 (s, 1H), 8.39 (d, J=1.3 Hz, 1H), 8.28 (s, 1H), 7.60 (d, J=7.8 Hz, 1H), 7.32 (d, J=11.5 Hz, 1H), 6.70 (d, J=1.4 Hz, 1H), 3.84-3.77 (m, 4H), 3.55-3.45 (m, 4H), 2.48 (s, 3H), 2.30 (s, 3H), 1.68 (s, 9H).

Example 304: 2-Tert-butyl-N-{5-[2-cyclopropyl-5-(morpholin-4-yl)-[1,2,4]triazolo[1,5-a]pyridin-7-yl]-2-fluoro-4-methylphenyl}-1,3-oxazole-5-carboxamide

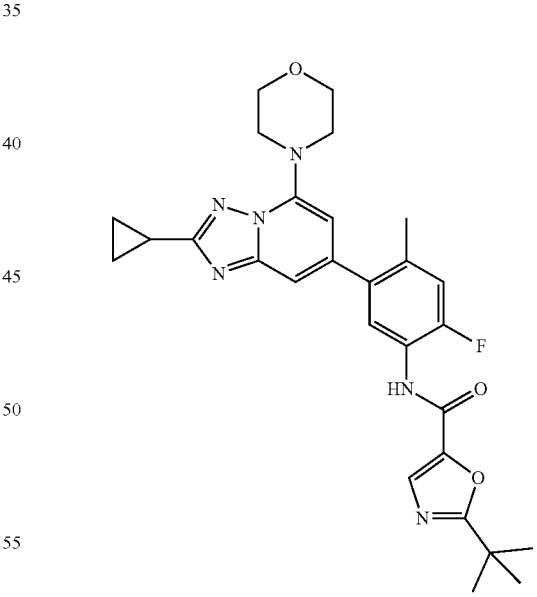

Step 1: To a stirred solution of amino 2,4,6-trimethylbenzenesulfonate (2.51 g, 11.65 mmol) in DCM (30 mL) was added 4,6-dichloropyridin-2-amine (950 mg, 5.82 mmol) in DCM (30 mL) dropwise at 0° C. under nitrogen atmosphere. The reaction mixture was allowed to stir for 2 h at 50° C. under nitrogen atmosphere. The resulting mixture was concentrated in vacuo to afford 1,2-diamino-4,6-dichloropyridin-i-ium 2,4,6-trimethylbenzenesulfonate (960 mg, 43%) as a white solid. MS ESI calculated for C$_{14}$H$_{17}$C$_{12}$N$_3$O$_3$ [M

- 199], 177.99, found 178.10; ¹H NMR (400 MHz, DMSO-d₆) δ 8.93 (s, 2H), 7.45 (d, J=2.4 Hz, 1H), 7.10 (d, J=2.4 Hz, 1H), 6.74 (s, 2H), 6.47 (s, 2H), 2.49 (s, 6H), 2.17 (s, 3H).

Step 2: To a stirred mixture of 1,2-diamino-4,6-dichloropyridin-1-ium 2,4,6-trimethylbenzenesulfonate (1.5 g, 3.97 mmol) and Cu(OAc)₂ (0.36 g, 1.98 mmol) in AcOH (8 mL) and MeOH (4 mL) was added cyclopropanecarbaldehyde (0.83 g, 11.90 mmol) dropwise at room temperature. The reaction mixture was purged with nitrogen three times and stirred for 1 h at 70° C. The resulting mixture was concentrated in vacuo and the residue diluted with EA (20 mL). The resulting mixture was basified to pH 7 with NaOH (aq.) and extracted with EtOAc (3×50 mL). The combined organic layers were washed with brine (2×30 mL), dried over anhydrous Na₂SO₄ and filtered. The filtrate was concentrated in vacuo and the residue purified by silica gel column chromatography (PE/EA, 3:1). The fractions containing the desired product were combined and concentrated to afford 5,7-dichloro-2-cyclopropyl-[1,2,4]triazolo[1,5-a]pyridine (510 mg, 54.19%) as a light yellow solid. MS ESI calculated for C₉H₇Cl₂N₃[M+H]⁺, 228.00 found 228.00; ¹H NMR (400 MHz, Chloroform-d) δ 7.57 (d, J=1.9 Hz, 1H), 7.07 (d, J=1.9 Hz, 1H), 2.29-2.24 (m, 1H), 1.24-1.09 (m, 4H).

Step 3: To a stirred solution of 5,7-dichloro-2-cyclopropyl-[1,2,4]triazolo[1,5-a]pyridine (510 mg, 2.24 mmol) and K₂CO₃ (618.07 mg, 4.47 mmol) in DMSO (10 mL) was added morpholine (195.46 mg, 2.24 mmol) dropwise at room temperature. The reaction mixture was allowed to stir for 1 h at 100° C. under nitrogen atmosphere. The resulting mixture was diluted with water (30 mL) and extracted with EtOAc (3×50 mL). The combined organic layers were washed with brine (2×50 mL), dried over anhydrous Na₂SO₄ and filtered. The filtrate was concentrated in vacuo and the residue purified by silica gel column chromatography (PE/EA, 1:1). The fractions containing the desired product were combined and concentrated to afford 4-{7-chloro-2-cyclopropyl-[1,2,4]triazolo[1,5-a]pyridin-5-yl}morpholine (560 mg, 89%) as an off-white solid. MS ESI calculated for C₁₃H₁₅ClN₄O [M+H]⁺, 279.09, 281.09, found 279.10, 281.10; ¹H NMR (400 MHz, Chloroform-d) δ 7.31-7.24 (m, 1H), 6.28-6.23 (m, 1H), 4.03-3.96 (m, 4H), 3.52 (t, J=4.6 Hz, 4H), 2.23-2.18 (m, 1H), 1.27-1.06 (m, 4H).

Step 4: To a stirred mixture of 4-{7-chloro-2-cyclopropyl-[1,2,4]triazolo[1,5-a]pyridin-5-yl}morpholine (280 mg, 1.00 mmol), 2-fluoro-4-methyl-5-(4,4,5,5-tetramethyl-1,3,2-dioxaborolan-2-yl)aniline (302.69 mg, 1.21 mmol) and K₃PO₄ (639.67 mg, 3.01 mmol) in THF (3 mL) and water (0.3 mL) was added 2nd Generation XPhos precatalyst (79.04 mg, 0.10 mmol) in portions at room temperature. The reaction mixture was purged with nitrogen three times and stirred for 1 h at 80° C. The resulting mixture was concentrated in vacuo and the residue purified by silica gel column chromatography (PE/EA, 1:1). The fractions containing the desired product were combined and concentrated to afford 5-[2-cyclopropyl-5-(morpholin-4-yl)-[1,2,4]triazolo[1,5-a]pyridin-7-yl]-2-fluoro-4-methylaniline (230 mg, 62%) as a light yellow solid. MS ESI calculated for C₂₀H₂₂FN₅O[M+H]⁺, 368.18, found 368.35; ¹H NMR (400 MHz, Chloroform-d) δ 7.18-7.15 (m, 1H), 6.93 (d, J=11.8 Hz, 1H), 6.71 (d, J=9.0 Hz, 1H), 6.21 (d, J=1.6 Hz, 1H), 4.01 (t, J=4.7 Hz, 4H), 3.52 (t, J=4.7 Hz, 4H), 2.28-2.24 (m, 1H), 2.18 (s, 3H), 1.19-1.14 (m, 2H), 1.11-1.08 (m, 2H).

Step 5: To a stirred mixture of 5-[2-cyclopropyl-5-(morpholin-4-yl)-[1,2,4]triazolo[1,5-a]pyridin-7-yl]-2-fluoro-4-methylaniline (100 mg, 0.27 mmol) in T₃P (0.5 mL, 50% in EA) was added 2-tert-butyl-1,3-oxazole-5-carboxylic acid (92.09 mg, 0.54 mmol) in Pyridine (0.5 mL) at room temperature. The reaction mixture was allowed to stir for 1 h at room temperature. The resulting mixture was concentrated in vacuo and the residue purified by reversed-phase flash chromatography with the following conditions: column, C18 silica gel; mobile phase, ACN in water (Plus 10 mmol/L NH₄HCO₃), 35% to 65% gradient in 15 min; detector, UV 254 nm. The fractions containing the desired product were combined and concentrated to afford the title compound (58.4 mg, 41%) as a white solid. MS ESI calculated for C₂₈H₃₁FN₆O₃[M+H]⁺, 519.24, found 519.40; ¹H NMR (400 MHz, DMSO-d4) δ 10.22 (s, 1H), 7.86 (s, 1H), 7.53 (d, J=7.8 Hz, 1H), 7.33 (d, J=11.3 Hz, 1H), 7.21 (d, J=1.6 Hz, 1H), 6.38 (d, J=1.7 Hz, 1H), 3.87-3.80 (m, 4H), 3.49-3.39 (m, 4H), 2.31 (s, 3H), 2.20-2.15 (m, 1H), 1.38 (s, 9H), 1.09-1.00 (m, 4H).

Example 305: 2-(Tert-butyl)-N-(5-(2-ethyl-5-morpholino-[1,2,4]triazolo[1,5-a]pyridin-7-yl)-2-fluoro-4-methylphenyl)oxazole-5-carboxamide

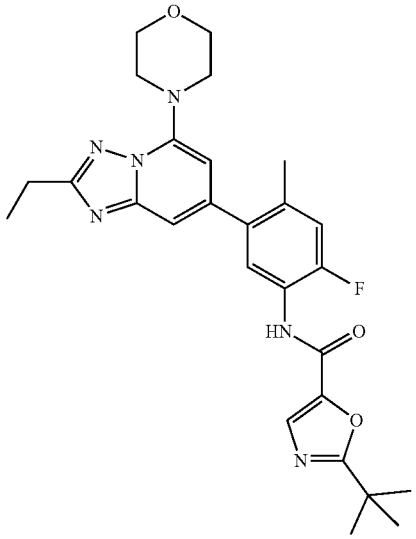 [SMILES: CCc1nc2cc(-c3cc(NC(=O)c4cnc(C(C)(C)C)o4)c(F)cc3C)cc(N3CCOCC3)n2n1]

Step 1: To a stirred mixture of 4-{7-chloro-2-ethyl-[1,2,4]triazolo[1,5-a]pyridin-5-yl}morpholine (190 mg, 0.71 mmol), 2-fluoro-4-methyl-5-(4,4,5,5-tetramethyl-1,3,2-dioxaborolan-2-yl)aniline (214.65 mg, 0.85 mmol) and K₃PO₄ (453.61 mg, 2.14 mmol) in THF (2 mL) and water (0.2 mL) was added XPhos Pd G2 (56.05 mg, 0.07 mmol) in portions at room temperature. The reaction mixture was purged with nitrogen three times and stirred for 1 h at 80° C. The resulting mixture was concentrated in vacuo and the residue purified by silica gel column chromatography (PE/EA, 1:3). The fractions containing the desired product were combined and concentrated to afford 5-[2-ethyl-5-(morpholin-4-yl)-[1,2,4]triazolo[1,5-a]pyridin-7-yl]-2-fluoro-4-methylaniline (100 mg, 39%) as a light yellow oil. MS ESI calculated for C₁₉H₂₂FN₅O[M+H]⁺, 356.18, found 356.35; ¹H NMR (400 MHz, Chloroform-d) δ 7.24 (d, J=1.6 Hz, 1H), 6.94 (d, J=11.8 Hz, 1H), 6.72 (d, J=9.0 Hz, 1H), 6.24 (d, J=1.7 Hz, 1H), 4.02-3.95 (m, 4H), 3.56-3.49 (m, 4H), 3.00-2.94 (m, 2H), 2.19 (s, 3H), 1.47 (t, J=7.6 Hz, 3H).

Step 2: To a stirred solution of 2-tert-butyl-1,3-oxazole-5-carboxylic acid (38.08 mg, 0.23 mmol) in T₃P (0.2 mL, 50% in EA) was added 5-[2-ethyl-5-(morpholin-4-yl)-[1,2,4]triazolo[1,5-a]pyridin-7-yl]-2-fluoro-4-methylaniline (80 mg, 0.23 mmol) in Pyridine (0.2 mL) dropwise at room temperature. The reaction mixture was allowed to stir for 1 h at 30° C. The resulting mixture was concentrated in vacuo and purified by reversed-phase flash chromatography with the following conditions: column, C18 silica gel; mobile phase, MeCN in Water (Plus 10 mmol/L $NH_4HCO_3$), 20% to 50% gradient in 30 min; detector, UV 254 nm. The fractions containing the desired product were combined and concentrated to afford 2-tert-butyl-N-{5-[2-ethyl-5-(morpholin-4-yl)-[1,2,4]triazolo[1,5-a]pyridin-7-yl]-2-fluoro-4-methylphenyl}-1,3-oxazole-5-carboxamide (63.8 mg, 55%) as a white solid. MS ESI calculated for $C_7H_{31}FN_6O_3$ [M+H]$^+$, 507.24, found 507.40; $^1$H NMR (400 MHz, DMSO-d$_6$) δ 10.22 (s, 1H), 7.85 (s, 1H), 7.54 (d, J=7.9 Hz, 1H), 7.34 (d, J=11.3 Hz, 1H), 7.27 (d, J=1.6 Hz, 1H), 6.40 (d, J=1.7 Hz, 1H), 3.83 (t, J=4.6 Hz, 4H), 3.48 (t, J=4.6 Hz, 4H), 2.85-2.78 (m, 2H), 2.32 (s, 3H), 1.38 (s, 9H), 1.33 (t, J=7.6 Hz, 3H).

Example 306: N-(1-(tert-Butyl)-5-fluoro-1H-pyrazol-4-yl)-5-(2-ethyl-5-morpholino-[1,2,4]triazolo[1,5-a]pyridin-7-yl)-2-fluoro-4-methylbenzamide

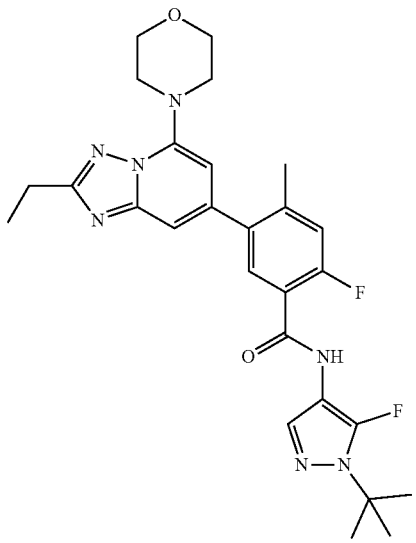 [SMILES: CCc1nc2cc(-c3cc(C(=O)Nc4cnn(C(C)(C)C)c4F)c(F)cc3C)cc(N3CCOCC3)n2n1]

Step 1: To a stirred mixture of 1,2-diamino-4,6-dichloropyridin-1-ium 2,4,6-trimethylbenzenesulfonate (1.5 g, 3.96 mmol) and Cu(OAc)$_2$ (0.36 g, 1.98 mmol) in AcOH (8 mL) and MeOH (4 mL) was added propionaldehyde (0.69 g, 11.89 mmol) dropwise at room temperature under nitrogen atmosphere. The reaction mixture was purged with nitrogen three times and stirred for 1 h at 70° C. The resulting mixture was concentrated in vacuo and the reaction mixture was basified to pH 7 with NaOH (aq.). The resulting mixture was extracted with EtOAc (3×50 mL). The combined organic layers were washed with brine (2×30 mL), dried over anhydrous Na$_2$SO$_4$ and filtered. The filtrate was concentrated in vacuo and the residue purified by silica gel column chromatography (PE/EA, 3:1). The fractions containing the desired product were combined and concentrated to afford 5,7-dichloro-2-ethyl-[1,2,4]triazolo[1,5-a]pyridine (300 mg, 33%) as a light yellow solid. MS ESI calculated for $C_8H_7Cl_2N_3$[M+H]$^+$, 216.07, found 216.15; $^1$H NMR (400 MHz, Chloroform-d) δ 7.66 (d, J=2.0 Hz, 1H), 7.12 (d, J=2.0 Hz, 1H), 3.01-2.96 (m, 2H), 1.45 (t, J=7.6 Hz, 3H).

Step 2: To a stirred mixture of 5,7-dichloro-2-ethyl-[1,2,4]triazolo[1,5-a]pyridine (270 mg, 1.25 mmol) and morpholine (163.30 mg, 1.87 mmol) in DMSO (3 mL) was added K$_2$CO$_3$ (345.40 mg, 2.50 mmol) in portions at room temperature under nitrogen atmosphere. The reaction mixture was allowed to stir for 2 h at 100° C. under nitrogen atmosphere. The resulting mixture was diluted with water (20 mL) and extracted with EA (3×30 mL). The resulting mixture was concentrated in vacuo and the residue purified by silica gel column chromatography (PE/EA, 2:1). The fractions containing the desired product were combined and concentrated to afford 4-{7-chloro-2-ethyl-[1,2,5-a]pyridin-5-yl}morpholine (320 mg, 96%) as an off-white solid. MS ESI calculated for $C_{12}H_{15}ClN_4O$. [M+H]$^+$, 267.09, found 267.30; $^1$H NMR (400 MHz, Chloroform-d) δ 7.34 (d, J=2.0 Hz, 1H), 6.29 (d, J=1.9 Hz, 1H), 4.03-3.97 (m, 4H), 3.54-3.48 (m, 4H), 3.01-2.96 (m, 2H), 1.44 (t, J=7.6 Hz, 3H).

Step 3: To a stirred mixture of 4-{7-chloro-2-ethyl-[1,2,4]triazolo[1,5-a]pyridin-5-yl}morpholine (300 mg, 1.12 mmol), methyl 2-fluoro-4-methyl-5-(4,4,5,5-tetramethyl-1,3,2-dioxaborolan-2-yl)benzoate (330.82 mg, 1.12 mmol) and XPhos Pd G2 (88.50 mg, 0.11 mmol) in THF (2 mL) was added K$_3$PO$_4$ (4 mL, 2.00 mmol, 0.5 M) dropwise at room temperature. The reaction mixture was purged with nitrogen three times and stirred for 2 h at 40° C. The resulting mixture was concentrated in vacuo and the residue purified by silica gel column chromatography, eluted with PE/EA (1/1). The fractions containing the desired product were combined and concentrated to afford methyl 5-[2-ethyl-5-(morpholin-4-yl)-[1,2,4]triazolo[1,5-a]pyridin-7-yl]-2-fluoro-4-methylbenzoate (300 mg, 67%) as an off-white solid. MS ESI calculated for $C_{21}H_{23}FN_4O_3$[M+H]$^+$, 399.18, found 399.40; $^1$H NMR (400 MHz, Chloroform-d) δ 7.88 (d, J=7.3 Hz, 1H), 7.34-7.31 (m, 1H), 7.13 (d, J=11.3 Hz, 1H), 6.28-6.25 (m, 1H), 4.02 (t, J=4.8 Hz, 4H), 3.96 (s, 3H), 3.57 (t, J=4.8 Hz, 4H), 3.05-2.98 (m, 2H), 2.36 (s, 3H), 1.50 (t, J=7.6 Hz, 3H).

Step 4: To a stirred mixture of methyl 5-[2-ethyl-5-(morpholin-4-yl)-[1,2,4]triazolo[1,5-a]pyridin-7-yl]-2-fluoro-4-methylbenzoate (270 mg, 0.68 mmol) in THF (2 mL) and MeOH (2 mL) was added NaOH (81.31 mg, 2.03 mmol) in H$_2$O (2 mL) dropwise at room temperature. The reaction mixture was allowed to stir for 1 h at room temperature. The resulting mixture was concentrated in vacuo and to afford 5-[2-ethyl-5-(morpholin-4-yl)-[1,2,4]triazolo[1,5-a]pyridin-7-yl]-2-fluoro-4-methylbenzoic acid (390 mg, crude) as an off-white solid. MS ESI calculated for $C_{20}H_{21}FN_4O_3$. [M+H]$^+$, 385.16, found 385.00.

Step 5: To a stirred mixture of 5-[2-ethyl-5-(morpholin-4-yl)-[1,2,4]triazolo[1,5-a]pyridin-7-yl]-2-fluoro-4-methylbenzoic acid (350 mg, 0.91 mmol), EDCI (259.89 mg, 1.36 mmol), HOBT (184.55 mg, 1.36 mmol) and NH$_4$Cl (194.81 mg, 3.64 mmol) in DMF (4 mL) was added DIEA (941.42 mg, 7.28 mmol) dropwise at room temperature. The resulting mixture was allowed to stir for 30 min at 50° C. The resulting mixture was concentrated in vacuo and the residue purified by silica gel column chromatography (DCM/MeOH, 10:1). The fractions containing the desired product were combined and concentrated to afford 5-[2-ethyl-5-(morpholin-4-yl)-[1,2,4]triazolo[1,5-a]pyridin-7-yl]-2-fluoro-4-methylbenzamide (230 mg, 66%) as an off-white solid. MS ESI calculated for $C_{20}H_{22}FN_5O_2$[M+H]$^+$, 384.18, found 384.40; $^1$H NMR (400 MHz, Chloroform-d) δ 8.05 (d, J=8.1 Hz, 1H), 7.23 (d, J=1.6 Hz, 1H), 7.10 (d, J=12.6 Hz, 1H), 6.70 (d, J=11.4 Hz, 1H), 6.21 (d, J=1.6 Hz, 1H), 5.86

(s, 1H), 4.05-3.97 (m, 4H), 3.53-3.45 (m, 4H), 2.99-2.95 (m, 2H), 2.35 (s, 3H), 1.46 (t, J=7.6 Hz, 3H).

Step 6: To a stirred mixture of 5-[2-ethyl-5-(morpholin-4-yl)-[1,2,4]triazolo[1,5-a]pyridin-7-yl]-2-fluoro-4-methylbenzamide (200 mg, 0.52 mmol), methyl[2-(methylamino) ethyl]amine (45.98 mg, 0.52 mmol) and CuI (99.34 mg, 0.52 mmol) in dioxane (4 mL) was added 4-bromo-1-(tert-butyl)-5-fluoro-1H-pyrazole (230.63 mg, 1.04 mmol) in dioxane (4 mL) dropwise at room temperature. The reaction mixture was purged with nitrogen atmosphere for three times and stirred for 16 h at 100° C. The mixture was allowed to cool to room temperature. The resulting mixture was concentrated in vacuo and the residue purified by silica gel column chromatography (PE/EA, 1:4) to afford the crude product. The crude product was purified by reverse phase Flash chromatography with the following conditions: Column: WelFlash TM C18-I, 20-40 μm, 40 g; Eluent A: Water (Plus 10 mmol/L $NH_4HCO_3$); Eluent B: ACN; Gradient: 35% to 60% B in 25 min; Flow rate: 35 mL/min; Detector: 220/254 nm. The faster peak contained desired product were combined and concentrated to afford the title compound (109.7 mg, 39%) as an off-white solid. MS ESI calculated for $C_{27}H_{31}F_2N_7O_2$ [M+H]$^+$, 524.25, found 524.40; $^1$H NMR (400 MHz, Chloroform-d) δ 8.11 (d, J=7.9 Hz, 1H), 7.99 (d, J=15.3 Hz, 1H), 7.79 (d, J=2.3 Hz, 1H), 7.60-7.56 (m, 1H), 7.20 (d, J=12.7 Hz, 1H), 6.50-6.45 (m, 1H), 4.05-3.94 (m, 4H), 3.63-3.52 (m, 4H), 3.15-3.12 (m, 2H), 2.41 (s, 3H), 1.65 (s, 9H), 1.56 (t, J=7.6 Hz, 3H).

Example 307: N-(1-(tert-butyl)-5-fluoro-1H-pyrazol-4-yl)-5-(2-cyclopropyl-5-morpholino-[1,2,4] triazolo[1,5-a]pyridin-7-yl)-2-fluoro-4-methylbenzamide

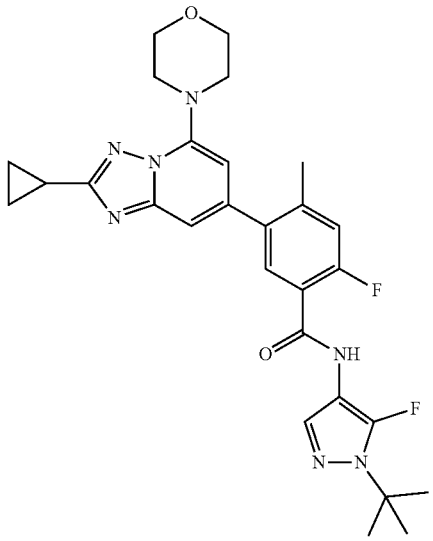 [SMILES: Cc1cc(F)c(C(=O)Nc2cnn(C(C)(C)C)c2F)cc1-c1cc(N2CCOCC2)n2nc(C3CC3)nc2c1]

Step 1: To a stirred mixture of 4-{7-Chloro-2-cyclopropyl-[1,2,4]triazolo[1,5-a]pyridin-5-yl}morpholine (560 mg, 2.01 mmol), Methyl 2-fluoro-4-methyl-5-(4,4,5,5-tetramethyl-1,3,2-dioxaborolan-2-yl)benzoate (709.10 mg, 2.41 mmol) and $K_3PO_4$ (852.90 mg, 4.02 mmol) in THF (10 mL) and $H_2O$ (1 mL) was added XPhos Pd G2 (158.08 mg, 0.20 mmol) in portions at room temperature. The reaction mixture was purged with nitrogen three times and stirred for 1 h at 80° C. The resulting mixture was diluted with water (100 mL). The resulting mixture was diluted with water (20 mL) and extracted with EtOAc (3×50 mL). The combined organic layers were washed with brine (2×30 mL), dried over anhydrous $Na_2SO_4$ and filtered. The filtrate was concentrated in vacuo and the residue purified by silica gel column chromatography (PE/EA, 1:2). The fractions containing the desired product were combined and concentrated to afford methyl 5-[2-cyclopropyl-5-(morpholin-4-yl)-[1,2,4]triazolo[1,5-a]pyridin-7-yl]-2-fluoro-4-methylbenzoate (580 mg, 70.34%) as an off-white solid. MS ESI calculated for $C_{22}H_{23}FN_4O_3$[M+H]$^+$, 411.18, found 411.30.

Step 2: To a stirred mixture of methyl 5-[2-Cyclopropyl-5-(morpholin-4-yl)-[1,2,4]triazolo[1,5-a]pyridin-7-yl]-2-fluoro-4-methylbenzoate (550 mg, 1.34 mmol) in THF (3 mL), MeOH (3 mL) and $H_2O$ (3 mL) was added LiOH $H_2O$ (224.90 mg, 5.36 mmol) at room temperature. The reaction mixture was allowed to stir for 1 h at room temperature. The resulting mixture was concentrated in vacuo to afford 5-[2-cyclopropyl-5-(morpholin-4-yl)-[1,2,4]triazolo[1,5-a]pyridin-7-yl]-2-fluoro-4-methylbenzoic acid (400 mg, crude). MS ESI calculated for $C_{21}H_{21}FN_4O_3$[M+H]$^+$, 397.16, found 397.35; $^1$H NMR (400 MHz, DMSO-d$_6$) δ 7.52 (d, J=7.5 Hz, 1H), 7.14-7.09 (m, 1H), 6.98 (d, J=11.0 Hz, 1H), 6.33-6.28 (m, 1H), 3.83 (t, J=4.6 Hz, 4H), 3.47 (t, J=4.6 Hz, 4H), 2.25 (s, 3H), 2.18-2.13 (m, 1H), 1.03-0.96 (m, 4H).

Step 3: To a stirred mixture of 5-[2-Cyclopropyl-5-(morpholin-4-yl)-[1,2,4]triazolo[1,5-a]pyridin-7-yl]-2-fluoro-4-methylbenzoic acid (400 mg, 1.01 mmol), HATU (575.50 mg, 1.51 mmol) and DIEA (652.07 mg, 5.05 mmol) in THF (6 mL) was added $NH_4Cl$ (80.96 mg, 1.51 mmol). The reaction mixture was allowed to stir for 2 h at room temperature. The resulting mixture was diluted with water (30 mL) and extracted with EtOAc (3×50 mL). The combined organic layers were washed with brine (2×40 mL), dried over anhydrous $Na_2SO_4$ and filtered. The filtrate was concentrated in vacuo and the residue purified by silica gel column chromatography (DCM/MeOH, 15:1). The fractions containing the desired product were combined and concentrtated to afford 5-[2-Cyclopropyl-5-(morpholin-4-yl)-[1,2,4]triazolo[1,5-a]pyridin-7-yl]-2-fluoro-4-methylbenzamide (320 mg, 80%) as an off-white solid. MS ESI calculated for $C_{21}H_{22}FN_5O_2$[M+H]$^+$, 396.18, found 396.15; $^1$H NMR (400 MHz, Chloroform-d) δ 8.06 (d, J=8.0 Hz, 1H), 7.20 (d, J=1.6 Hz, 1H), 7.12 (d, J=12.6 Hz, 1H), 6.23 (d, J=1.6 Hz, 1H), 4.02 (t, J=4.6 Hz, 4H), 3.55 (t, J=4.6 Hz, 4H), 2.36 (s, 3H), 2.29-2.23 (m, 1H), 1.25-1.09 (m, 4H).

Step 4: To a stirred solution of 5-[2-Cyclopropyl-5-(morpholin-4-yl)-[1,2,4]triazolo[1,5-a]pyridin-7-yl]-2-fluoro-4-methylbenzamide (100 mg, 0.25 mmol), 4-bromo-1-(tert-butyl)-5-fluoro-1H-pyrazole (72.68 mg, 0.33 mmol) and $K_3PO_4$ (112.72 mg, 0.53 mmol) in dioxane (2 mL) were added Methyl[2-(methylamino)ethyl]amine (22.29 mg, 0.25 mmol) and CuI (48.16 mg, 0.25 mmol) in portions at room temperature. The reaction mixture was purged with nitrogen three times and stirred for 16 h at 100° C. The resulting mixture was diluted with water (20 mL) and $NH_3H_2O$ (5 mL). The resulting mixture was extracted with EtOAc (3×40 mL). The combined organic layers were washed with brine (2×30 mL), dried over anhydrous $Na_2SO_4$ and filtered. The filtrate was concentrated in vacuo and the residue purified by silica gel column chromatography (PE/EA, 1:1) to afford the crude product (40 mg). The crude product (40 mg) was purified by reverse phase flash chromatography with the following conditions: Column: Spherical C18, 20-40 um, 40 g; Mobile Phase A: Water (Plus 10 mmol/L $NH_4HCO_3$); Mobile Phase B: ACN; Flow rate: 40 mL/min; Gradient: 30% B to 60% B gradient in 25 min; Detector: 220 nm. The fractions containing the desired product were combined and concentrated to afford the title compound (30.2 mg, 22%) as a white solid. MS ESI calculated for C$_{28}$H$_{31}$F$_2$N$_7$O$_2$[M+H]$^+$, 536.25, found 536.40; $^1$H NMR (400 MHz, DMSO-d$_6$) δ 9.94 (s, 1H), 7.63 (d, J=7.3 Hz, 1H), 7.58 (d, J=2.4 Hz, 1H), 7.36 (d, J=11.3 Hz, 1H), 7.27 (d, J=1.7 Hz, 1H), 6.42 (d, J=1.8 Hz, 1H), 3.87-3.80 (m, 4H), 3.50-3.43 (m, 4H), 2.36 (s, 3H), 2.21-2.07 (m, 1H), 1.55 (s, 9H), 1.09-0.95 (m, 4H).

Example 308: N-(1-(tert-Butyl)-5-fluoro-1H-pyrazol-4-yl)-2-fluoro-5-(2-isopropyl-8-morpholino-[1,2,4]triazolo[1,5-a]pyridin-6-yl)-4-methylbenzamide

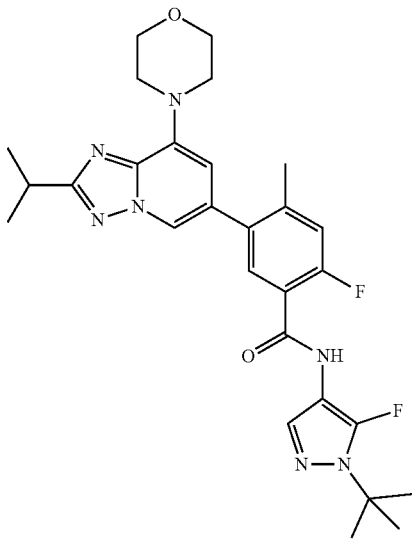 [SMILES: Cc1cc(F)c(C(=O)Nc2cnn(C(C)(C)C)c2F)cc1-c1cc(N2CCOCC2)c2nc(C(C)C)nn2c1]

Step 1: To a stirred solution of 5-bromo-3-(morpholin-4-yl)pyridin-2-amine (6 g, 23.25 mmol) in dioxane (60 mL) was added ethyl N-carbothioylcarbamate (3.05 g, 23.25 mmol) at room temperature. The reaction mixture was allowed to stir for 2 h at room temperature. The resulting mixture was concentrated in vacuo and the residue purified by trituration with MTBE (20 mL) and cyclohexane (10 mL). The precipitated solids were collected by filtration and washed with MTBE (3×10 mL) to afford ethyl N-{[5-bromo-3-(morpholin-4-yl)pyridin-2-yl]carbamothioyl}carbamate (8.4 g, 93%) as a brown solid. MS ESI calculated for C$_{13}$H$_{17}$BrN$_4$O3S [M+H]$^+$, 389.02, 391.02, found 389.25, 391.25; $^1$H NMR (400 MHz, Chloroform-d) δ 8.28 (s, 1H), 7.57 (s, 1H), 4.33-4.26 (m, 2H), 3.92 (t, J=4.4 Hz, 4H), 2.94 (t, J=4.4 Hz, 4H), 1.38 (t, J=7.2 Hz, 3H).

Step 2: To a stirred solution of ethyl N-{[5-bromo-3-(morpholin-4-yl)pyridin-2-yl]carbamothioyl}carbamate (8.4 g, 21.58 mmol) in MeOH (50 mL), EtOH (50 mL) and THF (50 mL) were added NH$_2$OH HCl (8.10 g, 116.53 mmol) and DIEA (13.95 g, 107.90 mmol) at room temperature. The reaction mixture was allowed to stir for 2 h at 60° C. The resulting mixture was diluted with water (150 mL) and basified to pH 8 with saturated NaHCO$_3$ (10%.). The resulting mixture was allowed to stir for 10 min at room temperature. The precipitated solids were collected by filtration and washed with water (3×30 mL) and Et$_2$O (3×15 mL) to afford 6-bromo-8-(morpholin-4-yl)-[1,2,4]triazolo[1,5-a]pyridin-2-amine (4.35 g, crude) as a brown yellow solid.

MS ESI calculated for C$_{10}$H$_{12}$BrN$_5$O [M+H]$^+$, 298.02, 300.02, found 298.25, 300.25; $^1$H NMR (400 MHz, Chloroform-d) δ 8.09 (d, J=1.6 Hz, 1H), 6.70 (d, J=1.6 Hz, 1H), 4.47 (s, 2H), 3.96-3.93 (m, 4H), 3.50-3.47 (m, 4H).

Step 3: To a stirred solution of 6-bromo-8-(morpholin-4-yl)-[1,2,4]triazolo[1,5-a]pyridin-2-amine (3 g, 10.06 mmol) and methyl 2-fluoro-4-methyl-5-(4,4,5,5-tetramethyl-1,3,2-dioxaborolan-2-yl)benzoate (2.96 g, 10.06 mmol) in dioxane (24 mL) and H$_2$O (6 mL) were added Na$_2$CO$_3$ (3.20 g, 30.19 mmol) and Pd(PPh$_3$)$_2$C$_{12}$ (706 mg, 1.00 mmol) at room temperature. The reaction mixture was purged with nitrogen three times and stirred for 1 h at 80° C. The resulting mixture was diluted with water (40 mL) and extracted with EtOAc (3×40 mL). The combined organic layers were washed with brine (3×40 mL), dried over anhydrous Na$_2$SO$_4$ and filtered. The filtrate was concentrated in vacuo and the residue purified by silica gel column chromatography (DCM/MeOH, 10:1) to afford the crude product. The crude product was purified by trituration (PE/EA, 1:1) to afford methyl 5-[2-amino-8-(morpholin-4-yl)-[1,2,4]triazolo[1,5-a]pyridin-6-yl]-2-fluoro-4-methylbenzoate (1.68 g, 43%) as a light yellow solid. MS ESI calculated for C$_{19}$H$_2$OFN$_5$O$_3$[M+H]$^+$, 386.39, found 386.25; $^1$H NMR (400 MHz, DMSO-d$_6$) δ 8.17-8.13 (m, 1H), 7.76 (d, J=7.4 Hz, 1H), 7.36 (d, J=12.0 Hz, 1H), 6.61-6.58 (m, 1H), 6.00 (s, 2H), 3.85 (s, 3H), 3.77 (t, J=4.8 Hz, 4H), 3.45 (t, J=4.8 Hz, 4H), 2.33 (s, 3H).

Step 4: To a stirred solution of methyl 5-[2-amino-8-(morpholin-4-yl)-[1,2,4]triazolo[1,5-a]pyridin-6-yl]-2-fluoro-4-methylbenzoate (1.63 g, 4.23 mmol) and CuI (1.61 g, 8.46 mmol) in MeCN (20 mL) was added t-BuONO (2.18 g, 21.15 mmol) at room temperature. The reaction mixture was allowed to stir for 20 min at room temperature Then the reaction mixture was warmed to 55° C. and stirred for 30 min under nitrogen atmosphere. The resulting mixture was filtered, the filter cake was washed with ACN (3×20 mL). The filtrate was concentrated in vacuo and the residue was diluted with water (100 mL) and basified to pH 8 with NaOH (aq.).

The resulting mixture was extracted with CH$_2$Cl$_2$ (3×100 mL). The combined organic layers were washed with brine (3×70 mL), dried over anhydrous Na$_2$SO$_4$ and filtered. The filtrate was concentrated in vacuo and the residue purified by silica gel column chromatography (DCM/EA, 3:1). The fractions containing the desired product were combined and concentrated to afford methyl 2-fluoro-5-[2-iodo-8-(morpholin-4-yl)-[1,2,4]triazolo[1,5-a]pyridin-6-yl]-4-methylbenzoate (766 mg, 36%) as an off-white solid. MS ESI calculated for C$_{19}$H$_{18}$FIN$_4$O$_3$[M+H]$^+$, 497.04, found 497.25; $^1$H NMR (400 MHz, Chloroform-d) δ 8.09 (s, 1H), 7.86 (d, J=7.2 Hz, 1H), 7.12 (d, J=11.2 Hz, 1H), 6.59 (s, 1H), 4.00-3.96 (m, 4H), 3.95 (s, 3H), 3.61-3.59 (m, 4H), 2.33 (s, 3H). $^{19}$F NMR (376 MHz, CDCl$_3$) δ -110.16 (1F).

Step 5: To a stirred mixture of methyl 2-fluoro-5-[2-iodo-8-(morpholin-4-yl)-[1,2,4]triazolo[1,5-a]pyridin-6-yl]-4-methylbenzoate (300 mg, 0.60 mmol), 4,4,5,5-tetramethyl-2-(prop-1-en-2-yl)-1,3,2-dioxaborolane (152.37 mg, 0.91 mmol) and Na$_2$CO$_3$ (192.21 mg, 1.81 mmol) in dioxane (5 mL) and H$_2$O (1 mL) was added Pd(dppf)Cl$_2$CH$_2$Cl$_2$ (49.24 mg, 0.06 mmol) in portions at room temperature. The reaction mixture was purged with nitrogen three times and stirred for 1 h at 80° C. The resulting mixture was concentrated in vacuo and the residue purified by silica gel column chromatography (PE/EA/EtOH, 5:3:1). The fractions containing the desired product were combined and concentrated to afford methyl 2-fluoro-4-methyl-5-(8-morpholino-2-(prop-1-en-2-yl)-[1,2,4]triazolo[1,5-a]pyridin-6-yl)benzoate (240 mg, 87%) as a pink solid. MS ESI calculated for C₂₂H₂₃FN₄O₃[M+H]⁺, 411.18, found 411.40; ¹H NMR (400 MHz, Chloroform-d) δ 8.09 (d, J=1.4 Hz, 1H), 7.86 (d, J=7.2 Hz, 1H), 7.10 (d, J=11.4 Hz, 1H), 6.55 (d, J=1.4 Hz, 1H), 6.30 (d, J=7.8 Hz, 1H), 5.43-5.38 (m, 1H), 4.02-3.97 (m, 4H), 3.93 (s, 3H), 3.63-3.57 (m, 4H), 1.26 (s, 3H), 0.87 (s, 3H).

Step 6: To a stirred mixture of methyl 2-fluoro-4-methyl-5-(8-morpholino-2-(prop-1-en-2-yl)-[1,2,4]triazolo[1,5-a]pyridin-6-yl)benzoate (230 mg, 0.56 mmol) in MeOH (3 mL) was added Pd/C (230.19 mg, 2.16 mmol, 10%) in portions at room temperature. The reaction mixture was allowed to stir for 1 h under hydrogen atmosphere at room temperature. The resulting mixture was filtered, the filter cake was washed with MeOH (3×20 mL). The filtrate was concentrated in vacuo to afford methyl 2-fluoro-5-(2-isopropyl-8-morpholino-[1,2,4]triazolo[1,5-a]pyridin-6-yl)-4-methylbenzoate (210 mg, crude) as a white solid. MS ESI calculated for C₂₂H₂₅FN₄O₃[M+H]⁺, 413.19, found 413.30; ¹H NMR (400 MHz, Chloroform-d) δ 8.07 (d, J=1.4 Hz, 1H), 7.85 (d, J=7.3 Hz, 1H), 7.10 (d, J=11.4 Hz, 1H), 6.55-6.53 (m, 1H), 4.02-3.95 (m, 5H), 3.93 (s, 3H), 3.58-3.51 (m, 4H), 2.32 (s, 3H), 1.46 (d, J=6.8 Hz, 6H).

Step 7: To a stirred mixture of methyl 2-fluoro-5-(2-isopropyl-8-morpholino-[1,2,4]triazolo[1,5-a]pyridin-6-yl)-4-methylbenzoate (200 mg, 0.49 mmol) in THF (2 mL) and MeOH (2 mL) was added NaOH (96.97 mg, 2.43 mmol) in H₂O (2 mL) dropwise at room temperature. The reaction mixture was allowed to stir for 1 h at room temperature. The resulting mixture was concentrated in vacuo to afford 2-fluoro-5-(2-isopropyl-8-morpholino-[1,2,4]triazolo[1,5-a]pyridin-6-yl)-4-methylbenzoic acid (300 mg, crude) as a white solid. MS ESI calculated for C₂₁H₂₃FN₄O₃[M+H]⁺, 399.18, found 399.35.

Step 8: To a stirred mixture of 2-fluoro-5-(2-isopropyl-8-morpholino-[1,2,4]triazolo[1,5-a]pyridin-6-yl)-4-methylbenzoic acid (280 mg, 0.70 mmol), EDCI (202.07 mg, 1.05 mmol), HOBT (142.44 mg, 1.05 mmol) and NH₄Cl (187.95 mg, 3.52 mmol) in DMF (5 mL) was added DIEA (908.28 mg, 7.03 mmol) dropwise at room temperature. The reaction mixture was allowed to stir for 1 h at 50° C. The resulting mixture was concentrated in vacuo and the residue purified by silica gel column chromatography (PE/EA, 4:1). The fractions containing the desired product were combined and concentrated to afford 2-fluoro-5-(2-isopropyl-8-morpholino-[1,2,4]triazolo[1,5-a]pyridin-6-yl)-4-methylbenzamide (100 mg, 35%) as a white solid. MS ESI calculated for C₂₁H₂₄FN₅O₂[M+H]⁺, 398.19, found 398.35; ¹H NMR (400 MHz, Chloroform-d) δ 8.10-8.06 (m, 1H), 8.00 (s, 2H), 7.12 (d, J=12.5 Hz, 1H), 6.65-6.61 (m, 1H), 5.81-5.74 (m, 1H), 4.00-3.95 (m, 4H), 2.92-2.87 (m, 5H), 2.32 (s, 3H), 1.47 (d, J=6.8 Hz, 6H).

Step 9: To a stirred mixture of 2-fluoro-5-(2-isopropyl-8-morpholino-[1,2,4]triazolo[1,5-a]pyridin-6-yl)-4-methylbenzamide (90 mg, 0.23 mmol), K₃PO₄ (100.94 mg, 0.48 mmol) and CuI (86.25 mg, 0.45 mmol) in dioxane (1 mL) was added methyl[2-(methylamino)ethyl]amine (39.92 mg, 0.45 mmol) and 4-bromo-1-(tert-butyl)-5-fluoro-1H-pyrazole (200.24 mg, 0.90 mmol) at room temperature. The reaction mixture was allowed to stir for 16 h at 100° C. The resulting mixture was concentrated in vacuo and the residue purified by Prep-TLC (PE/EA, 1:3) to afford the crude product. The crude product (80 mg) was purified by Prep-HPLC with the following conditions: Column: XBridge Prep OBD C18 Column, 30×150 mm, 5 m; Mobile Phase A: water (Plus 10 mmol/L NH₄HCO₃), Mobile Phase B: ACN; Flow rate: 60 mL/min; Gradient: 50% B to 80% B in 7 min; Wave Length: 254 nm/220 nm; RT1: 6.1 min. The fractions containing the desired product were combined and concentrated to afford the title compound (8.6 mg, 7%) as a white solid. MS ESI calculated for C₂₈H₃₃F₂N₇O₂[M+H]⁺, 538.27, found 538.45; ¹H NMR (400 MHz, Chloroform-d) δ 8.25 (d, J=15.6 Hz, 1H), 8.13-8.07 (m, 3H), 7.17 (d, J=12.8 Hz, 1H), 6.55 (d, J=1.4 Hz, 1H), 4.01-3.98 (m, 4H), 3.62-3.59 (m, 4H), 3.31-3.27 (m, 1H), 2.38 (s, 3H), 1.57 (s, 9H), 1.47 (d, J=7.0 Hz, 6H).

Example 309: N-(1-(tert-Butyl)-5-fluoro-1H-pyrazol-4-yl)-5-(2-(dimethylamino)-8-morpholino-[1,2,4]triazolo[1,5-a]pyridin-6-yl)-2-fluoro-4-methylbenzamide

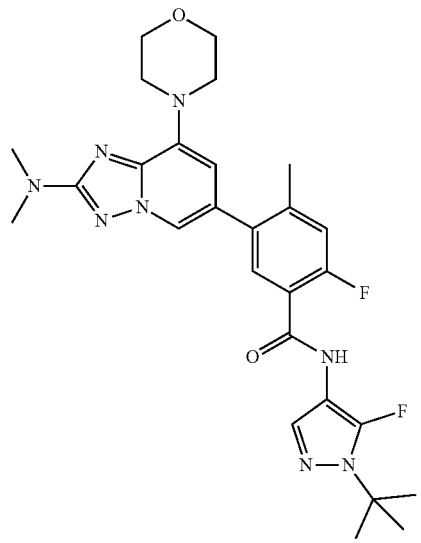 [SMILES: Cc1cc(F)c(C(=O)Nc2cnn(C(C)(C)C)c2F)cc1-c1cc(N2CCOCC2)c2nc(N(C)C)nn2c1]

Step 1: To a stirred solution of methyl 5-[2-amino-8-(morpholin-4-yl)-[1,2,4]triazolo[1,5-a]pyridin-6-yl]-2-fluoro-4-methylbenzoate (300 mg, 0.78 mmol) in DMF (15 mL) was added NaH (93.40 mg, 2.33 mmol, 60%) in portions at 0° C. under nitrogen atmosphere. The reaction mixture was allowed to stir for 30 min at room temperature under nitrogen atmosphere. To the above mixture was added CH₃I (441.95 mg, 3.11 mmol) dropwise at 0° C. The reaction mixture was allowed to stir for additional 1 h at room temperature. The resulting mixture was quenched with sat. NH₄Cl (aq.) at room temperature and diluted with water (30 mL) and extracted with EtOAc (3×50 mL). The combined organic layers were washed with brine (2×30 mL), dried over anhydrous Na₂SO₄. The residue was purified by silica gel column chromatography (PE/EA, 2:1). The residue was purified by reversed-phase flash chromatography with the following conditions: column, C18 silica gel; mobile phase, MeCN in water (Plus 10 mmol/L NH₄HCO₃), 25% to 55% gradient in 30 min; detector, UV 254 nm. The fractions containing the desired product were combined and concentrated to afford methyl 5-[2-(dimethylamino)-8-(morpholin-4-yl)-[1,2,4]triazolo[1,5-a]pyridin-6-yl]-2-fluoro-4-methylbenzoate (150 mg, 46%) as a white solid. MS ESI calculated for C₂₁H₂₄FN₅O₃[M+H]⁺, 414.19, found 414.35; ¹H NMR (400 MHz, DMSO-d4) δ 8.27-8.24 (m, 1H), 7.76 (d, J=7.5 Hz, 1H), 7.37 (d, J=11.9 Hz, 1H), 6.64-6.60 (m, 1H), 3.85 (s, 3H), 3.79 (t, J=4.6 Hz, 4H), 3.48 (t, J=4.6 Hz, 4H), 3.03 (s, 6H), 2.33 (s, 3H).

Step 2: To a stirred solution of methyl 5-[2-(dimethylamino)-8-(morpholin-4-yl)-[1,2,4]triazolo[1,5-a]pyridin-6-yl]-2-fluoro-4-methylbenzoate (120 mg, 0.29 mmol) in THF (1.2 mL) and MeOH (1.2 mL) was added NaOH (58.04 mg, 1.45 mmol) in H$_2$O (1.2 mL) dropwise at room temperature. The reaction mixture was allowed to stir for 16 h at room temperature. The resulting mixture was concentrated in vacuo to afford 5-[2-(dimethylamino)-8-(morpholin-4-yl)-[1,2,4]triazolo[1,5-a]pyridin-6-yl]-2-fluoro-4-methylbenzoic acid (210 mg, crude) as a white solid. MS ESI calculated for C$_{20}$H$_{22}$FN$_5$O$_3$[M+H]$^+$, 400.17, found 400.25.

Step 3: To a stirred solution of 5-[2-(dimethylamino)-8-(morpholin-4-yl)-[1,2,4]triazolo[1,5-a]pyridin-6-yl]-2-fluoro-4-methylbenzoic acid (180 mg, 0.32 mmol, 70%), EDCI (90.71 mg, 0.47 mmol), HOBT (63.94 mg, 0.47 mmol) and NH$_4$Cl (84.37 mg, 1.58 mmol) in DMF (3.6 mL) was added DIEA (0.55 mL, 3.15 mmol) dropwise at room temperature. The reaction mixture was allowed to stir for 2 h at 50° C. The resulting mixture was diluted with water (30 mL) and extracted with EtOAc (3×50 mL). The combined organic layers were washed with brine (2×30 mL), dried over anhydrous Na$_2$SO$_4$. The residue was purified by silica gel column chromatography (PE/EA, 1:2). The fractions containing the desired product were combined and concentrated to afford 5-[2-(dimethylamino)-8-(morpholin-4-yl)-[1,2,4]triazolo[1,5-a]pyridin-6-yl]-2-fluoro-4-methylbenzamide (75 mg, 59%) as a white solid. MS ESI calculated for C$_{20}$H$_{23}$FN$_6$O$_2$[M+H]$^+$, 399.19, found 399.35; $^1$H NMR (400 MHz, Chloroform-d) δ 8.03 (d, J=8.2 Hz, 1H), 7.92 (d, J=1.6 Hz, 1H), 7.08 (d, J=12.6 Hz, 1H), 6.49 (d, J=1.7 Hz, 1H), 3.96 (t, J=4.7 Hz, 4H), 3.51 (t, J=4.7 Hz, 4H), 3.14 (s, 6H), 2.33 (s, 3H).

Step 4: To a stirred solution of 5-[2-(dimethylamino)-8-(morpholin-4-yl)-[1,2,4]triazolo[1,5-a]pyridin-6-yl]-2-fluoro-4-methylbenzamide (75 mg, 0.19 mmol), methyl[2-(methylamino)ethyl]amine (16.59 mg, 0.19 mmol), K$_3$PO$_4$ (83.91 mg, 0.40 mmol) and CuI (35.85 mg, 0.19 mmol) in dioxane (1 mL) was added 4-bromo-1-(tert-butyl)-5-fluoro-1H-pyrazole (62.42 mg, 0.28 mmol) dropwise at room temperature. The reaction mixture was purged with nitrogen three times and stirred for 16 h at 100° C. The resulting mixture was concentrated in vacuo and the residue purified by Prep-TLC (PE/EA, 1:9) to afford the crude product. The crude product was purified by Prep-HPLC with the following conditions: Column: XBridge Prep OBD C18 Column, 30×150 mm, 5 m; Mobile Phase A: water (Plus 10 mmol/L NH$_4$HCO$_3$), Mobile Phase B: ACN; Flow rate: 60 mL/min; Gradient: 37% B to 67% B in 7 min; Wave Length: 254 nm/220 nm. The fractions containing the desired product were combined and concentrated to afford the title compound (30.6 mg, 30%) as a white solid. MS ESI calculated for C$_{27}$H$_{32}$F$_2$N$_8$O$_2$[M+H]$^+$, 539.26, found 539.45; $^1$H NMR (400 MHz, DMSO-d$_6$) δ 9.91 (s, 1H), 8.30-8.28 (m, 1H), 7.60 (d, J=7.4 Hz, 1H), 7.57 (d, J=2.3 Hz, 1H), 7.33 (d, J=11.3 Hz, 1H), 6.67-6.65 (m, 1H), 3.80 (t, J=4.6 Hz, 4H), 3.49 (t, J=4.6 Hz, 4H), 3.03 (s, 6H), 2.35 (s, 3H), 1.54 (s, 9H).

Example 310: 2-Fluoro-N-[3-fluoro-1-(1-methylcyclopropyl)pyrazol-4-yl]-4-methyl-5-[2-methyl-8-(morpholin-4-yl)-[1,2,4]triazolo[1,5-a]pyridin-6-yl]benzamide

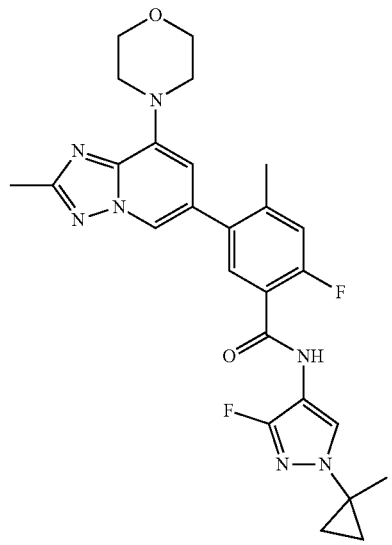

Step 1: To a stirred solution of 4-bromo-3-fluoro-1H-pyrazole (1 g, 6.06 mmol), Cu(OAc)$_2$ (1.10 g, 6.06 mmol) and Na$_2$CO$_3$ (1.28 g, 12.12 mmol) in DCE (20 mL) was added 2,2'-bipyridine (0.95 g, 6.06 mmol) at room temperature. The reaction mixture was purged with oxygen for three times. To the above mixture was added 4,4,5,5-tetramethyl-2-(prop-1-en-2-yl)-1,3,2-dioxaborolane (2.04 g, 12.12 mmol) in DCE (6 mL) dropwise at room temperature. The resulting mixture was allowed to stir for 16 h at 70° C. The resulting mixture was quenched with saturated aqueous NH$_4$Cl (100 mL) and extracted with EA (3×70 mL). The combined organic layers were washed with brine (50 mL), dried over anhydrous Na$_2$SO$_4$ and filtered. The filtrate was concentrated in vacuo and the residue purified by silica gel column chromatography (PE/DCM, 1:1). The fractions containing the desired product were combined and concentrated to afford 4-bromo-3-fluoro-1-(prop-1-en-2-yl)pyrazole (850 mg, 68%) as a light yellow oil. MS ESI calculated for C$_6$H$_6$BrFN$_2$ [M+H]$^+$, 204.97, 206.97, found 204.95, 206.95; $^1$H NMR (400 MHz, Chloroform-d) δ 7.55 (d, J=2.0 Hz, 1H), 5.28-5.26 (m, 1H), 4.70-4.68 (m, 1H), 2.19 (s, 3H).

Step 2: To a stirred solution of 4-bromo-3-fluoro-1-(prop-1-en-2-yl)pyrazole (850 mg, 4.15 mmol) in DCM (10 mL) was added diethylzinc (12.5 mL, 12.44 mmol) (1 M in THF) dropwise at 0° C. The reaction mixture was purged with nitrogen three times and stirred for 0.5 h at 0° C. To the above mixture was added CH$_2$I$_2$(5.55 g, 20.73 mmol) dropwise at 0° C. The reaction mixture was allowed to stir for additional 16 h at room temperature. The resulting mixture was quenched with saturated aqueous NH$_4$Cl (100 mL) and extracted with dichloromethane (3×100 mL). The combined organic layers were washed with brine (50 mL), dried over anhydrous Na$_2$SO$_4$ and filtered. The filtrate was concentrated in vacuo and the residue purified by silica gel column chromatography (PE/DCM, 2:1) (detector: UV 227 nm). The fractions containing the desired product were combined and concentrated to afford 4-bromo-3-fluoro-1-(1-methylcyclopropyl)pyrazole (100 mg, 11%) as a light yellow oil.

MS ESI calculated for $C_7H_8BrFN_2$ [M+H]$^+$, 218.99, 220.99, found 219.00, 221.00; $^1$H NMR (400 MHz, Chloroform-d) δ 7.34 (d, J=2.0 Hz, 1H), 1.56 (s, 3H), 1.21-1.18 (m, 2H), 0.86-0.85 (m, 2H).

Step 3: To a stirred mixture of 2-fluoro-4-methyl-5-[2-methyl-8-(morpholin-4-yl)-[1,2,4]triazolo[1,5-a]pyridin-6-yl]benzamide (110 mg, 0.30 mmol) and CuI (57 mg, 0.30 mmol) in dioxane (3 mL) were added $K_3PO_4$ (139 mg, 0.66 mmol), methyl[2-(methylamino)ethyl]amine (26 mg, 0.30 mmol) and 4-bromo-3-fluoro-1-(1-methylcyclopropyl)pyrazole (78 mg, 0.36 mmol) at room temperature. The reaction mixture was purged with nitrogen three times and stirred for additional 16 h at 100° C. The resulting mixture was diluted with water (30 mL) and extracted with ea (3×50 mL). The combined organic layers were washed with saturated brine (2×30 mL), dried over anhydrous $Na_2SO_4$ and filtered. The filtrate was concentrated in vacuo and the residue purified by Prep-TLC (DCM/MeOH, 20:1) to afford the crude product. The crude product was purified by reverse flash chromatography with the following conditions: column, C18 silica gel; mobile phase, ACN in water (Plus 10 mmol/L $NH_4HCO_3$), 20% to 60% gradient in 20 min; detector, UV 254 nm. The fractions containing the desired product were combined and concentrated to afford the title compound (47.1 mg, 31%) as an off-white solid. MS ESI calculated for $C_{26}H_{27}F_2N_7O_2$ [M+H]$^+$, 508.22, found 508.35; $^1$H NMR (400 MHz, Chloroform-d) δ 8.25 (d, J=15.6 Hz, 1H), 8.10-8.07 (m, 3H), 7.18 (d, J=12.8 Hz, 1H), 7.65 (s, 1H), 4.02-4.00 (m, 4H), 3.57-3.55 (m, 4H), 2.68 (s, 3H), 2.38 (s, 3H), 1.60 (s, 3H), 1.27-1.24 (m, 2H), 0.91-0.88 (m, 2H).

The following compounds in Table 8 were prepared using procedures similar to those described above using appropriate starting materials.

TABLE 8

| Ex. | Compound Name | Exact Mass [M + H]$^+$ | Chiral separation conditions |
|---|---|---|---|
| 37 | N-(3-(8-Hydroxy-8-methyl-4-morpholino-6,7,8,9-tetrahydrobenzo[4,5]imidazo[1,2-a]pyridin-2-yl)-4-methylphenyl)-2-(trifluoromethyl)isonicotinamide | Calc'd 566.23, found 566.10 | |
| 39 | 2-Tert-butyl-N-{2-fluoro-4-methyl-5-[8-(morpholin-4-yl)imidazo[1,2-a]pyridin-6-yl]phenyl}pyridine-4-carboxamide | Calc'd 488.24, found 488.20 | |
| 40 | (S)-N-(2-Fluoro-4-methyl-5-(3-methyl-8-morpholinoimidazo[1,2-a]pyridin-6-yl)phenyl)-3-(2,2,2-trifluoroethyl)pyrrolidine-1-carboxamide | Calc'd 520.23, found 520.20 | |
| 41 | N-(2-Fluoro-4-methyl-5-(8-morpholinoimidazo[1,2-a]pyridin-6-yl)phenyl)-2-(trifluoromethyl)isonicotinamide | Calc'd 500.16, found 500.20 | |
| 42 | N-(2-Fluoro-4-methyl-5-(2-methyl-8-morpholinoimidazo[1,2-a]pyridin-6-yl)phenyl)-2-(trifluoromethyl)isonicotinamide | Calc'd 514.18, found 514.30 | |
| 44 | (S)-N-(2-Fluoro-4-methyl-5-(6-morpholino-3,4-dihydro-1H-pyrano[4',3':4,5]imidazo[1,2-a]pyridin-8-yl)phenyl)-3-(2,2,2-trifluoroethyl)pyrrolidine-1-carboxamide | Calc'd 562.24, found 562.35 | |
| 45 | (S)-N-(2-Fluoro-5-(2-(2-methoxyethyl)-8-morpholinoimidazo[1,2-a]pyridin-6-yl)-4-methylphenyl)-3-(2,2,2-trifluoroethyl)pyrrolidine-1-carboxamide | Calc'd 564.25, found 564.25 | |
| 47 | (S)-N-(2-Fluoro-4-methyl-5-(8-morpholinoimidazo[1,2-a]pyridin-6-yl)phenyl)-1-(2,2,2-trifluoroethyl)pyrrolidine-3-carboxamide | Calc'd 506.21, found 506.20 | CHIRALPAK IG, Hex (0.5% 2M $NH_3$—MeOH)/ (MeOH:DCM = 1:1) = 80/20, 2$^{ed}$ peak |
| 48 | N-(2-Fluoro-4-methyl-5-(6-morpholino-3,4-dihydro-1H-pyrano[4',3':4,5]imidazo[1,2-a]pyridin-8-yl)phenyl)-2-(trifluoromethyl)isonicotinamide | Calc'd 556.19, found 556.15 | |
| 49 | N-(2-Fluoro-4-methyl-5-(8-morpholinoimidazo[1,2-a]pyridin-6-yl)phenyl)-1-(2,2,2-trifluoroethyl)-1H-pyrrole-3-carboxamide | Calc'd 502.18, found 502.10 | |
| 51 | 2-(tert-Butyl)-N-(2-fluoro-4-methyl-5-(8-morpholinoimidazo[1,2-a]pyridin-6-yl)phenyl)morpholine-4-carboxamide | Calc'd 496.26, found 496.25 | CHIRAL ART Amylose-SA, Hex (0.5% 2M $NH_3$—MeOH)/ (MeOH:DCM = 1:1) = 80/20, 2$^{ed}$ peak |
| 52 | 1-(3,3-Dimethylbutyl)-3-(2-fluoro-4-methyl-5-(8-morpholinoimidazo[1,2-a]pyridin-6-yl)phenyl)-1-methylurea | Calc'd 468.27, found 468.25 | |
| 53 | (S)-N-(2-Fluoro-4-methyl-5-(9-morpholino-3,4-dihydro-1H-pyrano[3',4':4,5]imidazo[1,2-a]pyridin-7-yl)phenyl)-3-(2,2,2-trifluoroethyl)pyrrolidine-1-carboxamide | Calc'd 562.24, found 562.30 | |

TABLE 8-continued

| Ex. | Compound Name | Exact Mass [M + H]⁺ | Chiral separation conditions |
|---|---|---|---|
| 54 | 1-(Tert-butyl)-N-(2-fluoro-4-methyl-5-(8-morpholinoimidazo[1,2-a]pyridin-6-yl)phenyl)-1H-pyrazole-4-carboxamide | Calc'd 477.23, found 477.25 | |
| 55 | N-(2-Fluoro-4-methyl-5-(8-morpholinoimidazo[1,2-a]pyridin-6-yl)phenyl)-1-isopropyl-1H-pyrrole-3-carboxamide | Calc'd 462.22, found 462.25 | |
| 56 | 1-Cyclopropyl-N-(2-fluoro-4-methyl-5-(8-morpholinoimidazo[1,2-a]pyridin-6-yl)phenyl)-1H-pyrrole-3-carboxamide | Calc'd 460.21, found 460.20 | |
| 57 | 1-(Tert-butyl)-N-(2-fluoro-4-methyl-5-(2-methyl-8-morpholinoimidazo[1,2-a]pyridin-6-yl)phenyl)-1H-pyrrole-3-carboxamide | Calc'd 490.25, found 490.25 | |
| 58 | N-(2-Fluoro-4-methyl-5-(8-morpholinoimidazo[1,2-a]pyridin-6-yl)phenyl)-2-(1,1,1-trifluoro-2-methylpropan-2-yl)isonicotinamide | Calc'd 542.21, found 542.25 | |
| 59 | N-(2-Fluoro-4-methyl-5-(8-morpholinoimidazo[1,2-a]pyridin-6-yl)phenyl)-2-(1,1,1-trifluoropropan-2-yl)isonicotinamide | Calc'd 528.19, found 528.20 | |
| 60 | 2-Fluoro-4-methyl-5-(8-morpholinoimidazo[1,2-a]pyridin-6-yl)phenyl 2-(1-(trifluoromethyl)cyclopropyl)isonicotinate | Calc'd 540.53, found 540.20 | |
| 63 | N-(2-Fluoro-4-methyl-5-(8-morpholinoimidazo[1,2-a]pyridin-6-yl)phenyl)-1-(1-methylcyclopropyl)-1H-pyrazole-4-carboxamide | Calc'd 475.22, found 475.20 | |
| 64 | (S)-N-(5-(2-(2,2-Difluoroethyl)-8-morpholinoimidazo[1,2-a]pyridin-6-yl)-2-fluoro-4-methylphenyl)-3-(2,2,2-trifluoroethyl)pyrrolidine-1-carboxamide | Calc'd 570.22, found 570.30 | |
| 65 | N-(2-Fluoro-4-methyl-5-(8-morpholinoimidazo[1,2-a]pyridin-6-yl)phenyl)-1-(trifluoromethyl)-1H-pyrrole-3-carboxamide | Calc'd 488.16, found 488.20 | |
| 68 | (S)-N-(5-(2-(1,1-Difluoroethyl)-8-morpholinoimidazo[1,2-a]pyridin-6-yl)-2-fluoro-4-methylphenyl)-3-(2,2,2-trifluoroethyl)pyrrolidine-1-carboxamide | Calc'd 570.22, found 570.30 | |
| 71 | N-(2-fluoro-4-methyl-5-(8-morpholinoimidazo[1,2-a]pyridin-6-yl)phenyl)-1-(1,1,1-trifluoropropan-2-yl)-1H-pyrazole-4-carboxamide | Calc'd 516.50, found 517.20 | CHIRAL ART Cellulose-SB, Hex (0.5% 2M NH₃—MeOH)/(EtOH/DCM = 1/1) = 70/30, 1ˢᵗ peak |
| 72 | N-(2-fluoro-4-methyl-5-(8-morpholinoimidazo[1,2-a]pyridin-6-yl)phenyl)-1-(1,1,1-trifluoropropan-2-yl)-1H-pyrazole-4-carboxamide | Calc'd 516.50, found 517.20 | CHIRAL ART Cellulose-SB, Hex (0.5% 2M NH₃—MeOH)/(EtOH/DCM = 1/1) = 70/30, 2ᵉᵈ peak |
| 76 | N-(1-(tert-Butyl)-3-fluoro-1H-pyrazol-4-yl)-5-(2-ethyl-5-morpholino-[1,2,4]triazolo[1,5-a]pyridin-7-yl)-2-fluoro-4-methylbenzamide | Calc'd 524.25, found 524.45 | |
| 77 | (R)-N-(2-Fluoro-4-methyl-5-(8-morpholinoimidazo[1,2-a]pyridin-6-yl)phenyl)-3-isopropylpyrrolidine-1-carboxamide | Calc'd 466.57, found, 466.30 | |
| 78 | (S)-N-(2-Fluoro-4-methyl-5-(8-morpholinoimidazo[1,2-a]pyridin-6-yl)phenyl)-3-isopropylpyrrolidine-1-carboxamide | Calc'd 466.25, found 466.20 | |
| 79 | 3-(tert-butyl)-N-(2-fluoro-4-methyl-5-(8-morpholinoimidazo[1,2-a]pyridin-6-yl)phenyl)pyrrolidine-1-carboxamide | Calc'd 480.27, found 480.30 | CHIRALPAK IG, 2 × 25 cm, 5 µm, Hex (0.5% 2M NH₃—MeOH)/(EtOH:DCM = 1:1) = 85/15, 1ˢᵗ peak |
| 80 | 3-(tert-butyl)-N-(2-fluoro-4-methyl-5-(8-morpholinoimidazo[1,2-a]pyridin-6-yl)phenyl)pyrrolidine-1-carboxamide | Calc'd 480.27, found 480.30 | CHIRALPAK IG, 2 × 25 cm, 5 µm, Hex (0.5% 2M NH₃—MeOH)/(EtOH:DCM = 1:1) = 85/15, 2ᵉᵈ peak |

TABLE 8-continued

| Ex. | Compound Name | Exact Mass [M + H]+ | Chiral separation conditions |
|---|---|---|---|
| 81 | N-(2-fluoro-4-methyl-5-(8-morpholinoimidazo[1,2-a]pyridin-6-yl)phenyl)-3-(1,1,1-trifluoropropan-2-yl)pyrrolidine-1-carboxamide | Calc'd 519.23, found 520.30 | CHIRAL ART Cellulose-SB, Hex (0.5% 2M NH$_3$—MeOH)/ (EtOH:DCM = 1:1) = 70/30, 1$^{st}$ peak |
| 82 | N-(2-fluoro-4-methyl-5-(8-morpholinoimidazo[1,2-a]pyridin-6-yl)phenyl)-3-(1,1,1-trifluoropropan-2-yl)pyrrolidine-1-carboxamide | Calc'd 519.23, found 520.30 | CHIRAL ART Cellulose-SB, Hex (0.5% 2M NH$_3$—MeOH)/ (EtOH:DCM = 1:1) = 70/30, 2$^{ed}$ peak |
| 83 | 1-(Tert-butyl)-N-(4-methyl-3-(8-morpholinoimidazo[1,2-a]pyridin-6-yl)phenyl)-1H-imidazole-4-carboxamide | Calc'd 459.56, found 459.25 | |
| 85 | N-(2-Fluoro-4-methyl-5-(8-morpholinoimidazo[1,2-a]pyridin-6-yl)phenyl)-5-(2-fluoropropan-2-yl)nicotinamide | Calc'd 492.21, found 492.20 | |
| 93 | 3-fluoro-N-(2-fluoro-4-methyl-5-(8-morpholinoimidazo[1,2-a]pyridin-6-yl)phenyl)-3-(2-fluoropropan-2-yl)pyrrolidine-1-carboxamide | Calc'd 502.24, Found 502.25 | CHIRALPAK IH, Hex (0.5% 2M NH$_3$—MeOH)/ (MeOH:DCM = 1:1) = 85/15, 1$^{st}$ peak |
| 94 | 1-(Tert-butyl)-N-(2-fluoro-5-(3-fluoro-8-morpholinoimidazo[1,2-a]pyridin-6-yl)-4-methylphenyl)-1H-pyrrole-3-carboxamide | Calc'd 494.23 Found 494.30 | |
| 96 | 1-(Tert-butyl)-2-fluoro-N-(2-fluoro-4-methyl-5-(8-morpholinoimidazo[1,2-a]pyridin-6-yl)phenyl)-1H-pyrrole-3-carboxamide | Calc'd 494.23, found 494.25 | |
| 97 | 1-(Tert-butyl)-2-fluoro-N-(2-fluoro-4-methyl-5-(8-morpholinoimidazo[1,2-a]pyridin-6-yl)phenyl)-1H-pyrrole-3-carboxamide | Calc'd 526.16, found 526.10 | |
| 100 | (S)-N-(2-fluoro-4-methyl-5-(8-morpholinoimidazo[1,2-a]pyridin-6-yl)phenyl)-3-(2,2,2-trifluoroethyl)pyrrolidine-1-carboxamide | Calc'd 506.2 found 506.2 | |
| 101 | N-(2-fluoro-5-(3-fluoro-8-morpholinoimidazo[1,2-a]pyridin-6-yl)-4-methylphenyl)-3-(1,1,1-trifluoro-2-methylpropan-2-yl)pyrrolidine-1-carboxamide | Calc'd 552.52, found 552.25 | CHIRAL ART Cellulose-SB, Hex (0.5% 2M NH$_3$—MeOH)/ (IPA:DCM = 1:1) = 80/20, 2$^{ed}$ peak |
| 102 | N-(2-fluoro-5-(3-fluoro-8-morpholinoimidazo[1,2-a]pyridin-6-yl)-4-methylphenyl)-3-(1,1,1-trifluoro-2-methylpropan-2-yl)pyrrolidine-1-carboxamide | Calc'd 552.52, found 552.25 | CHIRAL ART Cellulose-SB, Hex (0.5% 2M NH$_3$—MeOH)/ (IPA:DCM = 1:1) = 80/20, 1$^{st}$ peak |
| 104 | (S)-N-(4-Chloro-3-(8-morpholinoimidazo[1,2-a]pyridin-6-yl)phenyl)-3-(2,2,2-trifluoroethyl)pyrrolidine-1-carboxamide | Calc'd 508.16 found 508.30 | |
| 105 | 1-(Tert-butyl)-N-(2,4-difluoro-5-(8-morpholinoimidazo[1,2-a]pyridin-6-yl)phenyl)-5-fluoro-1H-pyrazole-4-carboxamide | Calc'd 499.20, found 499.30 | |
| 106 | 1-(Tert-butyl)-5-fluoro-N-(4-fluoro-3-(8-morpholinoimidazo[1,2-a]pyridin-6-yl)phenyl)-1H-pyrazole-4-carboxamide | Calc'd 481.21, found 481.30 | |
| 107 | N-(2-fluoro-5-(3-fluoro-8-morpholinoimidazo[1,2-a]pyridin-6-yl)-4-methylphenyl)-3-(1-methylcyclopropyl)pyrrolidine-1-carboxamide | Calc'd 496.24, found 496.25 | CHIRAL ART Amylose-SA, Hex (0.5% 2M NH$_3$—MeOH)/ (EtOH:DCM = 1:1) = 80/20, 1$^{st}$ peak |
| 108 | N-(2-fluoro-5-(3-fluoro-8-morpholinoimidazo[1,2-a]pyridin-6-yl)-4-methylphenyl)-3-(1-methylcyclopropyl)pyrrolidine-1-carboxamide | Calc'd 496.24, found 496.25 | CHIRAL ART Amylose-SA, Hex (0.5% 2M NH$_3$—MeOH)/ (EtOH:DCM = 1:1) = 80/20, 2$^{ed}$ peak |
| 109 | 1-(1,1-Difluoropropan-2-yl)-N-(2-fluoro-4-methyl-5-(8-morpholinoimidazo[1,2-a]pyridin-6-yl)phenyl)-1H-pyrazole-4-carboxamide | Calc'd 499.20, found 499.10 | |

TABLE 8-continued

| Ex. | Compound Name | Exact Mass [M + H]+ | Chiral separation conditions |
|---|---|---|---|
| 115 | 1-(Tert-butyl)-N-(4-chloro-3-(8-morpholinoimidazo[1,2-a]pyridin-6-yl)phenyl)-3-fluoro-1H-pyrazole-4-carboxamide | Calc'd 497.18, found 497.20 | |
| 116 | 1-(Tert-butyl)-N-(2-fluoro-4-methyl-5-(8-morpholinoimidazo[1,2-a]pyridin-6-yl)phenyl)-2-methyl-1H-imidazole-4-carboxamide | Calc'd 491.25, found 491.25 | |
| 117 | 1-(Tert-butyl)-N-(4-methyl-3-(8-morpholinoimidazo[1,2-a]pyridin-6-yl)phenyl)-1H-imidazole-4-carboxamide | Calc'd 459.56, found 459.25 | |
| 126 | 1-(Tert-butyl)-5-fluoro-N-(3-(3-fluoro-8-morpholinoimidazo[1,2-a]pyridin-6-yl)-4-methylphenyl)-1H-pyrazole-4-carboxamide | Calc'd 494.54, found 495.25 | |
| 127 | 1-(Tert-butyl)-3-fluoro-N-(3-(3-fluoro-8-morpholinoimidazo[1,2-a]pyridin-6-yl)-4-methylphenyl)-1H-pyrazole-4-carboxamide | Calc'd 494.54, found 495.25 | |
| 128 | 1-(Tert-butyl)-3-fluoro-N-(2-fluoro-5-(3-fluoro-8-morpholinoimidazo[1,2-a]pyridin-6-yl)-4-methylphenyl)-1H-pyrazole-4-carboxamide | Calc'd 513.21, found 513.30 | |
| 129 | 2-(Tert-butyl)-N-(2-fluoro-4-methyl-5-(8-morpholinoimidazo[1,2-a]pyridin-6-yl)phenyl)thiazole-5-carboxamide | Calc'd 494.19, found 494.15 | |
| 130 | 2-(Tert-butyl)-N-(4-methyl-3-(8-morpholinoimidazo[1,2-a]pyridin-6-yl)phenyl)thiazole-5-carboxamide | Calc'd 476.20, found 476.10 | |
| 131 | 1-(Tert-butyl)-N-(2-fluoro-4-methyl-5-(8-morpholinoimidazo[1,2-a]pyridin-6-yl)phenyl)-1H-pyrazole-3-carboxamide | Calc'd 477.23, found 477.15 | |
| 132 | 3-(Tert-butyl)-N-(2-fluoro-4-methyl-5-(8-morpholinoimidazo[1,2-a]pyridin-6-yl)phenyl)-1,2,4-oxadiazole-5-carboxamide | Calc'd 479.21, found 479.15 | |
| 133 | 3-(Tert-butyl)-N-(4-methyl-3-(8-morpholinoimidazo[1,2-a]pyridin-6-yl)phenyl)-1,2,4-oxadiazole-5-carboxamide | Calc'd 461.22, found 461.15 | |
| 134 | 1-(Tert-butyl)-N-(4-methyl-3-(8-morpholinoimidazo[1,2-a]pyridin-6-yl)phenyl)-1H-pyrazole-3-carboxamide | Calc'd 459.24, found 459.15 | |
| 135 | 3-(1-Cyclopropylethyl)-N-(2-fluoro-4-methyl-5-(8-morpholinoimidazo[1,2-a]pyridin-6-yl)phenyl)pyrrolidine-1-carboxamide | Calc'd 492.27, found 492.30 | |
| 138 | 1-Tert-butyl-5-fluoro-N-{6-methyl-5-[8-(morpholin-4-yl)imidazo[1,2-a]pyridin-6-yl]pyridin-3-yl}pyrazole-4-carboxamide | Calc'd 478.23, found 478.20 | |
| 144 | 1-(Tert-butyl)-5-fluoro-N-(3-fluoro-4-methyl-5-(8-morpholinoimidazo[1,2-a]pyridin-6-yl)phenyl)-lH-pyrazole-4-carboxamide | Calc'd 495.22, found 495.20 | |
| 145 | 1-Tert-butyl-N-{4-chloro-2-fluoro-5-[8-(morpholin-4-yl)imidazo[1,2-a]pyridin-6-yl]phenyl}imidazole-4-carboxamide | Calc'd 497.18, found 497.15 | |
| 146 | 3-(tert-Butyl)-N-(2-fluoro-4-methyl-5-(8-morpholinoimidazo[1,2-a]pyridin-6-yl)phenyl)cyclopentane-1-carboxamide | Calc'd 479.27, found 479.25 | CHIRAL ART Cellulose-SB, Hex (0.2% DEA):(EtOH:DCM = 1:1) = 85/15, 1st peak |
| 147 | 3-(tert-Butyl)-N-(2-fluoro-4-methyl-5-(8-morpholinoimidazo[1,2-a]pyridin-6-yl)phenyl)cyclopentane-1-carboxamide | Calc'd 479.27, found 479.25 | CHIRAL ART Cellulose-SB, Hex (0.2% DEA):(EtOH:DCM = 1:1) = 85/15, 2ed peak |

TABLE 8-continued

| Ex. Compound Name | Exact Mass [M + H]+ | Chiral separation conditions |
|---|---|---|
| 149 1-Tert-butyl-5-fluoro-N-{2-fluoro-4-methyl-3-[8-(morpholin-4-yl)imidazo[1,2-a]pyridin-6-yl]phenyl}pyrazole-4-carboxamide | Calc'd 495.22, found 495.15 | |
| 150 1-(Tert-butyl)-N-(4-chloro-3-fluoro-5-(8-morpholinoimidazo[1,2-a]pyridin-6-yl)phenyl)-5-fluoro-1H-pyrazole-4-carboxamide | Calc'd 515.17, found 515.25 | |
| 152 (3S)-N-{2-fluoro-4-methyl-5-[7-(morpholin-4-yl)pyrazolo[1,5-a]pyridin-5-yl]phenyl}-3-(2,2,2-trifluoroethyl)pyrrolidine-1-carboxamide | Calc'd 506.21, found 506.15 | |
| 154 N-(2-Fluoro-4-methyl-5-(8-morpholinoimidazo[1,2-a]pyridin-6-yl)phenyl)-4,5,6,7-tetrahydropyrazolo[1,5-a]pyridine-3-carboxamide | Calc'd 475.22, found 475.10 | |
| 155 N-(2-fluoro-4-methyl-5-(8-morpholinoimidazo[1,2-a]pyridin-6-yl)phenyl)-5,6-dihydro-4H-pyrrolo[1,2-b]pyrazole-3-carboxamide | Calc'd 461.20, found 461.20 | |
| 156 N-(2-fluoro-4-methyl-5-(8-morpholinoimidazo[1,2-a]pyridin-6-yl)phenyl)-1-methyl-1H-pyrrolo[2,3-b]pyridine-4-carboxamide | Calc'd 485.20, found 485.15 | |
| 157 2-Tert-butyl-N-{2-fluoro-4-methyl-5-[8-(morpholin-4-yl)imidazo[1,2-a]pyridin-6-yl]phenyl}-1,3-thiazole-5-carboxamide | Calc'd 494.19, found 494.15 | |
| 158 2-Tert-butyl-N-{4-methyl-3-[8-(morpholin-4-yl)imidazo[1,2-a]pyridin-6-yl]phenyl}-1,3-thiazole-5-carboxamide | Calc'd 476.20, found 476.10 | |
| 161 1-(Tert-butyl)-5-fluoro-N-(4-methyl-3-(8-morpholinoimidazo[1,2-a]pyridin-6-yl)phenyl)-1H-imidazole-4-carboxamide | Calc'd 477.23, found 477.20 | |
| 165 2-Tert-butyl-N-{2-fluoro-4-methyl-5-[8-(morpholin-4-yl)imidazo[1,2-a]pyridin-6-yl]phenyl}-1,2,3,4-tetrazole-5-carboxamide | Calc'd 479.22, found 479.15 | |
| 167 2-(Dimethylamino)-N-{2-fluoro-4-methyl-5-[8-(morpholin-4-yl)imidazo[1,2-a]pyridin-6-yl]phenyl}pyridine-4-carboxamide | Calc'd 475.22, found 475.20 | |
| 168 N-(5-(8-(2-oxa-6-azaspiro[3.3]heptan-6-yl)imidazo[1,2-a]pyridin-6-yl)-2-fluoro-4-methylphenyl)-1-(tert-butyl)-5-fluoro-1H-pyrazole-4-carboxamide | Calc'd 507.22, found 507.20 | |
| 169 1-(Tert-butyl)-2-fluoro-N-(4-methyl-3-(8-morpholinoimidazo[1,2-a]pyridin-6-yl)phenyl)-1H-imidazole-4-carboxamide | Calc'd 477.23, found 477.20 | |
| 170 (3R,4S)-3-Tert-butyl-4-fluoro-N-{2-fluoro-4-methyl-5-[8-(morpholin-4-yl)imidazo[1,2-a]pyridin-6-yl]phenyl}pyrrolidine-1-carboxamide | Calc'd 498.26, found 498.30 | |
| 171 (3R,4R)-3-Tert-butyl-4-fluoro-N-{2-fluoro-4-methyl-5-[8-(morpholin-4-yl)imidazo[1,2-a]pyridin-6-yl]phenyl}pyrrolidine-1-carboxamide | Calc'd 498.26, found 498.30 | |
| 172 3-(tert-butyl)-N-(2-fluoro-4-methyl-5-(8-morpholinoimidazo[1,2-a]pyridin-6-yl)phenyl)cyclopentane-1-carboxamide | Calc'd 479.27, found 479.25 | |
| 173 N-(2-fluoro-4-methyl-5-(8-morpholinoimidazo[1,2-a]pyridin-6-yl)phenyl)-3-isopropyl-2,5-dihydro-1H-pyrrole-1-carboxamide | Calc'd 464.24, found 464.30 | |
| 174 1-Tert-butyl-N-{2,6-difluoro-4-methyl-3-[8-(morpholin-4-yl)imidazo[1,2-a]pyridin-6-yl]phenyl}-5-fluoropyrazole-4-carboxamide | Calc'd 513.21, found 513.25 | |
| 175 2-Tert-butyl-N-{4-methyl-3-[8-(morpholin-4-yl)imidazo[1,2-a]pyridin-6-yl]phenyl}-1,3-oxazole-4-carboxamide | Calc'd 460.23, found 460.20 | |

TABLE 8-continued

| Ex. | Compound Name | Exact Mass [M + H]+ | Chiral separation conditions |
|---|---|---|---|
| 176 | N-(5-(8-(6-oxabicyclo[3.1.1]heptan-3-yl)imidazo[1,2-a]pyridin-6-yl)-2-fluoro-4-methylphenyl)-1-(tert-butyl)-5-fluoro-1H-pyrazole-4-carboxamide | Calc'd 507.20, found 507.20 | |
| 177 | 1-Tert-butyl-5-fluoro-N-(2-fluoro-4-methyl-5-{8-[(1S,4S)-2-oxa-5-azabicyclo[2.2.1]heptan-5-yl]imidazo[1,2-a]pyridin-6-yl}phenyl)pyrazole-4-carboxamide | Calc'd 507.22, found 507.20 | |
| 178 | 1-Tert-butyl-5-fluoro-N-(2-fluoro-4-methyl-5-{8-[(1R,4R)-2-oxa-5-azabicyclo[2.2.1]heptan-5-yl]imidazo[1,2-a]pyridin-6-yl}phenyl)pyrazole-4-carboxamide | Calc'd 507.22, found 507.20 | |
| 179 | N-(5-(8-(3-oxa-6-azabicyclo[3.1.1]heptan-6-yl)imidazo[1,2-a]pyridin-6-yl)-2-fluoro-4-methylphenyl)-1-(tert-butyl)-5-fluoro-1H-pyrazole-4-carboxamide | Calc'd 507.22, found 507.20 | |
| 182 | 2-{2-Azabicyclo[2.1.1]hexan-2-yl}-N-{2-fluoro-4-methyl-5-[8-(morpholin-4-yl)imidazo[1,2-a]pyridin-6-yl]phenyl}pyridine-4-carboxamide | Calc'd 513.23, found 513.20 | |
| 186 | 2-(Tert-butyl)-N-(4-methyl-3-(8-morpholinoimidazo[1,2-a]pyridin-6-yl)phenyl)-2H-1,2,3-triazole-4-carboxamide | Calc'd 460.24, found 460.25 | |
| 190 | 1-Tert-butyl-N-{2-fluoro-4-methyl-5-[7-(morpholin-4-yl)pyrazolo[1,5-a]pyridin-5-yl]phenyl}imidazole-4-carboxamide | Calc'd 478.23, found 478.25 | |
| 191 | 1-(Tert-butyl)-N-(4-methyl-3-(5-morpholino-[1,2,4]triazolo[4,3-a]pyridin-7-yl)phenyl)-1H-imidazole-4-carboxamide | Calc'd 460.24, found 460.25 | |
| 192 | 1-Tert-butyl-5-fluoro-N-{2-fluoro-4-methyl-5-[5-(morpholin-4-yl)-[1,2,4]triazolo[4,3-a]pyridin-7-yl]phenyl}pyrazole-4-carboxamide | Calc'd 496.22, found 496.25 | |
| 193 | 1-Tert-butyl-N-{2-fluoro-4-methyl-5-[5-(morpholin-4-yl)-[1,2,4]triazolo[4,3-a]pyridin-7-yl]phenyl}imidazole-4-carboxamide | Calc'd 478.23, found 478.30 | |
| 194 | 1-Tert-butyl-5-fluoro-N-{2-fluoro-4-methyl-5-[4-(morpholin-4-yl)pyrazolo[1,5-a]pyridin-6-yl]phenyl}pyrazole-4-carboxamide | Calc'd 495.22, found 495.30 | |
| 195 | 1-Tert-butyl-5-fluoro-N-{4-methyl-3-[5-(morpholin-4-yl)imidazo[1,2-a]pyridin-7-yl]phenyl}pyrazole-4-carboxamide | Calc'd 477.23, found 477.30 | |
| 196 | 1-Tert-butyl-5-fluoro-N-{4-methyl-3-[5-(morpholin-4-yl)-[1,2,4]triazolo[1,5-a]pyridin-7-yl]phenyl}pyrazole-4-carboxamide | Calc'd 478.35, found 478.54 | |
| 197 | 1-Tert-butyl-3-fluoro-N-{4-methyl-3-[5-(morpholin-4-yl)-[1,2,4]triazolo[1,5-a]pyridin-7-yl]phenyl}pyrazole-4-carboxamide | Calc'd 478.35, found 478.54 | |
| 198 | 1-Tert-butyl-N-{2-fluoro-4-methyl-5-[5-(morpholin-4-yl)imidazo[1,2-a]pyridin-7-yl]phenyl}imidazole-4-carboxamide | Calc'd 478.23, found 478.15 | |
| 199 | 1-Tert-butyl-N-{4-methyl-3-[5-(morpholin-4-yl)imidazo[1,2-a]pyridin-7-yl]phenyl}imidazole-4-carboxamide | Calc'd 459.24, found 459.30 | |
| 200 | 1-(Tert-butyl)-N-(4-methyl-3-(5-morpholino-[1,2,4]triazolo[1,5-a]pyridin-7-yl)phenyl)-1H-imidazole-4-carboxamide | Calc'd 460.24, found 460.30 | |
| 201 | 1-Tert-butyl-5-fluoro-N-{4-methyl-3-[5-(morpholin-4-yl)-[1,2,4]triazolo[4,3-a]pyridin-7-yl]phenyl}pyrazole-4-carboxamide | Calc'd 478.23, found 478.40 | |
| 202 | (3R)-N-{2-fluoro-4-methyl-5-[8-(morpholin-4-yl)imidazo[1,2-a]pyridin-6-yl]phenyl}-1-isopropylpyrrolidine-3-carboxamide | Calc'd 466.30, found 466.57 | CHIRALPAK IG, Hex:DCM = 3:1 (0.5% 2M NH3—MeOH)/ IPA = 80/20, 1st peak |

TABLE 8-continued

| Ex. Compound Name | Exact Mass [M + H]+ | Chiral separation conditions |
|---|---|---|
| 203 (3S)-N-{2-fluoro-4-methyl-5-[8-(morpholin-4-yl)imidazo[1,2-a]pyridin-6-yl]phenyl}-1-isopropylpyrrolidine-3-carboxamide | Calc'd 466.30, found 466.57 | CHIRALPAK IG, Hex:DCM = 3:1 (0.5% 2M NH$_3$—MeOH)/ IPA = 80/20, 2ed peak |
| 207 3-Tert-butyl-N-{2-fluoro-4-methyl-5-[8-(morpholin-4-yl)imidazo[1,2-a]pyridin-6-yl]phenyl}-2,5-dihydropyrrole-1-carboxamide | Calc'd 478.25, found 478.30 | |
| 208 1-(Tert-butyl)-5-fluoro-N-(2-fluoro-4-methyl-5-(8-morpholino-[1,2,4]triazolo[4,3-a]pyridin-6-yl)phenyl)-1H-pyrazole-4-carboxamide | Calc'd 496.22, found 496.30 | |
| 209 1-(Tert-butyl)-3-fluoro-N-(2-fluoro-4-methyl-5-(8-morpholino-[1,2,4]triazolo[4,3-a]pyridin-6-yl)phenyl)-1H-pyrazole-4-carboxamide | Calc'd 496.22, found 496.30 | |
| 210 1-Tert-butyl-5-fluoro-N-{2-fluoro-4-methyl-5-[5-(morpholin-4-yl)imidazo[1,2-a]pyridin-7-yl]phenyl}pyrazole-4-carboxamide | Calc'd 495.22, found 495.30 | |
| 211 1-Tert-butyl-3-fluoro-N-{2-fluoro-4-methyl-5-[5-(morpholin-4-yl)imidazo[1,2-a]pyridin-7-yl]phenyl}pyrazole-4-carboxamide | Calc'd 495.22, found 495.30 | |
| 212 1-Tert-butyl-5-fluoro-N-{4-methyl-3-[7-(morpholin-4-yl)pyrazolo[1,5-a]pyridin-5-yl]phenyl}pyrazole-4-carboxamide | Calc'd | |
| 213 1-Tert-butyl-3-fluoro-N-{4-methyl-3-[7-(morpholin-4-yl)pyrazolo[1,5-a]pyridin-5-yl]phenyl}pyrazole-4-carboxamide | Calc'd 477.23, found 477.20 | |
| 214 1-Tert-butyl-N-{2-fluoro-4-methyl-5-[7-(morpholin-4-yl)pyrazolo[1,5-a]pyridin-5-yl]phenyl}imidazole-4-carboxamide | Calc'd 477.23, found 477.35 | |
| 215 1-Tert-butyl-N-{4-methyl-3-[5-(morpholin-4-yl)imidazo[1,5-a]pyridin-7-yl]phenyl}imidazole-4-carboxamide | Calc'd 459.24, found 459.30 | |
| 216 1-Tert-butyl-N-{4-methyl-3-[7-(morpholin-4-yl)pyrazolo[1,5-a]pyridin-5-yl]phenyl}imidazole-4-carboxamide | Calc'd 459.24, found 459.30 | |
| 217 N-(2-fluoro-4-methyl-5-(8-morpholinoimidazo[1,2-a]pyridin-6-yl)phenyl)-7-methyl-4,5,6,7-tetrahydropyrazolo[1,5-a]pyridine-3-carboxamide | Calc'd 489.23, found 489.35 | |
| 218 1-Tert-butyl-N-{2-fluoro-4-methyl-5-[8-(morpholin-4-yl)imidazo[1,2-a]pyridin-6-yl]phenyl}pyrrolo[2,3-b]pyridine-4-carboxamide | Calc'd 527.25, found 527.35 | |
| 219 2-(3,3-Difluoropyrrolidin-1-yl)-N-{2-fluoro-4-methyl-5-[8-(morpholin-4-yl)imidazo[1,2-a]pyridin-6-yl]phenyl}pyridine-4-carboxamide | Calc'd 537.21, found 537.35 | |
| 221 1-(Tert-butyl)-5-fluoro-N-(2-fluoro-4-methyl-5-(5-morpholinoimidazo[1,5-a]pyridin-7-yl)phenyl)-1H-pyrazole-4-carboxamide | Calc'd 495.22, found 495.35 | |
| 222 1-(Tert-butyl)-3-fluoro-N-(2-fluoro-4-methyl-5-(5-morpholinoimidazo[1,5-a]pyridin-7-yl)phenyl)-1H-pyrazole-4-carboxamide | Calc'd 495.22, found 495.35 | |
| 223 1-(Tert-butyl)-N-(2-fluoro-4-methyl-5-(5-morpholinoimidazo[1,5-a]pyridin-7-yl)phenyl)-1H-imidazole-4-carboxamide | Calc'd 477.23, found 477.30 | |
| 224 1-(Tert-butyl)-5-fluoro-N-(4-(8-morpholinoimidazo[1,2-a]pyridin-6-yl)-5-(trifluoromethyl)pyridin-2-yl)-1H-pyrazole-4-carboxamide | Calc'd 532.20, found 532.35 | |
| 225 1-(Tert-butyl)-3-fluoro-N-(4-(8-morpholinoimidazo[1,2-a]pyridin-6-yl)-5-(trifluoromethyl)pyridin-2-yl)-1H-pyrazole-4-carboxamide | Calc'd 532.20, found 532.35 | |

TABLE 8-continued

| Ex. Compound Name | Exact Mass [M + H]+ | Chiral separation conditions |
|---|---|---|
| 226 1-(Tert-butyl)-N-(5-chloro-4-(8-morpholinoimidazo[1,2-a]pyridin-6-yl)pyridin-2-yl)-3-fluoro-1H-pyrazole-4-carboxamide | Calc'd 498.17, 500.17, found 498.25, 500.25 | |
| 228 1-(Tert-butyl)-3-fluoro-N-(2-fluoro-4-methyl-5-(8-morpholinoimidazo[1,2-a]pyrazin-6-yl)phenyl)-1H-pyrazole-4-carboxamide | Calc'd 496.22, found 496.35 | |
| 230 1-(Tert-butyl)-N-(2-fluoro-4-methyl-5-(8-morpholinoimidazo[1,2-b]pyridazin-6-yl)phenyl)-1H-imidazole-4-carboxamide | Calc'd 478.23, found 478.30 | |
| 231 1-(Tert-butyl)-N-(2-fluoro-4-methyl-5-(8-morpholinoimidazo[1,2-a]pyrazin-6-yl)phenyl)-1H-imidazole-4-carboxamide | Calc'd 478.23, found 478.20 | |
| 232 4-(Tert-butyl)-3,3-difluoro-N-(2-fluoro-4-methyl-5-(8-morpholinoimidazo[1,2-a]pyridin-6-yl)phenyl)pyrrolidine-1-carboxamide | Calc'd 516.25, found 516.40 | |
| 233 1-(Tert-butyl)-5-fluoro-N-(4-methyl-3-(5-morpholinoimidazo[1,5-a]pyridin-7-yl)phenyl)-1H-pyrazole-4-carboxamide | Calc'd 477.23, found 477.30 | |
| 234 1-(Tert-butyl)-5-fluoro-N-(6-fluoro-5-methyl-4-(8-morpholinoimidazo[1,2-a]pyridin-6-yl)pyridin-2-yl)-1H-pyrazole-4-carboxamide | Calc'd 496.22, found 496.15 | |
| 235 1-(Tert-butyl)-3-fluoro-N-(6-fluoro-5-methyl-4-(8-morpholinoimidazo[1,2-a]pyridin-6-yl)pyridin-2-yl)-1H-pyrazole-4-carboxamide | Calc'd 496.22, found 496.30 | |
| 237 1-(Tert-butyl)-5-fluoro-N-(5-fluoro-4-(8-morpholinoimidazo[1,2-a]pyridin-6-yl)pyridin-2-yl)-1H-pyrazole-4-carboxamide | Calc'd 482.20, found 482.35 | |
| 238 1-(Tert-butyl)-3-fluoro-N-(5-fluoro-4-(8-morpholinoimidazo[1,2-a]pyridin-6-yl)pyridin-2-yl)-1H-pyrazole-4-carboxamide | Calc'd 482.20, found 482.30 | |
| 240 1-(Tert-butyl)-3-fluoro-N-(2-fluoro-4-methyl-5-(8-morpholinoimidazo[1,2-b]pyridazin-6-yl)phenyl)-1H-pyrazole-4-carboxamide | Calc'd 496.22, found 496.30 | |
| 241 1-(Tert-butyl)-5-fluoro-N-(2-fluoro-5-(8-(4-fluorotetrahydro-2H-pyran-4-yl)imidazo[1,2-a]pyridin-6-yl)-4-methylphenyl)-1H-pyrazole-4-carboxamide | Calc'd 512.22, found 512.40 | |
| 242 1-(Tert-butyl)-N-(5-(8-(3,6-dihydro-2H-pyran-4-yl)imidazo[1,2-b]pyridazin-6-yl)-2-fluoro-4-methylphenyl)-5-fluoro-1H-pyrazole-4-carboxamide | Calc'd 493.21, found 493.35 | |
| 244 1-(Tert-butyl)-N-(5-(8-(3,6-dihydro-2H-pyran-4-yl)imidazo[1,2-b]pyridazin-6-yl)-2-fluoro-4-methylphenyl)-3-fluoro-1H-pyrazole-4-carboxamide | Calc'd 493.21, found 493.35 | |
| 245 1-(Tert-butyl)-N-(2,5-difluoro-4-methyl-3-(8-morpholinoimidazo[1,2-a]pyridin-6-yl)phenyl)-5-fluoro-1H-pyrazole-4-carboxamide | Calc'd 513.21, found 513.35 | |
| 246 1-(Tert-butyl)-5-fluoro-N-(2-fluoro-4-methyl-5-(8-(pyrimidin-4-yl)imidazo[1,2-a]pyridin-6-yl)phenyl)-1H-pyrazole-4-carboxamide | Calc'd 488.19, found 488.10 | |
| 249 1-(Tert-butyl)-3-fluoro-N-(2-fluoro-5-(8-(4-fluorotetrahydro-2H-pyran-4-yl)imidazo[1,2-a]pyridin-6-yl)-4-methylphenyl)-1H-pyrazole-4-carboxamide | Calc'd 512.22, found 512.35 | |
| 251 1-Tert-butyl-3-fluoro-N-{2-fluoro-4-methyl-5-[2-methyl-8-(morpholin-4-yl)-[1,2,4]triazolo[1,5-a]pyridin-6-yl]phenyl}pyrazole-4-carboxamide | Calc'd 510.24, found 510.25 | |

TABLE 8-continued

| Ex. Compound Name | Exact Mass [M + H]+ | Chiral separation conditions |
|---|---|---|
| 250 1-(Tert-butyl)-5-fluoro-N-(2-fluoro-4-methyl-5-(2-methyl-5-morpholinoimidazo[1,2-a]pyridin-7-yl)phenyl)-1H-pyrazole-4-carboxamide | Calc'd 509.24, found 509.20 | |
| 254 N-(1-(Tert-butyl)-5-fluoro-1H-pyrazol-4-yl)-4-methyl-3-(8-morpholinoimidazo[1,2-a]pyridin-6-yl)benzamide | Calc'd 477.23, found 477.35 | |
| 255 1-(Tert-butyl)-5-fluoro-N-(2-fluoro-4-methyl-5-(8-(pyridin-4-yl)imidazo[1,2-a]pyridin-6-yl)phenyl)-1H-pyrazole-4-carboxamide | Calc'd 487.20, found 487.35 | |
| 256 1-(Tert-butyl)-3-fluoro-N-(2-fluoro-4-methyl-5-(8-(pyridin-4-yl)imidazo[1,2-a]pyridin-6-yl)phenyl)-1H-pyrazole-4-carboxamide | Calc'd 487.20, found 487.05 | |
| 257 1-(Tert-butyl)-3-fluoro-N-(2-fluoro-4-methyl-5-(8-(pyrimidin-4-yl)imidazo[1,2-a]pyridin-6-yl)phenyl)-1H-pyrazole-4-carboxamide | Calc'd 488.19, found 488.30 | |
| 258 1-(Tert-butyl)-5-fluoro-N-(2-fluoro-4-methyl-5-(1-morpholinopyrrolo[1,2-a]pyrazin-3-yl)phenyl)-1H-pyrazole-4-carboxamide | Calc'd 495.22, found 495.35 | |
| 259 N-(1-(Tert-butyl)-3-fluoro-1H-pyrazol-4-yl)-4-methyl-3-(8-morpholinoimidazo[1,2-a]pyridin-6-yl)benzamide | Calc'd 477.23, found 477.35 | |
| 261 N-(1-(Tert-butyl)-5-fluoro-1H-pyrazol-4-yl)-4-methyl-3-(8-morpholinoimidazo[1,2-b]pyridazin-6-yl)benzamide | Calc'd 478.23, found 478.35 | |
| 262 7,7-difluoro-N-(2-fluoro-4-methyl-5-(8-morpholinoimidazo[1,2-a]pyridin-6-yl)phenyl)-6,7-dihydro-5H-cyclopenta[b]pyridine-4-carboxamide | Calc'd 508.19, found 508.20 | |
| 264 1-(Tert-butyl)-N-(5-(difluoromethyl)-4-(8-morpholinoimidazo[1,2-a]pyridin-6-yl)pyridin-2-yl)-5-fluoro-1H-pyrazole-4-carboxamide | Calc'd 514.21, found 514.35 | |
| 268 N-(1-(Tert-butyl)-5-fluoro-1H-pyrazol-4-yl)-3-(3-fluoro-8-morpholinoimidazo[1,2-a]pyridin-6-yl)-4-methylbenzamide | Calc'd 495.22, found 495.40 | |
| 269 N-(1-(Tert-butyl)-5-fluoro-1H-pyrazol-4-yl)-4-methyl-3-(2-methyl-8-morpholinoimidazo[1,2-a]pyridin-6-yl)benzamide | Calc'd 491.25, found 491.40 | |
| 270 N-(1-(Tert-butyl)-5-fluoro-1H-pyrazol-4-yl)-2-fluoro-4-methyl-5-(5-morpholinoimidazo[1,5-a]pyridin-7-yl)benzamide | Calc'd 495.22, found 495.35 | |
| 271 N-(1-(Tert-butyl)-3-fluoro-1H-pyrazol-4-yl)-2-fluoro-4-methyl-5-(5-morpholinoimidazo[1,5-a]pyridin-7-yl)benzamide | Calc'd 495.22, found 495.15 | |
| 272 N-(1-(Tert-butyl)-5-fluoro-1H-pyrazol-4-yl)-4-methyl-3-(5-morpholinoimidazo[1,5-a]pyridin-7-yl)benzamide | Calc'd 477.23, found 477.35 | |
| 276 N-(1-(Tert-butyl)-5-fluoro-1H-pyrazol-4-yl)-3-(3-fluoro-2-methyl-8-morpholinoimidazo[1,2-a]pyridin-6-yl)-4-methylbenzamide | Calc'd 509.24, found 509.40 | |
| 277 5-(Tert-butyl)-N-(2-fluoro-4-methyl-5-(8-morpholinoimidazo[1,2-a]pyridin-6-yl)phenyl)oxazole-2-carboxamide | Calc'd 478.22, found 478.30 | |
| 278 N-(5-(2-amino-8-morpholino-[1,2,4]triazolo[1,5-a]pyridin-6-yl)-2-fluoro-4-methylphenyl)-1-(tert-butyl)-5-fluoro-1H-pyrazole-4-carboxamide | Calc'd 511.23, found 511.40 | |
| 279 N-(2-(Tert-butyl)oxazol-5-yl)-3-(3-fluoro-2-methyl-8-morpholinoimidazo[1,2-a]pyridin-6-yl)-4-methylbenzamide | Calc'd 492.23, found 492.40 | |

TABLE 8-continued

| Ex. | Compound Name | Exact Mass [M + H]+ | Chiral separation conditions |
|---|---|---|---|
| 280 | N-(2-(Tert-butyl)oxazol-5-yl)-2-fluoro-5-(3-fluoro-2-methyl-8-morpholinoimidazo[1,2-a]pyridin-6-yl)-4-methylbenzamide | Calc'd 510.22, found 510.20 | |
| 281 | 4-(Tert-butyl)-N-(2-fluoro-4-methyl-5-(8-morpholinoimidazo[1,2-a]pyridin-6-yl)phenyl)oxazole-2-carboxamide | Calc'd 478.22, found 478.20 | |
| 284 | N-(1-(Tert-butyl)-5-fluoro-1H-pyrazol-4-yl)-4-methyl-3-(2-methyl-5-morpholino-[1,2,4]triazolo[1,5-a]pyridin-7-yl)benzamide | Calc'd 492.24, found 490.35 | |
| 286 | N-(2-(Tert-butyl)oxazol-5-yl)-3-(3-fluoro-8-morpholinoimidazo[1,2-a]pyridin-6-yl)-4-methylbenzamide | Calc'd 478.22, found 478.35 | |
| 287 | N-(2-(Tert-butyl)oxazol-5-yl)-2-fluoro-5-(3-fluoro-8-morpholinoimidazo[1,2-a]pyridin-6-yl)-4-methylbenzamide | Calc'd 496.21, found 496.35 | |
| 288 | N-(1-(Tert-butyl)-5-fluoro-1H-pyrazol-4-yl)-5-methyl-4-(8-morpholinoimidazo[1,2-a]pyridin-6-yl)picolinamide | Calc'd 478.23, found 478.40 | |
| 289 | N-(1-(Tert-butyl)-5-fluoro-1H-pyrazol-4-yl)-4-(3-fluoro-8-morpholinoimidazo[1,2-a]pyridin-6-yl)-5-methylpicolinamide | Calc'd 496.22, found 496.35 | |
| 290 | 1-(Tert-butyl)-5-fluoro-N-(4-(3-fluoro-8-morpholinoimidazo[1,2-a]pyridin-6-yl)-5-methylpyridin-2-yl)-1H-pyrazole-4-carboxamide | Calc'd 496.22, found 496.35 | |
| 295 | N-(2-(Tert-butyl)oxazol-5-yl)-2-fluoro-4-methyl-5-(2-methyl-8-morpholino-[1,2,4]triazolo[1,5-a]pyridin-6-yl)benzamide | Calc'd 493.23, found 493.25 | |
| 296 | N-(2-Tert-butyl-1,3-oxazol-5-yl)-5-methyl-4-[2-methyl-8-(morpholin-4-yl)-[1,2,4]triazolo[1,5-a]pyridin-6-yl]pyridine-2-carboxamide | Calc'd 476.23, found 476.25 | |
| 297 | N-(1-Tert-butyl-5-fluoropyrazol-4-yl)-5-methyl-4-[2-methyl-8-(morpholin-4-yl)-[1,2,4]triazolo[1,5-a]pyridin-6-yl]pyridine-2-carboxamide | Calc'd 493.24, found 493.40 | |
| 298 | N-(1-Tert-butyl-5-fluoropyrazol-4-yl)-5-methyl-4-[2-methyl-5-(morpholin-4-yl)-[1,2,4]triazolo[1,5-a]pyridin-7-yl]pyridine-2-carboxamide | Calc'd 491.24, found 491.40 | |
| 300 | 1-Tert-butyl-5-fluoro-N-{2-fluoro-5-[3-fluoro-8-(morpholin-4-yl)imidazo[1,2-a]pyridin-6-yl]-6-methylpyridin-3-yl}pyrazole-4-carboxamide | Calc'd 514.21, found 514.35, | |
| 301 | N-(1-Tert-butyl-5-fluoropyrazol-4-yl)-2-fluoro-6-methyl-5-[8-(morpholin-4-yl)imidazo[1,2-a]pyridin-6-yl]pyridine-3-carboxamide | Calc'd 496.22, found 496.20 | |
| 302 | N-(4-Tert-butyl-1,3-oxazol-2-yl)-4-[3-fluoro-8-(morpholin-4-yl)imidazo[1,2-a]pyridin-6-yl]-5-methylpyridine-2-carboxamide | Calc'd 479.21, found 479.35 | |

II. Biological Evaluation

Example 1: Kinase Assay Protocol

Enzymatic BRAF Kinase Activity Determination:
Small molecule inhibition of the BRAF kinases was measured using ADP-Glo assay. In the assay, ADP is converted to ATP in the presence of test kinase and substrate, resulting in luciferase reaction and luminescent readout with light generated proportional to the relative kinase activity. Compounds diluted in DMSO were used in 10-point, 3-fold dose curve for both assays. Final concentrations of 6 nM BRAF (CarnaBio, Cat. 09-122) or 3 nM RAF1 (CarnaBio, Cat. 09-125) and 30 nM MEK1 substrate (Millipore, Cat. 14-420) were incubated with 3 M ATP, 10 mM MgCl2, 0.003% Brij-35, 2 mM DTT, 0.05% BSA, 1 mM EGTA, and 50 mM HEPES for 90 minutes at room temp prior to addition of ADP-Glo reagent (Promega, Cat. V9102) for 40 minutes, and detection reagent for 45 minutes. Luminescence was read on an Envision plate reader (PerkinElmer) and percent remaining activity was used to calculate IC50 using a four-parameter fit model using Dotmatics Knowledge Solutions Studies curve fitting (Dotmatics, Bishops Stortford, UK, CM23).

Representative data for exemplary compounds is presented in Table 9.

TABLE 9

| Synthetic Chemistry Example | BRAF IC$_{50}$ |
|---|---|
| 1 | B |
| 16 | B |
| 17 | B |
| 22 | B |
| 23 | B |
| 33 | B |
| 34 | B |
| 35 | B |
| 36 | B |
| 38 | B |
| 43 | B |
| 46 | B |
| 50 | B |
| 60 | B |
| 61 | C |
| 66 | B |
| 67 | B |
| 69 | B |
| 70 | B |
| 73 | B |
| 74 | B |
| 75 | B |
| 76 | B |
| 84 | B |
| 86 | B |
| 87 | B |
| 88 | B |
| 89 | C |
| 90 | C |
| 91 | B |
| 92 | B |
| 95 | C |
| 98 | B |
| 99 | C |
| 103 | B |
| 110 | B |
| 111 | C |
| 112 | C |
| 113 | B |
| 114 | B |
| 118 | B |
| 119 | B |
| 120 | B |
| 121 | B |
| 122 | B |
| 123 | B |
| 124 | B |
| 125 | B |
| 136 | B |
| 137 | B |
| 138 | B |
| 140 | B |
| 141 | B |
| 142 | B |
| 143 | B |
| 148 | B |
| 151 | B |
| 153 | B |
| 159 | B |
| 160 | B |
| 162 | B |
| 163 | B |
| 164 | B |
| 166 | B |
| 180 | B |
| 181 | B |
| 183 | B |
| 184 | B |
| 185 | B |
| 186 | B |
| 188 | B |
| 186 | B |

TABLE 9-continued

| Synthetic Chemistry Example | BRAF IC$_{50}$ |
|---|---|
| 188 | B |
| 189 | B |
| 204 | B |
| 205 | C |
| 206 | B |
| 220 | C |
| 226 | B |
| 228 | B |
| 236 | C |
| 239 | B |
| 242 | B |
| 247 | C |
| 253 | C |
| 260 | B |
| 263 | B |
| 265 | B |
| 267 | B |
| 273 | B |
| 274 | B |
| 275 | A |
| 282 | C |
| 283 | B |
| 285 | B |
| 291 | C |
| 292 | C |
| 293 | B |
| 294 | C |
| 303 | B |
| 304 | B |
| 305 | C |
| 306 | B |
| 307 | B |
| 308 | B |
| 309 | B |
| 310 | B |

Note:
Biochemical assay IC$_{50}$ data are designated within the following ranges:
A: ≤0.001 μM
B: >0.001 μM to ≤0.010 μM
C: >0.010 μM to ≤0.100 μM
D: >0.100 μM to ≤1 μM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, having the structure of Formula (Ia):

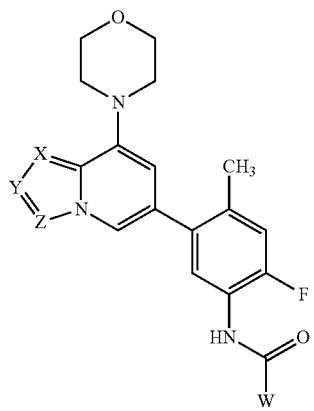

(Ia)

wherein,
X is N or C—R¹;
Y is N or C—R²;
Z is N or C—R³;
R¹, R², and R³ are independently selected from H, —CN, halogen, optionally substituted alkyl, optionally substituted cycloalkyl, or optionally substituted cycloalkylalkyl; and
W is an optionally substituted nitrogen-containing heterocyclyl, optionally substituted nitrogen-containing heteroaryl, optionally substituted aryl, optionally substituted nitrogen-containing heterocyclyl further substituted with an optionally substituted cycloalkyl, optionally substituted nitrogen-containing heteroaryl further substituted with an optionally substituted cycloalkyl, or optionally substituted aryl further substituted with an optionally substituted cycloalkyl.

2. The compound of claim 1, or pharmaceutically acceptable salt or solvate thereof, wherein X is C—R¹.

3. The compound of claim 2, or pharmaceutically acceptable salt or solvate thereof, wherein Y is N, and Z is N.

4. The compound of claim 2, or pharmaceutically acceptable salt or solvate thereof, wherein Y is C—R², and Z is N.

5. The compound of claim 2, or pharmaceutically acceptable salt or solvate thereof, wherein Y is N, and Z is C—R³.

6. The compound of claim 2, or pharmaceutically acceptable salt or solvate thereof, wherein Y is C—R², and Z is C—R³.

7. The compound of claim 1, or pharmaceutically acceptable salt or solvate thereof, wherein Y is C—R².

8. The compound of claim 7, or pharmaceutically acceptable salt or solvate thereof, wherein X is N, and Z is N.

9. The compound of claim 7, pharmaceutically acceptable salt or solvate thereof, wherein X is C—R¹, and Z is N.

10. The compound of claim 7, or pharmaceutically acceptable salt or solvate thereof, wherein X is N, and Z is C—R³.

11. The compound of claim 7, or pharmaceutically acceptable salt or solvate thereof, wherein X is C—R¹, and Z is C—R³.

12. The compound of claim 1, or pharmaceutically acceptable salt or solvate thereof, wherein Z is C—R³.

13. The compound of claim 12, or pharmaceutically acceptable salt or solvate thereof, wherein X is N, and Y is N.

14. The compound of claim 12, or pharmaceutically acceptable salt or solvate thereof, wherein X is C—R¹, and Y is N.

15. The compound of claim 1, or pharmaceutically acceptable salt or solvate thereof, wherein X is N, and Y is C—R².

16. The compound of claim 12, or pharmaceutically acceptable salt or solvate thereof, wherein X is C—R¹, and Y is C—R².

17. The compound of claim 1, or pharmaceutically acceptable salt or solvate thereof, wherein R² is H.

18. The compound of claim 1, or pharmaceutically acceptable salt or solvate thereof, wherein R² is halogen.

19. The compound of claim 1, or pharmaceutically acceptable salt or solvate thereof, wherein R² is optionally substituted alkyl.

20. The compound of claim 1, or pharmaceutically acceptable salt or solvate thereof, wherein R² is optionally substituted cycloalkyl.

21. The compound of claim 1, or pharmaceutically acceptable salt or solvate thereof, wherein R³ is H.

22. The compound of claim 1, or pharmaceutically acceptable salt or solvate thereof, wherein R³ is halogen.

23. The compound of claim 1, or pharmaceutically acceptable salt or solvate thereof, wherein R³ is fluorine.

24. The compound of claim 1, or pharmaceutically acceptable salt or solvate thereof, wherein W is an optionally substituted nitrogen-containing heteroaryl.

25. The compound of claim 24, or pharmaceutically acceptable salt or solvate thereof, wherein W is an optionally substituted pyrazyl, optionally substituted imidazyl, optionally substituted triazyl, or optionally substituted tetrazyl.

26. The compound of claim 24, or pharmaceutically acceptable salt or solvate thereof, wherein W is an optionally substituted pyraz-3-yl, optionally substituted pyraz-4-yl, optionally substituted pyraz-5-yl, optionally substituted imidaz-4-yl, or optionally substituted imidaz-5-yl.

27. The compound of claim 24, or pharmaceutically acceptable salt or solvate thereof, wherein W is an optionally substituted oxaz-2-yl, optionally substituted oxaz-4-yl, or optionally substituted oxaz-5-yl.

28. The compound of claim 1, pharmaceutically acceptable salt or solvate thereof, wherein W is selected from:

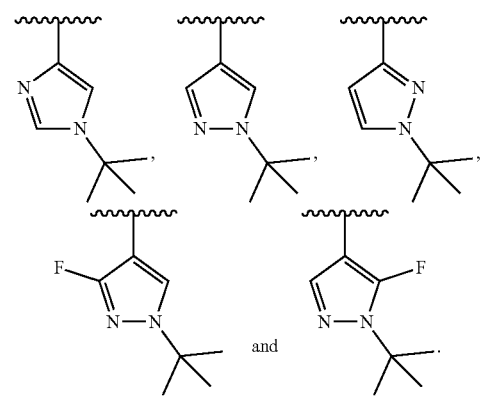

29. The compound of claim 1, or pharmaceutically acceptable salt or solvate thereof, wherein W is selected from:

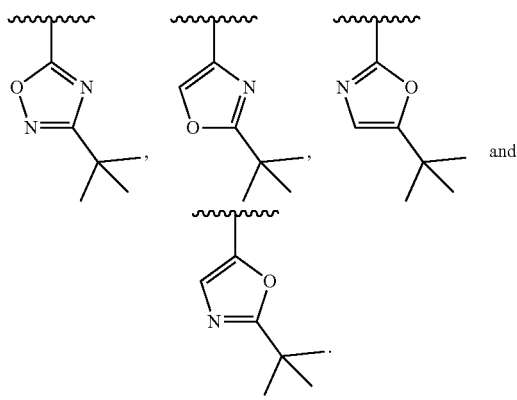
30. A pharmaceutical composition comprising a compound, or pharmaceutically acceptable salt or solvate thereof, as described in claim 1, and a pharmaceutically acceptable excipient.
* * * * *